US011239427B2

(12) United States Patent
Lee et al.

(10) Patent No.: US 11,239,427 B2
(45) Date of Patent: Feb. 1, 2022

(54) HETEROCYCLIC COMPOUND AND ORGANIC LIGHT EMITTING DEVICE USING SAME

(71) Applicant: LT MATERIALS CO., LTD., Yongin (KR)

(72) Inventors: Gi-Back Lee, Osan-si (KR); Han-Kook Oh, Osan-si (KR); Yong-Geun Jung, Seoul (KR); Jun-Tae Mo, Osan-si (KR); Won-Jang Jeong, Hwaseong-si (KR); Jin-Seok Choi, Suwon-si (KR); Dae-Hyuk Choi, Yongin-si (KR); Joo-Dong Lee, Seongnam-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 412 days.

(21) Appl. No.: 16/315,485

(22) PCT Filed: Jul. 6, 2017

(86) PCT No.: PCT/KR2017/007250
§ 371 (c)(1),
(2) Date: Jan. 4, 2019

(87) PCT Pub. No.: WO2018/009007
PCT Pub. Date: Jan. 11, 2018

(65) Prior Publication Data

US 2019/0319195 A1 Oct. 17, 2019

(30) Foreign Application Priority Data

Jul. 6, 2016 (KR) ........................ 10-2016-0085748

(51) Int. Cl.
*C07D 221/06* (2006.01)
*H01L 51/00* (2006.01)
*H01L 51/50* (2006.01)

(52) U.S. Cl.
CPC ........ *H01L 51/0067* (2013.01); *C07D 221/06* (2013.01); *H01L 51/0052* (2013.01);
(Continued)

(58) Field of Classification Search
None
See application file for complete search history.

(56) References Cited

U.S. PATENT DOCUMENTS

| | | | |
|---|---|---|---|
| 8,114,529 | B2 | 2/2012 | Kitazawa et al. |
| 2012/0280613 | A1 | 11/2012 | Kang et al. |
| 2013/0256637 | A1 | 10/2013 | Seo et al. |

FOREIGN PATENT DOCUMENTS

| | | | |
|---|---|---|---|
| CN | 101077971 A | 11/2007 | |
| EP | 2182002 A1 | 5/2010 | |

(Continued)

OTHER PUBLICATIONS

Zhou et al. "Altering the Position of Phenyl Substitution to Adjust Film Morphology and Memory Device Performance." Chemistry—An Asian Journal 10, No. 7 (2015): 1474-1479. (Year: 2015).*

(Continued)

*Primary Examiner* — Robert S Loewe
(74) *Attorney, Agent, or Firm* — Birch, Stewart, Kolasch & Birch, LLP

(57) ABSTRACT

The present application provides a hetero-cyclic compound capable of significantly enhancing lifespan, efficiency, electrochemical stability and thermal stability of an organic light emitting device, and an organic light emitting device containing the hetero-cyclic compound in an organic compound layer.

8 Claims, 3 Drawing Sheets

(52) U.S. Cl.
CPC ...... *H01L 51/0072* (2013.01); *H01L 51/0073* (2013.01); *H01L 51/0074* (2013.01); *H01L 51/5072* (2013.01); *H01L 51/5092* (2013.01); *H01L 51/5096* (2013.01)

(56) References Cited

FOREIGN PATENT DOCUMENTS

| | | | |
|---|---|---|---|
| JP | 2008-177459 | A | 7/2008 |
| JP | 2008-243932 | A | 10/2008 |
| JP | 2013-509390 | A | 3/2013 |
| JP | 2013-229322 | A | 11/2013 |
| JP | 2014-508130 | A | 4/2014 |
| KR | 10-1148460 | B1 | 5/2012 |
| KR | 10-2015-0103967 | A | 9/2015 |
| KR | 10-2015-0124000 | A | 11/2015 |
| KR | 10-2016-0008946 | A | 1/2016 |
| WO | WO 2011/051749 | A1 | 5/2011 |

OTHER PUBLICATIONS

Xiang-Shan et al. "A highly selective method for the synthesis of 1,3-diarylbenzo[f]quinoline derivatives catalyzed by silver triflate" Monatsh Chem 2012, 143, 935-938. (Year: 2012).*

International Search Report for PCT/KR2017/007250(PCT/ISA/210) dated Oct. 20, 2017.

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole-Transport Materials", Advanced Materials, vol. 6, No. 9, 1994, p. 677-679.

Qiao et al., "High-efficiency orange to near-infrared emissions from bis-cyclometalated iridium complexes with phenyl-benzoquinoline isomers as ligands", Journal of Material Chemistry, vol. 19, 2009, p. 6573-6580.

Chemical Abstract compound, STN express, RN 344249-16-7, Entered STN: Jul. 1, 2001, 2 pages.

Chemical Abstract compound, STN express, RN 344249-22-5, Entered STN: Jul. 1, 2001, 2 pages.

Chemical Abstract compound, STN express, RN 344249-29-2, Entered STN: Jul. 1, 2001, 2 pages.

Extended European Search Report, dated Nov. 25, 2019, for European Application No. 17824563.5.

Doklady Akademi Nauk BSSR, 1969, 13(7), p. 614-616.

Doklady Akademnii Nauk BSSR, 1976, 20(8), p. 714-716.

Dyes and Pigments, 2014, 109, p. 155-162.

Japanese Office Action dated Jun. 1, 2021 for Japanese Application No. 2019-500236 with English translation.

Khimiya Geterosiklicheskikh Soedinenii, 1979, (4), p. 520-526.

Vestsi Akademii Nauk BSSR, Seryya Khimichnykh Navuk, 1968, (5), p. 104-106.

European Comerunication pursuant to Article 94(3) EPC for European Application No. 17824563.5, dated Mar. 24, 2021.

* cited by examiner

【FIG. 1】
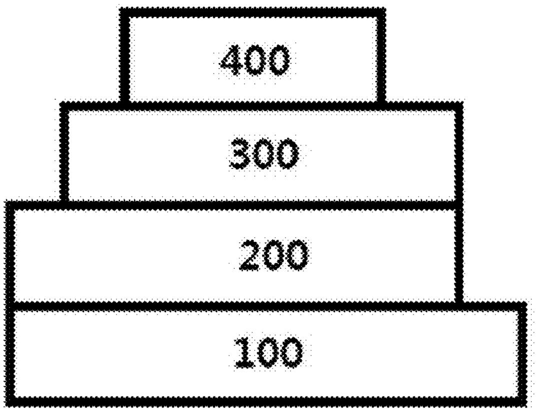
【FIG. 2】
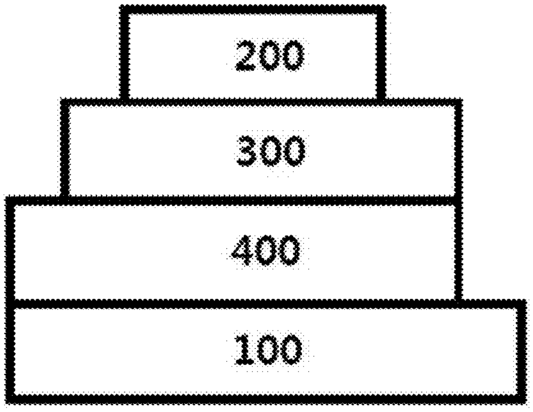

【FIG. 3】
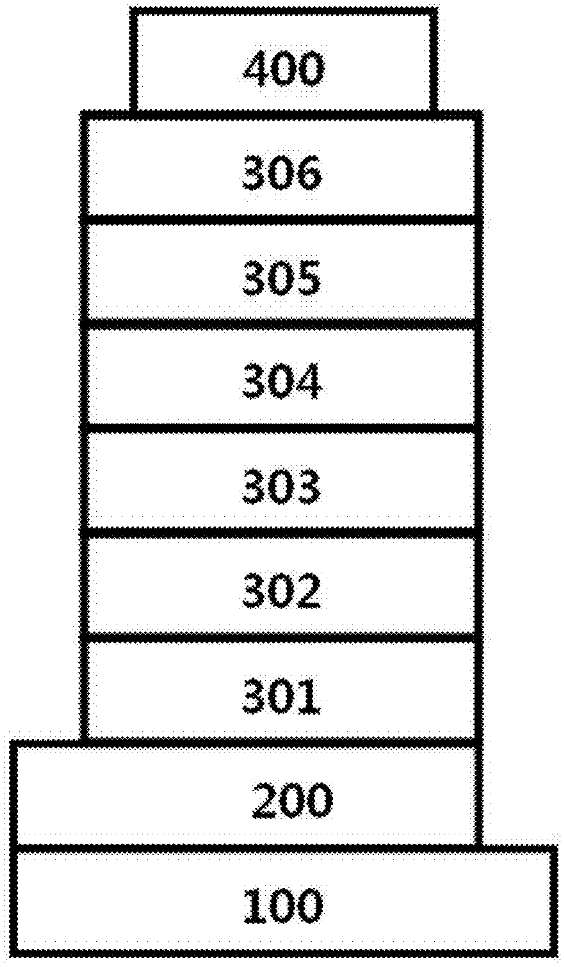

【FIG. 4】

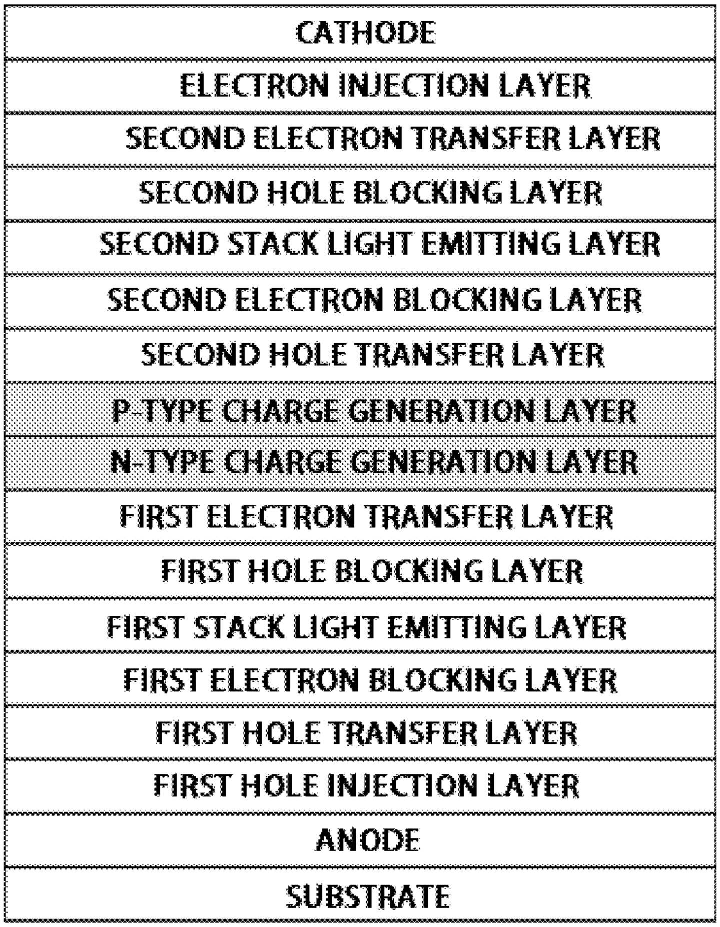

[FIG. 4]

| CATHODE |
|---|
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT EMITTING DEVICE USING SAME

TECHNICAL FIELD

This application claims priority to and the benefits of Korean Patent Application No. 10-2016-0085748, filed with the Korean Intellectual Property Office on Jul. 6, 2016, the entire contents of which are incorporated herein by reference.

The present application relates to a hetero-cyclic compound and an organic light emitting device using the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

the organic thin film, compounds capable of forming a light emitting layer themselves may be used alone, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifespan or efficiency of an organic light emitting device.

PRIOR ART DOCUMENTS

Patent Documents

U.S. Pat. No. 4,356,429

DISCLOSURE

Technical Problem

Researches for an organic light emitting device comprising a compound capable of satisfying conditions required for materials usable in an organic light emitting device, for example, a proper energy level, electrochemical stability, thermal stability and the like, and having a chemical structure that may perform various roles required in an organic light emitting device depending on substituents have been required.

Technical Solution

One embodiment of the present application provides a hetero-cyclic compound represented by the following Chemical Formula 1:

[Chemical Formula 1]

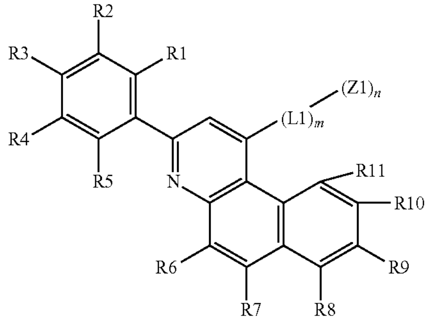

in Chemical Formula 1,

L1 is a direct bond; a substituted or unsubstituted $C_6$ to $C_{60}$ arylene group; or a $C_2$ to $C_{60}$ heteroarylene group, Z1 is selected from the group consisting of hydrogen; deuterium; a halogen group; —CN; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, m is an integer of 0 to 4, n is an integer of 1 to 4, R1 to R11 are the same as or different from each other, and each independently selected from the group consisting of hydrogen; deuterium; a halogen group; —CN; a substituted or unsubstituted $C_1$ to $C_{60}$ alkyl group; a substituted or unsubstituted $C_2$ to $C_{60}$ alkenyl group; a substituted or unsubstituted $C_2$ to $C_{60}$ alkynyl group; a substituted or unsubstituted $C_1$ to $C_{60}$ alkoxy group; a substituted or unsubstituted $C_3$ to $C_{60}$ cycloalkyl group; a substituted or unsubstituted $C_2$ to $C_{60}$ heterocycloalkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, or two or more groups adjacent to each other bond to each other to form a substituted or unsubstituted aliphatic or aromatic hydrocarbon ring, and R, R' and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

Another embodiment of the present application provides an organic light emitting device comprising an anode, a cathode and one or more organic material layers provided between the anode and the cathode, wherein one or more layers of the organic material layers comprise the hetero-cyclic compound represented by Chemical Formula 1.

Advantageous Effects

A hetero-cyclic compound according to one embodiment of the present application can be used as an organic material layer material of an organic light emitting device. The hetero-cyclic compound can be used as a material of a hole injection layer, a hole transfer layer, a light emitting layer, an electron transfer layer, an electron injection layer, a charge generation layer or the like in an organic light emitting device. Particularly, the hetero-cyclic compound represented by Chemical Formula 1 can be used as a material of an electron transfer layer or a charge generation layer in an organic light emitting device. In addition, using the hetero-cyclic compound represented by Chemical Formula 1 in an organic light emitting device lowers a driving voltage of the device, enhances light efficiency, and can enhance a lifespan property of the device with thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

A hetero-cyclic compound according to one embodiment of the present application is represented by Chemical Formula 1. More specifically, the hetero-cyclic compound represented by Chemical Formula 1 is capable of being used as an organic material layer material of an organic light emitting device with such a core structure and structural characteristics of substituents.

In one embodiment of the present application, when m of Chemical Formula 1 is 2 or greater, two or more L1s may be the same as or different from each other. In addition, when n of Chemical Formula 1 is 2 or greater, two or more Z1s may be the same as or different from each other.

In one embodiment of the present application, m of Chemical Formula 1 may be an integer of 1 to 4.

In one embodiment of the present application, at least one of R1 to R5 of Chemical Formula 1 may be represented by -(L2)p-(Z2)q. Herein, L2 has the same definition as L1 of Chemical Formula 1, Z2 has the same definition as Z1 of Chemical Formula 1, p is an integer of 0 to 4, and q is an integer of 1 to 4.

In another embodiment, one of R2 and R3 of Chemical Formula 1 may be represented by -(L2)p-(Z2)q, and the other one may be hydrogen. Herein, L2 has the same definition as L1 of Chemical Formula 1, Z2 has the same definition as Z1 of Chemical Formula 1, p is an integer of 0 to 4, and q is an integer of 1 to 4.

According to one embodiment of the present application, Chemical Formula 1 may be represented by the following Chemical Formula 2.

[Chemical Formula 2]

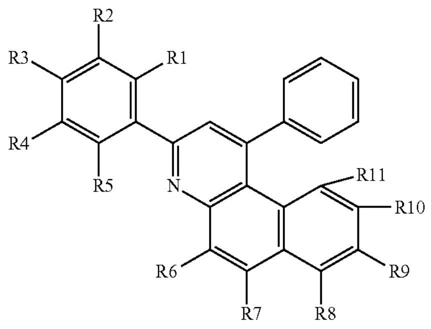

In Chemical Formula 2, at least one of R1 to R5 is represented by -(L2)p-(Z2)q, and the rest have the same definitions as in Chemical Formula 1, L2 has the same definition as L1 of Chemical Formula 1 and Z2 has the same definition as Z1 of Chemical Formula 1, p is an integer of 0 to 4, q is an integer of 1 to 4, and R6 to R11 have the same definitions as in Chemical Formula 1.

According to one embodiment of the present application, Chemical Formula 1 may be represented by the following Chemical Formula 3.

[Chemical Formula 3]

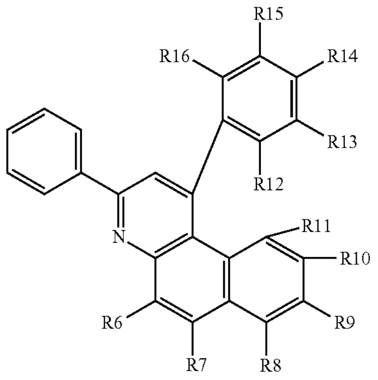

In Chemical Formula 3, at least one of R12 to R16 is represented by -(L3)r-(Z3)s, and the rest are selected from the group consisting of hydrogen; deuterium; a halogen group; —CN; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; —SiRR'R"; —P(=O)RR'; and an amine group unsubstituted or substituted with a $C_1$ to $C_{20}$ alkyl group, a $C_6$ to $C_{60}$ aryl group or a $C_2$ to $C_{60}$ heteroaryl group, L3 has the same definition as L1 of Chemical Formula 1 and Z3 has the same definition as Z1 of Chemical Formula 1, r is an integer of 0 to 3, s is an integer of 1 to 4, and R6 to R11 have the same definitions as in Chemical Formula 1.

In one embodiment of the present application, at least one of R1 to R5 of Chemical Formula 2 may be represented by -(L2)p-(Z2)q. Herein, L2 has the same definition as L1 of Chemical Formula 1, Z2 has the same definitions as Z1 of Chemical Formula 1, p is an integer of 0 to 4, and q is an integer of 1 to 4.

In another embodiment, one of R2 and R3 of Chemical Formula 2 may be represented by -(L2)p-(Z2)q, and the other one may be hydrogen. Herein, L2 has the same definition as L1 of Chemical Formula 1, Z2 has the same definition as Z1 of Chemical Formula 1, p is an integer of 0 to 4, and q is an integer of 1 to 4.

In one embodiment of the present application, at least one of R12 to R16 of Chemical Formula 3 may be represented by -(L3)r-(Z2)s. Herein, L3 has the same definition as L1 of Chemical Formula 1, Z3 has the same definition as Z1 of Chemical Formula 1, r is an integer of 0 to 3, and s is an integer of 1 to 4.

In another embodiment, one of R14 and R15 of Chemical Formula 3 may be represented by -(L3)r-(Z3)s, and the other one may be hydrogen. Herein, L3 has the same definition as L1 of Chemical Formula 1, Z3 has the same definition as Z1 of Chemical Formula 1, r is an integer of 0 to 3, and s is an integer of 1 to 4.

In one embodiment of the present application, R6 to R11 of Chemical Formulae 1 to 3 may be each independently hydrogen or deuterium.

In one embodiment of the present application, L1 to L3 of Chemical Formulae 1 to 3 may be a direct bond; a substituted or unsubstituted $C_6$ to $C_{60}$ arylene group; or a substituted or unsubstituted $C_2$ to $C_{60}$ heteroarylene group.

In another embodiment, L1 to L3 of Chemical Formulae 1 to 3 may be a direct bond; a $C_6$ to $C_{40}$ arylene group; or a $C_2$ to $C_{40}$ heteroarylene group.

In another embodiment, L1 to L3 of Chemical Formulae 1 to may be a direct bond; a phenylene group; a divalent anthracene group; a biphenylene group; or a naphthalene group.

In one embodiment of the present application, Z1 to Z3 of Chemical Formulae 1 to 3 may be each independently hydrogen; deuterium; a substituted or unsubstituted $C_6$ to $C_{60}$ aryl group; or a substituted or unsubstituted $C_2$ to $C_{60}$ heteroaryl group.

In one embodiment of the present application, Z1 to Z3 of Chemical Formulae 1 to 3 may be selected from the group consisting of hydrogen; a substituted or unsubstituted $C_1$ to $C_{60}$ alkyl group; a substituted or unsubstituted $C_6$ to $C_{60}$ aryl group; a substituted or unsubstituted $C_2$ to $C_{60}$ heteroaryl group; and —P(═O)RR'.

In another embodiment, Z1 to Z3 of Chemical Formulae 1 to 3 may be selected from the group consisting of hydrogen; a substituted or unsubstituted $C_6$ to $C_{40}$ aryl group; a substituted or unsubstituted $C_2$ to $C_{40}$ N, O, S-containing heteroaryl group; and —P(═O)RR'.

In another embodiment, Z1 to Z3 of Chemical Formulae 1 to 3 may be selected from the group consisting of hydrogen; a $C_6$ to $C_{40}$ aryl group unsubstituted or substituted with a $C_6$ to $C_{60}$ aryl group; a $C_2$ to $C_{40}$ N, O, S-containing heteroaryl group unsubstituted or substituted with one or more substituents selected from the group consisting of a $C_6$ to $C_{60}$ aryl group and a $C_2$ to $C_{60}$ heteroaryl group; and —P(═O)RR'.

In another embodiment, Z1 to Z3 of Chemical Formulae 1 to 3 may be selected from the group consisting of hydrogen; a phenyl group; a naphthyl group; a phenanthrene group; an anthracene group unsubstituted or substituted with one or more substituents selected from the group consisting of a phenyl group and a naphthyl group; a phenanthroline group unsubstituted or substituted with a phenyl group; a pyridine group unsubstituted or substituted with a pyridine group; a pyrimidine group unsubstituted or substituted with one or more substituents selected from the group consisting of a phenyl group, a biphenyl group, a naphthyl group and a pyridine group; a triazine group unsubstituted or substituted with one or more substituents selected from the group consisting of a phenyl group, a biphenyl group, a naphthyl group and a pyridine group; a quinoline group; a carbazole group unsubstituted or substituted with a phenyl group; a dibenzofuran group; a dibenzothiophene group; and —P(═O)RR'.

In one embodiment of the present application, R, R' and R" of Chemical Formulae 1 to 3 are the same as or different from each other, and may be each independently hydrogen; a substituted or unsubstituted $C_1$ to $C_{60}$ alkyl group; or a substituted or unsubstituted $C_6$ to $C_{60}$ aryl group.

In another embodiment, R, R' and R" of Chemical Formulae 1 to 3 are the same as or different from each other, and may be each independently a phenyl group.

In the present specification, the term “substituted or unsubstituted” means being substituted with one or more substituents selected from the group consisting of deuterium; a halogen group; —CN; a $C_1$ to $C_{60}$ alkyl group; a $C_2$ to $C_{60}$ alkenyl group; a $C_2$ to $C_{60}$ alkynyl group; a $C_3$ to $C_{60}$ cycloalkyl group; a $C_2$ to $C_{60}$ heterocycloalkyl group; a $C_6$ to $C_{60}$ aryl group; a $C_2$ to $C_{60}$ heteroaryl group; —SiRR'R"; —P(═O)RR'; a $C_1$ to $C_{20}$ alkylamine group; a $C_6$ to $C_{60}$ arylamine group; and a 02 to $C_{60}$ heteroarylamine group, or being unsubstituted, or being substituted with a substituent bonding two or more of the above-mentioned substituents, or being substituted, or being substituted with a substituent linking two or more substituents selected from among the above-mentioned substituents, or being unsubstituted. For example, “a substituent linking two or more substituents” may comprise a biphenyl group. In other words, a biphenyl group may be an aryl group, or may be interpreted as a substituent linking two phenyl groups. The additional substituents may be further substituted. R, R' and R" are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

According to one embodiment of the present application, the “substituted or unsubstituted” means being substituted with one or more substituents selected from the group consisting of deuterium, a halogen group, —CN, SiRR'R", P(═O)RR', a $C_1$ to $C_{20}$ linear or branched alkyl group, a $C_6$ to $C_{60}$ aryl group, and a $C_2$ to $C_{60}$ heteroaryl group, or being unsubstituted, and R, R' and R" are the same as or different from each other, and each independently hydrogen; deuterium; —CN; a $C_1$ to $C_{60}$ alkyl group unsubstituted or substituted with deuterium, a halogen group, —CN, a $C_1$ to $C_{20}$ alkyl group, a $C_6$ to $C_{60}$ aryl group and a $C_2$ to $C_{60}$ heteroaryl group; a $C_3$ to $C_{60}$ cycloalkyl group unsubstituted or substituted with deuterium, halogen, —CN, a $C_1$ to $C_{60}$ alkyl group, a $C_6$ to $C_{60}$ aryl group and a $C_2$ to $C_{60}$ heteroaryl group; a $C_6$ to $C_{60}$ aryl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group; or a $C_2$ to $C_{60}$ heteroaryl group unsubstituted or substituted with deuterium, halogen, —CN, a $C_1$ to $C_{20}$ alkyl group, a $C_6$ to $C_{60}$ aryl group and a $C_2$ to $C_{60}$ heteroaryl group.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, however, may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, however, may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, however, may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the spiro group is a group comprising a spiro structure, and may have 15 to 60 carbon atoms. For example, the spiro group may comprise a structure in which a 2,3-dihydro-1H-indene group or a cyclohexane group spiro bonds to a fluorenyl group. Specifically, the following Spiro group may comprise any one of the groups having the following structural formulae.

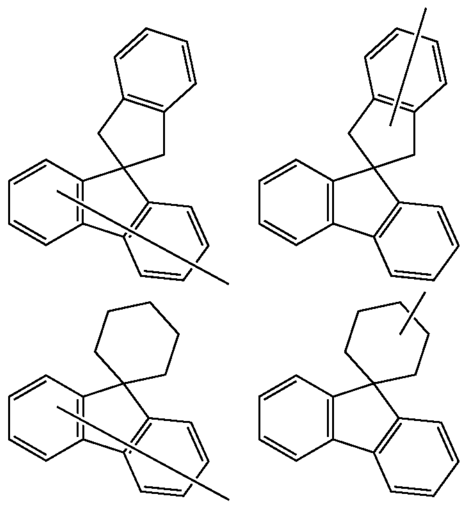

-continued

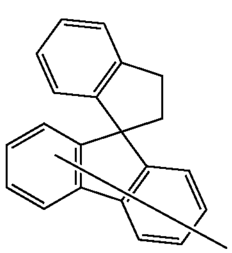

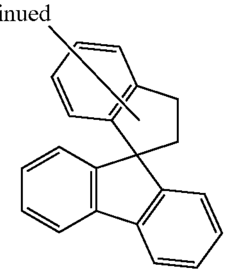

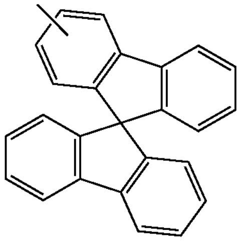

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, however, may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a triazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a triazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; $-NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

According to one embodiment of the present application, Chemical Formula 1 may be represented by any one of the following compounds, but is not limited thereto.

1

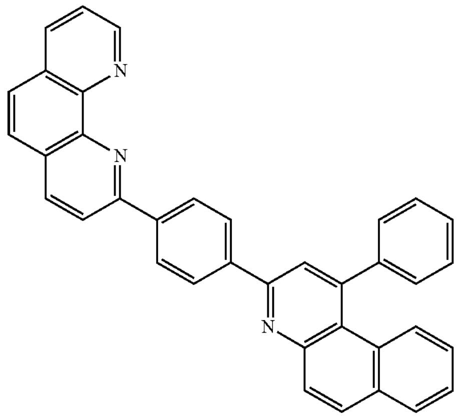

2

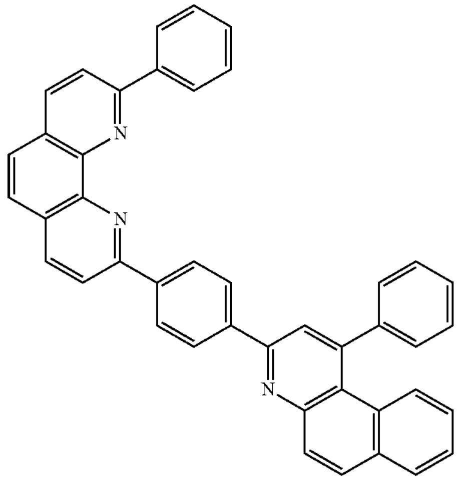

-continued
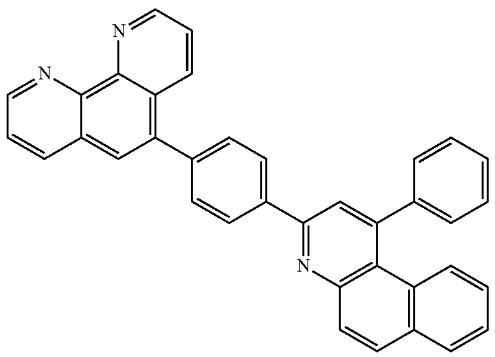
3
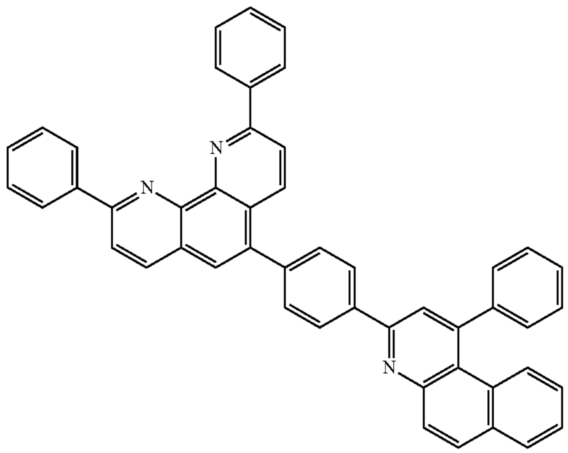
4
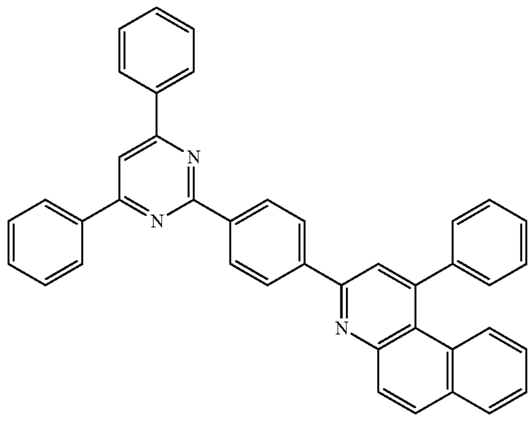
5
-continued
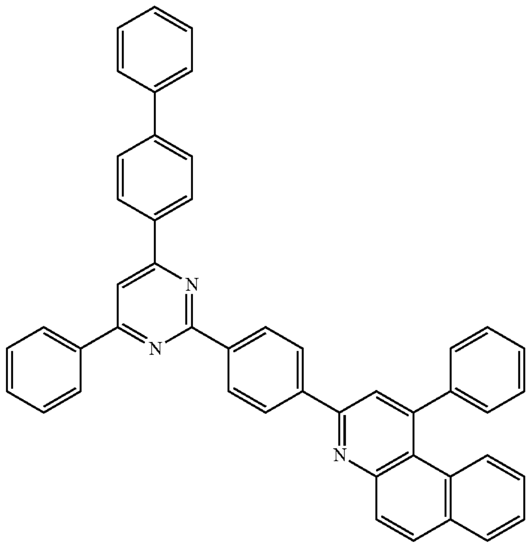
6
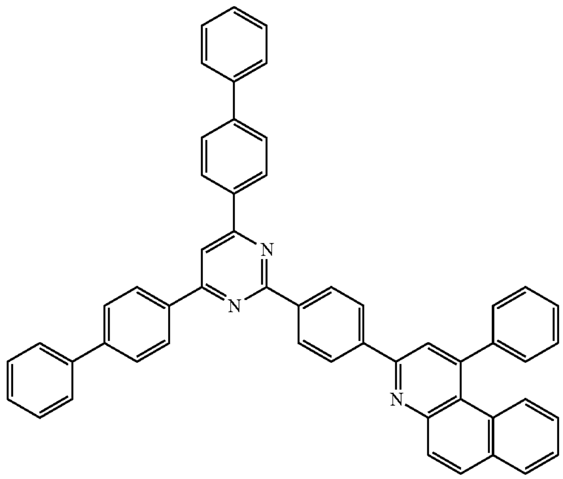
7
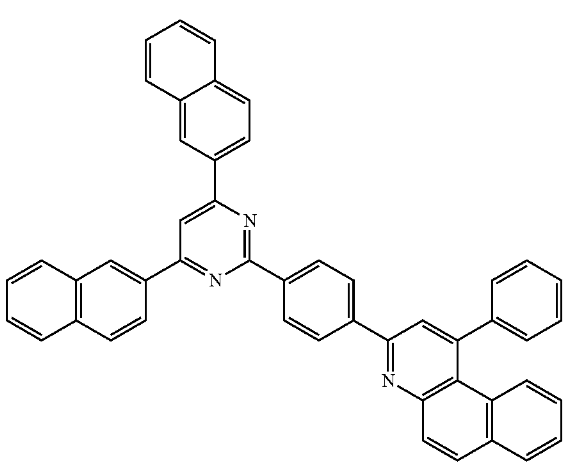
8

9
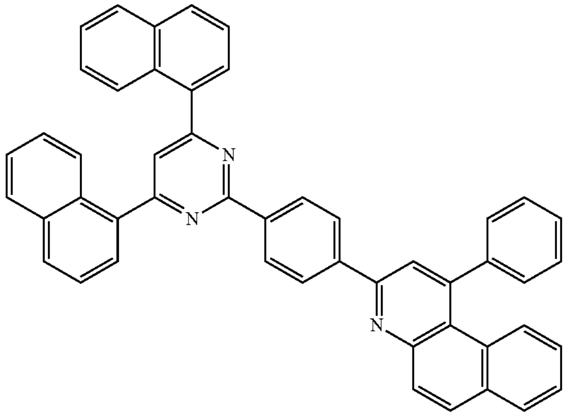
10
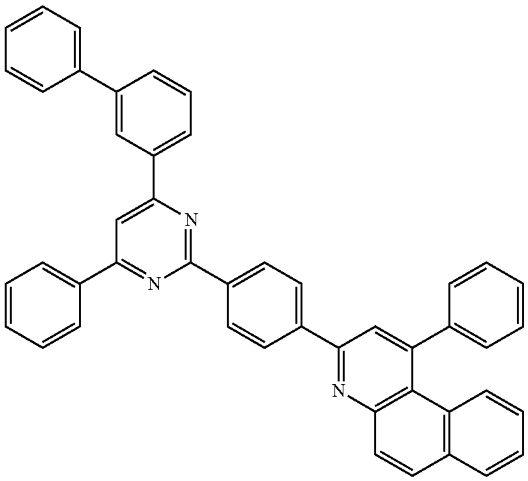
11
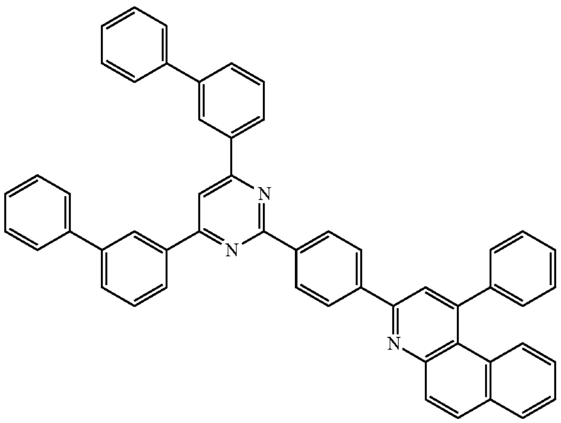
12
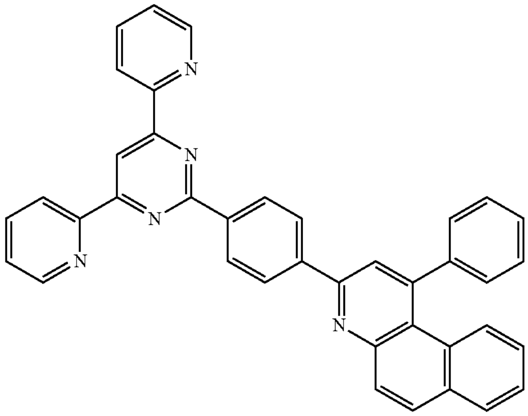
13
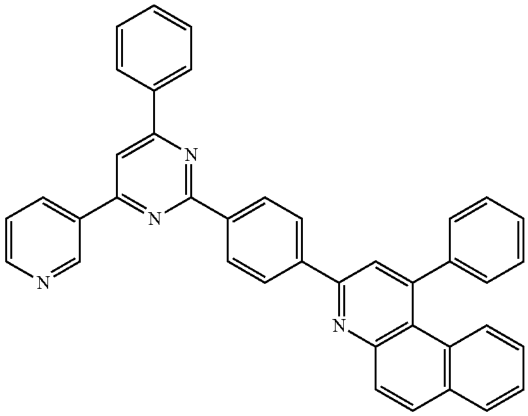
14
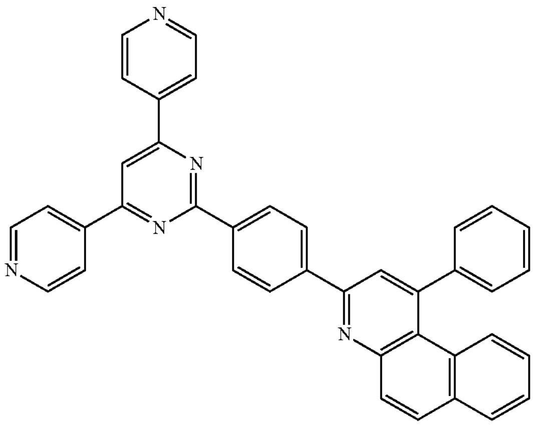

-continued
15
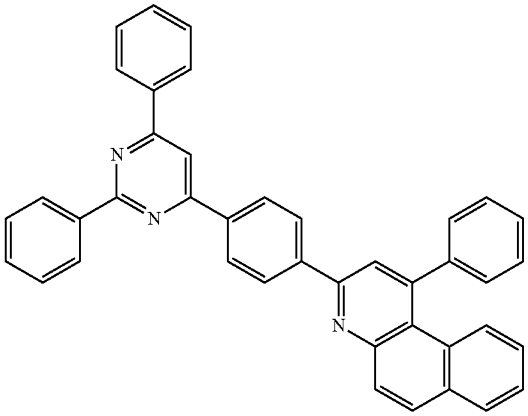
16
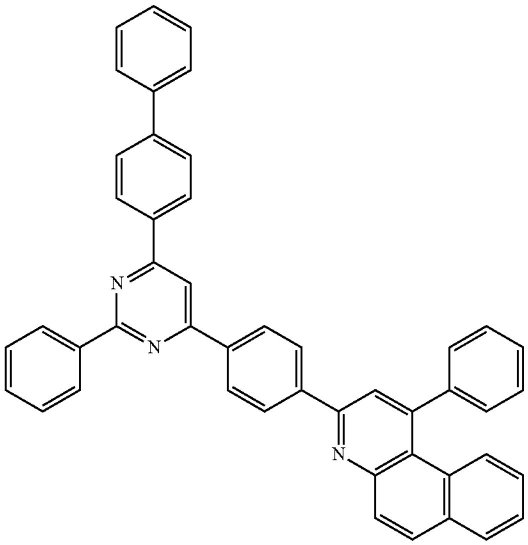
17
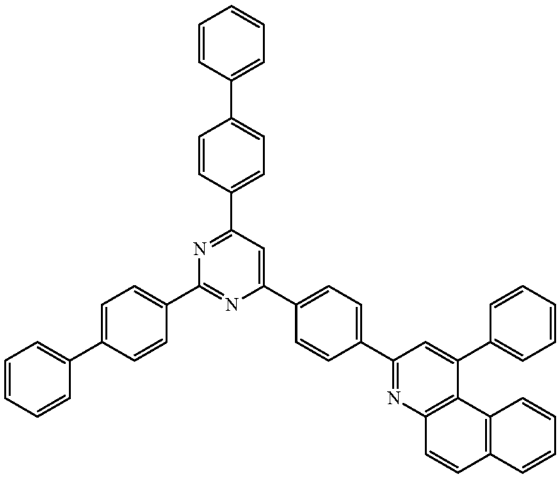
-continued
18
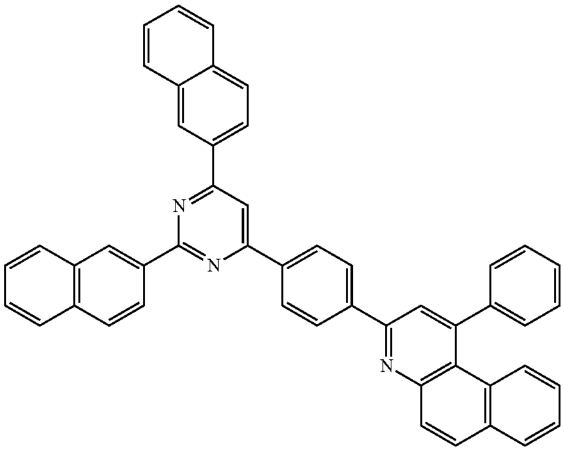
19
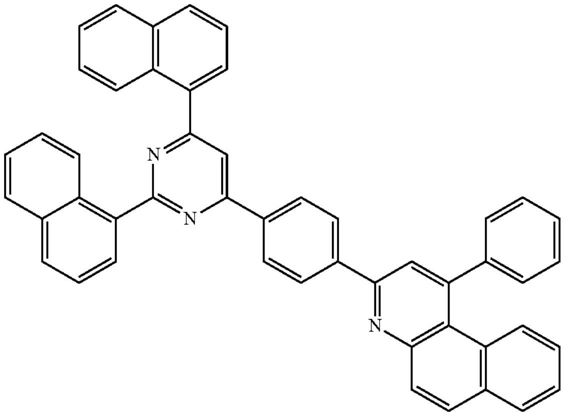
20
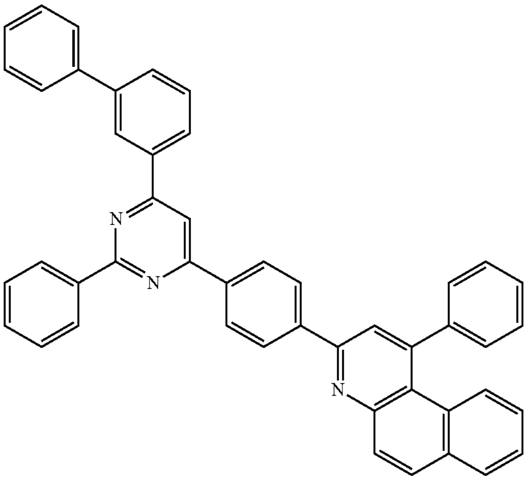

-continued
21
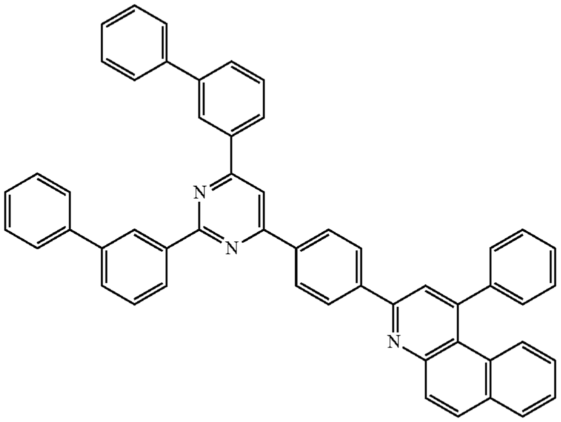
22
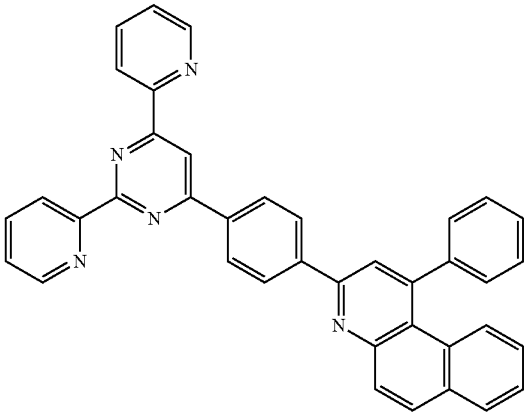
23
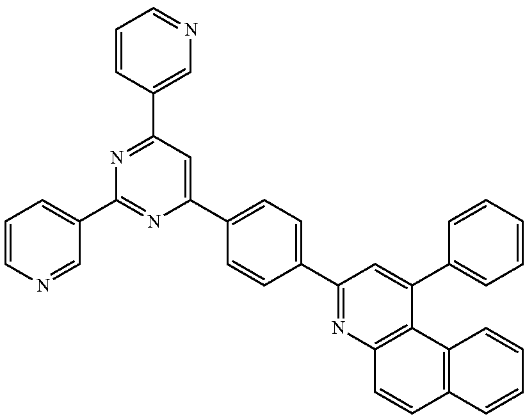
-continued
24
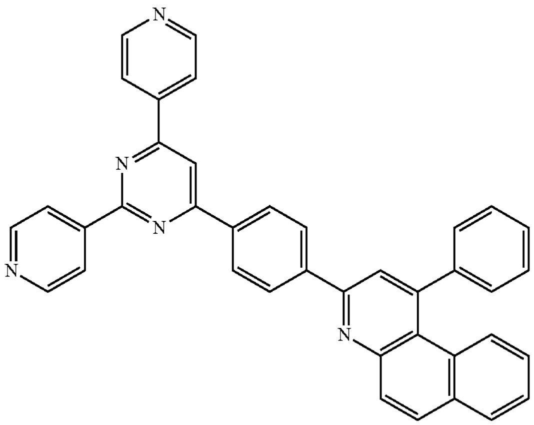
25
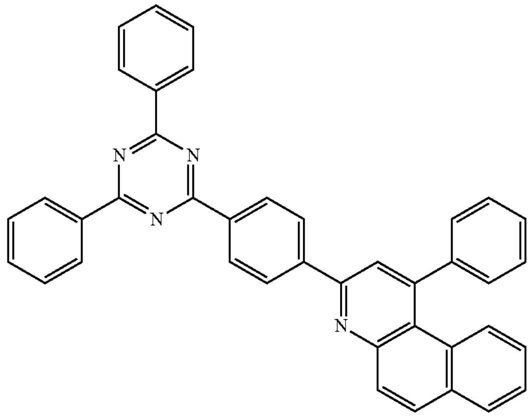
26
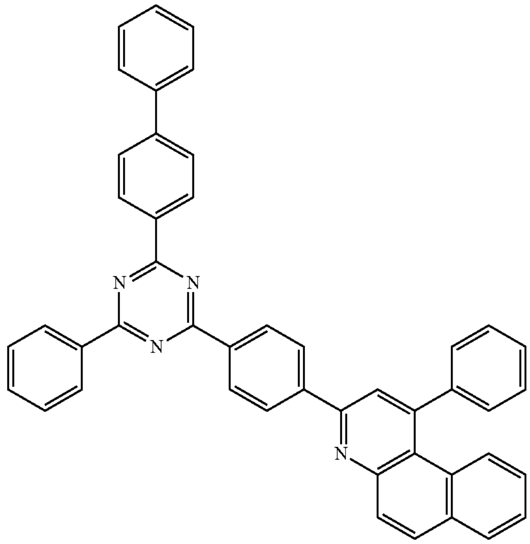

-continued
27
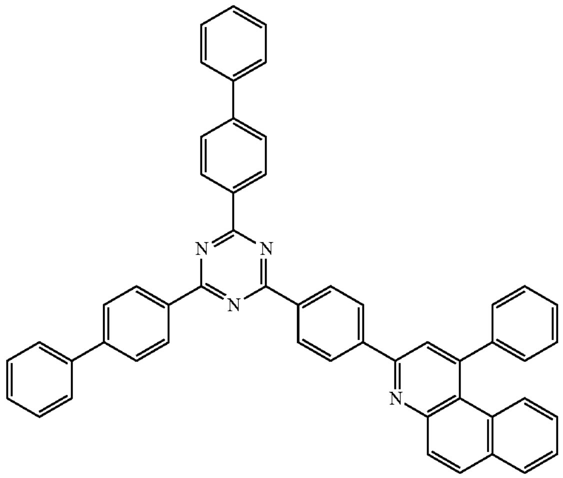
28
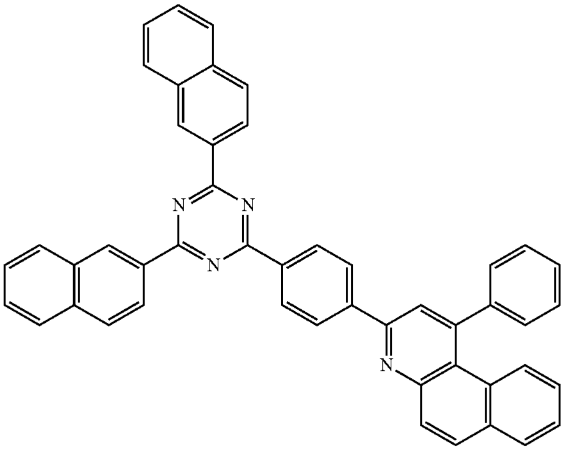
29
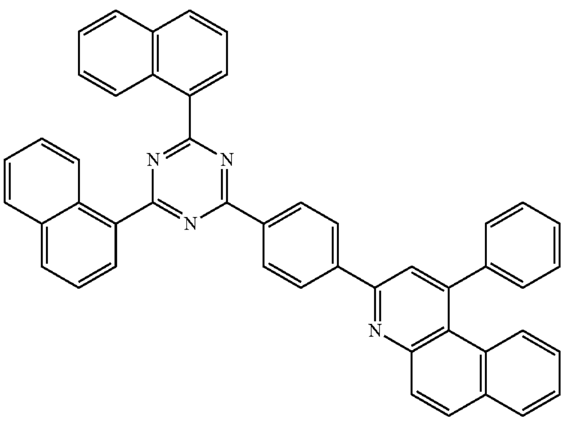
-continued
30
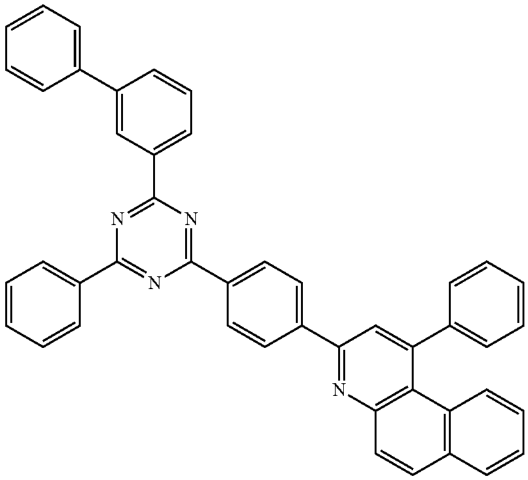
31
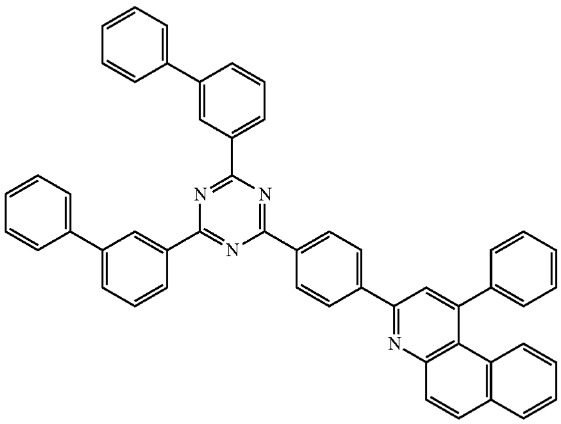
32
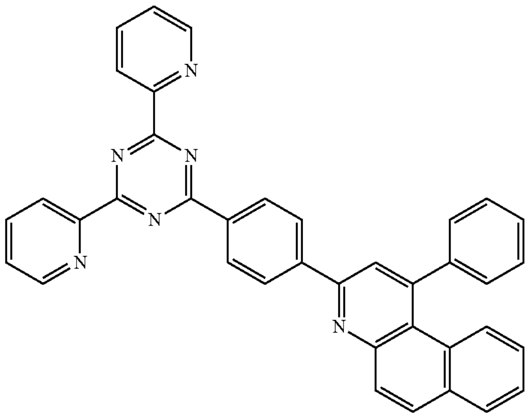

-continued
33
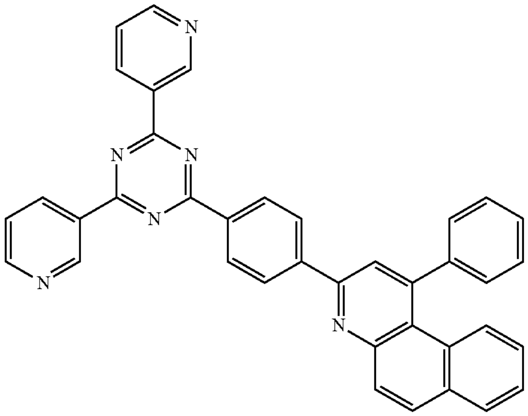
34
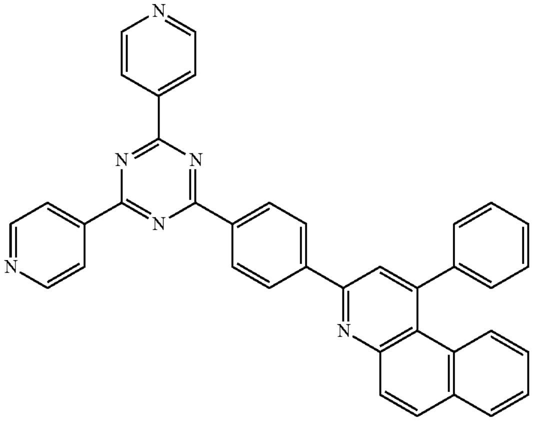
35
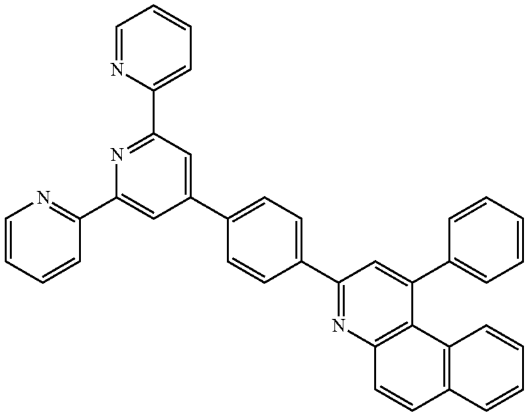
36
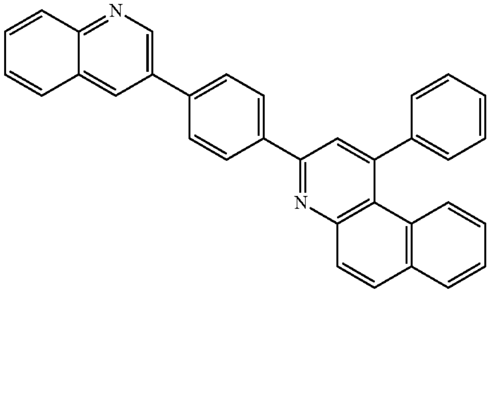
-continued
37
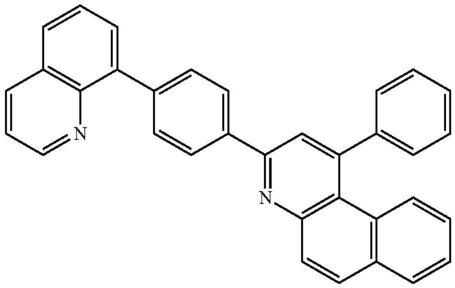
38
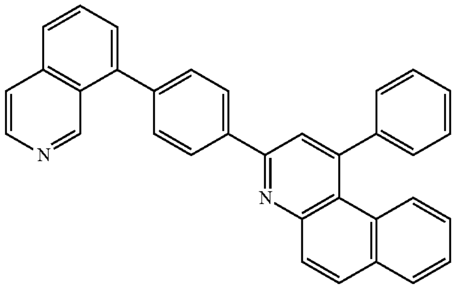
39
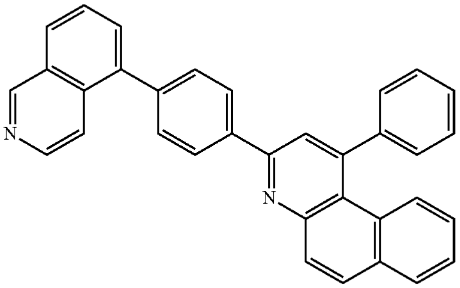
40
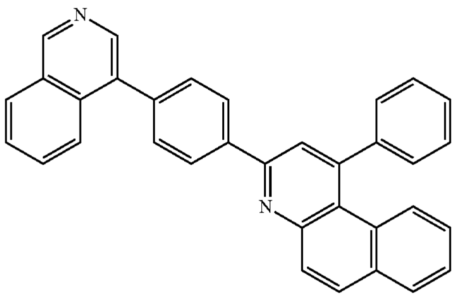
41
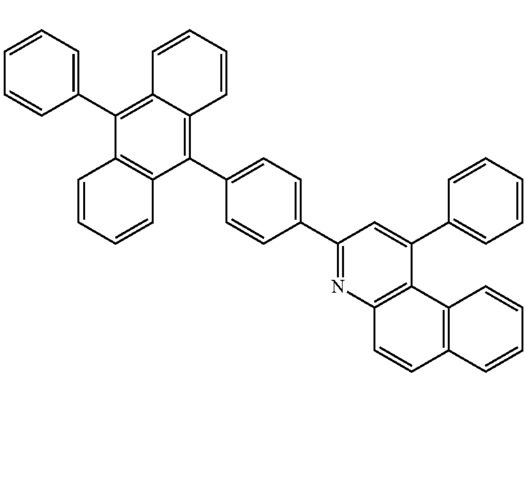

-continued
42
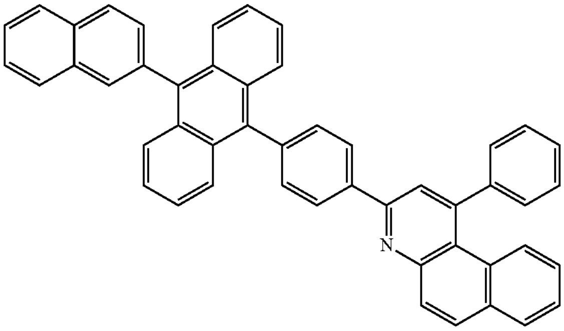
43
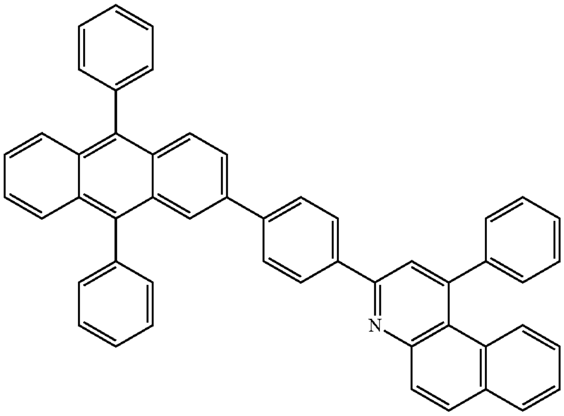
44
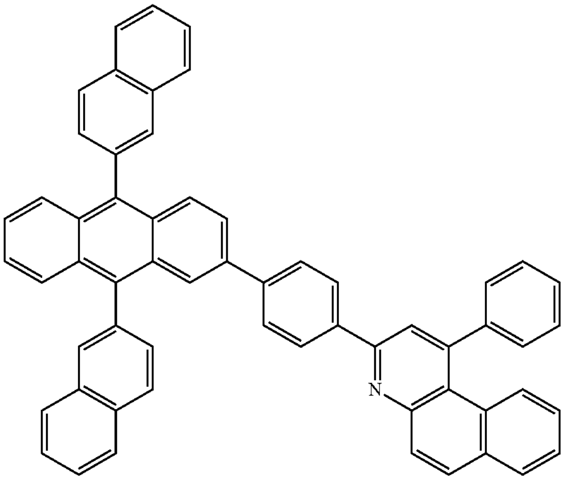
45
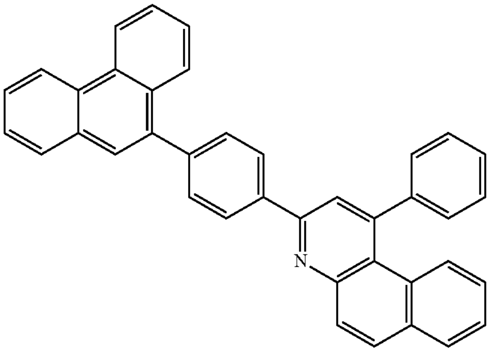
-continued
46
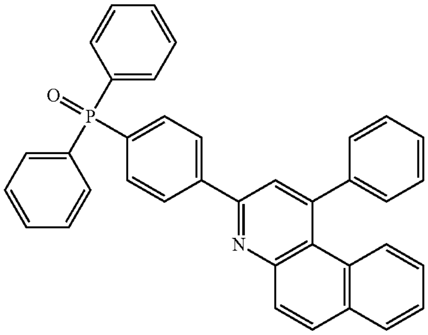
47
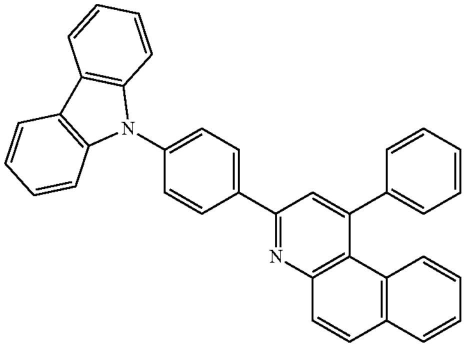
48
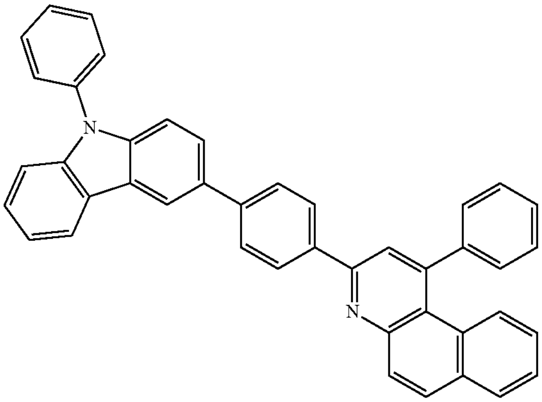
49
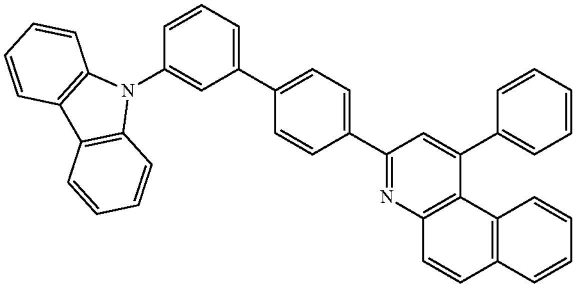

-continued
50
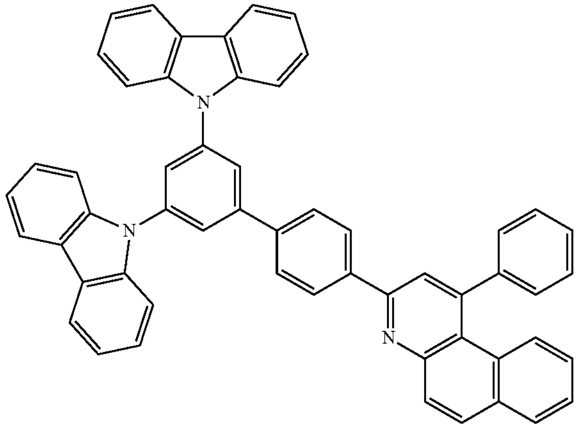
51
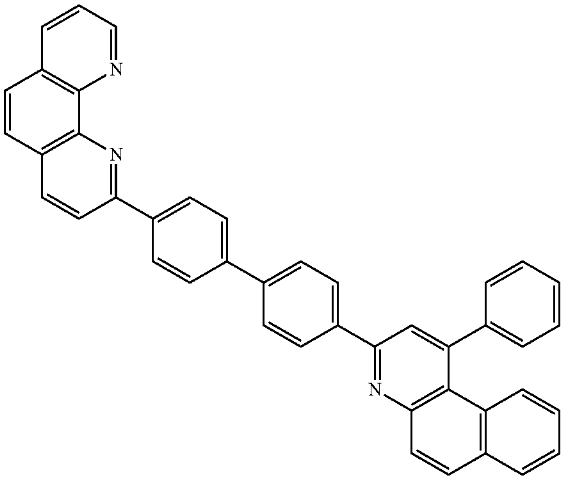
52
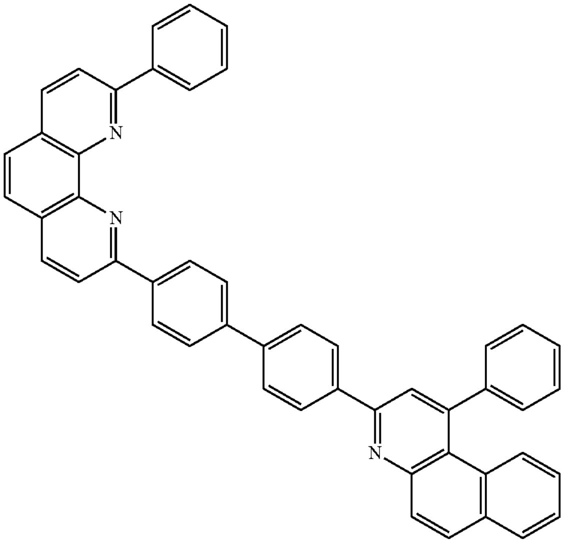
-continued
53
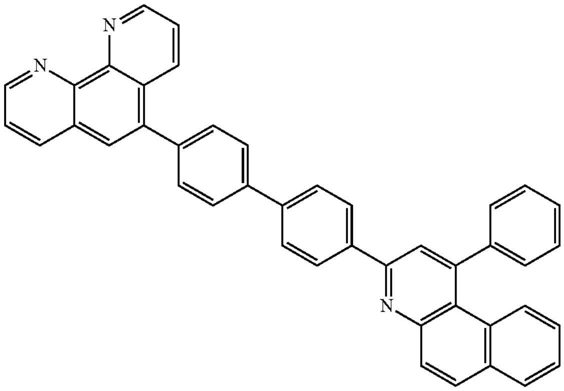
54
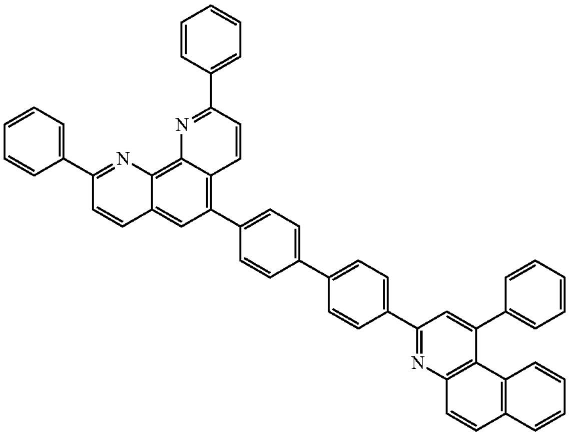
55
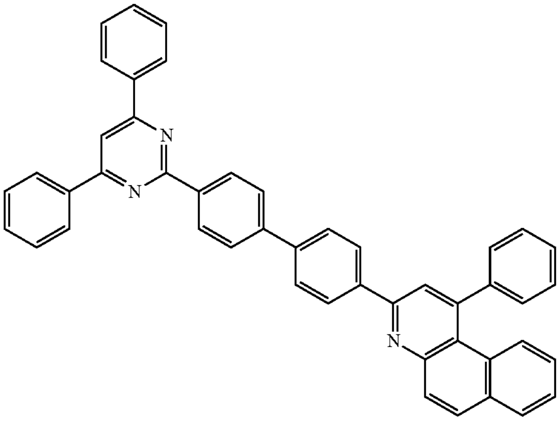

-continued
56
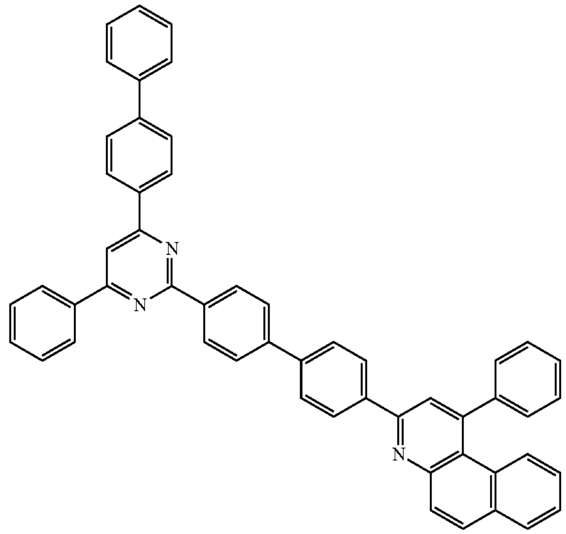
57
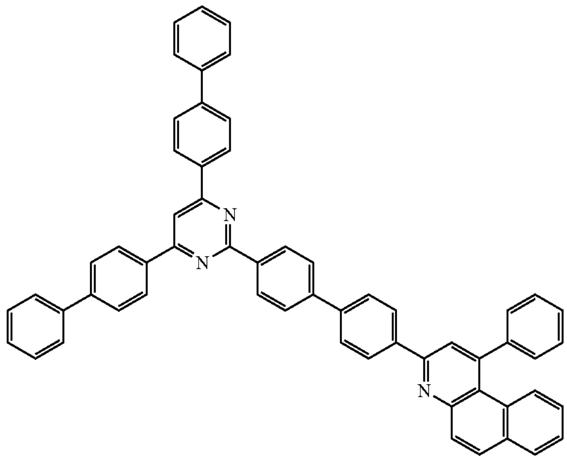
58
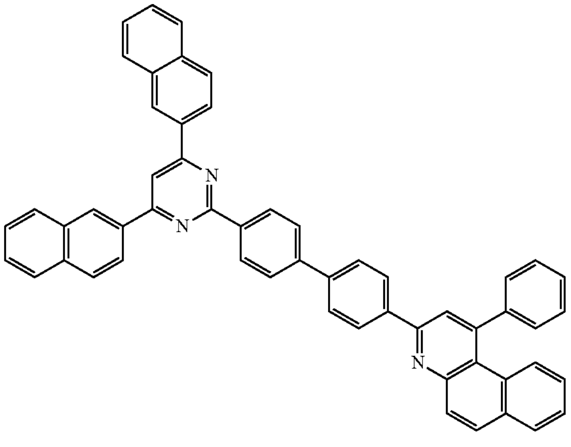
-continued
59
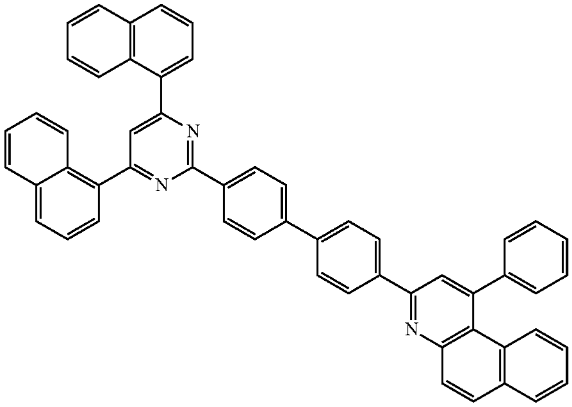
60
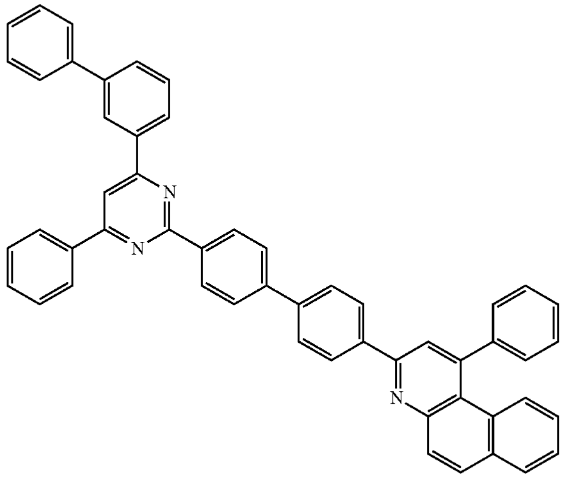
61
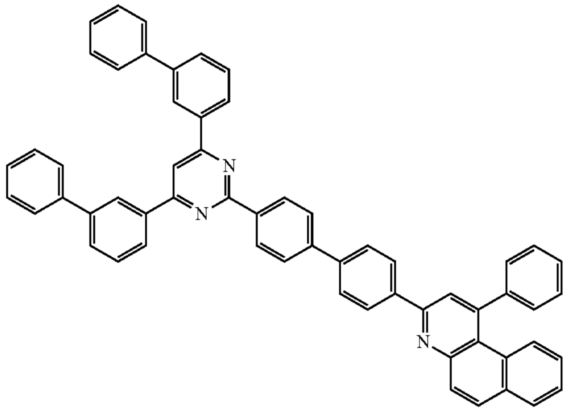

-continued
62
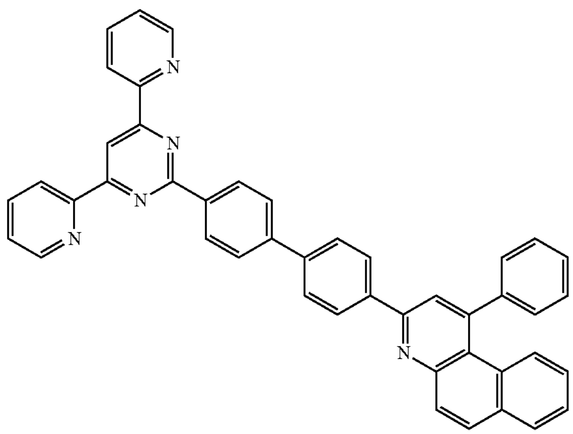
63
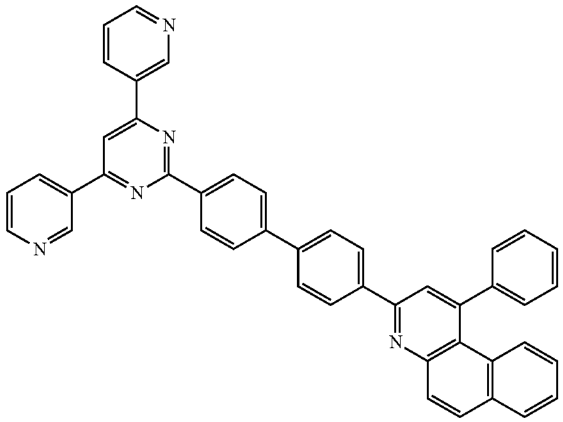
64
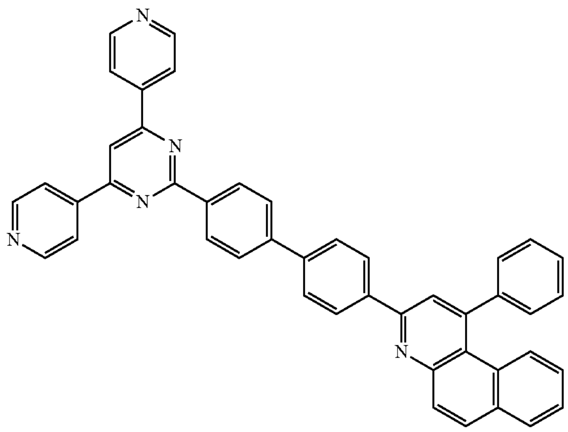
-continued
65
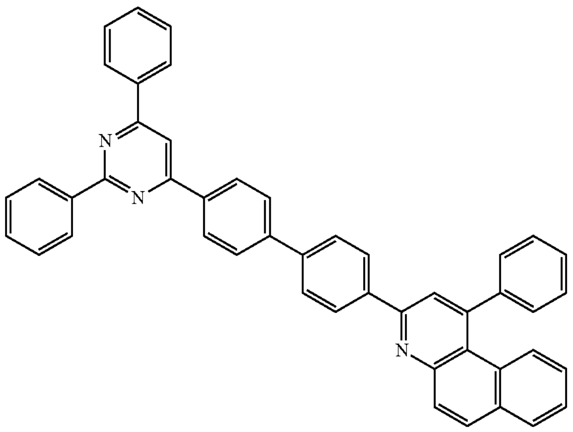
66
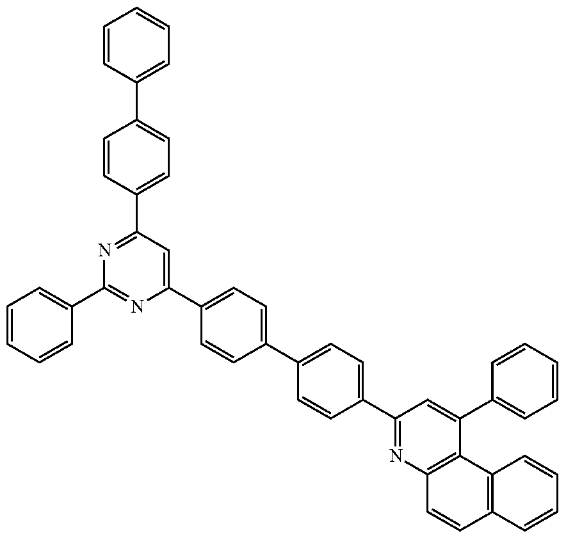
67
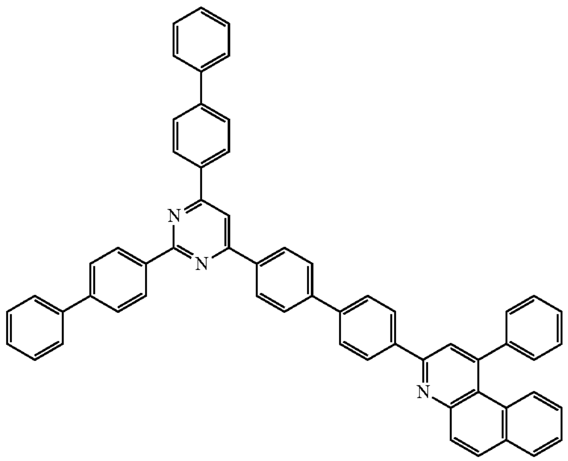

-continued
68
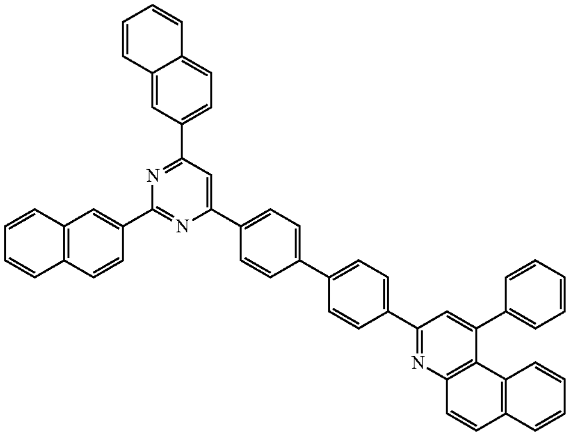
69
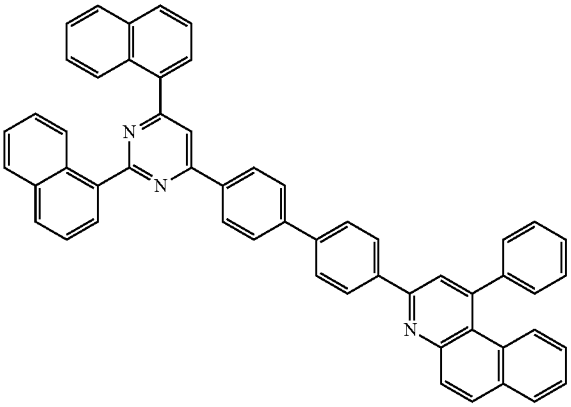
70
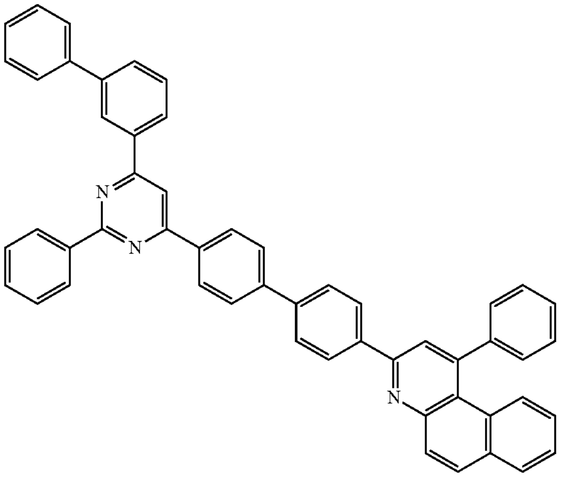
-continued
71
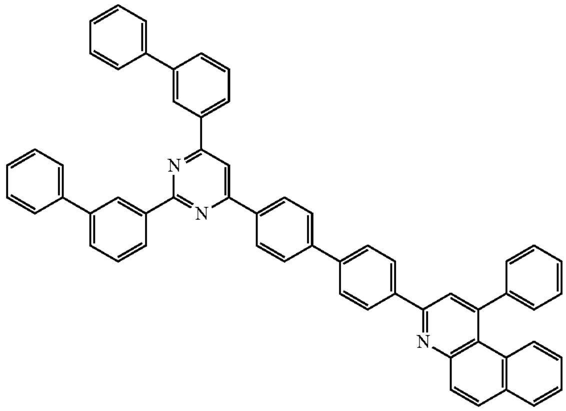
72
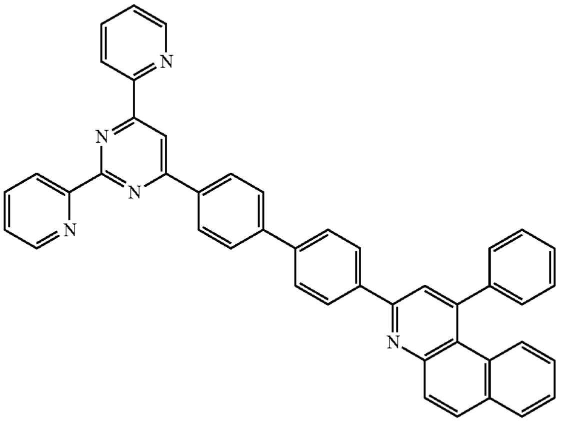
73
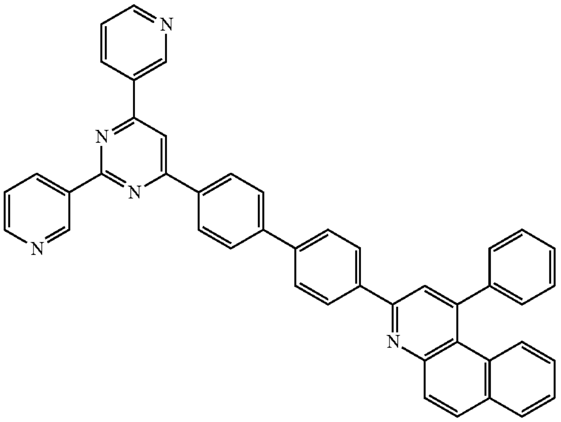

-continued
74
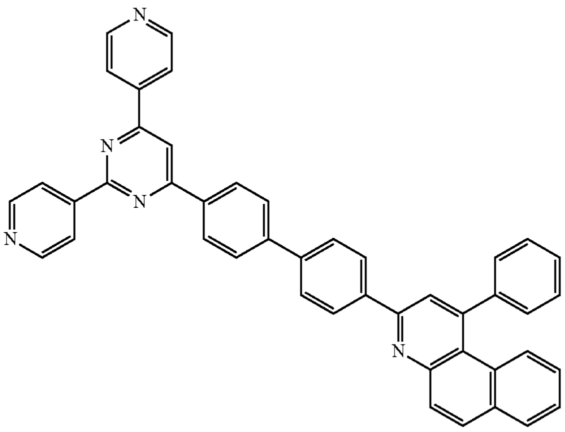
75
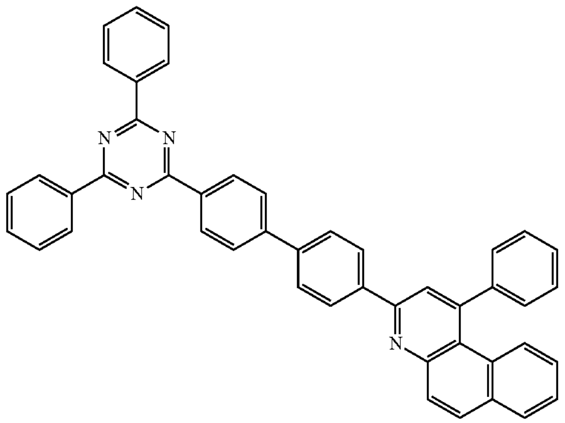
76
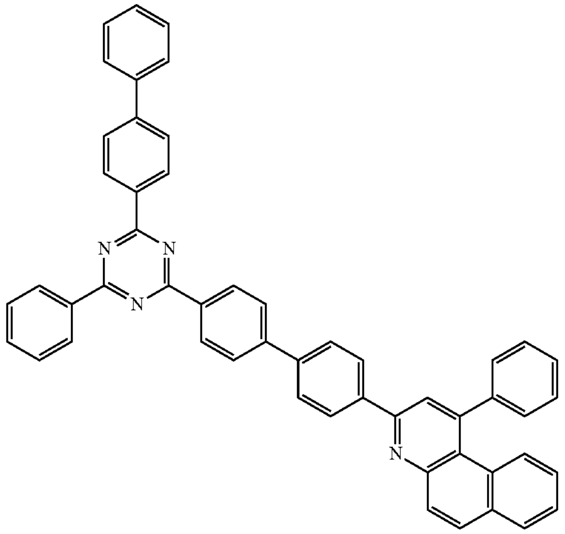
-continued
77
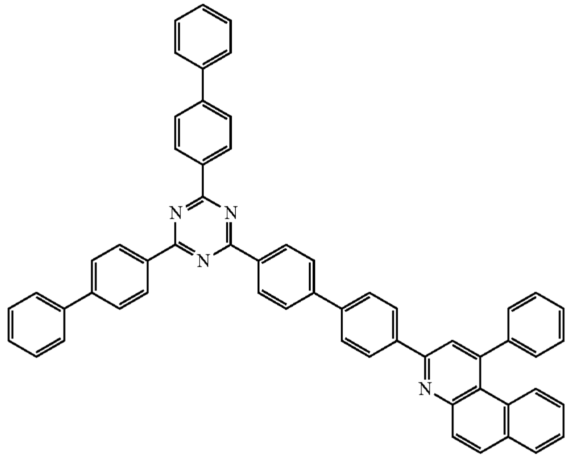
78
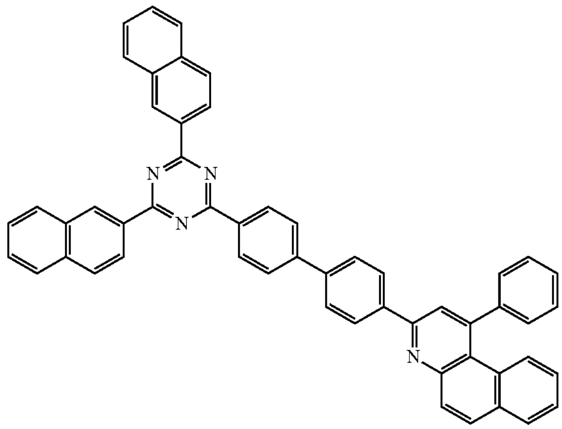
79
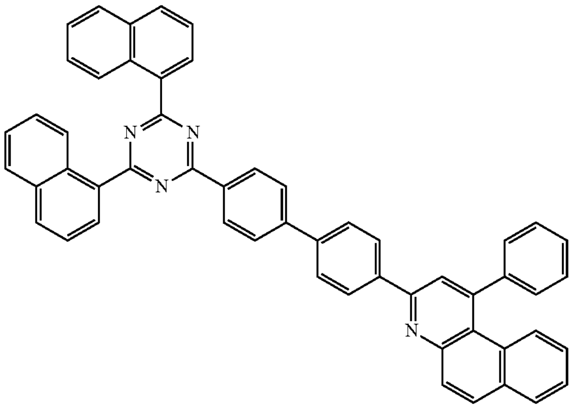

80
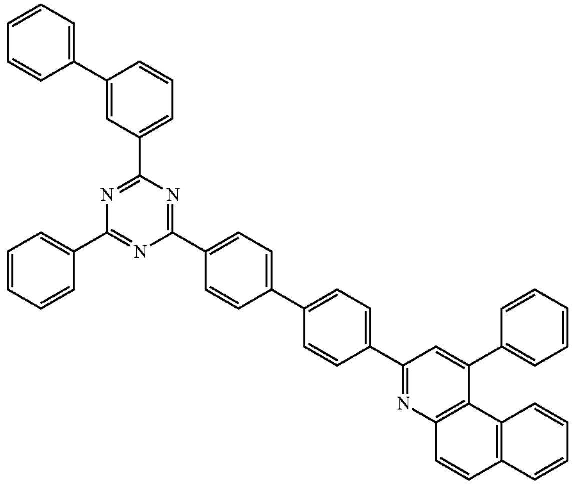
81
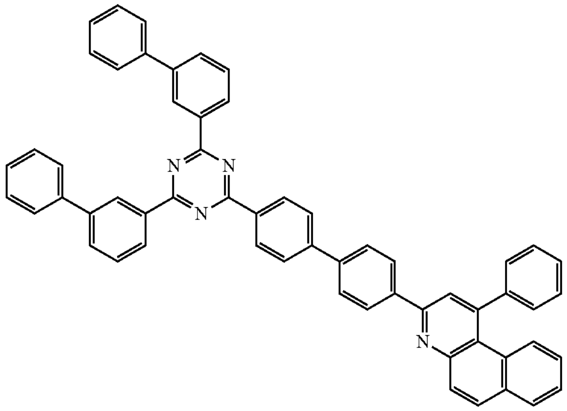
82
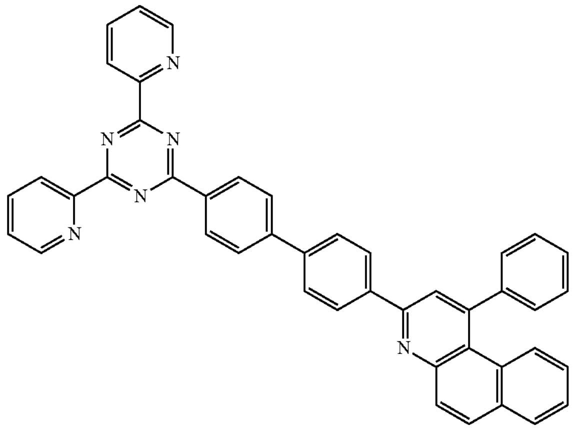
83
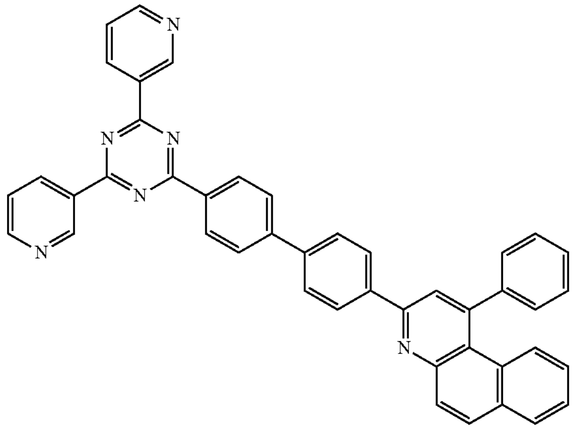
84
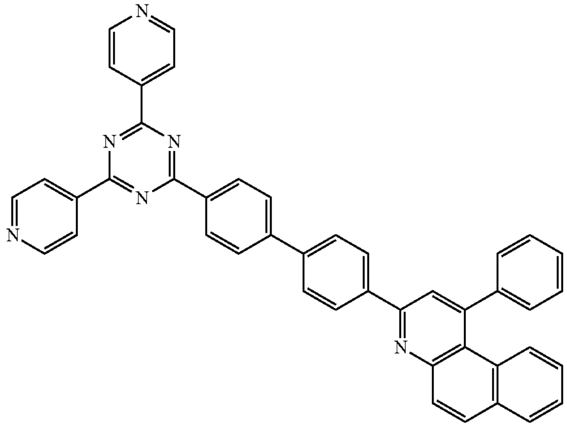
85
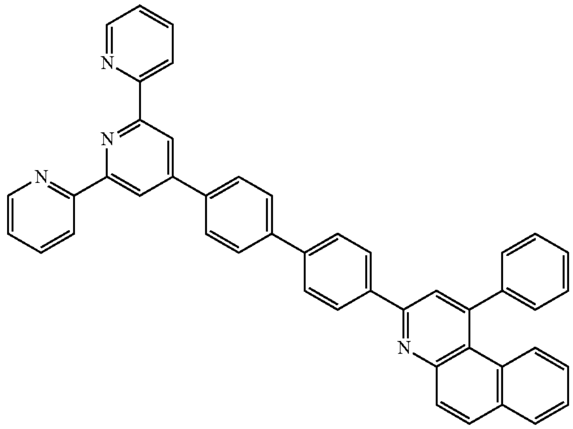

-continued
86
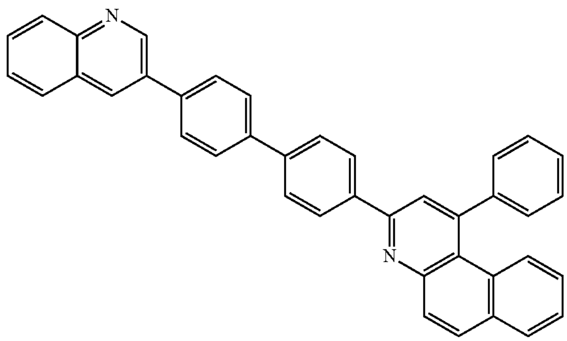
87
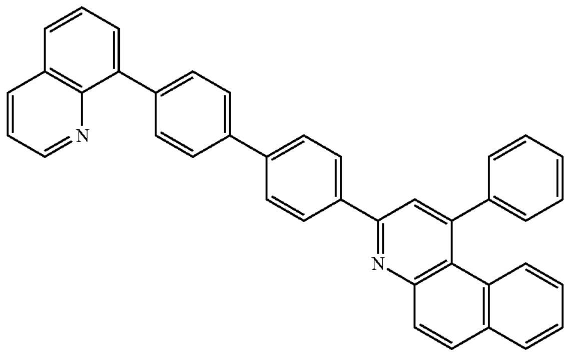
88
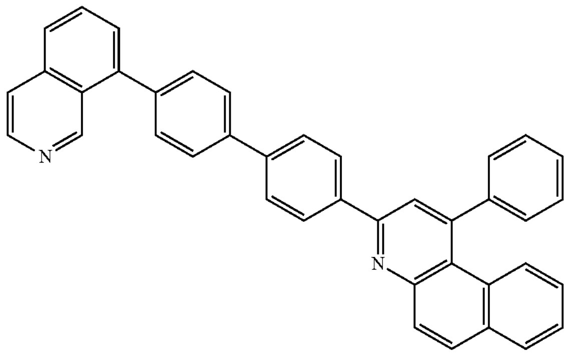
89
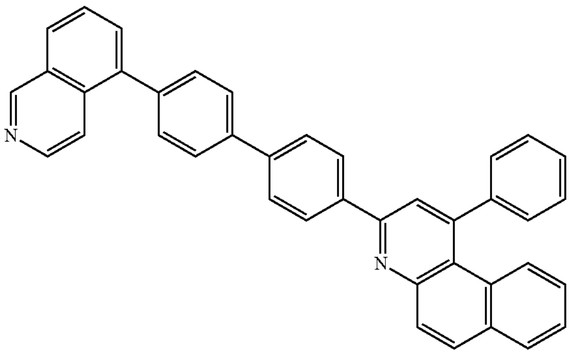
-continued
90
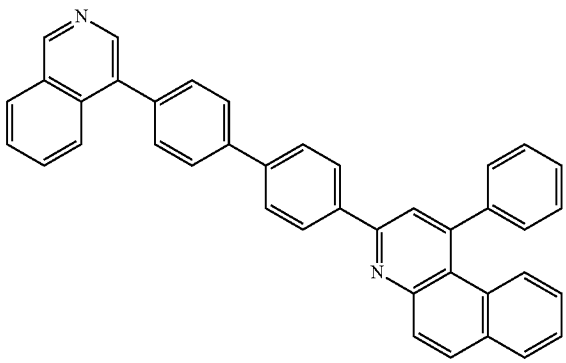
91
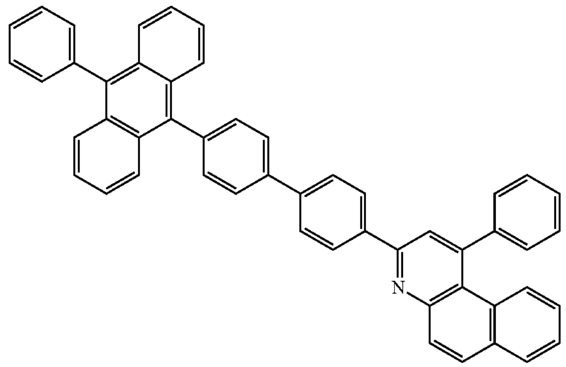
92
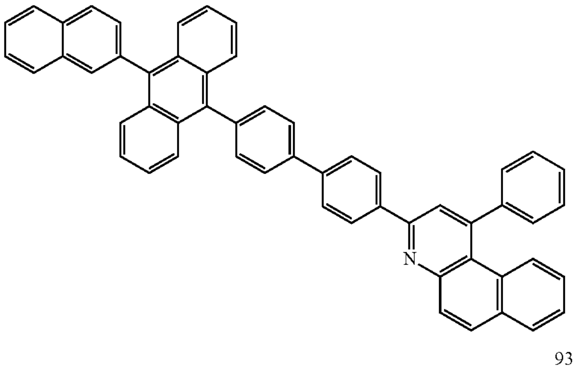
93
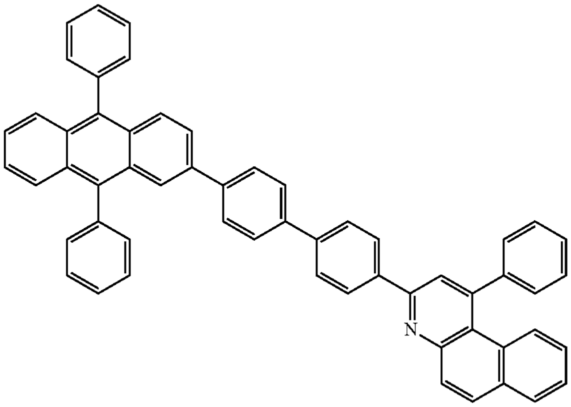

-continued
94
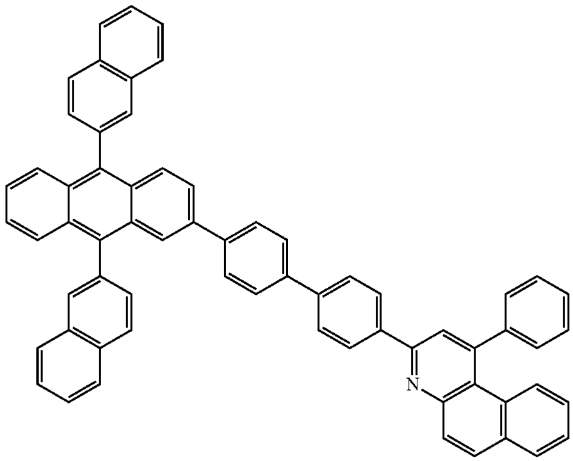
95
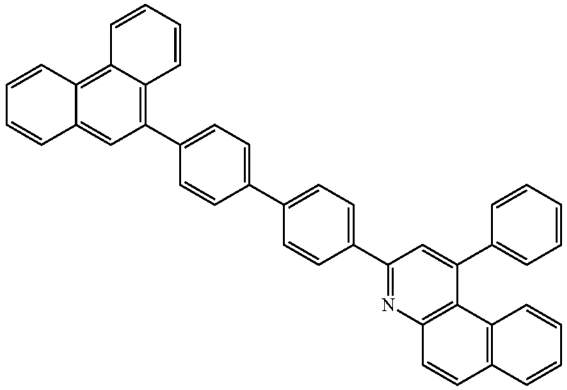
96
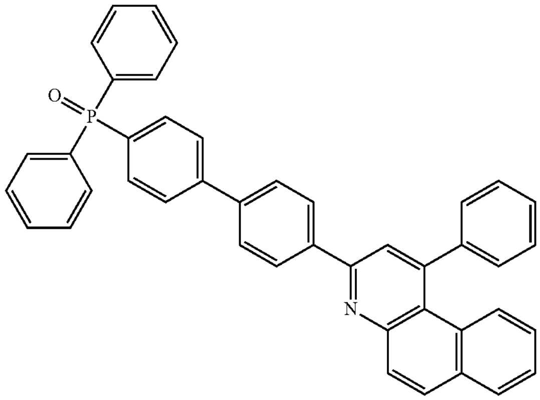
-continued
97
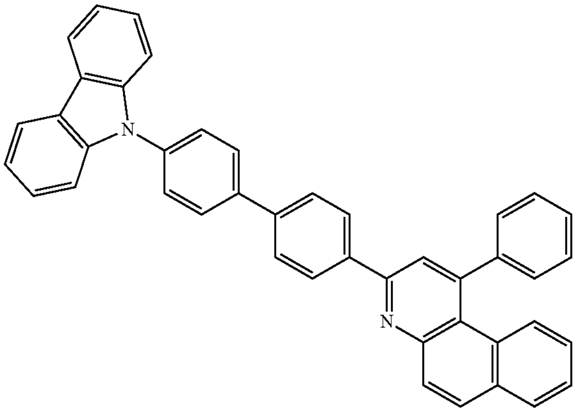
98
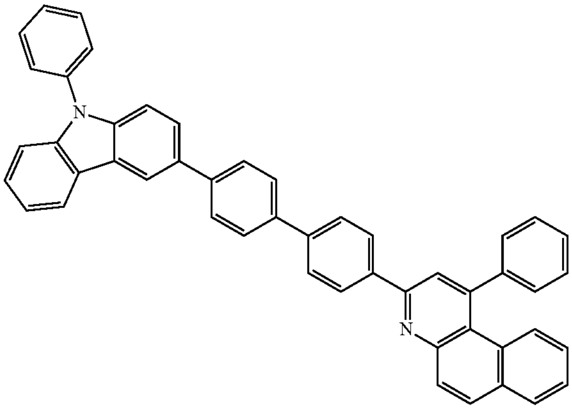
99
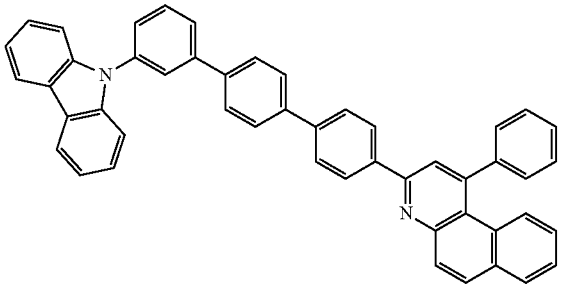
100
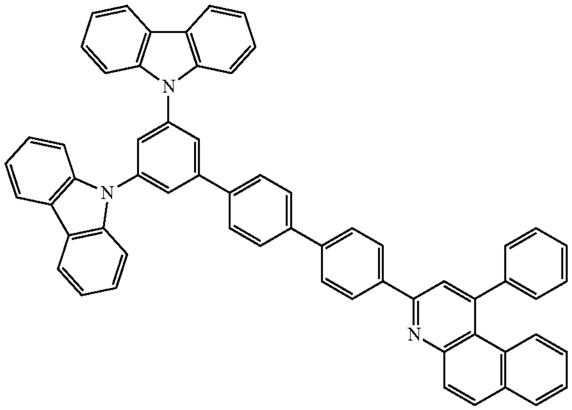

-continued
101
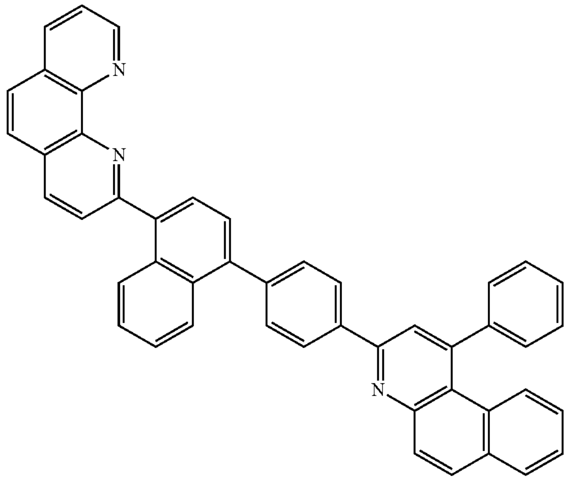
102
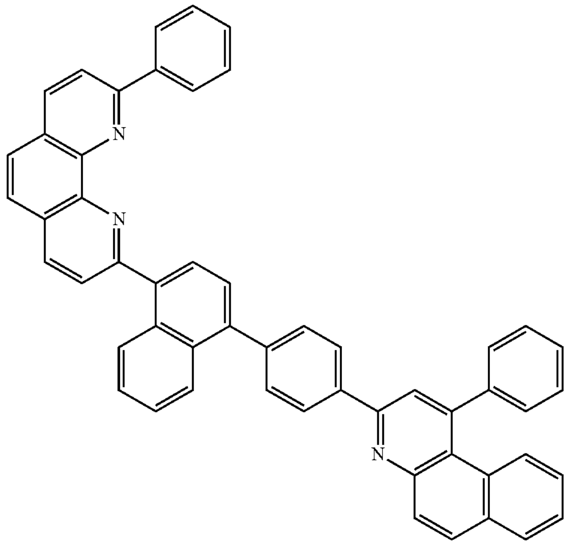
103
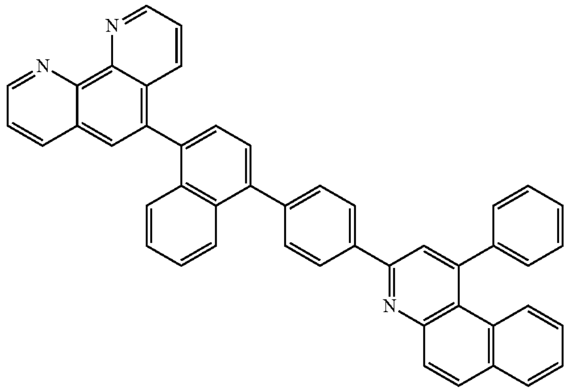
-continued
104
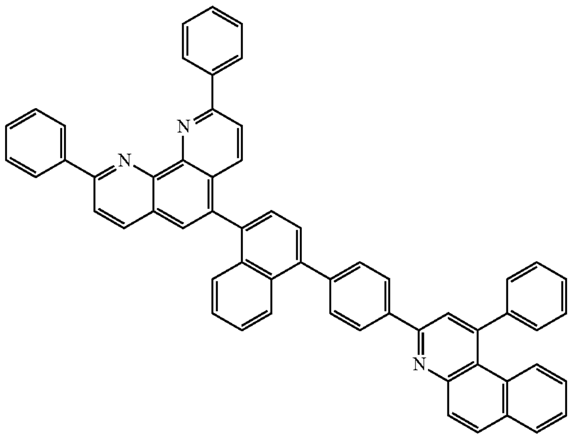
105
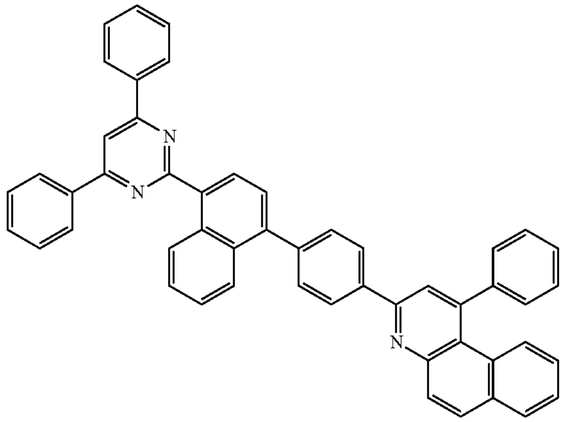
106
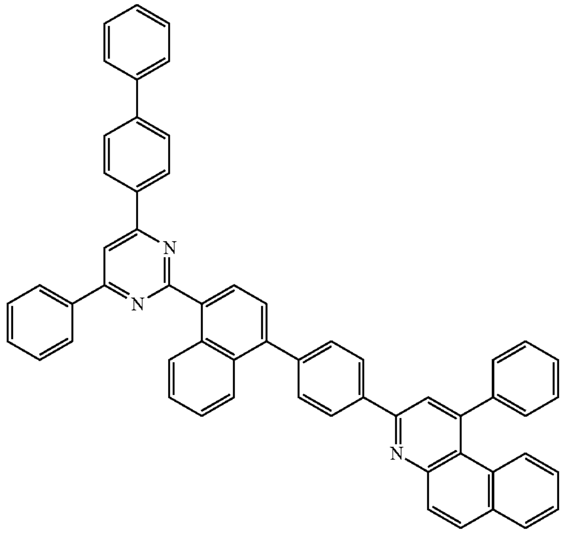

-continued
107
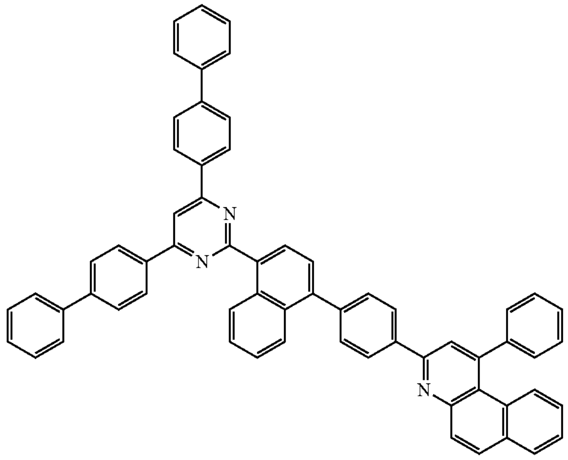
108
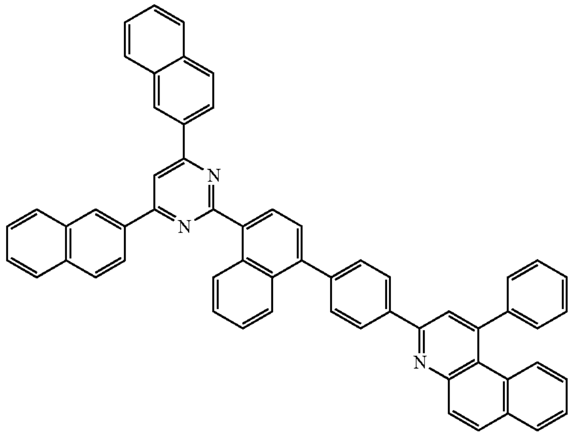
109
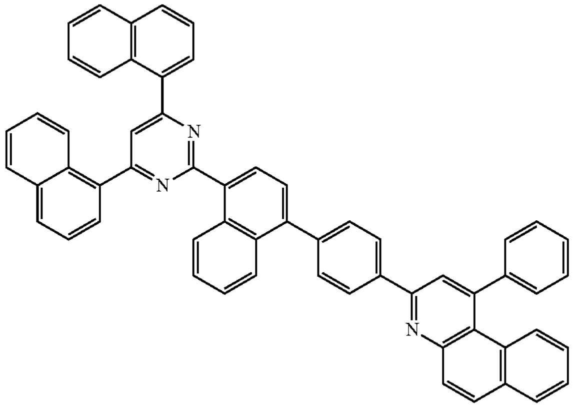
-continued
110
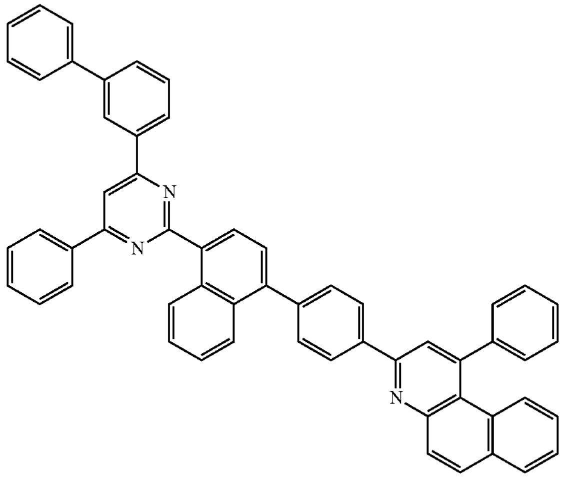
111
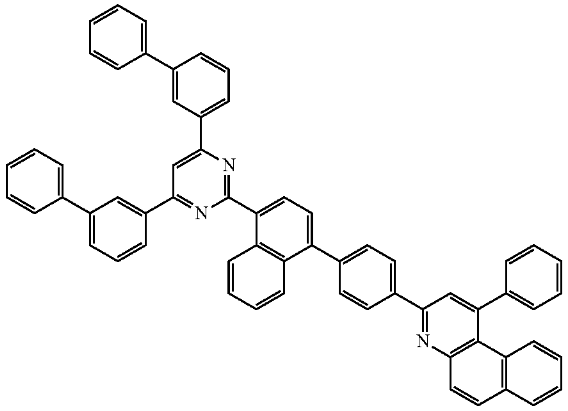
112
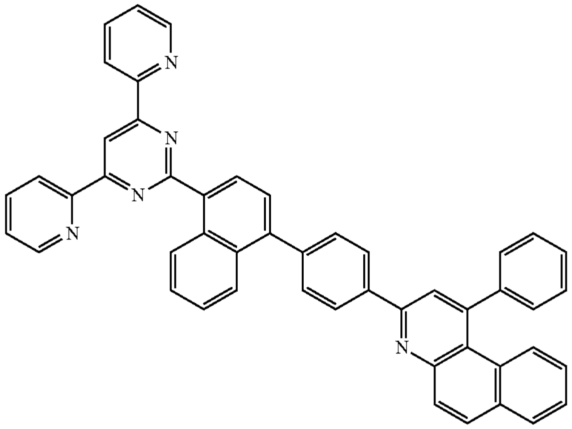

-continued
113
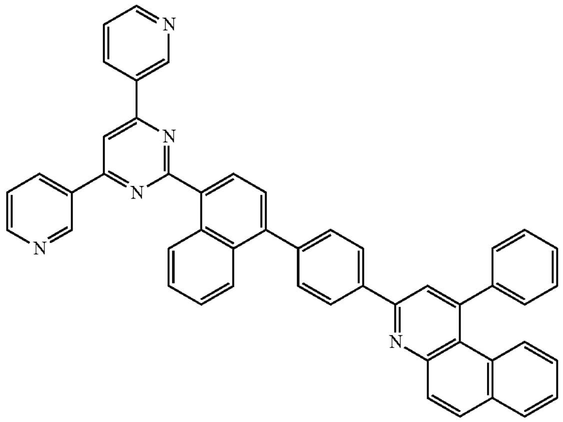
114
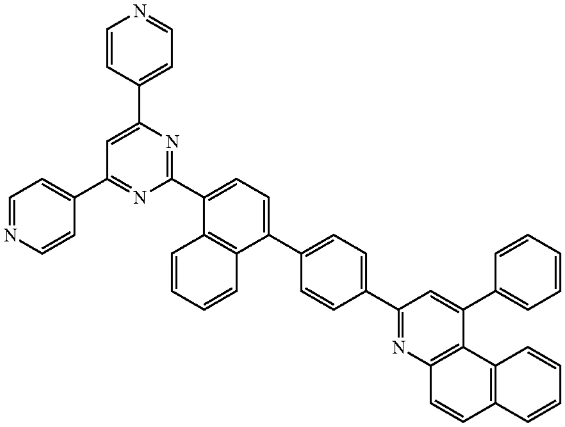
115
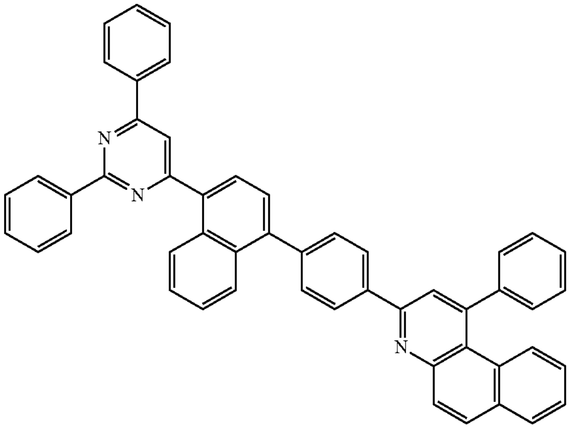
-continued
116
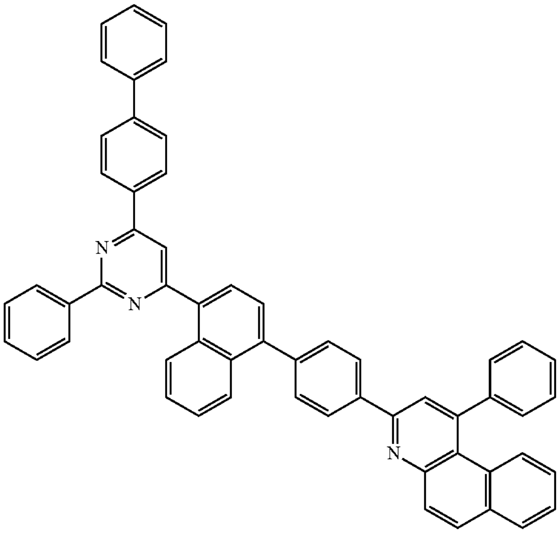
117
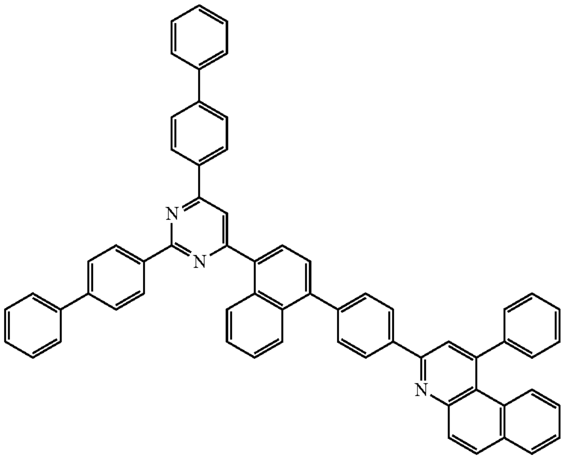
118
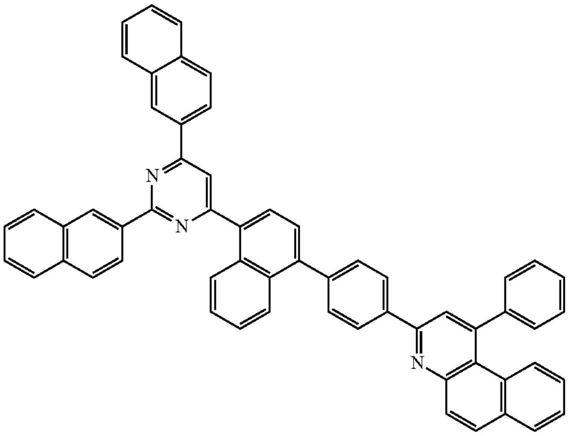

-continued
119
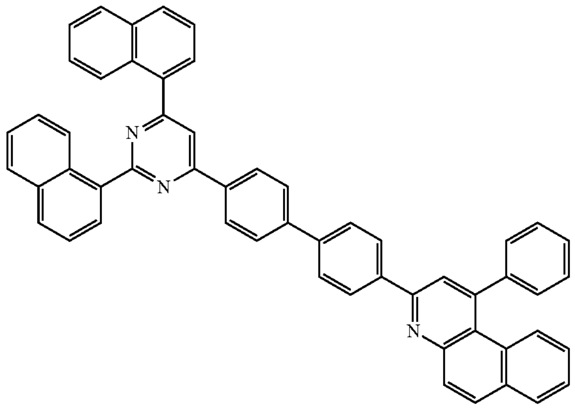
120
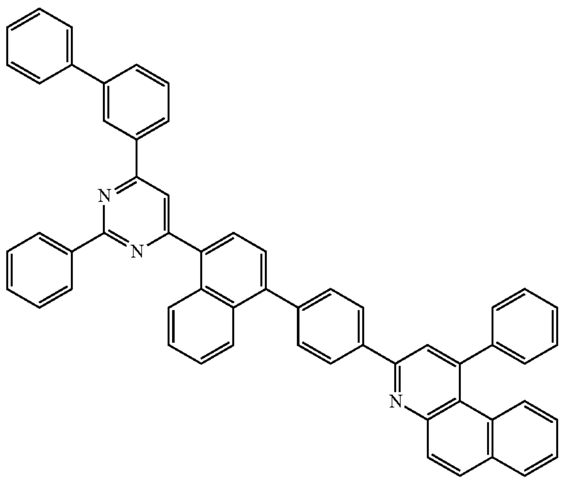
121
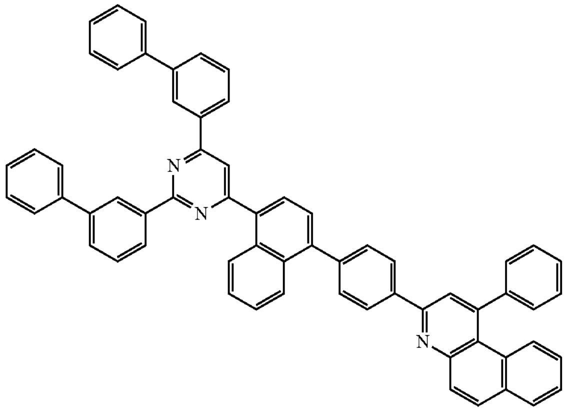
-continued
122
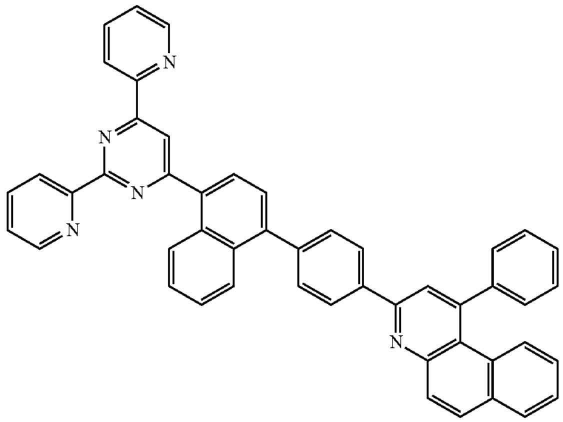
123
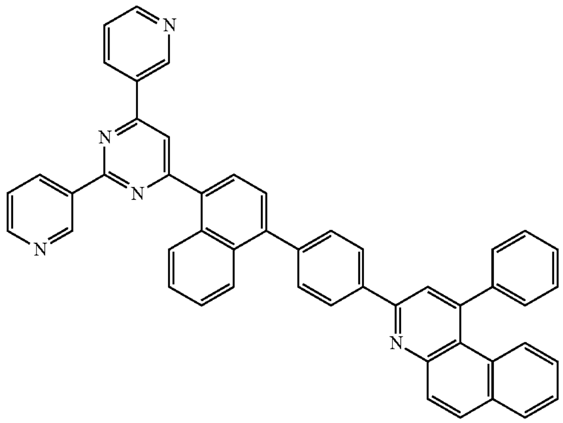
124
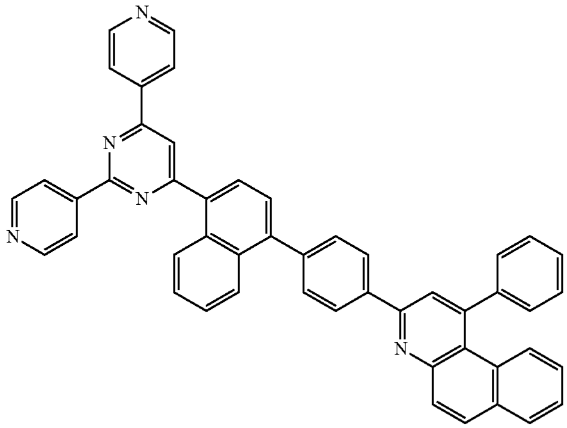

-continued
125
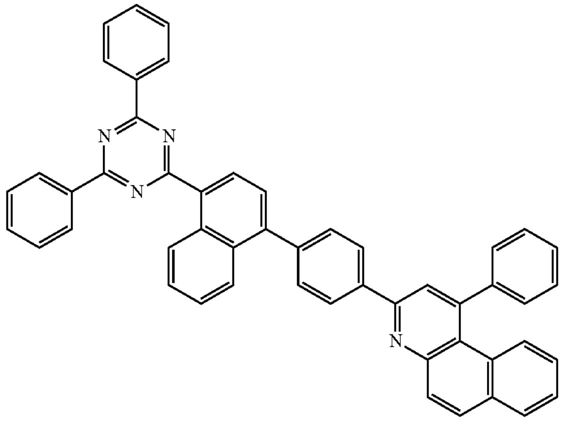
126
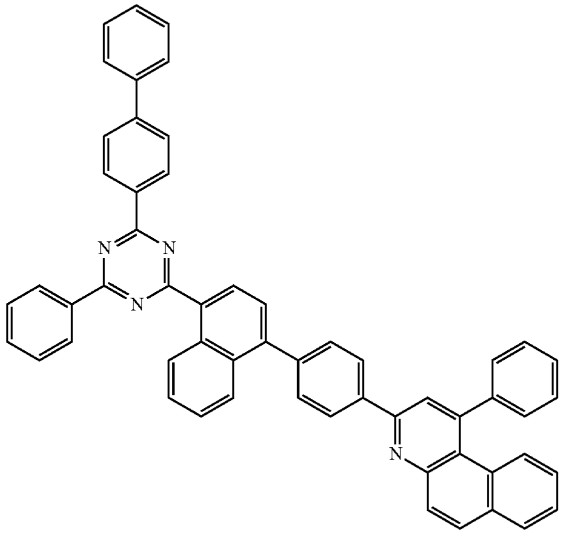
127
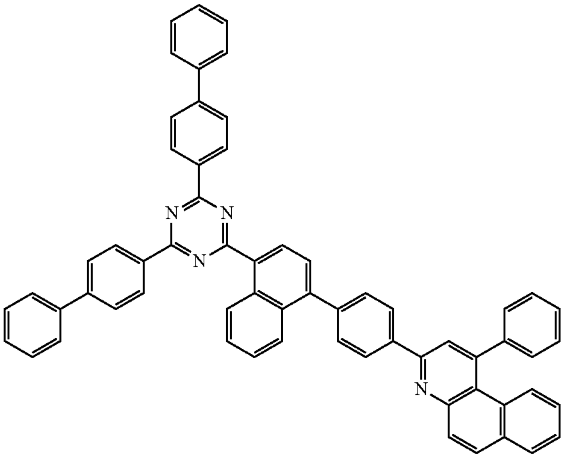
-continued
128
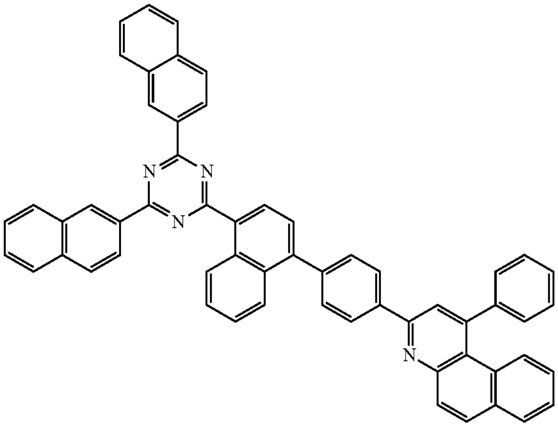
129
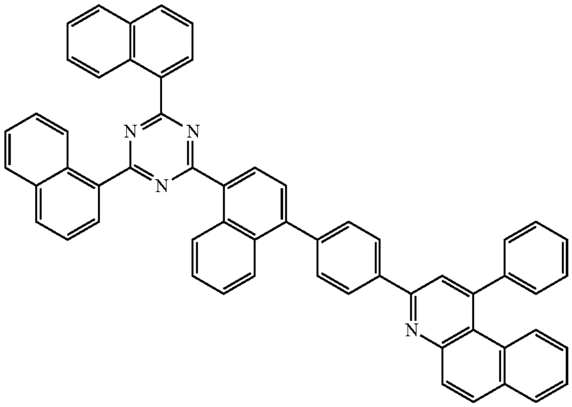
130
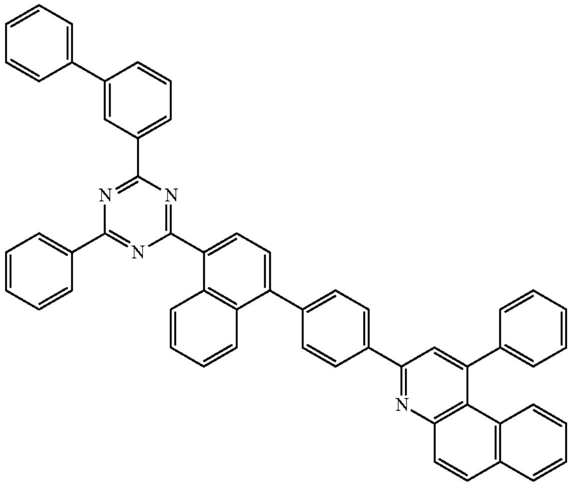

-continued
131
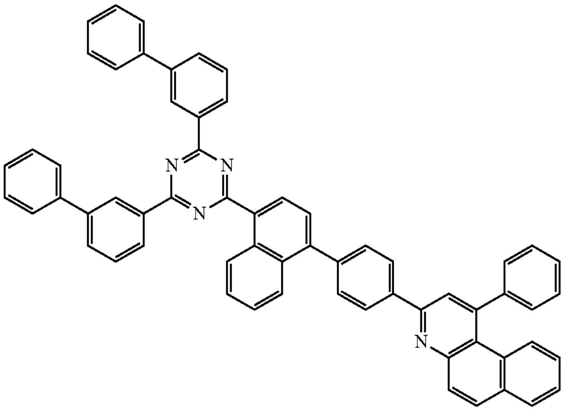
132
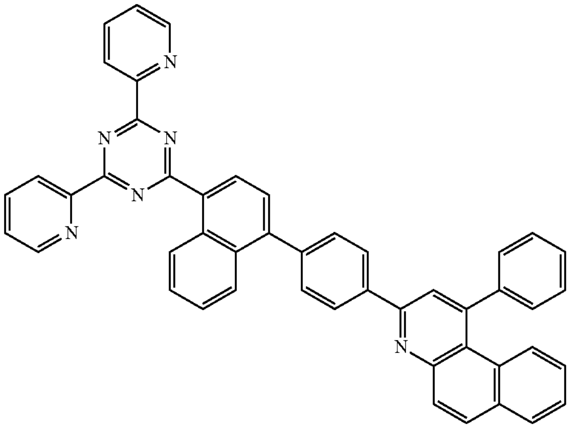
133
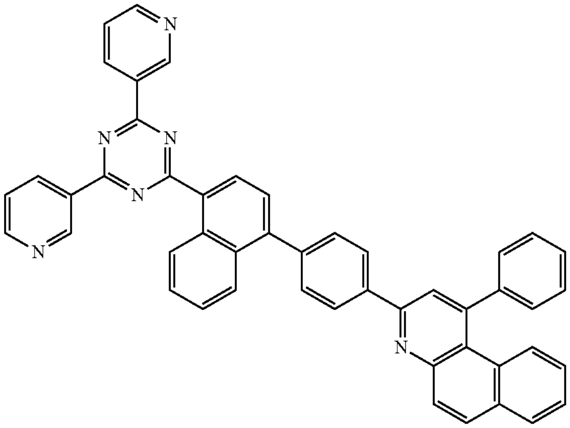
-continued
134
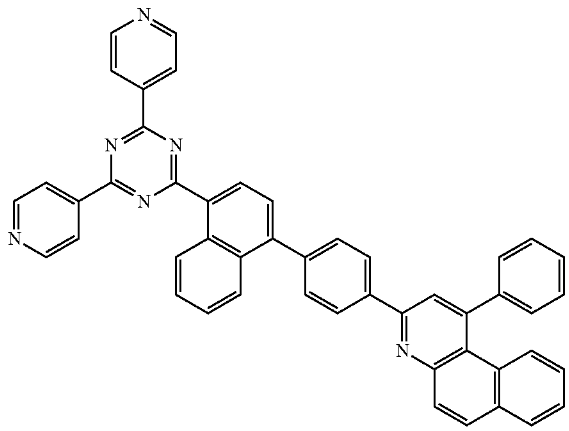
135
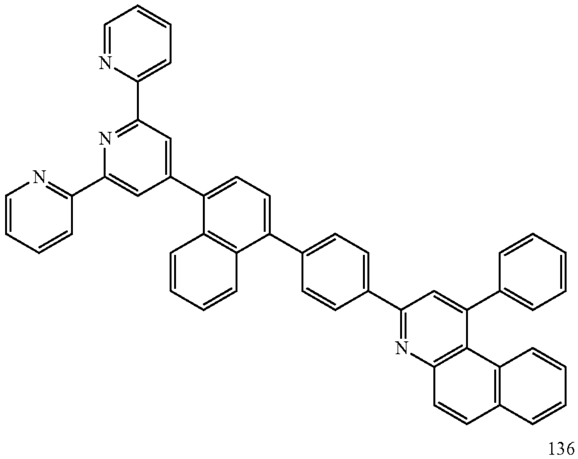
136
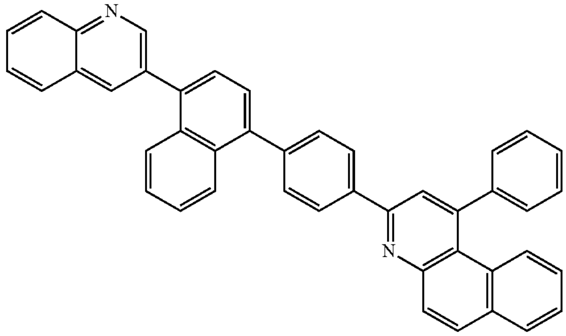
137
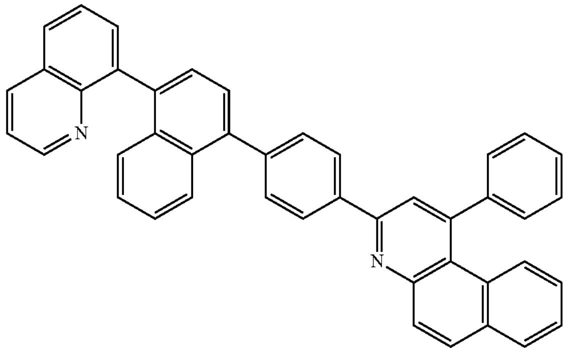

-continued
138
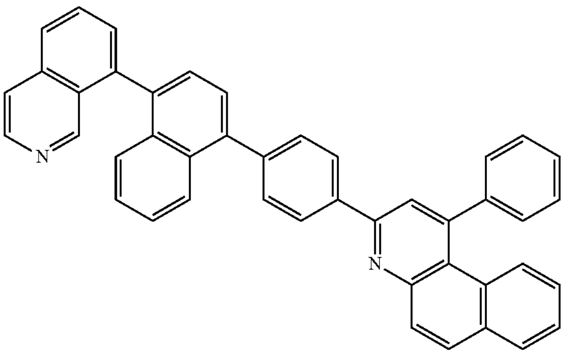
139
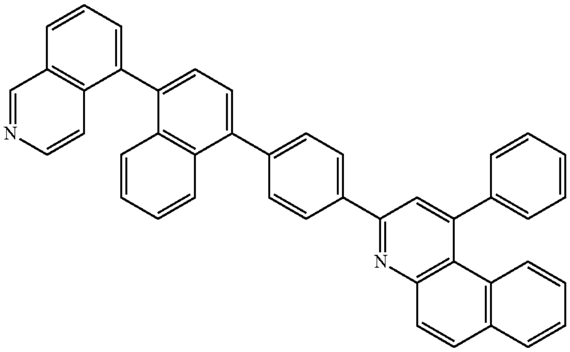
140
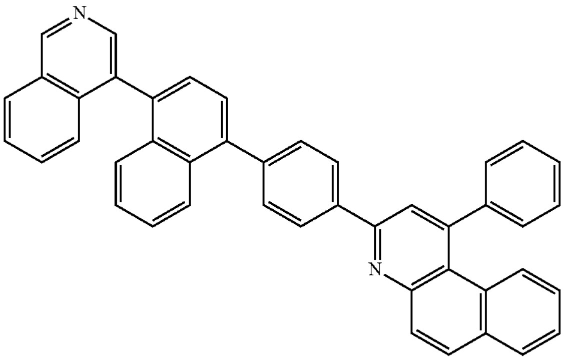
141
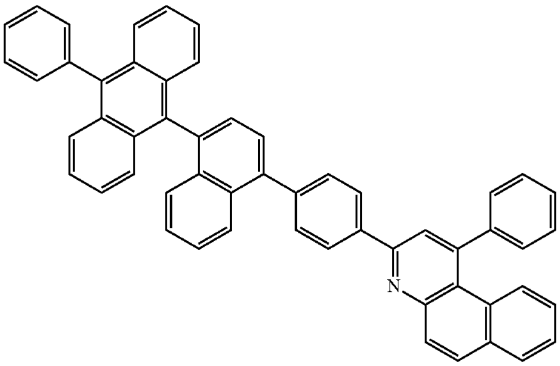
-continued
142
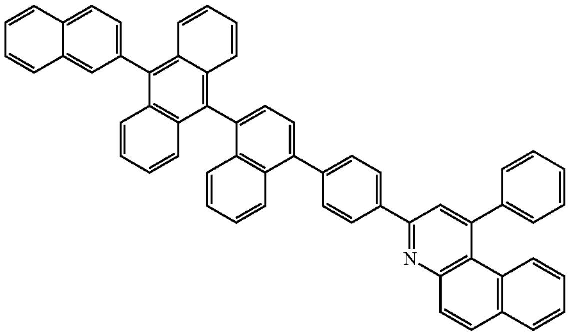
143
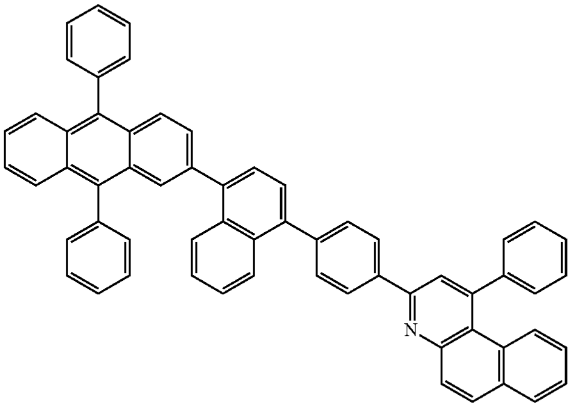
144
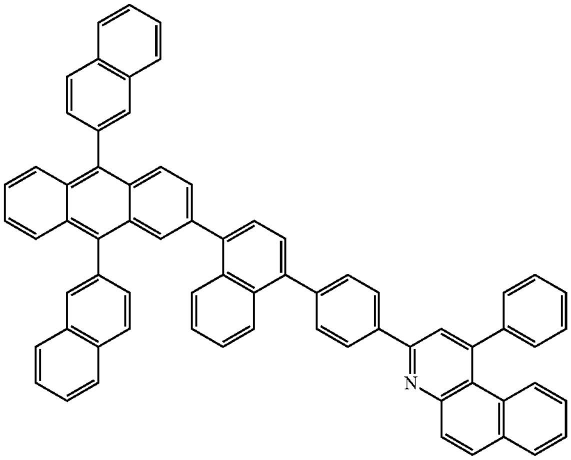

-continued
145
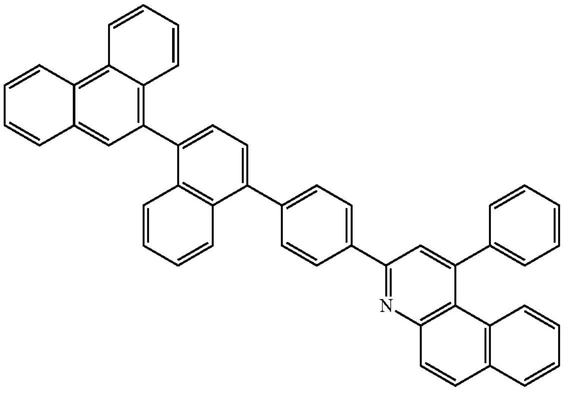
146
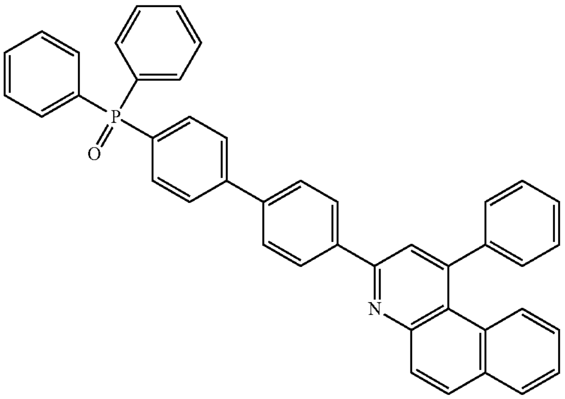
147
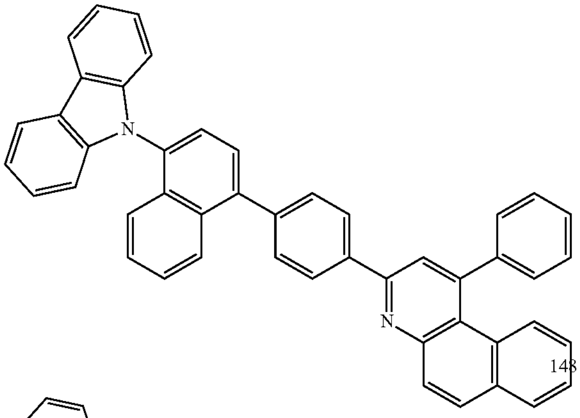
148
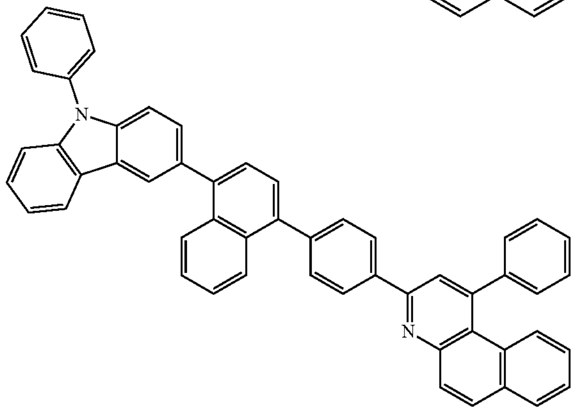
-continued
149
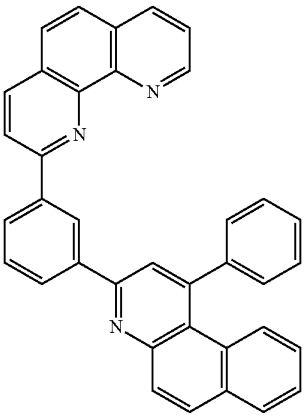
150
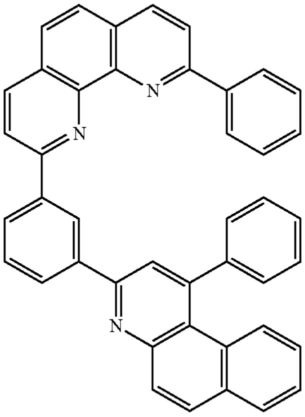
151
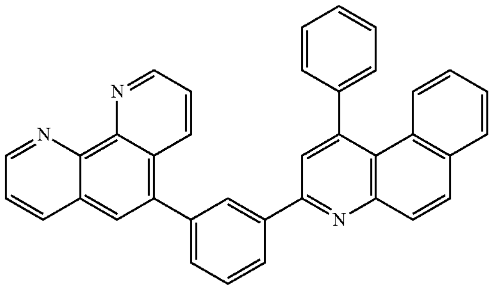
152
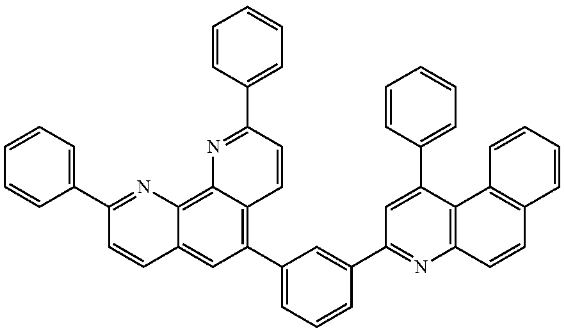

153
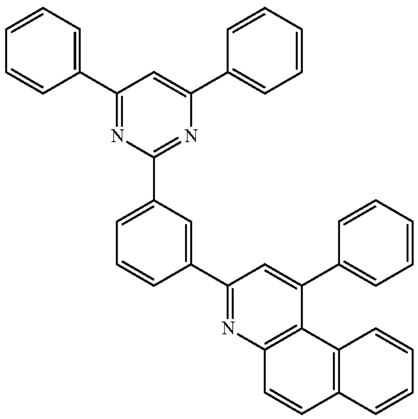
154
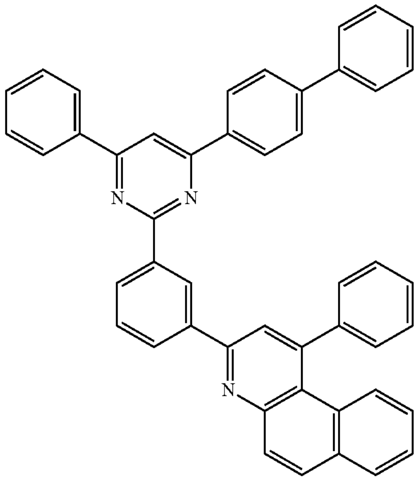
155
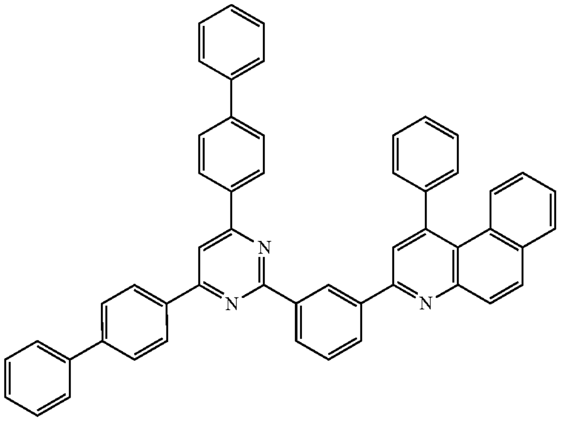
156
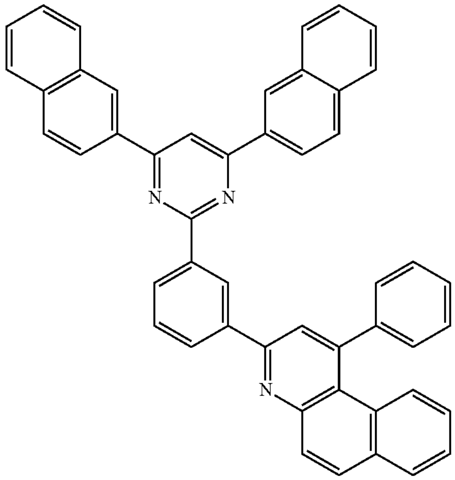
157
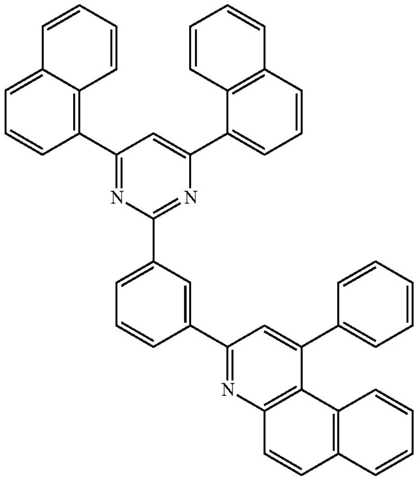
158
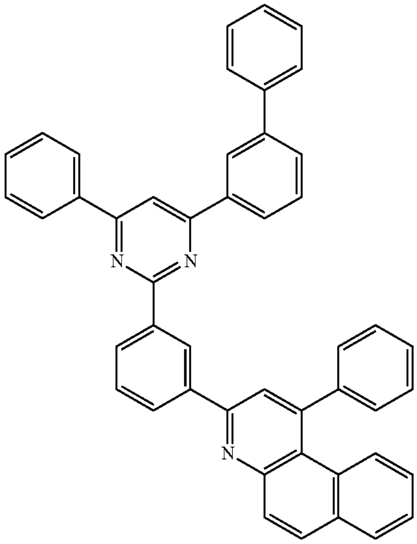

-continued
159
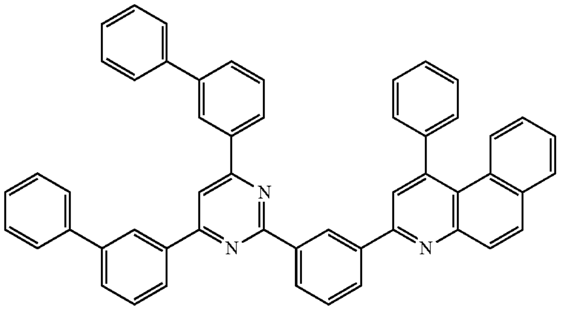
160
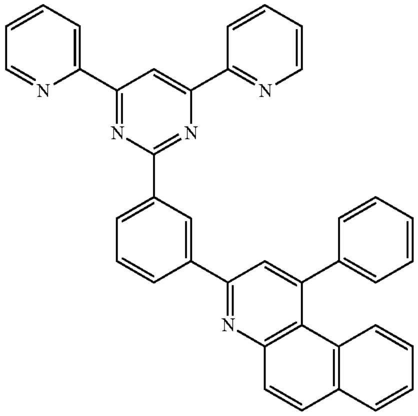
161
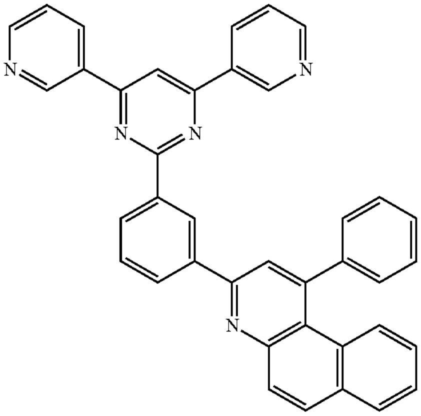
162
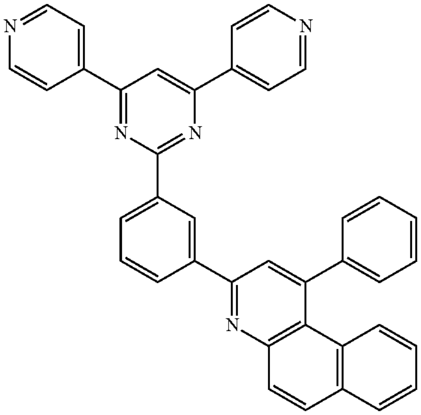
-continued
163
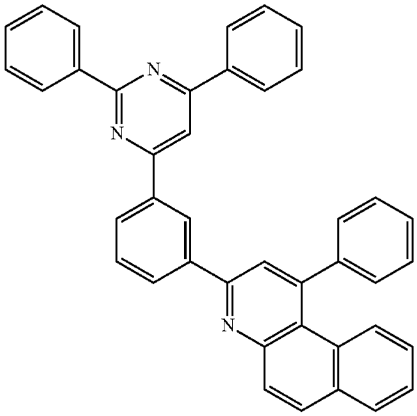
164
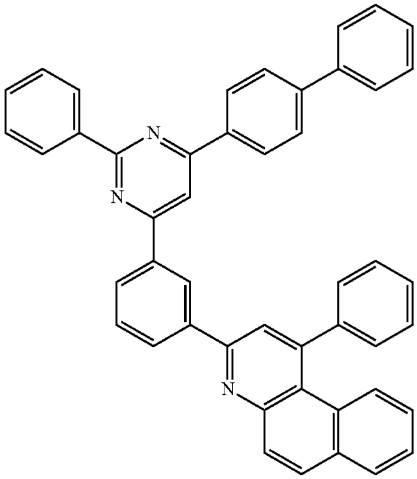
165
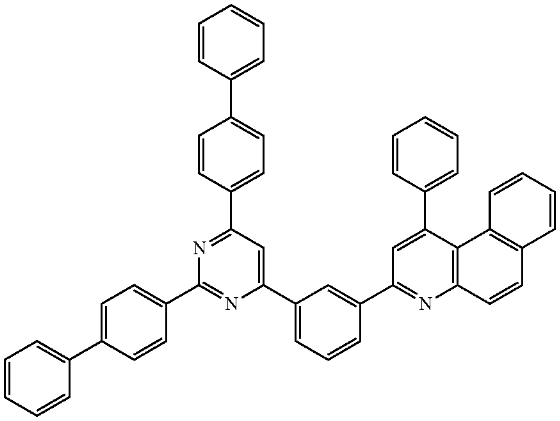

-continued
166
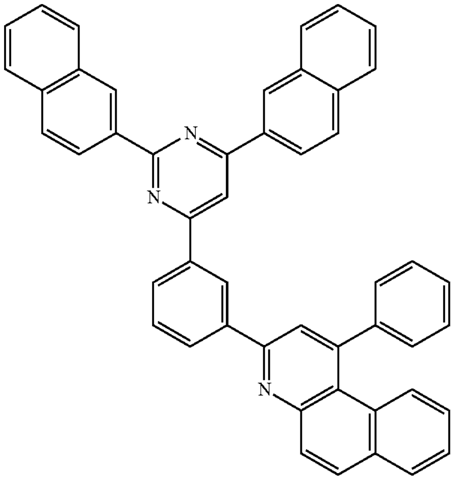
167
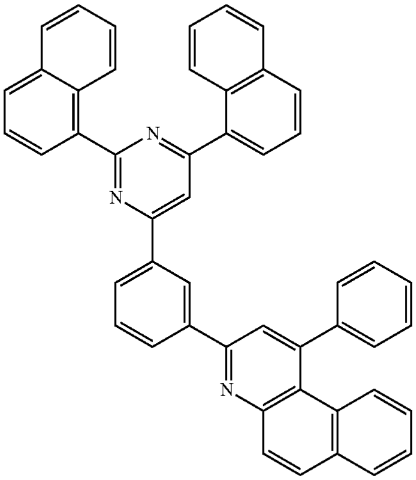
168
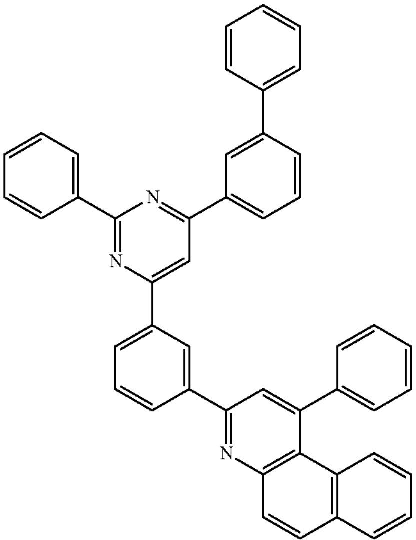
-continued
169
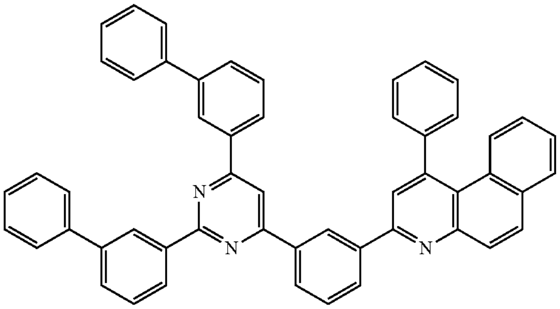
170
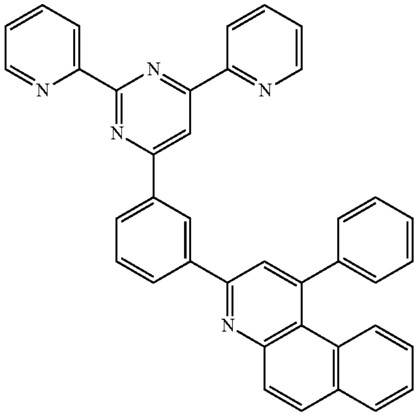
171
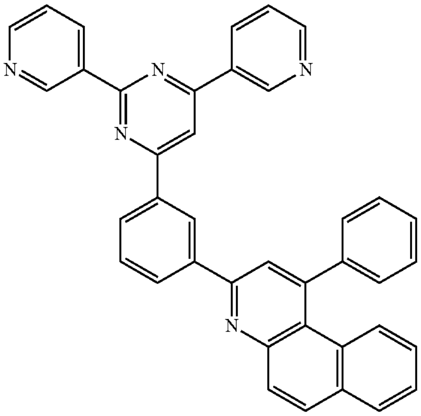
172
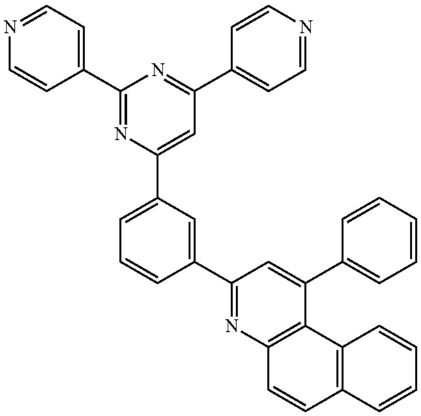

-continued
173
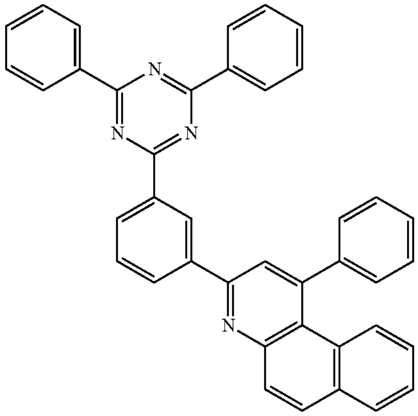
174
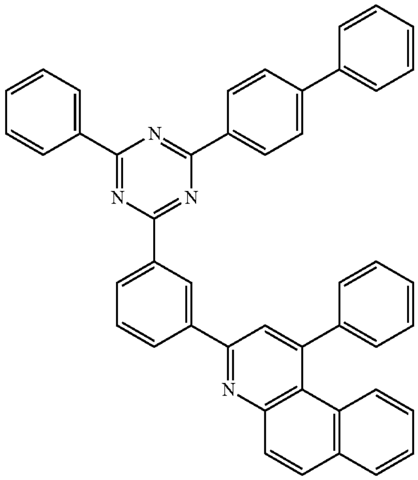
175
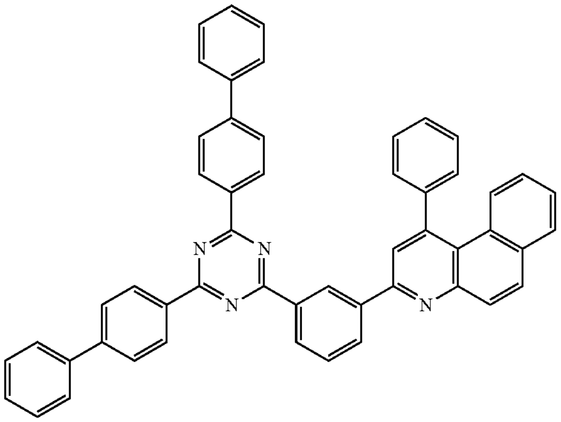
-continued
176
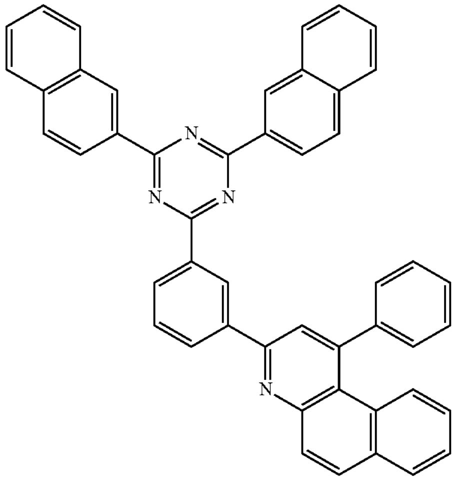
177
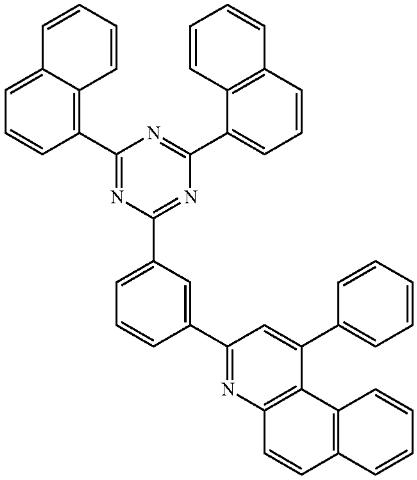
178
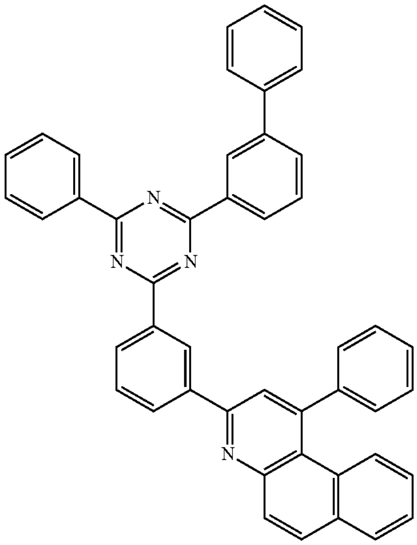

-continued
179
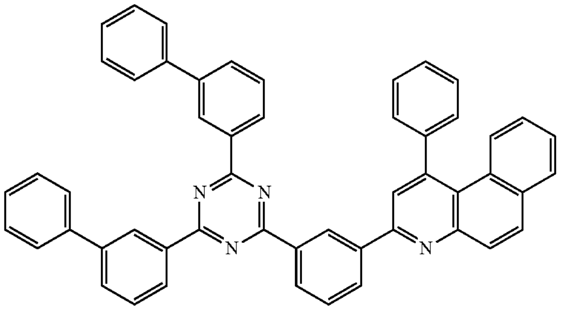
180
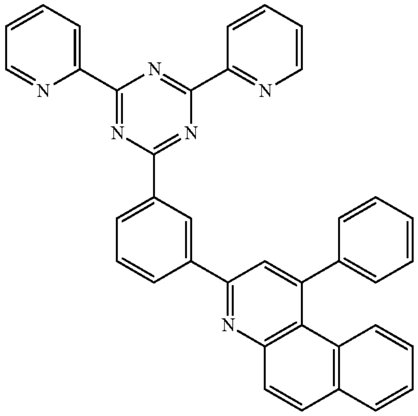
181
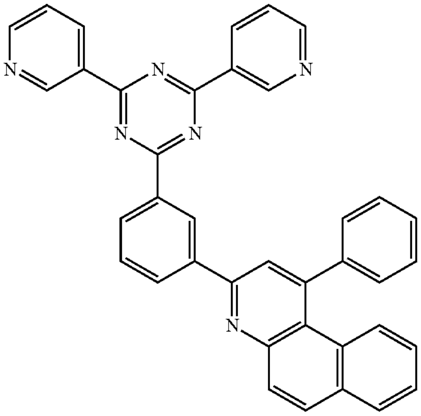
182
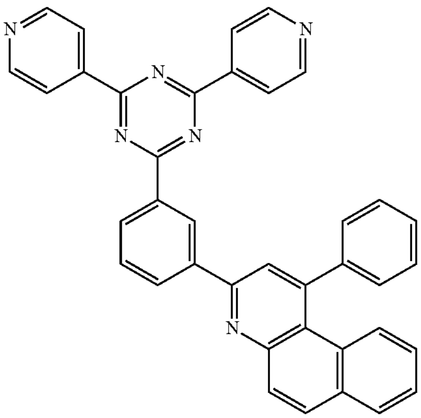
-continued
183
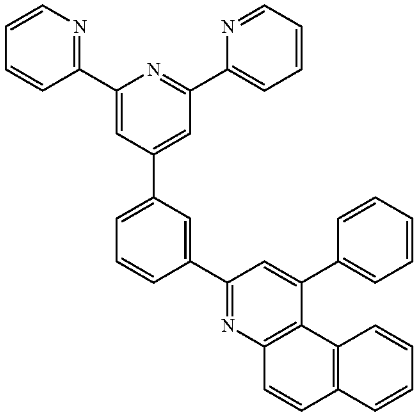
184
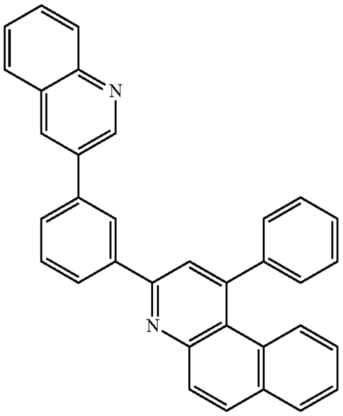
185
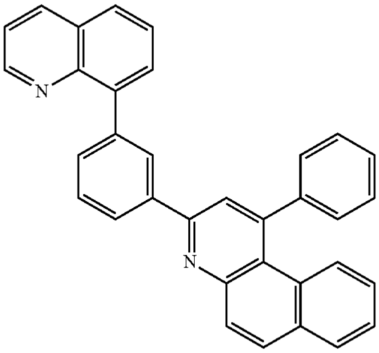
186
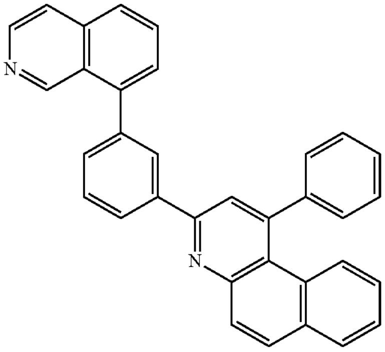

-continued
187
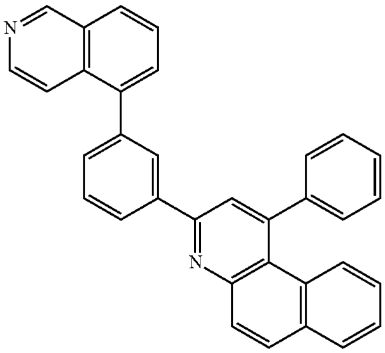
188
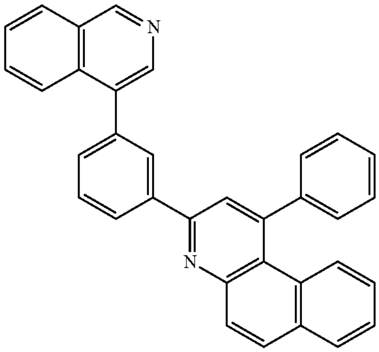
189
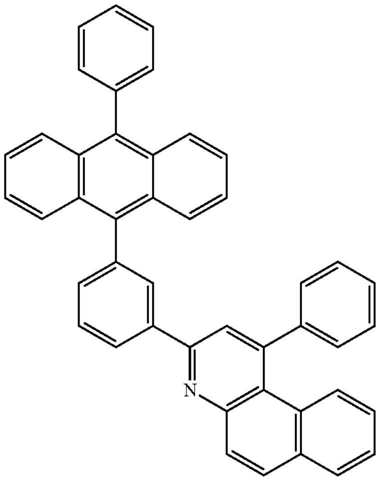
-continued
190
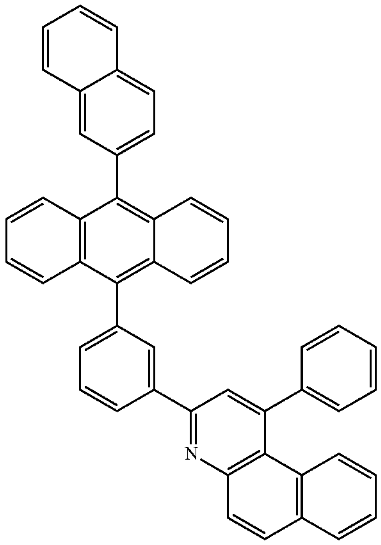
191
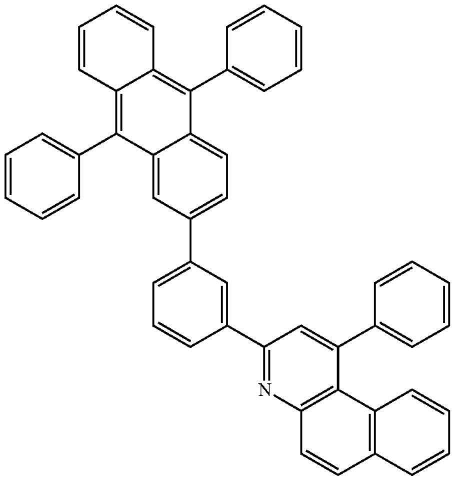
192
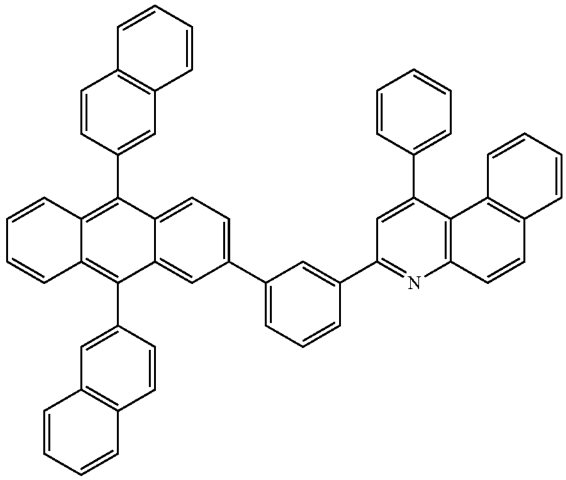

193
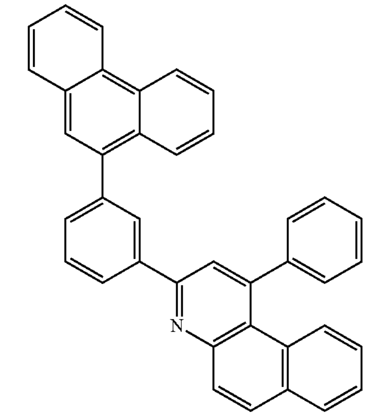
194
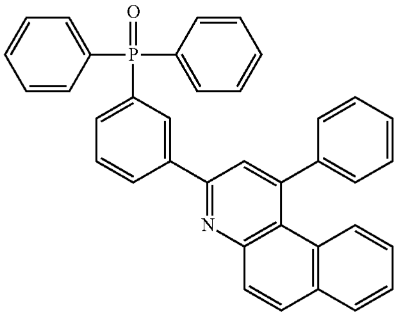
195
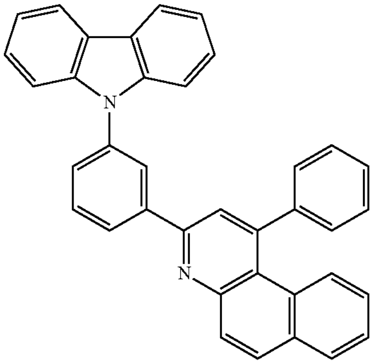
196
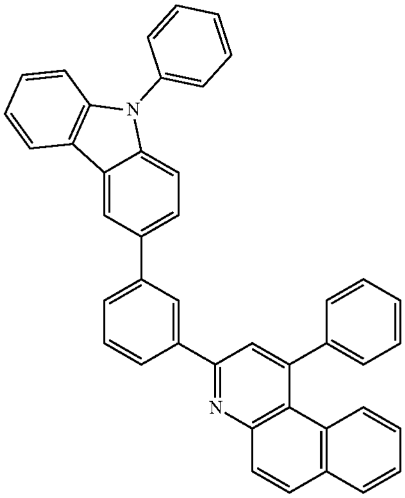
197
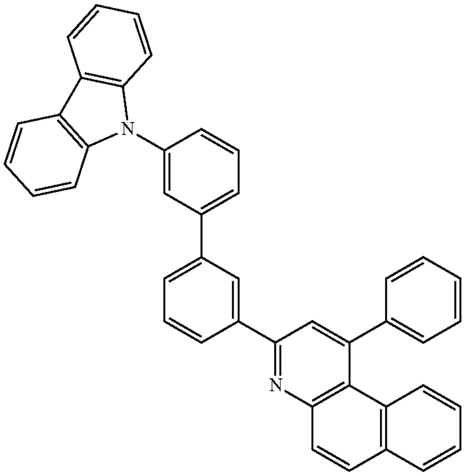
198
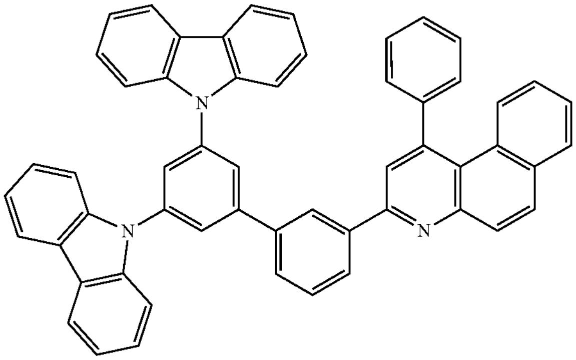
199
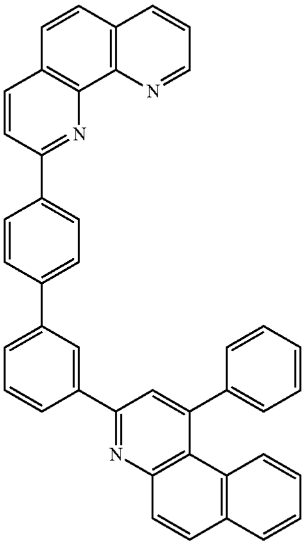

-continued
200
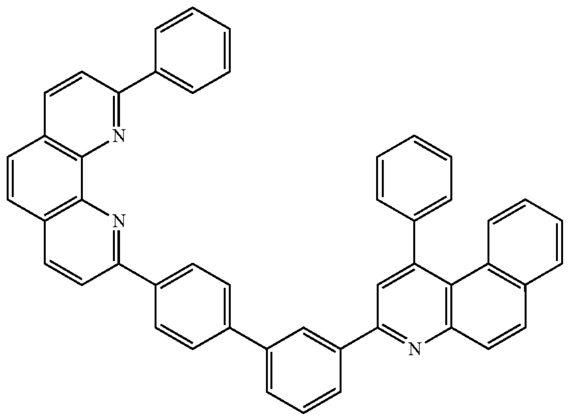
201
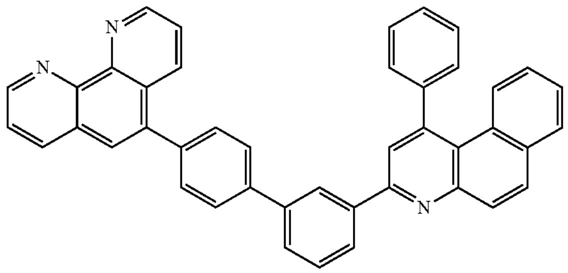
202
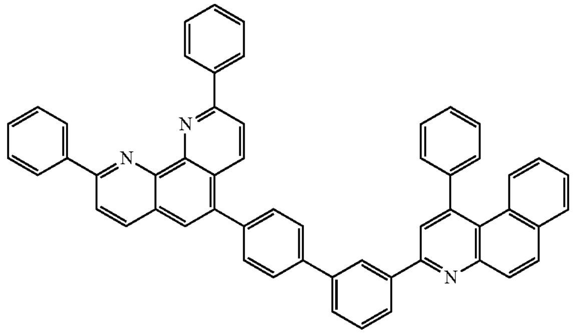
203
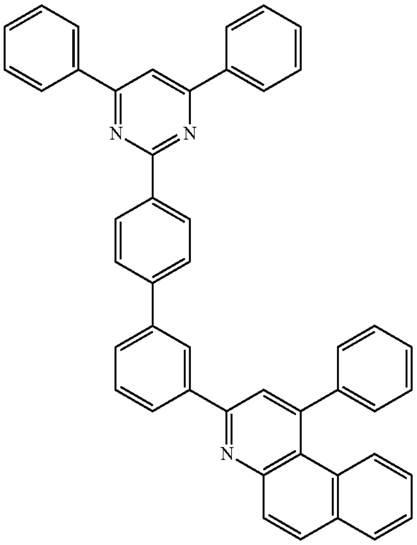
-continued
204
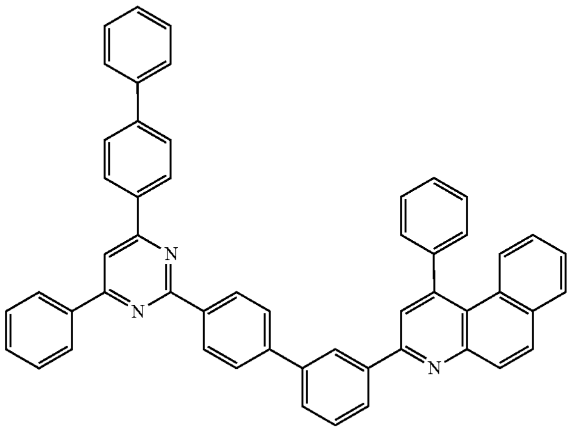
205
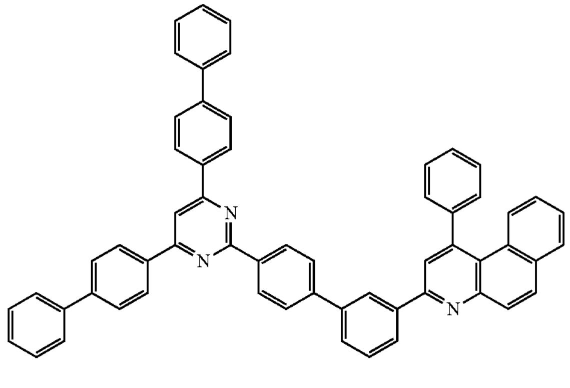
206
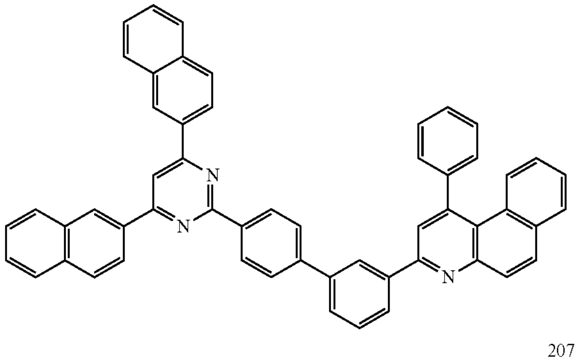
207
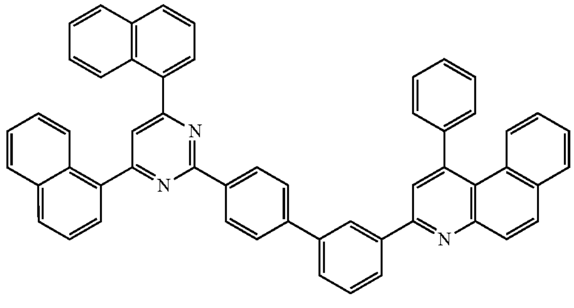

-continued
208
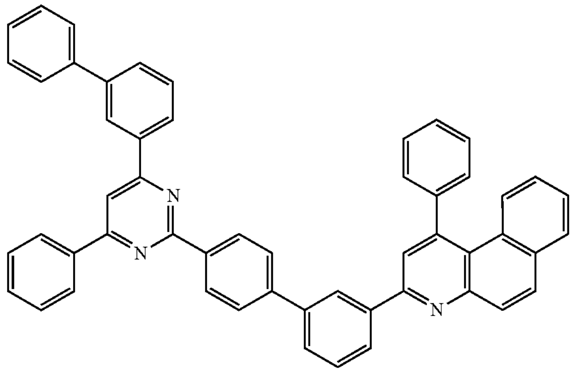
209
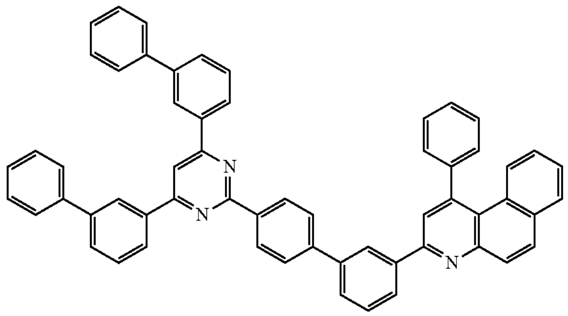
210
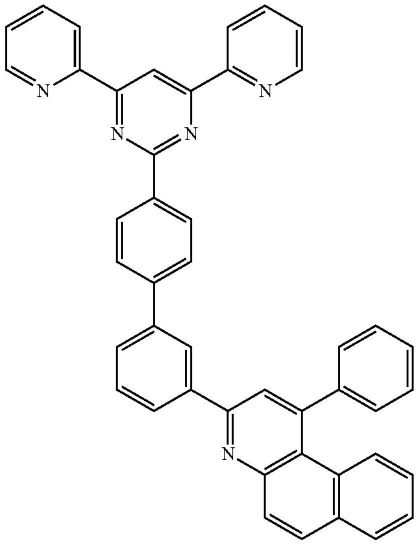
-continued
211
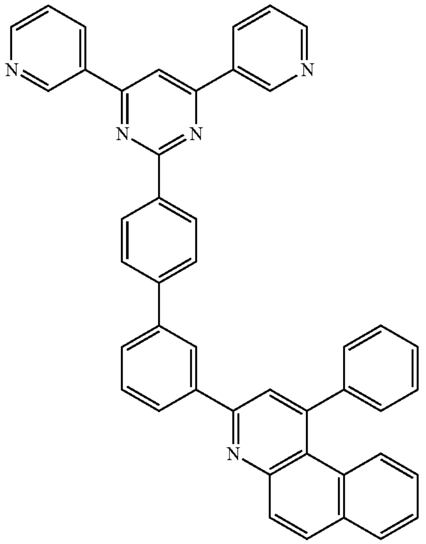
212
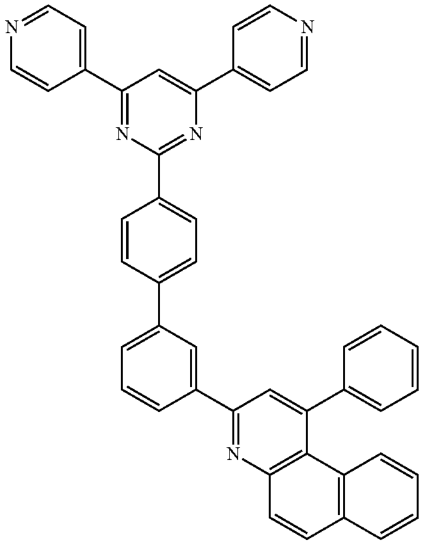
213
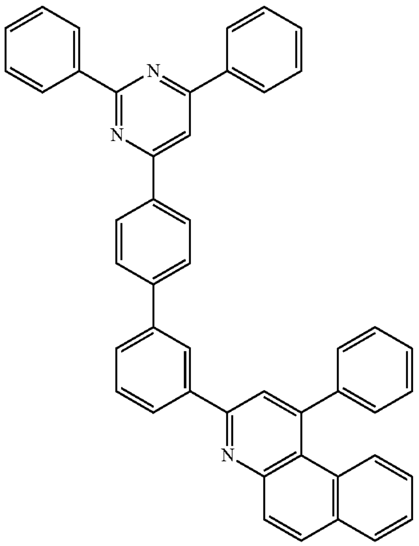

-continued
214
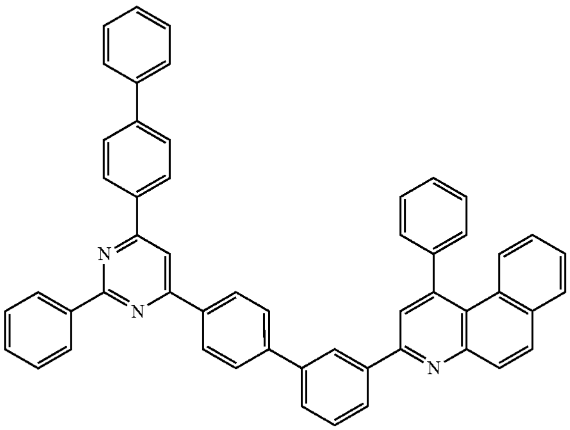
215
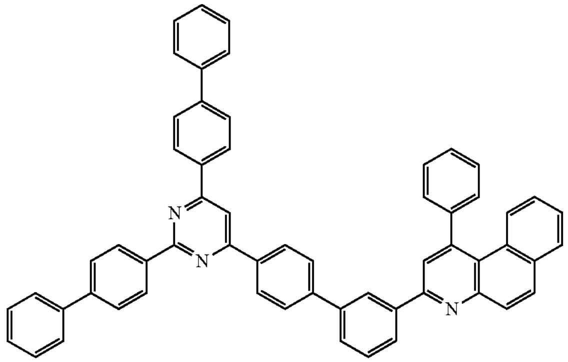
216
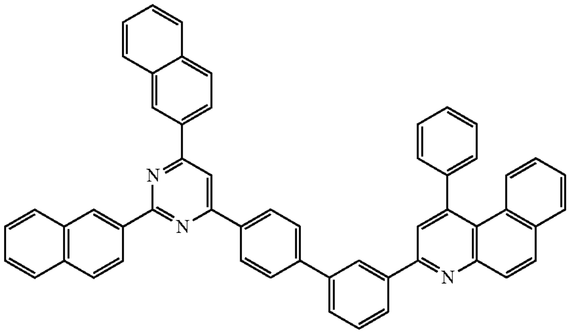
217
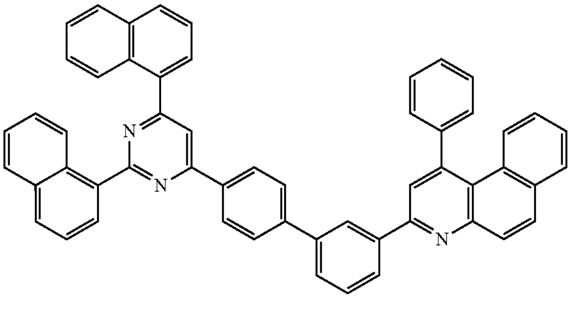
-continued
218
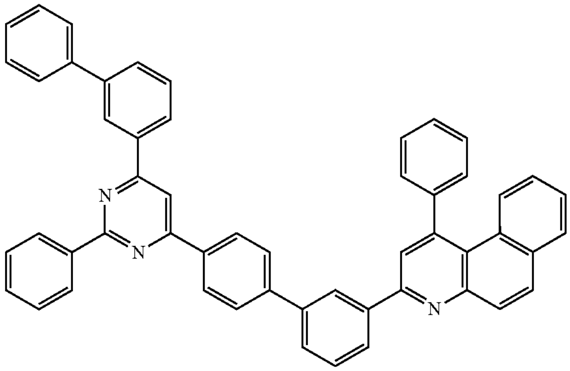
219
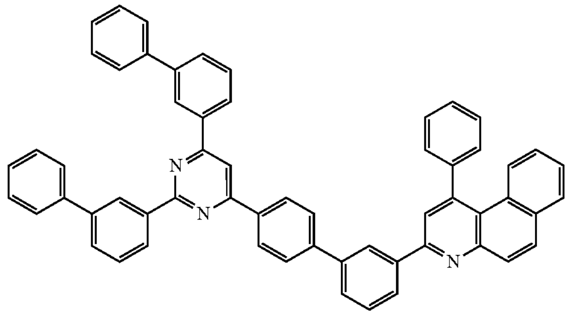
220
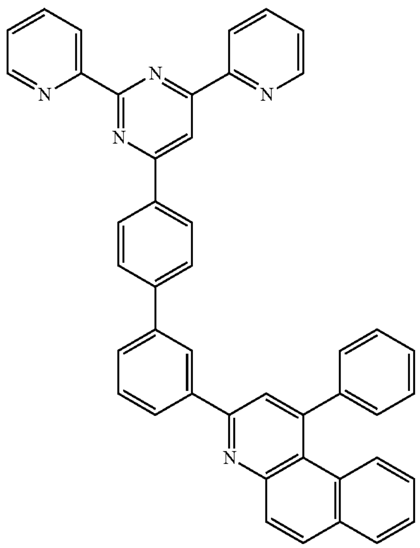

221
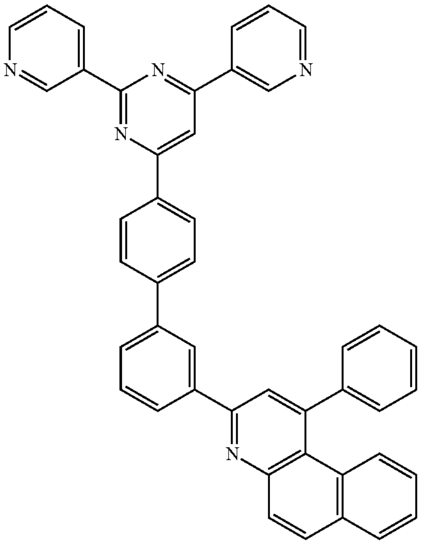
222
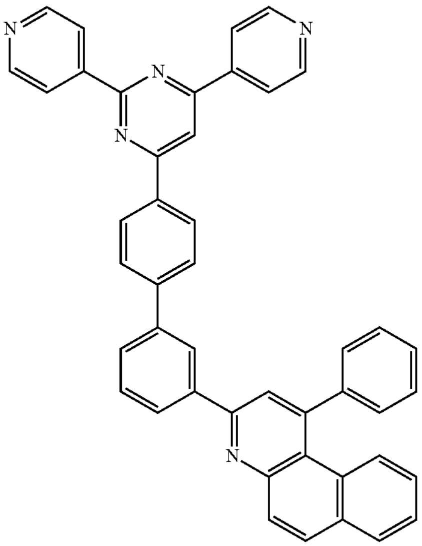
223
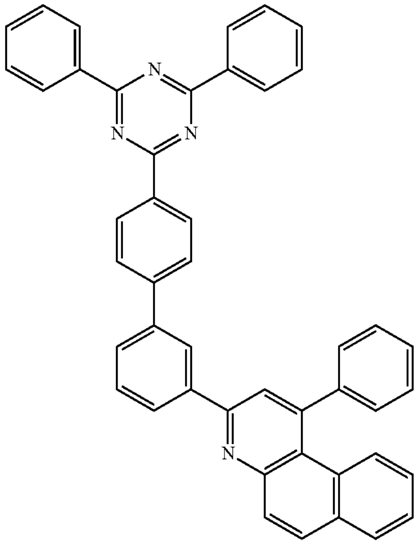
224
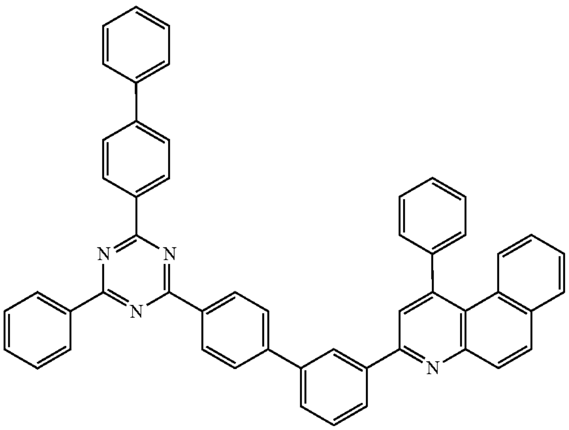
225
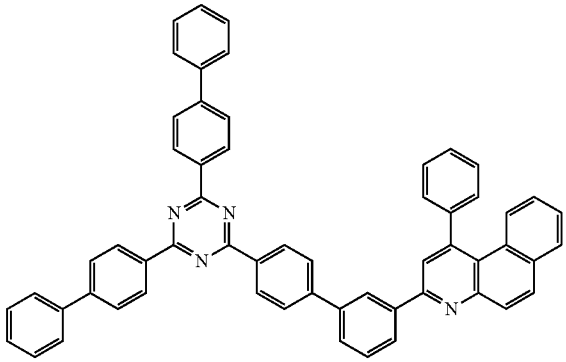
226
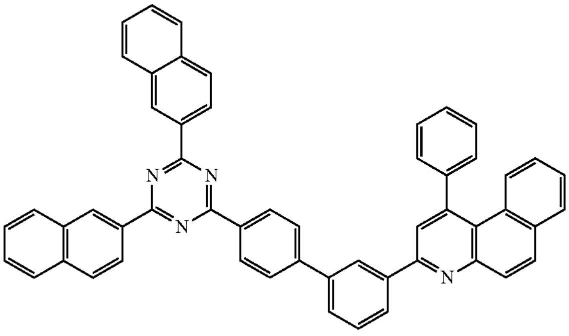
227
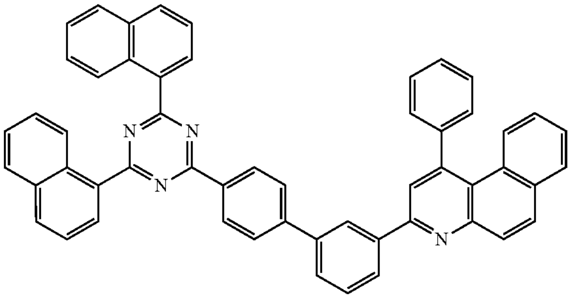

-continued
228
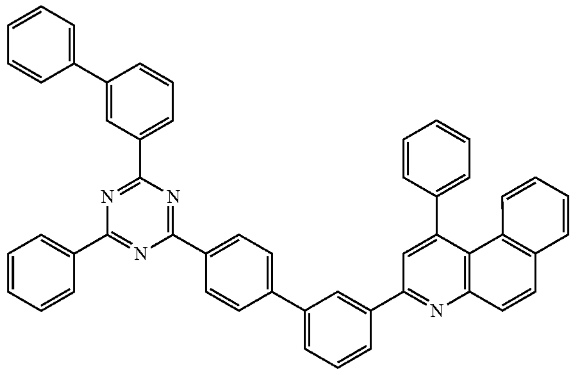
229
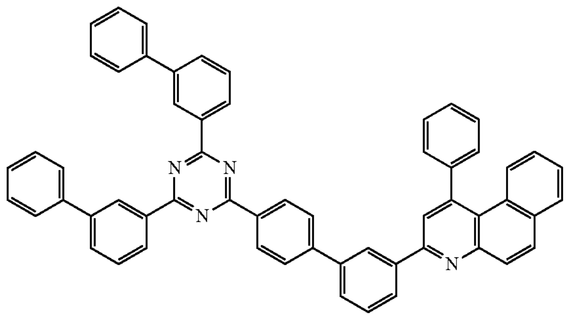
230
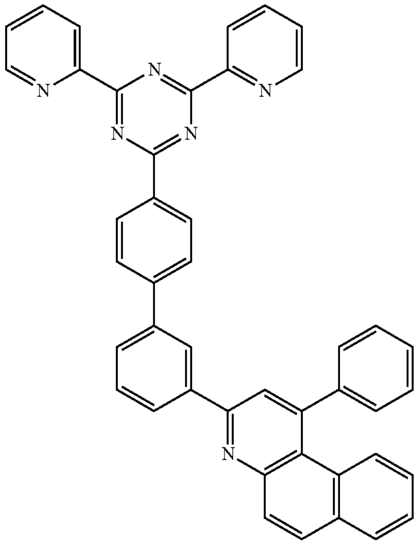
-continued
231
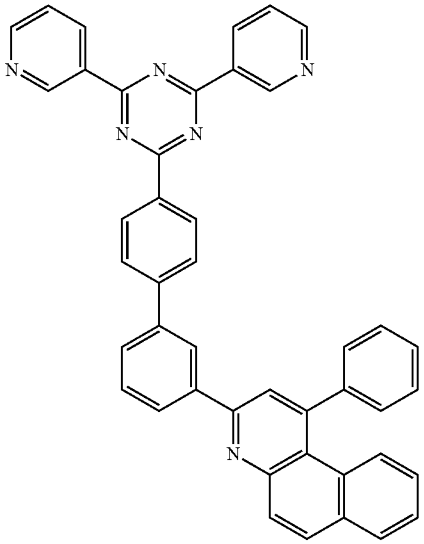
232
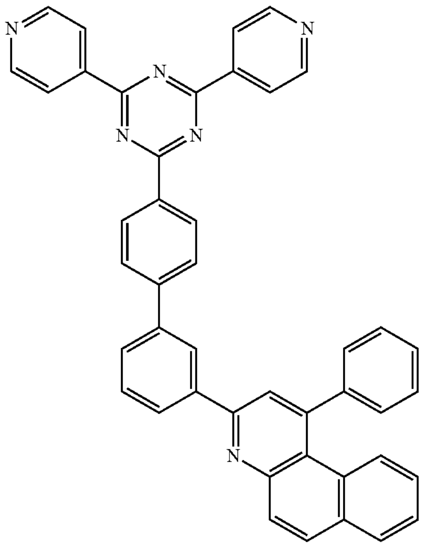
233
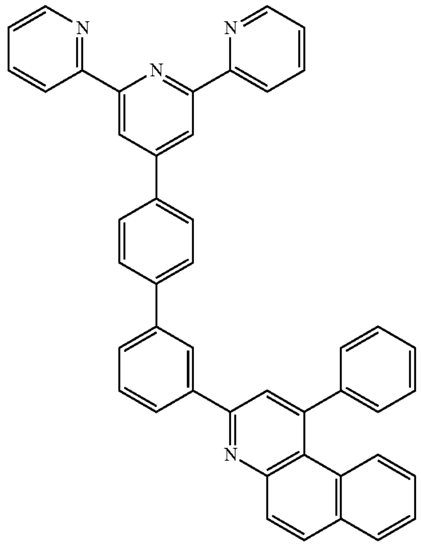

-continued
234
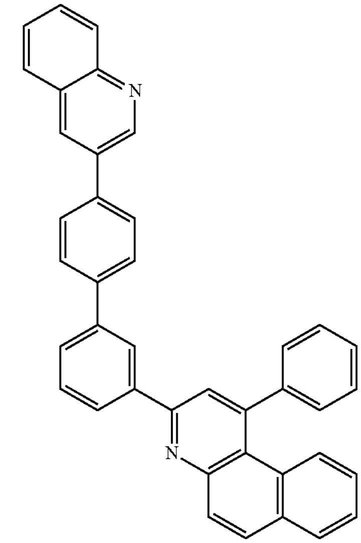
235
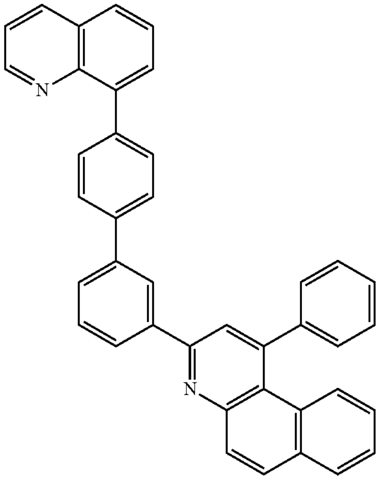
236
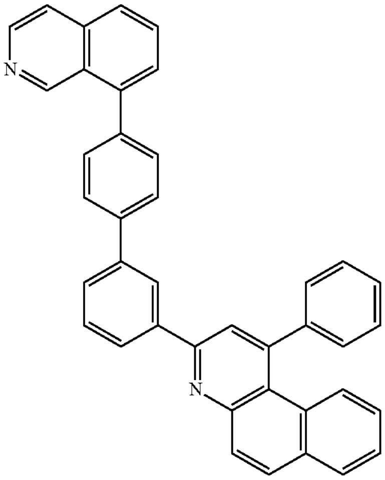
-continued
237
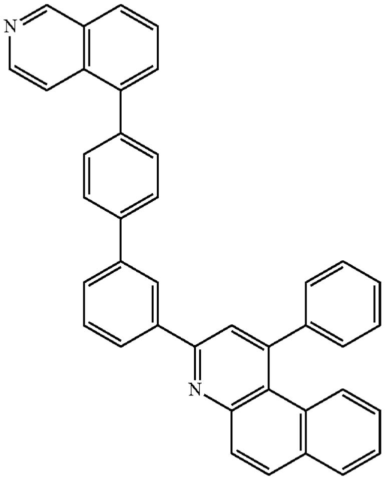
238
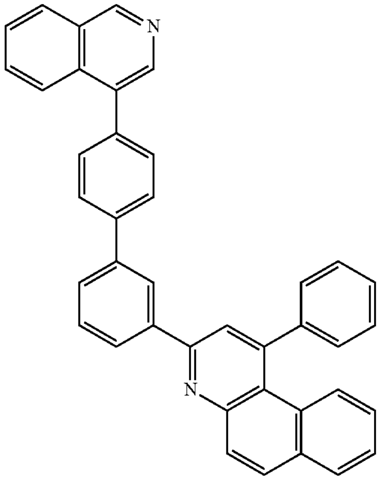
239
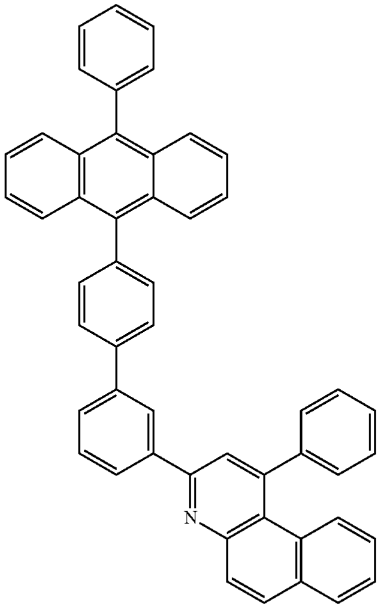

-continued
240
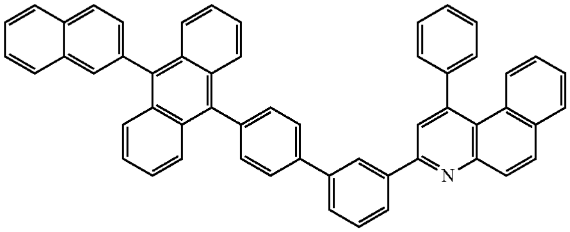
241
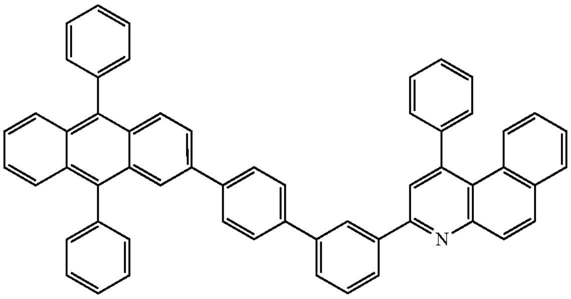
242
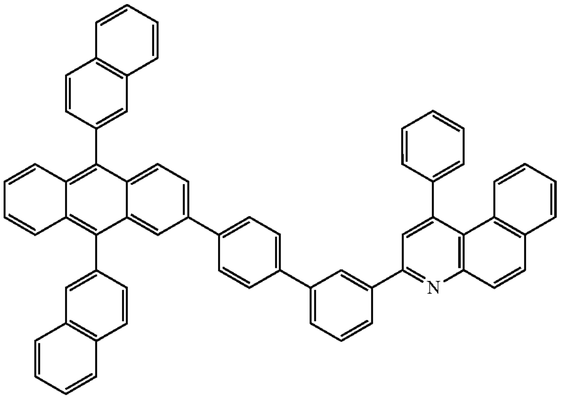
243
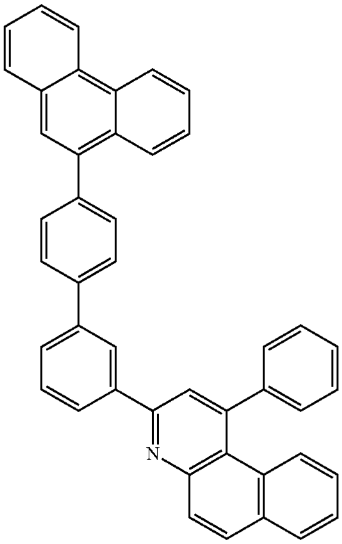
-continued
244
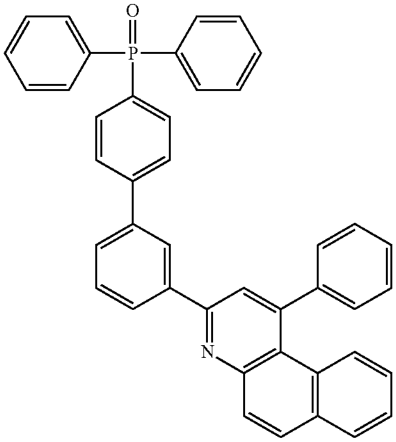
245
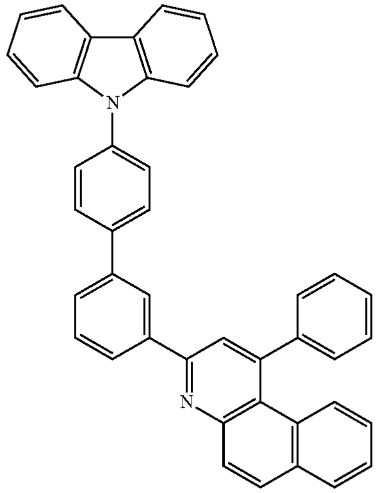
246
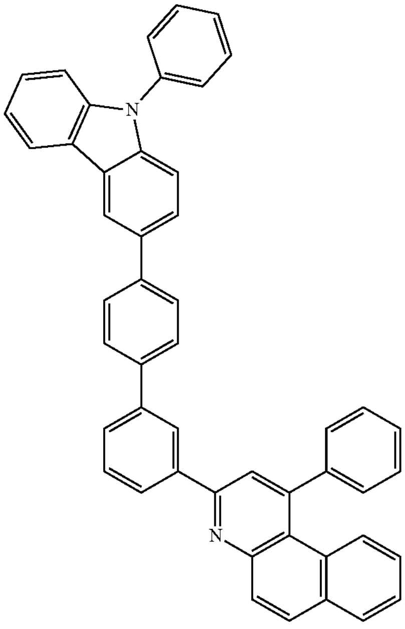

-continued
247
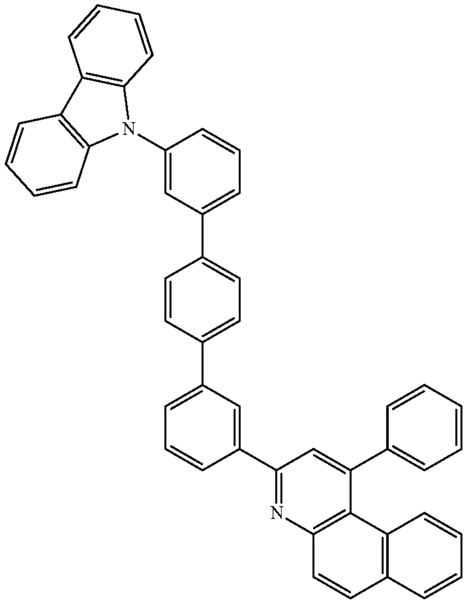
248
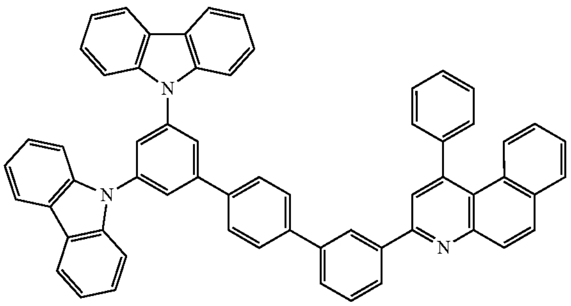
249
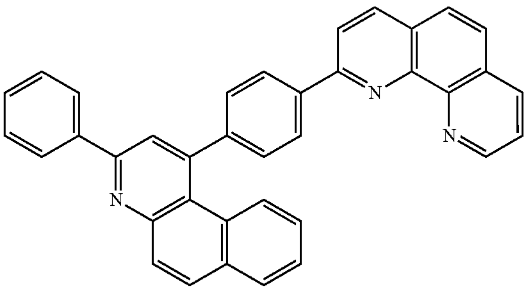
250
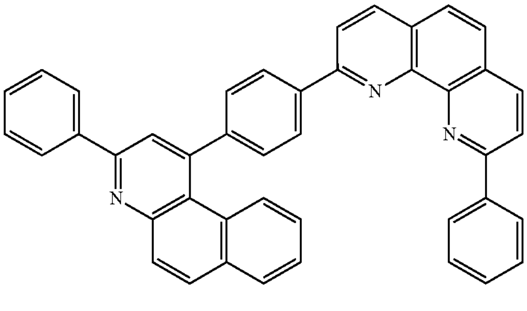
-continued
251
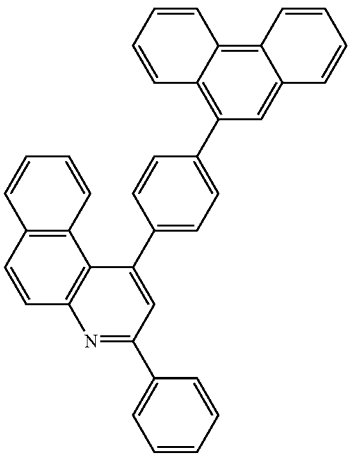
252
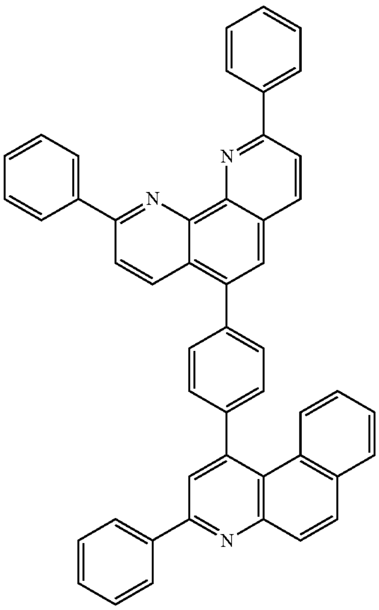
253
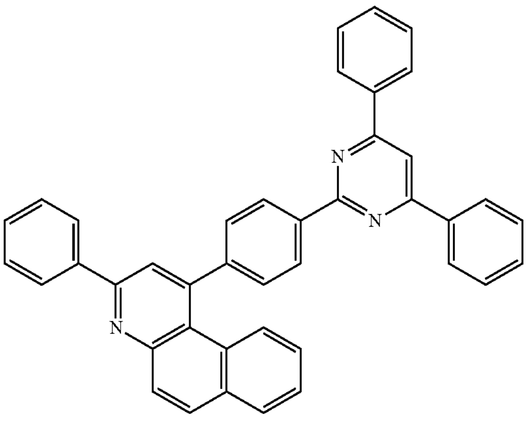

-continued
254
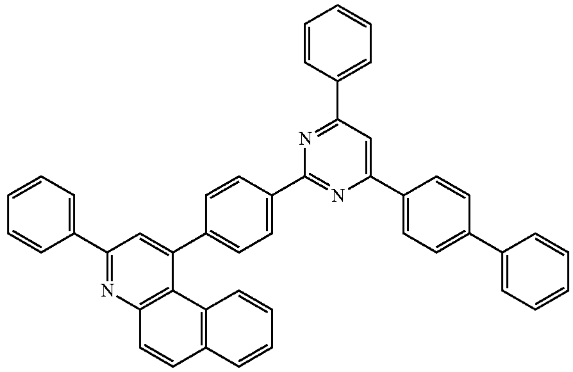
255
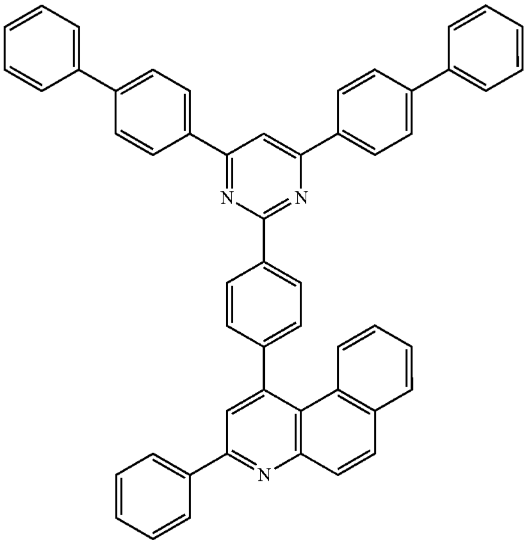
256
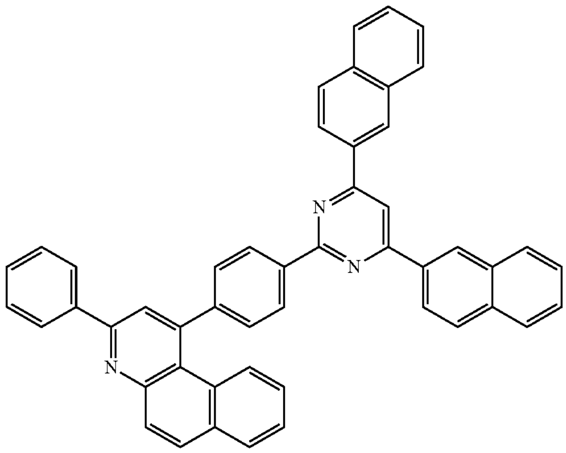
-continued
257
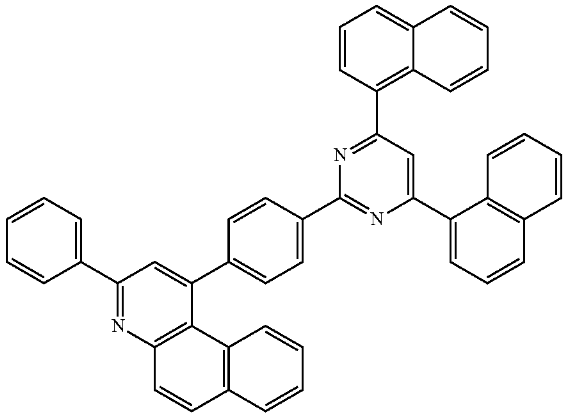
258
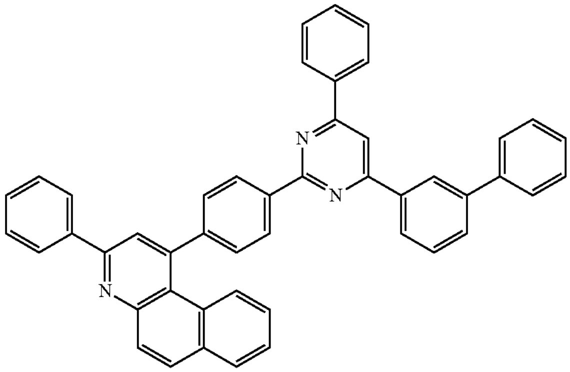
259
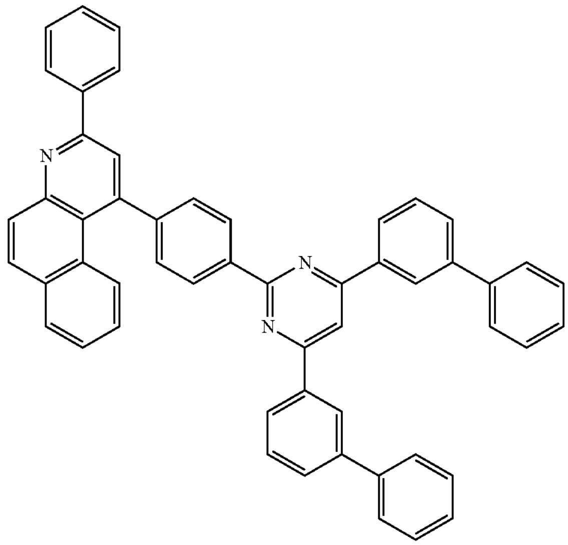

-continued
260
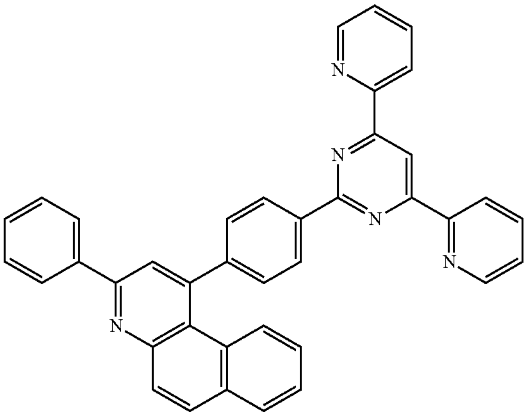
261
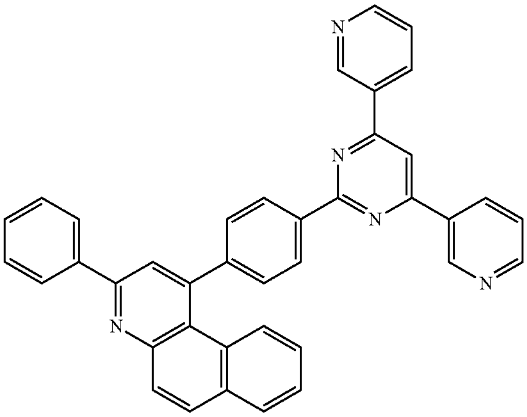
262
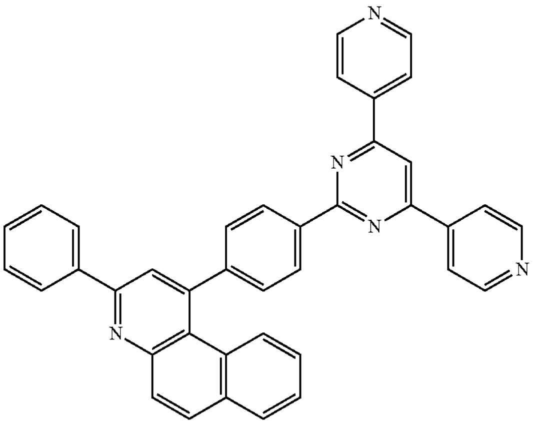
-continued
263
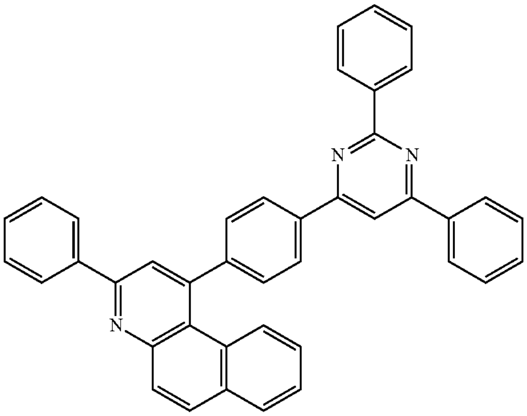
264
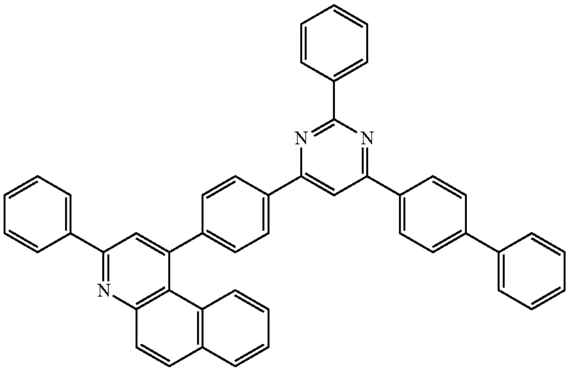
265
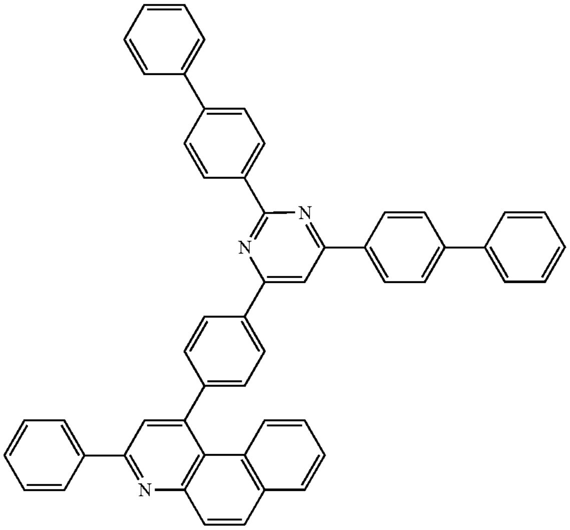

-continued
266
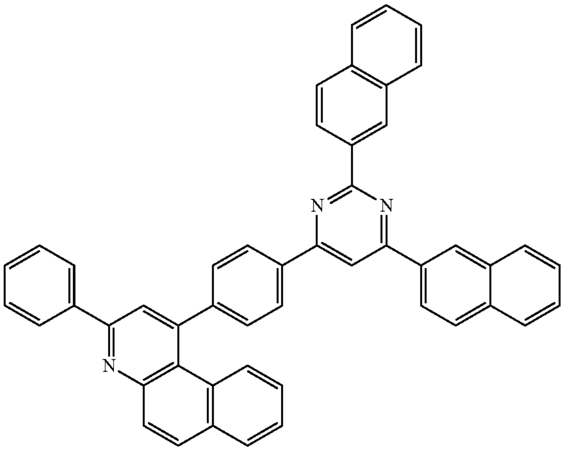
267
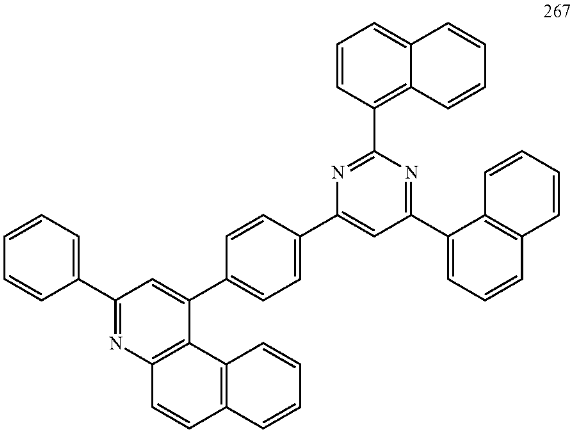
268
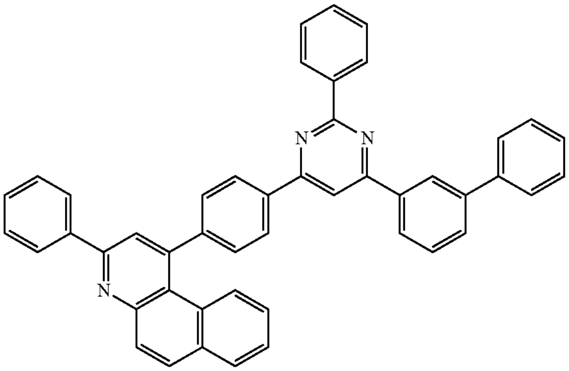
-continued
269
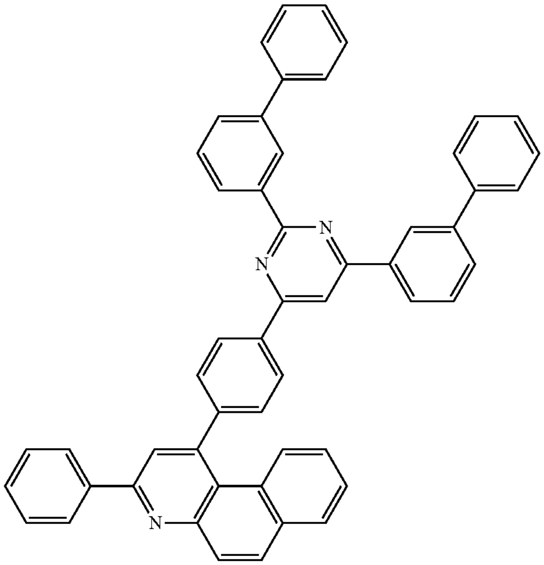
270
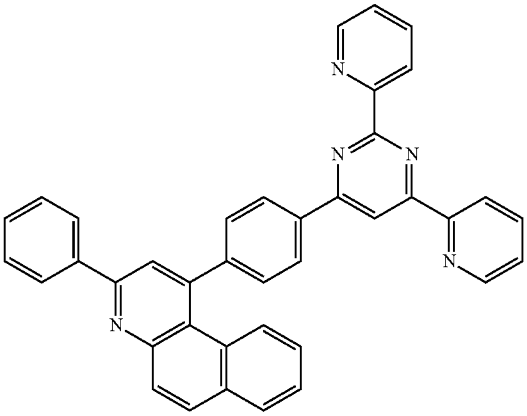
271
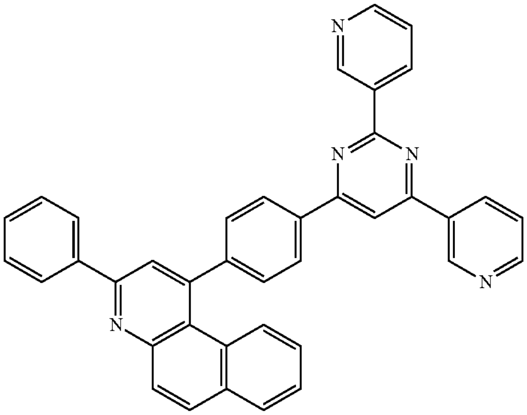

-continued
272
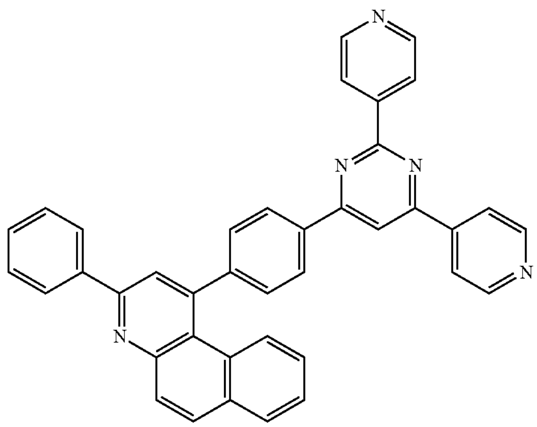
273
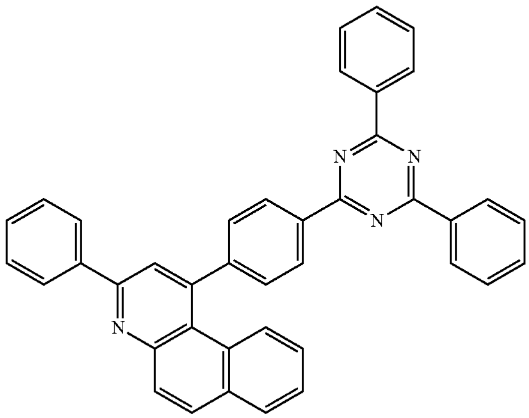
274
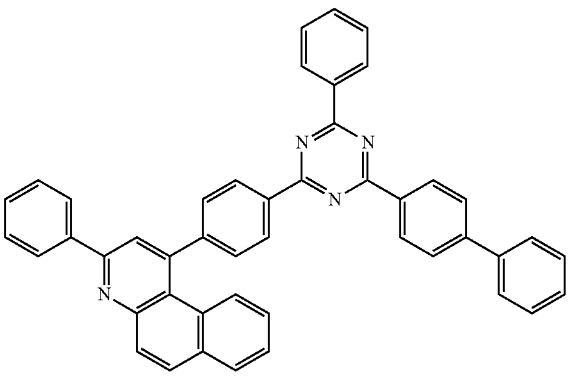
-continued
275
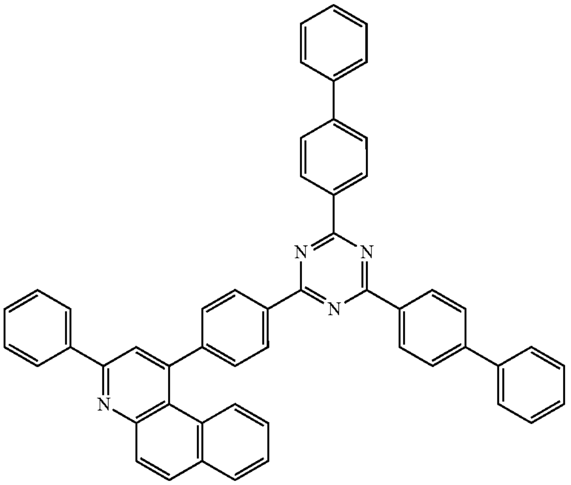
276
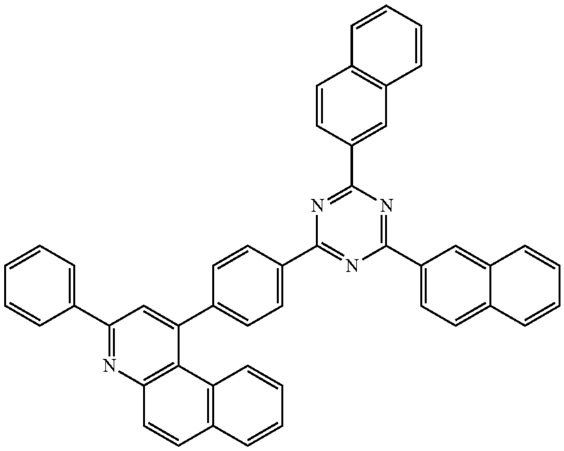
277
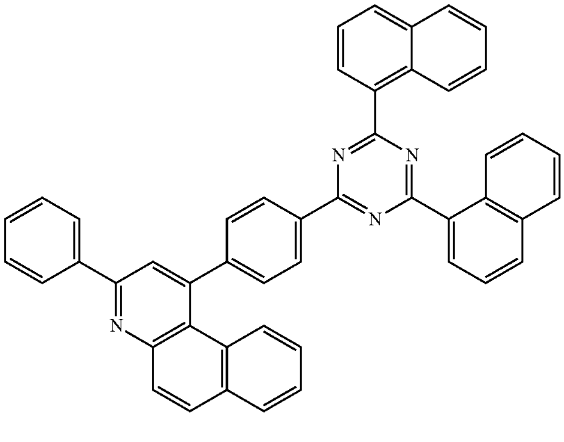

-continued
278
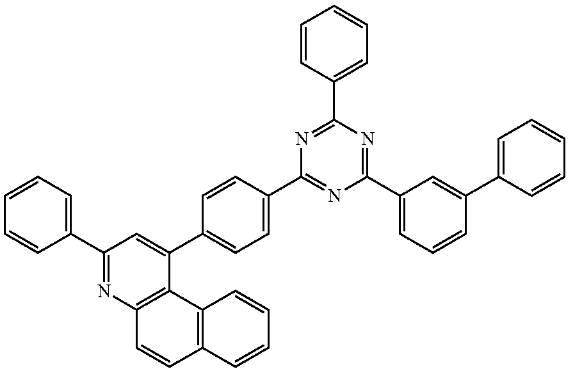
279
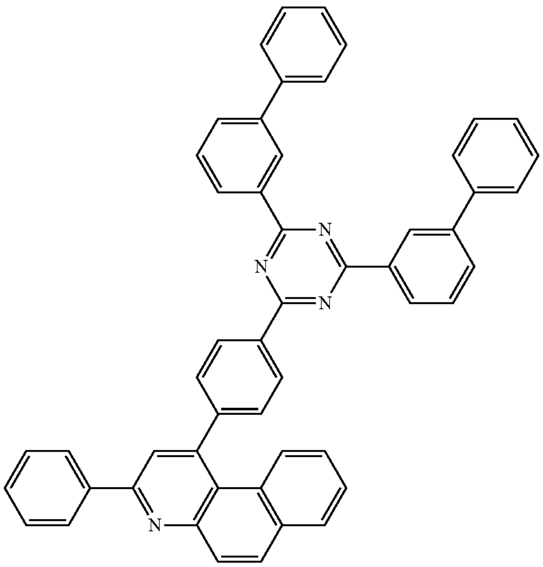
280
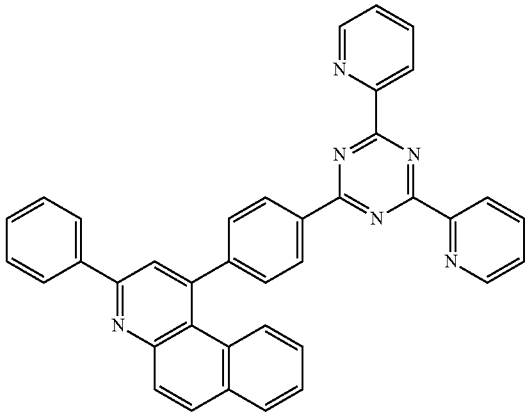
-continued
281
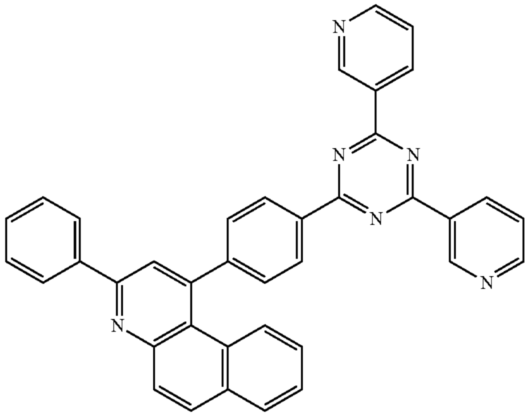
282
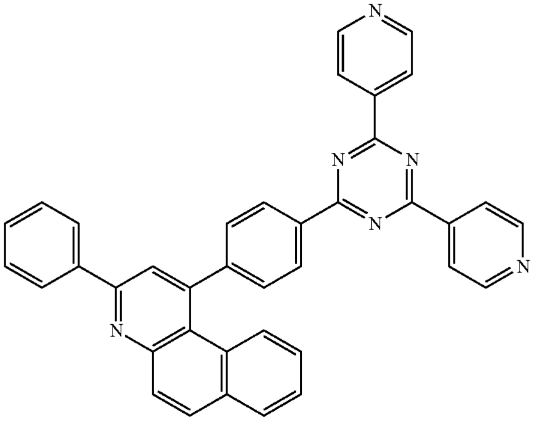
283
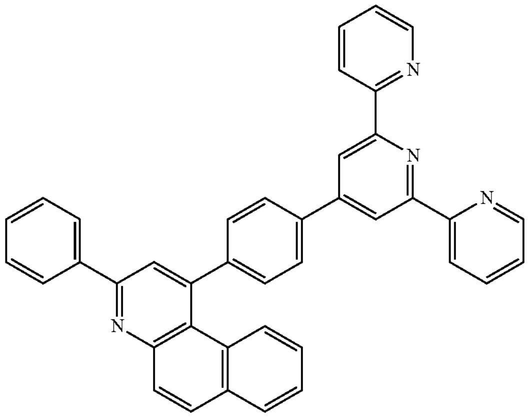
284
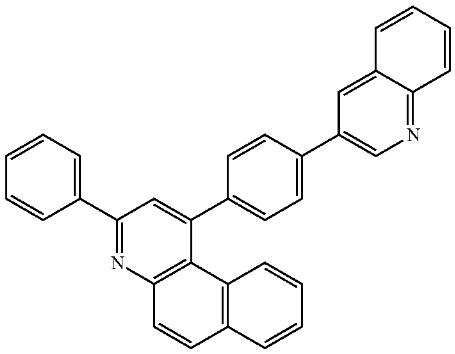

-continued
285
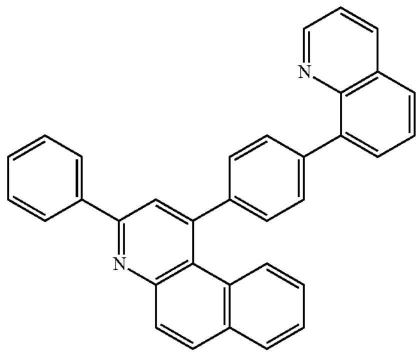
286
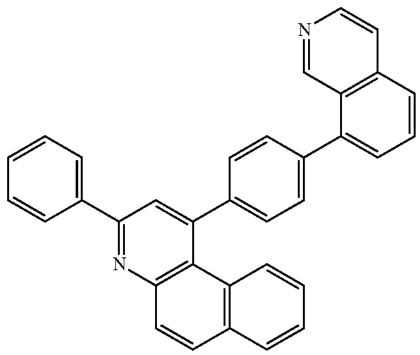
287
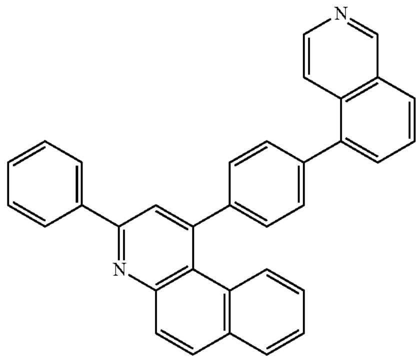
288
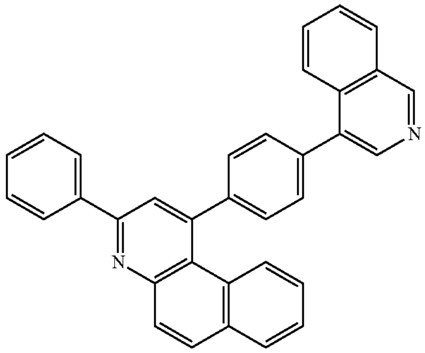
-continued
289
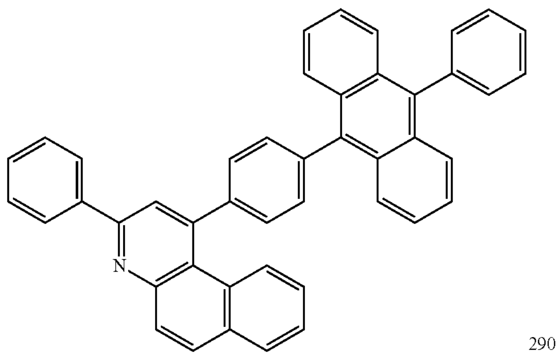
290
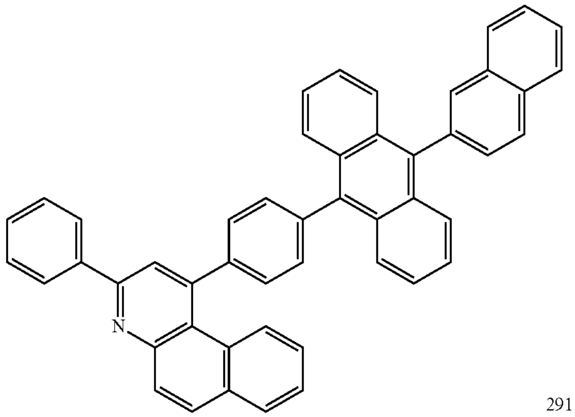
291
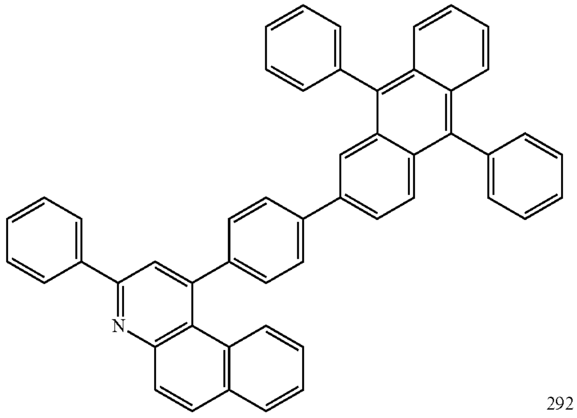
292
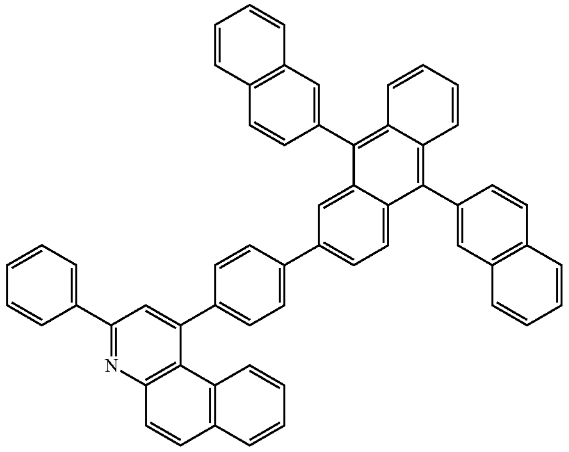

-continued
293
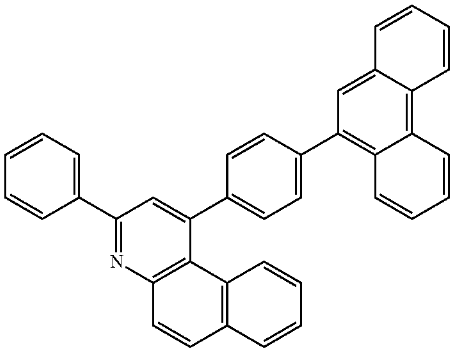
294
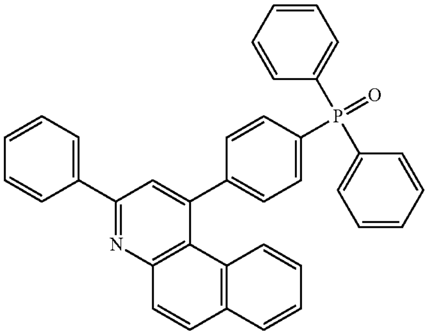
295
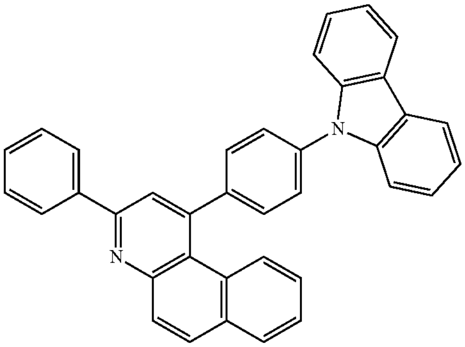
296
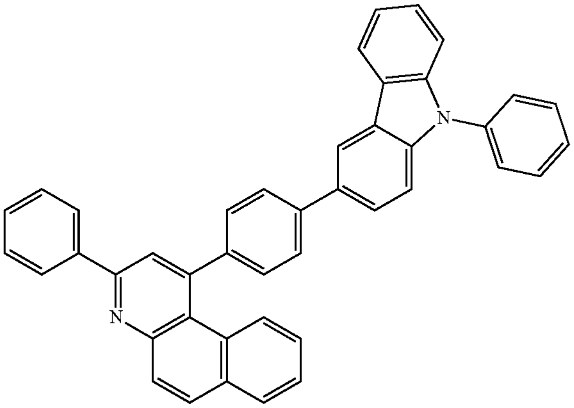
-continued
297
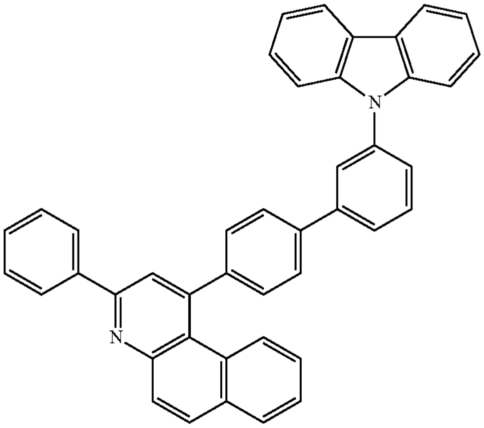
298
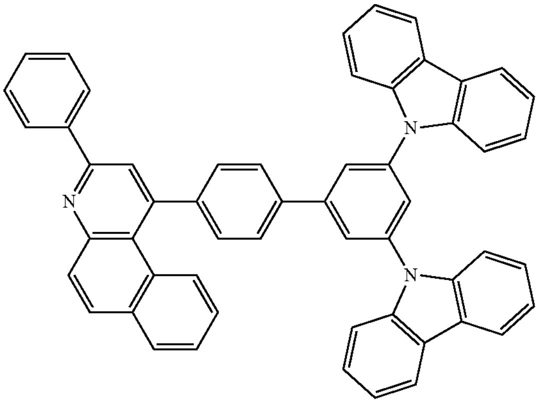
299
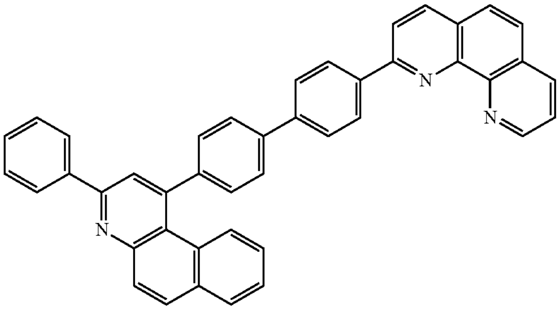
300
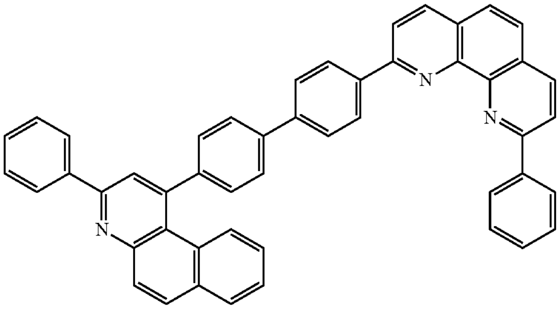

-continued
301
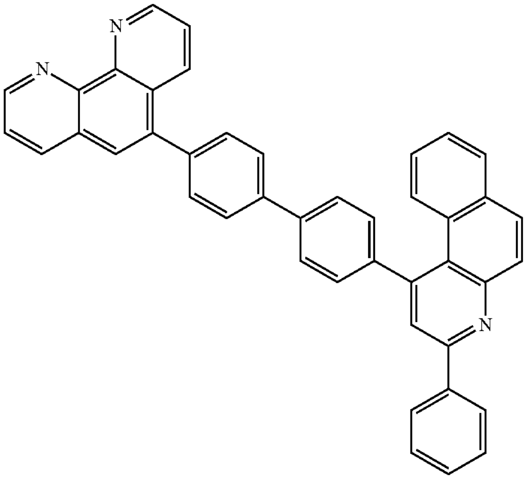
302
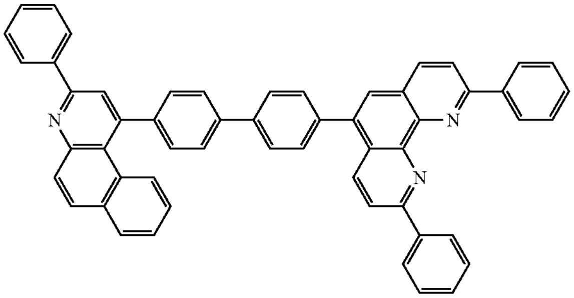
303
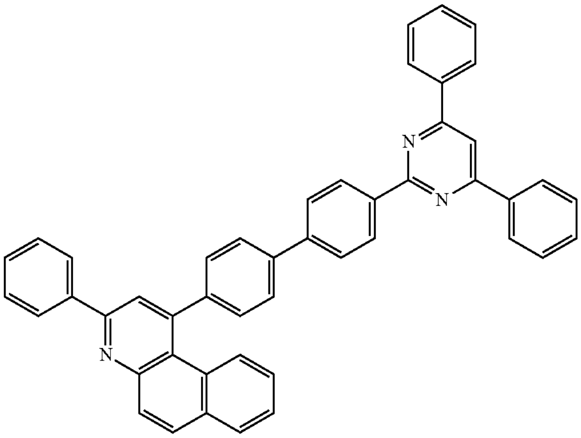
304
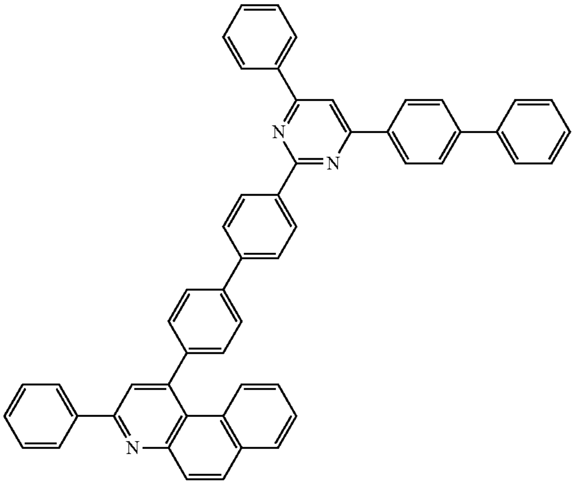
305
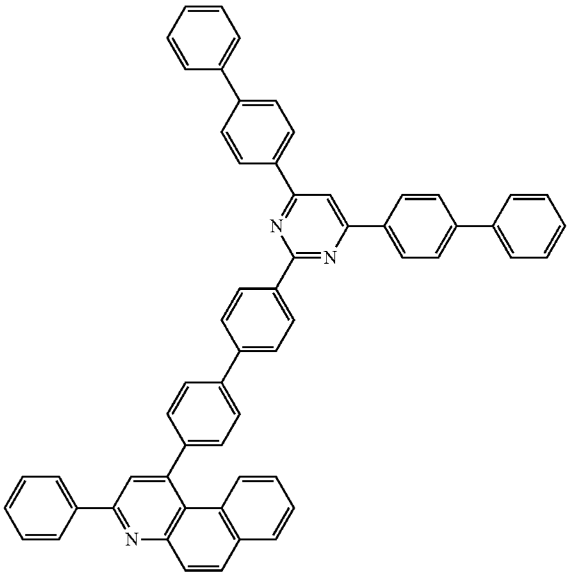
306
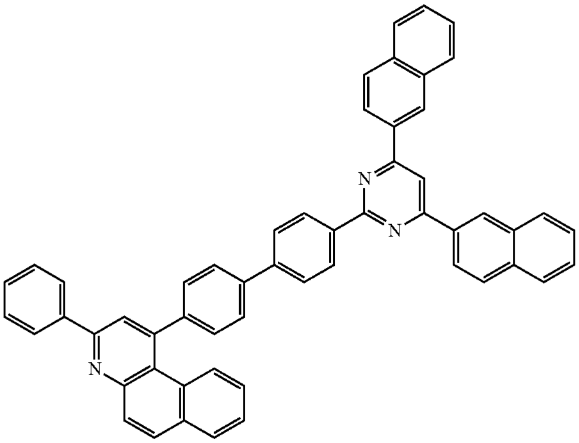

-continued
307
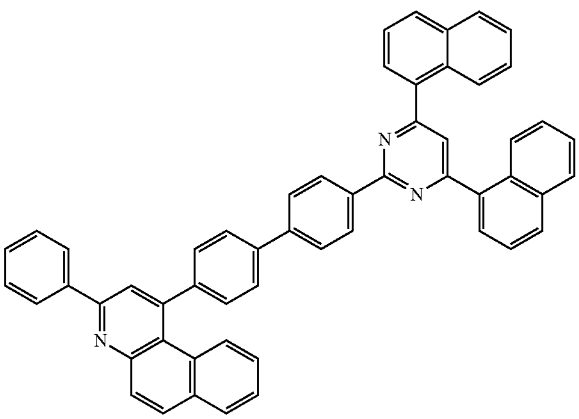
308
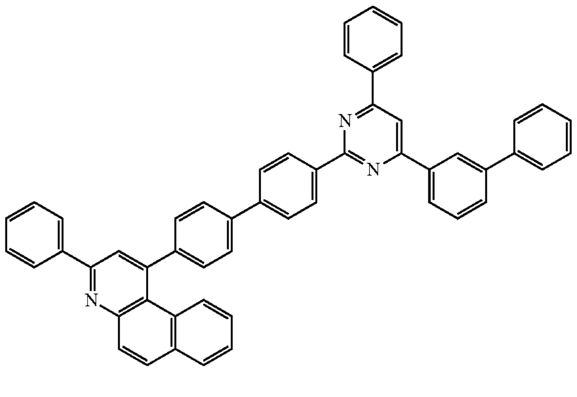
309
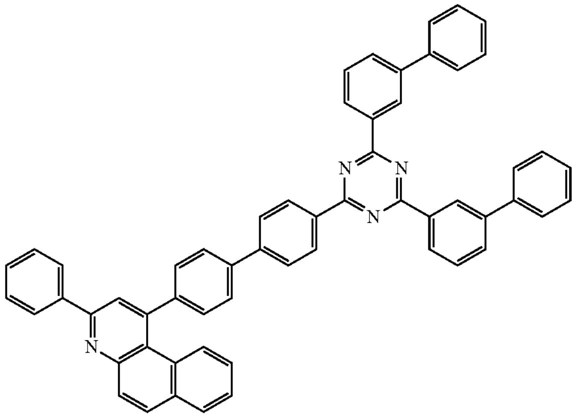
-continued
310
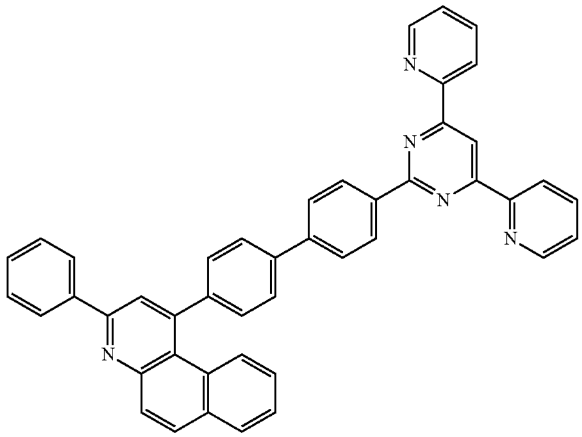
311
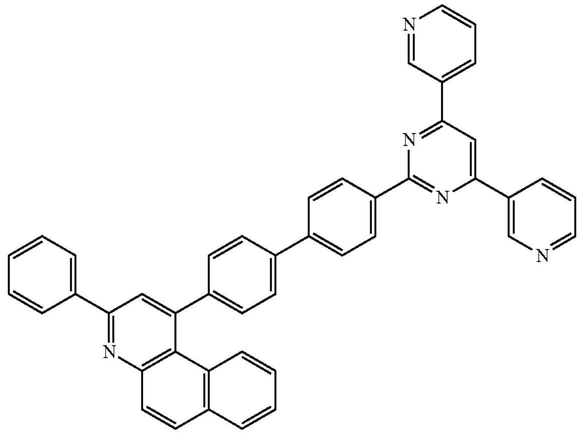
312
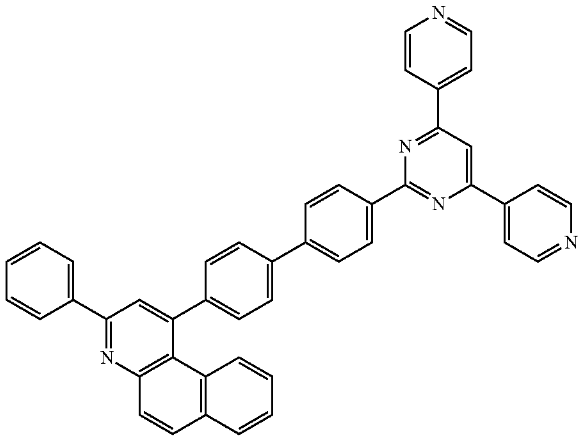

-continued
313
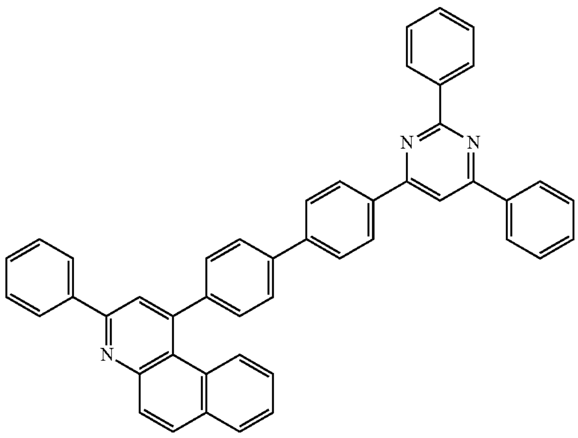
314
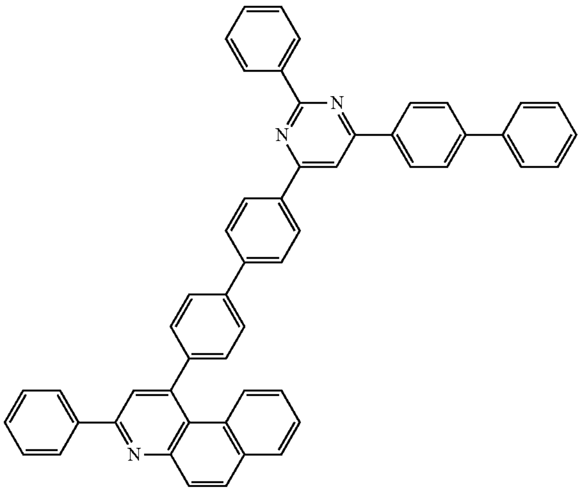
315
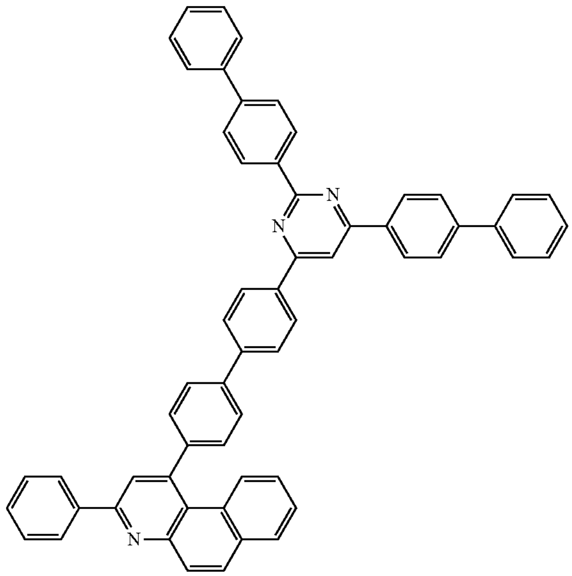
-continued
316
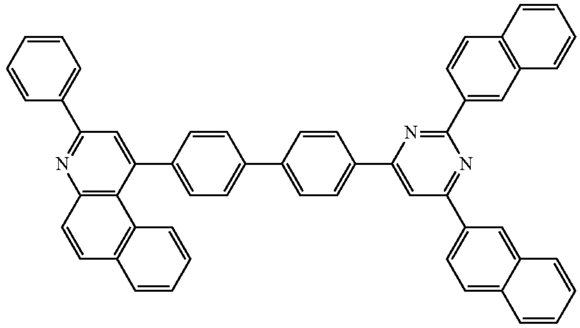
317
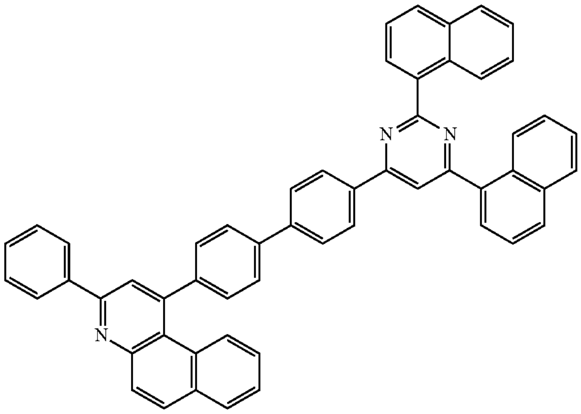
318
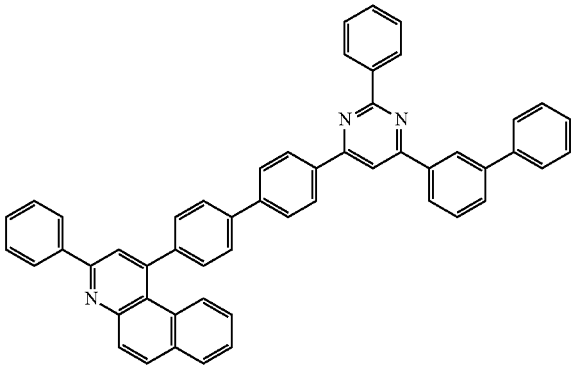
319
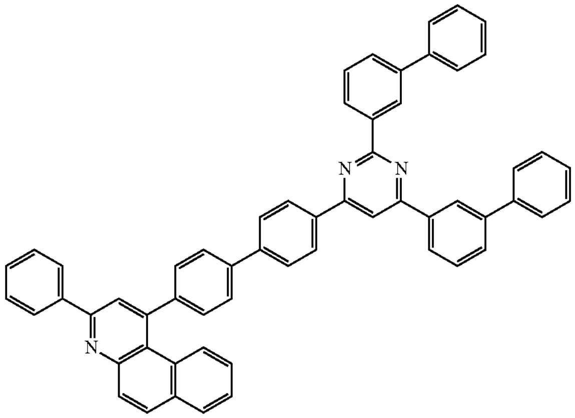

-continued
320
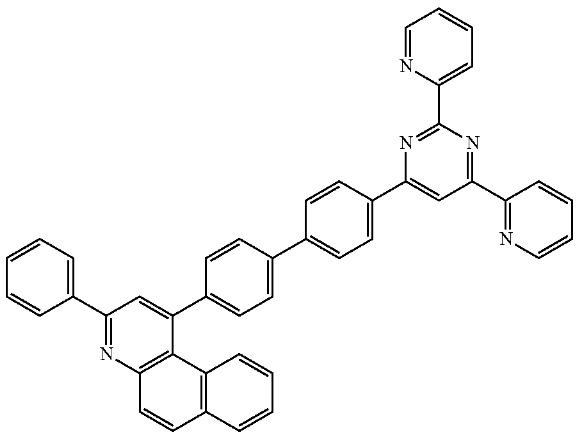
321
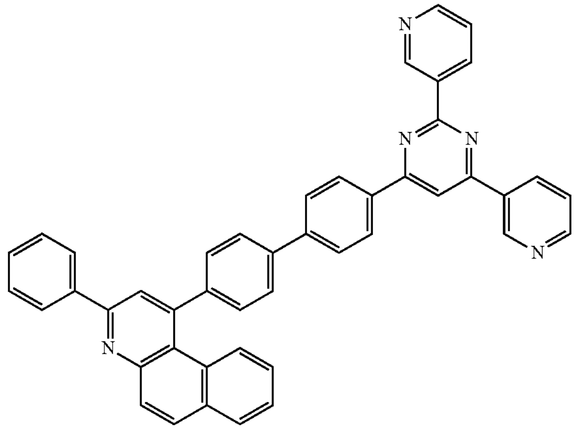
322
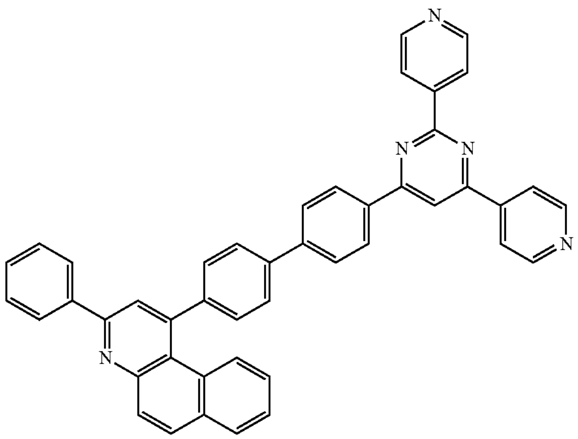
-continued
323
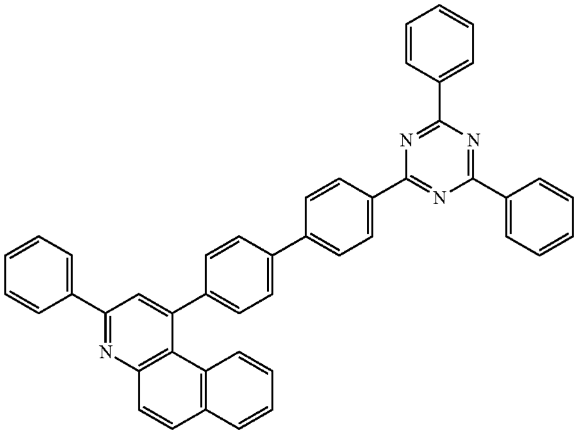
324
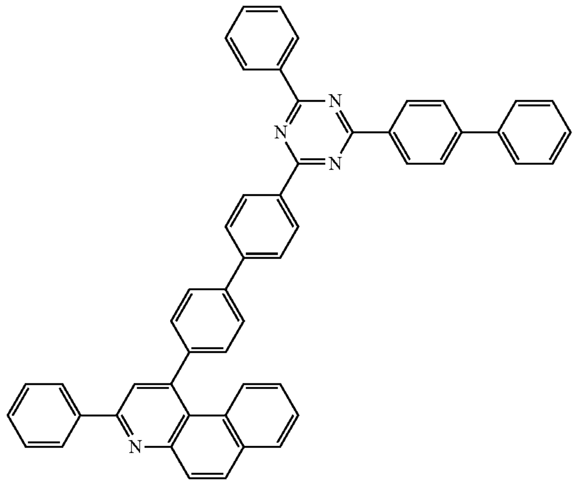
325
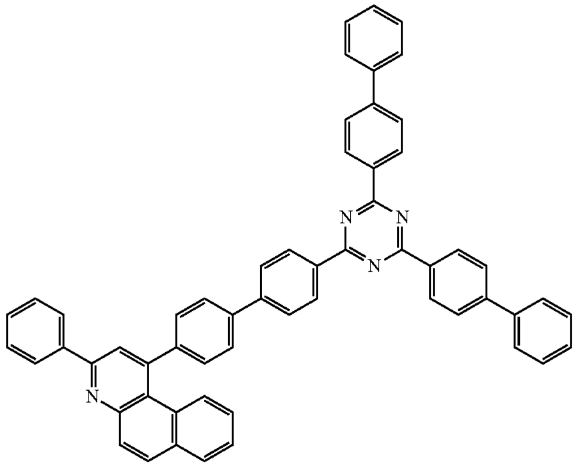

-continued
326
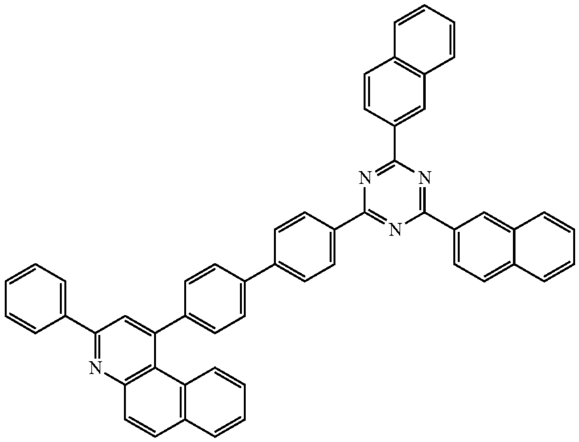
327
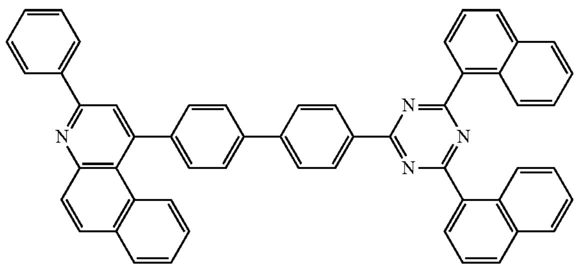
328
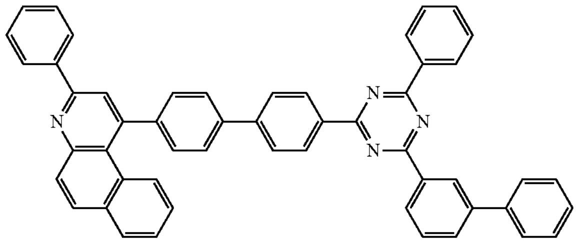
329
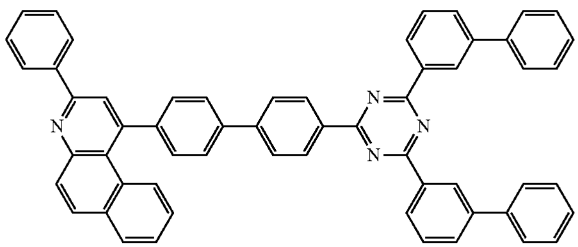
-continued
330
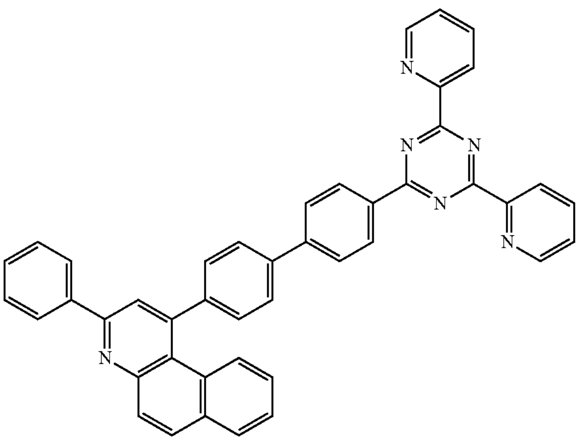
331
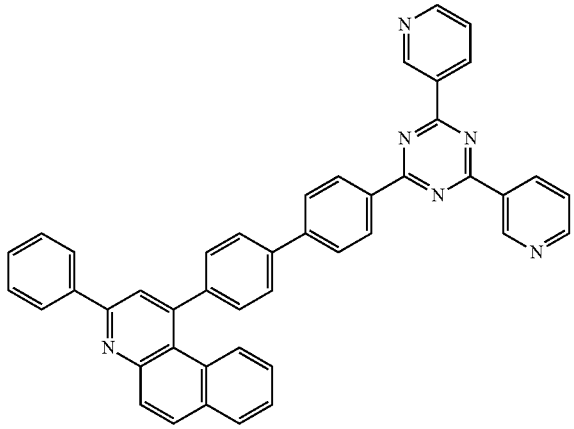
332
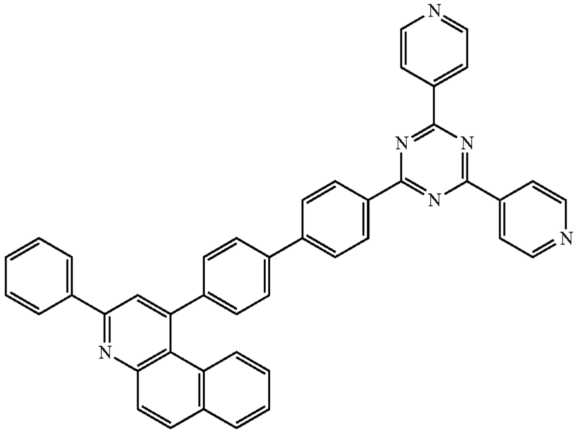

-continued
333
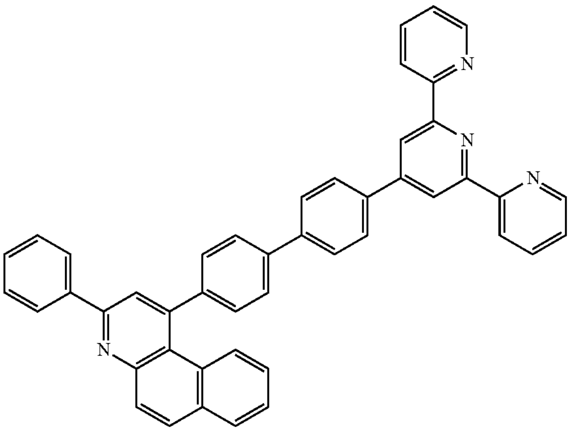
334
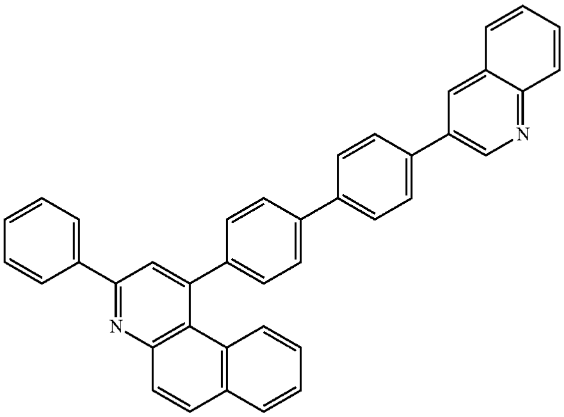
335
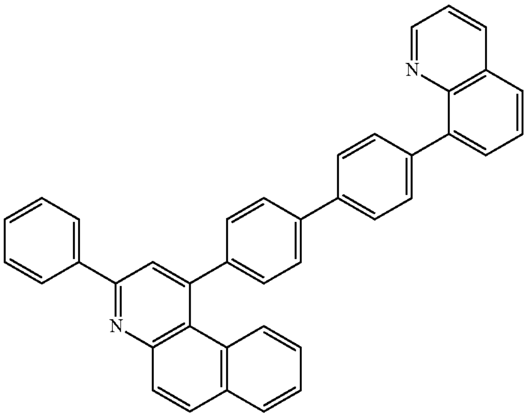
-continued
336
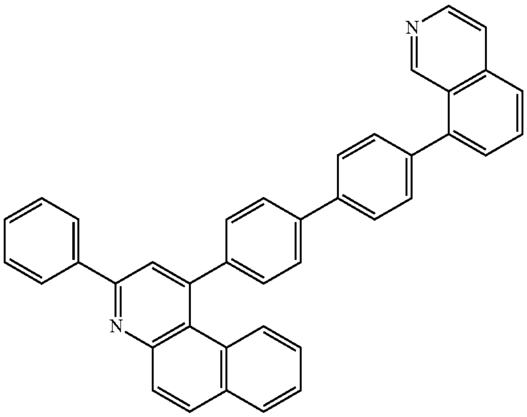
337
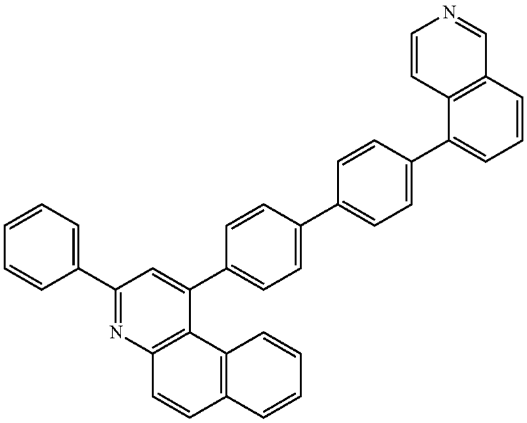
338
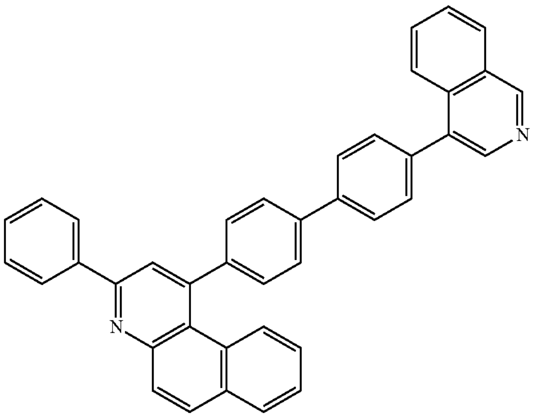

-continued
339
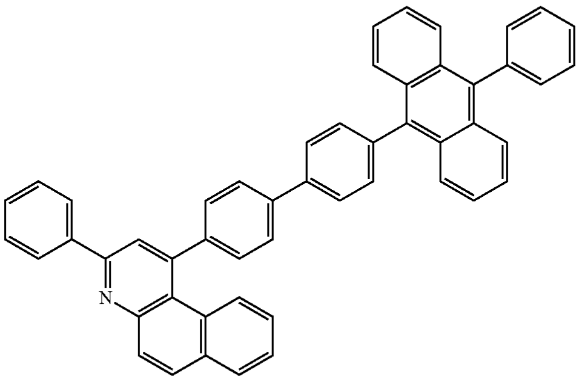
340
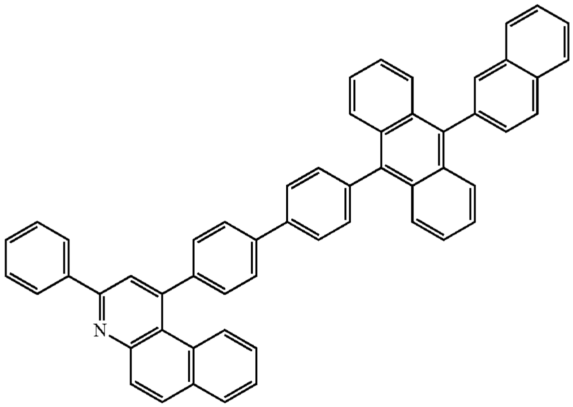
341
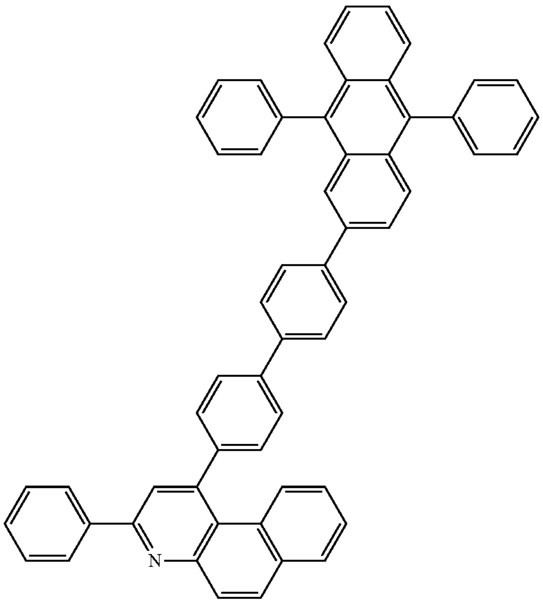
-continued
342
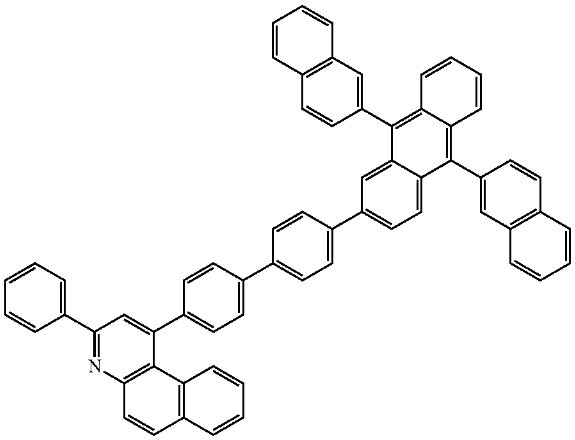
343
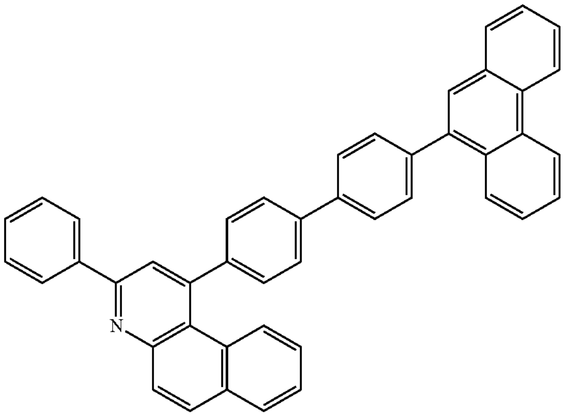
344
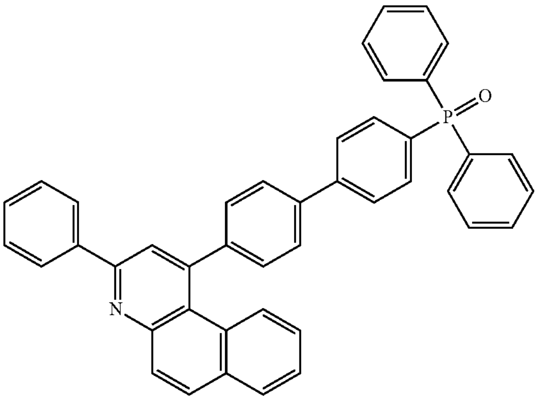

-continued
345
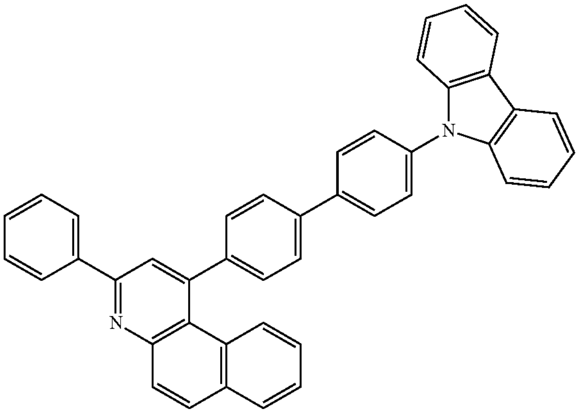
346
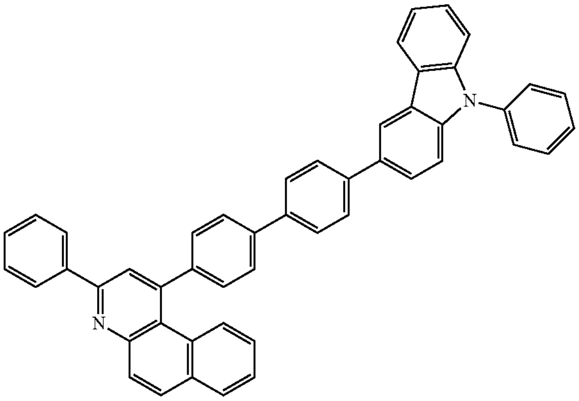
347
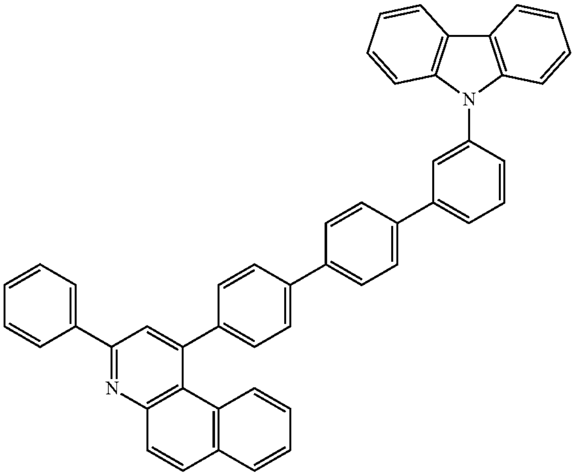
-continued
348
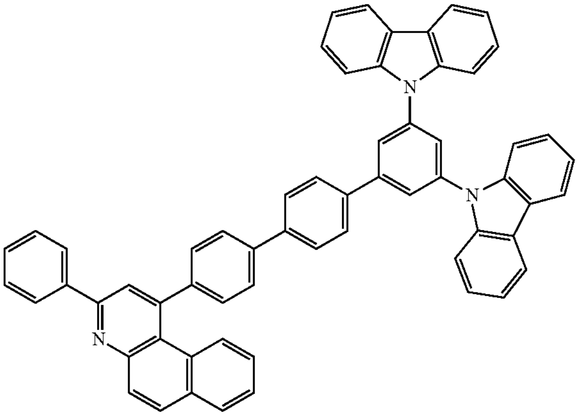
349
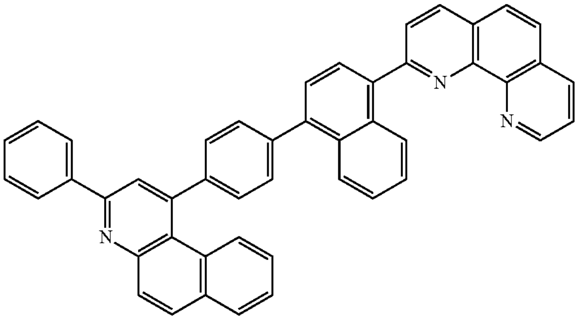
350
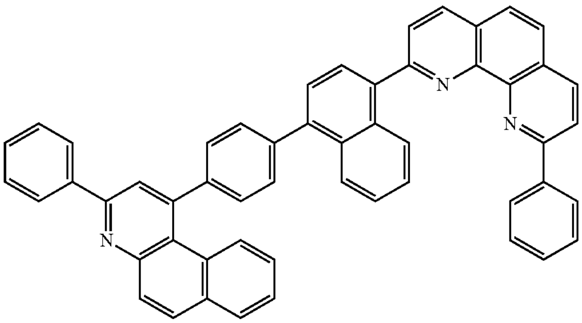
351
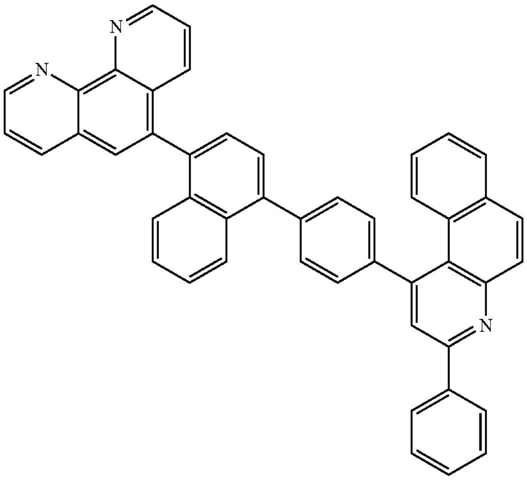

-continued
352
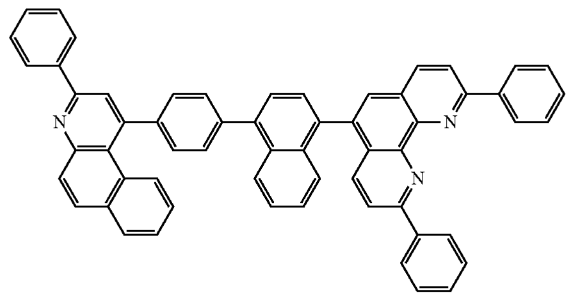
353
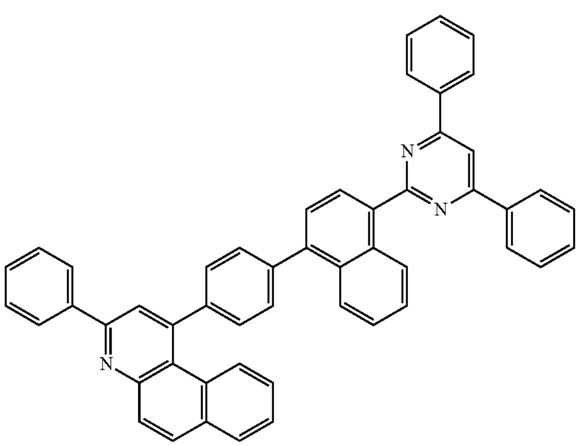
354
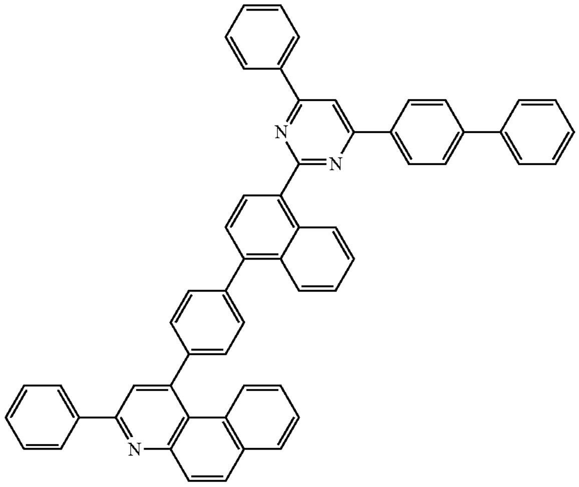
-continued
355
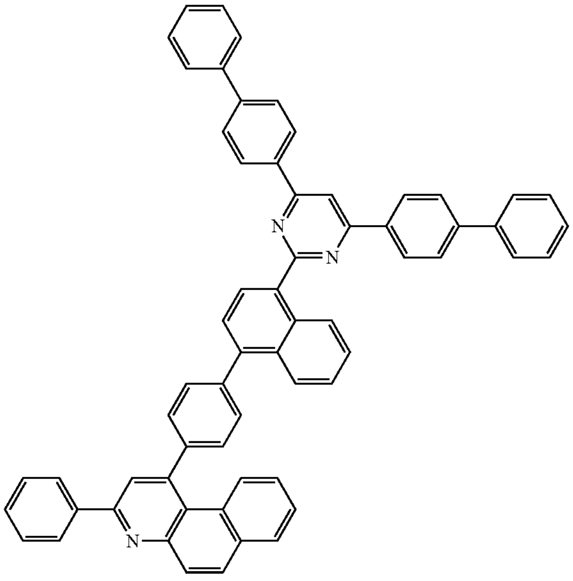
356
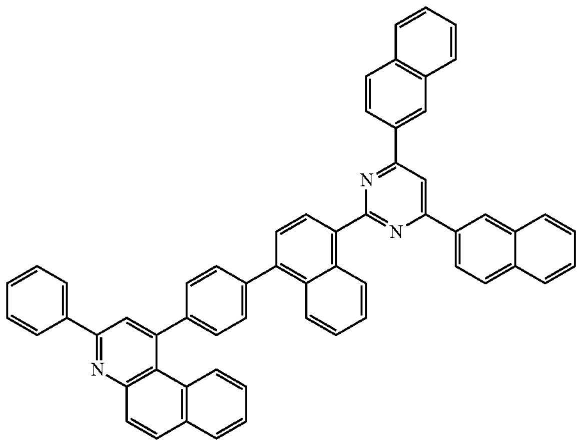
357
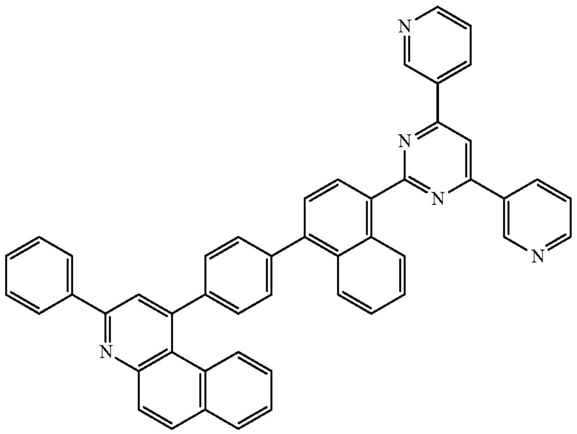

-continued
358
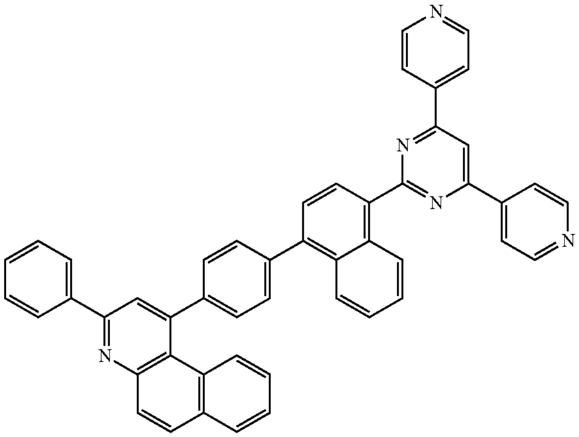
359
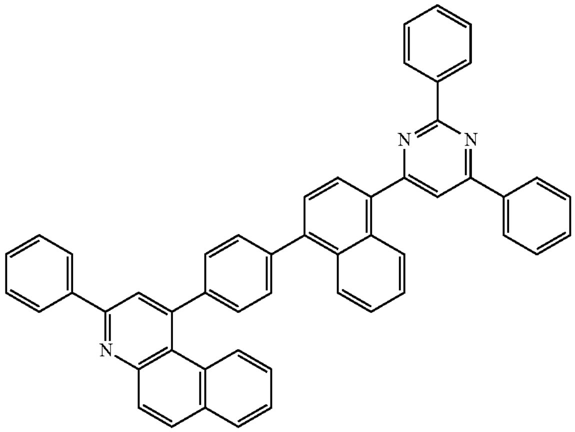
360
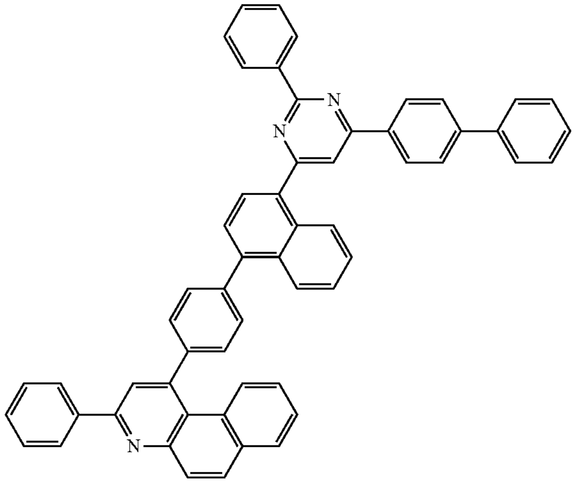
-continued
361
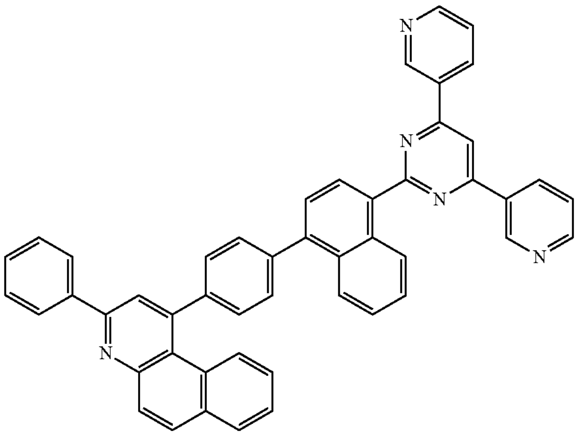
362
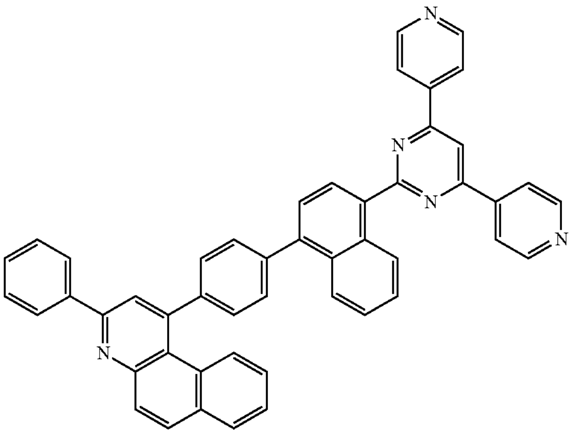
363
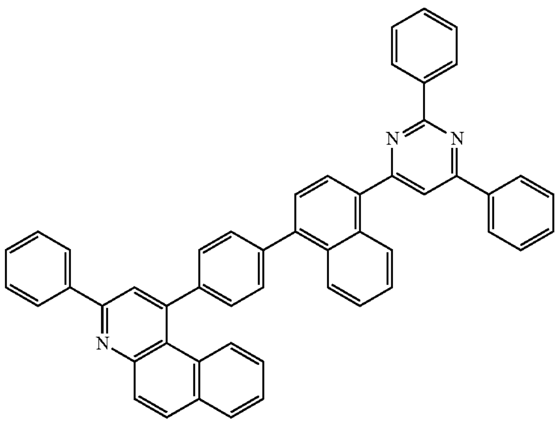

364
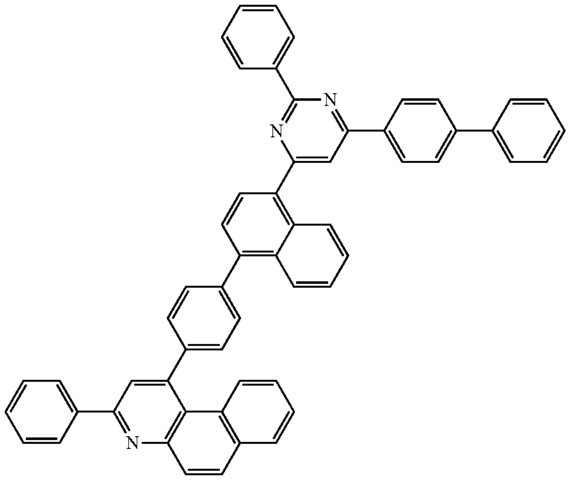
365
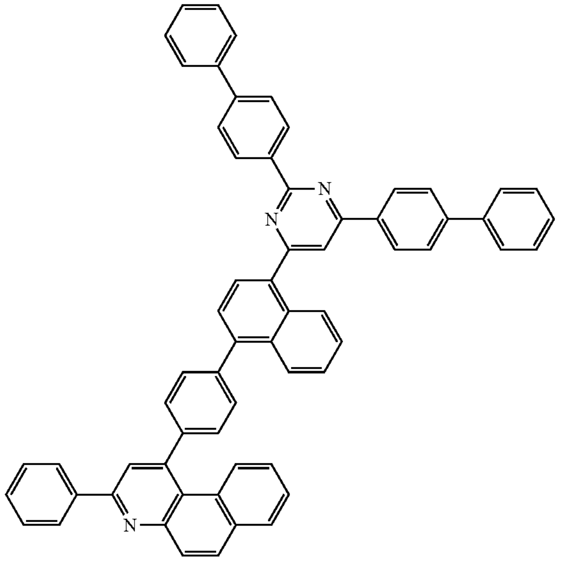
366
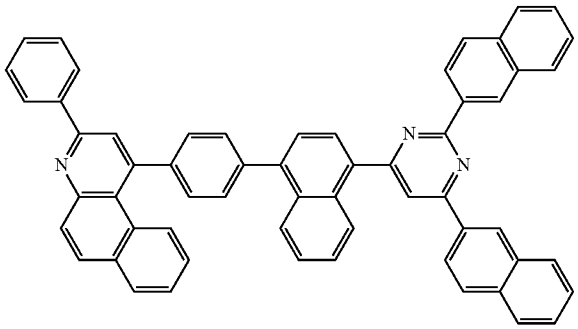
367
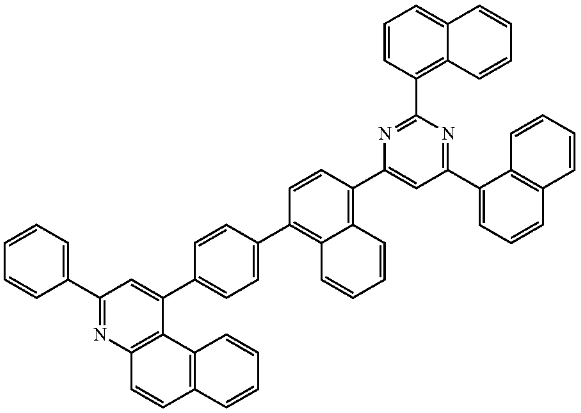
368
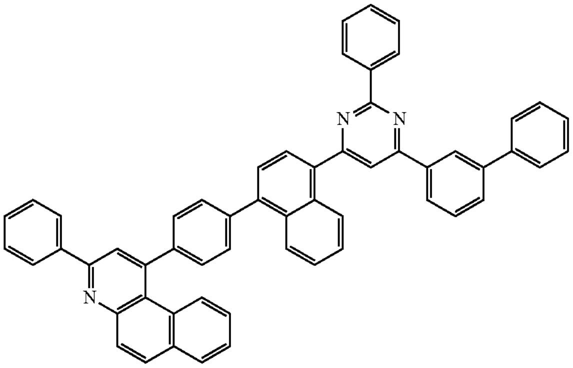
369
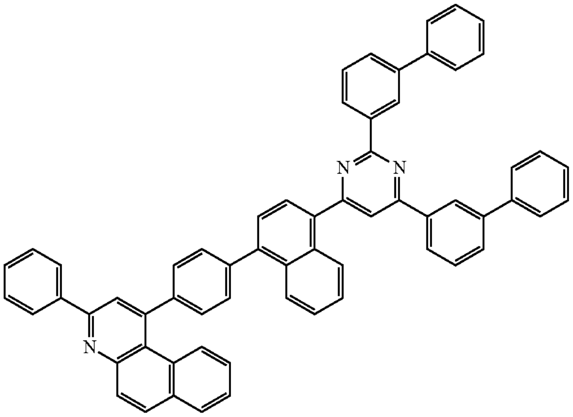

370
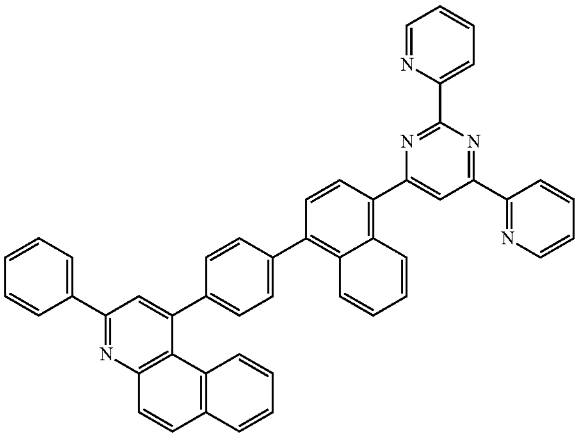
371
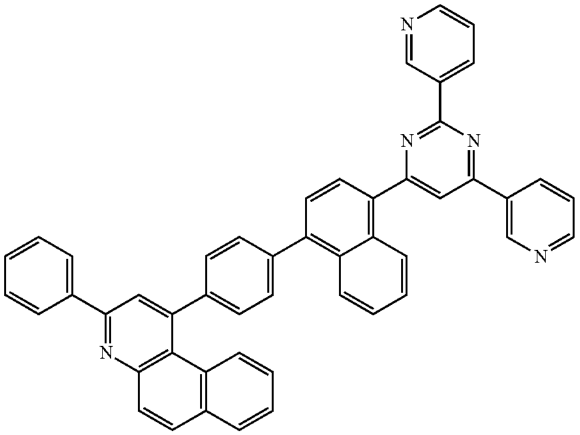
372
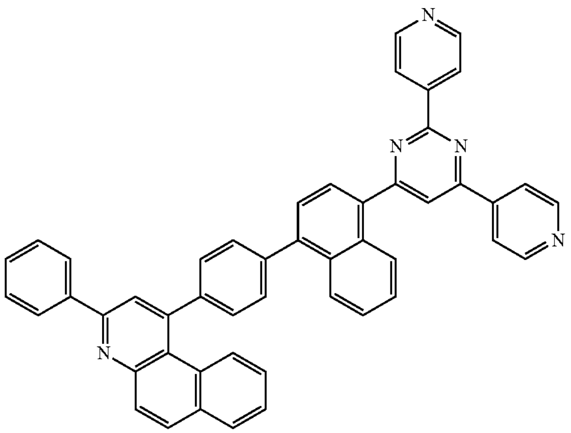
373
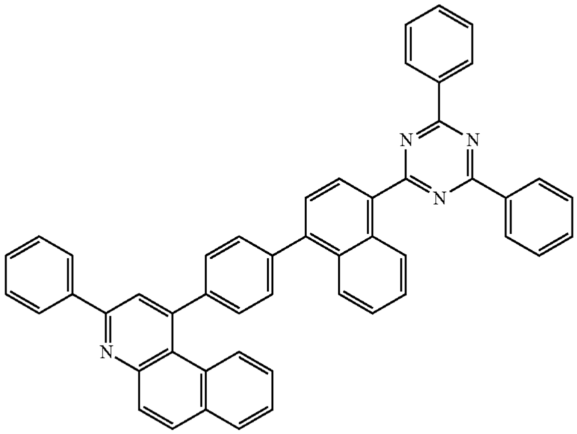
374
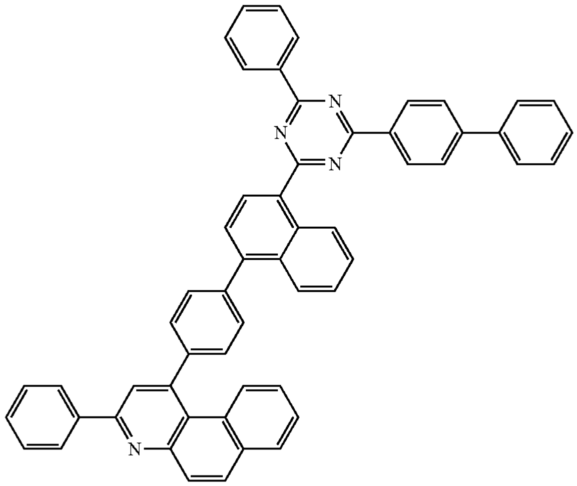
375
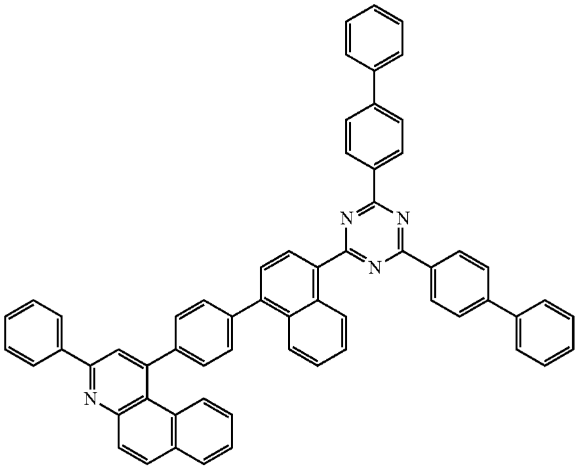

-continued
376
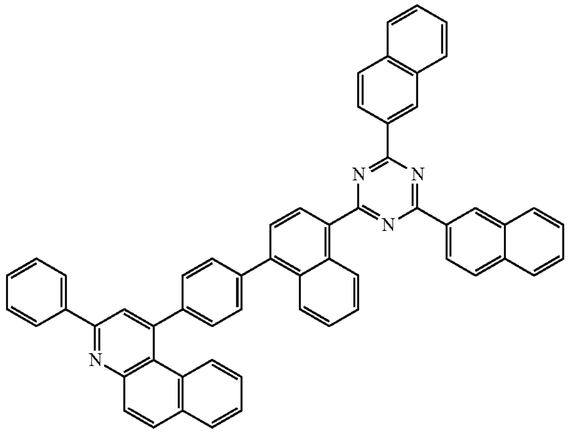
377
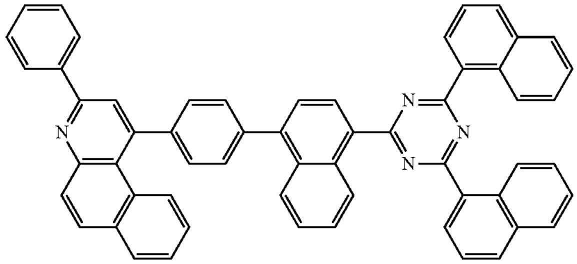
378
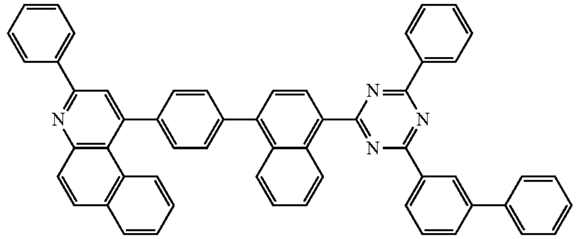
379
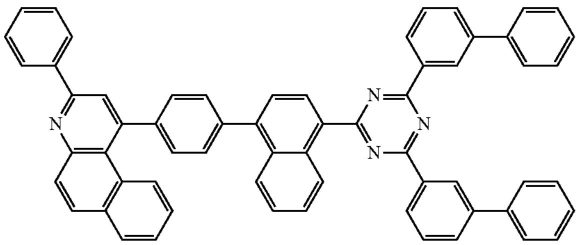
-continued
380
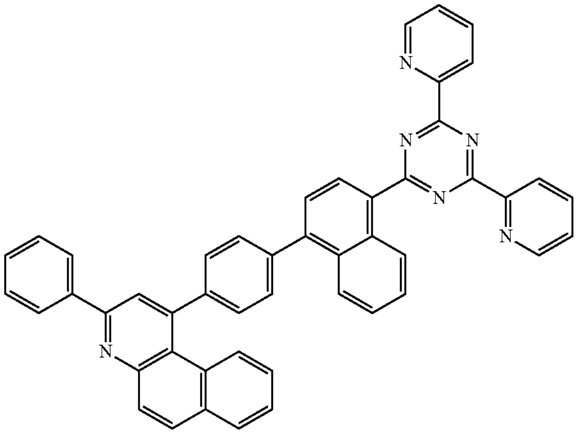
381
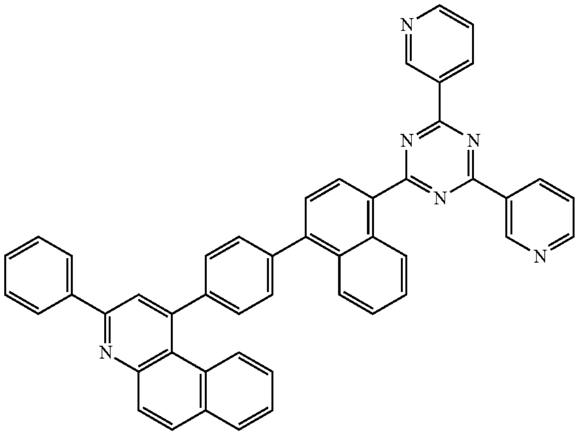
382
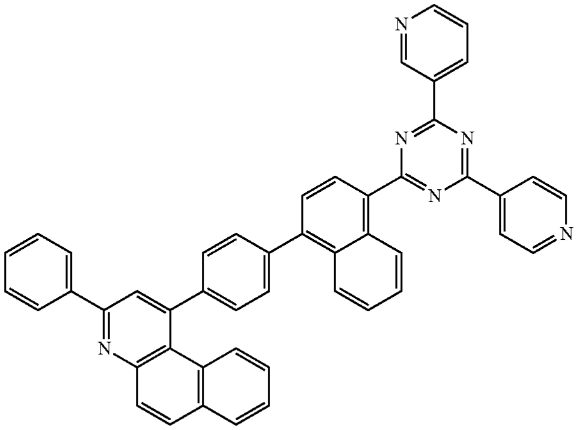

-continued
383
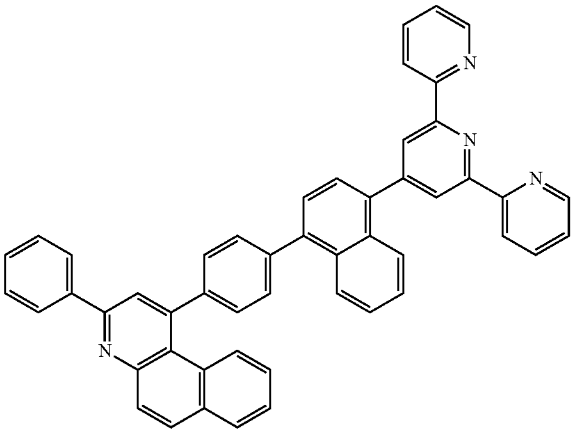
384
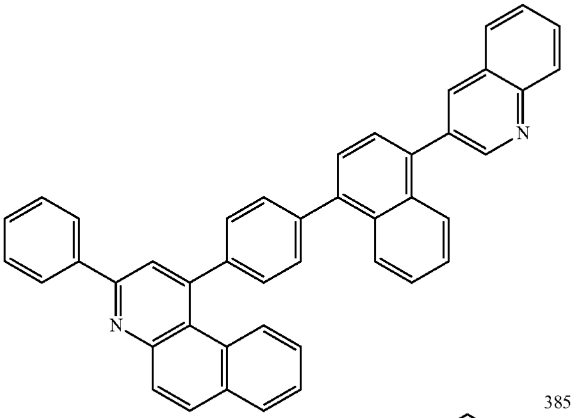
385
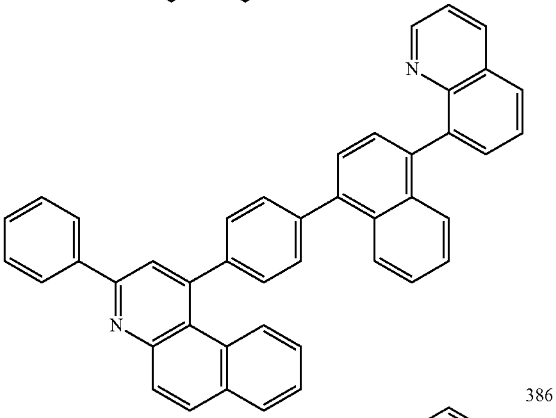
386
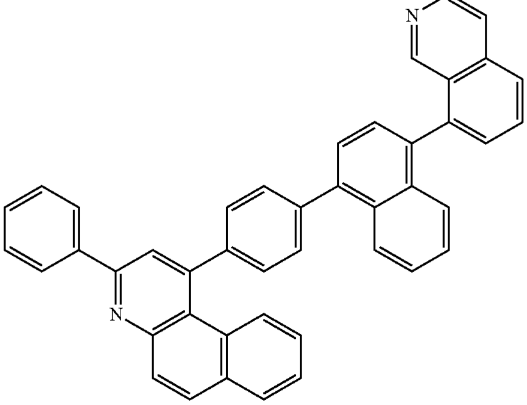
-continued
387
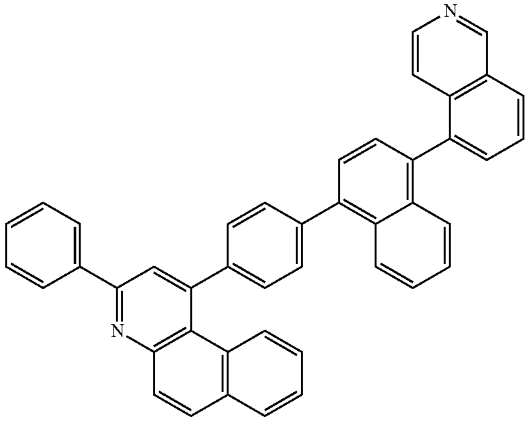
388
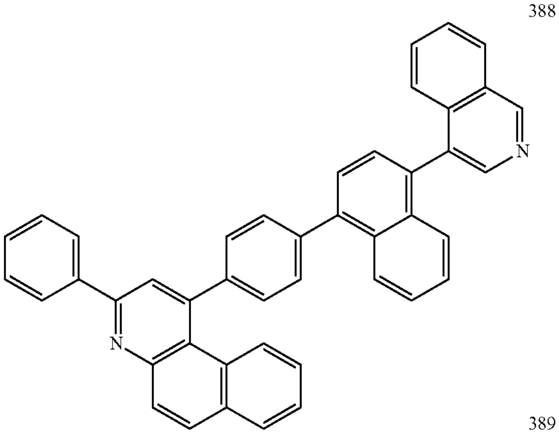
389
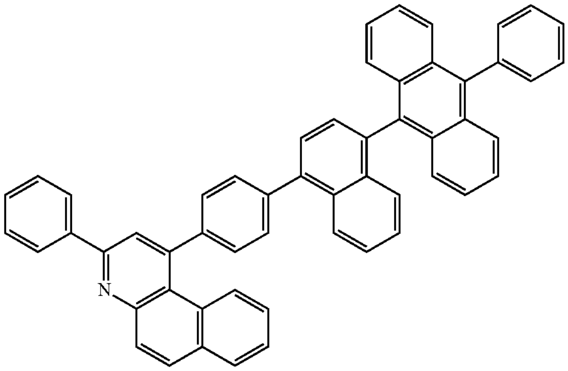
390
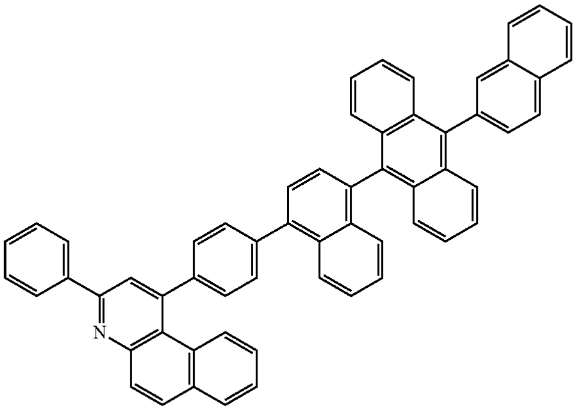

-continued
391
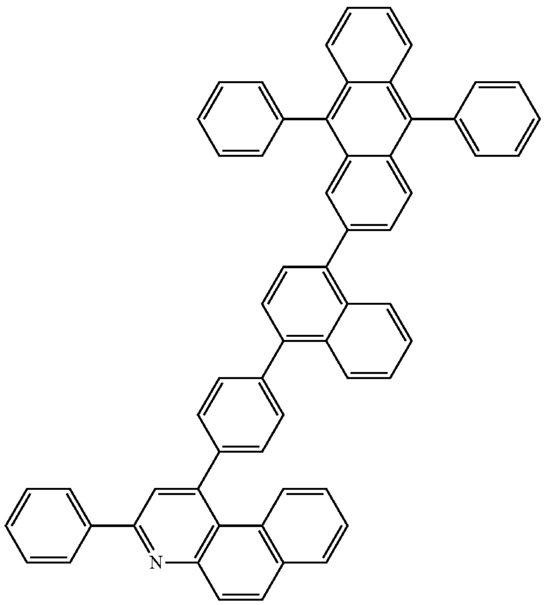
392
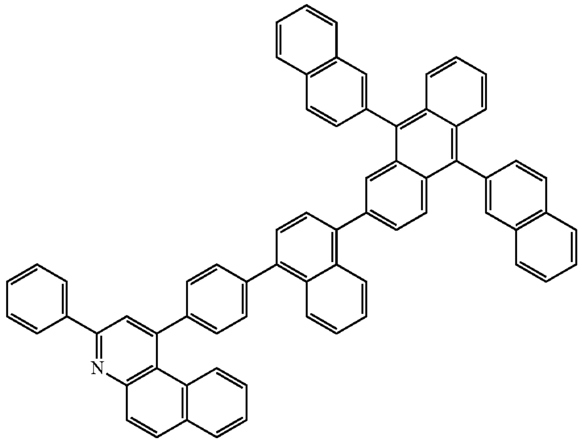
393
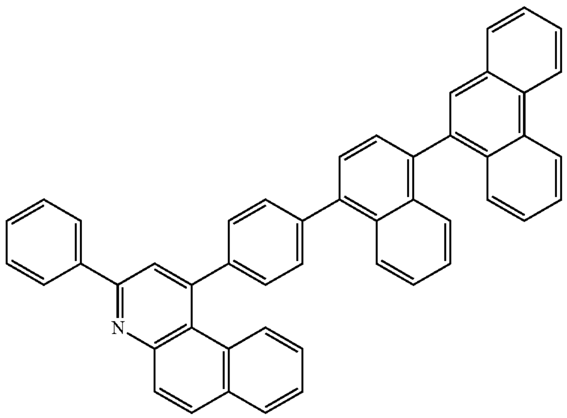
-continued
394
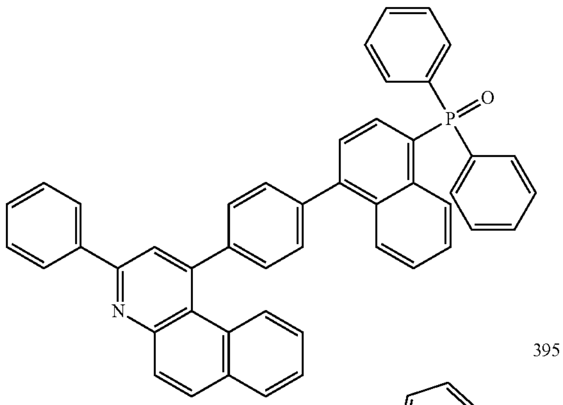
395
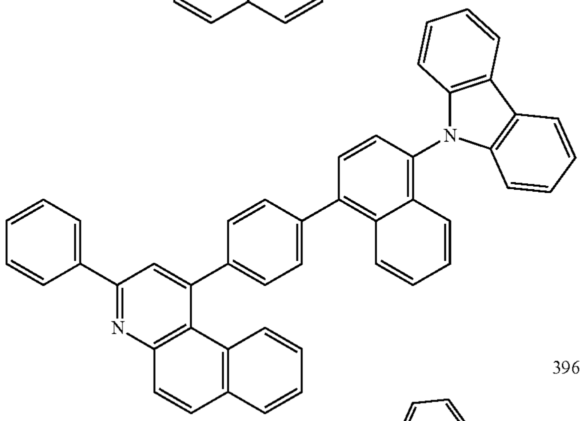
396
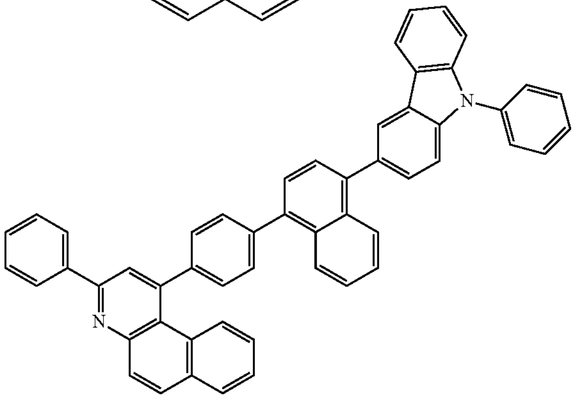
397
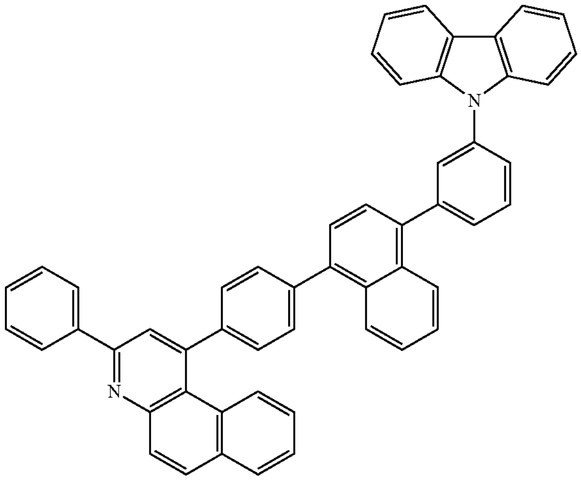

-continued
398
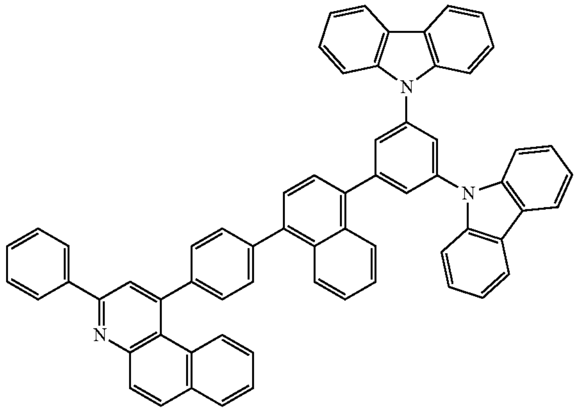
399
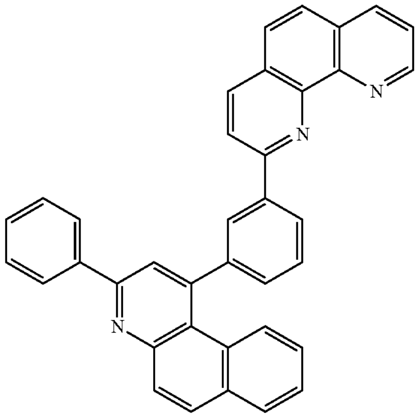
400
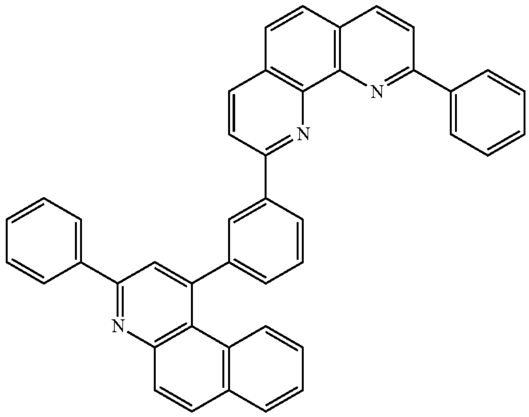
-continued
401
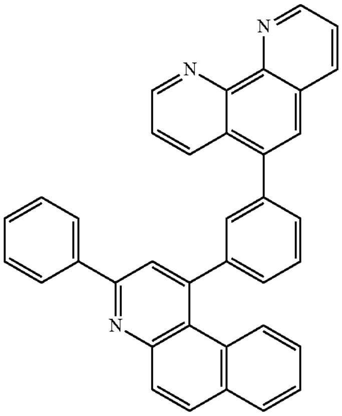
402
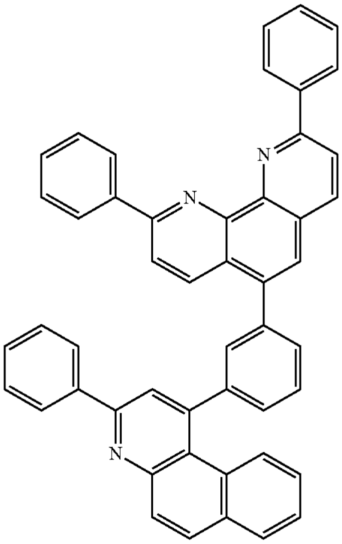
403
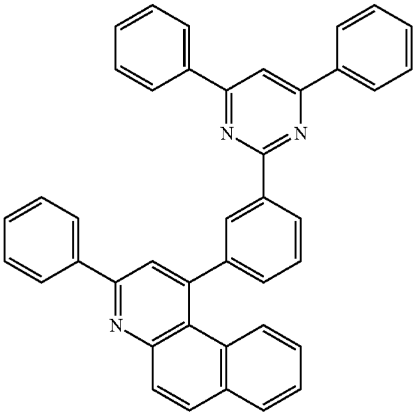

-continued
404
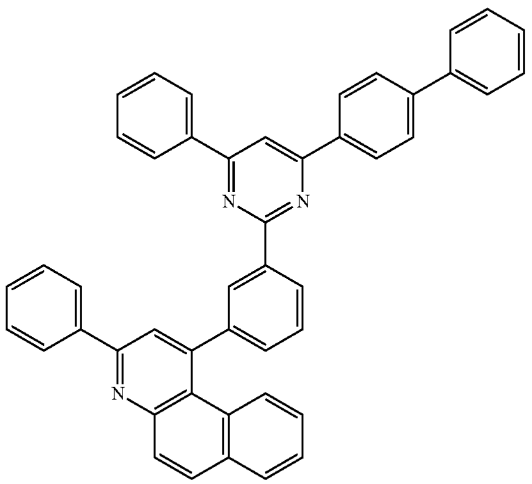
405
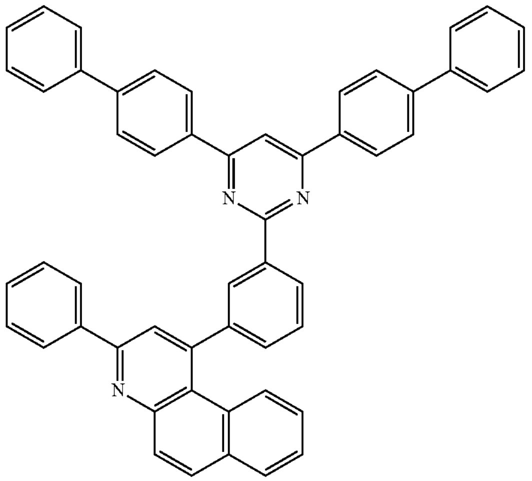
406
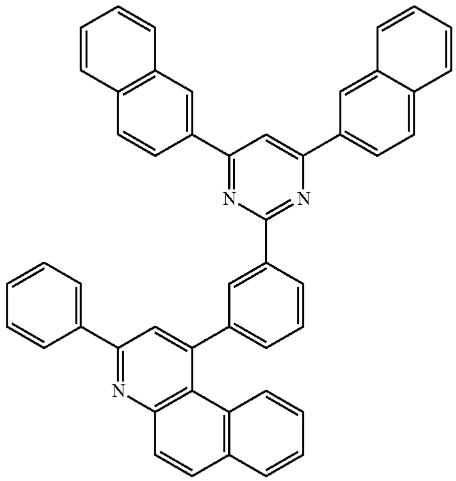
-continued
407
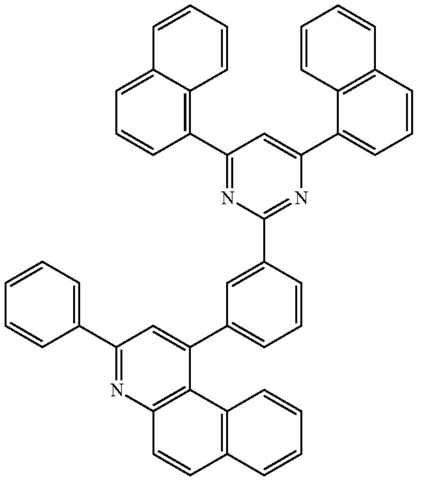
408
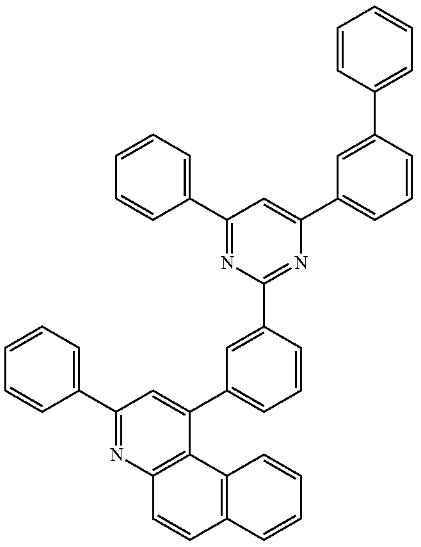
409
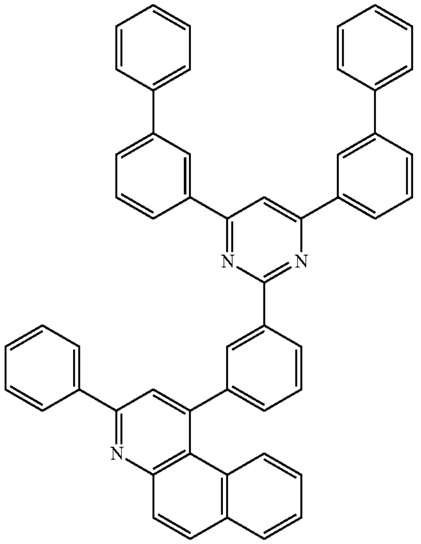

-continued
410
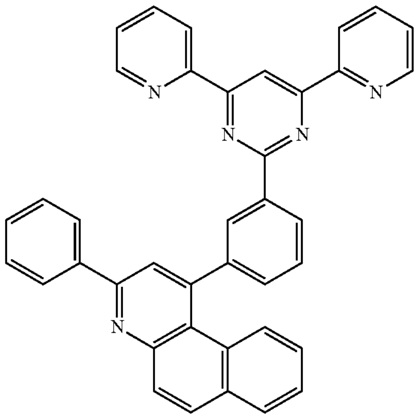
411
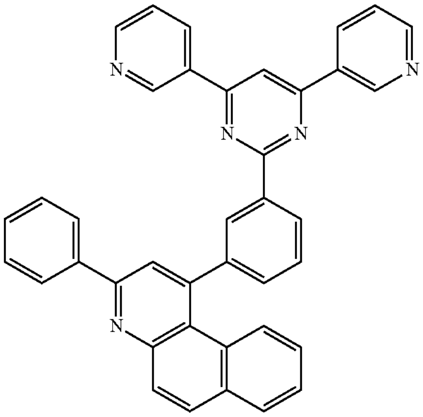
412
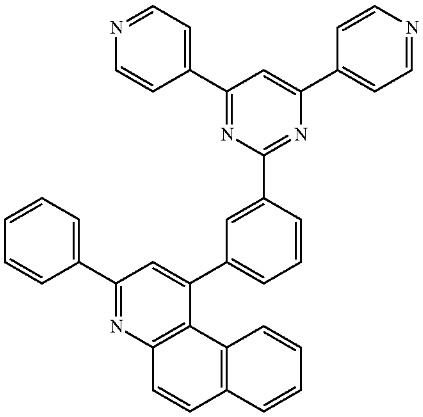
-continued
413
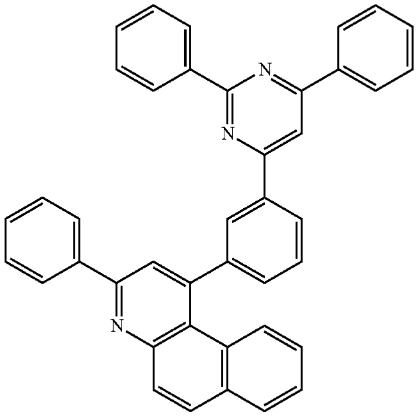
414
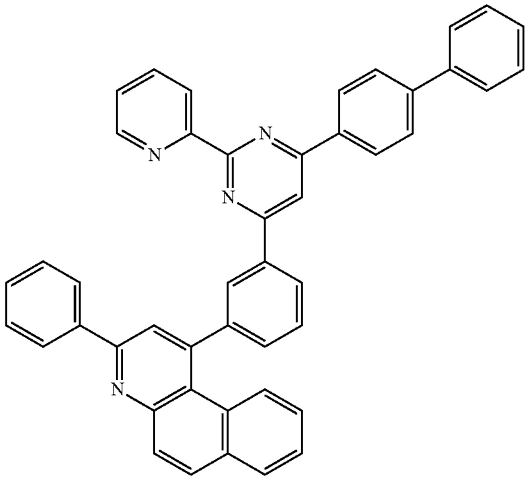
415
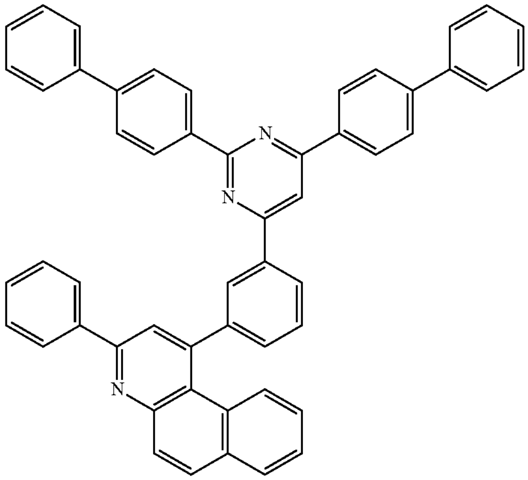

-continued
416
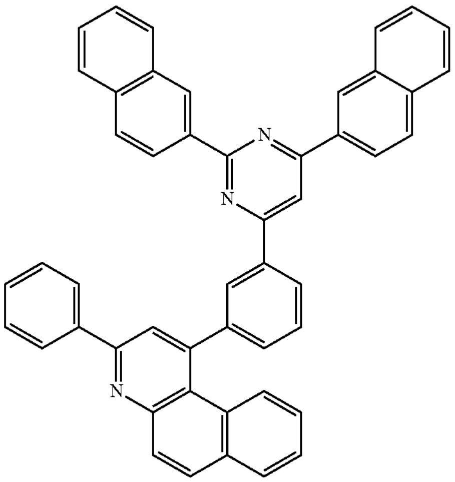
417
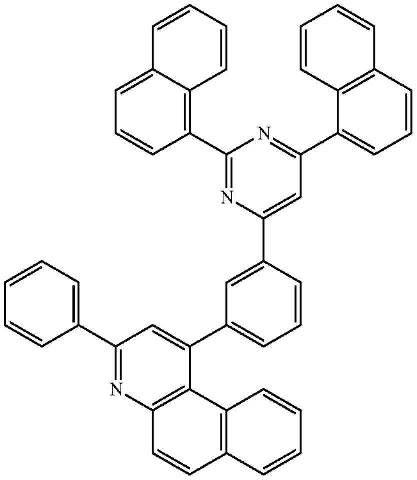
418
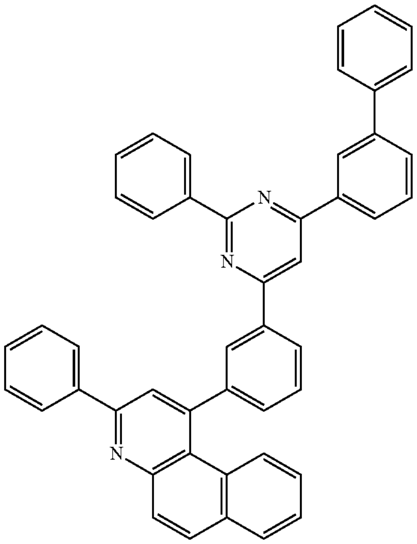
-continued
419
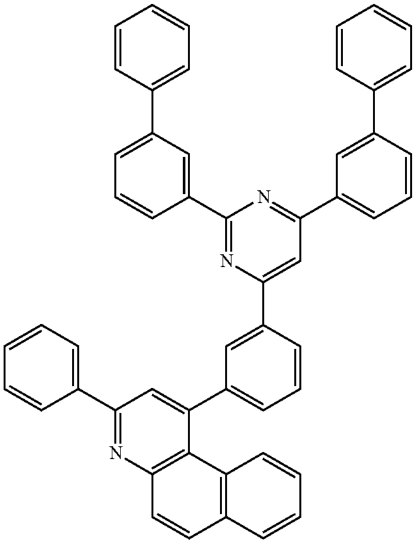
420
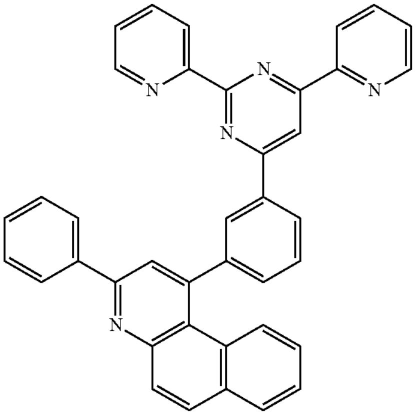
421
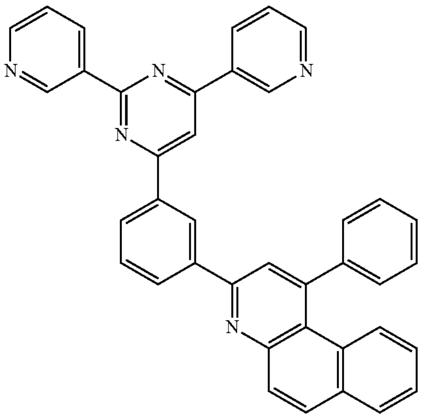

-continued
422
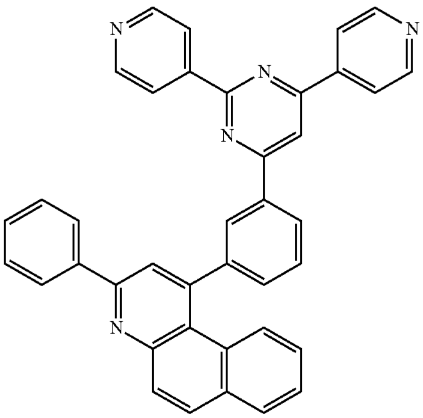
423
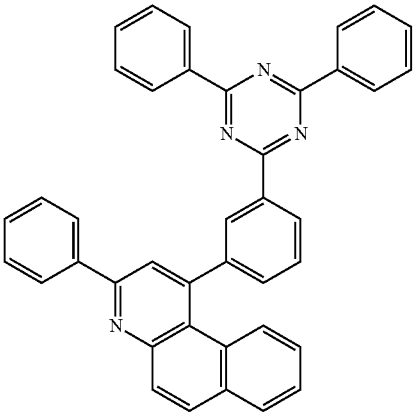
424
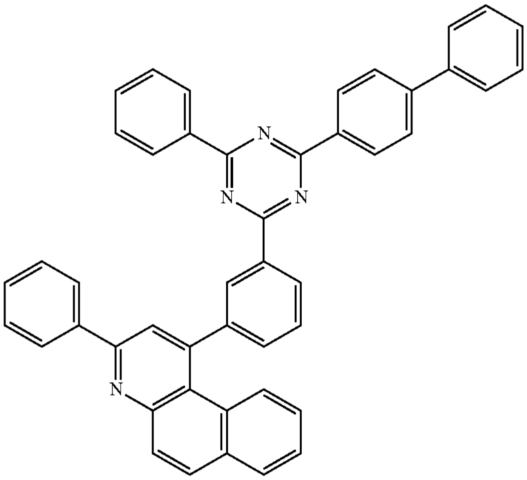
-continued
425
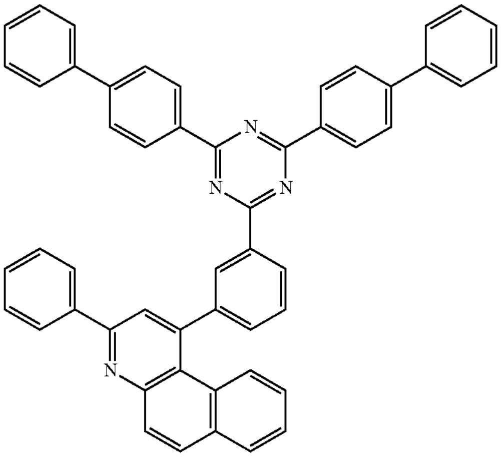
426
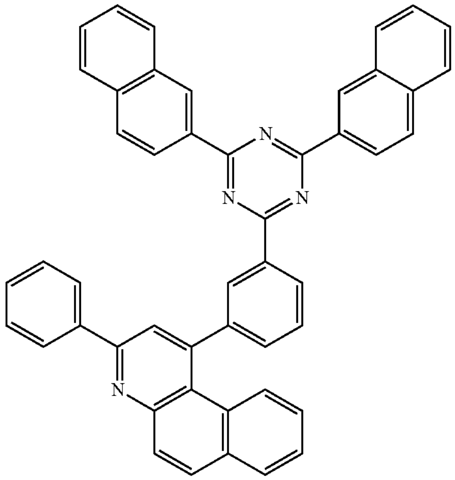
427
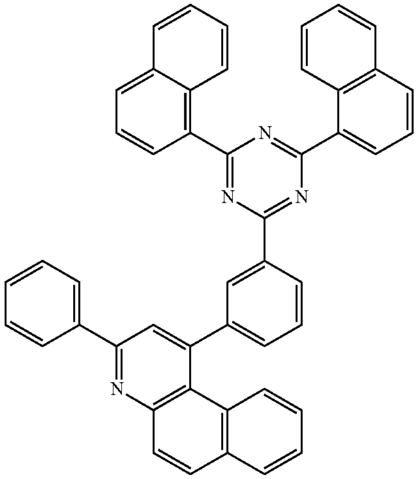

-continued
428
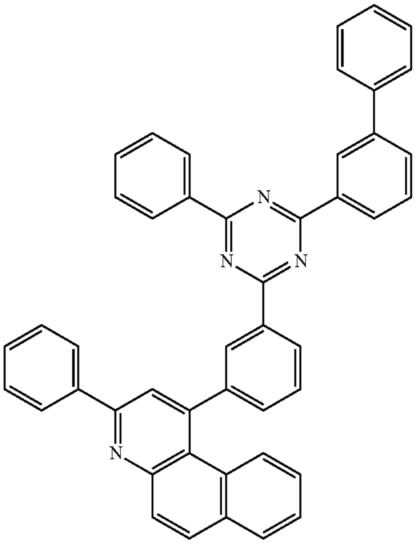
429
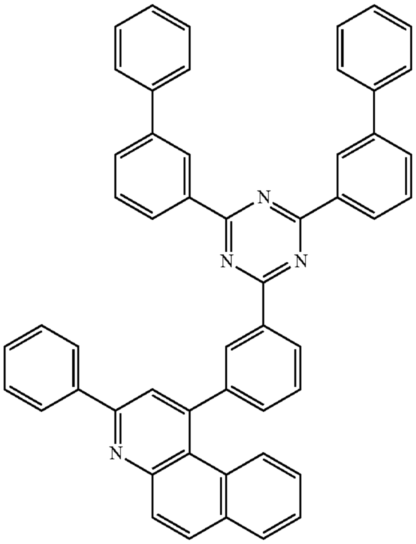
430
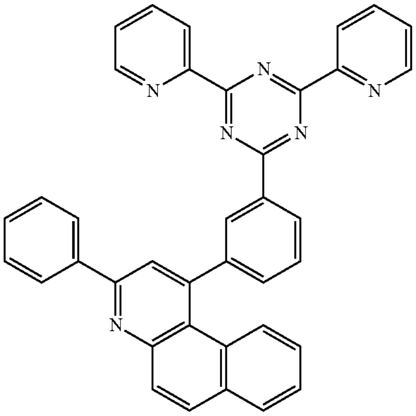
-continued
431
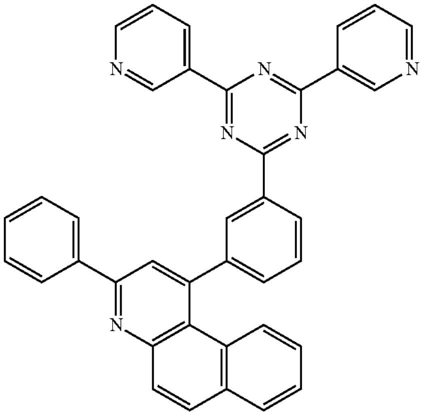
432
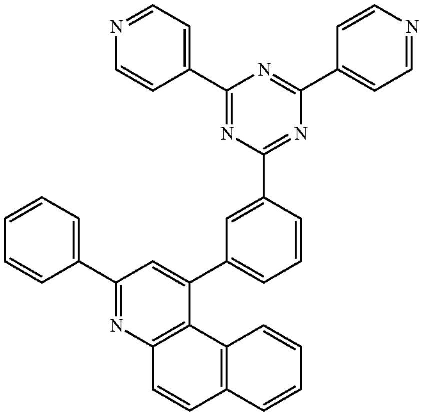
433
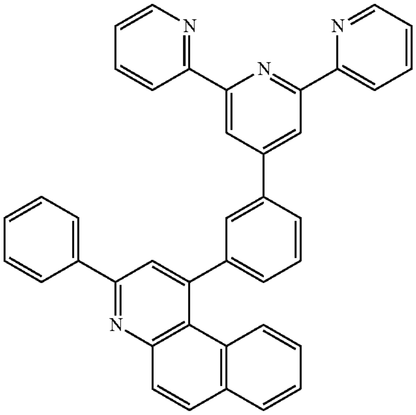

-continued
434
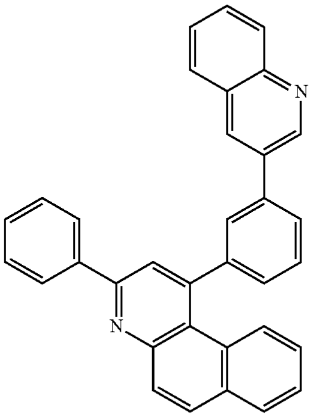
435
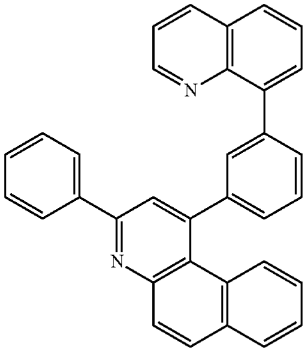
436
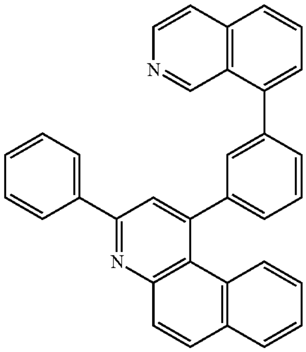
437
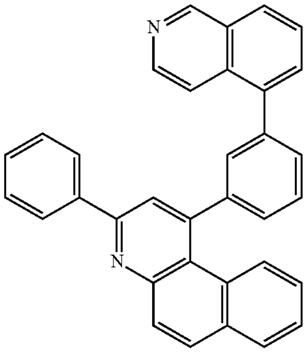
-continued
438
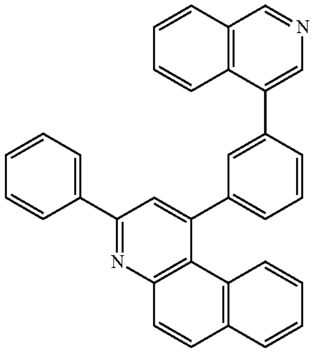
439
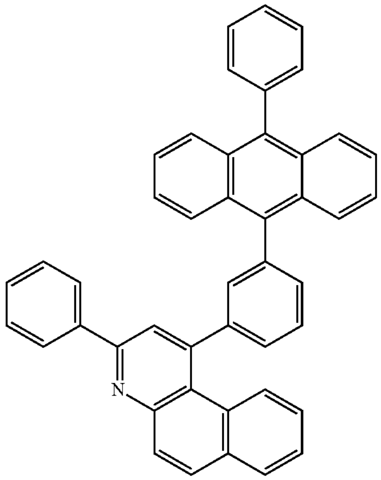
440
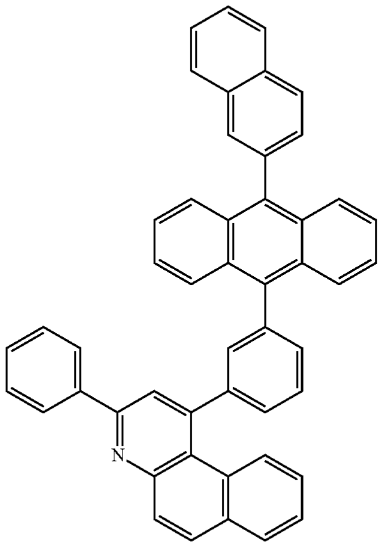

-continued
441
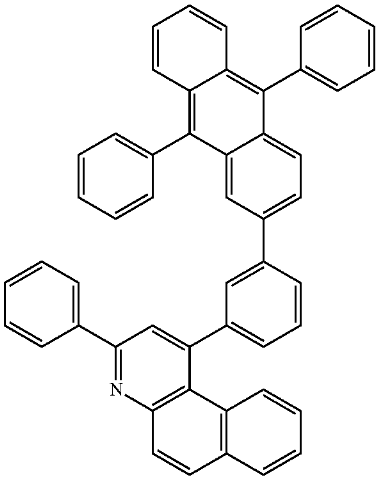
442
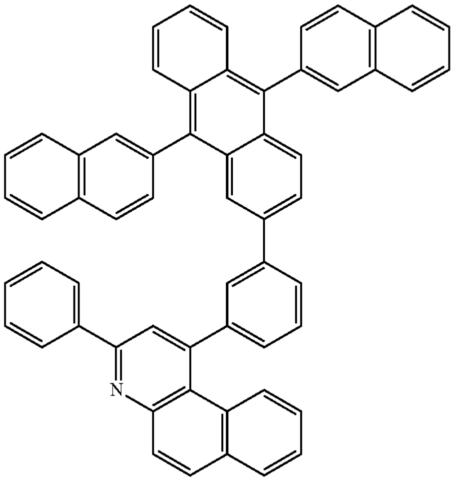
443
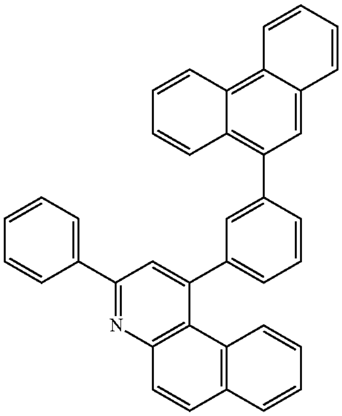
-continued
444
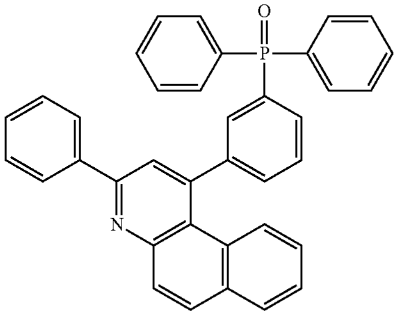
445
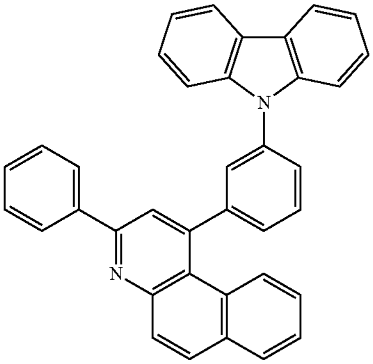
446
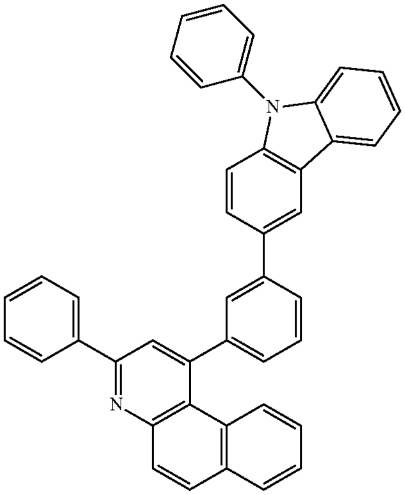

-continued
447
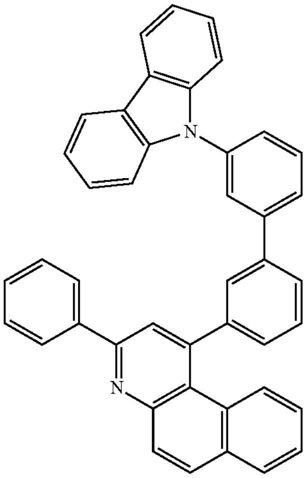
448
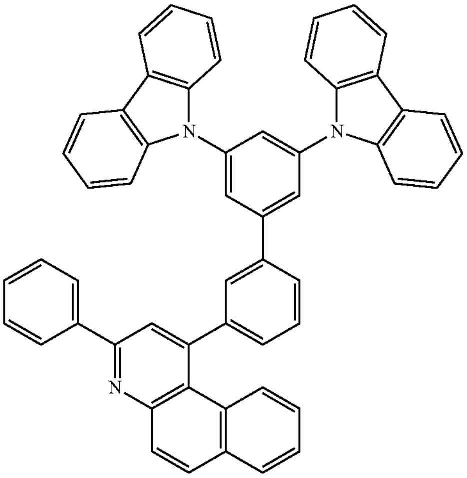
449
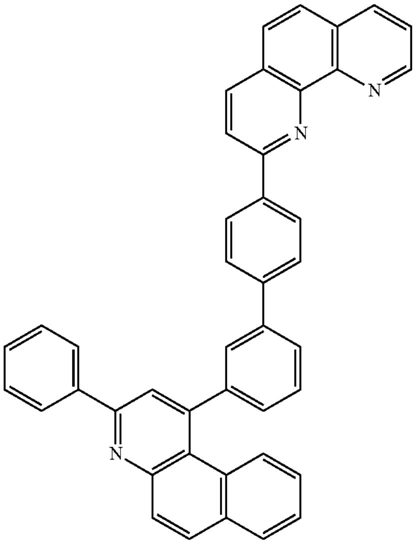
-continued
450
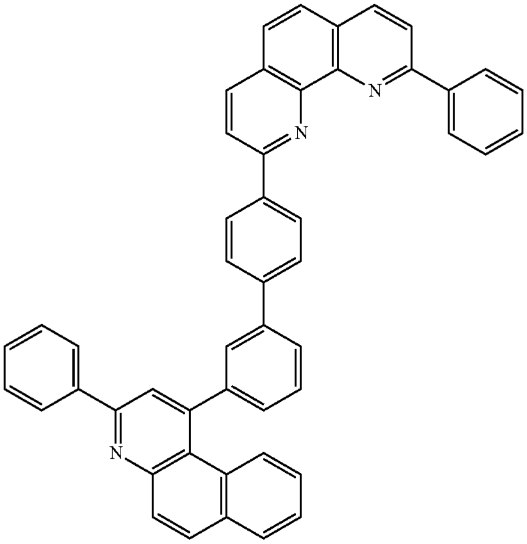
451
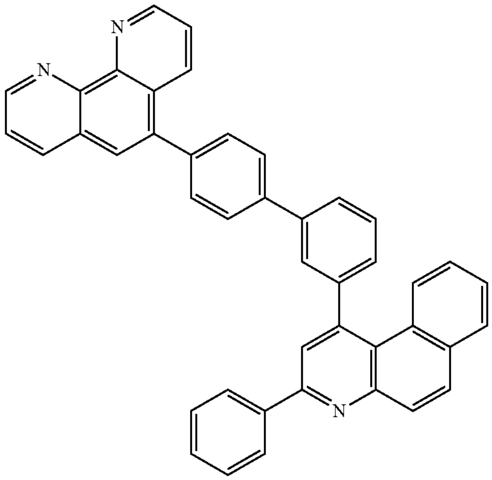
452
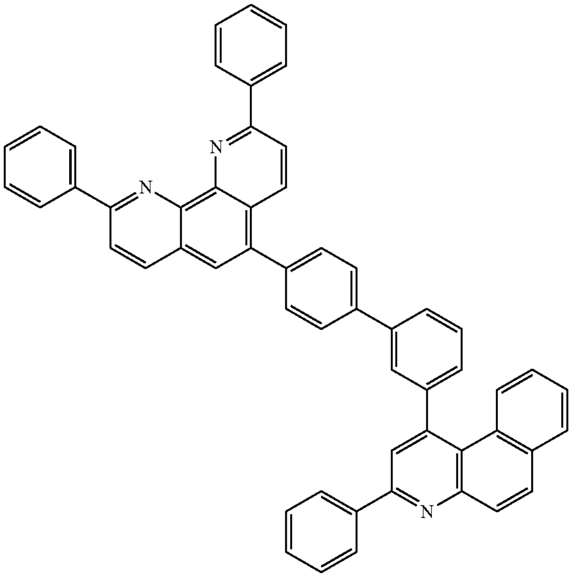

-continued
453
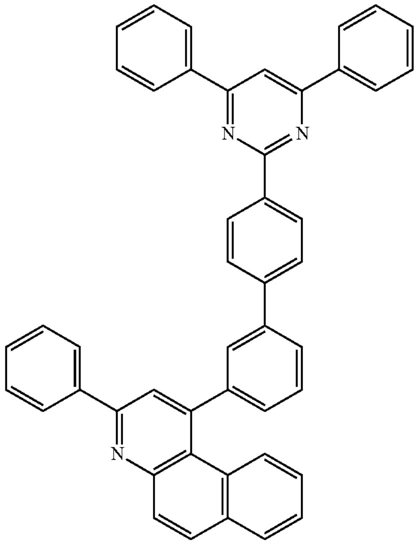
454
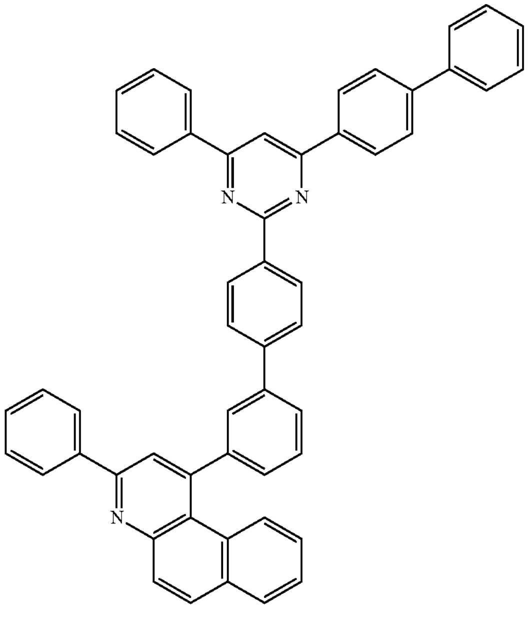
-continued
455
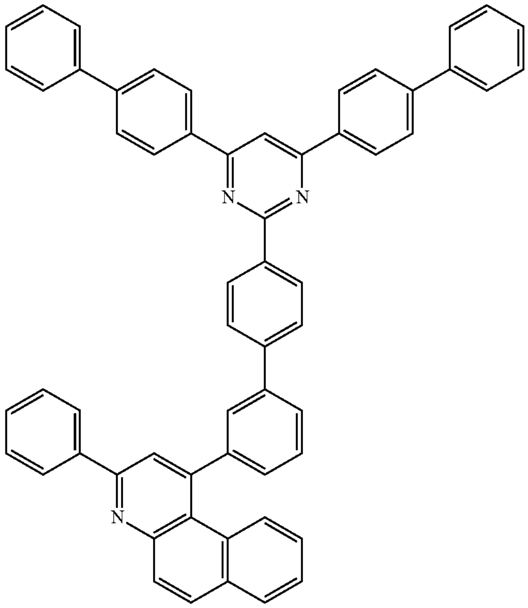
456
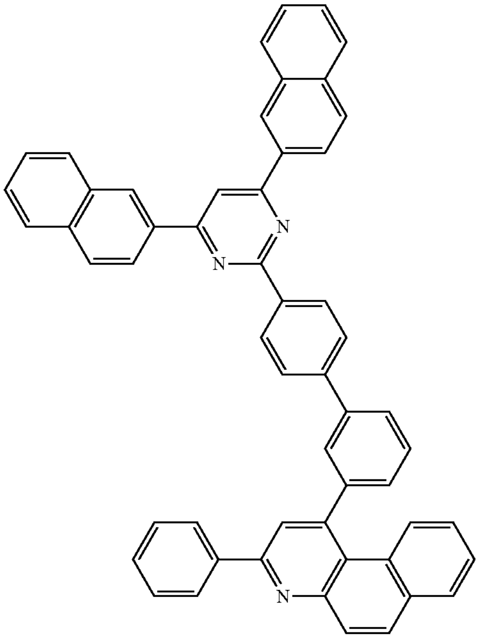

457
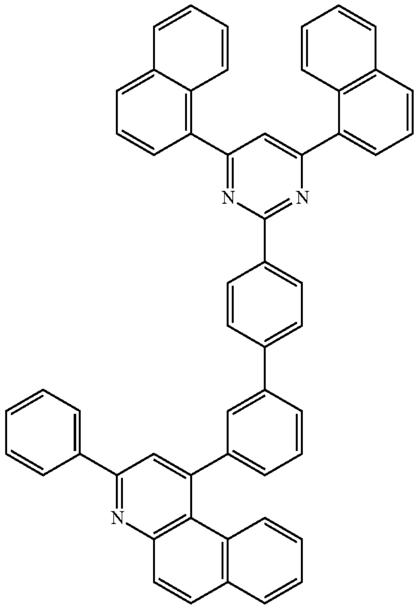
458
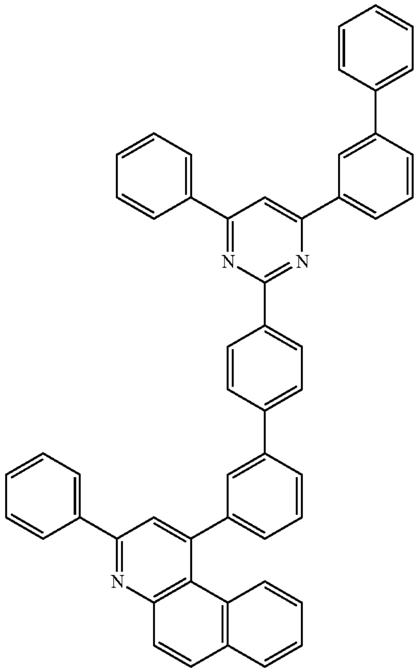
459
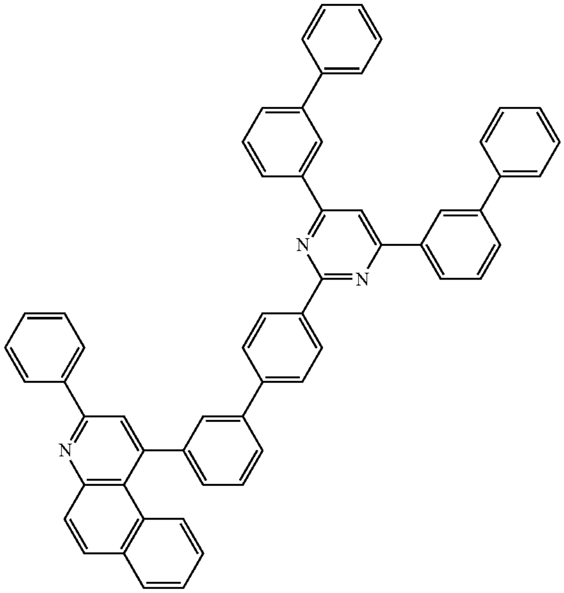
460
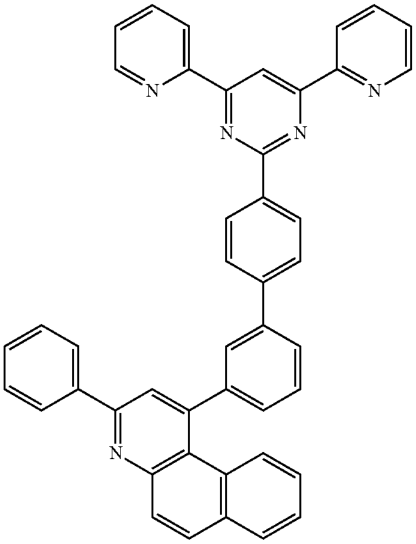

-continued
461
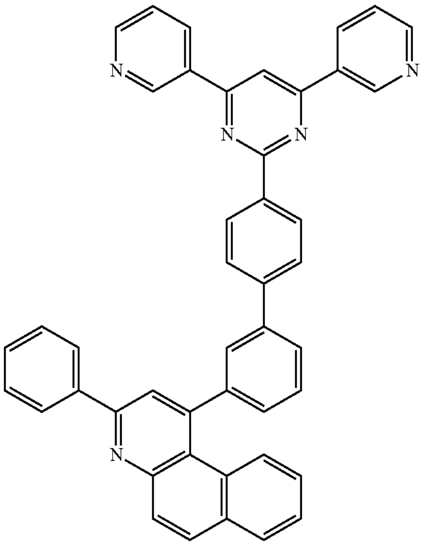
462
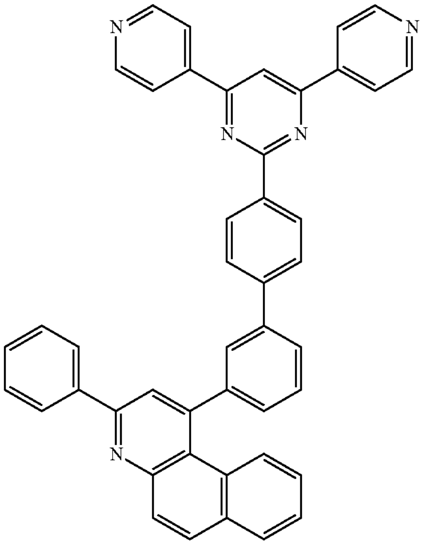
463
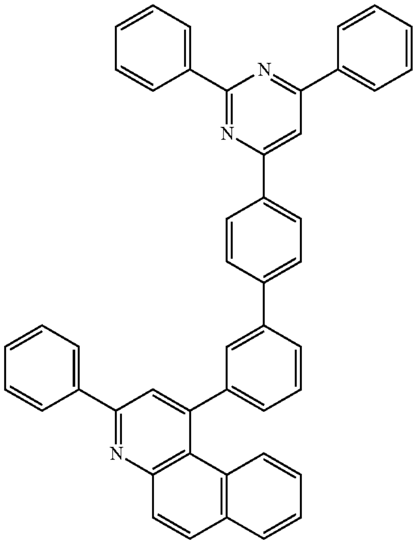
-continued
464
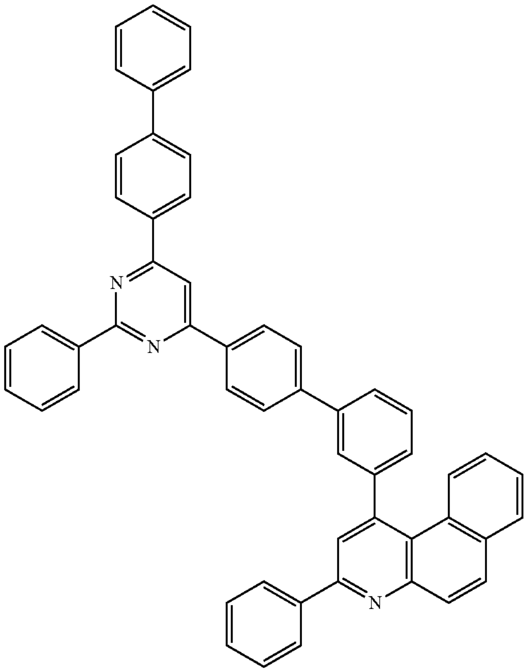
465
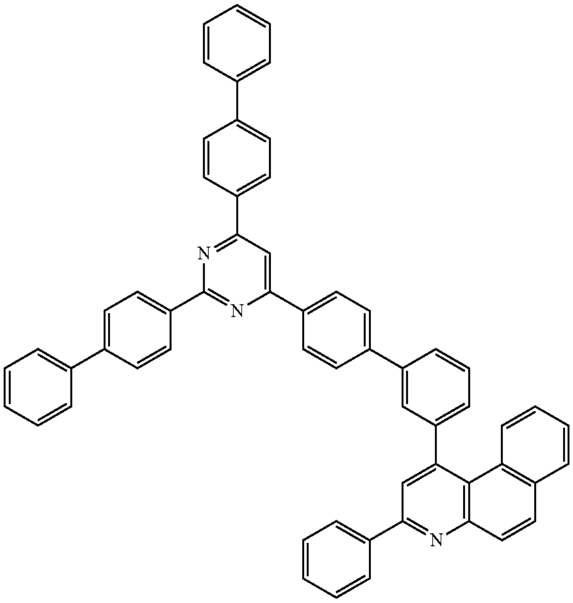

-continued
466
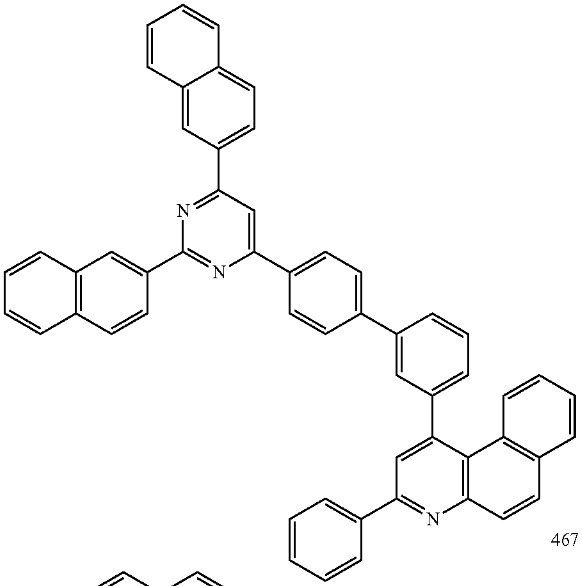
467
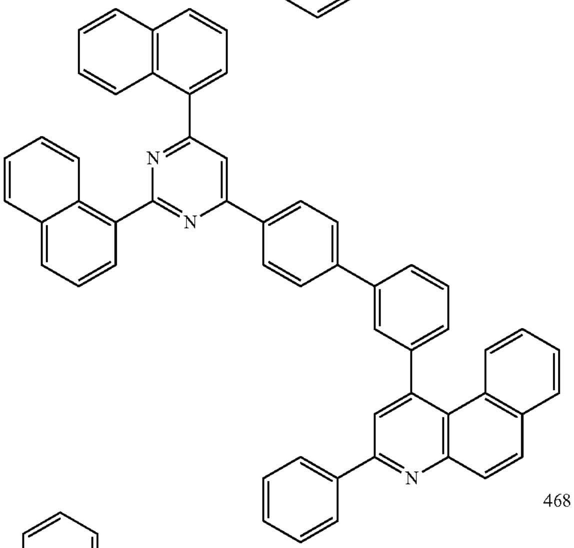
468
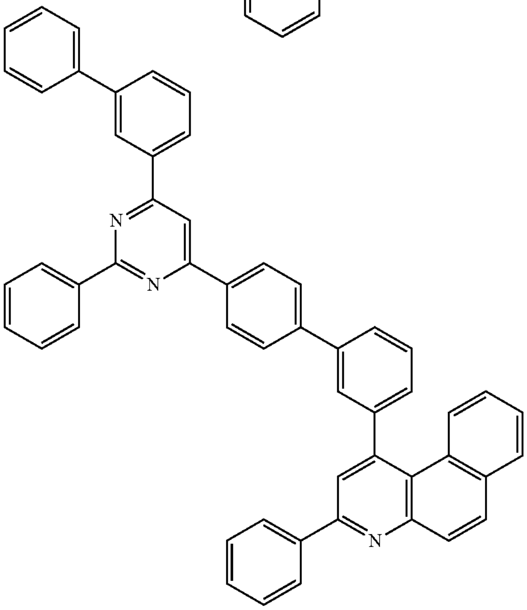
-continued
469
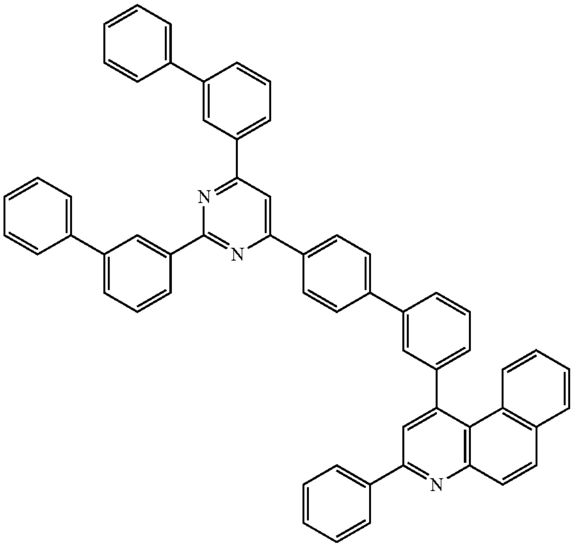
470
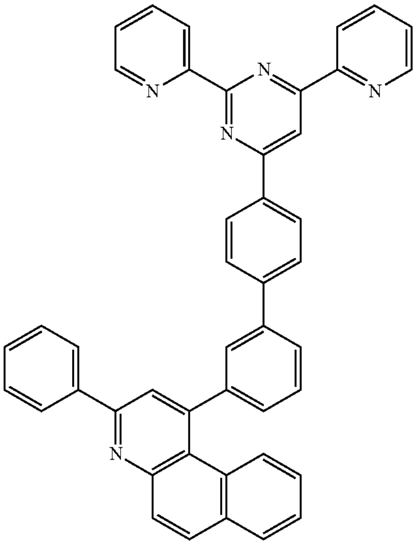
471
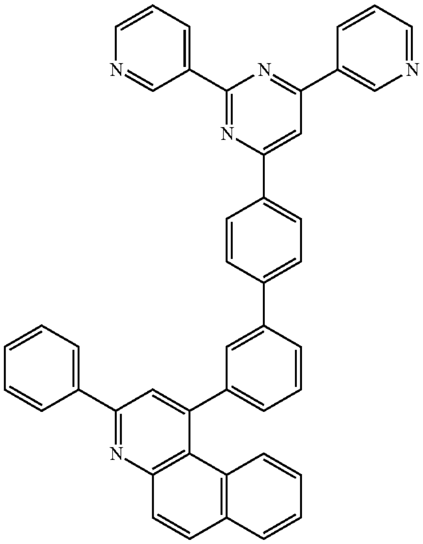

-continued
472
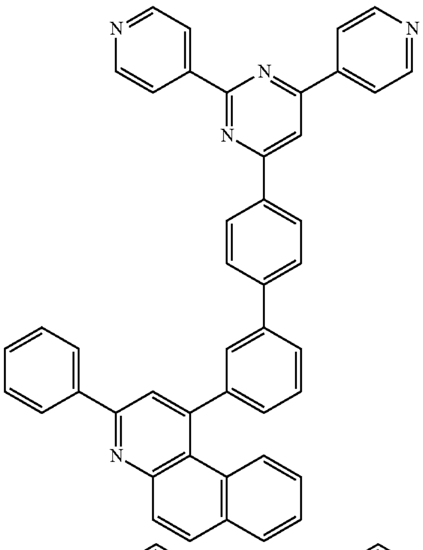
473
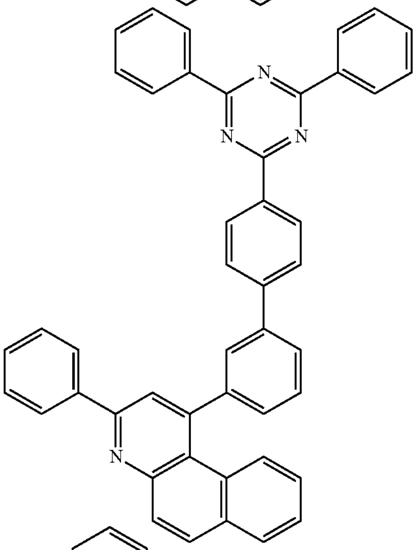
474
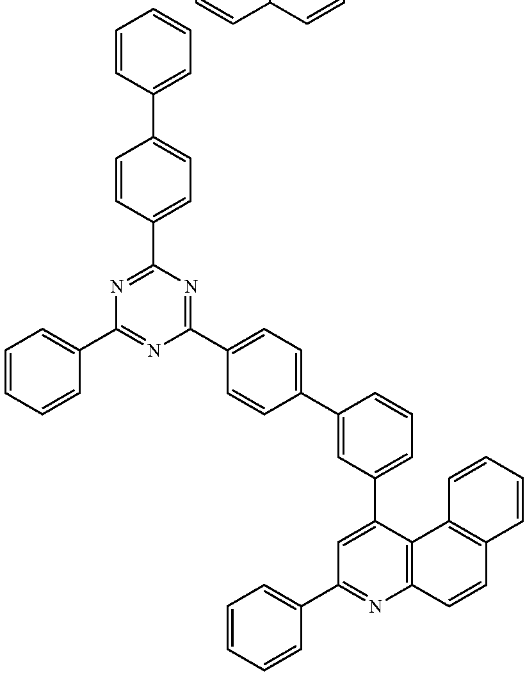
-continued
475
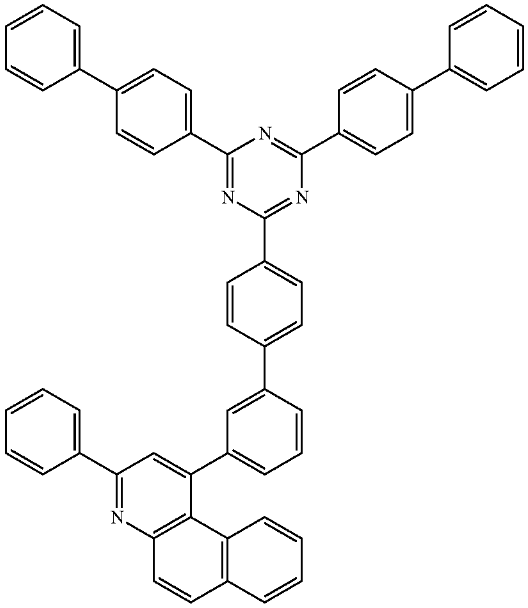
476
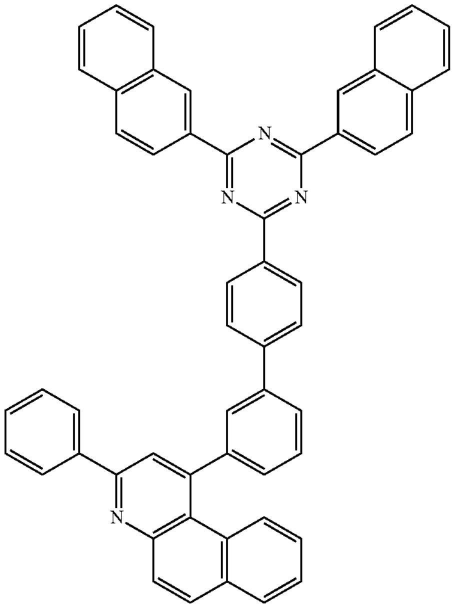

-continued
477
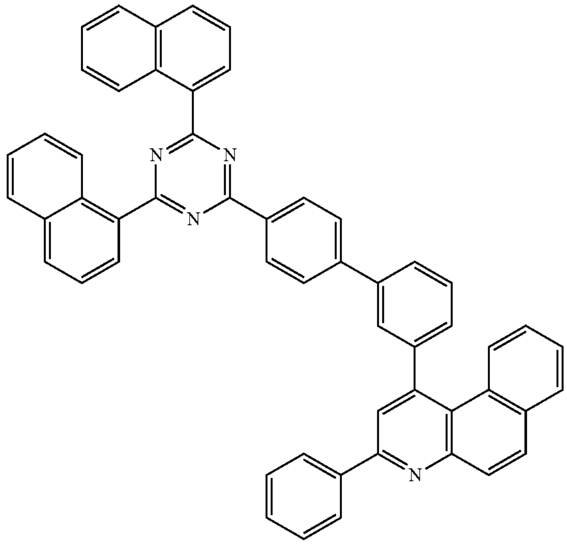
478
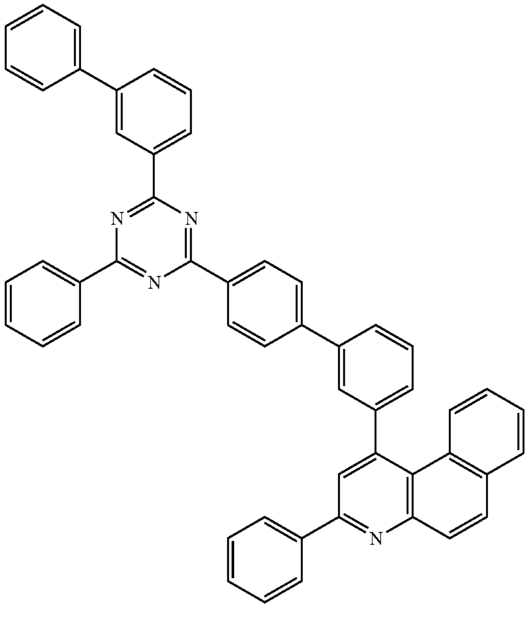
-continued
479
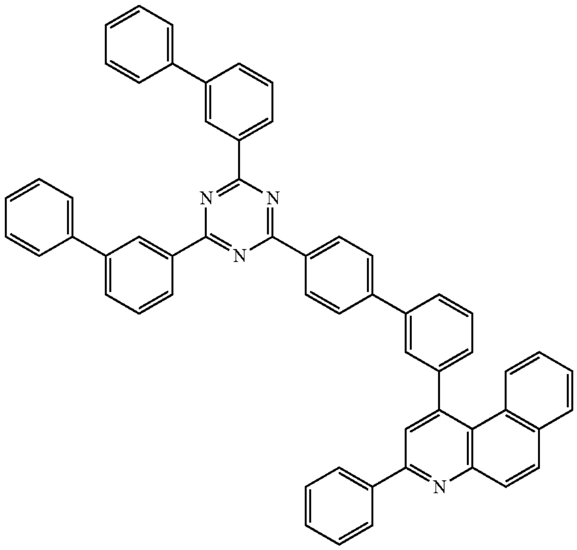
480
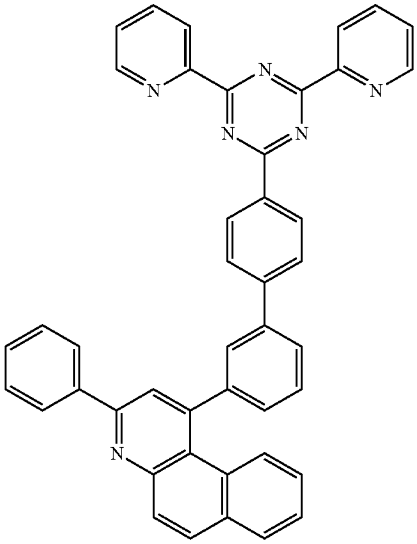
481
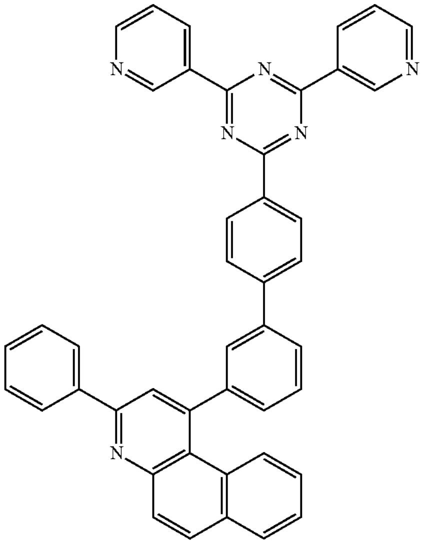

-continued
482
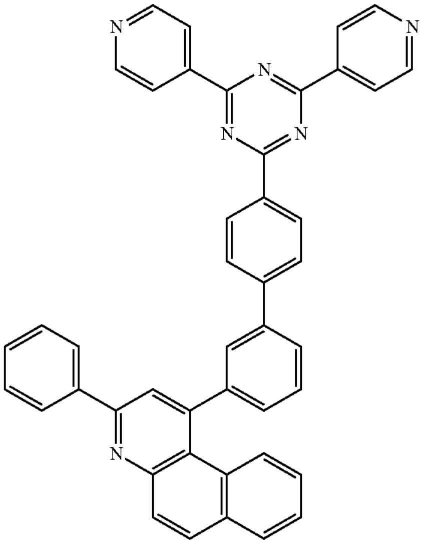
483
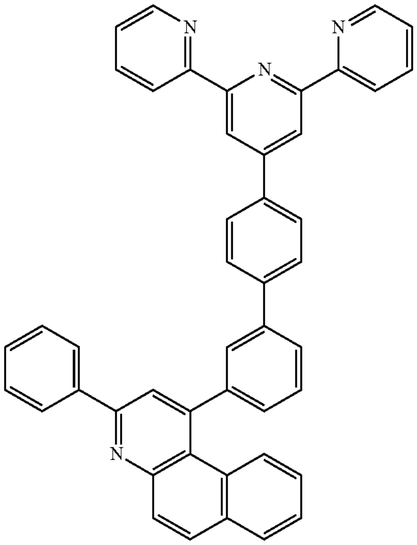
484
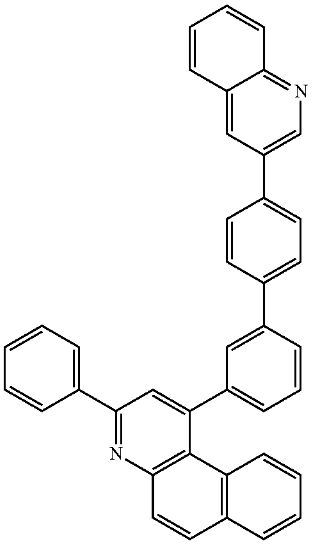
-continued
485
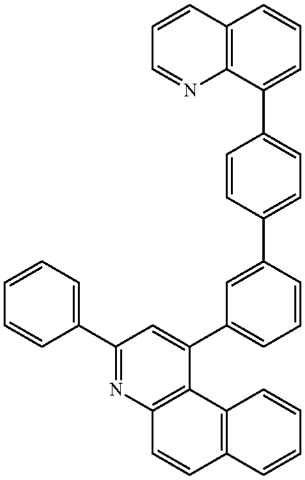
486
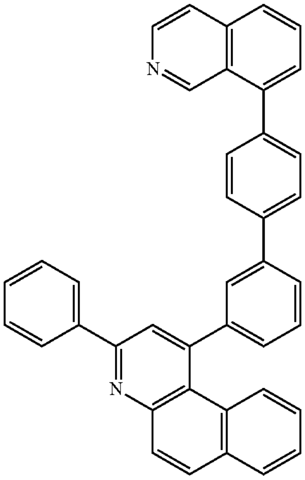
487
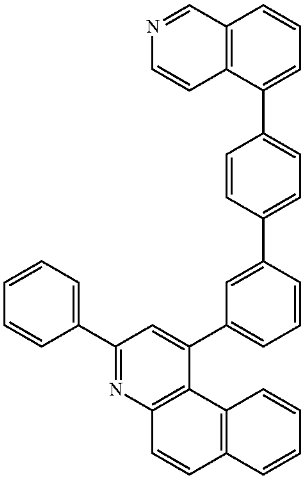

-continued
488
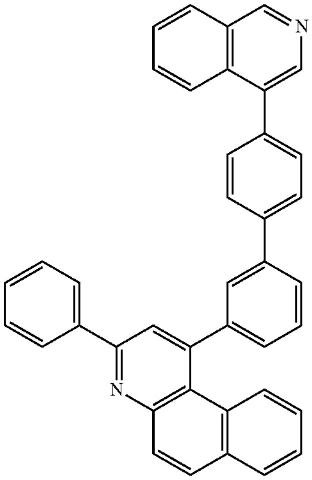
489
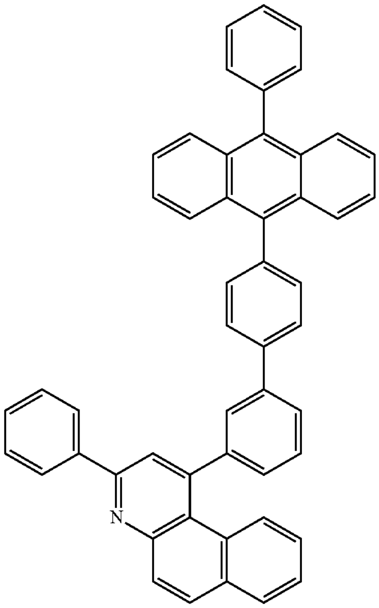
490
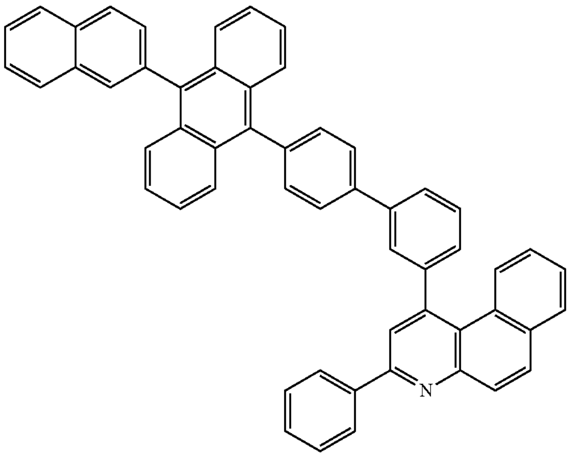
-continued
491
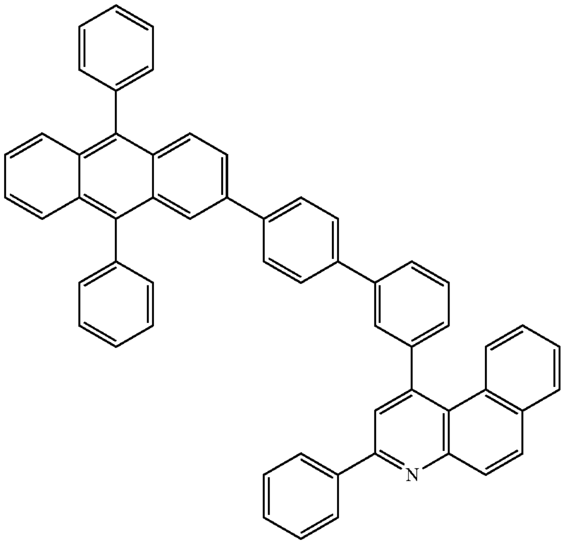
492
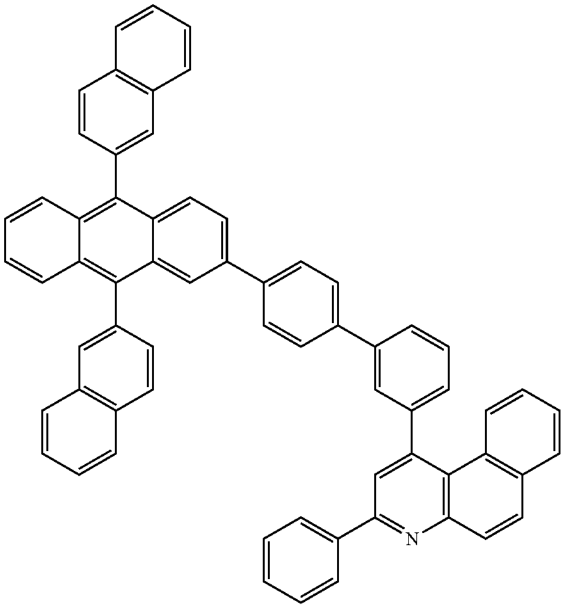

-continued
493
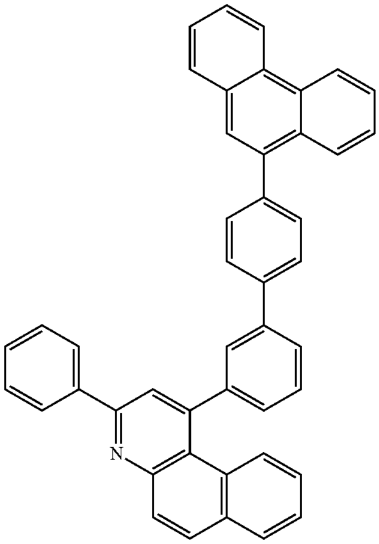
494
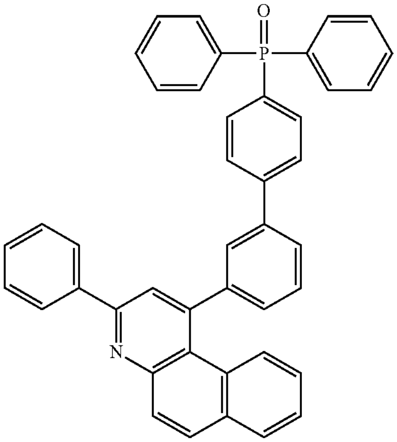
495
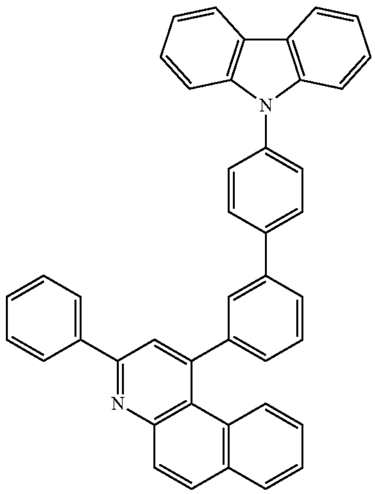
-continued
496
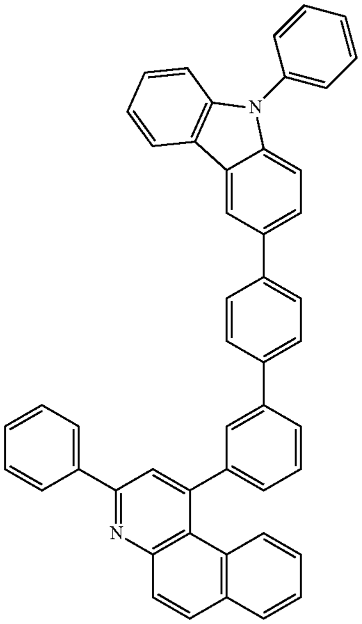
497
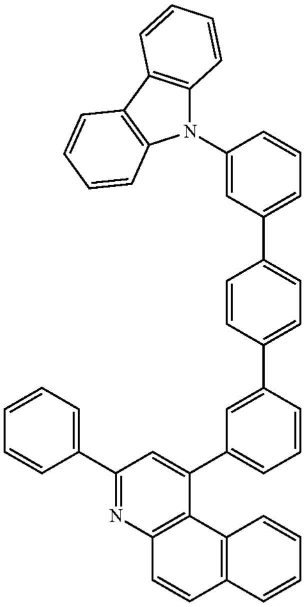

-continued
498
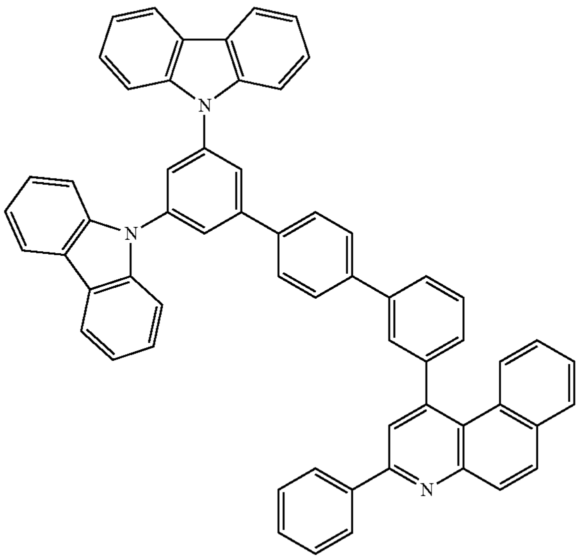
499
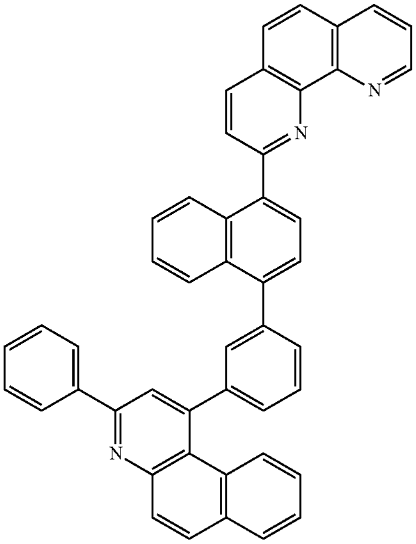
-continued
500
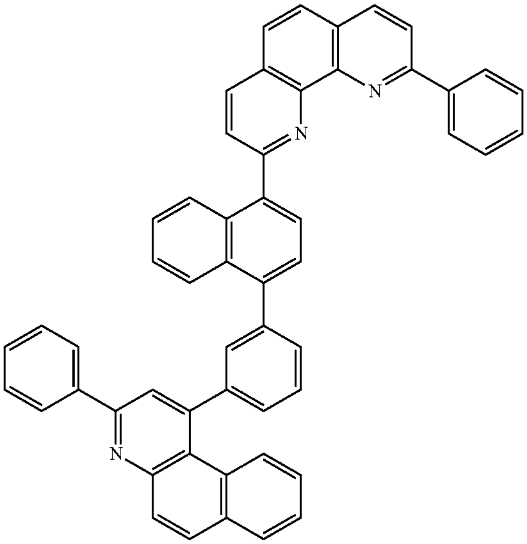
501
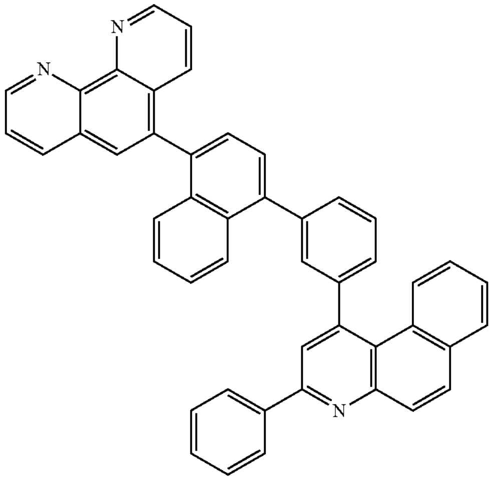
502
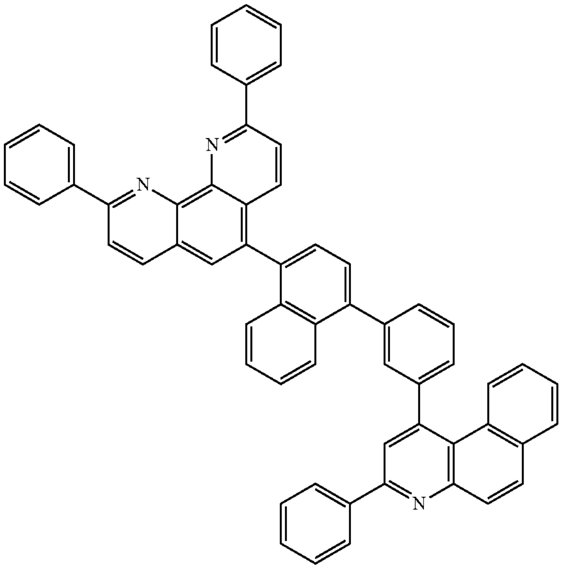

-continued
503
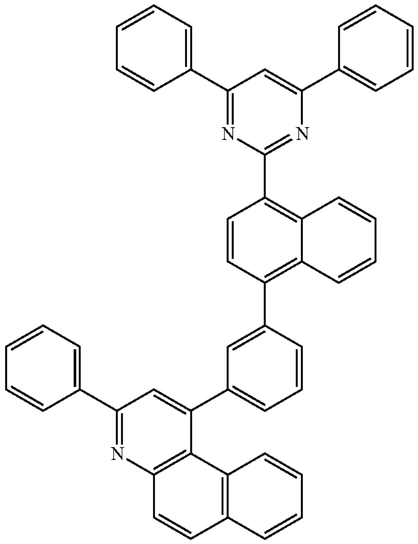
504
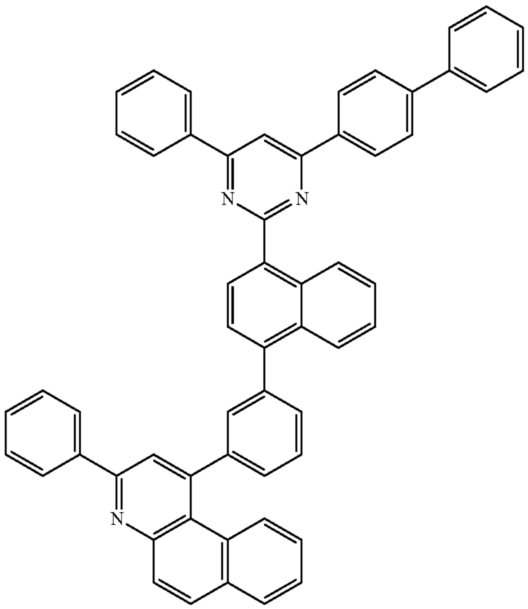
-continued
505
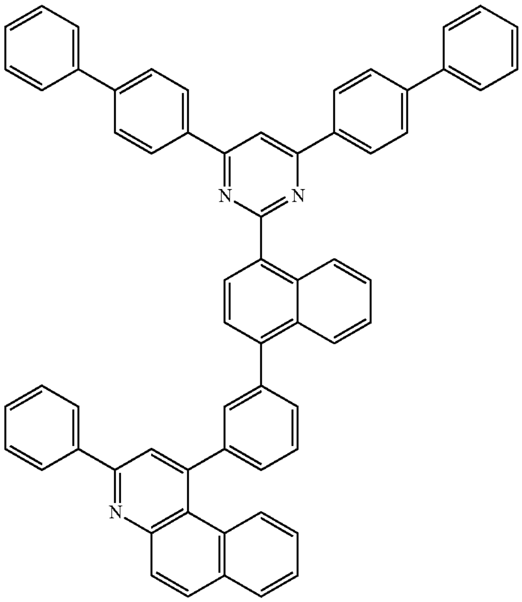
506
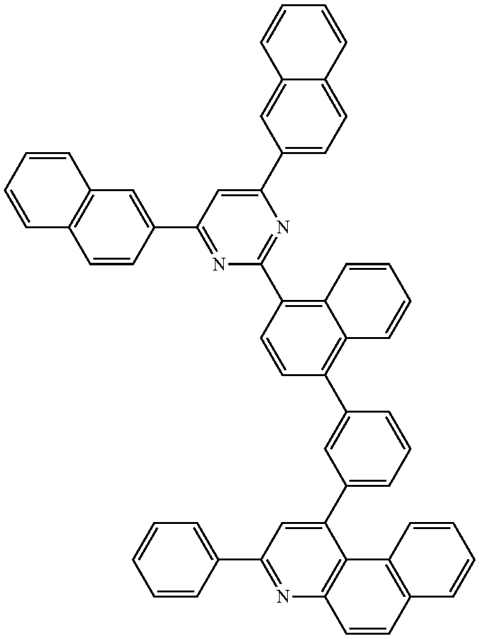

-continued
507
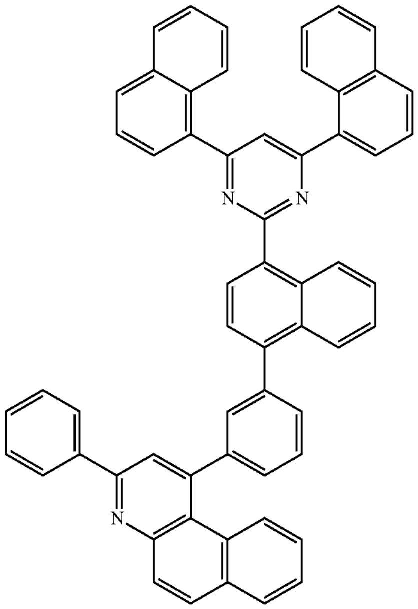
508
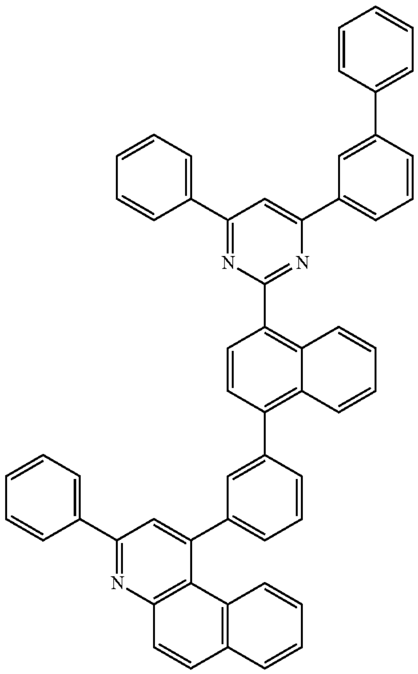
-continued
509
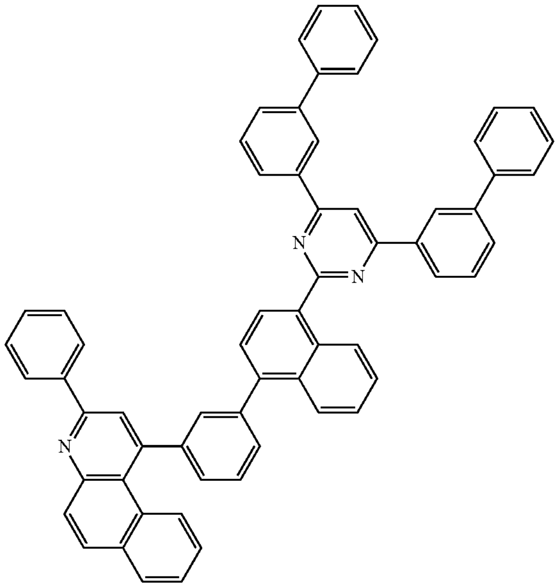
510
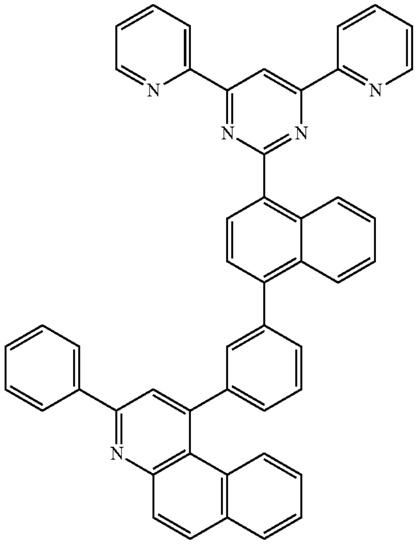

-continued
511
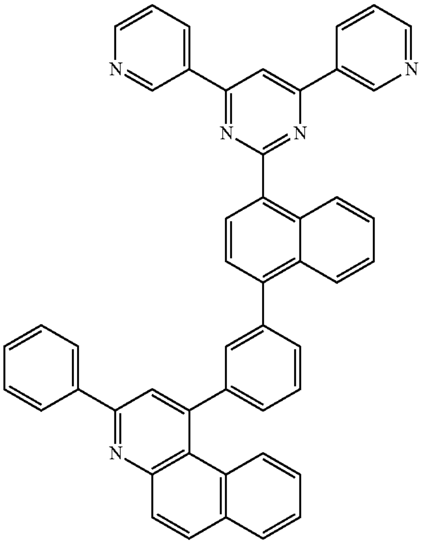
512
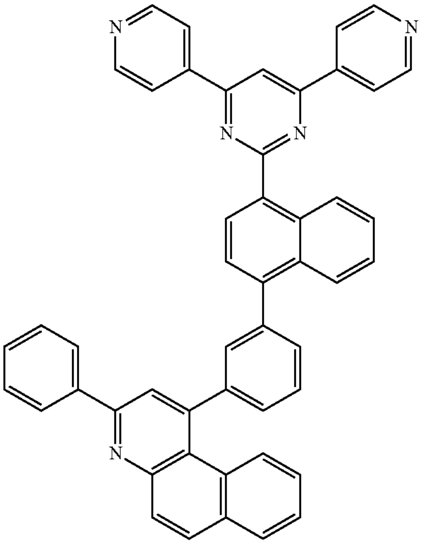
513
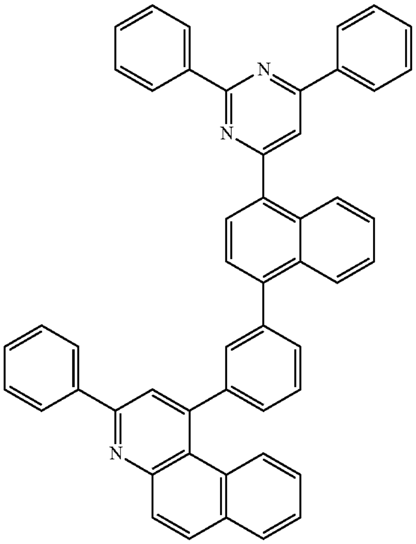
-continued
514
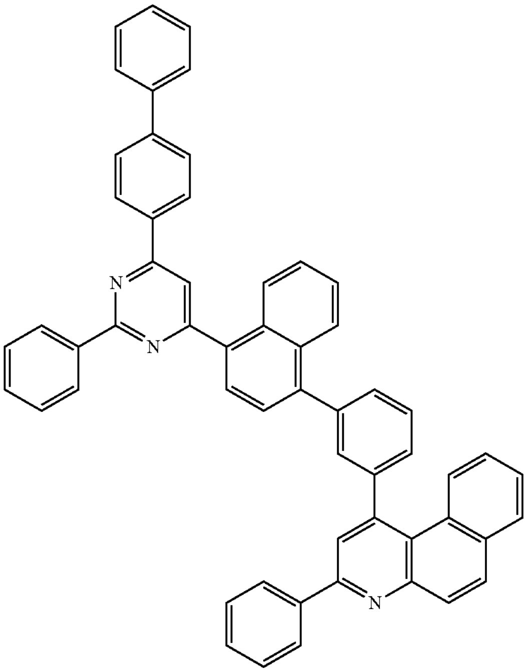
515
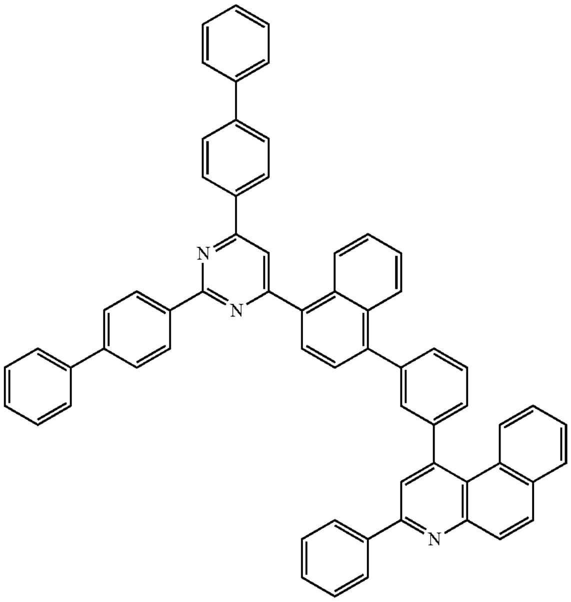

-continued
516
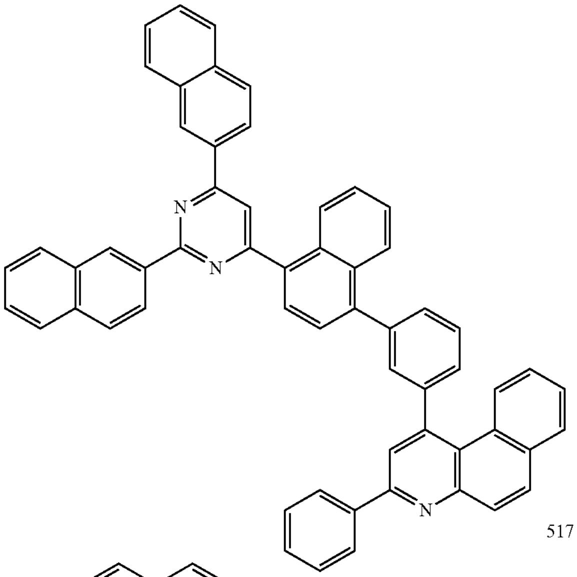
517
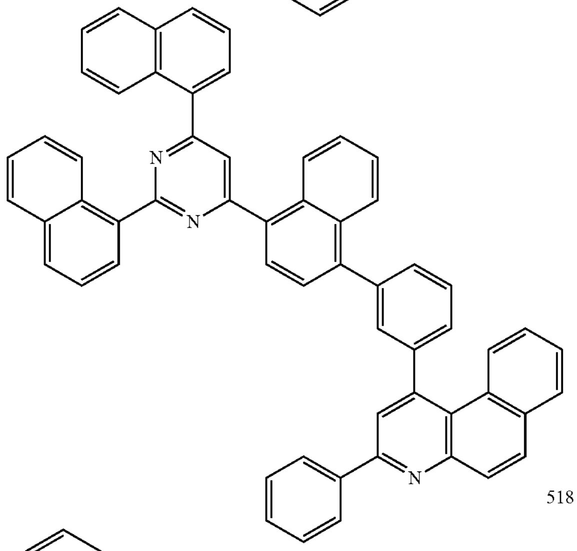
518
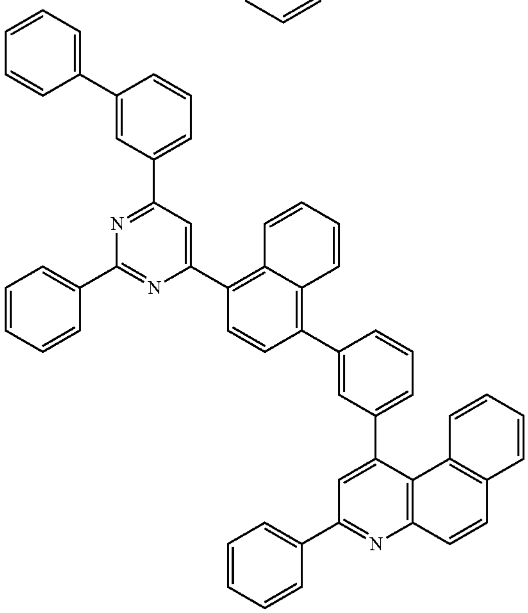
-continued
519
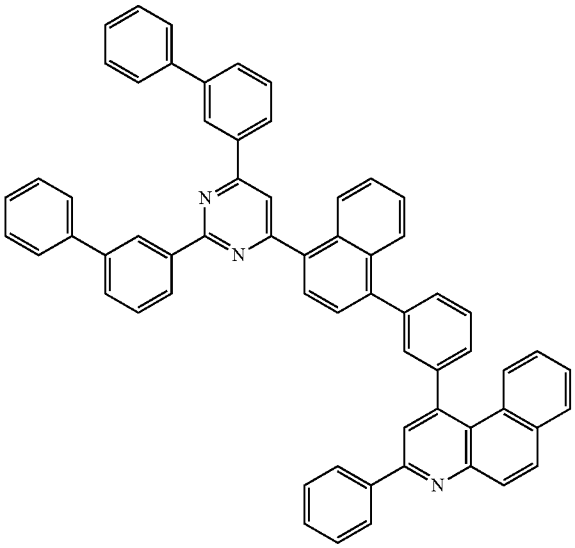
520
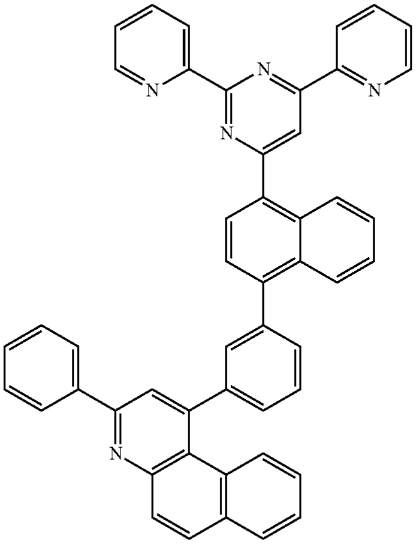
521
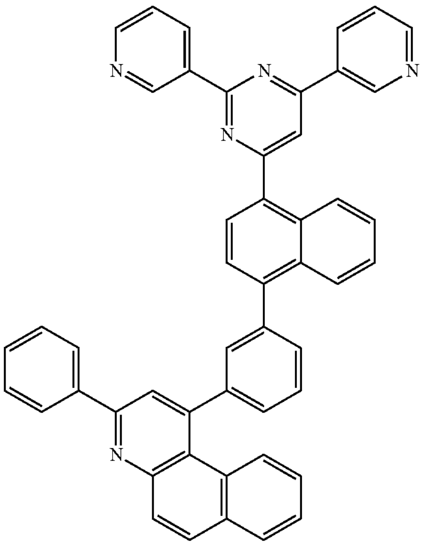

-continued
522
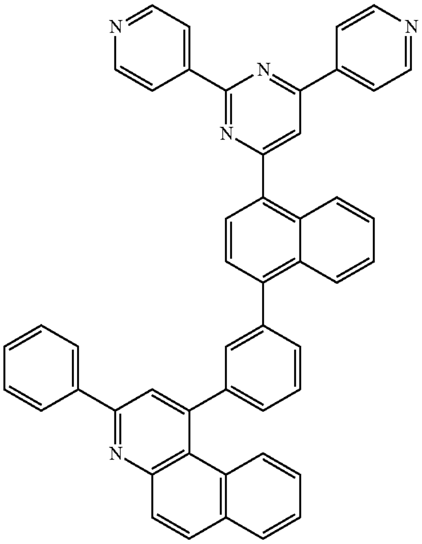
523
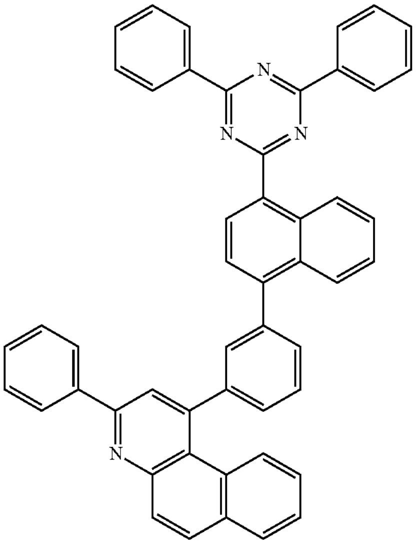
-continued
524
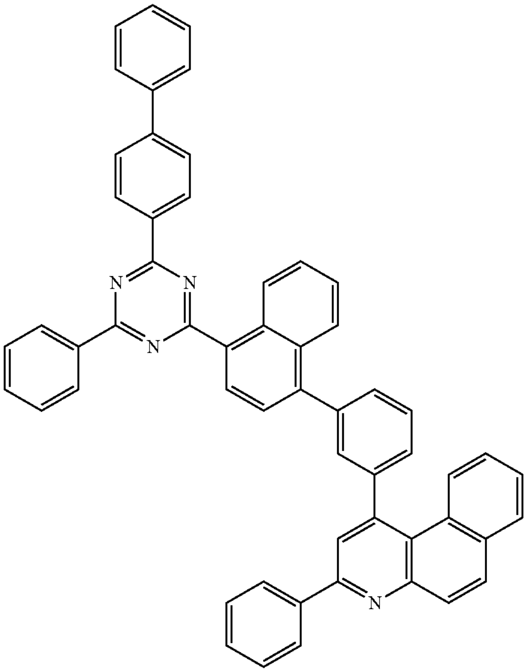
525
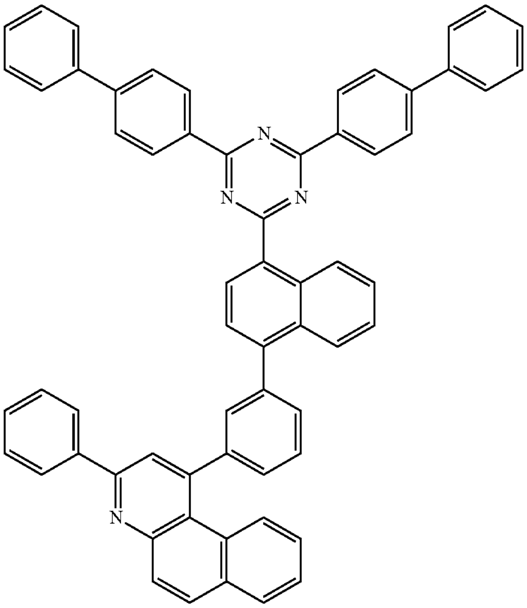

-continued
526
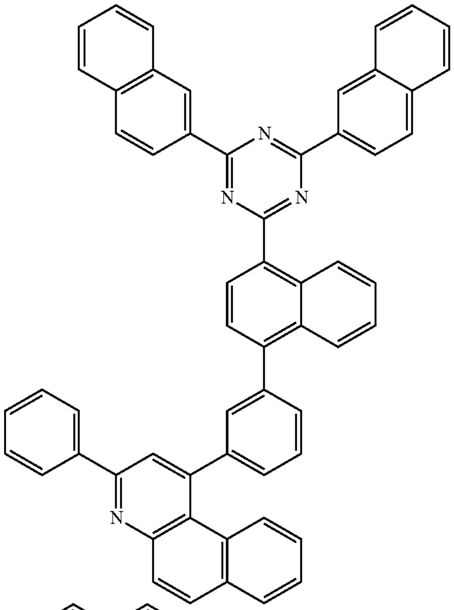
527
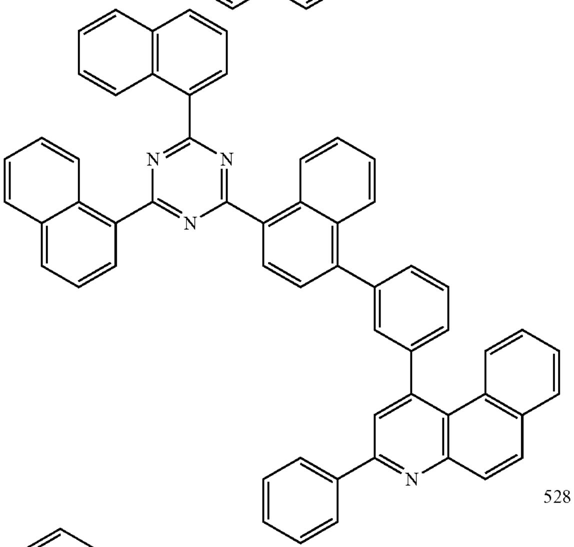
528
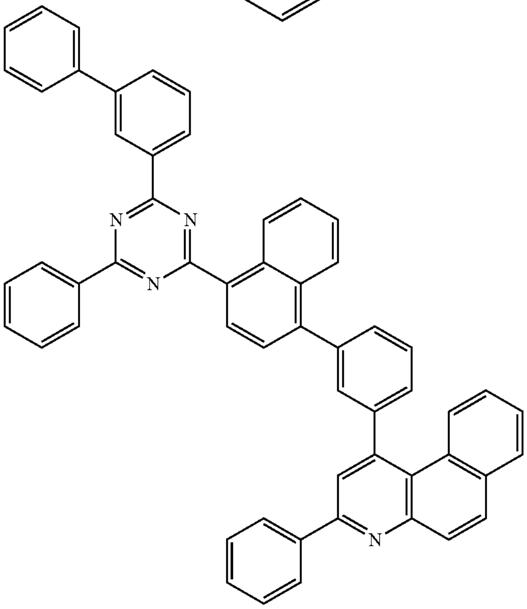
-continued
529
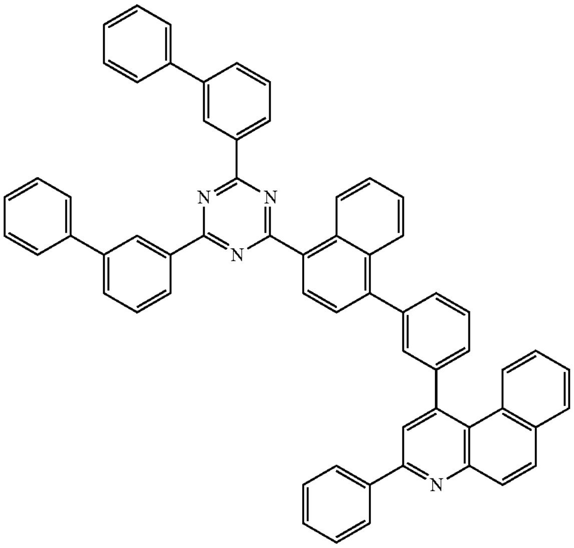
530
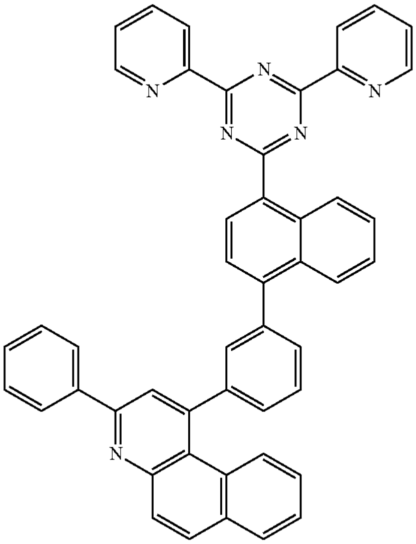
531
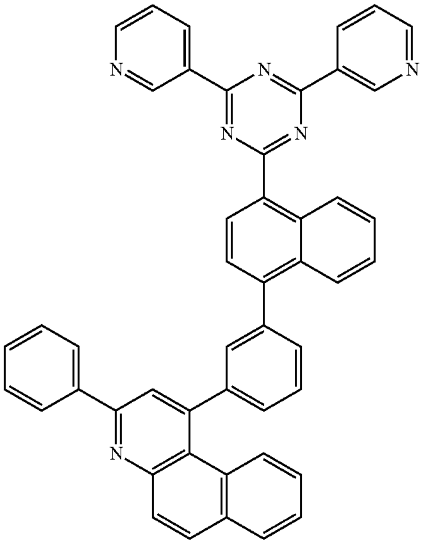

-continued
532
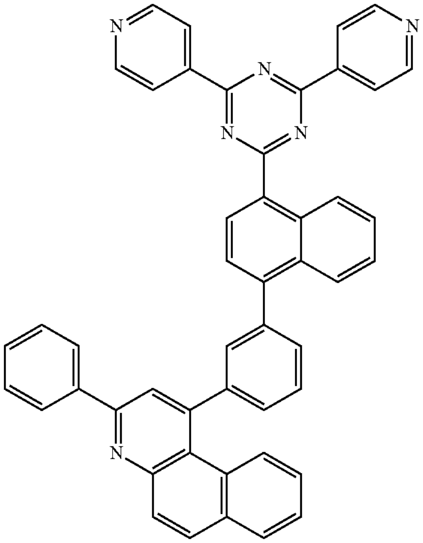
533
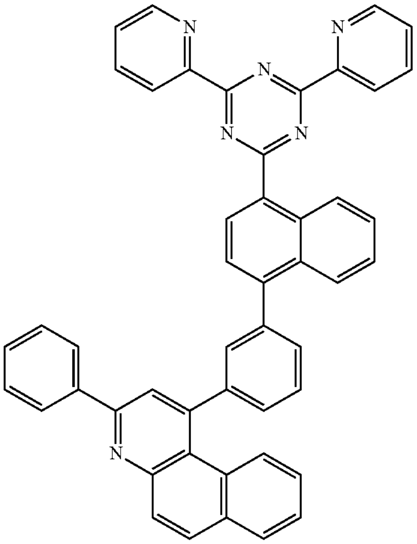
534
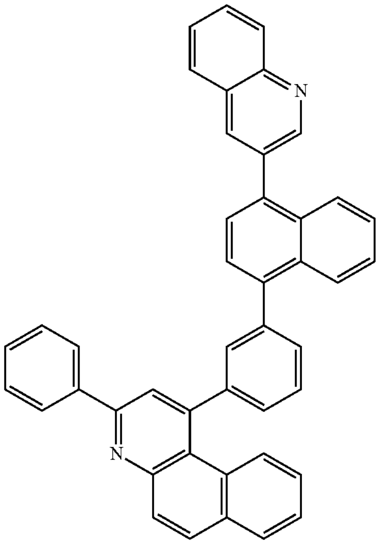
-continued
535
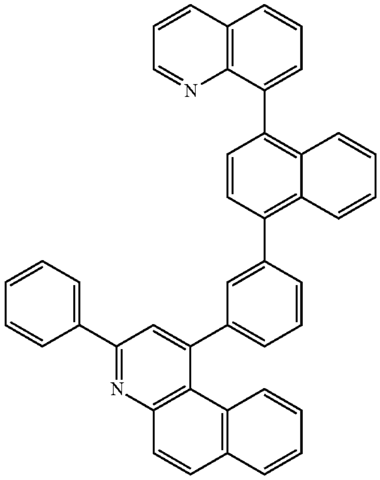
536
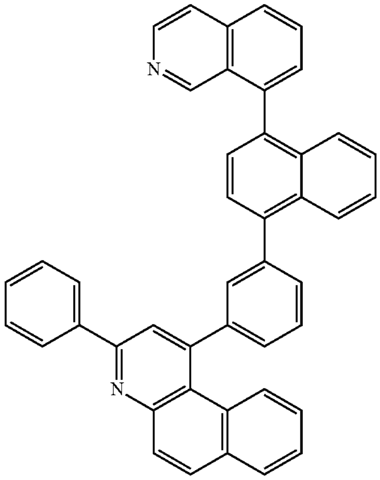
537
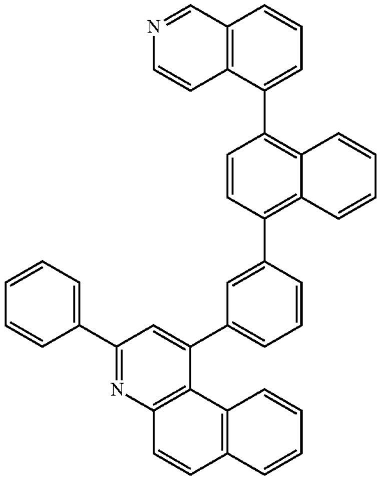

-continued
538
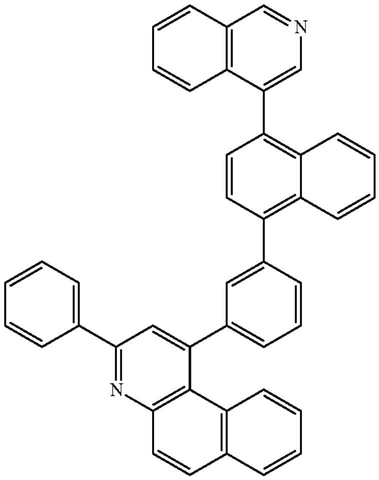
539
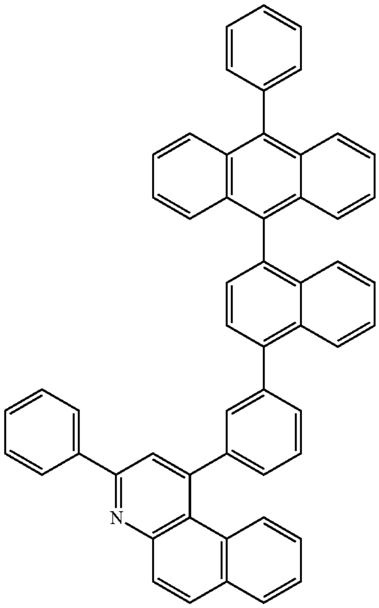
540
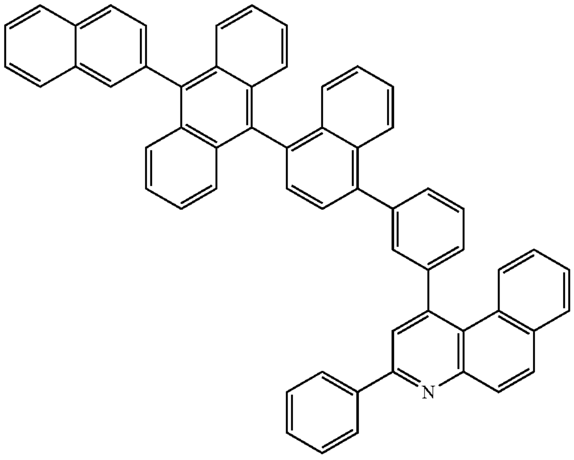
-continued
541
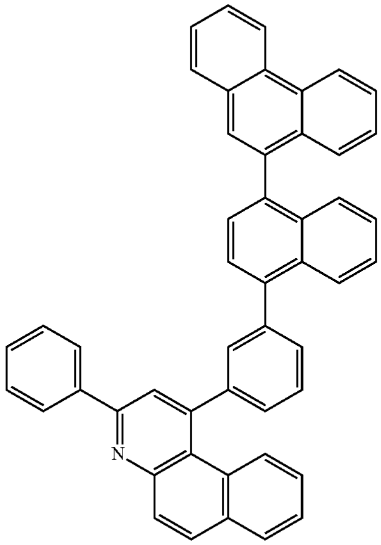
542
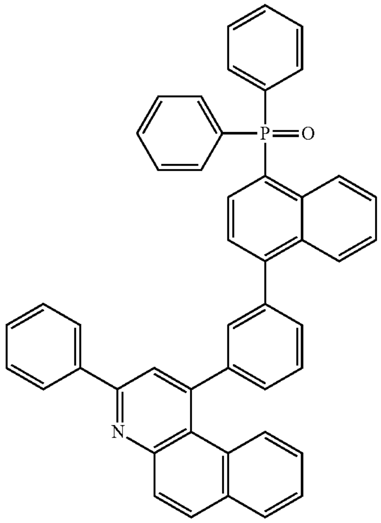
543
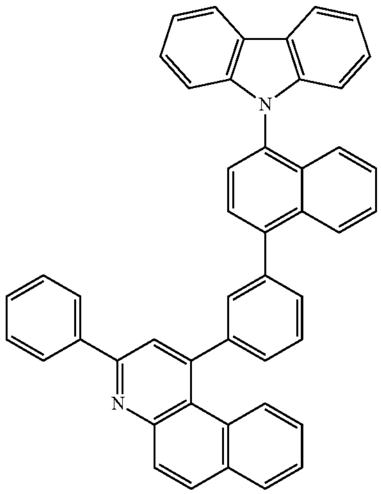

544
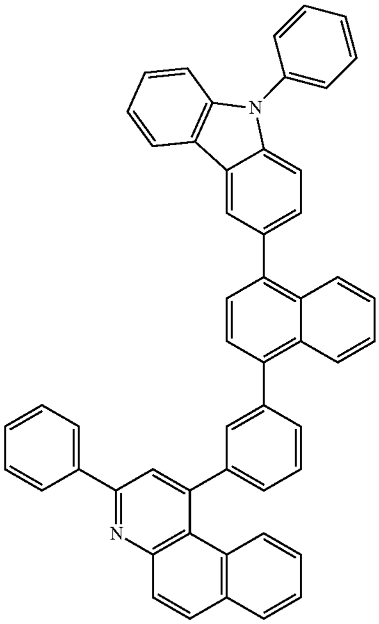
545
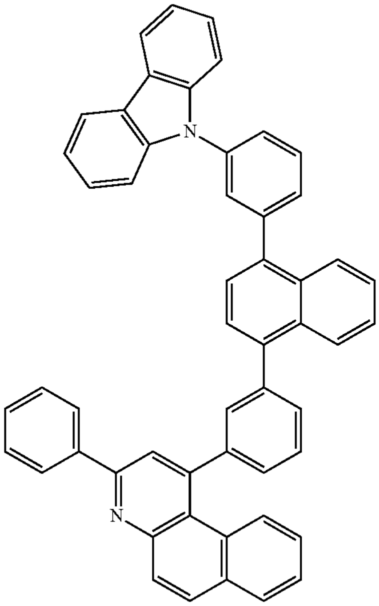
546
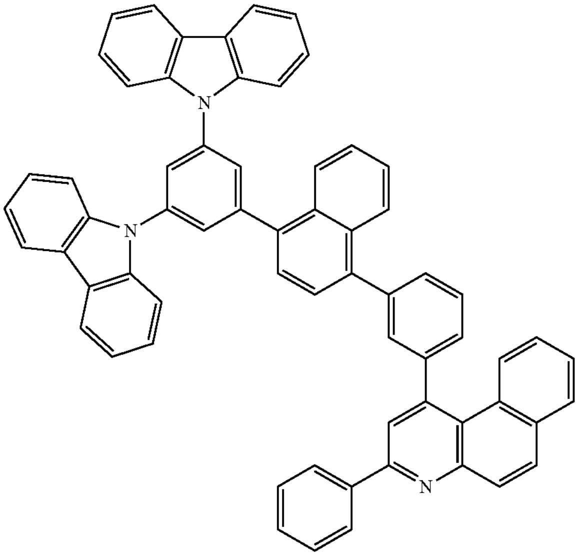
547
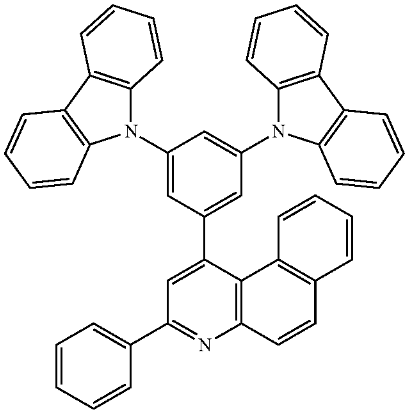
548
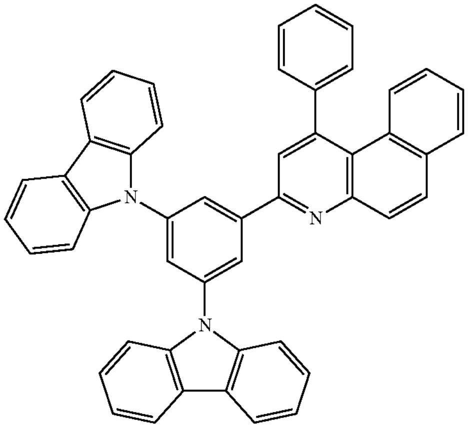

-continued
549
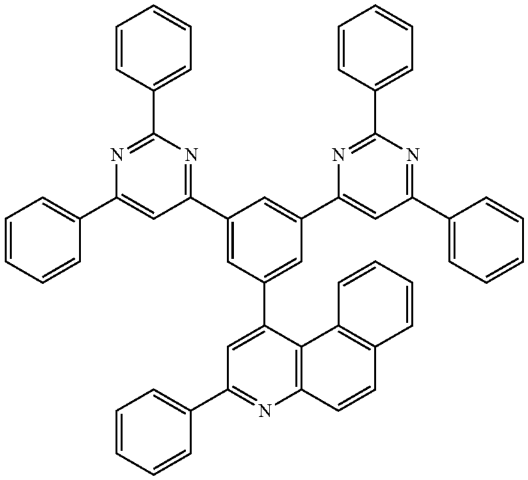
550
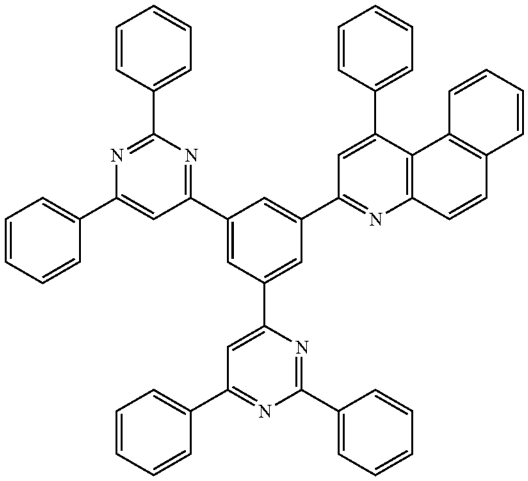
551
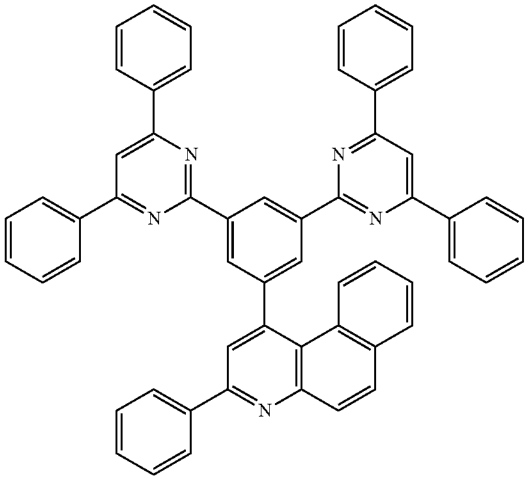
-continued
552
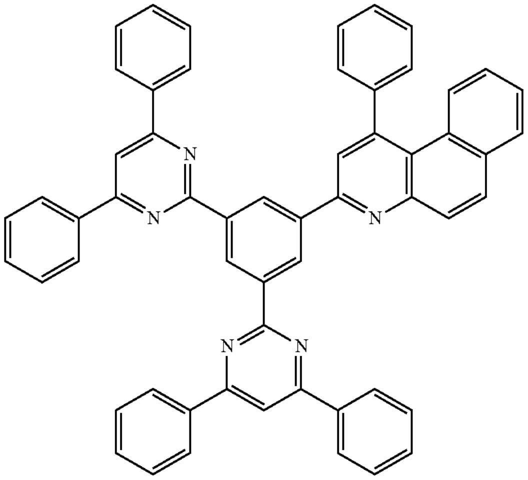
553
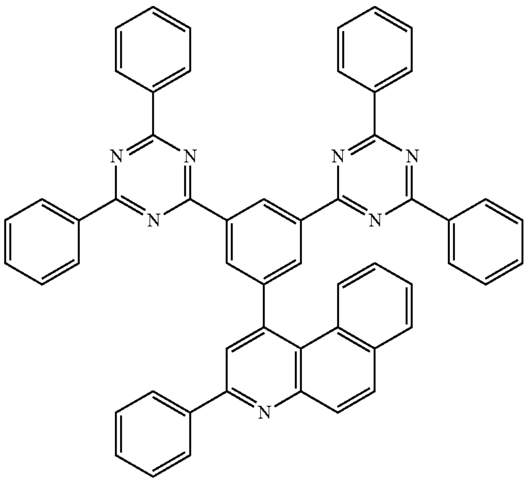
554
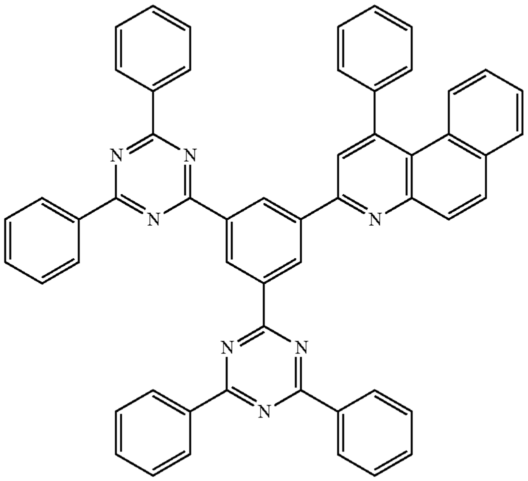

-continued
555
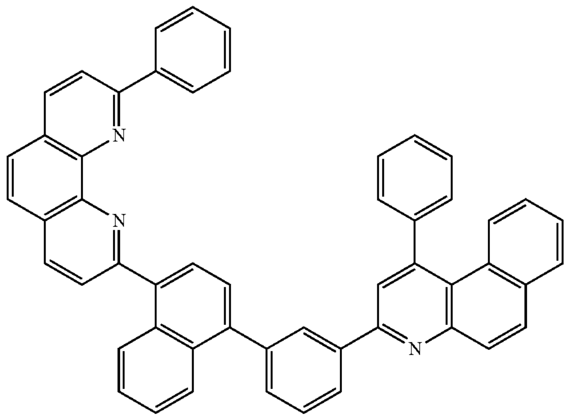
556
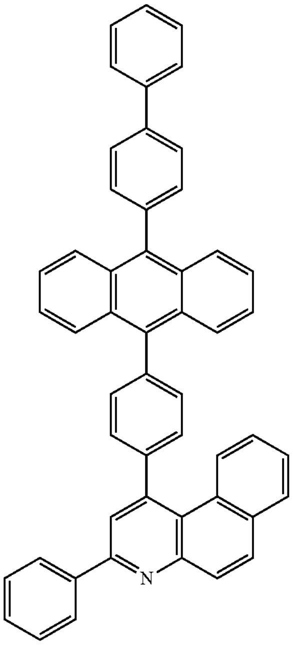
-continued
557
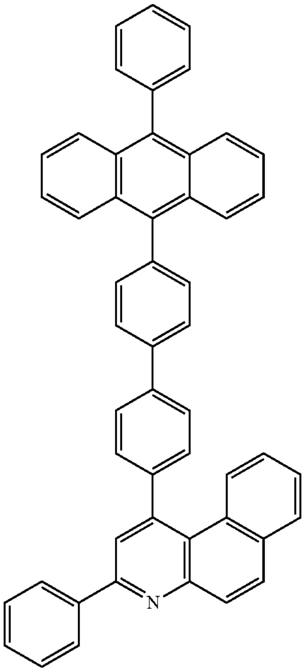
558
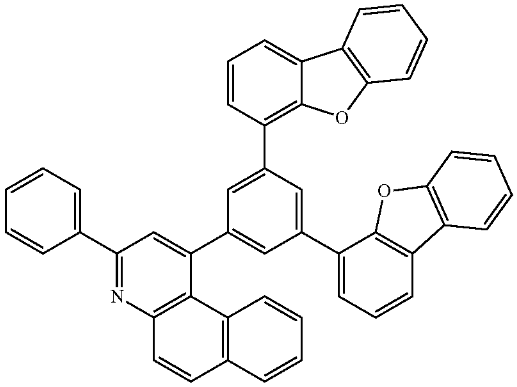
559
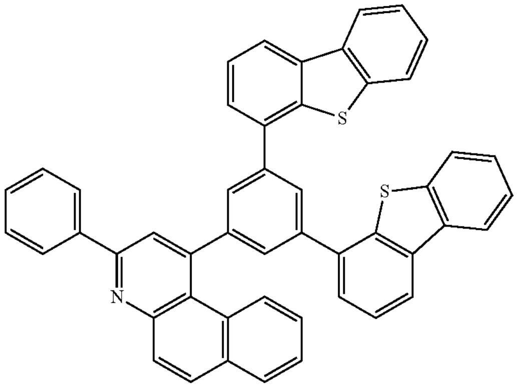

-continued
560
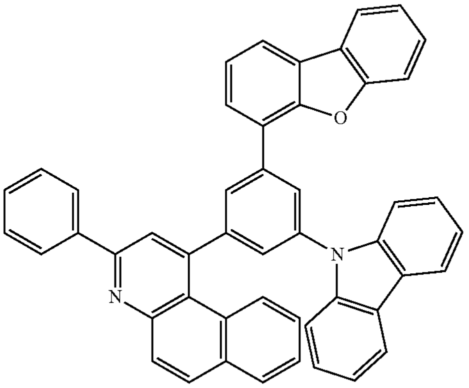
561
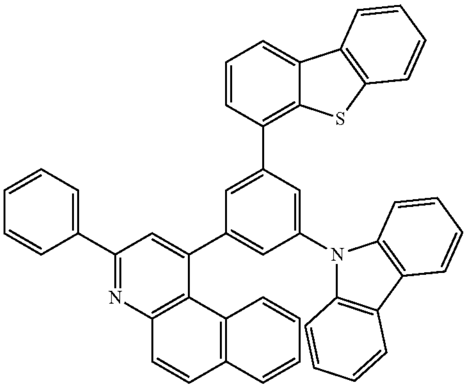
562
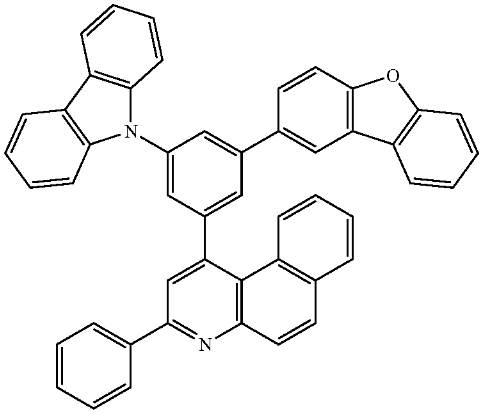
-continued
563
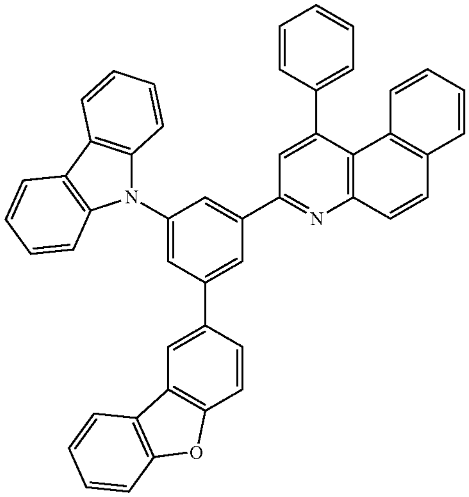
564
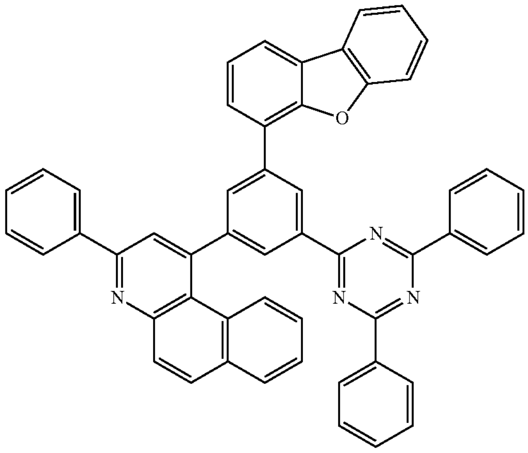
565
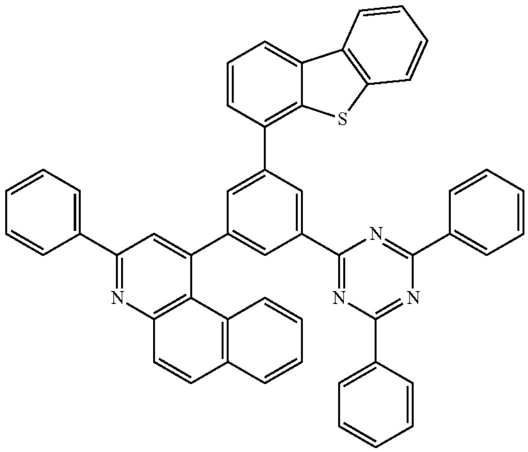

-continued
566
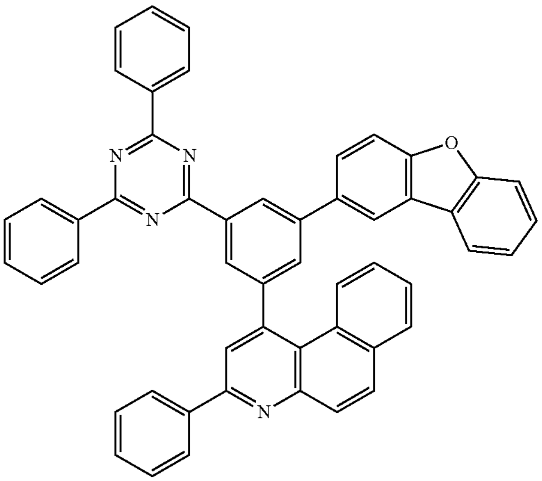
567
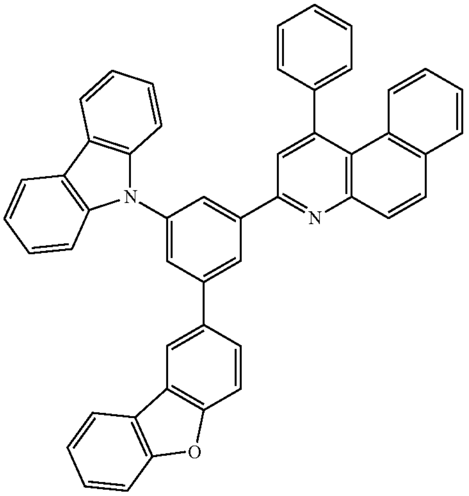
568
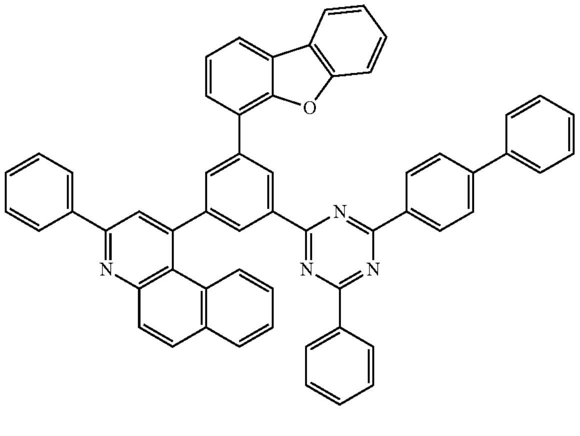
-continued
569
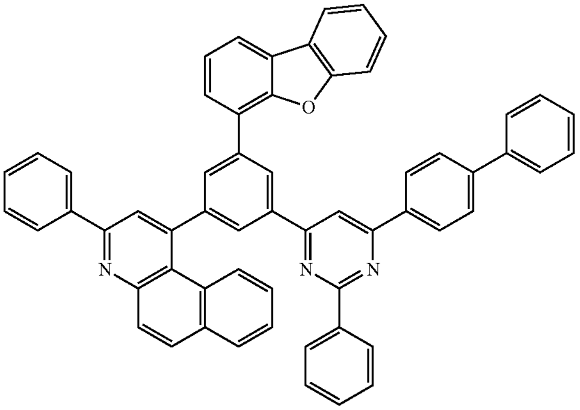
570
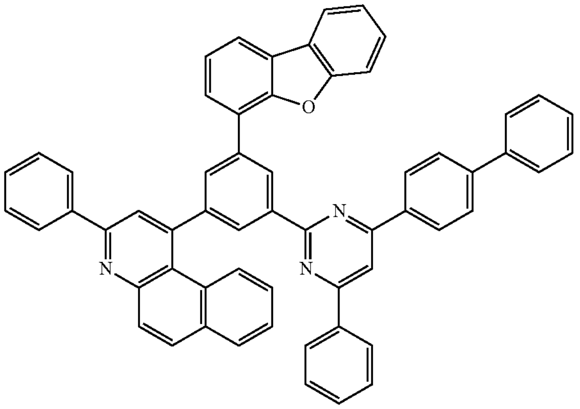
571
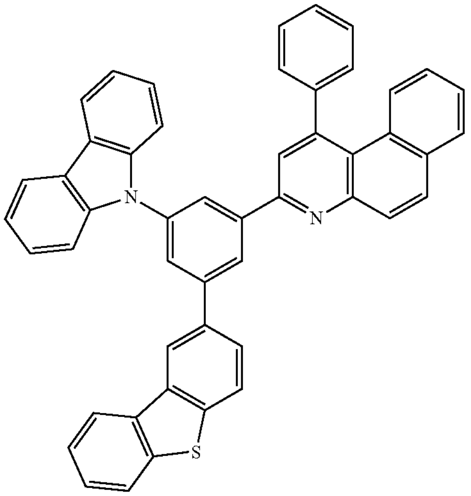

572
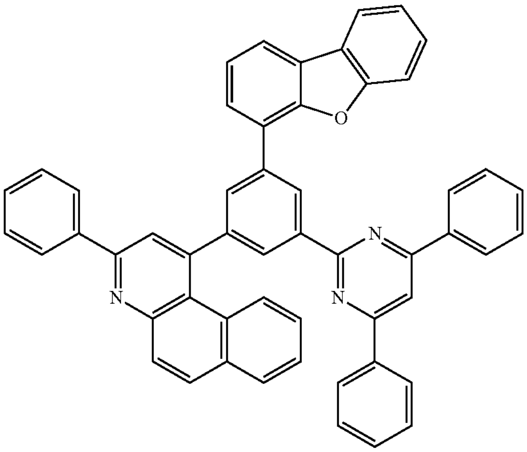
573
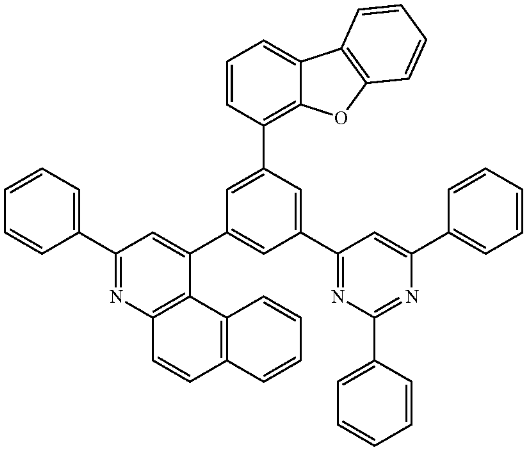
574
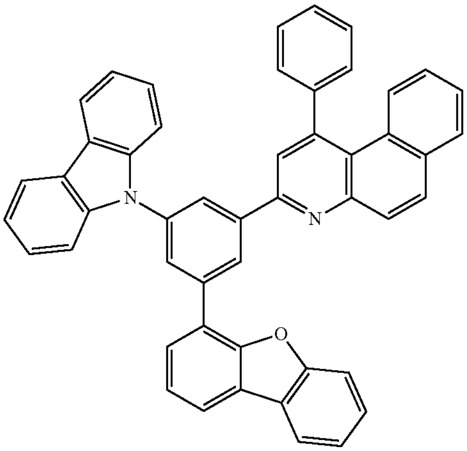
575
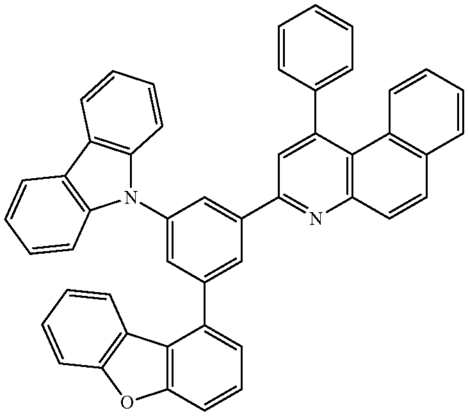
576
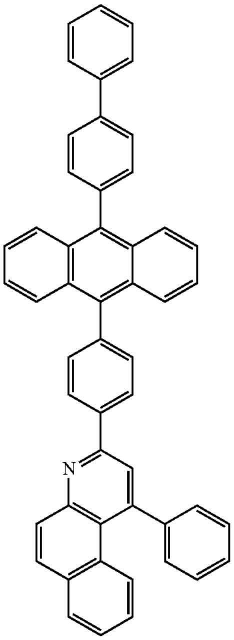

-continued
577
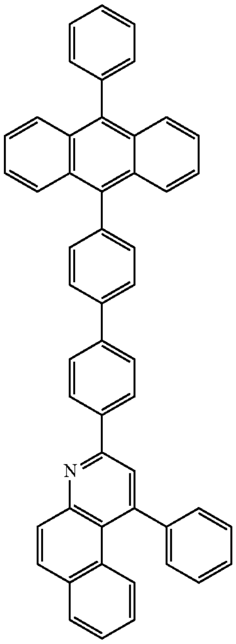
578
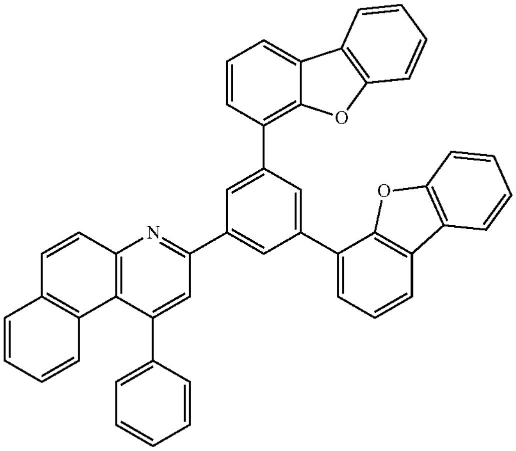
579
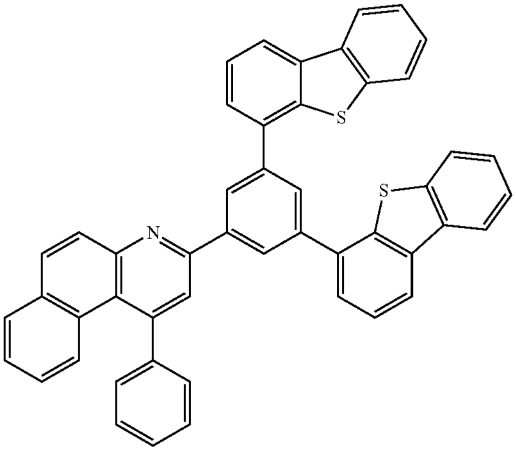
-continued
580
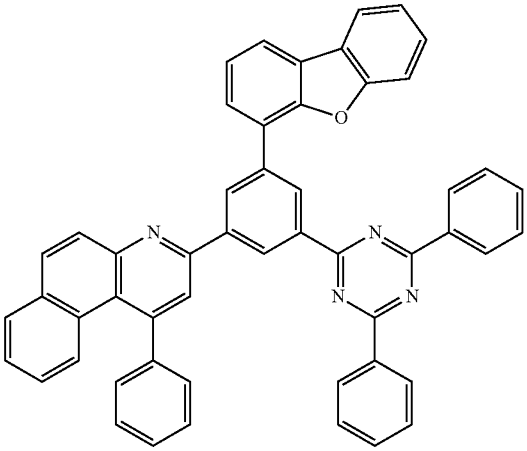
581
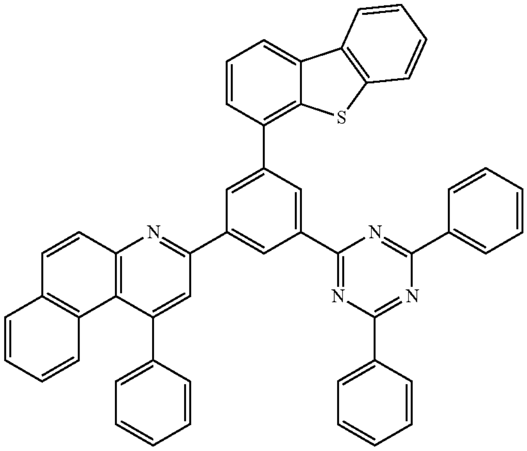
582
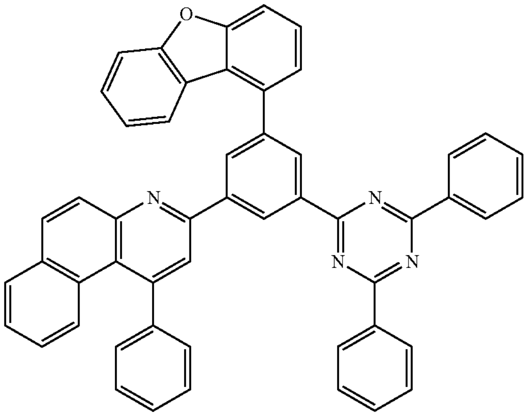

-continued
583
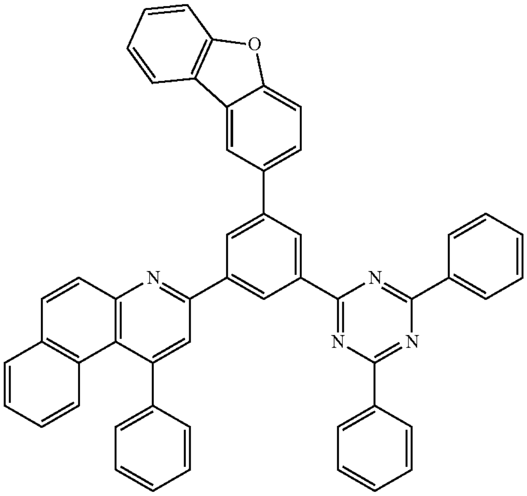
584
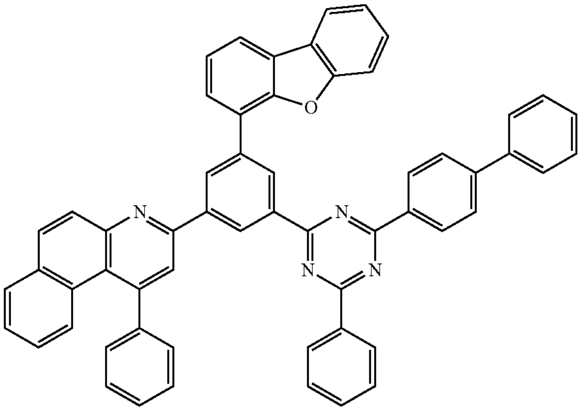
585
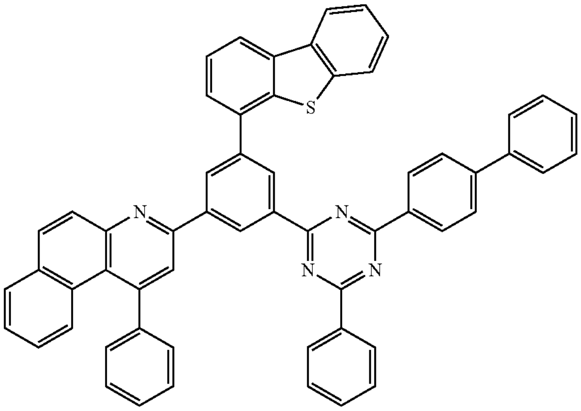
-continued
586
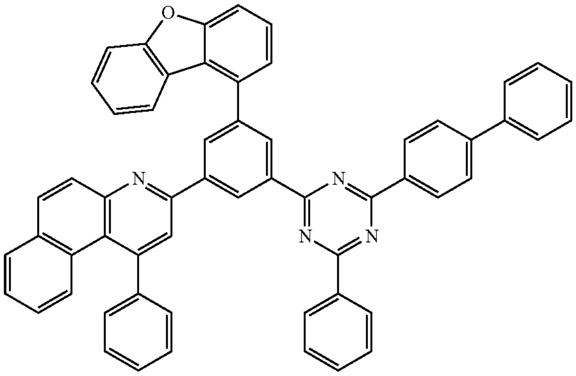
587
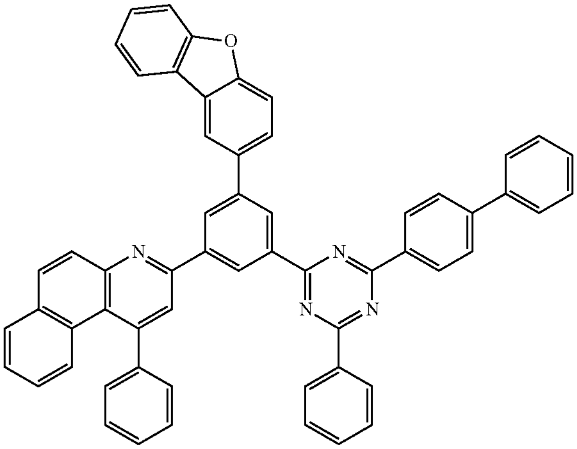
588
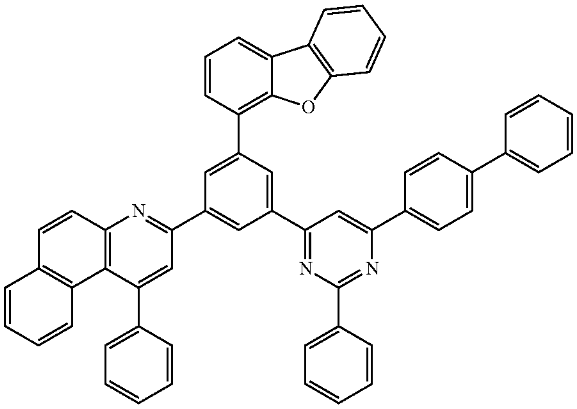

-continued
589
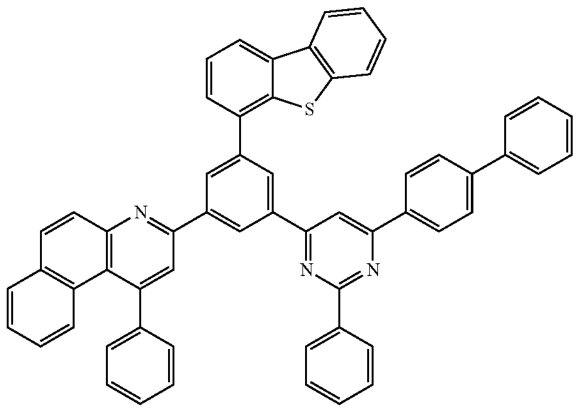
590
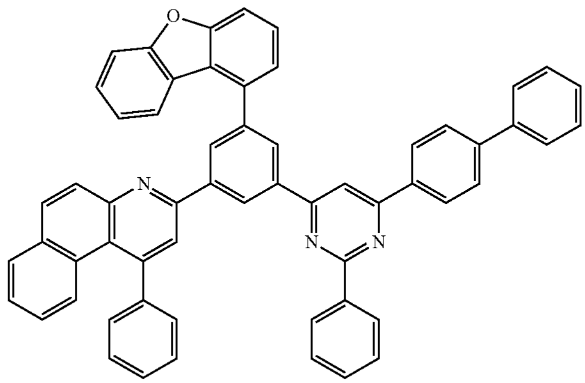
591
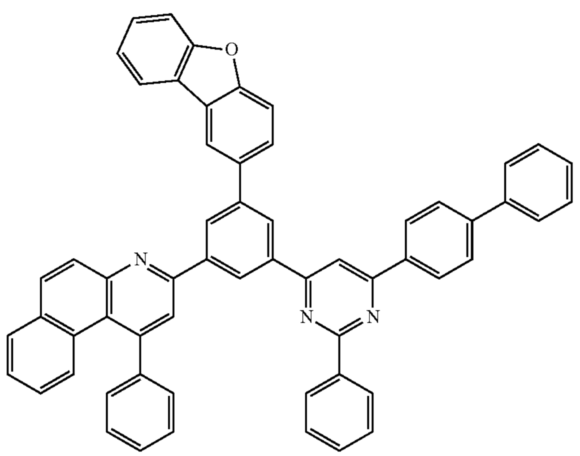
-continued
592
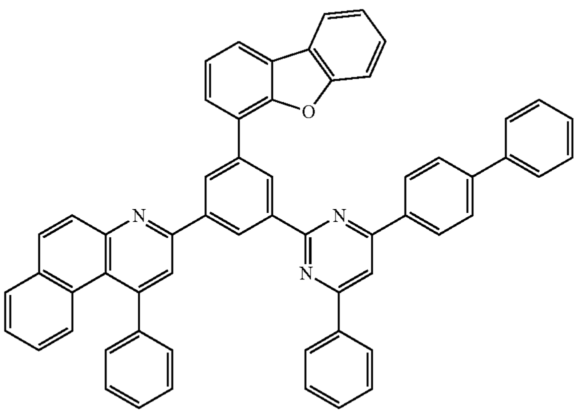
593
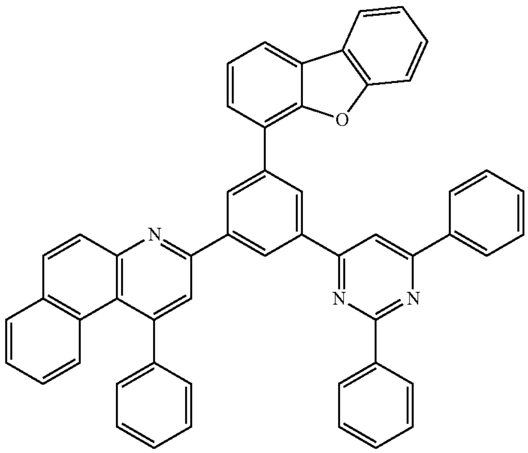
594
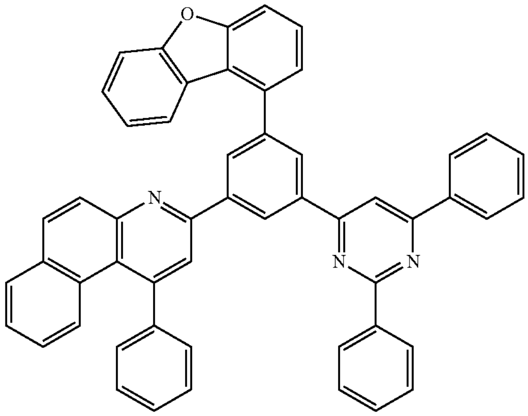

-continued

595

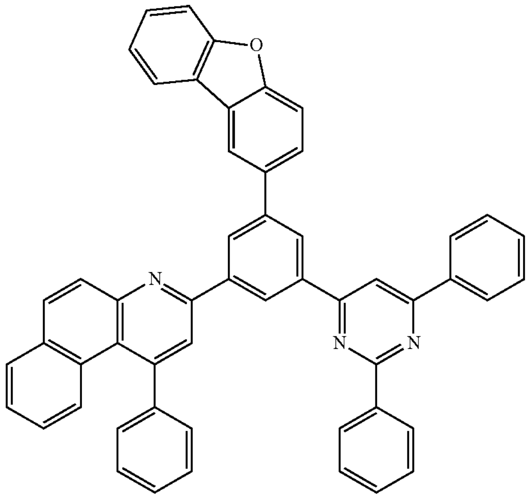

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the hetero-cyclic compound has excellent thermal stability with a high glass transition temperature (Tg). Such an increase in the thermal stability becomes an important factor in providing driving stability to a device.

The hetero-cyclic compound according to one embodiment of the present application may be prepared through a multistep chemical reaction. Some intermediate compounds are prepared first, and the compound of Chemical Formula 1 may be prepared from the intermediate compounds. More specifically, the hetero-cyclic compound according to one embodiment of the present application may be prepared based on preparation examples to be described below.

Another embodiment of the present application provides an organic light emitting device comprising the hetero-cyclic compound represented by Chemical Formula 1.

The organic light emitting device according to one embodiment of the present application may be manufactured using common organic light emitting device manufacturing methods and materials except that one or more organic material layers are formed using the hetero-cyclic compound described above.

The hetero-cyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

Specifically, the organic light emitting device according to one embodiment of the present application comprises an anode, a cathode, and one or more organic material layers provided between the anode and the cathode, wherein one or more layers of the organic material layers comprise the hetero-cyclic compound represented by Chemical Formula 1.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

In addition, the organic light emitting device according to one embodiment of the present application comprises an anode, a cathode, and two or more stacks provided between the anode and the cathode, wherein the two or more stacks each independently comprise a light emitting layer, a charge generation layer is included between the two or more stacks, and the charge generation layer comprises the hetero-cyclic compound represented by Chemical Formula 1.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the hetero-cyclic compound represented by Chemical Formula 1. In addition, the first stack and the second stack may each independently further comprise one or more types of the hole injection layer, the hole transfer layer, the hole blocking layer, the electron transfer layer, the electron injection layer described above and the like.

The charge generation layer may be an N-type charge generation layer, and the charge generation layer may further comprise a dopant known in the art in addition to the hetero-cyclic compound represented by Chemical Formula 1.

As the organic light emitting device according to one embodiment of the present application, an organic light emitting device having a 2-stack tandem structure is schematically illustrated in FIG. 4.

Herein, the first electron blocking layer, the first bole blocking layer, the second hole blocking layer and the like described in FIG. 4 may not be included in some cases.

The organic light emitting device according to the present specification may be manufactured using materials and methods known in the art except that one or more layers of the organic material layers comprise the hetero-cyclic compound represented by Chemical Formula 1.

The hetero-cyclic compound represented by Chemical Formula 1 may form one or more layers of the organic material layers of the organic light emitting device alone. However, as necessary, the hetero-cyclic compound represented by Chemical Formula 1 may be mixed with other materials to form the organic material layers.

The hetero-cyclic compound represented by Chemical Formula 1 may be used as a material of the charge generation layer in the organic light emitting device.

The hetero-cyclic compound represented by Chemical Formula 1 may be used as a material of the electron transfer layer, the hole blocking layer, the light emitting layer or the like in the organic light emitting device. As one example, the hetero-cyclic compound represented by Chemical Formula 1 may be used as a material of the electron transfer layer, the hole transfer layer or the light emitting layer in the organic light emitting device.

In addition, the hetero-cyclic compound represented by Chemical Formula 1 may be used as a material of the light emitting layer in the organic light emitting device. As one example, the hetero-cyclic compound represented by Chemical Formula 1 may be used as a phosphorescent host material of the light emitting layer in the organic light emitting device.

In the organic light emitting device according to one embodiment of the present application, materials other than the hetero-cyclic compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylcompound), poly[3,4-(ethylene-1,2-dioxy)compound] (PEDOT), polypyrrole and polyaniline, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

The organic light emitting device according to one embodiment of the present application may be a top-emission type, a bottom-emission type or a dual-emission type depending on the materials used.

The hetero-cyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

EXAMPLE

<Preparation Example 1> Preparation of Compound 1

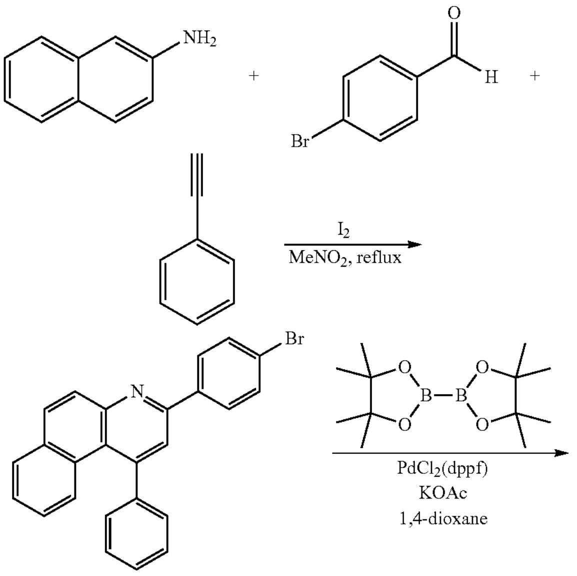

1-1

-continued

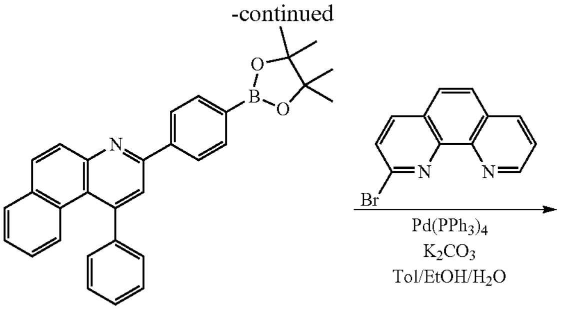

1-2

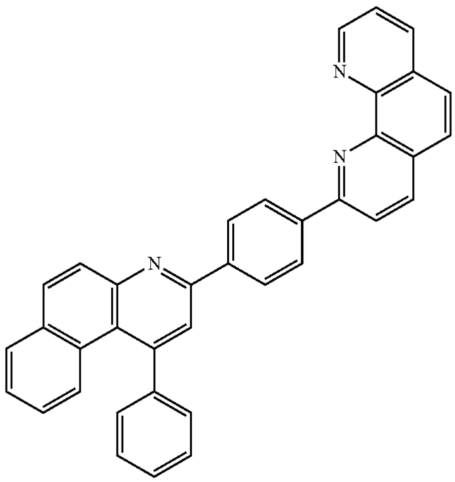

1

1) Preparation of Compound 1-1

Nitromethane (600 ml) was introduced to naphthalen-2-amine (60 g, 419.02 mmol, 1 eq.), 4-bromobenzaldehyde (77.5 g, 419.02 mmol, 1 eq.) and ethynylbenzene (64.2 g, 628.54 mmol, 1.5 eq.), iodine (10.6 g, 41.90 mmol, 0.1 eq.) was added thereto, and the result was stirred at 100° C.

MC was added to the reaction solution and dissolved, the result was extracted with water, and the organic layer was dried with anhydrous $Na_2SO_4$.

The result was separated using a silica-gel column (developing solvent EA:Hex=1:10→MC:EA=1:1).

The result was precipitated using MC/Hex→MC/MeOH to obtain 46 g of Compound 1-1 in a 27% yield.

2) Preparation of Compound 1-2

After dissolving Compound 1-1 (25 g, 60.93 mmol, 1 eq.) and bis(pinacolato)diboron (23.2 g, 91.39 mmol, 1.5 eq.) in 1,4-dioxane (250 ml), ($N_2$ condition) $PdCl_2$(dppf) (2.2 g, 3.05 mmol, 0.05 eq.) and KOAc (23.9 g, 243.72 mmol, 4 eq.) were added thereto, and the result was stirred for 6 hours at 100° C.

After extracting the result with MC and water, the organic layer was dried with anhydrous $Na_2SO_4$, and the result was silica-gel filtered.

The result was precipitated using MC/MeOH. The precipitates were filtered to obtain 24.5 g of Compound 1-2 in a 88% yield.

3) Preparation of Compound 1

After dissolving Compound 1-2 (20.1 g, 43.95 mmol, 1 eq.) and 2-bromo-1,10-phenanthroline (11.4 g, 43.95 mmol, 1 eq.) in 200 ml of Tol, 40 ml of EtOH and 40 ml of $H_2O$, ($N_2$ condition) $Pd(PPh_3)_4$ (2.5 g, 2.20 mmol, 0.05 eq.) and $K_2CO_3$ (12.2 g, 87.89 mmol, 2 eq.) were added thereto, and the result was stirred under reflux for 15 hours.

MC was introduced to the reaction solution and dissolved, the result was extracted with water, and the organic layer was dried with anhydrous $Na_2SO_4$.

The result was silica-gel filtered, and precipitated using MC/MeOH and MC/acetone.

The result was soxhlet extracted to obtain 10.47 g of Compound 1 in a 47% yield.

Target Compound A was synthesized in the same manner using, in Preparation Example 1, Intermediate A of the following Table 1 instead of 2-bromo-1,10-phenanthroline.

TABLE 1

| Compound Number | Intermediate A | Target Compound A | Yield |
|---|---|---|---|
| 2 | 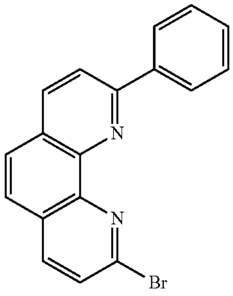 [SMILES: Brc1ccc2ccc3ccc(-c4ccccc4)nc3c2n1] | 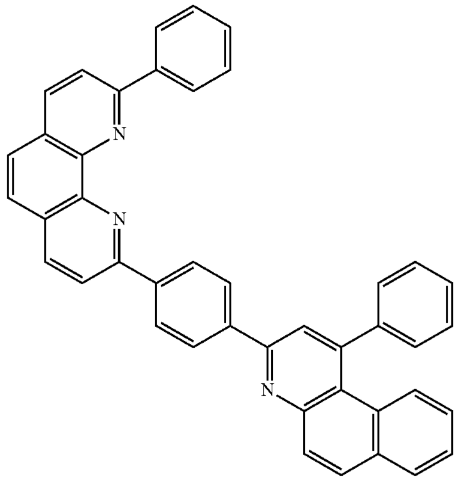 [SMILES: c1ccc(-c2ccc3ccc4ccc(-c5ccc(-c6cc(-c7ccccc7)c7c(ccc8ccccc87)n6)cc5)nc4c3n2)cc1] | 65% |

TABLE 1-continued
| Compound Number | Intermediate A | Target Compound A | Yield |
|---|---|---|---|
| 3 | 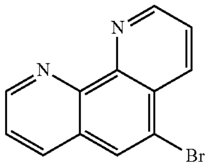 [SMILES: Brc1cc2cccnc2c2ncccc12] | 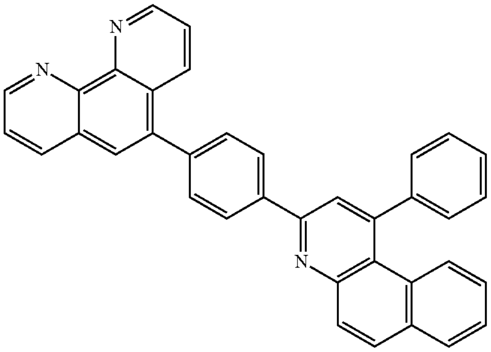 [SMILES: c1ccc(-c2cc(-c3ccc(-c4cc5cccnc5c5ncccc45)cc3)nc3ccc4ccccc4c23)cc1] | 71% |
| 5 | 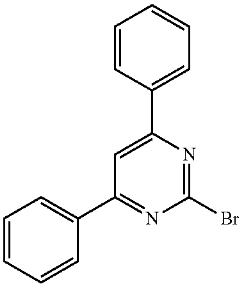 [SMILES: Brc1nc(-c2ccccc2)cc(-c2ccccc2)n1] | 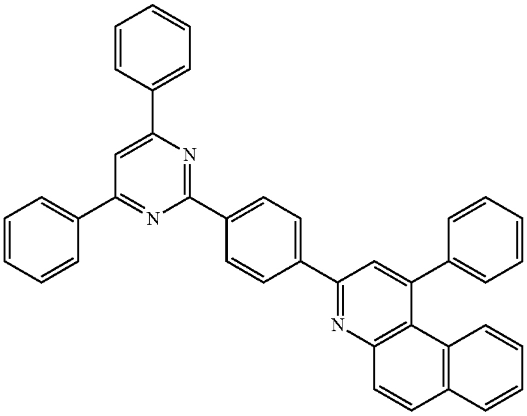 [SMILES: c1ccc(-c2cc(-c3ccccc3)nc(-c3ccc(-c4cc(-c5ccccc5)c5c(ccc6ccccc65)n4)cc3)n2)cc1] | 69% |
| 15 | 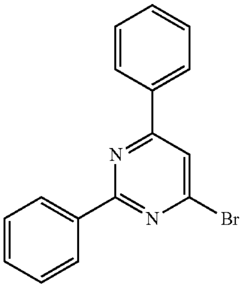 [SMILES: Brc1cc(-c2ccccc2)nc(-c2ccccc2)n1] | 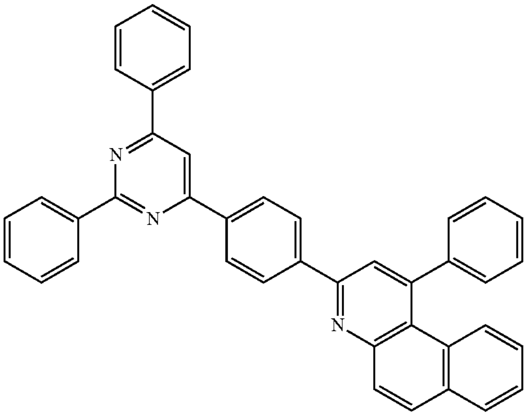 [SMILES: c1ccc(-c2cc(-c3ccc(-c4cc(-c5ccccc5)c5c(ccc6ccccc65)n4)cc3)nc(-c3ccccc3)n2)cc1] | 83% |

TABLE 1-continued
| Compound Number | Intermediate A | Target Compound A | Yield |
|---|---|---|---|
| 25 | 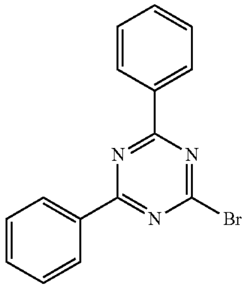 [SMILES: Brc1nc(-c2ccccc2)nc(-c2ccccc2)n1] | 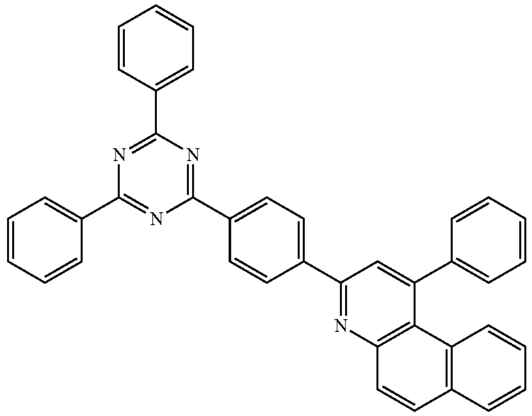 | 78% |
| 35 | 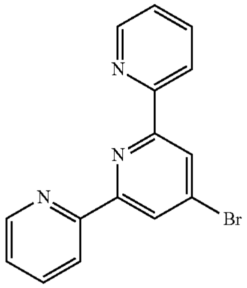 [SMILES: Brc1cc(-c2ccccn2)nc(-c2ccccn2)c1] | 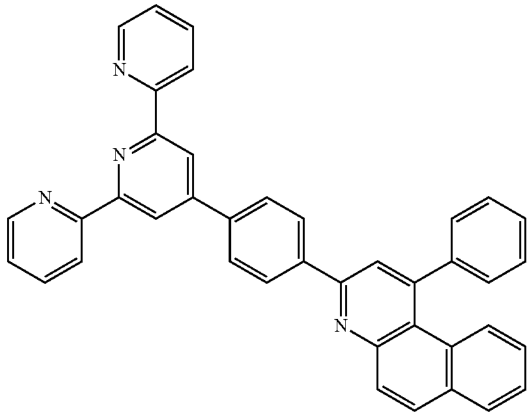 [SMILES: c1ccc(-c2cc(-c3ccc(-c4cc(-c5ccccn5)nc(-c5ccccn5)c4)cc3)nc3ccc4ccccc4c23)cc1] | 67% |
| 45 | 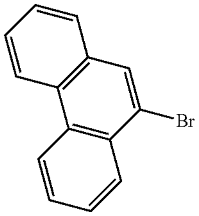 [SMILES: Brc1cc2ccccc2c2ccccc12] | 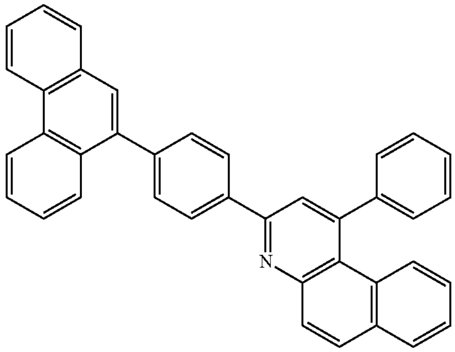 [SMILES: c1ccc(-c2cc(-c3ccc(-c4cc5ccccc5c5ccccc45)cc3)nc3ccc4ccccc4c23)cc1] | 70% |
| 46 | 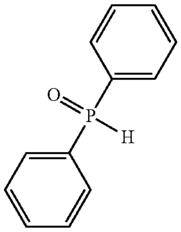 [SMILES: O=[PH](c1ccccc1)c1ccccc1] | 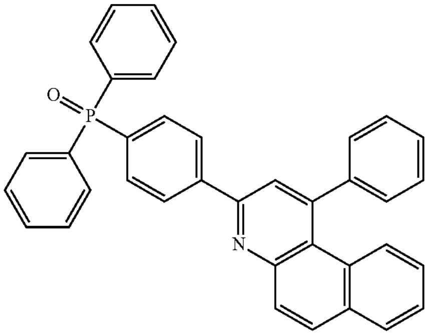 [SMILES: O=P(c1ccccc1)(c1ccccc1)c1ccc(-c2cc(-c3ccccc3)c3c(ccc4ccccc43)n2)cc1] | 62% |

TABLE 1-continued
| Compound Number | Intermediate A | Target Compound A | Yield |
|---|---|---|---|
| 50 | 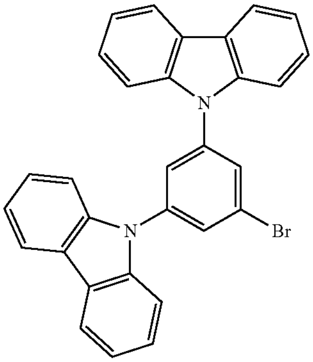 [SMILES: Brc1cc(-n2c3ccccc3c3ccccc32)cc(-n2c3ccccc3c3ccccc32)c1] | 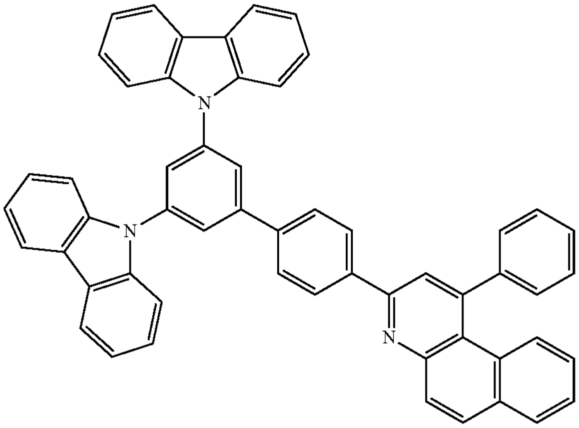 [SMILES: c1ccc(-c2cc(-c3ccc(-c4cc(-n5c6ccccc6c6ccccc65)cc(-n5c6ccccc6c6ccccc65)c4)cc3)nc3ccc4ccccc4c23)cc1] | 84% |
| 52 | 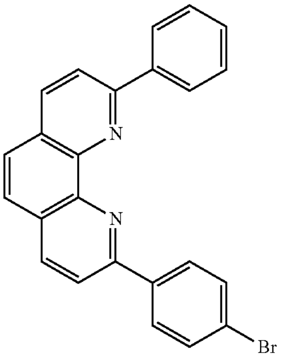 [SMILES: Brc1ccc(-c2ccc3ccc4ccc(-c5ccccc5)nc4c3n2)cc1] | 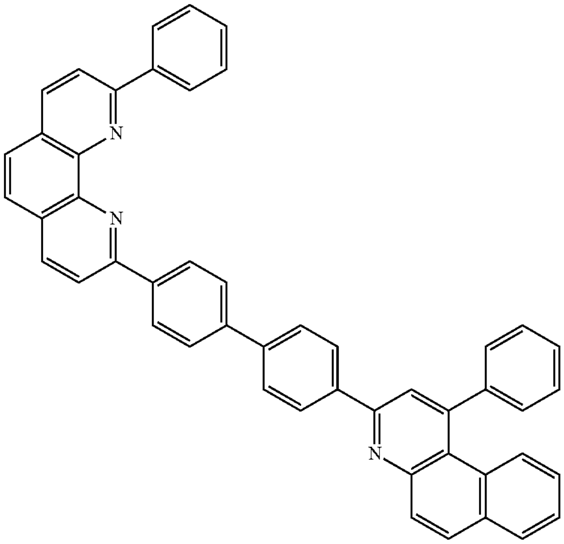 [SMILES: c1ccc(-c2ccc3ccc4ccc(-c5ccc(-c6ccc(-c7cc(-c8ccccc8)c8c(ccc9ccccc98)n7)cc6)cc5)nc4c3n2)cc1] | 71% |
| 102 | 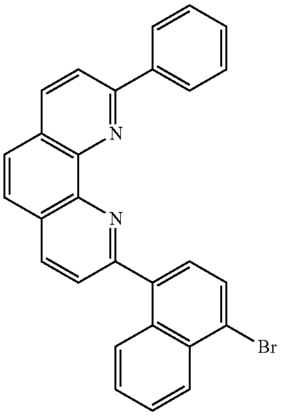 [SMILES: Brc1ccc(-c2ccc3ccc4ccc(-c5ccccc5)nc4c3n2)c2ccccc12] | 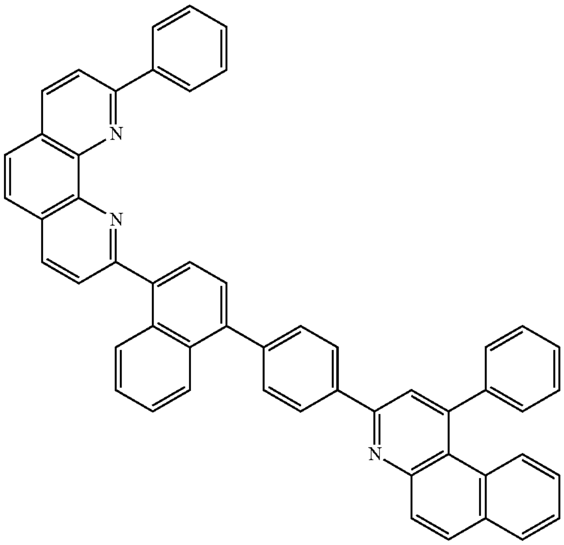 [SMILES: c1ccc(-c2ccc3ccc4ccc(-c5ccc(-c6ccc(-c7cc(-c8ccccc8)c8c(ccc9ccccc98)n7)cc6)c6ccccc56)nc4c3n2)cc1] | 74% |

<Preparation Example 2> Preparation of Compound 149

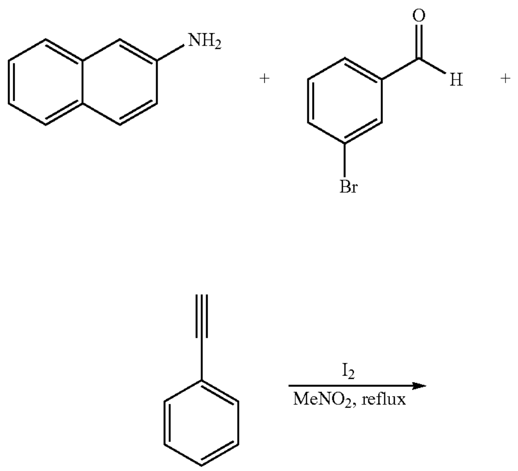

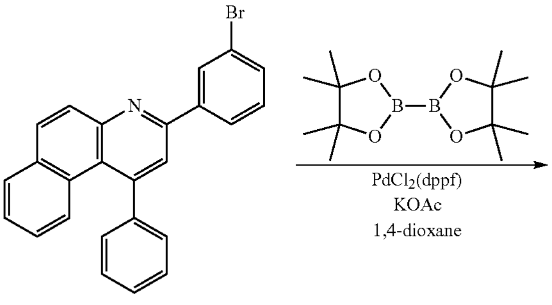

149-1

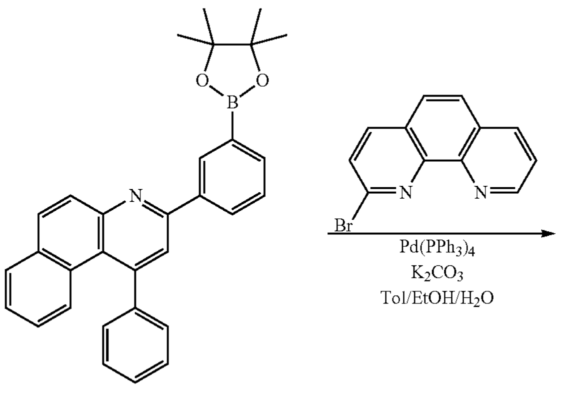

149-2

-continued

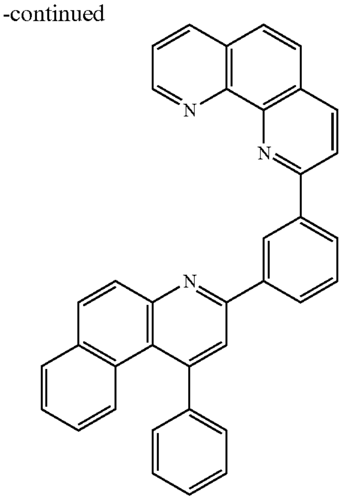

149

1) Preparation of Compound 149-1

Nitromethane (600 ml) was introduced to naphthalen-2-amine (60 g, 419.02 mmol, 1 eq.), 3-bromobenzaldehyde (77.5 g, 419.02 mmol, 1 eq.) and ethynylbenzene (64.2 g, 628.54 mmol, 1.5 eq.), iodine (10.6 g, 41.90 mmol, 0.1 eq.) was added thereto, and the result was stirred at 100° C.

MC was added to the reaction solution and dissolved, the result was extracted with water, and the organic layer was dried with anhydrous $Na_2SO_4$.

The result was separated using a silica-gel column (developing solvent EA:Hex=1:10→MC:EA→1:1).

The result was precipitated using MC/Hex→MC/MeOH to obtain 62 g of Compound 149-1 in a 36% yield.

2) Preparation of Compound 149-2

After dissolving Compound 149-1 (25 g 60.93 mmol, 1 eq.) and bis(pinacolato)diboron (23.2 g, 91.39 mmol, 1.5 eq.) in 1,4-dioxane (250 ml), ($N_2$ condition) $PdCl_2$(dppf) (2.2 g, 3.05 mmol, 0.05 eq.) and KOAc (23.9 g, 243.72 mmol, 4 eq.) were added thereto, and the result was stirred for 6 hours at 100° C.

After extracting the result with MC and water, the organic layer was dried with anhydrous $Na_2SO_4$, and the result was silica-gel filtered.

The result was precipitated using MC/MeOH. The precipitates were filtered to obtain 24 g of Compound 149-2 in a 86% yield.

3) Preparation of Compound 149

After dissolving Compound 149-2 (20.1 g, 43.95 mmol, 1 eq.) and 2-bromo-1,10-phenanthroline (11.4 g, 43.95 mmol, 1 eq.) in 200 ml of Tol, 40 ml of EtOH and 40 ml of $H_2O$, ($N_2$ condition) $Pd(PPh_3)_4$ (2.5 g, 2.20 mmol, 0.05 eq.) and $K_2CO_3$ (12.2 g, 87.89 mmol, 2 eq.) were added thereto, and the result was stirred under reflux for 15 hours.

MC was introduced to the reaction solution and dissolved, the result was extracted with water, and the organic layer was dried with anhydrous $Na_2SO_4$.

The result was silica-gel filtered, and precipitated using MC/MeOH and MC/acetone.

The result was soxhlet extracted to obtain 16 g of Compound 149 in a 71% yield.

Target Compound B was synthesized in the same manner using, in Preparation Example 2, Intermediate B of the following Table 2 instead of 2-bromo-1,10-phenanthroline.

TABLE 2
| Compound Number | Intermediate B | Target Compound B | Yield |
|---|---|---|---|
| 150 | 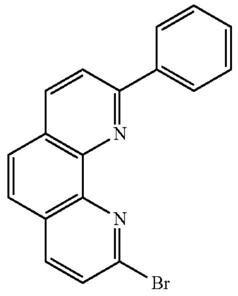 [SMILES: Brc1ccc2ccc3ccc(-c4ccccc4)nc3c2n1] | 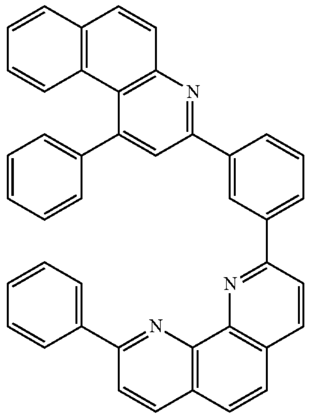 [SMILES: c1ccc(-c2ccc3ccc4ccc(-c5cccc(-c6cc(-c7ccccc7)c7c(ccc8ccccc87)n6)c5)nc4c3n2)cc1] | 69% |
| 151 | 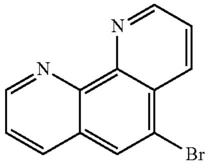 [SMILES: Brc1cc2cccnc2c2ncccc12] | 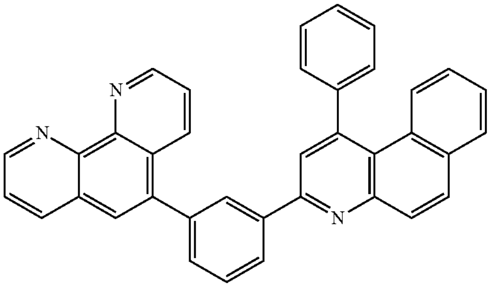 [SMILES: c1ccc(-c2cc(-c3cccc(-c4cc5cccnc5c5ncccc45)c3)nc3ccc4ccccc4c23)cc1] | 73% |
| 153 | 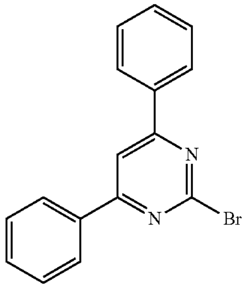 [SMILES: Brc1nc(-c2ccccc2)cc(-c2ccccc2)n1] | 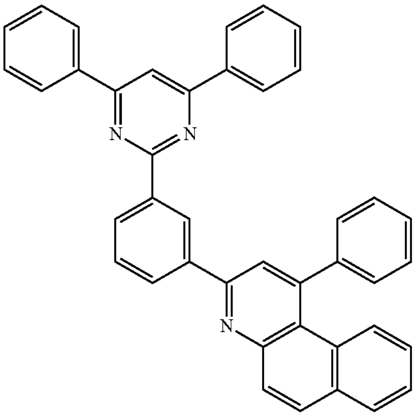 [SMILES: c1ccc(-c2cc(-c3ccccc3)nc(-c3cccc(-c4cc(-c5ccccc5)c5c(ccc6ccccc65)n4)c3)n2)cc1] | 64% |
| 163 | 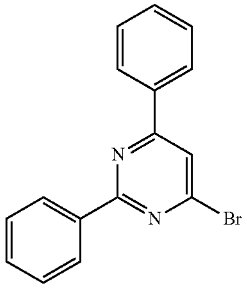 [SMILES: Brc1cc(-c2ccccc2)nc(-c2ccccc2)n1] | 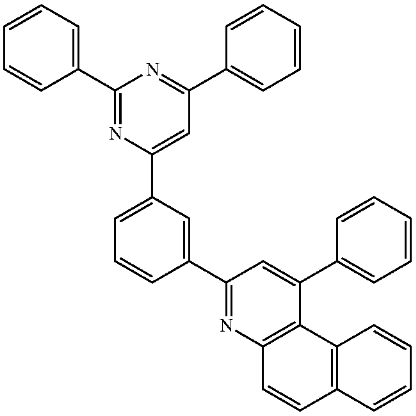 [SMILES: c1ccc(-c2cc(-c3cccc(-c4cc(-c5ccccc5)c5c(ccc6ccccc65)n4)c3)nc(-c3ccccc3)n2)cc1] | 88% |

TABLE 2-continued
| Compound Number | Intermediate B | Target Compound B | Yield |
|---|---|---|---|
| 173 | 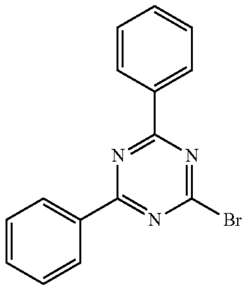 [SMILES: Brc1nc(-c2ccccc2)nc(-c2ccccc2)n1] | 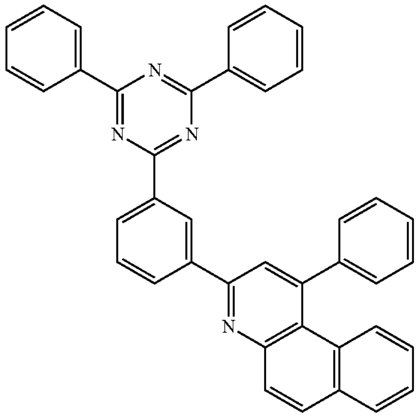 | 72% |
| 183 | 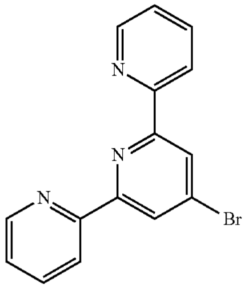 [SMILES: Brc1cc(-c2ccccn2)nc(-c2ccccn2)c1] | 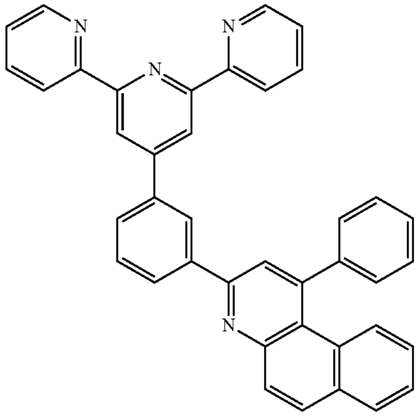 [SMILES: c1ccc(-c2cc(-c3cccc(-c4cc(-c5ccccn5)nc(-c5ccccn5)c4)c3)nc3ccc4ccccc4c23)cc1] | 69% |
| 194 | 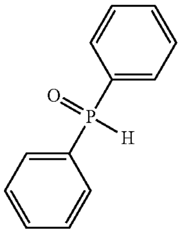 [SMILES: O=[PH](c1ccccc1)c1ccccc1] | 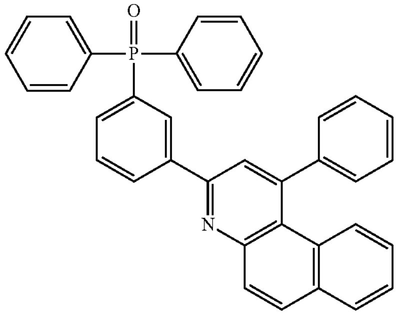 [SMILES: O=P(c1ccccc1)(c1ccccc1)c1cccc(-c2cc(-c3ccccc3)c3c(ccc4ccccc43)n2)c1] | 69% |
| 198 | 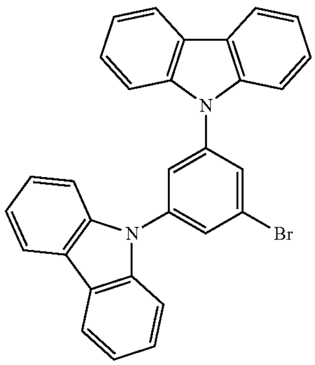 [SMILES: Brc1cc(-n2c3ccccc3c3ccccc32)cc(-n2c3ccccc3c3ccccc32)c1] | 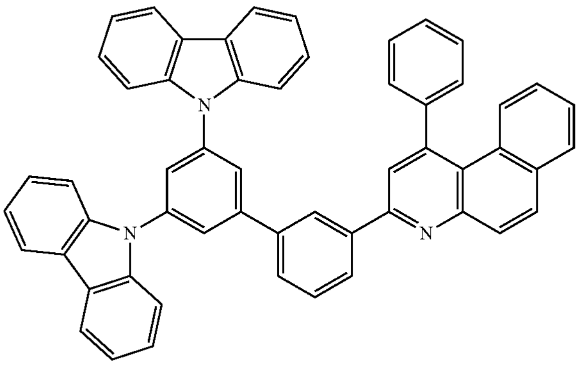 [SMILES: c1ccc(-c2cc(-c3cccc(-c4cc(-n5c6ccccc6c6ccccc65)cc(-n5c6ccccc6c6ccccc65)c4)c3)nc3ccc4ccccc4c23)cc1] | 81% |

TABLE 2-continued
| Compound Number | Intermediate B | Target Compound B | Yield |
|---|---|---|---|
| 199 | 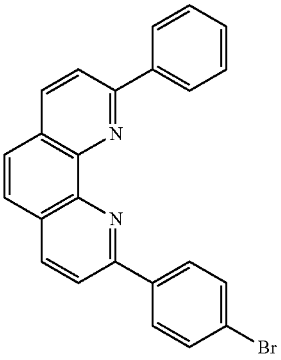 [SMILES: Brc1ccc(-c2ccc3ccc4ccc(-c5ccccc5)nc4c3n2)cc1] | 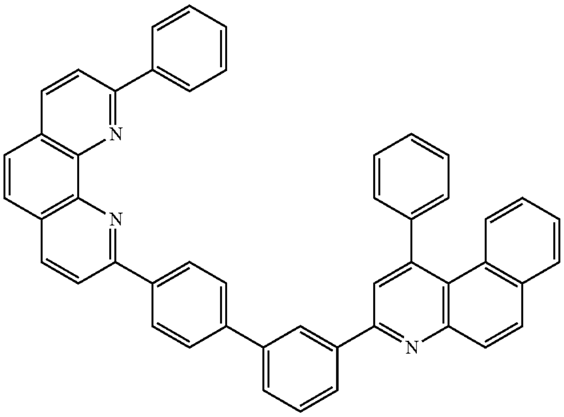 [SMILES: c1ccc(-c2ccc3ccc4ccc(-c5ccc(-c6cccc(-c7cc(-c8ccccc8)c8c(ccc9ccccc98)n7)c6)cc5)nc4c3n2)cc1] | 73% |
| 555 | 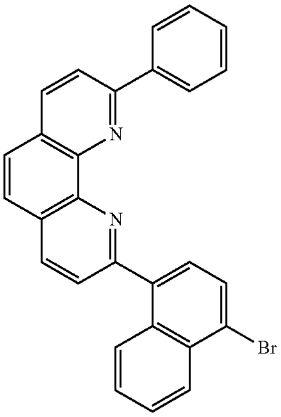 [SMILES: Brc1ccc(-c2ccc3ccc4ccc(-c5ccccc5)nc4c3n2)c2ccccc12] | 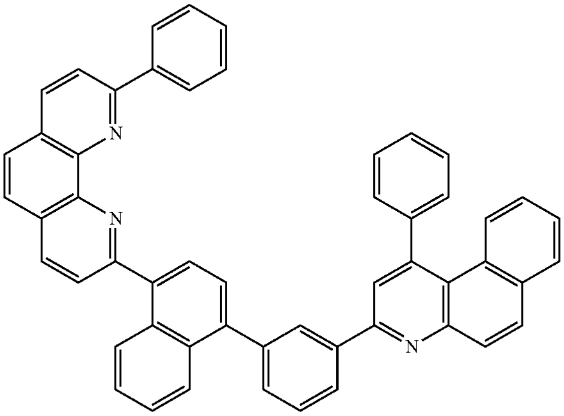 [SMILES: c1ccc(-c2ccc3ccc4ccc(-c5ccc(-c6cccc(-c7cc(-c8ccccc8)c8c(ccc9ccccc98)n7)c6)c6ccccc56)nc4c3n2)cc1] | 81% |
<Preparation Example 3> Preparation of Compound 249
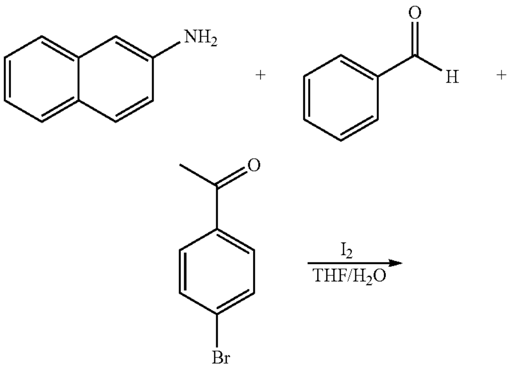
-continued
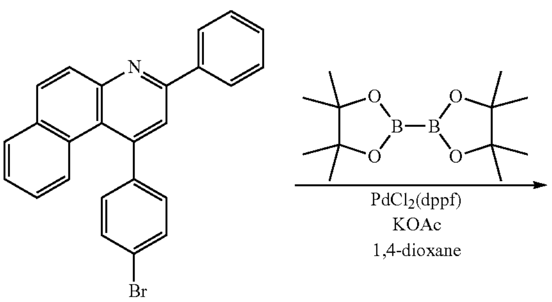
249-1

-continued

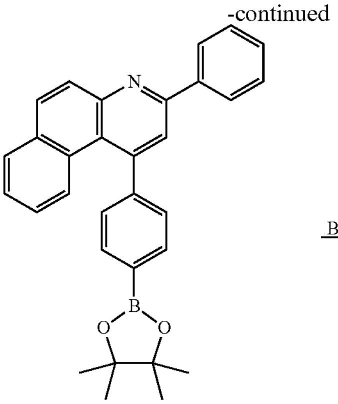

249-2

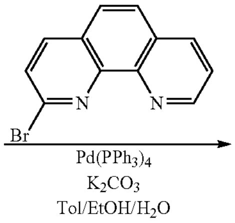

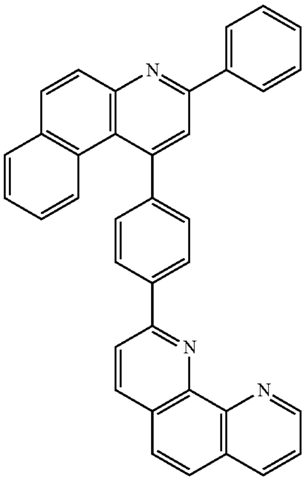

249

1) Preparation of Compound 249-1

Tetrahydrofuran (375 mL) and distilled water (3.75 mL) were introduced to naphthalen-2-amine (15 g, 0.104 mol, 1 eq.), 4-bromoacetophenone (20.75 g, 0.104 mol, 1 eq.) and benzaldehyde (11.12 g, 0.104 mol, 1.5 eq.), iodine (1.3 g, 0.0052 mol, 0.05 eq.) was added thereto, and the result was stirred at 80° C.

After removing the solvent from the reaction solution, $Na_2S_2O_3$, distilled water and acetone were added thereto, and the produced solids were filtered and washed with acetone to obtain 16 g of Compound 249-1 in a 38% yield.

2) Preparation of Compound 249-2

After dissolving Compound 249-1 (16 g, 0.0389 mol, 1 eq.) and bis(pinacolato)diboron (14.8 g, 0.0584 mol, 1.5 eq.) in 1,4-dioxane (240 ml), ($N_2$ condition) $PdCl_2$(dppf) (2.8 g, 0.0038 mol, 0.1 eq.) and KOAc (11.48 g, 0.116 mol, 3 eq.) were added thereto, and the result was stirred for 14 hours at 100° C.

After terminating the reaction using $H_2O$, the produced solids were filtered. The solids were dissolved in MC, silica-gel adsorbed, and column separated (developing solvent MC:Hex 1:1). After removing the solvent, the result was precipitated using MC/MeOH. The precipitates were filtered to obtain 13 g of Compound 249-2 in a 73% yield.

3) Preparation of Compound 249

After dissolving Compound 249-2 (13 g, 0.028 mol, 1 eq.) and 2-bromo-1,10-phenanthroline (7.36 g, 0.028 mol, 1 eq.) in 160 ml of Tol, 40 ml of EtOH and 40 ml of $H_2O$, ($N_2$ condition) $Pd(PPh_3)_4$ (1.6 g, 0.0014 mol, 0.05 eq.) and $K_2CO_3$ (7.85 g, 0.056 mol, 2 eq.) were added thereto, and the result was stirred under reflux for 8 hours.

MC was introduced to the reaction solution and dissolved, the result was extracted with water, and the organic layer was dried with anhydrous $Na_2SO_4$.

The result was silica-gel filtered, and precipitated using MC/MeOH and MC/acetone.

The result was soxhlet extracted to obtain 11 g of Compound 249 in a 76% yield.

Target Compound C was synthesized in the same manner using, in Preparation Example 3, Intermediate C of the following Table 3 instead of 2-bromo-1,10-phenanthroline.

TABLE 3

| Compound Number | Intermediate C | Target Compound C | Yield |
|---|---|---|---|
| 344 | 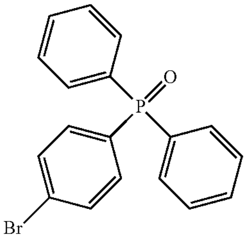 [SMILES: O=P(c1ccccc1)(c1ccccc1)c1ccc(Br)cc1] | 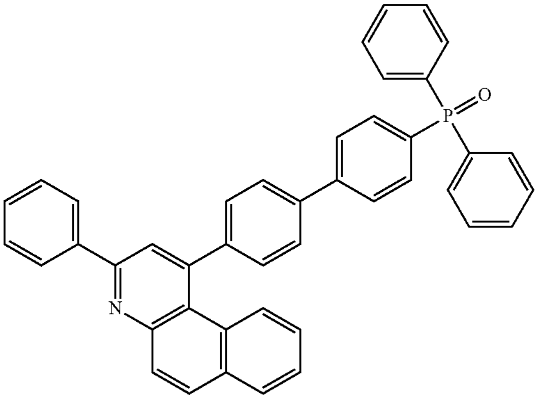 [SMILES: O=P(c1ccccc1)(c1ccccc1)c1ccc(-c2ccc(-c3cc(-c4ccccc4)nc4ccc5ccccc5c34)cc2)cc1] | 65% |

TABLE 3-continued

| Compound Number | Intermediate C | Target Compound C | Yield |
|---|---|---|---|
| 345 | 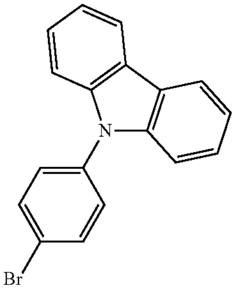 [SMILES: Brc1ccc(-n2c3ccccc3c3ccccc32)cc1] | 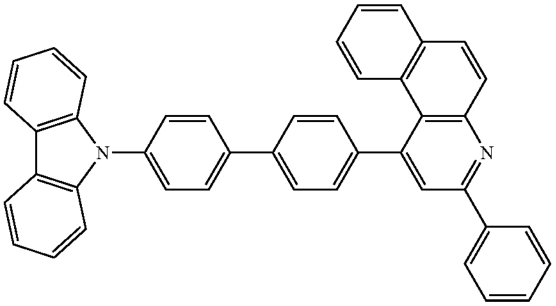 [SMILES: c1ccc(-c2cc(-c3ccc(-c4ccc(-n5c6ccccc6c6ccccc65)cc4)cc3)c3c(ccc4ccccc43)n2)cc1] | 70% |
| 556 | 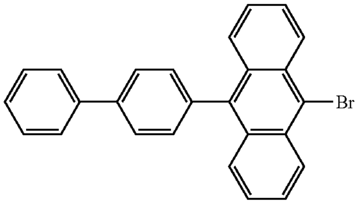 [SMILES: Brc1c2ccccc2c(-c2ccc(-c3ccccc3)cc2)c2ccccc12] | 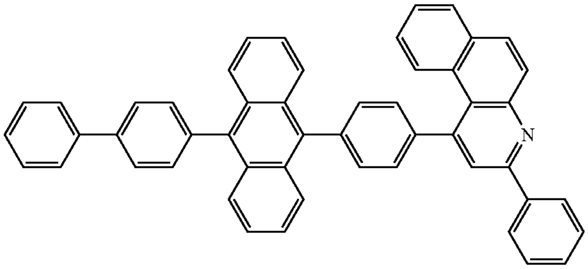 [SMILES: c1ccc(-c2ccc(-c3c4ccccc4c(-c4ccc(-c5cc(-c6ccccc6)nc6ccc7ccccc7c56)cc4)c4ccccc34)cc2)cc1] | 72% |

Compounds were prepared in the same manner as in the preparation examples, and the synthesis identification results are shown in Table 4 and Table 5. Table 4 shows measurement values of $^1H$ NMR ($CDCl_3$, 200 MHz), and Table 5 shows measurement values of field desorption mass spectrometry (FD-MS).

TABLE 4

| Compound | $^1H$ NMR ($CDCl_3$, 200 Mz) |
|---|---|
| 1 | δ = 8.84 (4H, dd), 8.83 (1H, d), 8.54 (1H, d), 8.38 (1H, d), 8.16 (1H, d), 8.10 (1H, d), 8.06 (1H, d), 7.99~7.98 (2H, m), 7.81~7.79 (3H, m), 7.67 (2H, m), 7.64 (1H, s), 7.58 (1H, m), 7.51 (2H, m), 7.41 (1H, m), 7.35 (1H, d) |
| 2 | δ = 8.84 (4H, dd), 8.54 (1H, d), 8.30 (2H, d), 8.16~8.06 (4H, m), 7.99~7.79 (5H, m), 7.67~7.64 (3H, m), 7.54~7.51 (4H, m), 7.47~7.41 (2H, m), 7.35 (2H, m) |
| 3 | δ = 8.83~8.81 (4H, m), 8.54 (1H, m), 8.38 (2H, m), 8.16 (1H, d), 7.99~7.98 (2H, m), 7.79 (2H, d), 7.67~7.64 (4H, m), 7.58~7.51 (4H, m), 7.41 (1H, m), 7.28 (2H, d) |
| 5 | δ = 8.81 (2H, d), 8.54 (1H, d), 8.23 (1H, s), 8.16 (1H, d), 7.99~7.98 (2H, dd), 7.88 (2H, d), 7.79 (6H, m), 7.67~7.64 (3H, m), 7.51 (6H, m), 7.41 (3H, m) |
| 15 | δ = 8.81 (2H, d), 8.54 (1H, d), 8.33~8.23 (5H, m), 8.16 (1H, d), 7.99~7.98 (2H, m), 7.79~7.64 (7H, m), 7.51 (6H, m), 7.41 (3H, m) |
| 25 | δ = 8.81 (2H, d), 8.54 (1H, d), 8.28 (4H, m), 8.16 (1H, m), 7.99~7.98 (2H, m), 7.88 (2H, d), 7.79 (2H, m), 7.67~7.64 (3H, m), 7.51 (6H, m), 7.41 (3H, m) |
| 35 | δ = 9.30~9.15 (4H, m), 8.81 (2H, d), 8.54~8.53 (3H, m), 8.16 (1H, m), 7.99~7.88 (4H, m), 7.79~7.64 (7H, m), 7.51 (2H, m), 7.14 (3H, m) |
| 45 | δ = 8.93 (2H, d), 8.81 (2H, d), 7.89 (1H, m), 8.16 (3H, m), 7.98~7.79 (9H, m), 7.67 (3H, m), 7.51 (3H, m), 7.28 (2H, m) |
| 46 | δ = 8.54 (1H, m), 8.30 (2H, d), 8.16 (1H, m), 7.99~7.98 (2H, m), 7.86~7.77 (8H, m), 7.67~7.64 (3H, m), 7.51 (2H, m), 7.45~7.41 (7H, m) |
| 50 | δ = 8.81 (2H, d), 8.55~8.54 (3H, m), 8.16~8.09 (5H, m), 7.99~7.94 (4H, m), 7.88~7.79 (4H, m), 7.67~7.63 (5H, m), 7.51~7.50 (4H, m), 7.41~7.40 (2H, m), 7.33~7.29 (4H, m), 7.25 (2H, m) |
| 52 | δ = 8.81 (4H, m), 8.54 (1H, m), 8.30 (2H, m), 8.16~7.98 (6H, m), 7.88~7.79 (7H, m), 7.67~7.51 (7H, m), 7.47~7.35 (4H, m) |
| 102 | δ = 8.81 (2H, d), 8.55~8.22 (4H, m), 8.30 (2H, m), 8.16~7.98 (7H, m), 7.81~7.79 (3H, m), 7.67~7.64 (3H, m), 7.55~7.41 (8H, m), 7.35~7.28 (4H, m) |

TABLE 4-continued

| Compound | $^1$H NMR ($CDCl_3$, 200 Mz) |
|---|---|
| 149 | δ = 8.83 (1H, d), 8.72 (1H, s), 8.54 (1H, m), 8.38~8.32 (3H, m), 8.16~8.06 (3H, m), 7.99~7.98 (2H, dd), 7.81~7.79 (3H, m), 7.67~7.63 (4H, m), 7.58~7.51 (3H, m), 7.41~7.35 (2H, m) |
| 150 | δ = 8.72 (1H, s), 8.54 (1H, m), 8.32~8.30 (4H, m), 8.16~7.98 (6H, m), 7.81~7.79 (3H, m), 7.67~7.35 (12H, m) |
| 151 | δ = 8.83 (2H, d), 8.54 (1H, m), 8.38 (2H, dd), 8.26~8.16 (3H, m), 7.99~7.98 (2H, m), 7.79 (2H, m), 7.67~7.41 (11H, m) |
| 153 | δ = 8.54 (1H, m), 8.30~8.16 (5H, m), 7.99~7.98 (2H, dd), 7.79 (613, dd), 7.67~7.41 (13H, m) |
| 163 | δ = 8.54 (1H, m), 8.28~8.16 (6H, m), 7.99~7.98 (2H, dd), 7.81~7.79 (5H, m), 7.67~7.41 (13H, m) |
| 173 | δ = 8.54 (1H, m), 8.30~8.16 (8H, m), 7.99~7.98 (2H, m), 7.79 (2H, m), 7.67~7.41 (13H, m) |
| 183 | δ = 9.30 (2H, dd), 9.15 (2H, s), 8.54~8.53 (3H, m), 8.26~8.16 (3H, m), 7.99~7.98 (2H, m), 7.79~7.41 (12H, m), 7.14 (2H, m) |
| 194 | δ = 8.54 (1H, m), 8.30 (1H, dd), 8.17~8.16 (2H, m), 7.99~7.98 (2H, m), 7.79~7.77 (7H, m), 7.67~7.64 (3H, m), 7.54~7.41 (10H, s) |
| 198 | δ = 8.55~8.54 (3H, m), 8.26~8.09 (7H, m), 7.99~7.94 (4H, m), 7.79 (2H, m), 7.67~7.25 (19H, m) |
| 199 | δ = 8.81 (2H, dd), 8.54 (1H, dd), 8.30~7.98 (10H, m), 7.88~7.79 (5H, m), 7.67~7.35 (13H, m) |
| 249 | δ = 8.81 (3H, m), 8.54 (1H, dd), 8.38 (3H, m), 8.16~7.98 (5H, m), 7.81 (1H, dd) 7.64~7.47 (7H, m) 7.28 (3H, m) |
| 344 | δ = 8.54 (1H, d), 8.30 (2H, m), 8.16 (1H, d), 7.98 (2H, d) 7.79~7.45 (20H, m), 7.25 (4H, m) |
| 345 | δ = 8.55 (2H, m), 8.30 (2H, m), 8.16 (2H, m), 7.98 (3H, m) 7.79 (2H, m) 7.67~7.54 (10H, m), 7.29 (7H, m) |
| 555 | δ = 8.55~8.52 (4H, m), 8.30~7.98 (11H, m), 7.81~7.79 (3H, m), 7.67~7.35 (15H, m) |
| 556 | δ = 8.54 (1H, d), 8.30 (2H, dd), 8.16 (1H, d), 7.91 (6H, m) 7.64~7.39 (15H, m) 7.25 (8H, m) |

TABLE 5

| Compound | FD-MS | Compound | FD-MS |
|---|---|---|---|
| 1 | m/z = 509.60 (C37H23N3 = 509.19) | 2 | m/z = 585.69 (C43H27N3 = 585.22) |
| 3 | m/z = 509.60 (C37H23N3 = 509.19) | 4 | m/z = 661.79 (C49H31N3 = 661.25) |
| 5 | m/z = 561.67 (C41H27N3 = 561.22) | 6 | m/z = 637.77 (C47H31N3 = 637.25) |
| 7 | m/z = 713.87 (C53H35N3 = 713.28) | 8 | m/z = 661.79 (C49H31N3 = 661.25) |
| 9 | m/z = 661.79 (C49H31N3 = 661.25) | 10 | m/z = 637.77 (C47H31N3 = 637.25) |
| 11 | m/z = 713.87 (C53H35N3 = 713.28) | 12 | m/z = 563.65 (C39H25N5 = 563.21) |
| 13 | m/z = 563.65 (C39H25N5 = 563.21) | 14 | m/z = 563.65 (C39H25N5 = 563.21) |
| 15 | m/z = 561.67 (C41H27N3 = 561.22) | 16 | m/z = 637.77 (C47H31N3 = 637.25) |
| 17 | m/z = 713.87 (C53H35N3 = 713.28) | 18 | m/z = 661.79 (C49H31N3 = 661.25) |
| 19 | m/z = 661.79 (C49H31N3 = 661.25) | 20 | m/z = 637.77 (C47H31N3 = 637.25) |
| 21 | m/z = 713.87 (C53H35N3 = 713.28) | 22 | m/z = 563.65 (C39H25N5 = 563.21) |
| 23 | m/z = 563.65 (C39H25N5 = 563.21) | 24 | m/z = 563.65 (C39H25N5 = 563.21) |
| 25 | m/z = 562.66 (C40H26N4 = 562.22) | 26 | m/z = 638.76 (C46H30N4 = 638.25) |
| 27 | m/z = 714.85 (C52H34N4 = 714.28) | 28 | m/z = 662.78 (C48H30N4 = 662.25) |
| 29 | m/z = 662.78 (C48H30N4 = 662.25) | 30 | m/z = 585.69 (C46H30N4 = 638.25) |
| 31 | m/z = 714.85 (C52H34N4 = 714.28) | 32 | m/z = 564.64 (C38H24N6 = 564.21) |
| 33 | m/z = 564.64 (C38H24N6 = 564.21) | 34 | m/z = 564.64 (C38H24N6 = 564.21) |
| 35 | m/z = 562.66 (C40H26N4 = 562.22) | 36 | m/z = 458.55 (C34H22N2 = 458.18) |

TABLE 5-continued

| Compound | FD-MS | Compound | FD-MS |
|---|---|---|---|
| 37 | m/z = 458.55 ($C_{34}H_{22}N_2$ = 458.18) | 38 | m/z = 458.55 ($C_{34}H_{22}N_2$ = 458.18) |
| 39 | m/z = 458.55 ($C_{34}H_{22}N_2$ = 458.18) | 40 | m/z = 458.55 ($C_{34}H_{22}N_2$ = 458.18) |
| 41 | m/z = 583.72 ($C_{45}H_{29}N$ = 583.23) | 42 | m/z = 633.78 ($C_{49}H_{31}N$ = 633.25) |
| 43 | m/z = 659.81 ($C_{51}H_{33}N$ = 659.26) | 44 | m/z = 759.93 ($C_{59}H_{37}N$ = 759.29) |
| 45 | m/z = 507.62 ($C_{39}H_{25}N$ = 507.20) | 46 | m/z = 531.58 ($C_{37}H_{26}NOP$ = 531.18) |
| 47 | m/z = 496.60 ($C_{37}H_{24}N_{23}$ = 496.19) | 48 | m/z = 572.70 ($C_{43}H_{28}N_2$ = 572.23) |
| 49 | m/z = 572.70 ($C_{43}H_{28}N_2$ = 572.23) | 50 | m/z = 737.89 ($C_{55}H_{35}N_3$ = 737.28) |
| 51 | m/z = 585.69 ($C_{43}H_{27}N_3$ = 585.22) | 52 | m/z = 661.79 ($C_{49}H_{31}N_3$ = 661.25) |
| 53 | m/z = 585.69 ($C_{43}H_{27}N_3$ = 585.22) | 54 | m/z = 737.89 ($C_{55}H_{35}N_3$ = 737.28) |
| 55 | m/z = 637.77 ($C_{47}H_{31}N_3$ = 637.25) | 56 | m/z = 713.87 ($C_{53}H_{35}N_3$ = 713.28) |
| 57 | m/z = 789.96 ($C_{59}H_{39}N_3$ = 789.31) | 58 | m/z = 737.89 ($C_{55}H_{35}N_3$ = 737.28) |
| 59 | m/z = 737.89 ($C_{55}H_{35}N_3$ = 737.28) | 60 | m/z = 713.87 ($C_{53}H_{35}N_3$ = 713.28) |
| 61 | m/z = 789.96 ($C_{59}H_{39}N_3$ = 789.31) | 62 | m/z = 639.75 ($C_{45}H_{29}N_5$ = 639.24) |
| 63 | m/z = 639.75 ($C_{45}H_{29}N_5$ = 639.24) | 64 | m/z = 639.75 ($C_{45}H_{29}N_5$ = 639.24) |
| 65 | m/z = 637.77 ($C_{47}H_{31}N_3$ = 637.25) | 66 | m/z = 713.87 ($C_{53}H_{35}N_3$ = 713.28) |
| 67 | m/z = 789.96 ($C_{59}H_{39}N_3$ = 789.31) | 68 | m/z = 737.89 ($C_{55}H_{35}N_3$ = 737.28) |
| 69 | m/z = 737.89 ($C_{55}H_{35}N_3$ = 737.28) | 70 | m/z = 713.87 ($C_{53}H_{35}N_3$ = 713.28) |
| 71 | m/z = 789.96 ($C_{59}H_{39}N_3$ = 789.31) | 72 | m/z = 639.75 ($C_{45}H_{29}N_5$ = 639.24) |
| 73 | m/z = 639.75 ($C_{45}H_{29}N_5$ = 639.24) | 74 | m/z = 639.75 ($C_{45}H_{29}N_5$ = 639.24) |
| 75 | m/z = 638.76 ($C_{46}H_{30}N_4$ = 638.25) | 76 | m/z = 714.85 ($C_{52}H_{34}N_4$ = 714.28) |
| 77 | m/z = 790.95 ($C_{58}H_{38}N_4$ = 790.31) | 78 | m/z = 738.87 ($C_{54}H_{34}N_4$ = 738.28) |
| 79 | m/z = 738.87 ($C_{54}H_{34}N_4$ = 738.28) | 80 | m/z = 714.85 ($C_{52}H_{34}N_4$ = 714.28) |
| 81 | m/z = 790.95 ($C_{58}H_{38}N_4$ = 790.31) | 82 | m/z = 640.73 ($C_{44}H_{28}N_6$ = 640.24) |
| 83 | m/z = 640.73 ($C_{44}H_{28}N_6$ = 640.24) | 84 | m/z = 640.73 ($C_{44}H_{28}N_6$ = 640.24) |
| 85 | m/z = 638.76 ($C_{46}H_{30}N_4$ = 638.25) | 86 | m/z = 534.65 ($C_{40}H_{26}N_2$ = 534.21) |
| 87 | m/z = 534.65 ($C_{40}H_{26}N_2$ = 534.21) | 88 | m/z = 534.65 ($C_{40}H_{26}N_2$ = 534.21) |
| 89 | m/z = 534.65 ($C_{40}H_{26}N_2$ = 534.21) | 90 | m/z = 534.65 ($C_{40}H_{26}N_2$ = 534.21) |
| 91 | m/z = 659.81 ($C_{51}H_{33}N$ = 659.26) | 92 | m/z = 709.87 ($C_{55}H_{35}N$ = 709.28) |
| 93 | m/z = 735.91 ($C_{57}H_{37}N$ = 735.29) | 94 | m/z = 836.03 ($C_{65}H_{41}N$ = 835.32) |
| 95 | m/z = 583.72 ($C_{45}H_{29}N$ = 583.23) | 96 | m/z = 607.68 ($C_{43}H_{30}NOP$ = 607.21) |
| 97 | m/z = 572.70 ($C_{43}H_{28}N_2$ = 572.23) | 98 | m/z = 648.79 ($C_{49}H_{32}N_2$ = 648.26) |
| 99 | m/z = 648.79 ($C_{49}H_{32}N_2$ = 648.26) | 100 | m/z = 813.98 ($C_{61}H_{39}N_3$ = 813.31) |
| 101 | m/z = 635.75 ($C_{47}H_{29}N_3$ = 635.24) | 102 | m/z = 711.85 ($C_{53}H_{33}N_3$ = 711.27) |
| 103 | m/z = 635.75 ($C_{47}H_{29}N_3$ = 635.24) | 104 | m/z = 787.95 ($C_{59}H_{37}N_3$ = 787.30) |
| 105 | m/z = 687.83 ($C_{51}H_{33}N_3$ = 687.27) | 106 | m/z = 763.92 ($C_{57}H_{37}N_3$ = 763.30) |
| 107 | m/z = 840.02 ($C_{63}H_{41}N_3$ = 839.33) | 108 | m/z = 787.95 ($C_{59}H_{37}N_3$ = 787.30) |
| 109 | m/z = 787.95 ($C_{59}H_{37}N_3$ = 787.30) | 110 | m/z = 763.92 ($C_{57}H_{37}N_3$ = 763.30) |
| 111 | m/z = 840.02 ($C_{63}H_{41}N_3$ = 839.33) | 112 | m/z = 689.80 ($C_{49}H_{31}N_5$ = 689.26) |
| 113 | m/z = 689.80 ($C_{49}H_{31}N_5$ = 689.26) | 114 | m/z = 689.80 ($C_{49}H_{31}N_5$ = 689.26) |

TABLE 5-continued

| Compound | FD-MS | Compound | FD-MS |
|---|---|---|---|
| 115 | m/z = 687.83<br>(C51H33N3 = 687.27) | 116 | m/z = 763.92<br>(C57H37N3 = 763.30) |
| 117 | m/z = 840.02<br>(C63H41N3 = 839.33) | 118 | m/z = 787.95<br>(C59H37N3 = 787.30) |
| 119 | m/z = 737.89<br>(C55H35N3 = 737.28) | 120 | m/z = 763.92<br>(C57H37N3 = 763.30) |
| 121 | m/z = 840.02<br>(C63H41N3 = 839.33) | 122 | m/z = 689.80<br>(C49H31N5 = 689.26) |
| 123 | m/z = 689.80<br>(C49H31N5 = 689.26) | 124 | m/z = 689.80<br>(C49H31N5 = 689.26) |
| 125 | m/z = 688.82<br>(C50H32N4 = 688.26) | 126 | m/z = 764.91<br>(C56H36N4 = 764.29) |
| 127 | m/z = 841.01<br>(C62H40N4 = 840.33) | 128 | m/z = 788.93<br>(C58H36N4 = 788.29) |
| 129 | m/z = 788.93<br>(C58H36N4 = 788.29) | 130 | m/z = 764.91<br>(C56H36N4 = 764 .29) |
| 131 | m/z = 841.01<br>(C62H40N4 = 840.33) | 132 | m/z = 690.79<br>(C48H30N6 = 690.25) |
| 133 | m/z = 690.79<br>(C48H30N6 = 690.25) | 134 | m/z = 690.79<br>(C48H30N6 = 690.25) |
| 135 | m/z = 688.82<br>(C50H32N4 = 688.26) | 136 | m/z = 584.71<br>(C44H28N2 = 584.23) |
| 137 | m/z = 584.71<br>(C44H28N2 = 584.23) | 138 | m/z = 584.71<br>(C44H28N2 = 584.23) |
| 139 | m/z = 584.71<br>(C44H28N2 = 584.23) | 140 | m/z = 584.71<br>(C44H28N2 = 584.23) |
| 141 | m/z = 709.87<br>(C55H35N = 709.28) | 142 | m/z = 759.93<br>(C59H37N = 759.29) |
| 143 | m/z = 785.97<br>(C61H39N = 785.31) | 144 | m/z = 886.09<br>(C69H43N = 885.34) |
| 145 | m/z = 633.78<br>(C49H31N = 633.25) | 146 | m/z = 657.74<br>(C47H32NOP = 657.22) |
| 147 | m/z = 622.75<br>(C47H30N2 = 622.24) | 148 | m/z = 698.85<br>(C53H34N2 = 698.27) |
| 149 | m/z = 509.60<br>(C37H23N3 = 509.19) | 150 | m/z = 585.69<br>(C43H27N3 = 585.22) |
| 151 | m/z = 509.60<br>(C37H23N3 = 509.19) | 152 | m/z = 661.79<br>(C49H31N3 = 661.25) |
| 153 | m/z = 561.67<br>(C41H27N3 = 561.22) | 154 | m/z = 637.77<br>(C47H31N3 = 637.25) |
| 155 | m/z = 713.87<br>(C53H35N3 = 713.28) | 156 | m/z = 661.79<br>(C49H31N3 = 661.25) |
| 157 | m/z = 661.79<br>(C49H31N3 = 661.25) | 158 | m/z = 637.77<br>(C47H31N3 = 637.25) |
| 159 | m/z = 713.87<br>(C53H35N3 = 713.28) | 160 | m/z = 563.65<br>(C39H25N5 = 563.21) |
| 161 | m/z = 563.65<br>(C39H25N5 = 563.21) | 162 | m/z = 563.65<br>(C39H25N5 = 563.21) |
| 163 | m/z = 561.67<br>(C41H27N3 = 561.22) | 164 | m/z = 637.77<br>(C47H31N3 = 637.25) |
| 165 | m/z = 713.87<br>(C53H35N3 = 713.28) | 166 | m/z = 661.79<br>(C49H31N3 = 661.25) |
| 167 | m/z = 661.79<br>(C49H31N3 = 661.25) | 168 | m/z = 637.77<br>(C47H31N3 = 637.25) |
| 169 | m/z = 713.87<br>(C53H35N3 = 713.28) | 170 | m/z = 563.65<br>(C39H25N5 = 563.21) |
| 171 | m/z = 563.65<br>(C39H25N5 = 563.21) | 172 | m/z = 563.65<br>(C39H25N5 = 563.21) |
| 173 | m/z = 562.66<br>(C40H26N4 = 562.22) | 174 | m/z = 638.76<br>(C46H30N4 = 638.25) |
| 175 | m/z = 714.85<br>(C52H34N4 = 714.28) | 176 | m/z = 662.78<br>(C48H30N4 = 662.25) |
| 177 | m/z = 662.78<br>(C48H30N4 = 662.25) | 178 | m/z = 638.76<br>(C46H30N4 = 638.25) |
| 179 | m/z = 714.85<br>(C52H34N4 = 714.28) | 180 | m/z = 564.64<br>(C38H24N6 = 564.21) |
| 181 | m/z = 564.64<br>(C38H24N6 = 564.21) | 182 | m/z = 564.64<br>(C38H24N6 = 564.21) |
| 183 | m/z = 562.66<br>(C40H26N4 = 562.22) | 184 | m/z = 458.55<br>(C34H22N2 = 458.18) |
| 185 | m/z = 458.55<br>(C34H22N2 = 458.18) | 186 | m/z = 458.55<br>(C34H22N2 = 458.18) |
| 187 | m/z = 458.55<br>(C34H22N2 = 458.18) | 188 | m/z = 458.55<br>(C34H22N2 = 458.18) |
| 189 | m/z = 583.72<br>(C45H29N = 583.23) | 190 | m/z = 633.78<br>(C49H31N = 633.25) |
| 191 | m/z = 659.81<br>(C51H33N = 659.26) | 192 | m/z = 759.93<br>(C59H37N = 759.29) |

TABLE 5-continued

| Compound | FD-MS | Compound | FD-MS |
|---|---|---|---|
| 193 | m/z = 507.62 (C39H25N = 507.20) | 194 | m/z = 531.58 (C37H26NOP = 531.18) |
| 195 | m/z = 496.60 (C37H24N2 = 496.19) | 196 | m/z = 572.70 (C43H28N2 = 572.23) |
| 197 | m/z = 572.70 (C43H28N2 = 572.23) | 198 | m/z = 737.89 (C55H35N3 = 737.28) |
| 199 | m/z = 585.69 (C43H27N3 = 585.22) | 200 | m/z = 661.79 (C49H31N3 = 661.25) |
| 201 | m/z = 585.69 (C43H27N3 = 585.22) | 202 | m/z = 737.89 (C55H35N3 = 737.28) |
| 203 | m/z = 637.77 (C47H31N3 = 637.25) | 204 | m/z = 713.87 (C53H35N3 = 713.28) |
| 205 | m/z = 789.96 (C59H39N3 = 789.31) | 206 | m/z = 737.89 (C55H35N3 = 737.28) |
| 207 | m/z = 737.89 (C55H35N3 = 737.28) | 208 | m/z = 713.87 (C53H35N3 = 713.28) |
| 209 | m/z = 789.96 (C59H39N3 = 789.31) | 210 | m/z = 639.75 (C45H29N5 = 639.24) |
| 211 | m/z = 639.75 (C45H29N5 = 639.24) | 212 | m/z = 639.75 (C45H29N5 = 639.24) |
| 213 | m/z = 637.77 (C47H31N3 = 637.25) | 214 | m/z = 713.87 (C53H35N3 = 713.28) |
| 215 | m/z = 789.96 (C59H39N3 = 789.31) | 216 | m/z = 737.89 (C55H35N3 = 737.28) |
| 217 | m/z = 737.89 (C55H35N3 = 737.28) | 218 | m/z = 713.87 (C53H35N3 = 713.28) |
| 219 | m/z = 789.98 (C59H39N3 = 789.31) | 220 | m/z = 639.76 (C45H29N5 = 639.24) |
| 221 | m/z = 639.76 (C45H29N5 = 639.24) | 222 | m/z = 639.76 (C45H29N5 = 639.24) |
| 223 | m/z = 638.77 (C46H30N4 = 638.24) | 224 | m/z = 714.87 (C52H34N4 = 714.27) |
| 225 | m/z = 790.97 (C58H38N4 = 790.31) | 226 | m/z = 738.89 (C54H34N4 = 738.27) |
| 227 | m/z = 738.89 (C54H34N4 = 738.27) | 228 | m/z = 714.87 (C52H34N4 = 714.27) |
| 229 | m/z = 790.97(C58H38N4 = 790.31) | 230 | m/z = 640.75 (C44H28N6 = 640.23) |
| 231 | m/z = 640.75 (C44H28N6 = 640.23) | 232 | m/z = 640.75 (C44H28N6 = 640.23) |
| 233 | m/z = 638.77 (C46H30N4 = 638.24) | 234 | m/z = 534.66 (C40H26N2 = 534.21) |
| 235 | m/z = 534.66 (C40H26N2 = 534.21) | 236 | m/z = 534.66 (C = 40H26N2 = 534.21) |
| 237 | m/z = 534.66 (C40H26N2 = 534.21) | 238 | m/z = 534.66 (C40H26N2 = 534.21) |
| 239 | m/z = 659.83 (C51H33N = 659.26) | 240 | m/z = 709.89 (C55H35N = 709.27) |
| 241 | m/z = 735.93 (C57H37N = 735.29) | 242 | m/z = 836.05 (C65H41N = 835.32) |
| 243 | m/z = 583.73 (C45H29N = 583.23) | 244 | m/z = 607.69 (C43N30NOP = 607.20) |
| 245 | m/z = 572.71 (C43H28N2 = 572.22) | 246 | m/z = 648.80 (C49H32N2 = 648.25) |
| 247 | m/z = 648.80 (C49H32N2 = 648.25) | 248 | m/z = 814.00 (C61H39N3 = 813.31) |
| 249 | m/z = 509.61 (C37H23N3 = 509.18) | 250 | m/z = 585.71 (C43H27N3 = 858.22) |
| 251 | m/z = 509.61 (C37H23N3 = 509.18) | 252 | m/z = 661.80 (C49H31N3 = 661.25) |
| 253 | m/z = 561.68 (C41H27N3 = 561.22) | 254 | m/z = 637.78 (C47H31N3 = 637.25) |
| 255 | m/z = 713.88 (C53H35N3 = 713.28) | 256 | m/z = 661.80 (C49H31N3 = 661.25) |
| 257 | m/z = 661.80 (C49H31N3 = 661.25) | 258 | m/z = 637.78 (C47J31N3 = 637.25) |
| 259 | m/z = 713.88 (C53H35N3 = 713.28) | 260 | m/z = 563.66 (C39H25N5 = 563.21) |
| 261 | m/z = 563.66 (C39H25N5 = 563.21) | 262 | m/z = 563.66 (C39H25N5 = 563.21) |
| 263 | m/z = 561.68 (C41H27N3 = 561.22) | 264 | m/z = 637.78 (C47H31N3 = 637.25) |
| 265 | m/z = 713.88 (C53H35N3 = 713.28) | 266 | m/z = 661.80 (C49H31N3 = 661.25) |
| 267 | m/z = 661.80 (C49H31N3 = 661.25) | 268 | m/z = 637.78 (C47H31N3 = 637.25) |
| 269 | m/z = 713.88 (C53H35N3 = 713.28) | 270 | m/z = 563.66 (C39H25N5 = 563.21) |

TABLE 5-continued

| Compound | FD-MS | Compound | FD-MS |
|---|---|---|---|
| 271 | m/z = 563.66 ($C_{39}H_{25}N_5$ = 563.21) | 272 | m/z = 563.66 ($C_{39}H_{25}N_5$ = 563.21) |
| 273 | m/z = 562.67 ($C_{40}H_{26}N_4$ = 562.21) | 274 | m/z = 638.77 ($C_{46}H_{30}N_4$ = 638.24) |
| 275 | m/z = 714.87 ($C_{52}H_{34}N_4$ = 714.27) | 276 | m/z = 662.79 ($C_{48}H_{30}N_4$ = 662.24) |
| 277 | m/z = 662.79 ($C_{48}H_{30}N_4$ = 662.24) | 278 | m/z = 638.77 ($C_{46}H_{30}N_4$ = 638.24) |
| 279 | m/z = 714.87 ($C_{52}H_{34}N_4$ = 714.27) | 280 | m/z = 564.65 ($C_{38}H_{24}N_6$ = 564.20) |
| 281 | m/z = 564.65 ($C_{38}H_{24}N_6$ = 564.20) | 282 | m/z = 564.65 ($C_{38}H_{24}N_6$ = 564.20) |
| 283 | m/z = 562.67 ($C_{40}H_{26}N_4$ = 562.21) | 284 | m/z = 458.56 ($C_{34}H_{22}N_2$ = 458.17) |
| 285 | m/z = 458.56 ($C_{34}H_{22}N_2$ = 458.17) | 286 | m/z = 458.56 ($C_{34}H_{22}N_2$ = 458.17) |
| 287 | m/z = 458.56 ($C_{34}H_{22}N_2$ = 458.17) | 288 | m/z = 458.56 ($C_{34}H_{22}N_2$ = 458.17) |
| 289 | m/z = 583.73 ($C_{45}H_{29}N$ = 583.23) | 290 | m/z = 633.79 ($C_{49}H_{31}N$ = 633.24) |
| 291 | m/z = 659.83 ($C_{51}H_{33}N$ = 659.26) | 292 | m/z = 759.95 ($C_{59}H_{37}N$ = 759.29) |
| 293 | m/z = 507.63 ($C_{39}H_{25}N$ = 507.19) | 294 | m/z = 531.59 ($C_{37}H_{26}NOP$ = 531.17) |
| 295 | m/z = 496.61 ($C_{37}H_{24}N_2$ = 496.19) | 296 | m/z = 572.71 ($C_{43}H_{28}N_2$ = 572.22) |
| 297 | m/z = 572.71 ($C_{43}H_{28}N_2$ = 572.22) | 298 | m/z = 737.90 ($C_{55}H_{35}N_3$ = 737.28) |
| 299 | m/z = 585.71 ($C_{43}H_{27}N_3$ = 585.22) | 300 | m/z = .661.80 ($C_{49}H_{31}N_3$ = 661.25) |
| 301 | m/z = 585.71 ($C_{43}H_{27}N_3$ = 585.22) | 302 | m/z = 737.90 ($C_{55}H_{35}N_3$ = 737.28) |
| 303 | m/z = 585.71 ($C_{43}H_{27}N_3$ = 585.22) | 304 | m/z = 737.90 ($C_{55}H_{35}N_3$ = 737.28) |
| 305 | m/z = 637.78 ($C_{47}H_{31}N_3$ = 637.25) | 306 | m/z = 713.88 ($C_{53}H_{35}N_3$ = 713.28) |
| 307 | m/z = 789.98 ($C_{59}H_{39}N_3$ = 789.31) | 308 | m/z = 737.90 ($C_{55}H_{35}N_3$ = 737.28) |
| 309 | m/z = 737.90 ($C_{55}H_{35}N_3$ = 737.28) | 310 | m/z = 713.88 ($C_{53}H_{35}N_3$ = 713.28) |
| 311 | m/z = 789.98 ($C_{59}H_{39}N_3$ = 789.31) | 312 | m/z = 639.76 ($C_{45}H_{29}N_5$ = 639.24) |
| 313 | m/z = 639.76 ($C_{45}H_{29}N_5$ = 639.24) | 314 | m/z = 639.76 ($C_{45}H_{29}N_5$ = 639.24) |
| 315 | m/z = 637.78 ($C_{47}H_{31}N_3$ = 637.25) | 316 | m/z = 713.88 ($C_{53}H_{35}N_3$ = 713.28) |
| 317 | m/z = 789.98 ($C_{59}H_{39}N_3$ = 789.31) | 318 | m/z = 737.90 ($C_{55}H_{35}N_3$ = 737.28) |
| 319 | m/z = 737.90 ($C_{55}H_{35}N_3$ = 737.28) | 320 | m/z = 713.88 ($C_{53}H_{35}N_3$ = 713.28) |
| 321 | m/z = 639.76 ($C_{45}H_{29}N_5$ = 639.24) | 322 | m/z = 639.76 ($C_{45}H_{29}N_5$ = 639.24) |
| 323 | m/z = 638.77 ($C_{46}H_{30}N_4$ = 638.24) | 324 | m/z = 714.87 ($C_{52}H_{34}N_4$ = 714.27) |
| 325 | m/z = 790.97 ($C_{58}H_{38}N_4$ = 790.31) | 326 | m/z = 738.89 ($C_{54}H_{34}N_4$ = 738.27) |
| 327 | m/z = 738.89 ($C_{54}H_{34}N_4$ = 738.27) | 328 | m/z = 714.87 ($C_{52}H_{34}N_4$ = 714.87) |
| 329 | m/z = 790.97 ($C_{58}H_{38}N_4$ = 790.31) | 330 | m/z = 640.75 ($C_{44}H_{28}N_6$ = 640.23) |
| 331 | m/z = 640.75 ($C_{44}H_{28}N_6$ = 640.23) | 332 | m/z = 640.75 ($C_{44}H_{28}N_6$ = 640.23) |
| 333 | m/z = 638.77 ($C_{46}H_{30}N_4$ = 638.24) | 334 | m/z = 534.66 ($C_{40}H_{26}N_2$ = 534.21) |
| 335 | m/z = 534.66 ($C_{44}H_{26}N_2$ = 534.21) | 336 | m/z = 534.66 ($C_{40}H_{26}N_2$ = 534.21) |
| 337 | m/z = 534.66 ($C_{40}H_{26}N_2$ = 534.21) | 338 | m/z = 534.66 ($C_{40}H_{26}N_2$ = 534.21) |
| 339 | m/z = 659.83 ($C_{51}H_{33}N$ = 659.26) | 340 | m/z = 709.89 ($C_{55}H_{35}N$ = 709.27) |
| 341 | m/z = 735.93 ($C_{57}H_{37}N$ = 735.29) | 342 | m/z = 836.05 ($C_{65}H_{41}N$ = 835.32) |
| 343 | m/z = 583.73 ($C_{45}H_{29}N$ = 583.23) | 344 | m/z = 607.69 ($C_{43}H_{30}NOP$ = 607.20) |
| 345 | m/z = 572.71 ($C_{43}H_{28}N_2$ = 572.22) | 346 | m/z = 648.80 ($C_{49}H_{32}N_2$ = 648.25) |
| 347 | m/z = 648.80 ($C_{49}H_{32}N_2$ = 648.25) | 348 | m/z = 814.00 ($C_{61}H_{39}N$# = 813.31) |

TABLE 5-continued

| Compound | FD-MS | Compound | FD-MS |
|---|---|---|---|
| 349 | m/z = 635.77 | 350 | m/z = 711.86 |
| | (C47H29N3 = 635.23) | | (C53H33N3 = 711.26) |
| 351 | m/z = 635.77 | 352 | m/z = 787.96 |
| | (C47H29N3 = 635.23) | | (C59H37N3 = 787.29) |
| 353 | m/z = 687.84 | 354 | m/z = 763.94 |
| | (C51H33N3 = 687.26) | | (C57H37N3 = 763.29) |
| 355 | m/z = 840.04 | 356 | m/z = 787.96 |
| | (C63H41N3 = 839.33) | | (C59H37N3 = 787.29) |
| 357 | m/z = 787.96 | 358 | m/z = 763.94 |
| | (C59H37N3 = 787.29) | | (C57H37N3 = 763.29) |
| 359 | m/z = 840.04 | 360 | m/z = 689.82 |
| | (C63H41N3 = 839.33) | | (C49H31N5 = 689.25) |
| 361 | m/z = 689.82 | 362 | m/z = 689.82 |
| | (C49H31N5 = 689.25) | | (C49H31N5 = 689.25) |
| 363 | m/z = 687.84 | 364 | m/z = 763.94 |
| | (C51H33N3 = 687.26) | | (C57H37N4 = 763.29) |
| 365 | m/z = 840.04 | 366 | m/z = 787.96 |
| | (C63H41N3 = 839.33) | | (C59H3N3 = 787.29) |
| 367 | m/z = 787.96 | 368 | m/z = 763.94 |
| | (C59H37N3 = 787.29) | | (C57H37N3 = 763.29) |
| 369 | m/z = 840.04 | 370 | m/z = 689.82 |
| | (C63H41N3 = 839.33) | 372 | (C49H31N5 = 689.25) |
| 371 | m/z = 689.82 | | m/z = 689.82 |
| | (C49H31N5 = 689.25) | 374 | (C49H31N5 = 689.25) |
| 373 | m/z = 688.83 | 374 | m/z = 764.93 |
| | (C50H32N4 = 688.26) | | (C56H36N4 = 764.29) |
| 375 | m/z = 841.03 | 376 | m/z = 788.95 |
| | (C62H40N4 = 840.32) | | (C58H36N4 = 788.29) |
| 377 | m/z = 788.95 | 378 | m/z = 764.93 |
| | (C58H36N4 = 788.29) | | (C56H36N4 = 764.29) |
| 379 | m/z = 841.03 | 380 | m/z = 690.81 |
| | (C62H40N4 = 840.32) | | (C48H30N6 = 690.25) |
| 381 | m/z = 690.81 | 382 | m/z = 690.81 |
| | (C48H30N6 = 690.25) | | (C48H30N6 = 690.25) |
| 383 | m/z = 688.83 | 384 | m/z = 584.72 |
| | (C50H32N4 = 688.26) | | (C44H28N2 = 584.22) |
| 385 | m/z = 584.72 | 386 | m/z = 584.72 |
| | (C44H28N2 = 584.22) | | (C44H28N2 = 584.22) |
| 387 | m/z = 584.72 | 388 | m/z = 584.72 |
| | (C44H28N2 = 584.22) | | (C44H28N2 = 584.22) |
| 389 | m/z = 709.89 | 390 | m/z = 759.95 |
| | (C55H35N = 709.27) | | (C59H37N = 759.29) |
| 391 | m/z = 785.99 | 392 | m/z = 886.11 |
| | (C61H39N = 785.30) | | (C69H43N = 885.34) |
| 393 | m/z = 633.79 | 394 | m/z = 657.75 |
| | (C49H31N = 633.24) | | (C47H32NOP = 657.22) |
| 395 | m/z = 622.77 | 396 | m/z = 698.86 |
| | (C47H30N2 = 622.24) | | (C53H34N2 = 698.27) |
| 397 | m/z = 698.86 | 398 | m/z = 864.06 |
| | (C53H34N2 = 698.27) | | (C65.41N3 = 863.33) |
| 399 | m/z = 509..61 | 400 | m/z = 585.71 |
| | (C37H23N3 = 509.18) | | (C43H27N3 = 585.22) |
| 401 | m/z = 509.61 | 402 | m/z = 661.80 |
| | (C37H23N3 = 509.18) | | (C49H31N3 = 661.25) |
| 403 | m/z = 561.68 | 404 | m/z = 637.78 |
| | (C41H27N3 = 561.22) | | (C47H31N3 = 637.25) |
| 405 | m/z = 713.88 | 406 | m/z = 661.80 |
| | (C53H35N3 = 713.28) | | (C49H31N3 = 661.25) |
| 407 | m/z = 661.80 | 408 | m/z = 637.78 |
| | (C49H31N3 = 661.25) | | (C47H31N3 = 637.25) |
| 409 | m/z = 713.88 | 410 | m/z = 563.66 |
| | (C53N35N3 = 713.28) | | (C39H25N5 = 563.21) |
| 411 | m/z = 563.66 | 412 | m/z = 563.66 |
| | (C39H25N5 = 563.21) | | (C39H25N5 = 563.21) |
| 413 | m/z = 561.68 | 414 | m/z = 637.78 |
| | (C41H27N3 = 561.22) | | (C47H31N3 = 637.25) |
| 415 | m/z = 713.88 | 416 | m/z = 661.80 |
| | (C53H35N3 = 713.28) | | (C49H31N3 = 661.25) |
| 417 | m/z = 661.80 | 418 | m/z = 637.78 |
| | (C49H31N3 = 661.25) | | (C47H31N3 = 637.25) |
| 419 | m/z = 713.88 | 420 | m/z = 563.66 |
| | (C53H35N3 = 713.28) | | (C39H25N5 = 563.21) |
| 421 | m/z = 563.66 | 422 | m/z = 563.66 |
| | (C39H25N5 = 563.21) | | (C39H25N5 = 563.21) |
| 423 | m/z = 562.67 | 424 | m/z = 638.77 |
| | (C40H26N4 = 562.21) | | (C46H30N4 = 638.24) |
| 425 | m/z = 714.87 | 426 | m/z = 662.79 |
| | (C52H34N4 = 714.27) | | (C48H30N4 = 662.24) |

TABLE 5-continued

| Compound | FD-MS | Compound | FD-MS |
|---|---|---|---|
| 427 | m/z = 662.79 (C48H30N4 = 662.24) | 428 | m/z = 638.77 (C46H30N4 = 638.24) |
| 429 | m/z = 714.87 (C52H34N4 = 714.27) | 430 | m/z = 564.65 (C38N24N6 = 564.20) |
| 431 | m/z = 564.65 (C38H24N6 = 564.20) | 432 | m/z = 564.65 (C38H24N6 = 564.20) |
| 433 | m/z = 562.67 (C40H26N4 = 562.21) | 434 | m/z = 458.56 (C34H22N2 = 458.17) |
| 435 | m/z = 458.56 (C34H22N2 = 458.17) | 436 | m/z = 458.56 (C34H22N2 = 458.17) |
| 437 | m/z = 458.56 (C34H22N2 = 458.17) | 438 | m/z = 458.56 (C34H22N2 = 458.17) |
| 439 | m/z = 583.73 (C45H29N = 583.23) | 440 | m/z = 633.79 (C49H31N = 633.24) |
| 441 | m/z = 659.83 (C51H33N = 659.26) | 442 | m/z = 759.95 (C59H37N = 859.29) |
| 443 | m/z = 507.63 (C39H25N = 507.19) | 444 | m/z = 531.59 (C37H26NOP = 531.17) |
| 445 | m/z = 496.61 (C37H24N2 = 496.19) | 446 | m/z = 572.71 (C43H28N2 = 572.22) |
| 447 | m/z = 572.71 (C43H28N2 = 572.22) | 448 | m/z = 737.90 (C55H35N3 = 737.28) |
| 449 | m/z = 585.71 (C43H27N3 = 585.22) | 450 | m/z = 661.80 (C49H31N3 = 661.25) |
| 451 | m/z = 585.71 (C43H27N3 = 585.22) | 452 | m/z = 737.90 (C55H35N3 = 737.28) |
| 453 | m/z = 637.78 (C47H31N3 = 637.25) | 454 | m/z = 713.88 (C55H35N3 = 713.28) |
| 455 | m/z = 789.98 (C59H39N3 = 789.31) | 456 | m/z = 737.90 (C55H35N3 = 737.28) |
| 457 | m/z = 737.90 (C55H35N3 = 737.28) | 458 | m/z = 713.88 (C53H35N3 = 714.28) |
| 459 | m/z = 789.98 (C59H39N3 = 789.31) | 460 | m/z = 639.76 (C45H29N5 = 639.24) |
| 461 | m/z = 639.76 (C45H29N5 = 639.24) | 462 | m/z = 639.76 (C45H29N5 = 639.24) |
| 463 | m/z = 637.78 (C47H31N3 = 637.25) | 464 | m/z = 713.88 (C53H35N3 = 713.28) |
| 465 | m/z = 789.98 (C59H39N3 = 789.31) | 466 | m/z = 737.90 (C55H35N3 = 737.28) |
| 467 | m/z = 737.90 (C55H35N3 = 737.28) | 468 | m/z = 713.88 (C53H35N3 = 713.28) |
| 469 | m/z = 789.98 (C59H39N3 = 789.31) | 470 | m/z = 639.76 (C45H29N5 = 639.24) |
| 471 | m/z = 639.76 (C45H29N5 = 639.24) | 472 | m/z = 639.76 (C45H29N5 = 639.24) |
| 473 | m/z = 683.77 (C46H30N4 = 638.24) | 474 | m/z = 714.87 (C52H34N4 = 714.27) |
| 475 | m/z = 790.97 (C58H36N4 = 790.31) | 476 | m/z = 738.89 (C54H34N4 = 738.27) |
| 477 | m/z = 738.89 (C54H34N4 = 738.27) | 478 | m/z = 714.87 (C52H34N4 = 714.27) |
| 479 | m/z = 790.97 (C58H38N4 = 790.31) | 480 | m/z = 640.75 (C44H28N6 = 640.23) |
| 481 | m/z = 640.75 (C44H28N6 = 640.23) | 482 | m/z = 640.75 (C44H28N6 = 640.23) |
| 483 | m/z = 638.77 (C46H30N4 = 638.24) | 484 | m/z = 534.66 (C40H26N2 = 534.21) |
| 485 | m/z = 534.66 (C40H26N2 = 534.21) | 486 | m/z = 534.66 (C40H26N2 = 534.21) |
| 487 | m/z = 534.66 (C40H26N2 = 534.21) | 488 | m/z = 534.66 (C40H26N2 = 534.21) |
| 489 | m/z = 659.83 (C51H33N = 659.26) | 490 | m/z = 709.86 (C55H35N = 709.27) |
| 491 | m/z = 735.93 (C57H37N = 735.29) | 492 | m/z = 836.05 (C65H41N = 835.32) |
| 493 | m/z = 583.73 (C45H29N = 583.23) | 494 | m/z = 608.69 (C43H30NOP = 607.20) |
| 495 | m/z = 572.71 (C43H28N2 = 572.22) | 496 | m/z = 648.80 (C49H32N2 = 648.25) |
| 497 | m/z = 648.80 (C49H32N2 = 648.25) | 498 | m/z = 814.00 (C61H39N3 = 813.31) |
| 499 | m/z = 635.77 (C47H29N3 = 635.23) | 500 | m/z = 711.86 (C53H33N3 = 711.26) |
| 501 | m/z = 635.77 (C47H29N3 = 635.23) | 502 | m/z = 787.96 (C59H37N3 = 787.29) |
| 503 | m/z = 687.84 (C51H33N3 = 687.26) | 504 | m/z = 763.94 (C57H37N3 = 763.29) |

TABLE 5-continued

| Compound | FD-MS | Compound | FD-MS |
|---|---|---|---|
| 505 | m/z = 840.04 (C63H41N3 = 839.33) | 506 | m/z = 787.96 (C59H37N3 = 787.29) |
| 507 | m/z = 787.96 (C59H37N3 = 787.29) | 508 | m/z = 763.94 (C57H37N3 = 763.29) |
| 509 | m/z = 840.04 (C63H41N3 = 839.33) | 510 | m/z = 689.82 (C49H31N5 = 689.25) |
| 511 | m/z = 689.82 (C49H31N5 = 689.25) | 512 | m/z = 689.82 (C49H31N5 = 689.25) |
| 513 | m/z = 687.84 (C51H33N3 = 687.26) | 514 | m/z = 763.94 (C57H37N3 = 763.29) |
| 515 | m/z = 840.04 (C63H41N3 = 839.33) | 516 | m/z = 787.96 (C59H37N3 = 787.29) |
| 517 | m/z = 787.96 (C59H37N3 = 787.29) | 518 | m/z = 763.94 (C57H37N3 = 763.29) |
| 519 | m/z = 840.04 (C63H41N3 = 839.33) | 520 | m/z = 689.82 (C49H31N5 = 689.25) |
| 521 | m/z = 689.82 (C49H31N5 = 689.25) | 522 | m/z = 689.82 (C49H31N5 = 689.25) |
| 523 | m/z = 688.83 (C50H32N4 = 688.26) | 524 | m/z = 764.93 (C56H36N4 = 764.29) |
| 525 | m/z = 841.03 (C62H40N4 = 840.32) | 526 | m/z = 788.95 (C58H36N4 = 788.29) |
| 527 | m/z = 788.95 (C58H36N4 = 788.29) | 528 | m/z = 764.93 (C56H36N4 = 764.29) |
| 529 | m/z = 841.03 (C62H40N4 = 840.32) | 530 | m/z = 690.81 (C48H30N6 = 690.25) |
| 531 | m/z = 690.81 (C48H30N6 = 690.25) | 532 | m/z = 690.81 (C48H30N6 = 690.25) |
| 533 | m/z = 688.83 (C50H32N4 = 688.26) | 534 | m/z = 584.72 (C44H28N2 = 584.22) |
| 535 | m/z = 584.72 (C44H28N2 = 584.22) | 536 | m/z = 584.72 (C44H28N2 = 584.22) |
| 537 | m/z = 584.72 (C44H28N2 = 584.22) | 538 | m/z = 584.72 (C44H28N2 = 584.22) |
| 539 | m/z = 709.89 (C55H35N = 709.27) | 540 | m/z = 759.95 (C59H37N = 759.29) |
| 541 | m/z = 673.85 (C52H35N = 673.27) | 542 | m/z = 657.75 (C47H32NOP = 657.22) |
| 543 | m/z = 622.77 (C44H30N2 = 622.24) | 544 | m/z = 698.86 (C53H34N2 = 698.27) |
| 545 | m/z = 698.86 (C53H34N2 = 698.27) | 546 | m/z = 865.06 (C65H41N3 = 863.33) |
| 547 | m/z = 661.80 (C49H31N3 = 661.25) | 548 | m/z = 661.80 (C49H31N3 = 661.25) |
| 549 | m/z = 791.95 (C57H37N5 = 791.30) | 550 | m/z = 791.95 (C57H37N5 = 791.30) |
| 551 | m/z = 791.95 (C57H37N5 = 791.30) | 552 | m/z = 791.95 (C57H37N5 = 791.30) |
| 553 | m/z = 793.93 (C55H35N7 = 793.29) | 554 | m/z = 793.93 (C55H35N7 = 793.29) |
| 555 | m/z = 711.02 (C53H33N3 = 711.27) | 556 | m/z = 659.01 (C51H33N = 659.26) |
| 557 | m/z = 659.02 (C51H33N = 659.26) | 558 | m/z = 662.96 (C49H28NO2 = 663.22) |
| 559 | m/z = 659.12 (C49H29NS2 = 659.17) | 560 | m/z = 662.19 (C49H30N2O = 662.24) |
| 561 | m/z = 678.17 (C49H30N2S = 678.21) | 562 | m/z = 662.19 (C49H30N2O = 662.24) |
| 563 | m/z = 662.19 (C49H30N2O = 662.24) | 564 | m/z = 728.21 (C52H32N4O = 728.26) |
| 565 | m/z = 744.18 (C52H32N4S = 774.23) | 566 | m/z = 728.21 (C52H32N4O = 728.26) |
| 567 | m/z = 662.19 (C49H30N2O = 662.24) | 568 | m/z = 804.23 (C58H36N4O = 804.29) |
| 569 | m/z = 803.24 (C59H37N3O = 803.29) | 570 | m/z = 803.23 (C59H37N3O = 803.29) |
| 571 | m/z = 678.16 (C49H30N2S = 678.21) | 572 | m/z = 727.20 (C53H33N3O = 727.26) |
| 573 | m/z = 727.19 (C53H33N3O = 727.26) | 574 | m/z = 662.19 (C49H30N2O = 662.24) |
| 575 | m/z = 662.20 (C49H30N2O = 662.24) | 576 | m/z = 659.21 (C51H33N = 659.26) |
| 577 | m/z = 659.20 (C51H33N = 659.26) | 578 | m/z = 663.17 (C49H29NO2 = 663.22) |
| 579 | m/z = 695.12 (C49H29NS2 = 695.17) | 580 | m/z = 728.22 (C52H32N4O = 728.26) |
| 581 | m/z = 744.18 (C52H32N4S = 744.23) | 582 | m/z = 728.20 (C52H32N4O = 728.26) |

TABLE 5-continued

| Compound | FD-MS | Compound | FD-MS |
|---|---|---|---|
| 583 | m/z = 728.21 (C52H32N4O = 728.26) | 584 | m/z = 804.23 (C58H36N4O = 804.29) |
| 585 | m/z = 820.22 (C58H36N4S = 820.27) | 586 | m/z = 728.21 (C52H36N4O = 728.26) |
| 587 | m/z = 804.21 (C58H36N4O = 804.29) | 588 | m/z = 804.22 (C58H36N4O = 804.29) |
| 589 | m/z = 803.23 (C59H37N3O = 803.29) | 590 | m/z = 819.21 (C59H37N3S = 819.27) |
| 591 | m/z = 803.22 (C59H37N3O = 803.29) | 592 | m/z = 727.21 (C53H33N3O = 727.26) |
| 593 | m/z = 727.21 (C53H33N3O = 727.26) | 594 | m/z = 727.22 (C53H33N3O = 727.26) |
| 595 | m/z = 727.22 (C53H33N3O = 727.26) | | |

EXPERIMENTAL EXAMPLE

Experimental Example 1

1) Manufacture of Organic Light Emitting Device

A glass substrate on which ITO was coated as a thin film to a thickness of 1500 Å was cleaned with distilled water and ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for removing ITO work function and remaining film, and the substrate was transferred to a thermal deposition apparatus for organic deposition.

On the ITO transparent electrode (anode), organic materials were formed in a two-stack white organic light emitting diode (WOLED) structure. As for the first stack, a M hole transfer layer was formed first by thermal vacuum depositing TAPC to a thickness of 300 Å. After forming the hole transfer layer, a light emitting layer was thermal vacuum deposited thereon as follows. The light emitting layer was deposited to 300 Å by doping Flrpic in 8% as a blue phosphorescent dopant to TCzl, a host. An electron transfer layer was formed to 400 Å using TmPyPB, and then a charge generation layer was formed to 100 Å by doping $Cs_2CO_3$ in 20% to a compound described in the following Table 6.

As for the second stack, a hole injection layer was formed first by thermal vacuum depositing $MoO_3$ to a thickness of 50 Å. A hole transfer layer, a common layer, was formed by doping $MoO_3$ to TAPC in 20% and forming to 100 Å, and then depositing TAPC to 300 Å. After depositing a light emitting layer to 300 Å thereon by doping Ir(ppy), a green phosphorescent dopant, in 8% to TCzl, a host, an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic light emitting device.

Meanwhile, all the organic compounds required to manufacture the OLED device were vacuum sublimation purified under $10^{-6}$ torr to $10^{-8}$ torr by each material to be used in the OLED manufacture.

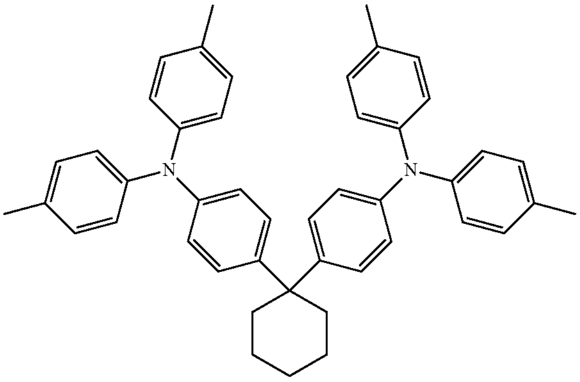

TAPC

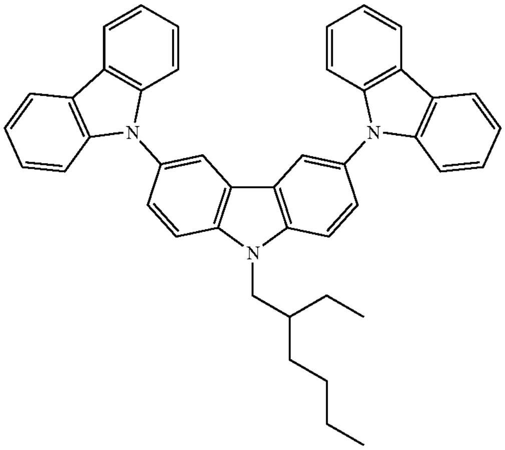

TCz1

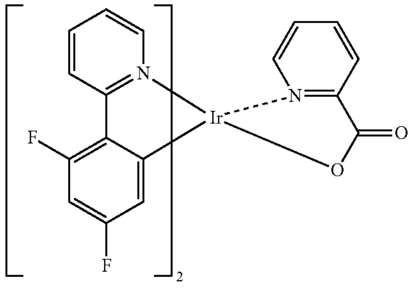

FIrpic

-continued

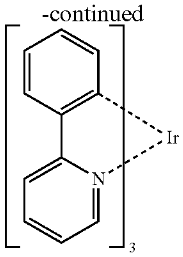

Ir(ppy)3

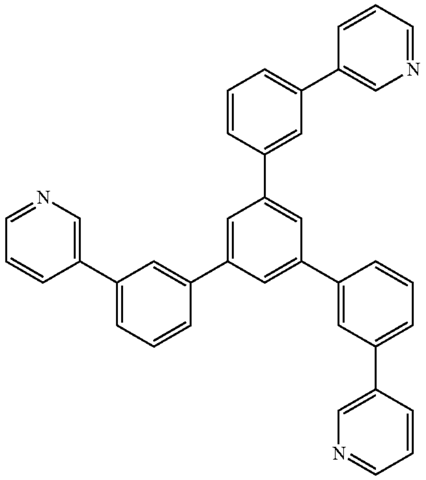

TmPyPB

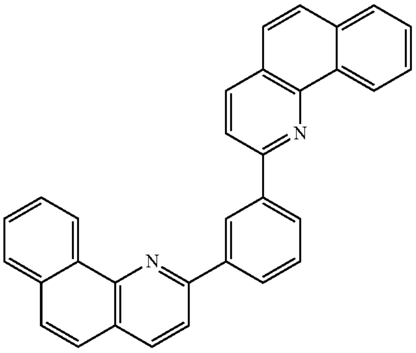

BBQB

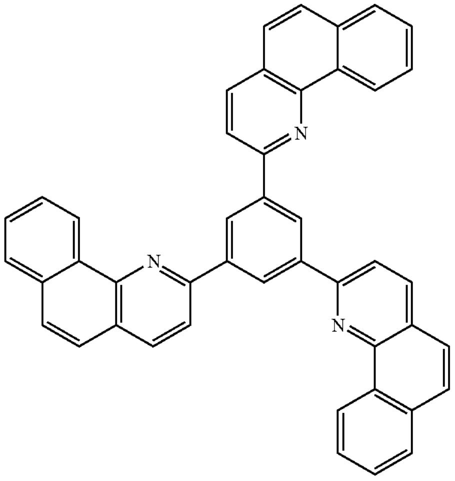

TBQB

2) Driving Voltage and Light Emission Efficiency of Organic Light Emitting Device For the organic light emitting devices manufactured as above, electroluminescent light emission (EL) characteristics were measured using M7000 manufactured by McScience Inc., and with the measurement results, T95 when standard luminance was 3,500 cd/$m^2$ was measured using a lifetime test system (M6000) manufactured by McScience Inc. Results of measuring a driving voltage, light emission efficiency, external quantum efficiency and a color coordinate (CIE) of the white organic light emitting devices manufactured according to the present disclosure are as shown in Table 6.

TABLE 6

| | Compound | Driving Voltage (V) | Light Emission Efficiency (cd/A) | CIE (x, y) | Lifespan (T95) |
|---|---|---|---|---|---|
| Example 1 | 1 | 7.13 | 69.21 | (0.221, 0.434) | 42 |
| Example 2 | 2 | 7.01 | 69.82 | (0.220, 0.440) | 43 |
| Example 3 | 3 | 7.10 | 69.45 | (0.219, 0.429) | 41 |
| Example 4 | 5 | 7.78 | 59.95 | (0.218, 0.427) | 27 |
| Example 5 | 15 | 7.95 | 59.45 | (0.220, 0.431) | 28 |
| Example 6 | 25 | 7.92 | 59.88 | (0.200, 0.421) | 29 |
| Example 7 | 35 | 7.17 | 66.23 | (0.205, 0.411) | 49 |
| Example 8 | 36 | 7.60 | 63.89 | (0.204, 0.413) | 36 |
| Example 9 | 44 | 7.55 | 62.77 | (0.210, 0.410) | 38 |
| Example 10 | 45 | 7.34 | 67.70 | (0.208, 0.420) | 35 |
| Example 11 | 46 | 7.74 | 58.52 | (0.212, 0.428) | 29 |
| Example 12 | 47 | 7.81 | 59.50 | (0.223, 0.415) | 32 |
| Example 13 | 48 | 7.72 | 58.81 | (0.219, 0.410) | 34 |
| Example 14 | 50 | 7.79 | 63.08 | (0.212, 0.429) | 30 |
| Example 15 | 51 | 7.60 | 62.00 | (0.213, 0.420) | 31 |
| Example 16 | 52 | 7.02 | 69.78 | (0.223, 0.433) | 41 |
| Example 17 | 75 | 7.89 | 58.98 | (0.219, 0.411) | 35 |
| Example 18 | 85 | 7.80 | 59.11 | (0.210, 0.412) | 35 |
| Example 19 | 86 | 7.65 | 58.54 | (0.211, 0.415) | 39 |
| Example 20 | 94 | 7.56 | 59.06 | (0.214, 0.420) | 33 |
| Example 21 | 95 | 7.80 | 54.22 | (0.215, 0.411) | 36 |
| Example 22 | 96 | 7.49 | 57.94 | (0.211, 0.419) | 37 |
| Example 23 | 97 | 7.66 | 58.26 | (0.209, 0.419) | 31 |
| Example 24 | 98 | 7.58 | 59.11 | (0.207, 0.409) | 38 |
| Example 25 | 100 | 7.50 | 56.66 | (0.208, 0.415) | 35 |
| Example 26 | 102 | 7.21 | 69.56 | (0.224, 0.429) | 40 |
| Example 27 | 149 | 7.07 | 70.01 | (0.225, 0.429) | 42 |
| Example 28 | 150 | 7.12 | 67.56 | (0.209, 0.415) | 44 |
| Example 29 | 151 | 7.00 | 69.89 | (0.231, 0.440) | 42 |
| Example 30 | 153 | 7.05 | 69.47 | (0.222, 0.435) | 41 |
| Example 31 | 163 | 7.87 | 65.84 | (0.218, 0.421) | 30 |
| Example 32 | 173 | 7.63 | 64.96 | (0.220, 0.421) | 28 |
| Example 33 | 183 | 7.37 | 67.13 | (0.221, 0.433) | 47 |
| Example 34 | 192 | 7.55 | 59.99 | (0.215, 0.422) | 40 |
| Example 35 | 193 | 7.80 | 57.11 | (0.214, 0.420) | 39 |
| Example 36 | 194 | 8.00 | 59.21 | (0.209, 0.432) | 26 |
| Example 37 | 195 | 7.44 | 57.84 | (0.210, 0.430) | 29 |
| Example 38 | 196 | 7.54 | 58.22 | (0.211, 0.428) | 30 |
| Example 39 | 198 | 7.74 | 67.32 | (0.230, 0.439) | 32 |
| Example 40 | 199 | 7.08 | 69.74 | (0.243, 0.442) | 43 |
| Example 41 | 200 | 7.60 | 59.08 | (0.231, 0.430) | 39 |
| Example 42 | 242 | 7.58 | 55.11 | (0.228, 0.428) | 31 |
| Example 43 | 243 | 7.70 | 54.01 | (0.210, 0.430) | 34 |
| Example 44 | 244 | 7.49 | 55.90 | (0.219, 0.422) | 34 |
| Example 45 | 245 | 7.66 | 56.10 | (0.229, 0.419) | 38 |
| Example 46 | 246 | 7.88 | 57.04 | (0.231, 0.418) | 37 |
| Example 47 | 248 | 7.85 | 55.28 | (0.227, 0.419) | 37 |
| Example 48 | 249 | 7.11 | 65.55 | (0.243, 0.442) | 39 |
| Example 49 | 250 | 7.34 | 61.00 | (0.234, 0.439) | 36 |
| Example 50 | 253 | 7.45 | 59.80 | (0.231, 0.423) | 39 |
| Example 51 | 263 | 7.44 | 57.20 | (0.234, 0.433) | 39 |
| Example 52 | 273 | 7.60 | 57.98 | (0.230, 0.421) | 35 |
| Example 53 | 292 | 7.51 | 52.17 | (0.228, 0.418) | 33 |

TABLE 6-continued

| | Compound | Driving Voltage (V) | Light Emission Efficiency (cd/A) | CIE (x, y) | Lifespan (T95) |
|---|---|---|---|---|---|
| Example 54 | 293 | 7.49 | 53.66 | (0.228, 0.418) | 38 |
| Example 55 | 294 | 7.55 | 53.90 | (0.230, 0.420) | 33 |
| Example 56 | 295 | 7.52 | 52.10 | (0.230, 0.424) | 35 |
| Example 57 | 296 | 7.49 | 53.82 | (0.231, 0.425) | 34 |
| Example 58 | 298 | 7.60 | 55.16 | (0.232, 0.425) | 34 |
| Example 59 | 299 | 7.72 | 54.67 | (0.233, 0.419) | 30 |
| Example 60 | 300 | 7.66 | 54.90 | (0.232, 0.421) | 39 |
| Example 61 | 301 | 7.56 | 55.10 | (0.238, 0.423) | 38 |
| Example 62 | 303 | 7.60 | 56.22 | (0.238, 0.421) | 38 |
| Example 63 | 313 | 7.55 | 56.88 | (0.239, 0.422) | 36 |
| Example 64 | 323 | 7.47 | 57.10 | (0.231, 0.423) | 39 |
| Example 65 | 333 | 7.51 | 56.12 | (0.232, 0.431) | 34 |
| Example 66 | 342 | 7.41 | 59.99 | (0.233, 0.433) | 31 |
| Example 67 | 343 | 7.44 | 58.89 | (0.238, 0.438) | 33 |
| Example 68 | 344 | 7.39 | 63.38 | (0.243, 0.442) | 40 |
| Example 69 | 345 | 7.22 | 66.22 | (0.243, 0.442) | 32 |
| Example 70 | 346 | 7.66 | 59.80 | (0.231, 0.423) | 36 |
| Example 71 | 348 | 7.55 | 59.10 | (0.238, 0.423) | 37 |
| Example 72 | 399 | 7.80 | 55.88 | (0.209, 0.419) | 37 |
| Example 73 | 400 | 7.79 | 56.18 | (0.210, 0.420) | 35 |
| Example 74 | 401 | 7.65 | 55.97 | (0.211, 0.421) | 38 |
| Example 75 | 403 | 7.45 | 56.45 | (0.212, 0.422) | 38 |
| Example 76 | 413 | 7.49 | 55.10 | (0.228, 0.418) | 38 |
| Example 77 | 423 | 7.54 | 56.89 | (0.231, 0.420) | 36 |
| Example 78 | 442 | 7.49 | 56.25 | (0.233, 0.419) | 35 |
| Example 79 | 443 | 7.80 | 56.25 | (0.229, 0.423) | 35 |
| Example 80 | 444 | 7.77 | 56.67 | (0.230, 0.421) | 38 |
| Example 81 | 445 | 7.69 | 54.20 | (0.231, 0.419) | 33 |
| Example 82 | 446 | 7.64 | 55.11 | (0.230, 0.423) | 34 |
| Example 83 | 448 | 7.65 | 53.10 | (0.231, 0.422) | 35 |
| Example 84 | 449 | 7.76 | 53.88 | (0.229. 0.424) | 35 |
| Example 85 | 450 | 7.68 | 54.10 | (0.230, 0.424) | 38 |
| Example 86 | 451 | 7.70 | 56.34 | (0.233, 0.419) | 38 |
| Example 87 | 453 | 7.75 | 56.38 | (0.231, 0.420) | 39 |
| Example 88 | 463 | 7.68 | 57.20 | (0.233, 0.421) | 35 |
| Example 89 | 473 | 7.71 | 57.11 | (0.232, 0.422) | 33 |
| Example 90 | 484 | 7.72 | 55.55 | (0.232, 0.421) | 32 |
| Example 91 | 492 | 7.76 | 55.40 | (0.232, 0.422) | 32 |
| Example 92 | 493 | 7.66 | 56.10 | (0.230, 0.420) | 33 |
| Example 93 | 494 | 7.56 | 56.88 | (0.231, 0.419) | 35 |
| Example 94 | 495 | 7.60 | 56.80 | (0.229, 0.423) | 36 |
| Example 95 | 496 | 7.58 | 56.15 | (0.228, 0.424) | 37 |
| Example 96 | 498 | 7.49 | 56.87 | (0.226, 0.434) | 37 |
| Example 97 | 499 | 7.48 | 55.87 | (0.228, 0.429) | 38 |
| Example 98 | 500 | 7.51 | 54.99 | (0.229, 0.430) | 30 |
| Example 99 | 555 | 7.02 | 68.99 | (0.228, 0.436) | 41 |
| Example 100 | 556 | 7.44 | 67.21 | (0.243, 0.442) | 38 |
| Comparative Example 1-1 | TmPyPB | 8.57 | 57.61 | (0.212, 0.433) | 24 |
| Comparative Example 1-2 | BBQB | 8.43 | 58.11 | (0.220, 0.429) | 27 |
| Comparative Example 1-3 | TBQB | 8.47 | 58.90 | (0.222, 0.430) | 28 |

As shown from the results of Table 6, the organic light emitting devices using the charge generation layer material of the 2-stack white organic light emitting device of the present disclosure had a low driving voltage and improved light emission efficiency compared to Comparative Example 1. Particularly, it was identified that Compounds 1, 2, 3, 35, 52, 102, 149, 150, 151, 183, 199 and 555 were significantly excellent in all of driving, efficiency and lifespan.

The presumed reason for such results is that the compound of the present disclosure used as an N-type charge generation layer formed with an invented skeleton having proper length, strength and flat property and a proper hetero-compound capable of binding with metals is doped with an alkali metal or an alkali-earth metal to form a gap state within the N-type charge generation layer, and electrons produced from a P-type charge generation layer are readily injected to the electron transfer layer through the gap state produced within the N-type charge generation layer. Accordingly, the P-type charge generation layer favorably carried out electron injection and electron transfer to the N-type charge generation layer, and as a result, it is considered that a driving voltage of the organic light emitting device decreased, and efficiency and lifespan were improved.

Experimental Example 2

1) Manufacture of Organic Light Emitting Device

A glass substrate on which ITO was coated as a thin film to a thickness of 1500 Å was cleaned with distilled water and ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for removing ITO work function and remaining film, and the substrate was transferred to a thermal deposition apparatus for organic deposition. On the ITO transparent electrode (anode), organic materials were formed in a single-stack structure. As a hole injection layer, HAT-CN was deposited to a thickness of 50 Å, and subsequently, a hole transfer layer was formed by doping DNTPD within 10% to NPD, depositing the result to a thickness of 1500 Å, and continuously depositing TCTA to a thickness of 200 Å. Subsequently, a light emitting layer comprising a t-Bu-perylene dopant in an ADN host was formed to a thickness of 250 Å. Next, $Alq_3$, an electron transfer layer, was formed to a thickness of 250 Å, and an N-type charge transfer layer was formed to a thickness of 100 Å by doping Li, an alkali metal, to a compound described in the following Table 7, and Al, a cathode, was formed to a thickness of approximately 1,000 Å to manufacture an organic light emitting device.

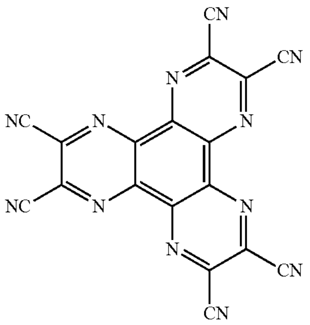

HAT-CN

-continued
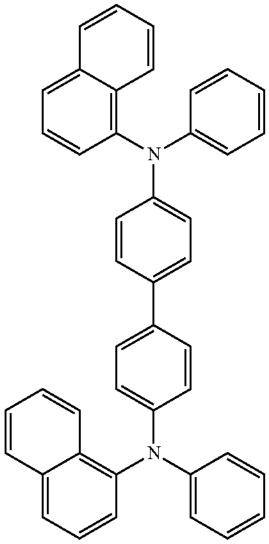
NPD
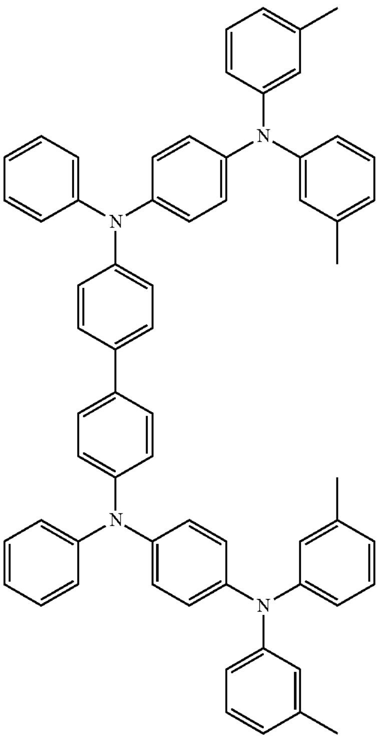
DNTPD
-continued
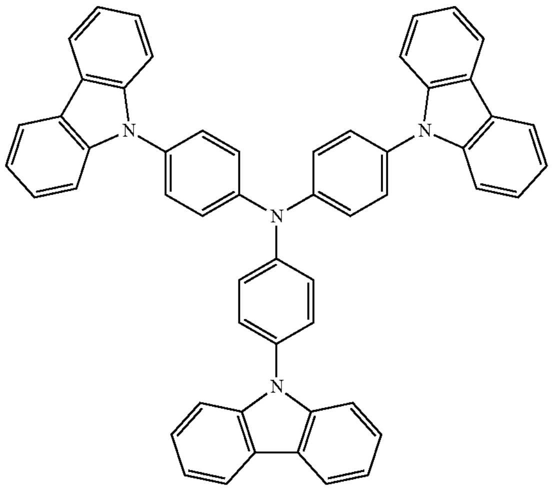
TCTA
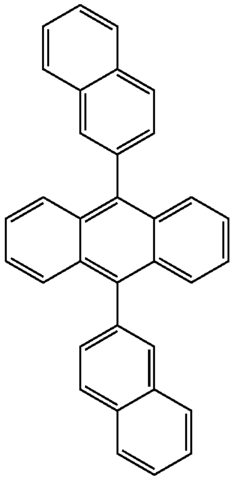
ADN
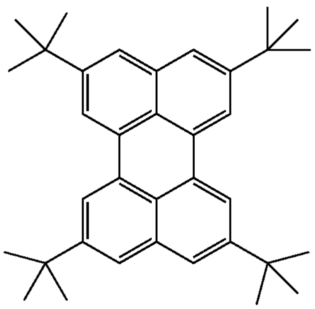
t-Bu-Perylene
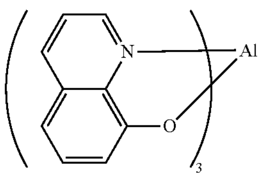
Alq3
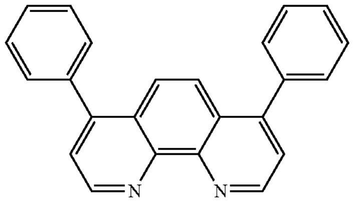
Bphen -continued

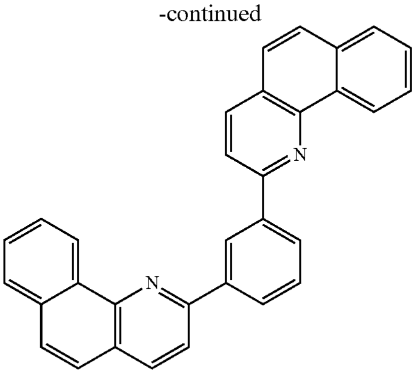

BBQB

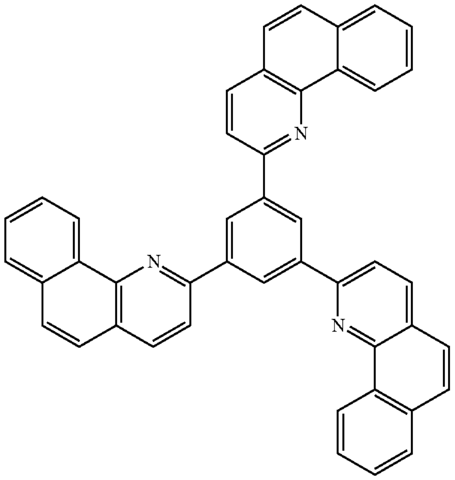

TBQB

2) Driving Voltage and Light Emission Efficiency of Organic Light Emitting Device For the organic light emitting devices manufactured as above, electroluminescent light emission (EL) characteristics were measured using M7000 manufactured by McScience Inc., and with the measurement results, $T_{95}$ when standard luminance was 750 cd/$m^2$ was measured using a lifetime test system (M6000) manufactured by McScience Inc. Results of measuring a driving voltage, light emission efficiency, external quantum efficiency and a color coordinate (CIE) of the white organic electroluminescent devices manufactured according to the present disclosure are as shown in Table 7.

TABLE 7

| | Compound | Driving Voltage (V) | Light Emission Efficiency (cd/A) | CIE (x, y) | Lifespan (T95) |
|---|---|---|---|---|---|
| Example 101 | 1 | 4.49 | 6.91 | (0.134, 0.101) | 40 |
| Example 102 | 2 | 4.50 | 6.92 | (0.134, 0.101) | 41 |
| Example 103 | 3 | 4.50 | 6.93 | (0.134, 0.100) | 42 |
| Example 104 | 5 | 4.92 | 6.21 | (0.134, 0.105) | 30 |
| Example 105 | 15 | 4.86 | 6.20 | (0.134, 0.105) | 29 |
| Example 106 | 25 | 4.95 | 6.22 | (0.134, 0.104) | 31 |
| Example 107 | 35 | 4.61 | 6.69 | (0.134, 0.099) | 47 |
| Example 108 | 36 | 4.97 | 6.15 | (0.134, 0.103) | 35 |
| Example 109 | 44 | 4.98 | 6.21 | (0.134, 0.102) | 34 |
| Example 110 | 45 | 4.80 | 6.10 | (0.134, 0.101) | 40 |
| Example 111 | 46 | 5.50 | 6.33 | (0.134, 0.101) | 41 |
| Example 112 | 47 | 5.20 | 6.29 | (0.134, 0.103) | 32 |

TABLE 7-continued

| | Compound | Driving Voltage (V) | Light Emission Efficiency (cd/A) | CIE (x, y) | Lifespan (T95) |
|---|---|---|---|---|---|
| Example 113 | 48 | 5.14 | 6.18 | (0.134, 0.102) | 34 |
| Example 114 | 50 | 5.02 | 6.51 | (0.134, 0.101) | 31 |
| Example 115 | 51 | 5.05 | 6.27 | (0.134, 0.104) | 33 |
| Example 116 | 52 | 4.62 | 6.91 | (0.134, 0.101) | 39 |
| Example 117 | 75 | 5.11 | 6.44 | (0.134, 0.104) | 35 |
| Example 118 | 85 | 5.21 | 6.47 | (0.134, 0.103) | 34 |
| Example 119 | 86 | 5.29 | 6.32 | (0.134, 0.102) | 35 |
| Example 120 | 94 | 5.20 | 6.33 | (0.134, 0.102) | 33 |
| Example 121 | 95 | 5.25 | 6.27 | (0.134, 0.104) | 33 |
| Example 122 | 96 | 5.18 | 6.29 | (0.134, 0.104) | 34 |
| Example 123 | 97 | 5.09 | 6.31 | (0.134, 0.102) | 37 |
| Example 124 | 98 | 5.04 | 6.14 | (0.134, 0.104) | 36 |
| Example 125 | 100 | 5.09 | 6.22 | (0.134, 0.101) | 37 |
| Example 126 | 102 | 4.46 | 6.84 | (0.134, 0.102) | 41 |
| Example 127 | 149 | 4.56 | 6.90 | (0.134, 0.101) | 40 |
| Example 128 | 150 | 4.51 | 6.94 | (0.134, 0.101) | 40 |
| Example 129 | 151 | 4.55 | 6.94 | (0.134, 0.100) | 42 |
| Example 130 | 153 | 4.60 | 6.98 | (0.134, 0.099) | 42 |
| Example 131 | 163 | 5.65 | 6.22 | (0.134, 0.104) | 34 |
| Example 132 | 173 | 5.68 | 6.15 | (0.134, 0.104) | 33 |
| Example 133 | 183 | 5.82 | 6.45 | (0.134, 0.105) | 30 |
| Example 134 | 192 | 5.50 | 6.45 | (0.134, 0.102) | 31 |
| Example 135 | 193 | 5.44 | 6.54 | (0.134, 0.103) | 32 |
| Example 136 | 194 | 5.80 | 6.62 | (0.134, 0.101) | 29 |
| Example 137 | 195 | 5.60 | 6.59 | (0.134, 0.102) | 30 |
| Example 138 | 196 | 5.49 | 6.50 | (0.134, 0.103) | 31 |
| Example 139 | 198 | 5.77 | 6.43 | (0.134, 0.101) | 30 |
| Example 140 | 199 | 4.40 | 6.98 | (0.134, 0.099) | 40 |
| Example 141 | 200 | 5.21 | 6.44 | (0.134, 0.101) | 35 |
| Example 142 | 242 | 5.44 | 6.43 | (0.134, 0.103) | 34 |
| Example 143 | 243 | 5.45 | 6.30 | (0.134, 0.102) | 34 |
| Example 144 | 244 | 5.55 | 6.29 | (0.134, 0.103) | 32 |
| Example 145 | 245 | 5.56 | 6.34 | (0.134, 0.102) | 31 |
| Example 146 | 246 | 5.46 | 6.38 | (0.134, 0.103) | 33 |
| Example 147 | 248 | 5.55 | 6.40 | (0.134, 0.101) | 30 |
| Example 148 | 249 | 4.99 | 6.34 | (0.134, 0.100) | 32 |
| Example 149 | 250 | 5.40 | 6.35 | (0.134, 0.102) | 33 |
| Example 150 | 253 | 5.44 | 6.40 | (0.134, 0.101) | 34 |
| Example 151 | 263 | 5.50 | 6.41 | (0.134, 0.102) | 35 |
| Example 152 | 273 | 5.34 | 6.38 | (0.134, 0.101) | 33 |
| Example 153 | 292 | 5.33 | 6.39 | (0.134, 0.103) | 32 |
| Example 154 | 293 | 5.45 | 6.40 | (0.134, 0.101) | 33 |
| Example 155 | 294 | 5.44 | 6.42 | (0.134, 0.103) | 31 |
| Example 156 | 295 | 5.34 | 6.44 | (0.134, 0.104) | 30 |
| Example 157 | 296 | 5.41 | 6.20 | (0.134, 0.103) | 30 |
| Example 158 | 298 | 5.39 | 6.38 | (0.134, 0.101) | 33 |
| Example 159 | 299 | 5.37 | 6.30 | (0.134, 0.103) | 32 |
| Example 160 | 300 | 5.35 | 6.29 | (0.134, 0.103) | 32 |
| Example 161 | 301 | 5.45 | 6.40 | (0.134, 0.101) | 33 |
| Example 162 | 303 | 5.51 | 6.33 | (0.134, 0.102) | 31 |
| Example 163 | 313 | 5.20 | 6.26 | (0.134, 0.102) | 34 |
| Example 164 | 323 | 5.33 | 6.24 | (0.134, 0.101) | 33 |
| Example 165 | 333 | 5.30 | 6.30 | (0.134, 0.101) | 33 |
| Example 166 | 342 | 5.20 | 6.34 | (0.134, 0.101) | 31 |
| Example 167 | 343 | 5.25 | 6.37 | (0.134, 0.102) | 31 |
| Example 168 | 344 | 5.10 | 6.62 | (0.134, 0.101) | 34 |
| Example 169 | 345 | 5.00 | 6.28 | (0.134, 0.100) | 39 |
| Example 170 | 346 | 5.35 | 6.30 | (0.134, 0.102) | 35 |
| Example 171 | 348 | 5.33 | 6.32 | (0.134, 0.103) | 34 |
| Example 172 | 399 | 5.44 | 6.20 | (0.134, 0.104) | 37 |
| Example 173 | 400 | 5.39 | 6.35 | (0.134, 0.101) | 35 |
| Example 174 | 401 | 5.44 | 6.33 | (0.134, 0.101) | 33 |
| Example 175 | 403 | 5.45 | 6.32 | (0.134, 0.104) | 35 |
| Example 176 | 413 | 5.46 | 6.35 | (0.134, 0.103) | 34 |
| Example 177 | 423 | 5.48 | 6.21 | (0.134, 0.103) | 37 |
| Example 178 | 442 | 5.44 | 6.33 | (0.134, 0.102) | 36 |
| Example 179 | 443 | 5.44 | 6.38 | (0.134, 0.102) | 36 |
| Example 180 | 444 | 5.41 | 6.20 | (0.134, 0.101) | 31 |
| Example 181 | 445 | 5.44 | 6.22 | (0.134, 0.101) | 32 |
| Example 182 | 446 | 5.50 | 6.34 | (0.134, 0.100) | 32 |
| Example 183 | 448 | 5.49 | 6.21 | (0.134, 0.104) | 34 |
| Example 184 | 449 | 5.48 | 6.24 | (0.134, 0.103) | 32 |
| Example 185 | 450 | 5.47 | 6.22 | (0.134, 0.104) | 32 |
| Example 186 | 451 | 5.43 | 6.38 | (0.134, 0.103) | 36 |
| Example 187 | 453 | 5.42 | 6.23 | (0.134, 0.102) | 34 |

TABLE 7-continued

| | Compound | Driving Voltage (V) | Light Emission Efficiency (cd/A) | CIE (x, y) | Lifespan (T95) |
|---|---|---|---|---|---|
| Example 188 | 463 | 5.46 | 6.29 | (0.134, 0.102) | 34 |
| Example 189 | 473 | 5.44 | 6.30 | (0.134, 0.101) | 35 |
| Example 190 | 484 | 5.41 | 6.22 | (0.134, 0.101) | 35 |
| Example 191 | 492 | 5.36 | 6.34 | (0.134, 0.103) | 37 |
| Example 192 | 493 | 5.45 | 6.31 | (0.134, 0.102) | 34 |
| Example 193 | 494 | 5.50 | 6.33 | (0.134, 0.102) | 33 |
| Example 194 | 495 | 5.49 | 6.25 | (0.134, 0.101) | 32 |
| Example 195 | 496 | 5.48 | 6.22 | (0.134, 0.101) | 35 |
| Example 196 | 498 | 5.55 | 6.34 | (0.134, 0.103) | 36 |
| Example 197 | 499 | 5.49 | 6.35 | (0.134, 0.104) | 34 |
| Example 198 | 500 | 5.42 | 6.30 | (0.134, 0.103) | 33 |
| Example 199 | 555 | 4.55 | 6.93 | (0.134, 0.100) | 41 |
| Example 200 | 556 | 4.79 | 6.44 | (0.134, 0.102) | 35 |
| Comparative Example 2-1 | Bphen | 5.82 | 6.23 | (0.134, 0.110) | 27 |
| Comparative Example 2-2 | BBQB | 5.80 | 6.32 | (0.134, 0.111) | 29 |
| Comparative Example 2-3 | TBQB | 5.84 | 6.39 | (0.134, 0.111) | 25 |

As shown from the results of Table 7, the organic light emitting devices using the charge generation layer material of the blue organic light emitting device of the present disclosure had a low driving voltage and improved light emission efficiency compared to Comparative Example 2. Particularly, it was identified that Compounds 1, 2, 3, 35, 52, 102, 149, 150, 151, 183, 199 and 555 were significantly excellent in all of driving, efficiency and lifespan.

The presumed reason for such results is that the compound of the present disclosure used as an N-type charge generation layer formed with an invented skeleton having proper length, strength and flat property and a proper hetero-compound capable of binding with metals is doped with an alkali metal or an alkali-earth metal to form a gap state within the N-type charge generation layer, and electrons produced from a P-type charge generation layer are readily injected to the electron transfer layer through the gap state produced within the N-type charge generation layer. Accordingly, the P-type charge generation layer favorably carried out electron injection and electron transfer to the N-type charge generation layer, and as a result, it is considered that a driving voltage of the organic light emitting device decreased, and efficiency and lifespan were improved.

Experimental Example 3

1) Manufacture of Organic Light Emitting Device

A transparent electrode ITO thin film obtained from glass for an OLED (manufactured by Samsung Corning Advanced Glass) was ultrasonic cleaned consecutively using trichloroethylene, acetone, ethanol and distilled water for 5 minutes each, placed in isopropanol and stored, and then used.

Next, the ITO substrate was installed in a substrate folder of vacuum deposition equipment, and the following 4,4',4"-tris(N,N-(2-naphthyl)-phenylamino)triphenyl amine (2-TNATA) was introduced to a cell in the vacuum deposition equipment.

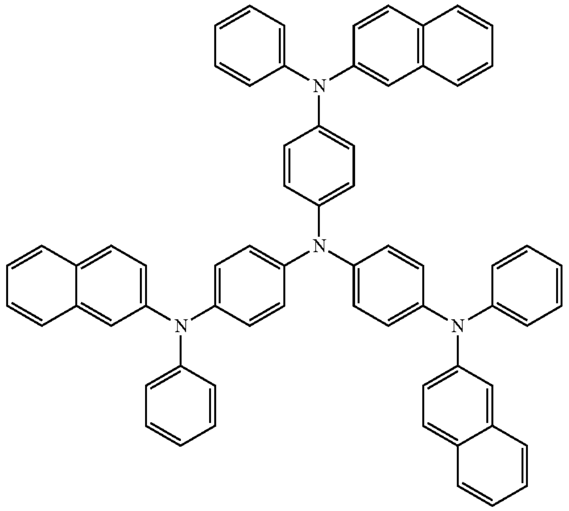

2-TNATA

Subsequently, the chamber was exhausted until the degree of vacuum inside the chamber reached $10^{-6}$ torr, and then a current was applied to the cell to evaporate the 2-TNATA to deposit a hole injection layer having a thickness of 600 Å on the ITO substrate.

The following N,N'-bis(α-naphthyl)-N,N'-diphenyl-4,4'-diamine (NPB) was introduced to a different cell in the vacuum deposition equipment, a current was applied to the cell to evaporate to deposit a hole transfer layer having a thickness of 300 Å on the hole injection layer.

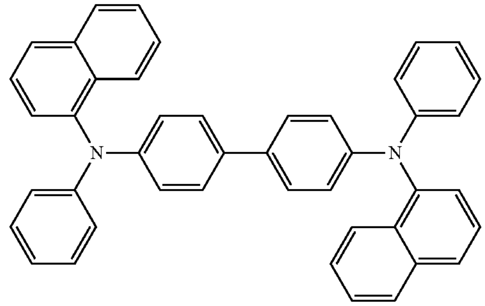

NPB

After forming the hole injection layer and the hole transfer layer as above, a blue light emitting material having a structure as follows was deposited thereon as a light emitting layer. Specifically, H1, a blue light emitting host material, was vacuum deposited to a thickness of 200 Å on one cell in the vacuum deposition equipment, and D1, a blue light emitting dopant material, was vacuum deposited thereon in 5% with respect to the host material.

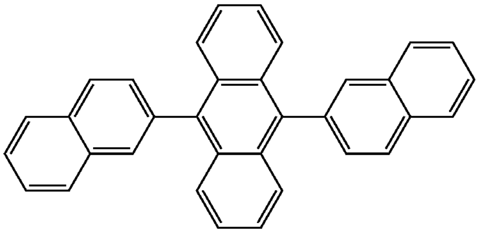

H1

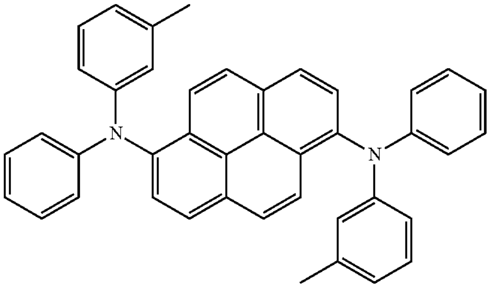

D1

Subsequently, a compound of the following structural formula E1 was deposited to a thickness of 300 Å as an electron transfer layer.

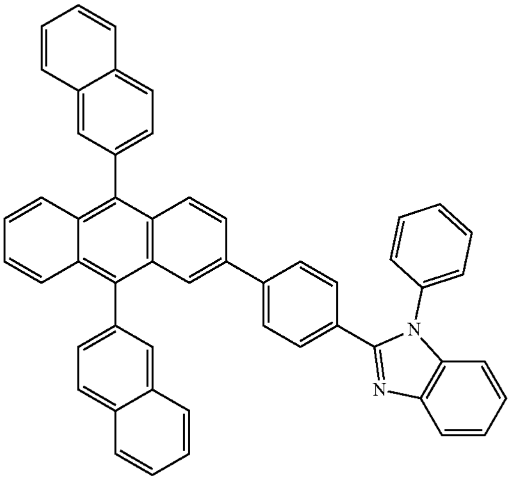

E1

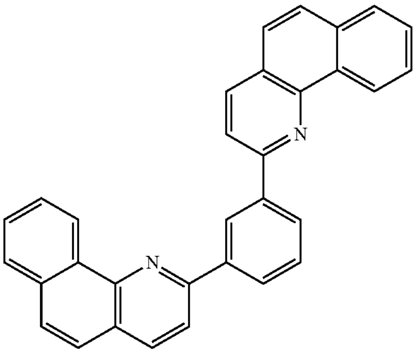

BBQB

-continued

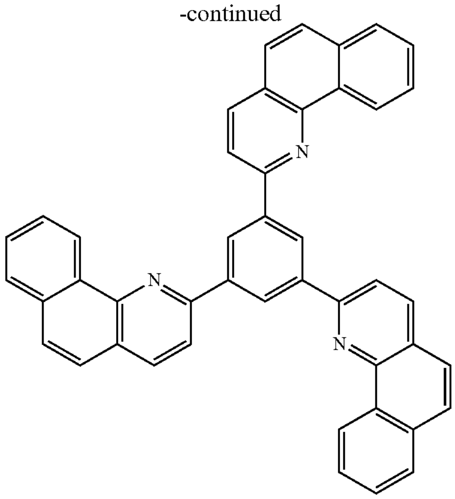

TBQB

As an electron injection layer, lithium fluoride (LiF) was deposited to a thickness of 10 Å, and an Al cathode was formed to a thickness of 1,000 Å to manufacture an OLED device.

Meanwhile, all the organic compounds required to manufacture the OLED device were vacuum sublimation purified under $10^{-6}$ torr to $10^{-8}$ torr by each material to be used in the OLED manufacture.

2) Driving Voltage and Light Emission Efficiency of Organic Light Emitting Device For the organic light emitting devices manufactured as above, electroluminescent light emission (EL) characteristics were measured using M7000 manufactured by McScience Inc., and with the measurement results, $T_{95}$ when standard luminance was 700 cd/$m^2$ was measured using a lifetime test system (M6000) manufactured by McScience Inc. Results of measuring a driving voltage, light emission efficiency, external quantum efficiency and a color coordinate (CIE) of the white organic light emitting devices manufactured according to the present disclosure are as shown in Table 8.

TABLE 8

| | Compound | Driving Voltage (V) | Light Emission Efficiency (cd/A) | CIE (x, y) | Lifespan (T95) |
|---|---|---|---|---|---|
| Example 201 | 1 | 5.48 | 6.02 | (0.134, 0.102) | 32 |
| Example 202 | 2 | 5.39 | 6.24 | (0.134, 0.102) | 31 |
| Example 203 | 3 | 5.35 | 6.34 | (0.134, 0.100) | 31 |
| Example 204 | 5 | 4.45 | 6.98 | (0.134, 0.100) | 40 |
| Example 205 | 15 | 4.50 | 6.99 | (0.134, 0.101) | 41 |
| Example 206 | 25 | 4.48 | 6.85 | (0.134, 0.099) | 40 |
| Example 207 | 35 | 5.38 | 5.64 | (0.134, 0.100) | 29 |
| Example 208 | 36 | 5.44 | 5.85 | (0.134, 0.100) | 33 |
| Example 209 | 44 | 5.38 | 5.90 | (0.134, 0.100) | 36 |
| Example 210 | 45 | 5.22 | 6.01 | (0.134, 0.100) | 28 |
| Example 211 | 46 | 4.70 | 6.67 | (0.134, 0.102) | 61 |
| Example 212 | 47 | 5.28 | 6.10 | (0.134, 0.100) | 40 |
| Example 213 | 48 | 5.30 | 6.20 | (0.134, 0.101) | 40 |
| Example 214 | 50 | 4.45 | 7.03 | (0.134, 0.100) | 33 |
| Example 215 | 51 | 5.44 | 6.14 | (0.134, 0.102) | 35 |
| Example 216 | 52 | 5.50 | 6.00 | (0.134, 0.102) | 31 |
| Example 217 | 75 | 5.40 | 6.21 | (0.134, 0.101) | 36 |
| Example 218 | 85 | 5.48 | 6.22 | (0.134, 0.101) | 38 |
| Example 219 | 86 | 5.44 | 6.25 | (0.134, 0.102) | 40 |
| Example 220 | 94 | 5.50 | 6.32 | (0.134, 0.101) | 33 |

TABLE 8-continued

| | Compound | Driving Voltage (V) | Light Emission Efficiency (cd/A) | CIE (x, y) | Lifespan (T95) |
|---|---|---|---|---|---|
| Example 221 | 95 | 5.44 | 6.44 | (0.134, 0.102) | 32 |
| Example 222 | 96 | 5.34 | 6.38 | (0.134, 0.101) | 31 |
| Example 223 | 97 | 5.38 | 6.20 | (0.134, 0.103) | 35 |
| Example 224 | 98 | 5.30 | 6.42 | (0.134, 0.102) | 34 |
| Example 225 | 100 | 5.35 | 6.30 | (0.134, 0.101) | 33 |
| Example 226 | 102 | 5.44 | 6.22 | (0.134, 0.102) | 30 |
| Example 227 | 149 | 5.32 | 5.95 | (0.134, 0.101) | 29 |
| Example 228 | 150 | 5.40 | 6.13 | (0.134, 0.101) | 31 |
| Example 229 | 151 | 5.44 | 5.89 | (0.134, 0.100) | 32 |
| Example 230 | 153 | 5.39 | 6.01 | (0.134, 0.101) | 29 |
| Example 231 | 163 | 4.56 | 6.88 | (0.134, 0.100) | 41 |
| Example 232 | 173 | 4.51 | 6.93 | (0.134, 0.100) | 40 |
| Example 233 | 183 | 4.41 | 6.95 | (0.134, 0.100) | 39 |
| Example 234 | 192 | 4.98 | 6.22 | (0.134, 0.100) | 40 |
| Example 235 | 193 | 5.02 | 6.34 | (0.134, 0.101) | 39 |
| Example 236 | 194 | 4.72 | 6.53 | (0.134, 0.102) | 66 |
| Example 237 | 195 | 5.05 | 6.14 | (0.134, 0.101) | 40 |
| Example 238 | 196 | 5.25 | 6.22 | (0.134, 0.100) | 41 |
| Example 239 | 198 | 5.59 | 6.19 | (0.134, 0.102) | 32 |
| Example 240 | 199 | 5.42 | 6.26 | (0.134, 0.101) | 32 |
| Example 241 | 200 | 5.11 | 6.11 | (0.134, 0.100) | 40 |
| Example 242 | 242 | 5.35 | 6.22 | (0.134, 0.102) | 38 |
| Example 243 | 243 | 5.34 | 6.20 | (0.134, 0.103) | 37 |
| Example 244 | 244 | 5.20 | 6.19 | (0.134, 0.100) | 37 |
| Example 245 | 245 | 5.22 | 6.05 | (0.134, 0.103) | 39 |
| Example 246 | 246 | 5.19 | 6.28 | (0.134, 0.102) | 40 |
| Example 247 | 248 | 5.33 | 6.01 | (0.134, 0.100) | 39 |
| Example 248 | 249 | 5.10 | 6.21 | (0.134, 0.101) | 40 |
| Example 249 | 250 | 5.40 | 6.05 | (0.134, 0.101) | 33 |
| Example 250 | 253 | 5.33 | 6.11 | (0.134, 0.100) | 33 |
| Example 251 | 263 | 5.31 | 6.21 | (0.134, 0.103) | 39 |
| Example 252 | 273 | 5.36 | 6.08 | (0.134, 0.101) | 32 |
| Example 253 | 292 | 5.30 | 5.98 | (0.134, 0.104) | 30 |
| Example 254 | 293 | 5.30 | 5.80 | (0.134, 0.100) | 35 |
| Example 255 | 294 | 5.11 | 6.22 | (0.134, 0.103) | 36 |
| Example 256 | 295 | 5.11 | 6.20 | (0.134, 0.100) | 40 |
| Example 257 | 296 | 5.24 | 6.10 | (0.134, 0.102) | 38 |
| Example 258 | 298 | 5.41 | 6.21 | (0.134, 0.100) | 39 |
| Example 259 | 299 | 5.33 | 6.19 | (0.134, 0.101) | 30 |
| Example 260 | 300 | 5.37 | 6.05 | (0.134, 0.100) | 28 |
| Example 261 | 301 | 5.18 | 6.03 | (0.134, 0.101) | 30 |
| Example 262 | 303 | 5.27 | 5.98 | (0.134, 0.100) | 33 |
| Example 263 | 313 | 5.39 | 6.05 | (0.134, 0.101) | 40 |
| Example 264 | 323 | 5.05 | 6.23 | (0.134, 0.101) | 41 |
| Example 265 | 333 | 5.18 | 6.20 | (0.134, 0.100) | 30 |
| Example 266 | 342 | 5.43 | 6.17 | (0.134, 0.102) | 34 |
| Example 267 | 343 | 5.40 | 6.21 | (0.134, 0.103) | 39 |
| Example 268 | 344 | 5.34 | 6.38 | (0.134, 0.100) | 38 |
| Example 269 | 345 | 5.27 | 6.40 | (0.134, 0.102) | 41 |
| Example 270 | 346 | 5.15 | 6.10 | (0.134, 0.103) | 39 |
| Example 271 | 348 | 5.20 | 6.15 | (0.134, 0.101) | 40 |
| Example 272 | 399 | 5.22 | 6.12 | (0.134, 0.101) | 33 |
| Example 273 | 400 | 5.05 | 6.20 | (0.134, 0.102) | 37 |
| Example 274 | 401 | 5.11 | 6.14 | (0.134, 0.102) | 38 |
| Example 275 | 403 | 5.22 | 6.22 | (0.134, 0.103) | 36 |
| Example 276 | 413 | 5.07 | 6.24 | (0.134, 0.100) | 33 |
| Example 277 | 423 | 5.05 | 6.31 | (0.134, 0.100) | 31 |
| Example 278 | 442 | 5.09 | 6.22 | (0.134, 0.101) | 32 |
| Example 279 | 443 | 5.11 | 6.05 | (0.134, 0.103) | 35 |
| Example 280 | 444 | 5.21 | 6.09 | (0.134, 0.101) | 33 |
| Example 281 | 445 | 5.32 | 6.12 | (0.134, 0.102) | 31 |
| Example 282 | 446 | 5.33 | 6.20 | (0.134, 0.101) | 28 |
| Example 283 | 448 | 5.34 | 6.25 | (0.134, 0.102) | 29 |
| Example 284 | 449 | 5.43 | 6.17 | (0.134, 0.102) | 30 |
| Example 285 | 450 | 5.29 | 6.18 | (0.134, 0.101) | 35 |
| Example 286 | 451 | 5.40 | 6.20 | (0.134, 0.103) | 33 |
| Example 287 | 453 | 5.38 | 6.11 | (0.134, 0.103) | 34 |
| Example 288 | 463 | 5.35 | 6.01 | (0.134, 0.102) | 33 |
| Example 289 | 473 | 5.37 | 6.05 | (0.134, 0.101) | 31 |
| Example 290 | 484 | 5.40 | 5.99 | (0.134, 0.102) | 37 |
| Example 291 | 492 | 5.51 | 5.90 | (0.134, 0.103) | 38 |
| Example 292 | 493 | 5.54 | 6.22 | (0.134, 0.102) | 33 |
| Example 293 | 494 | 5.34 | 6.19 | (0.134, 0.104) | 30 |
| Example 294 | 495 | 5.38 | 5.92 | (0.134, 0.104) | 28 |
| Example 295 | 496 | 5.27 | 6.11 | (0.134, 0.101) | 38 |

TABLE 8-continued

| | Compound | Driving Voltage (V) | Light Emission Efficiency (cd/A) | CIE (x, y) | Lifespan (T95) |
|---|---|---|---|---|---|
| Example 296 | 498 | 5.25 | 6.02 | (0.134, 0.102) | 34 |
| Example 297 | 499 | 5.44 | 6.00 | (0.134, 0.102) | 32 |
| Example 298 | 500 | 5.43 | 6.19 | (0.134, 0.101) | 31 |
| Example 299 | 555 | 5.48 | 6.35 | (0.134, 0.101) | 30 |
| Example 300 | 556 | 5.55 | 6.09 | (0.134, 0.100) | 40 |
| Comparative Example 3-1 | E1 | 5.56 | 5.91 | (0.134, 0.100) | 28 |
| Comparative Example 3-2 | BBQB | 5.50 | 6.10 | (0.134, 0.101) | 30 |
| Comparative Example 3-3 | TBQB | 5.51 | 6.15 | (0.134, 0.102) | 29 |

As shown from the results of Table 8, the organic light emitting devices using the electron transfer layer material of the blue organic light emitting device of the present disclosure had a low driving voltage and significantly improved light emission efficiency and lifespan compared to Comparative Example 3. Particularly, it was identified that Compounds 5, 15, 25, 46, 50, 153, 163, 173, 194 and 198 were significantly excellent in all of driving, efficiency and lifespan.

The presumed reason for such results is that, when the invented compound having proper length, strength and flat property is used as an electron transfer layer, a compound in an excited state is produced by receiving electrons under a specific condition, and particularly, when the excited state is formed in the heteroskeleton site of the compound, excited energy moves to a stable state before the excited heteroskeleton site goes through a different reaction, and the relatively stabilized compound is capable of efficiently transferring electrons without compound decomposition or destruction. As a reference, it is considered that those having a stable state when excited are aryl or acene series compounds or multicyclic hetero-compounds. Accordingly, it is considered that the compound of the present disclosure enhances electron-transport properties or improved stability resulting in excellency in all of driving, efficiency and lifespan.

The invention claimed is:

1. A hetero-cyclic compound represented by the following Chemical Formula] 2 or 3:

[Chemical Formula 2]

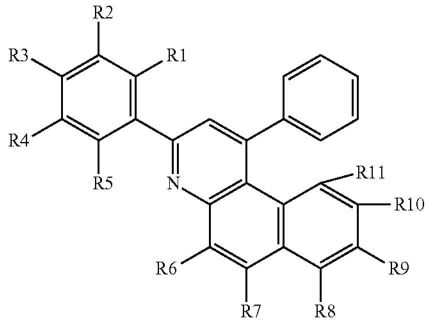

[Chemical Formula 3]

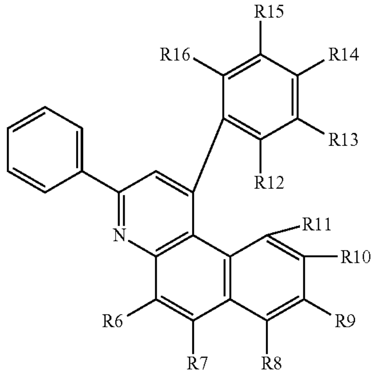

wherein, in Chemical Formula 2 and 3, at least one of R1 to R5 is represented by -(L2)p-(Z2)q and the rest are hydrogen; or deuterium, at least one of R12 to R16 is represented by -(L3)r-(Z3)s, and the rest are hydrogen; or deuterium, L2 and L3 are the same as or different from each other, and each independently a direct bond; or a substituted or unsubstituted $C_6$ to $C_{60}$ arylene group, Z2 and Z3 are the same as or different from each other, and each independently selected from the group consisting of a substituted or unsubstituted pyridine group; a substituted or unsubstituted pyrimidine group; a substituted or unsubstituted triazine group; a substituted or unsubstituted phenanthroline group; a substituted or unsubstituted quinoline group; a substituted or unsubstituted carbazole group; a substituted or unsubstituted dibenzofuran group; a substituted or unsubstituted dibenzothiophene group; a substituted or unsubstituted anthracene group; a substituted or unsubstituted phenanthrene group; a substituted or unsubstituted biphenyl group; a substituted or unsubstituted naphthyl group; and —P(═O)RR', p and r are an integer of 0 to 4;

q and s are an integer of 1 to 4;

R6 to R11 are hydrogen or deuterium; and

R, and R' are the same as or different from each other, and each independently hydrogen; deuterium; —CN; a substituted or unsubstituted $C_1$ to $C_{60}$ alkyl group; a substituted or unsubstituted $C_3$ to $C_{60}$ cycloalkyl group; a substituted or unsubstituted $C_6$ to $C_{60}$ aryl group; or a substituted or unsubstituted $C_2$ to $C_{60}$ heteroaryl group.

2. The hetero-cyclic compound of claim 1, wherein Chemical Formula 2 or 3 is represented by any one of the following compounds:

1

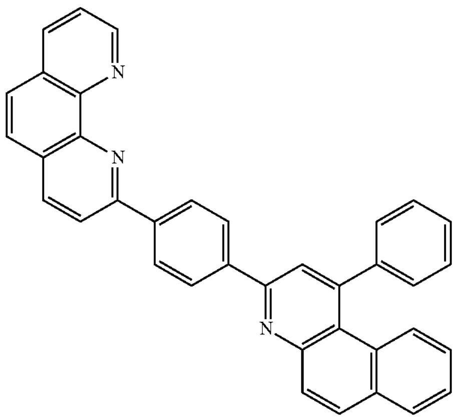

-continued

2

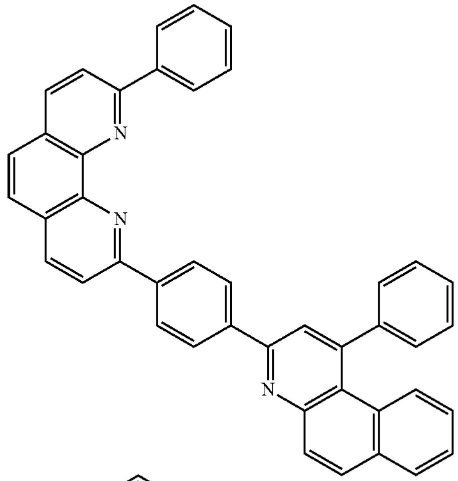

3

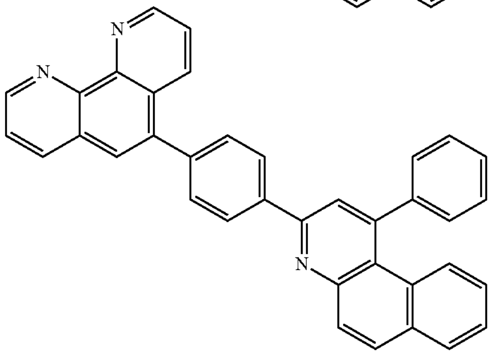

4

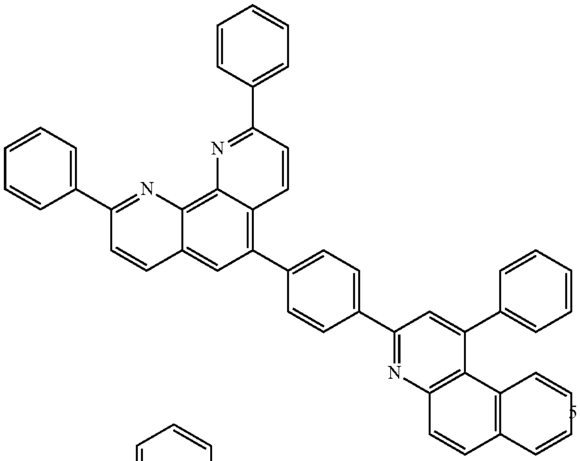

5

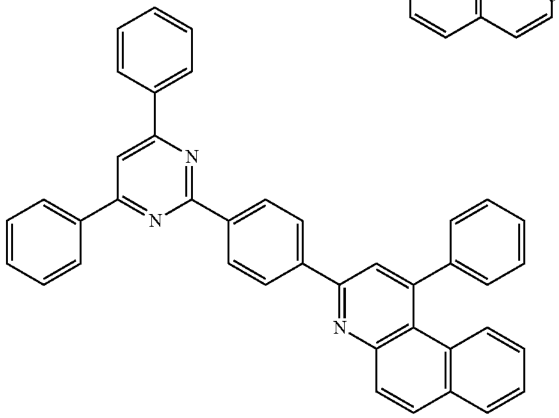

-continued
6
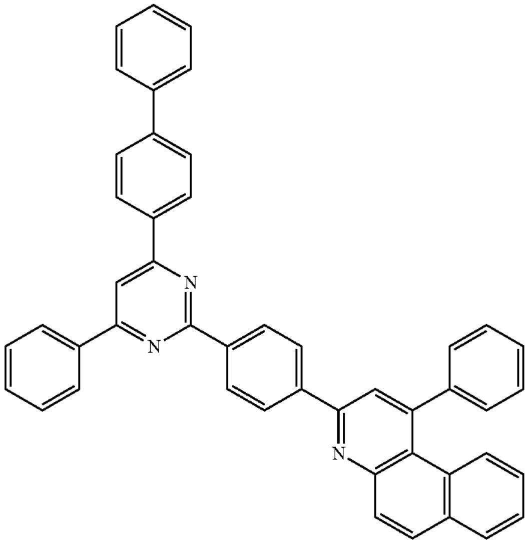
7
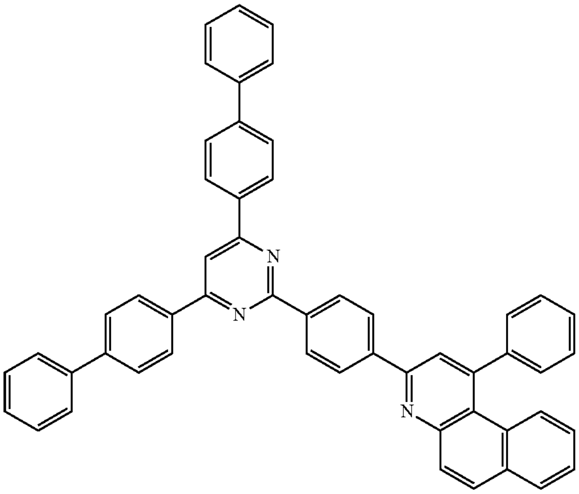
8
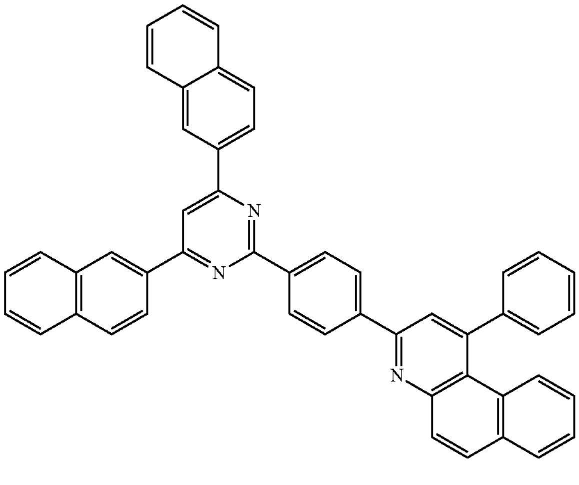
-continued
9
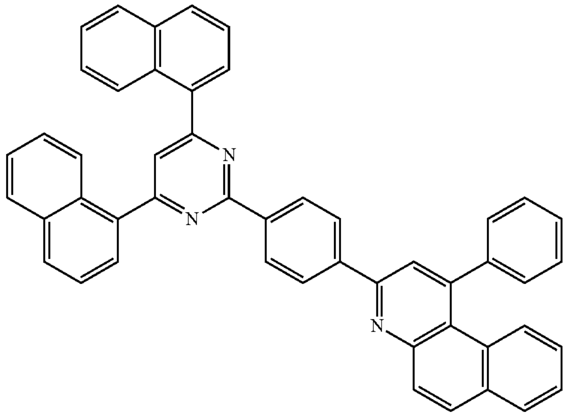
10
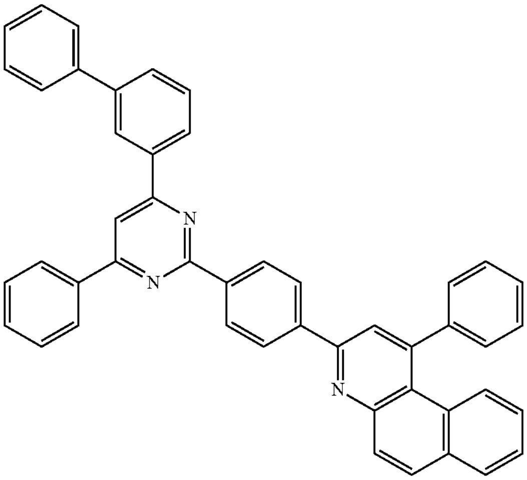
11
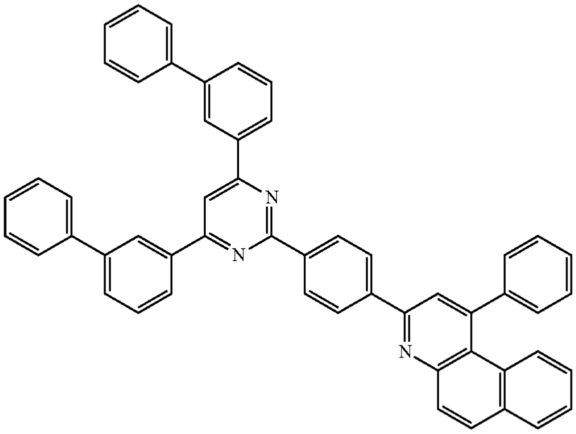

-continued
12
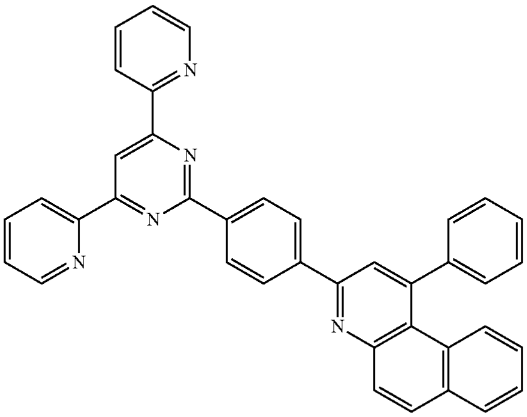
13
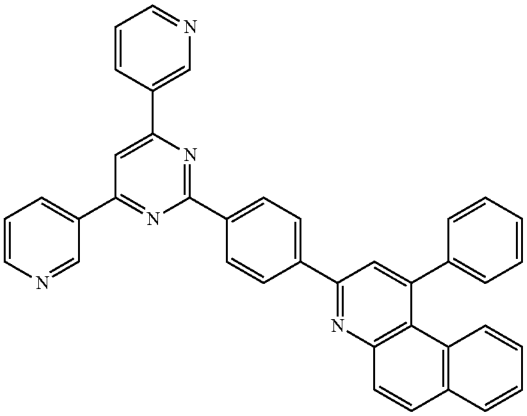
14
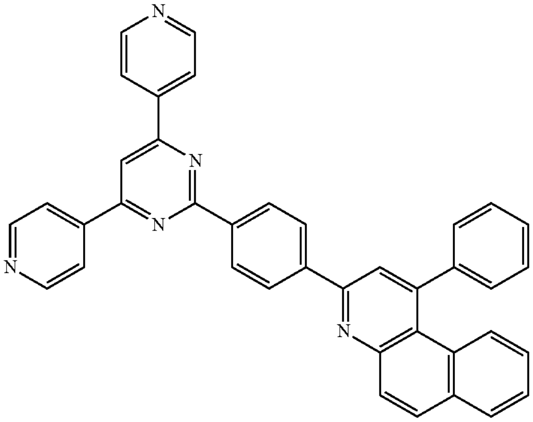
15
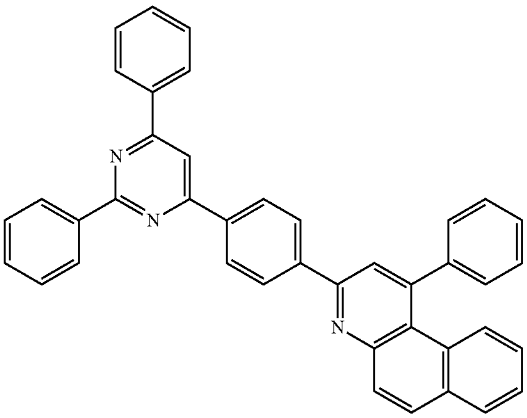
-continued
16
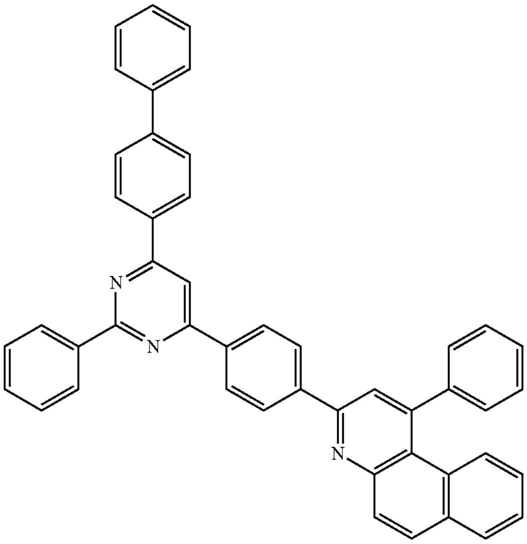
17
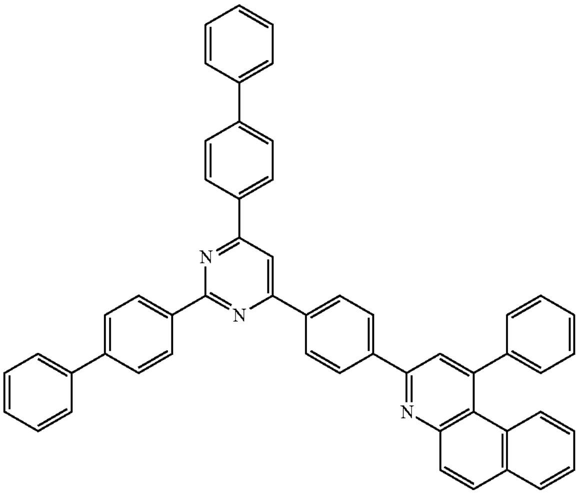
18
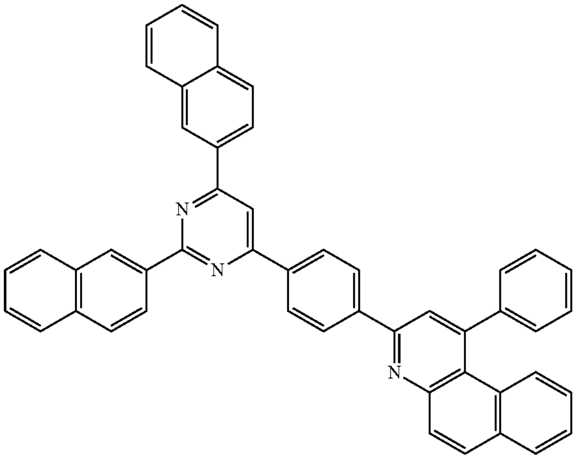

-continued
19
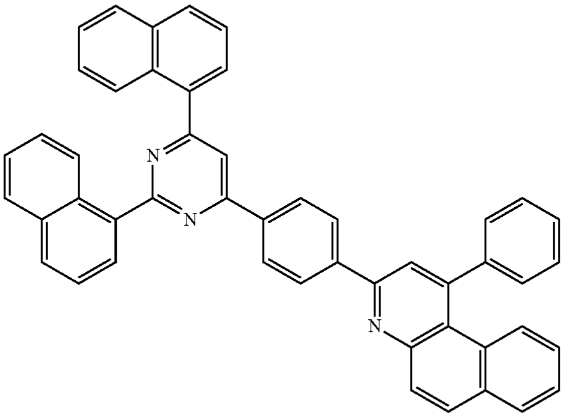
20
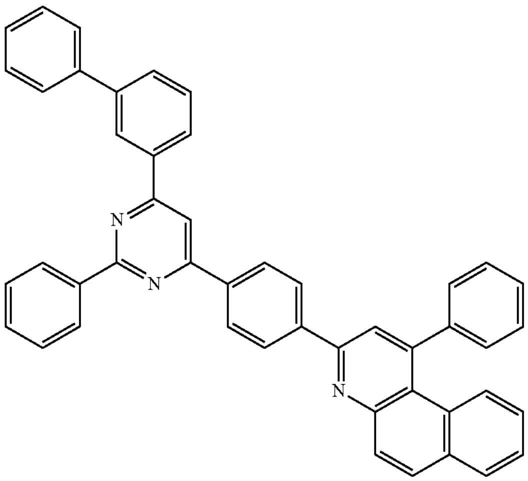
21
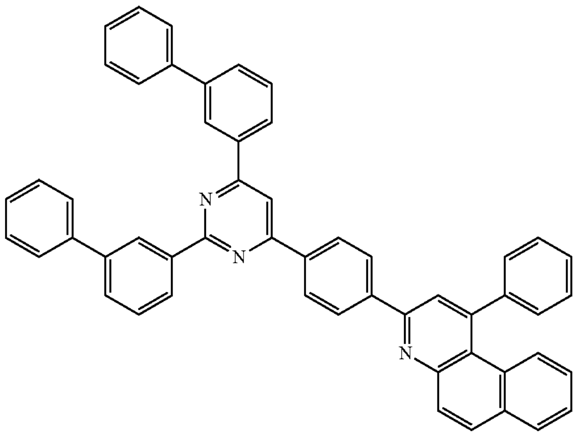
-continued
22
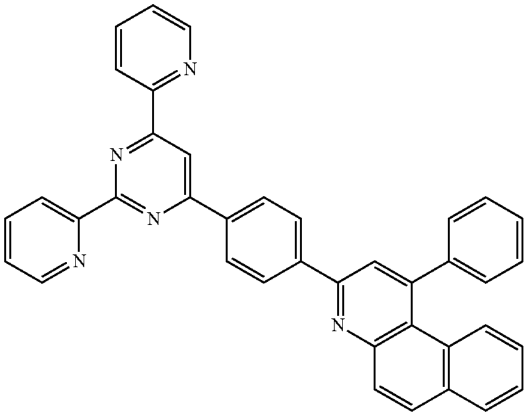
23
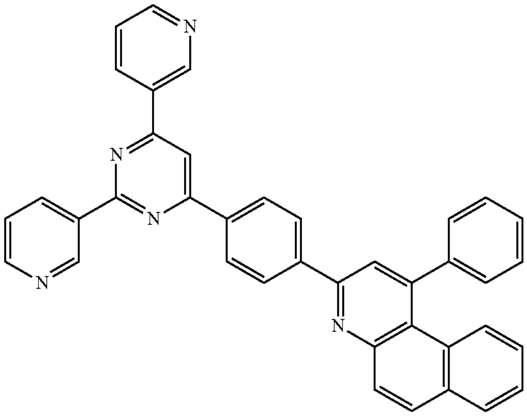
24
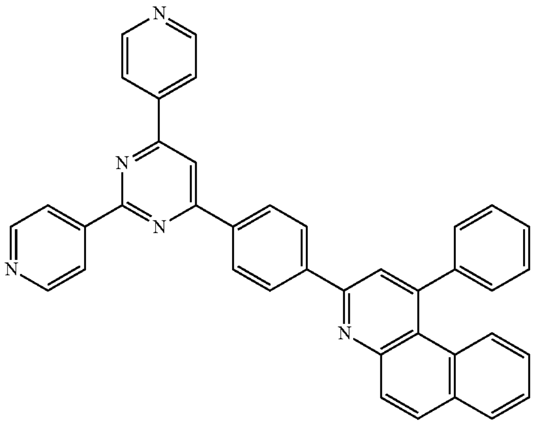
25
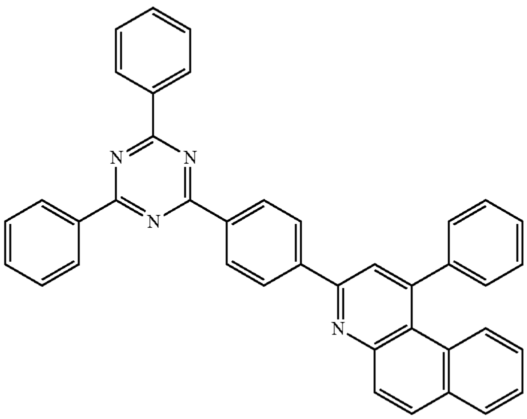

-continued
26
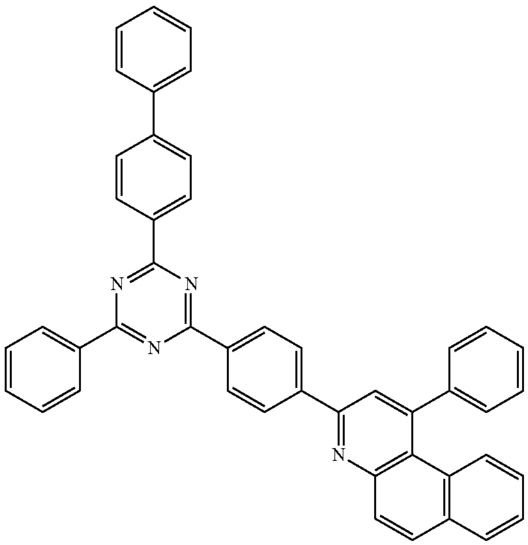
27
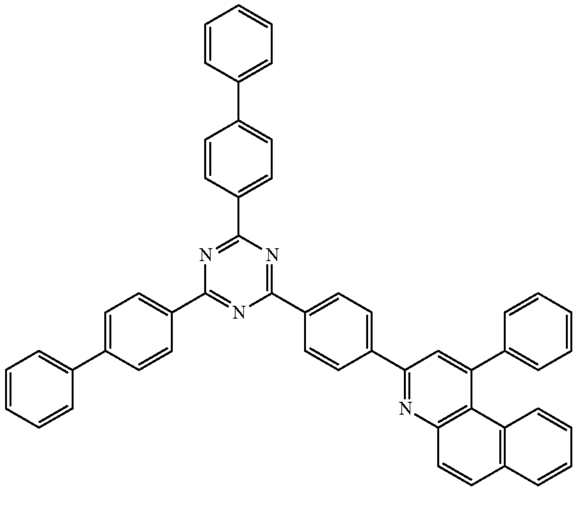
28
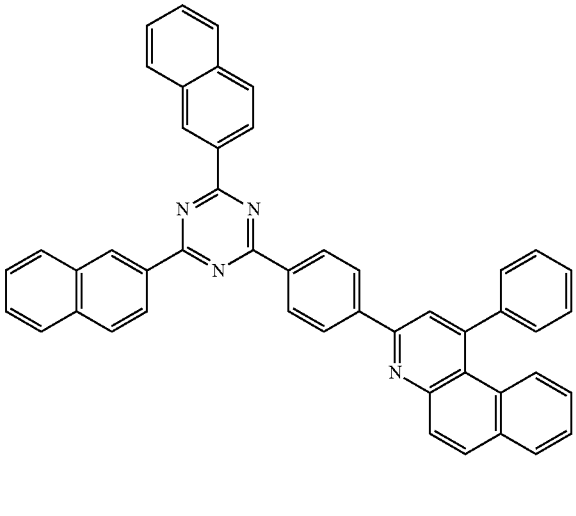
-continued
29
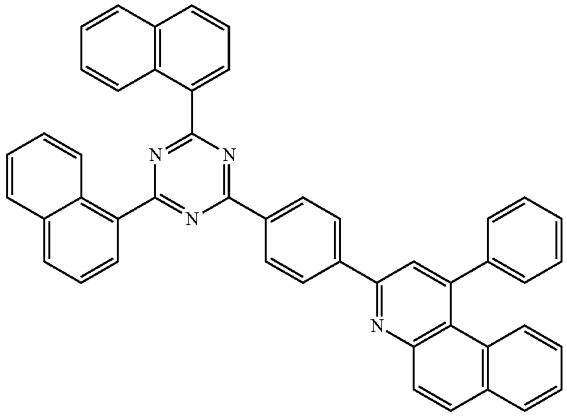
30
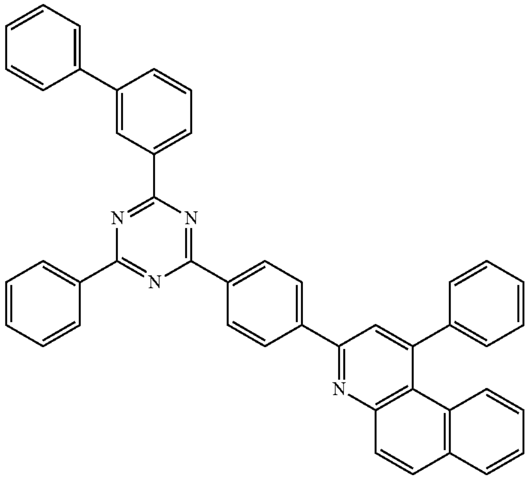
31
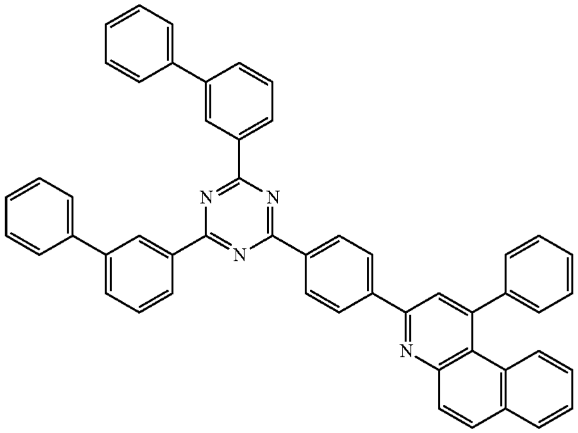

-continued
32
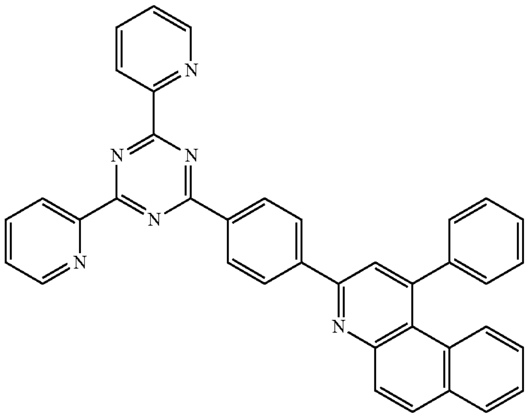
33
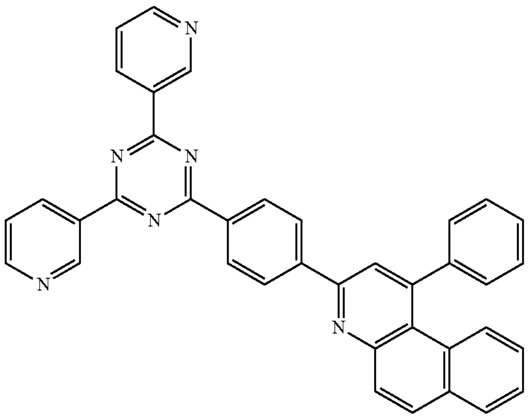
34
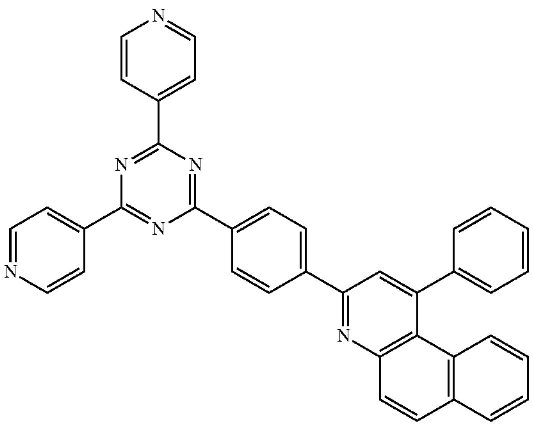
-continued
35
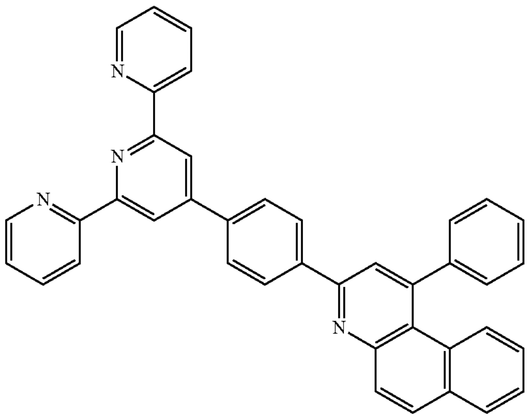
36
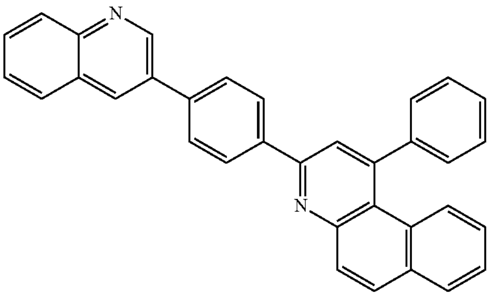
37
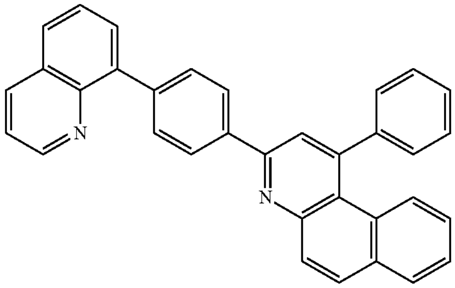
38
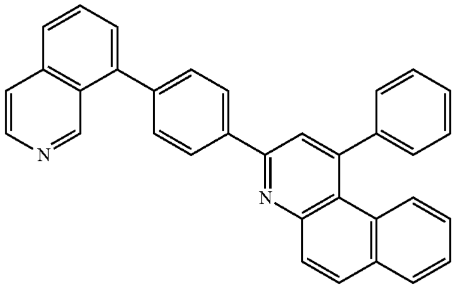
39
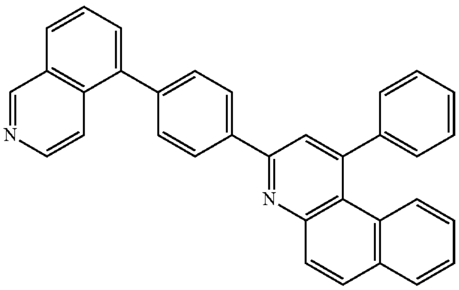

-continued
40
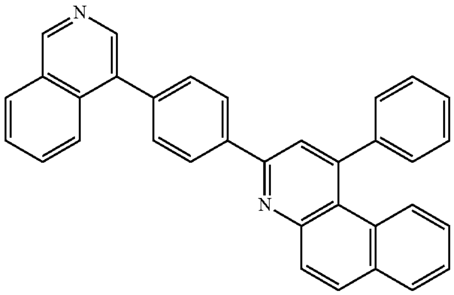
41
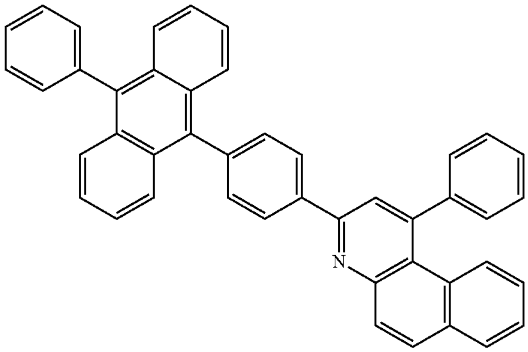
42
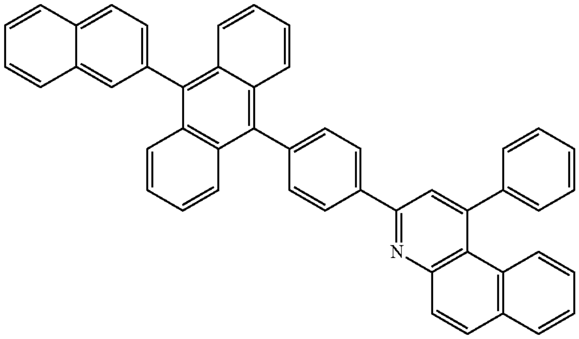
43
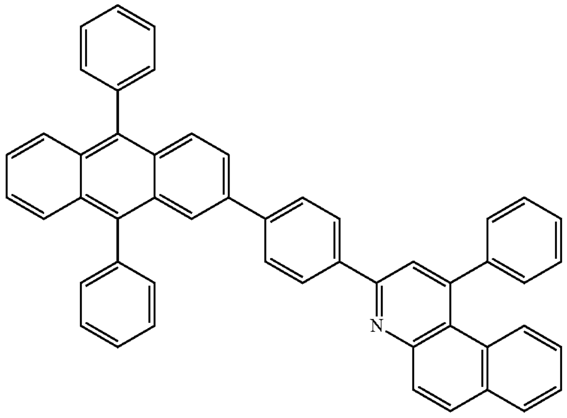
-continued
44
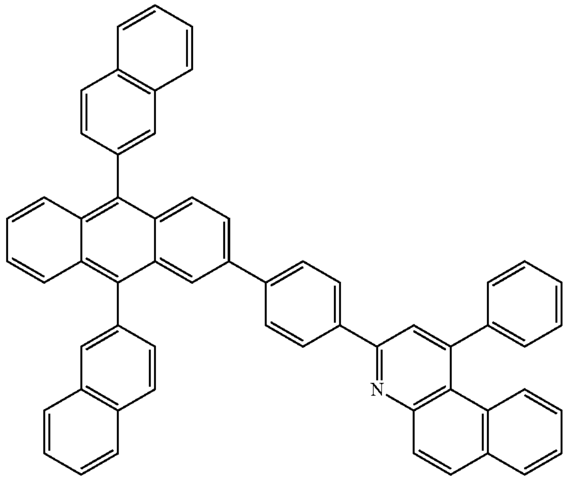
45
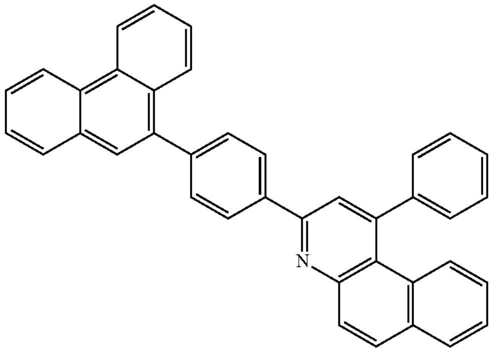
46
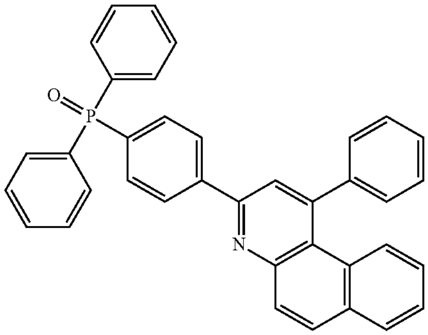
47
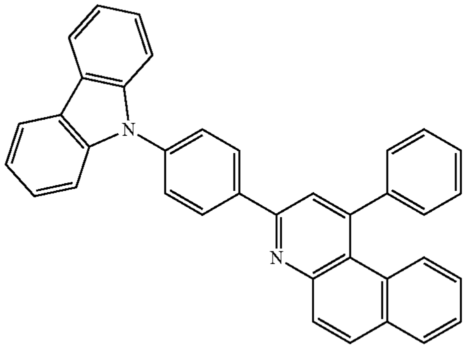

-continued
48
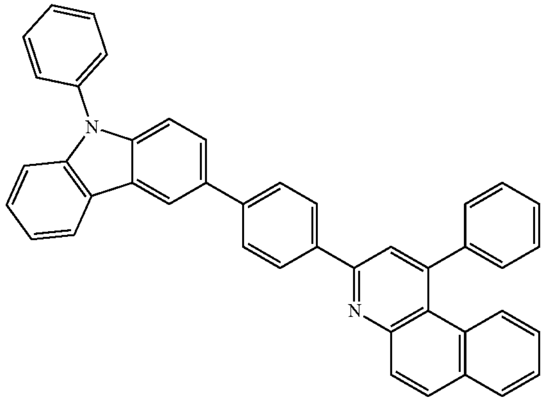
49
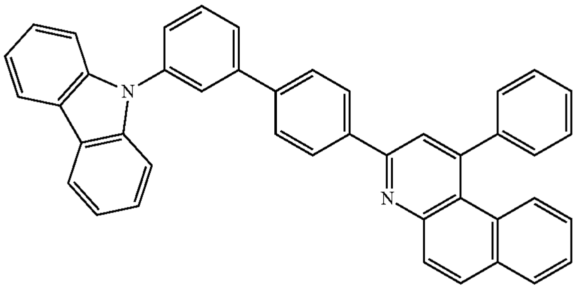
50
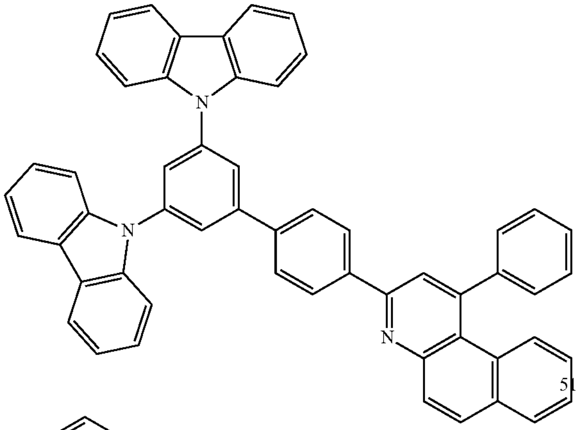
51
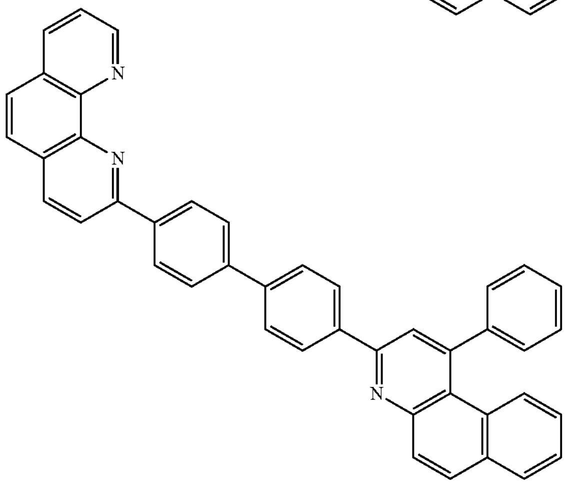
-continued
52
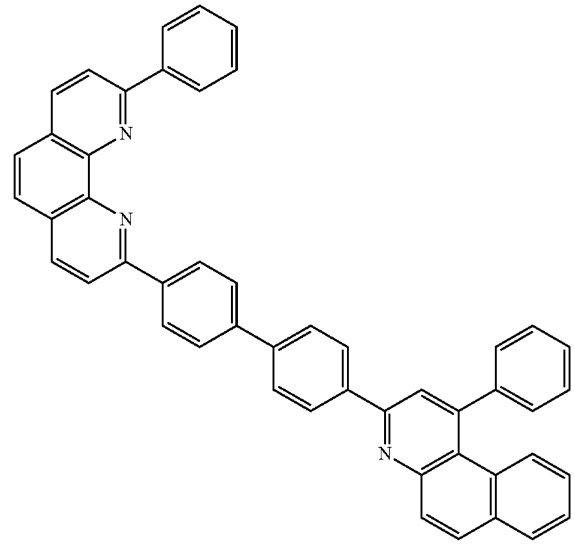
53
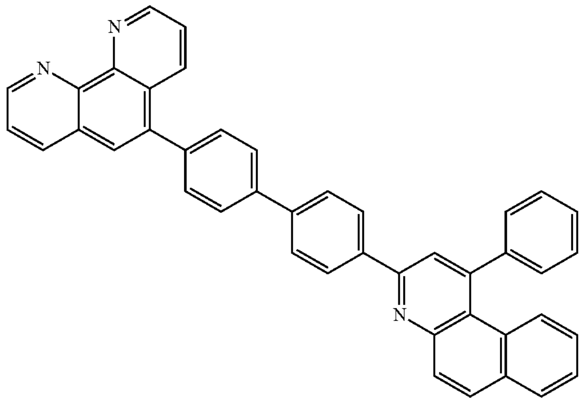
54
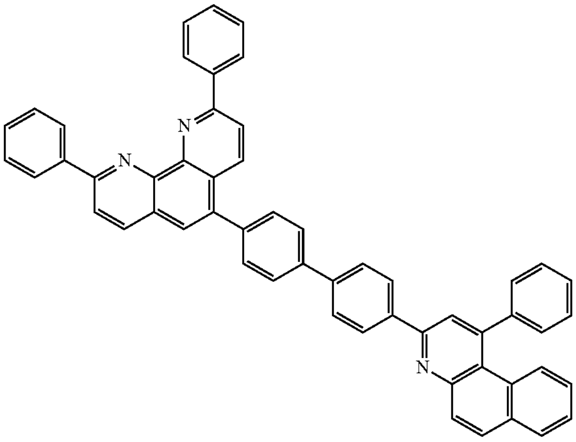

-continued
55
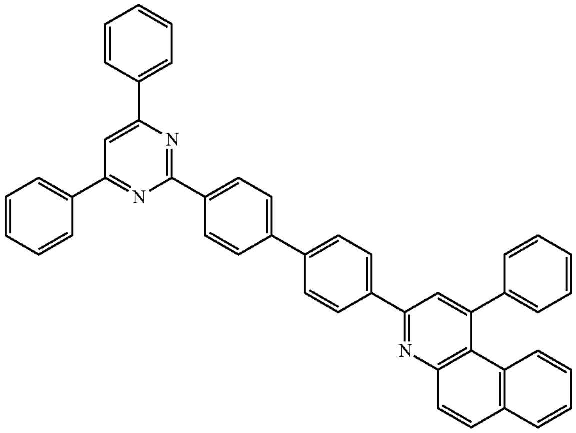
56
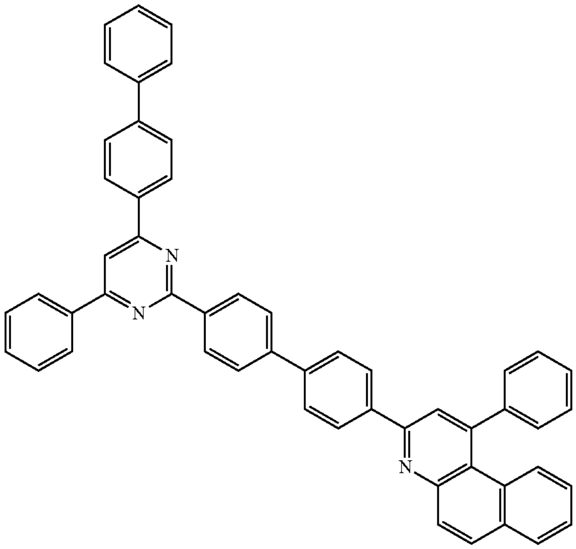
57
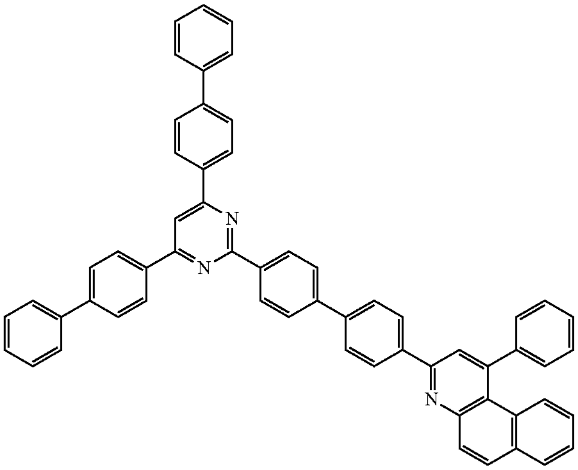
-continued
58
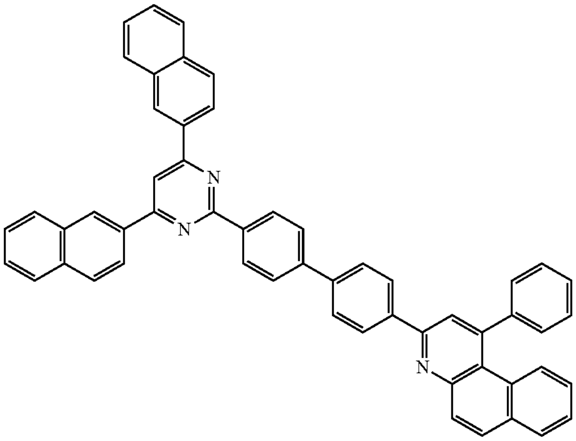
59
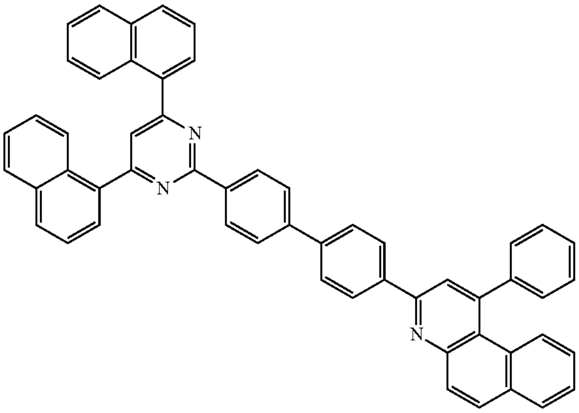
60
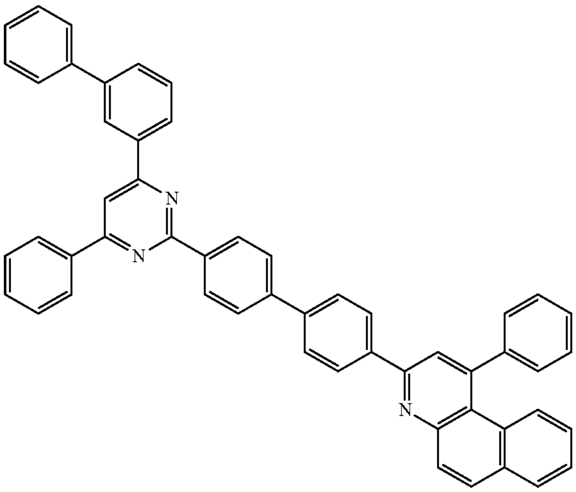

-continued
61
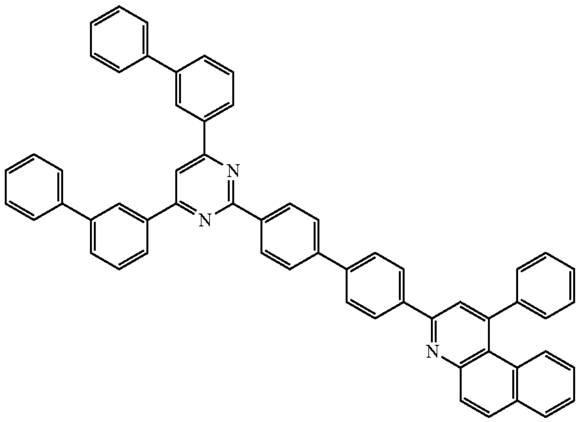
62
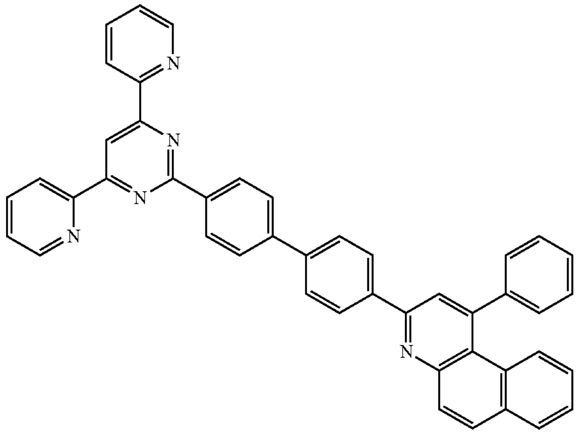
63
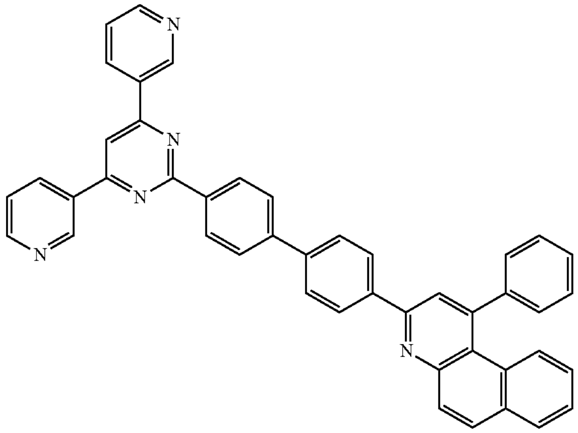
-continued
64
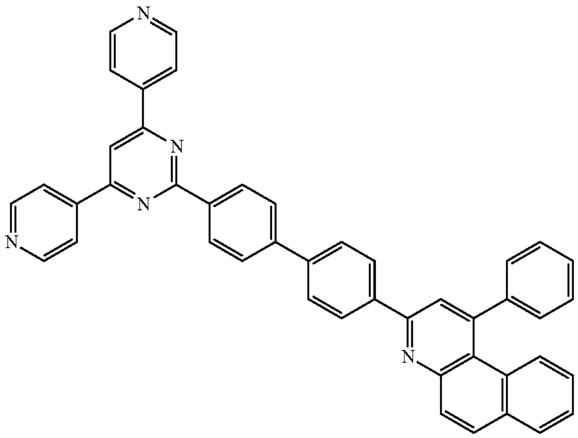
65
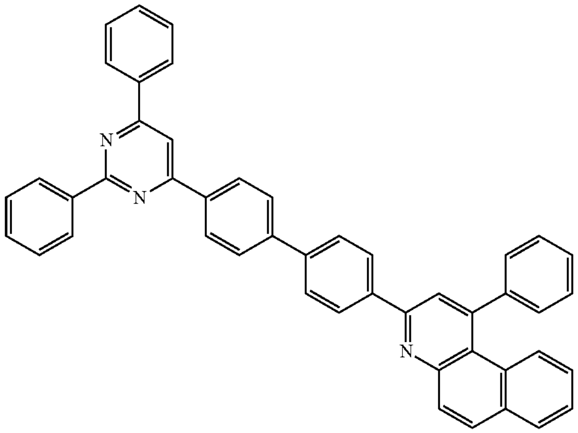
66
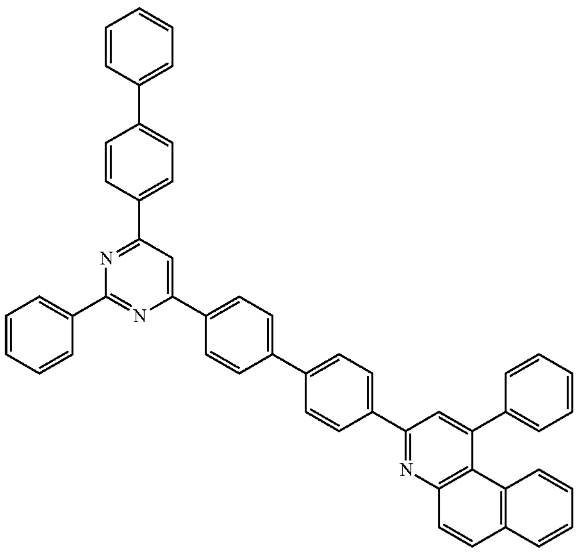

-continued
67
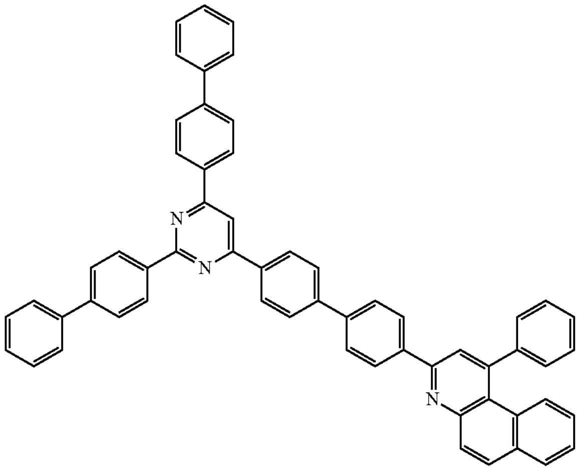
68
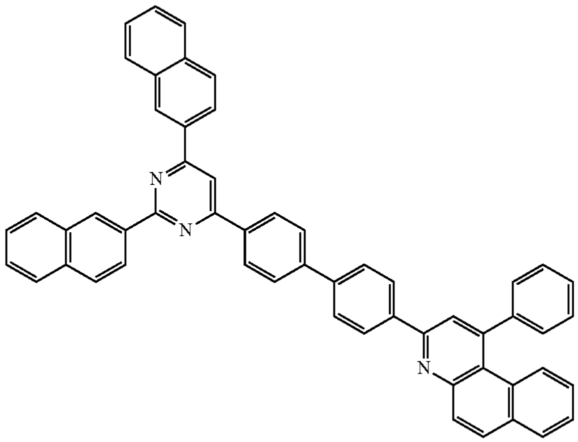
69
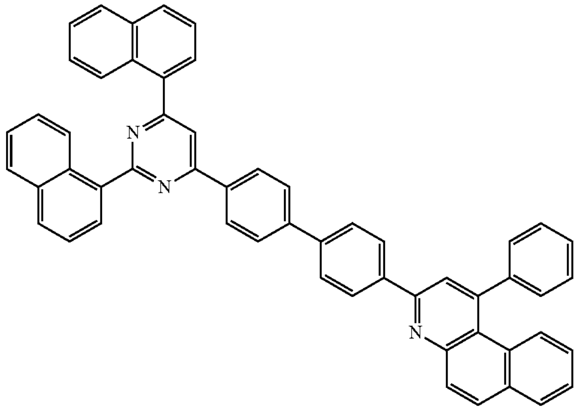
-continued
70
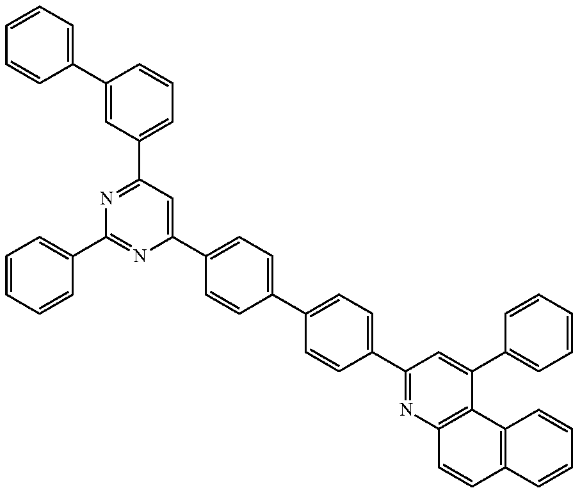
71
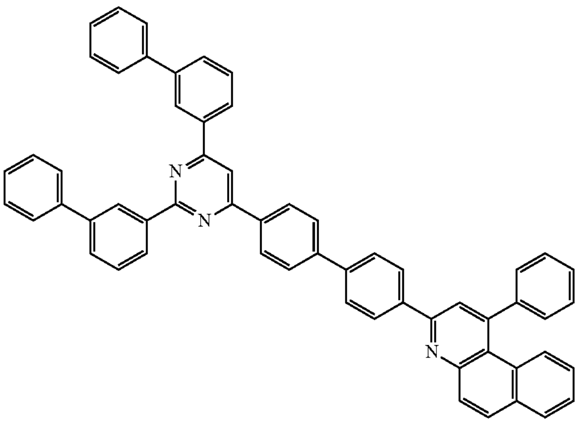
72
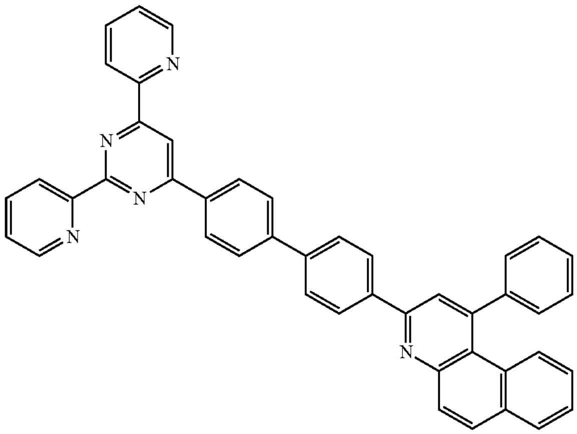

-continued
73
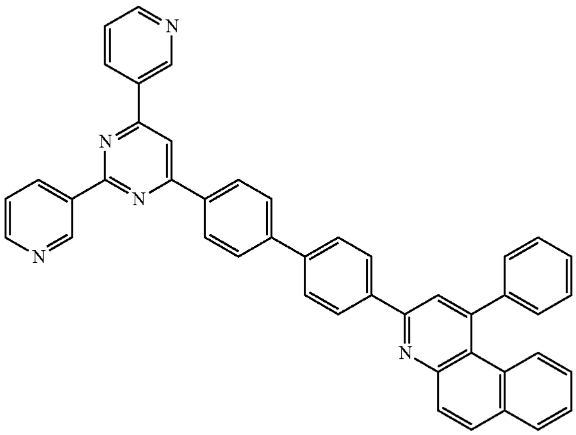
74
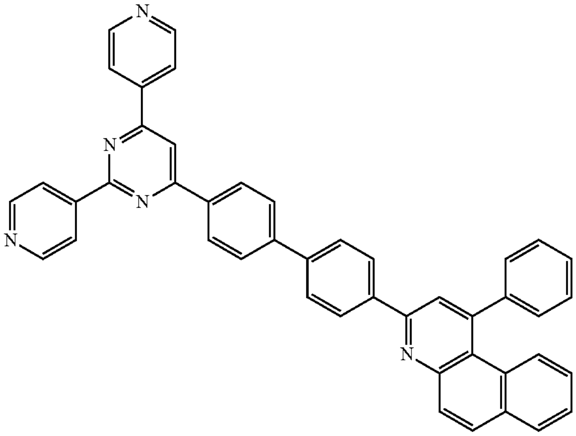
75
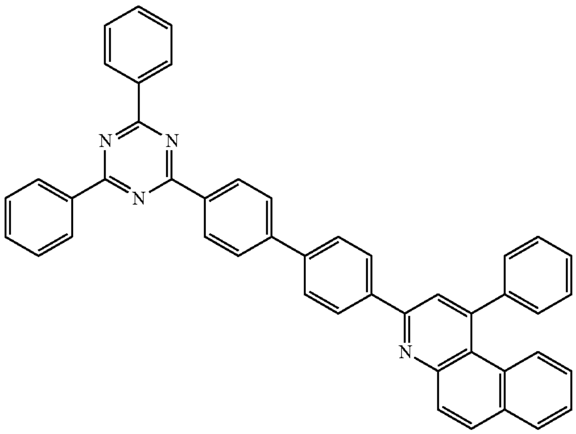
-continued
76
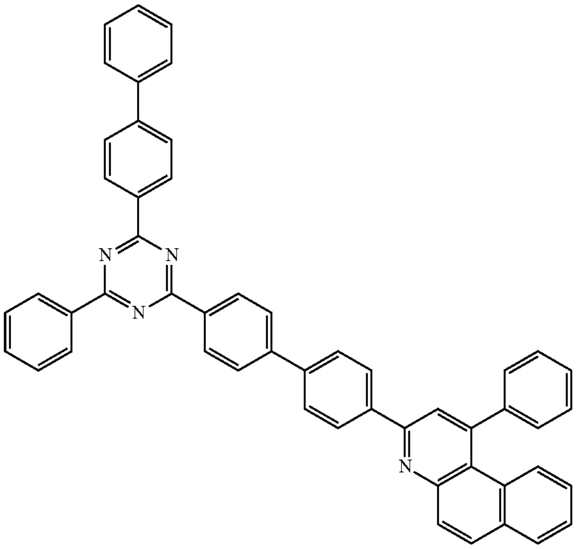
77
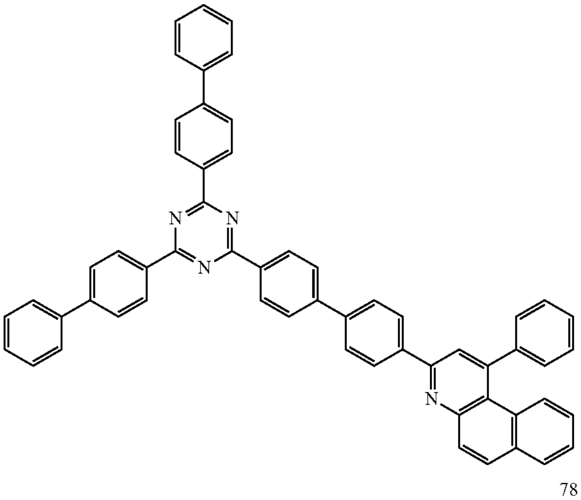
78
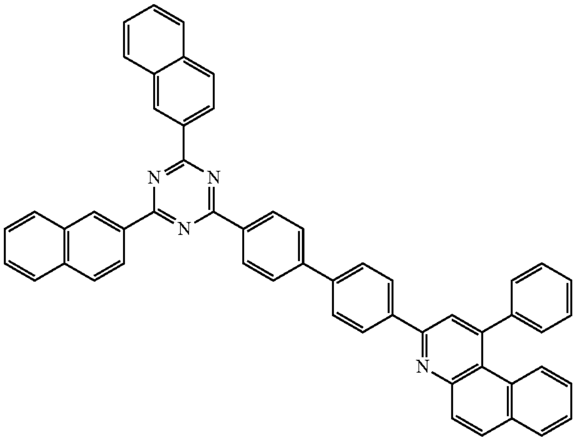

-continued
79
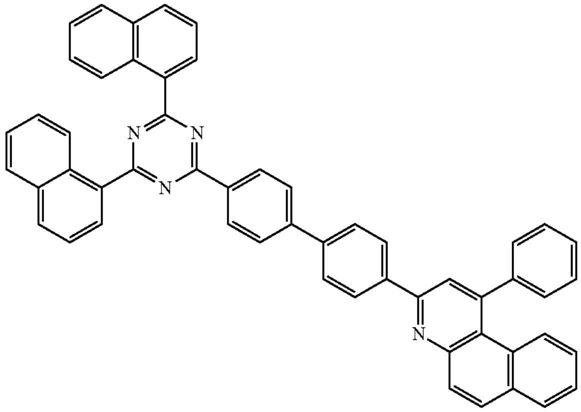
80
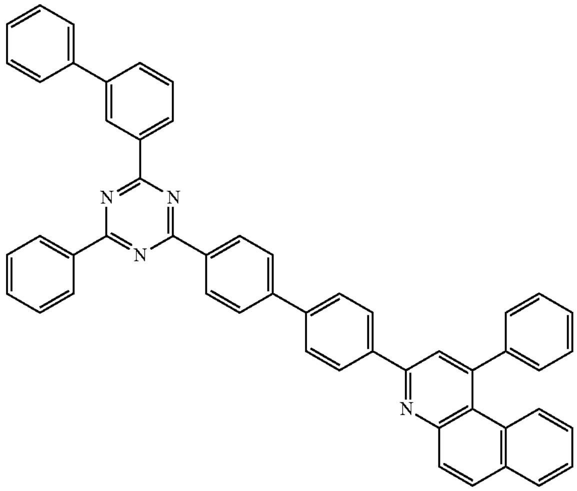
81
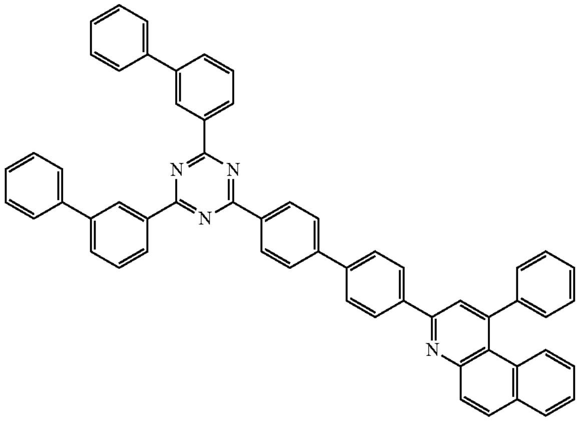
-continued
82
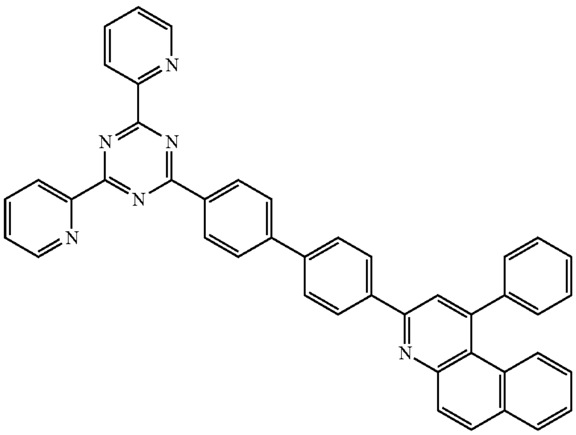
83
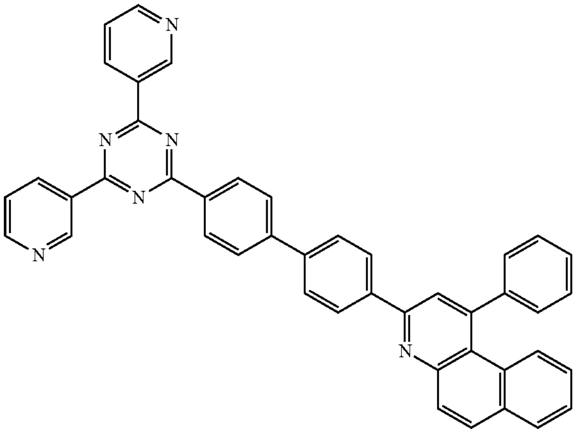
84
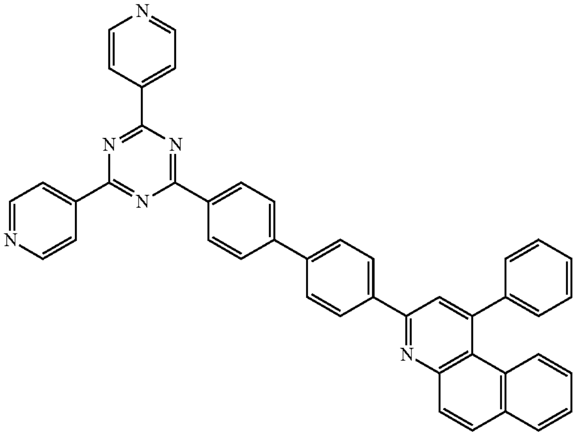

85
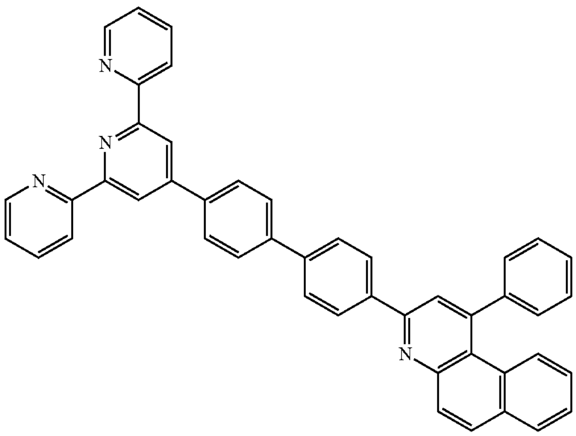
86
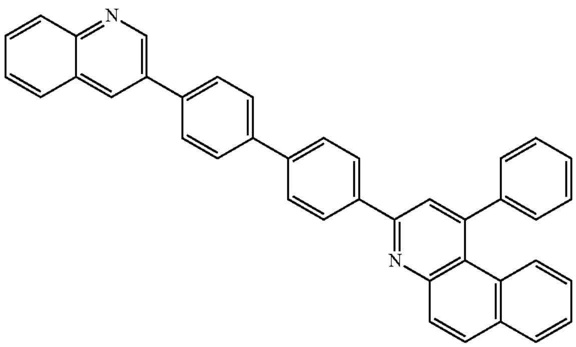
87
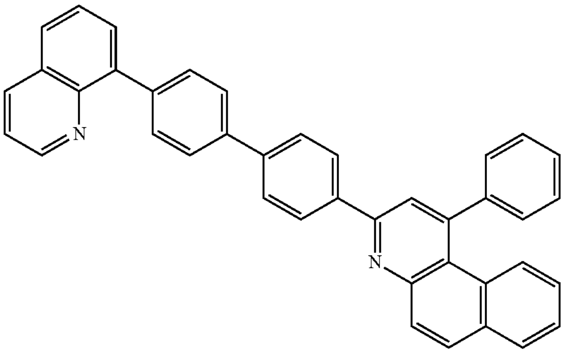
88
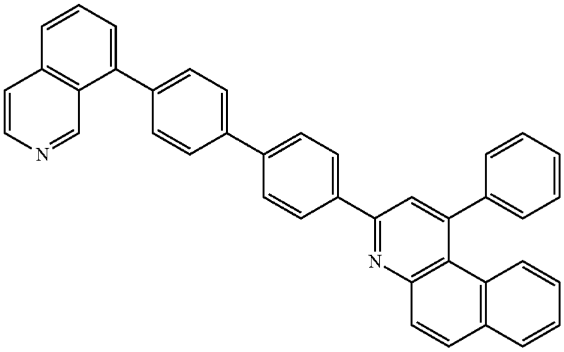
89
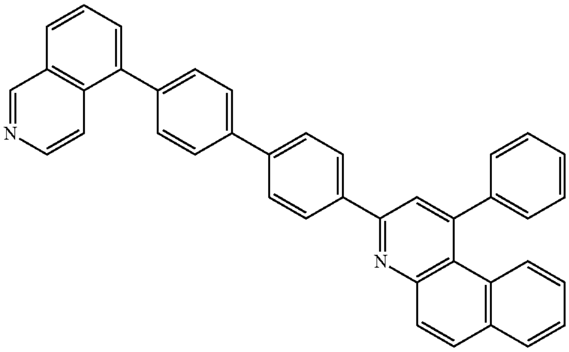
90
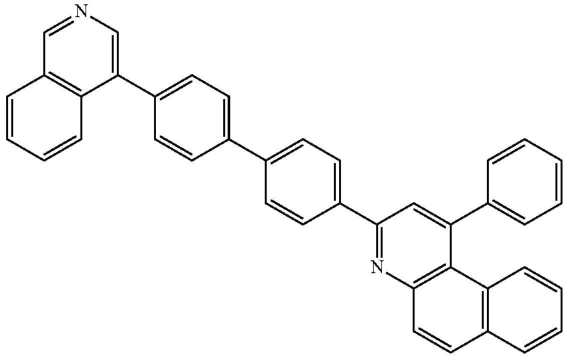
91
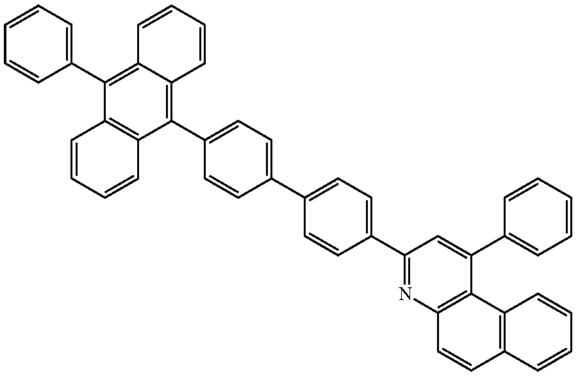
92
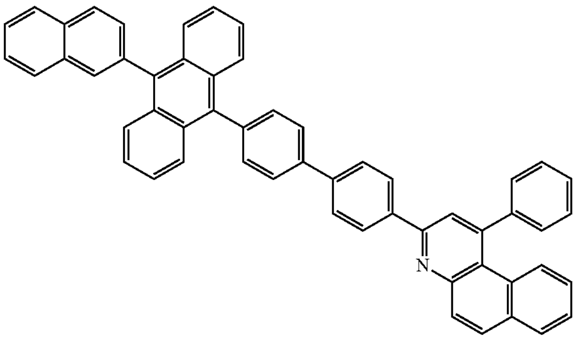

-continued
93
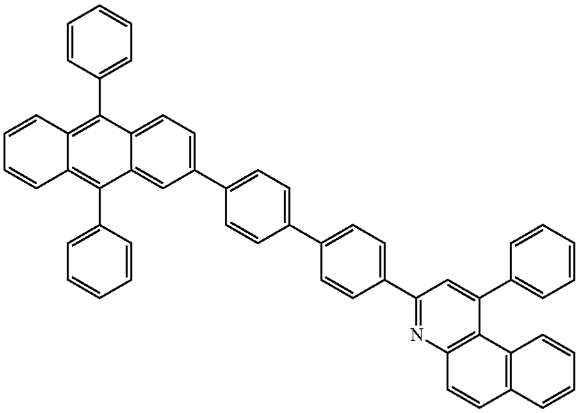
94
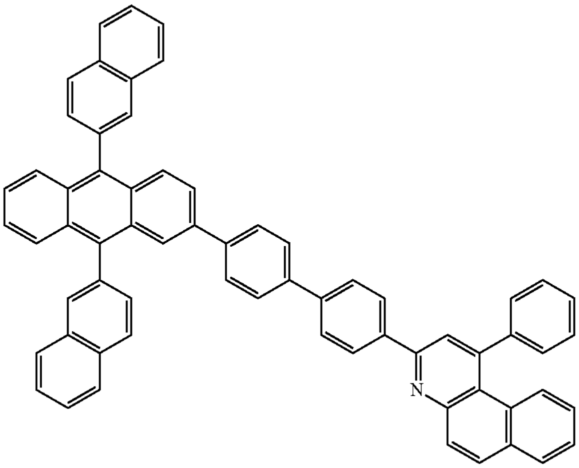
95
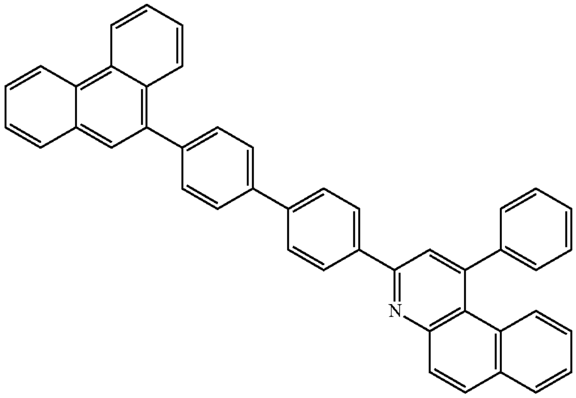
-continued
96
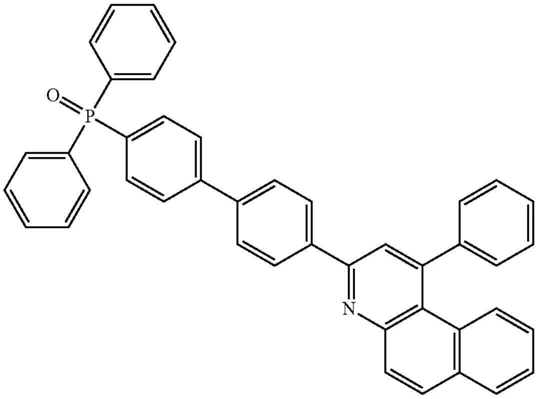
97
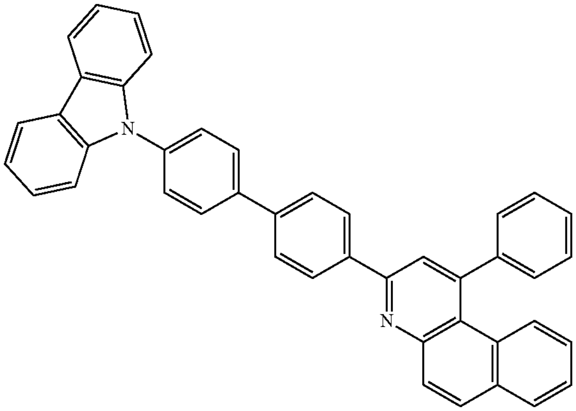
98
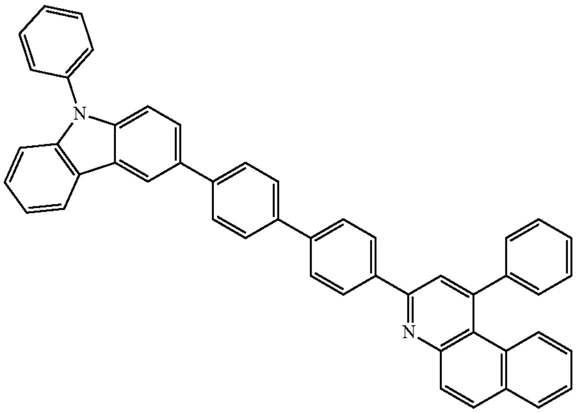
99
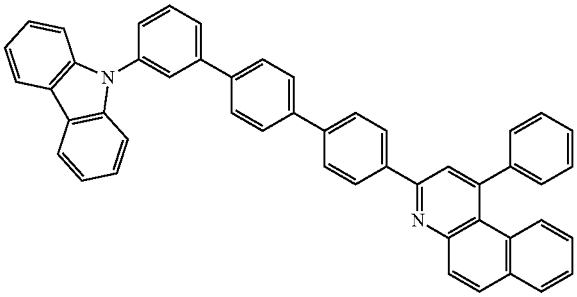

-continued
100
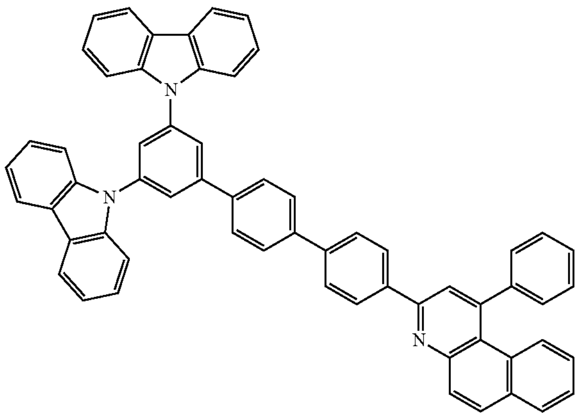
101
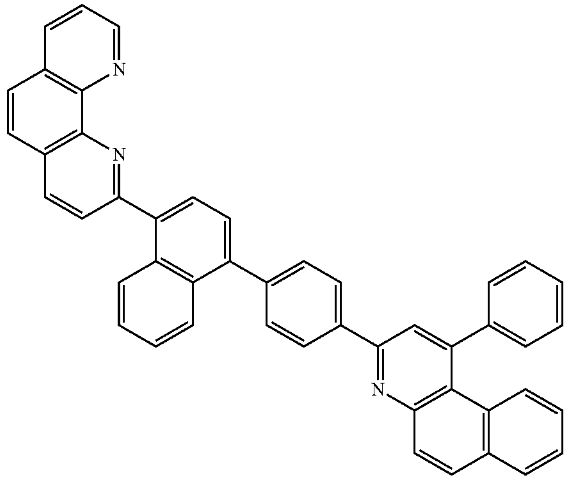
102
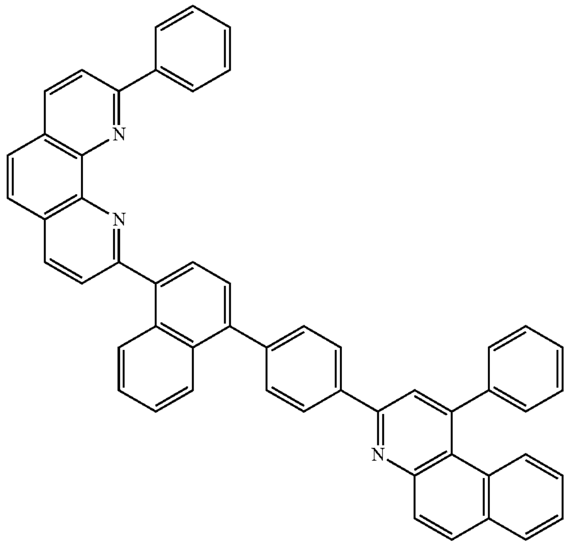
-continued
103
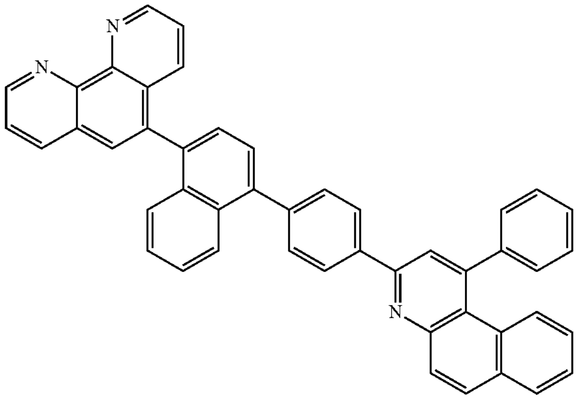
104
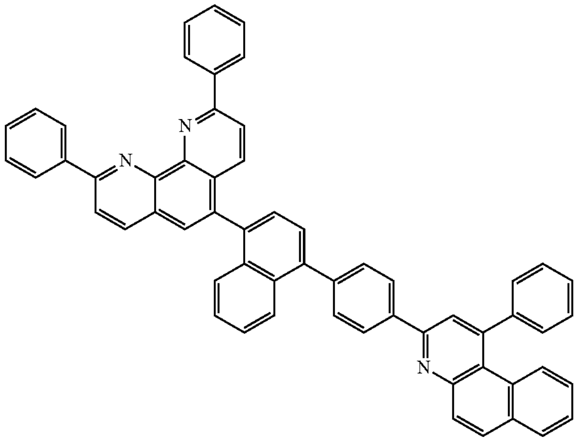
105
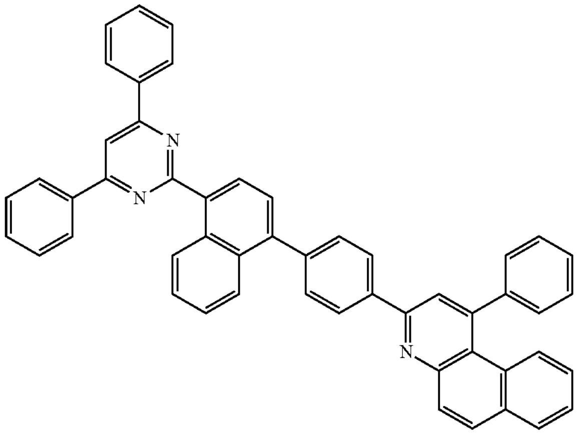

-continued
106
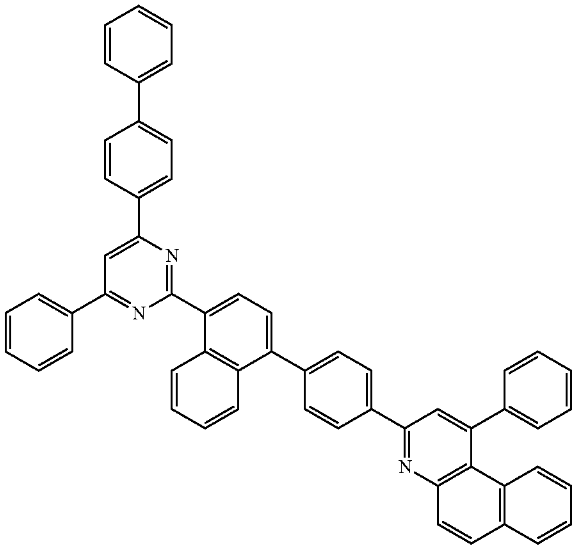
107
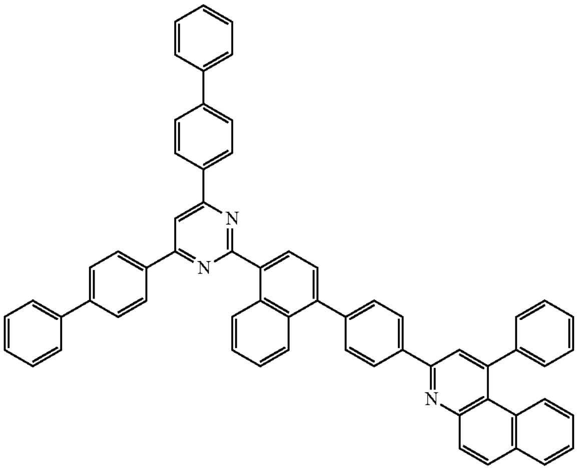
108
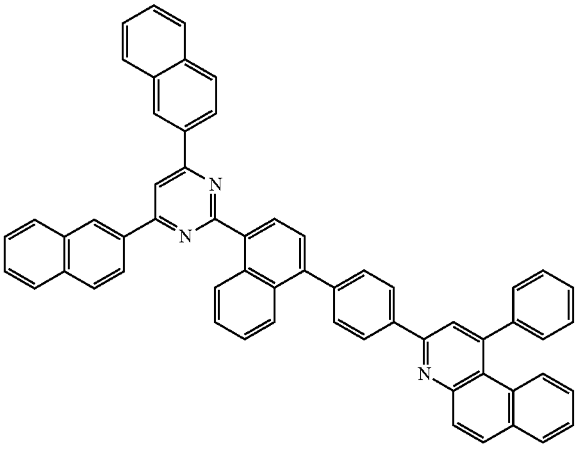
-continued
109
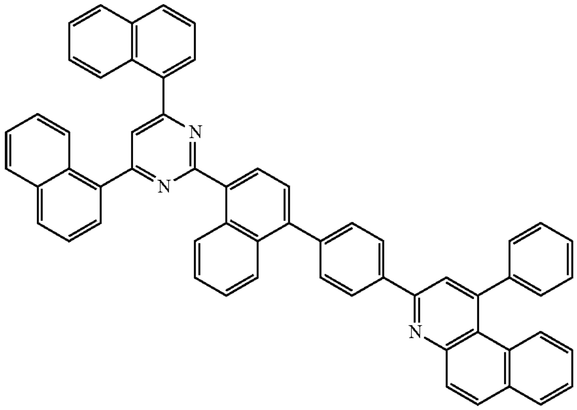
110
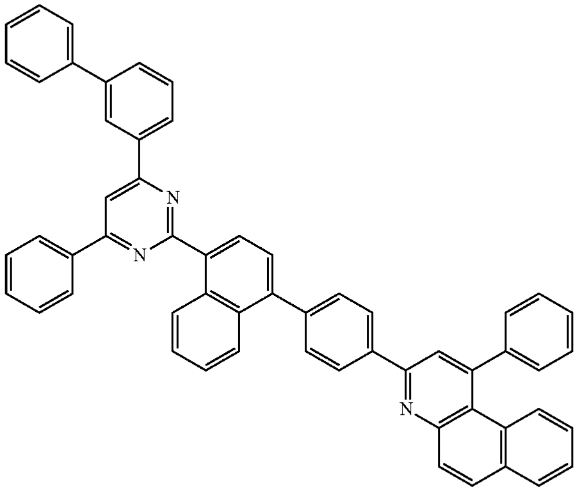
111
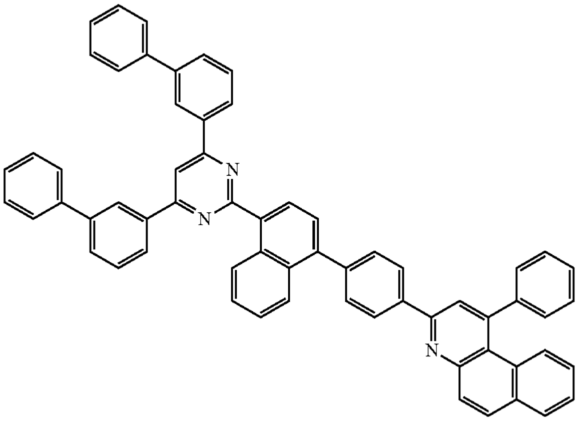

-continued
112
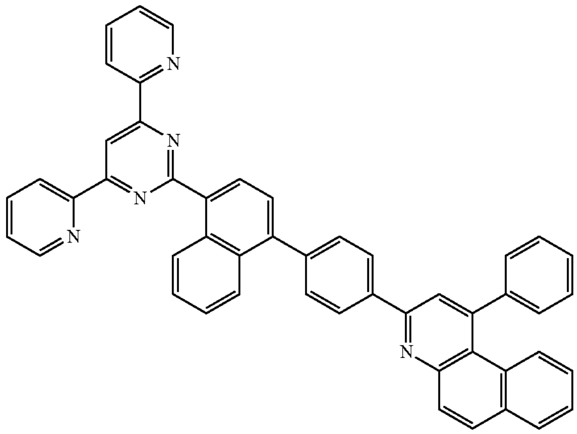
113
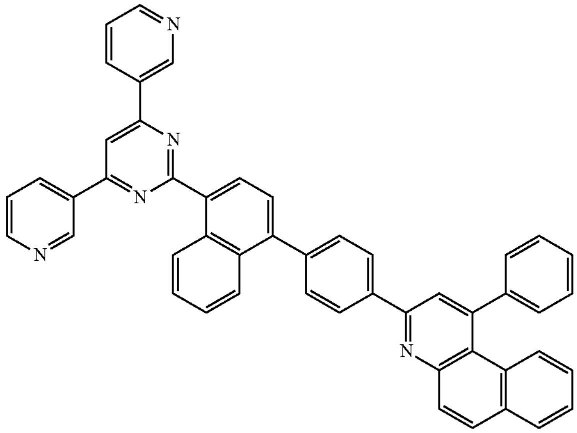
114
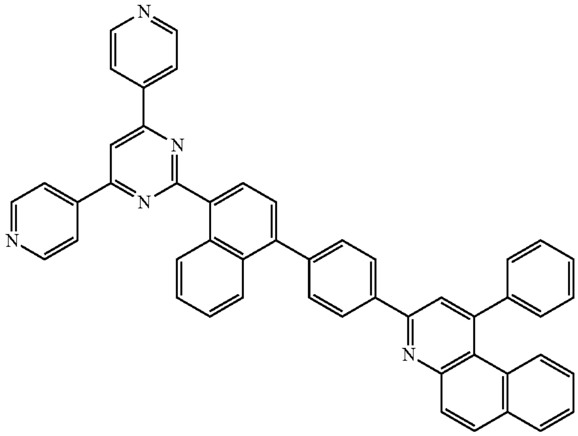
-continued
115
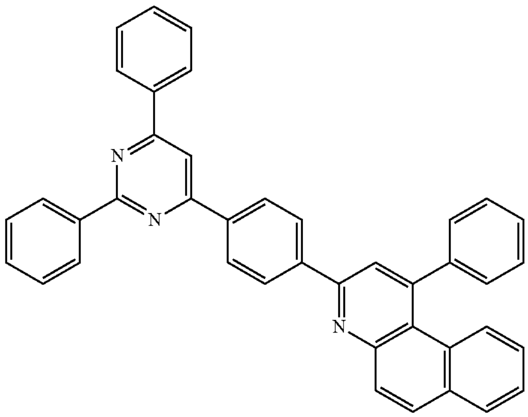
116
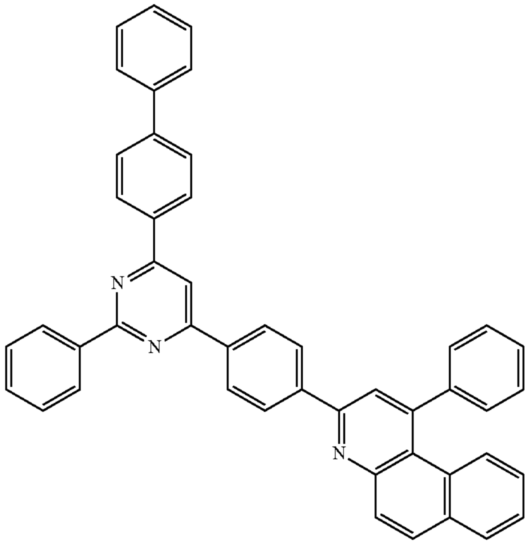
117
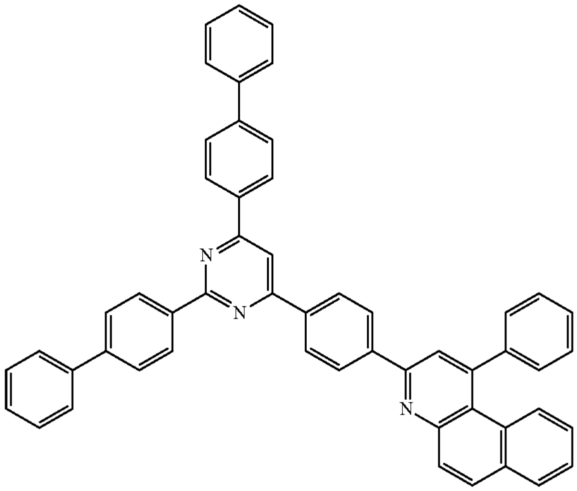

118
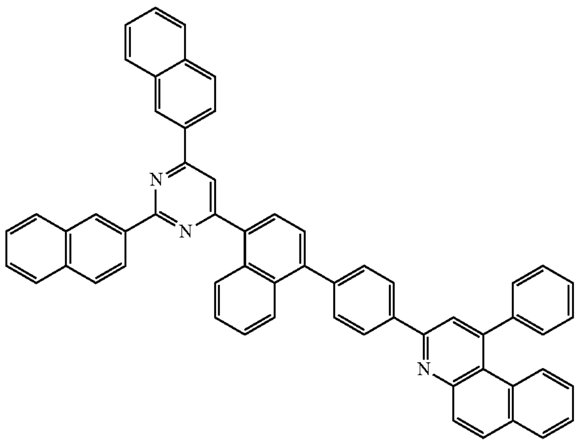
119
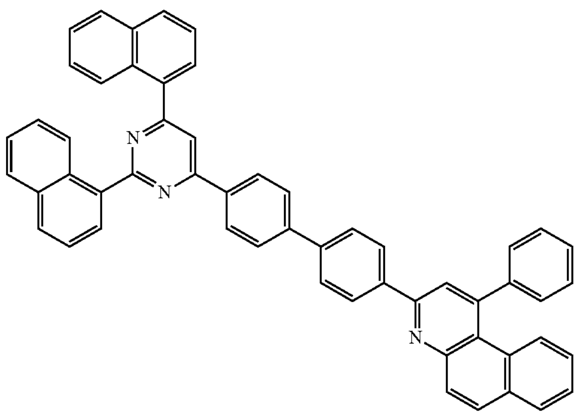
120
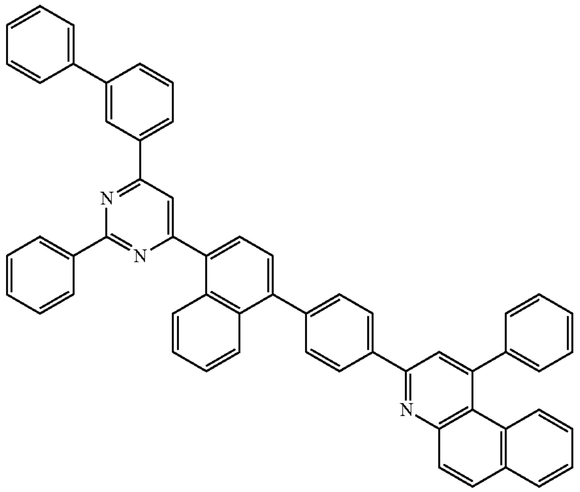
121
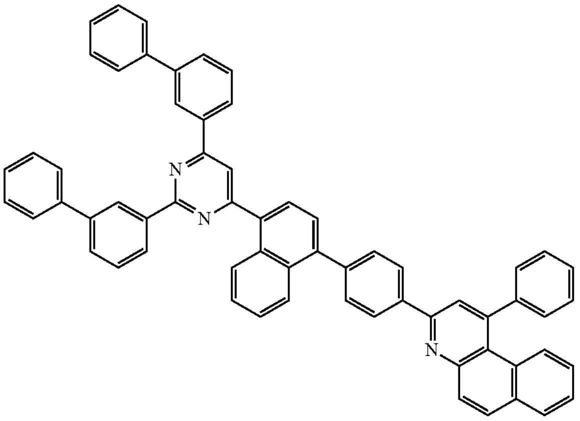
122
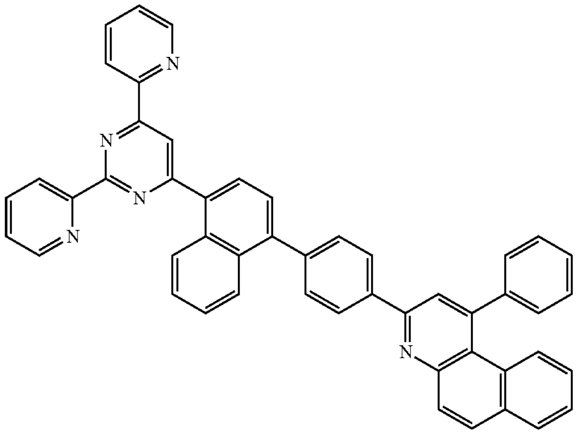
123
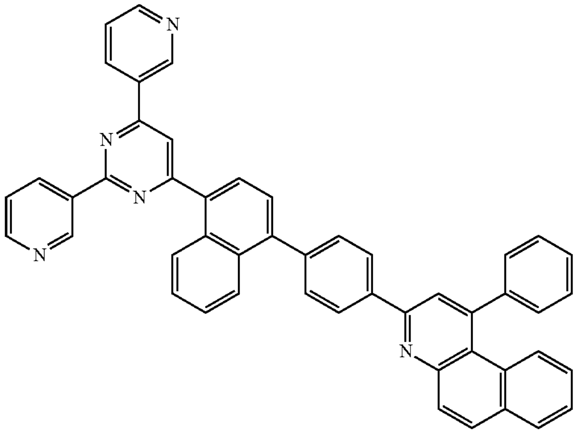

-continued
124
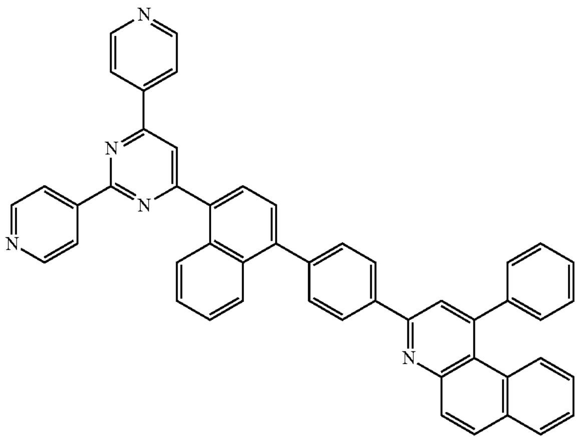
125
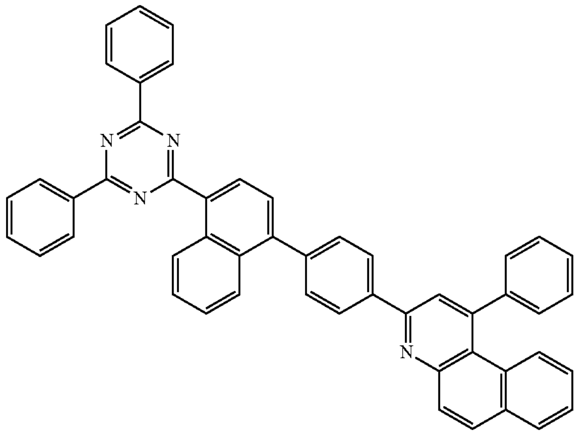
126
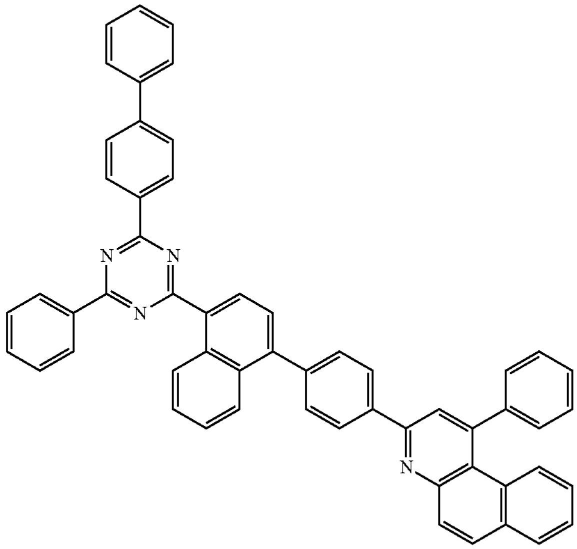
-continued
127
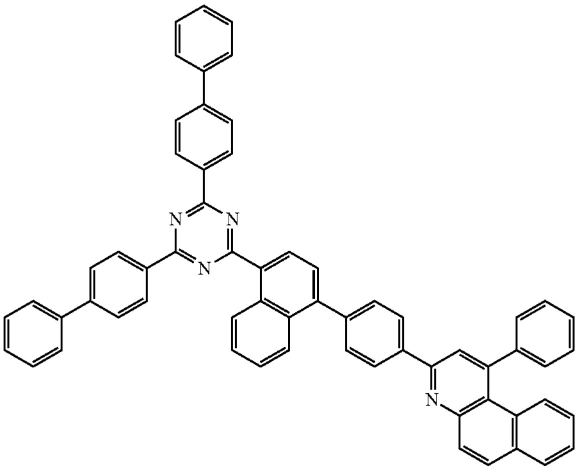
128
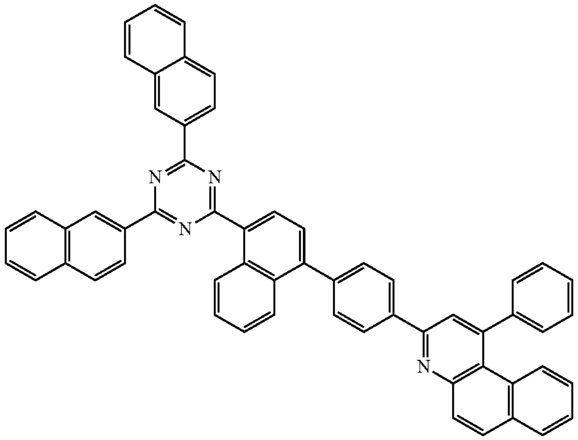
129
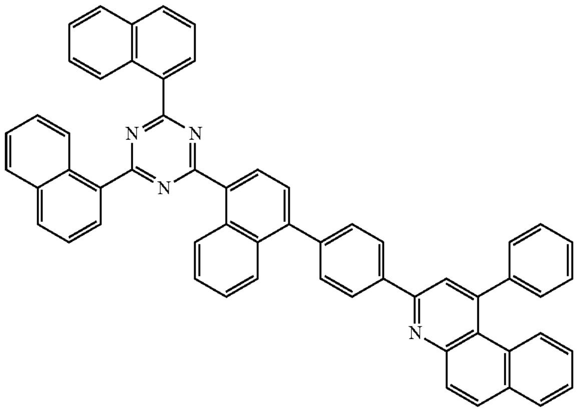

-continued
130
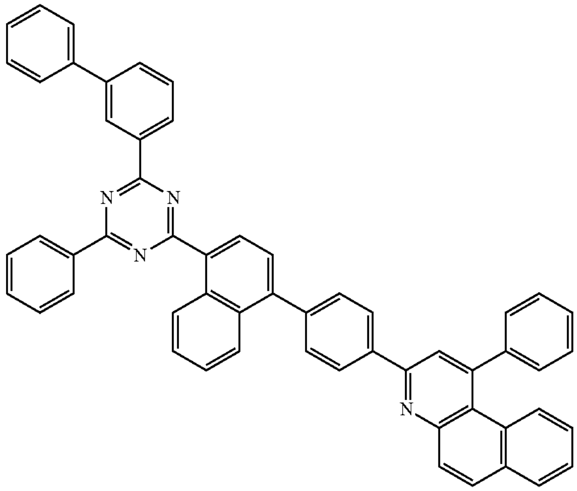
131
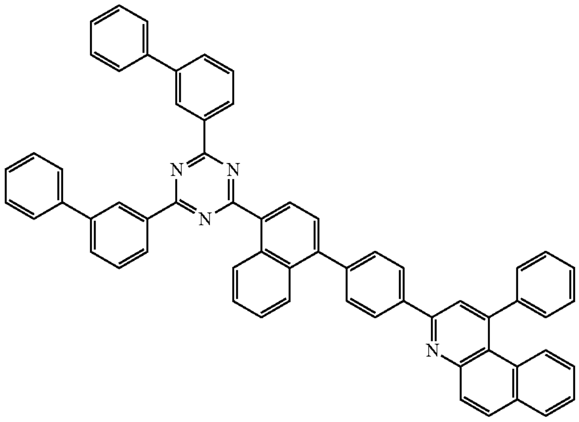
132
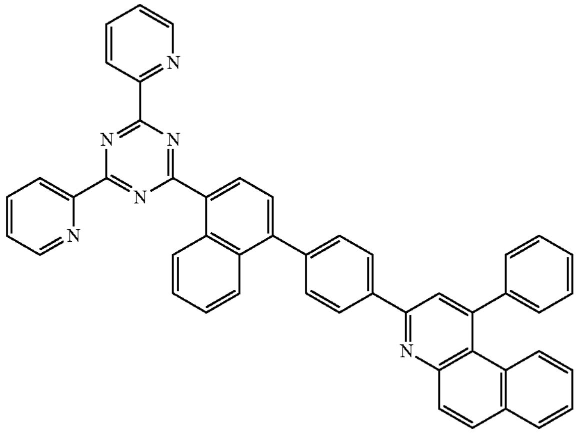
-continued
133
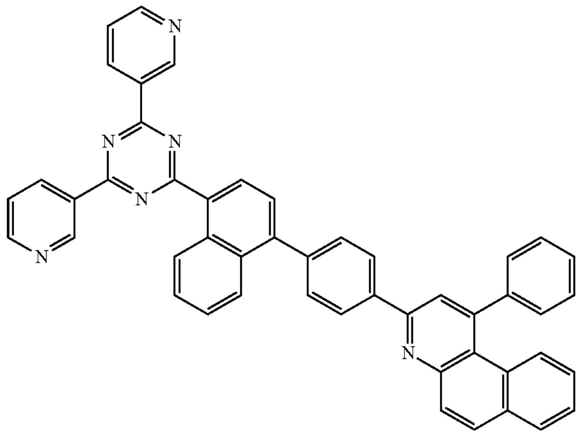
134
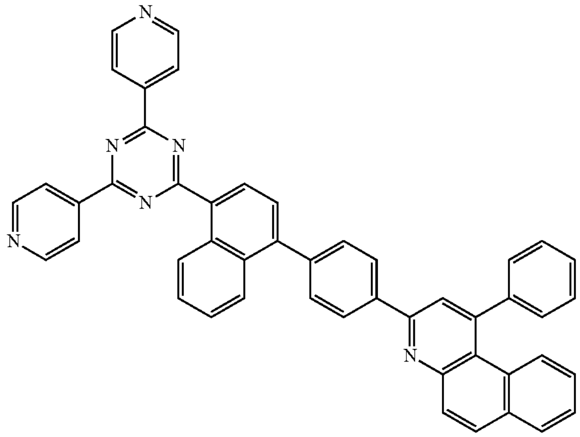
135
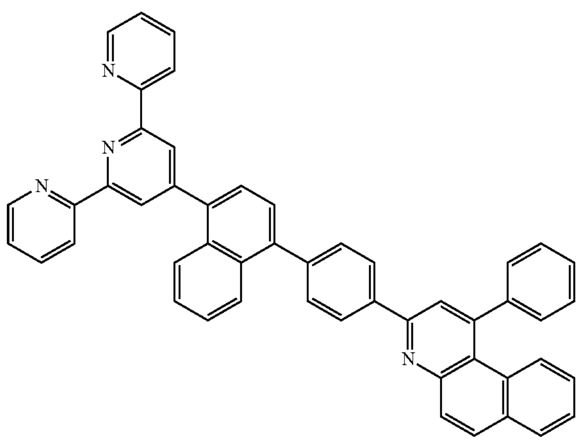

-continued
136
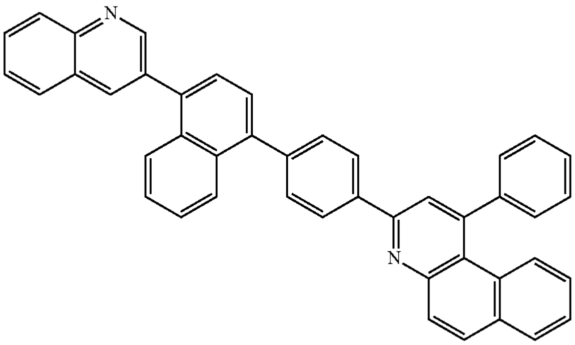
137
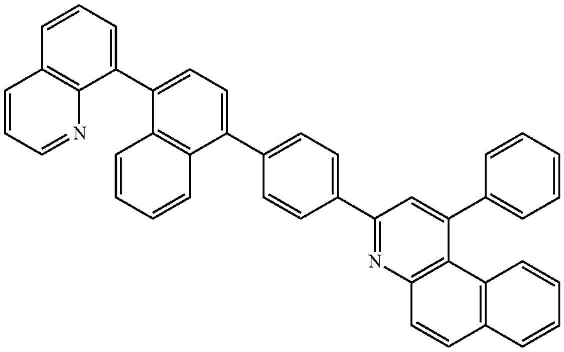
138
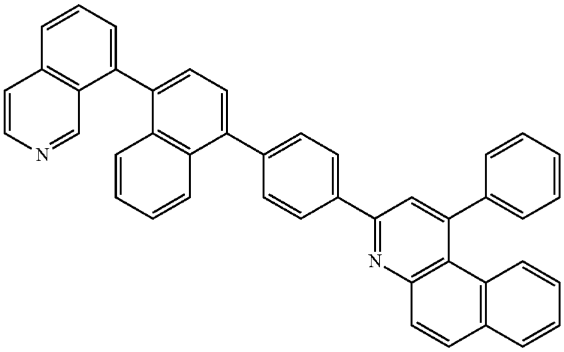
139
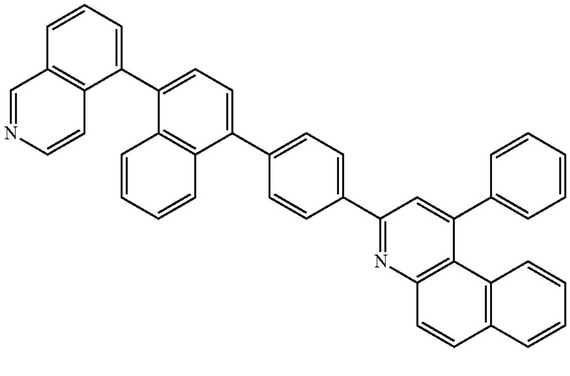
-continued
140
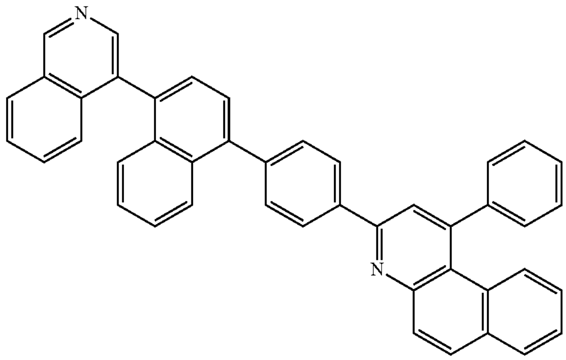
141
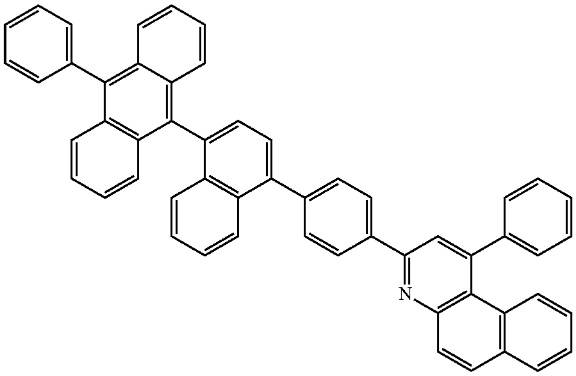
142
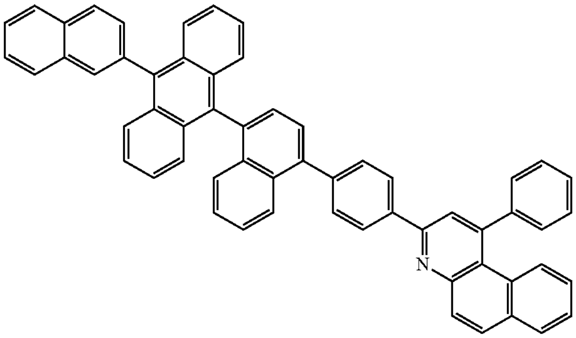
143
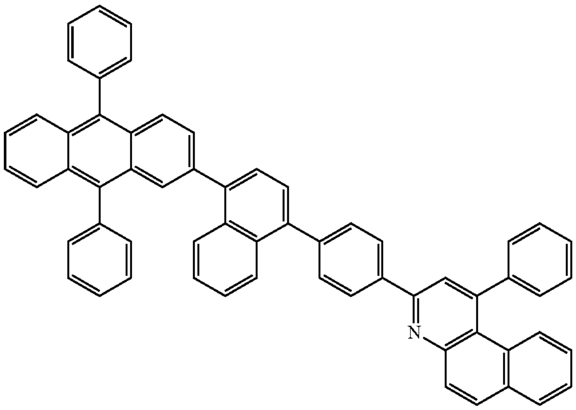

-continued
144
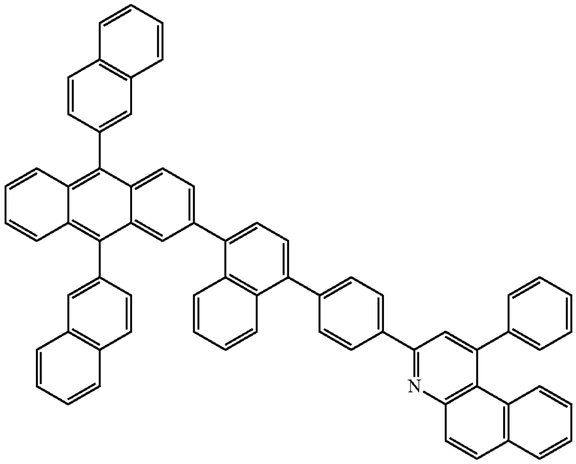
145
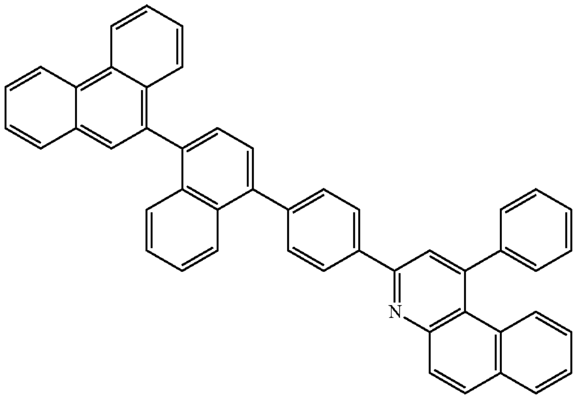
146
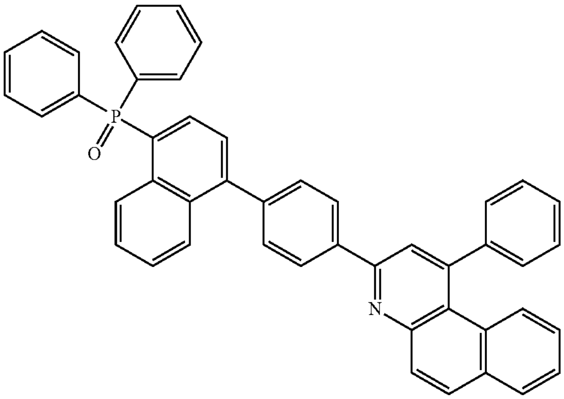
-continued
147
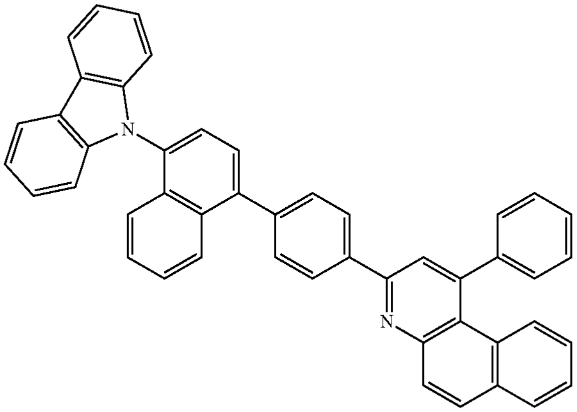
148
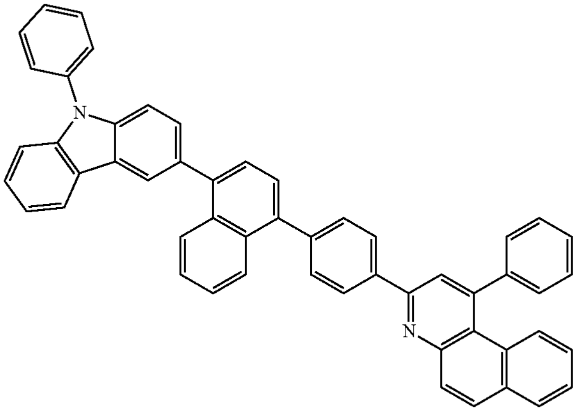
149
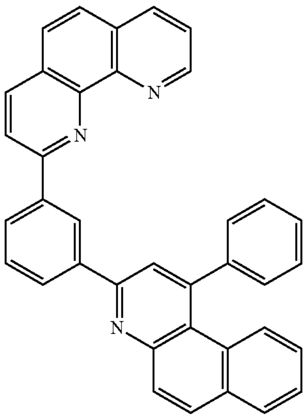

-continued
150
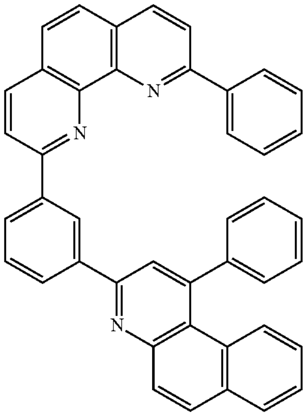
151
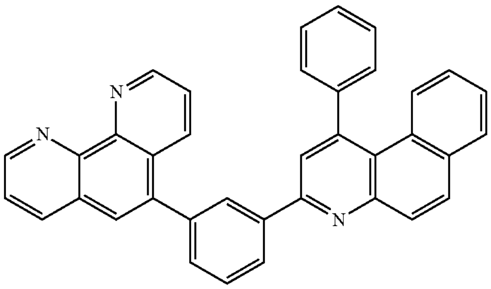
152
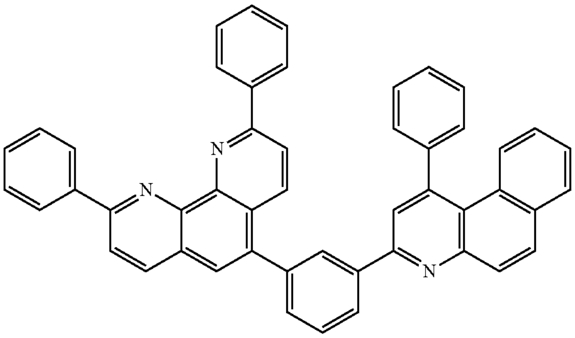
153
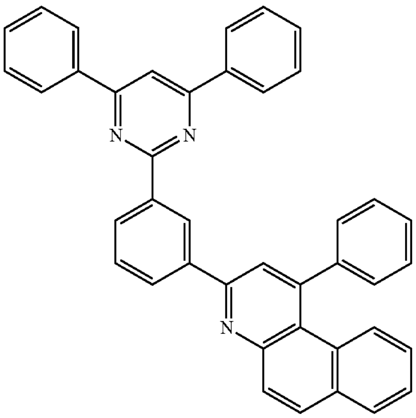
-continued
154
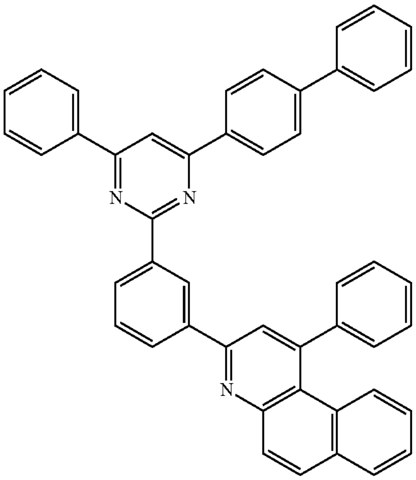
155
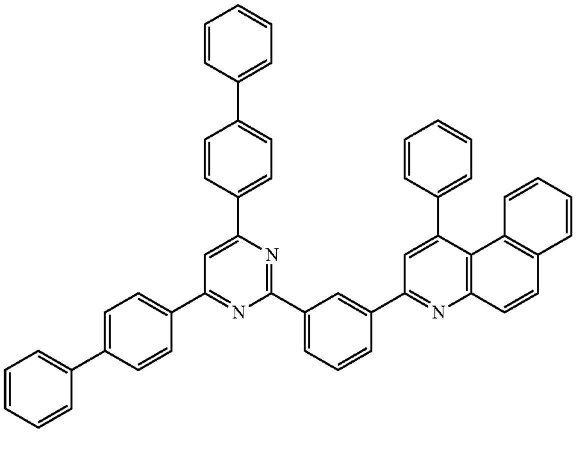
156
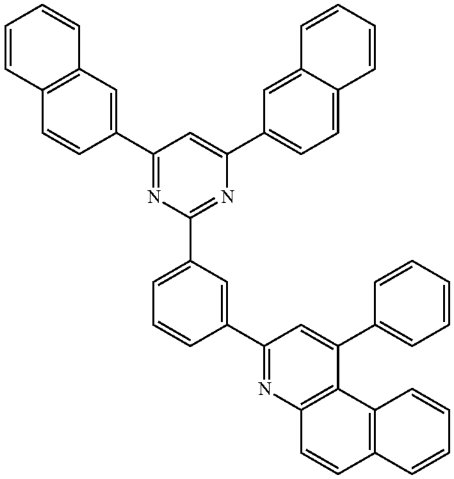

-continued
157
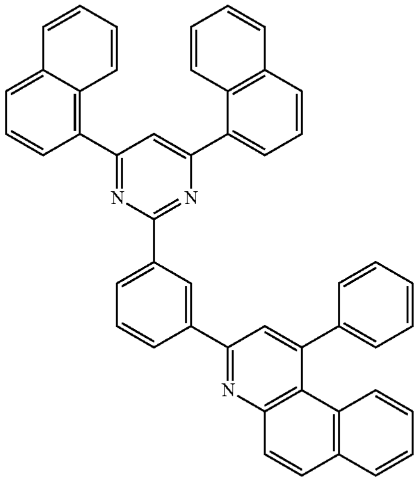
158
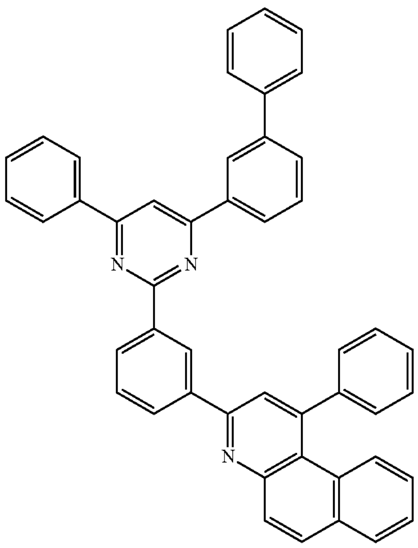
159
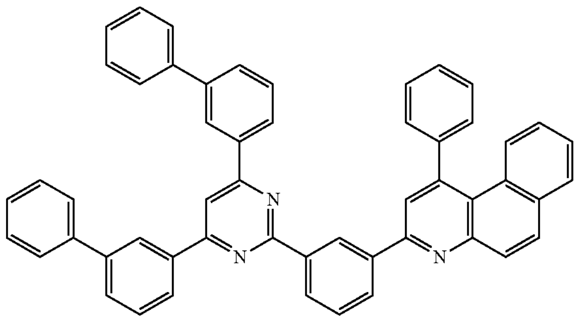
-continued
160
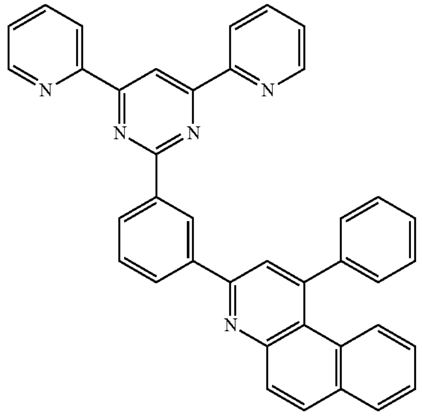
161
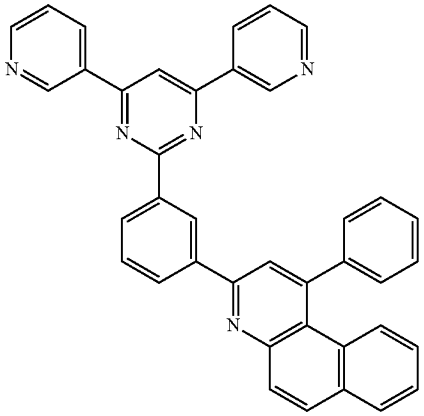
162
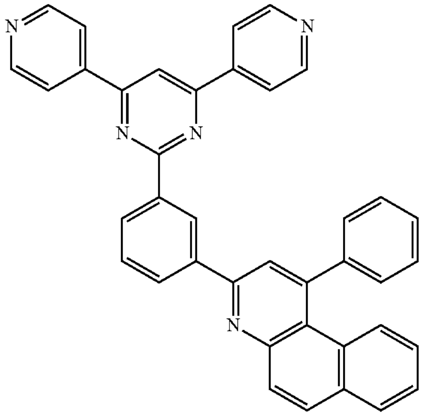

-continued
163
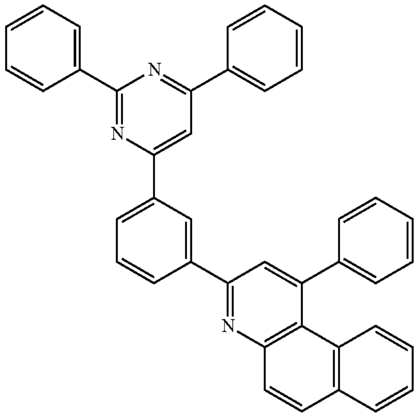
164
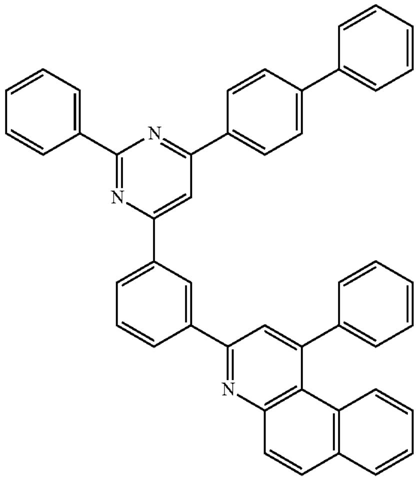
165
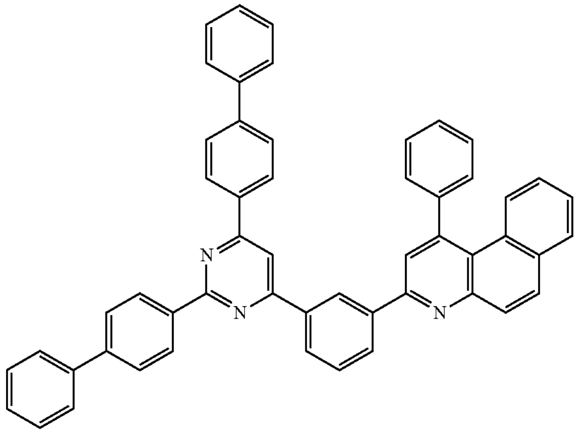
-continued
166
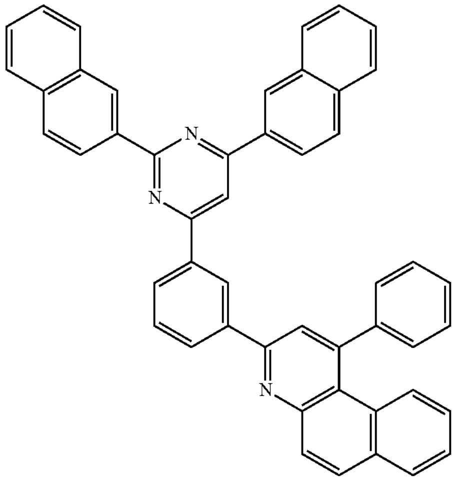
167
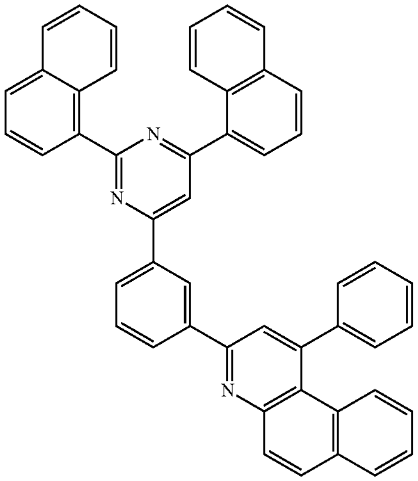
168
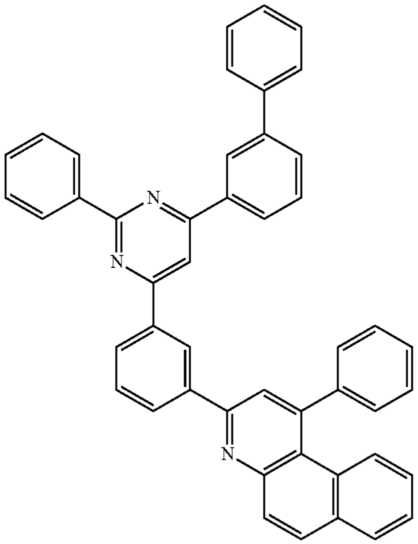

-continued
169
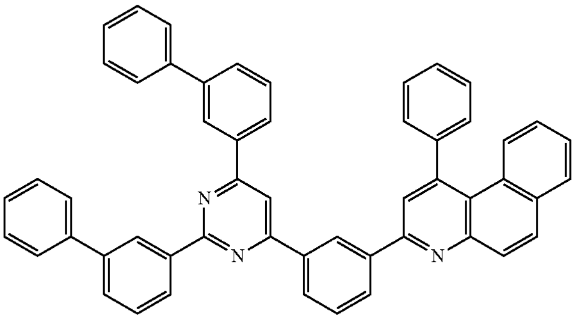
170
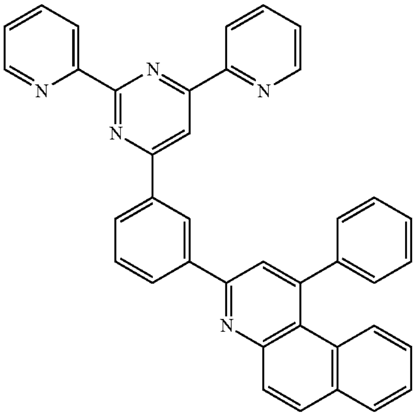
171
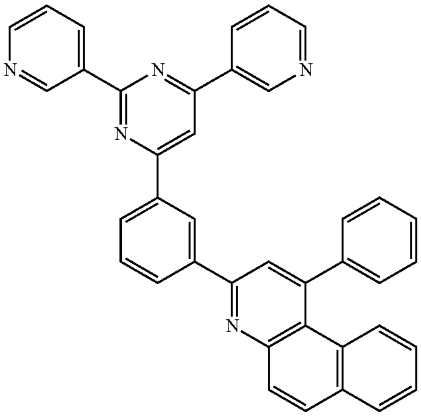
172
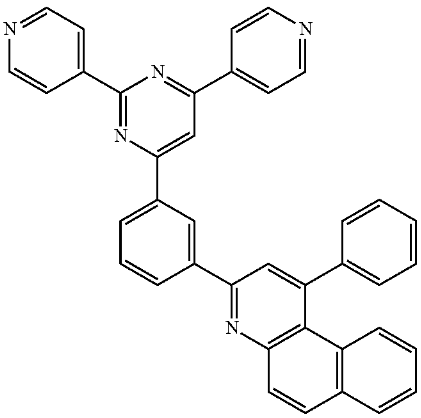
-continued
173
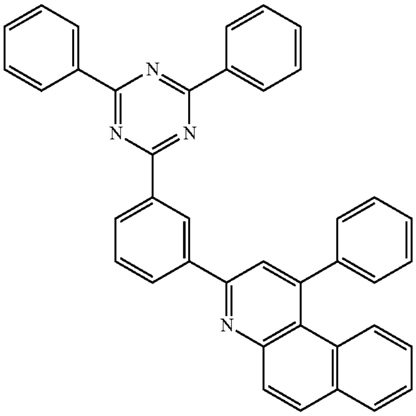
174
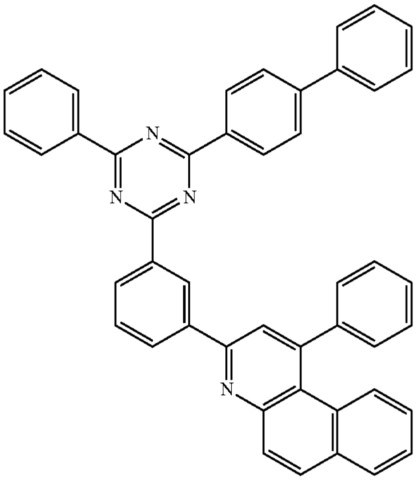
175
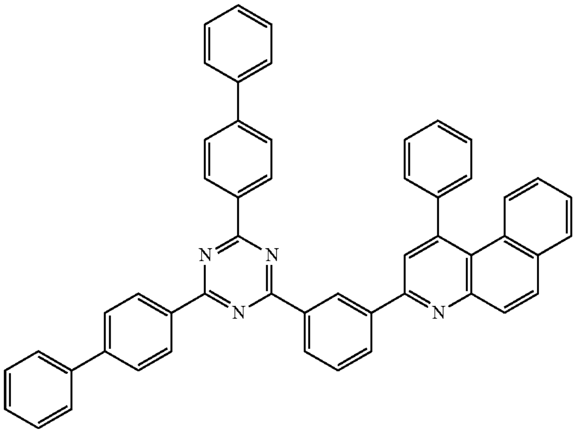

-continued
176
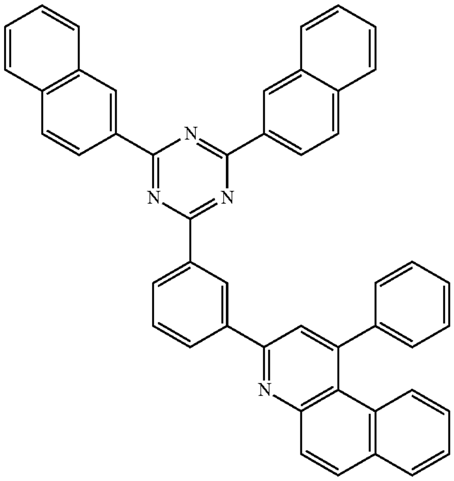
177
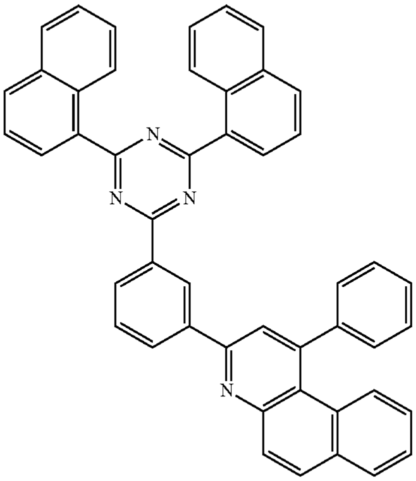
178
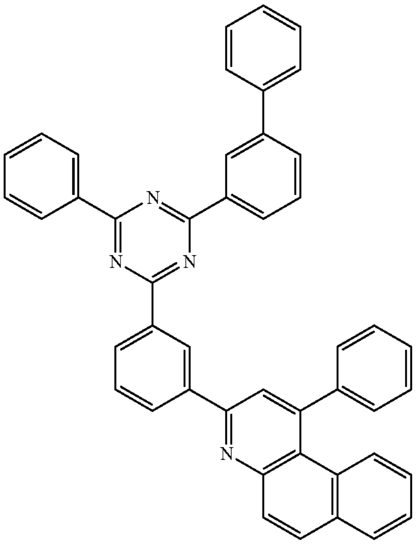
-continued
179
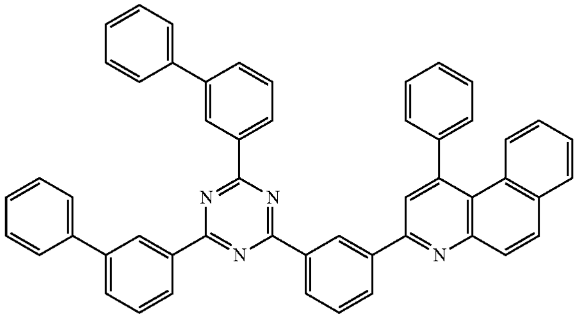
180
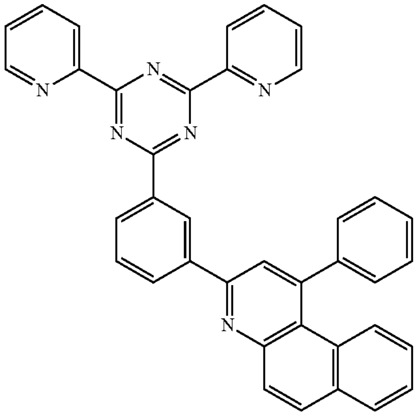
181
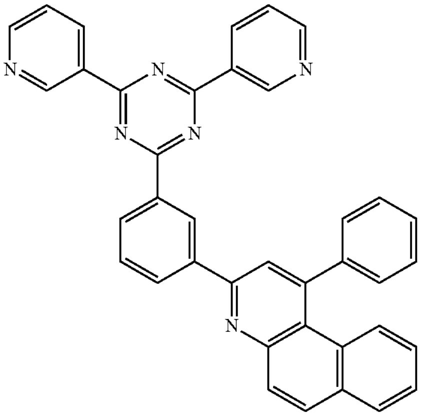
182
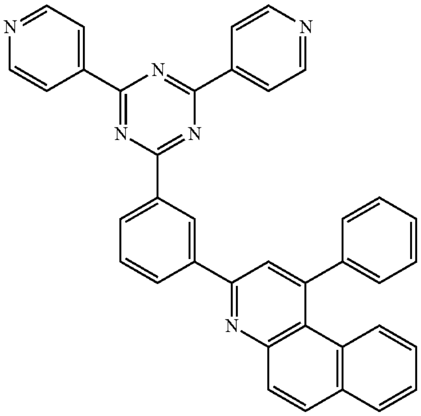

-continued
183
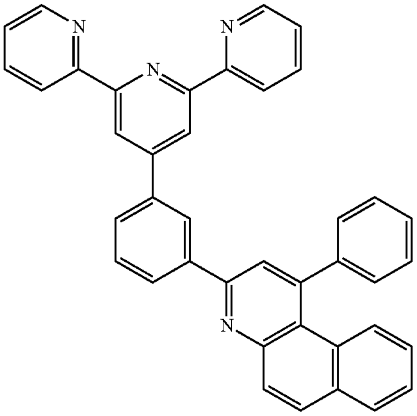
184
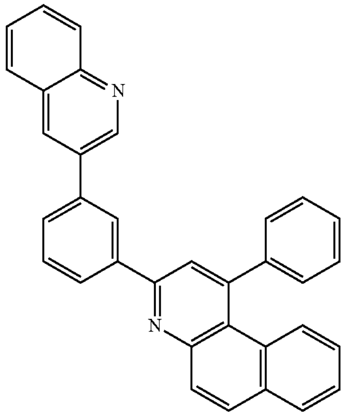
185
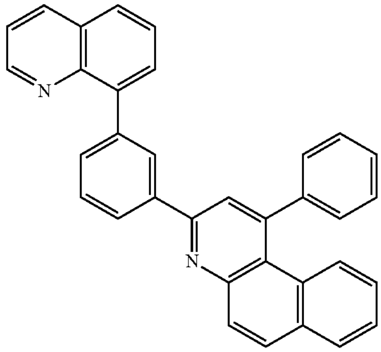
186
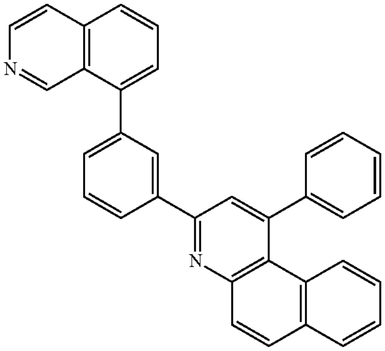
-continued
187
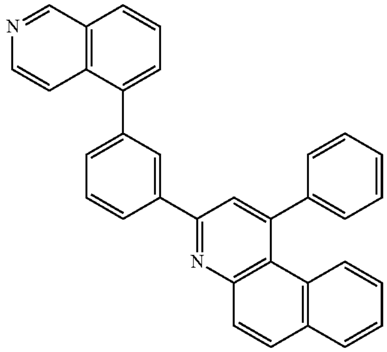
188
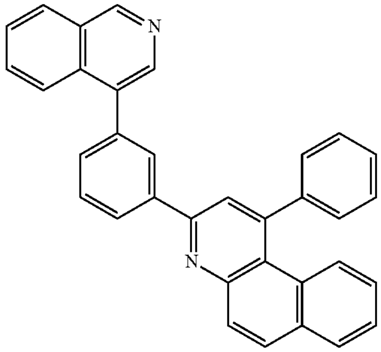
189
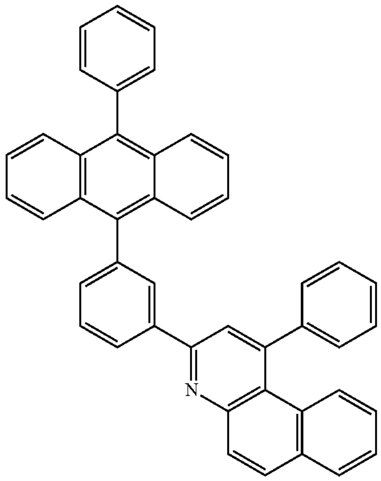

-continued
190
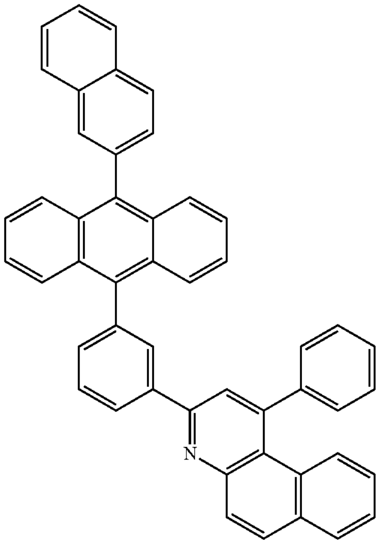
191
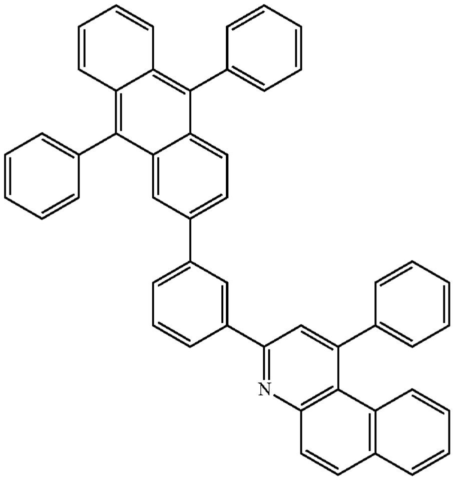
192
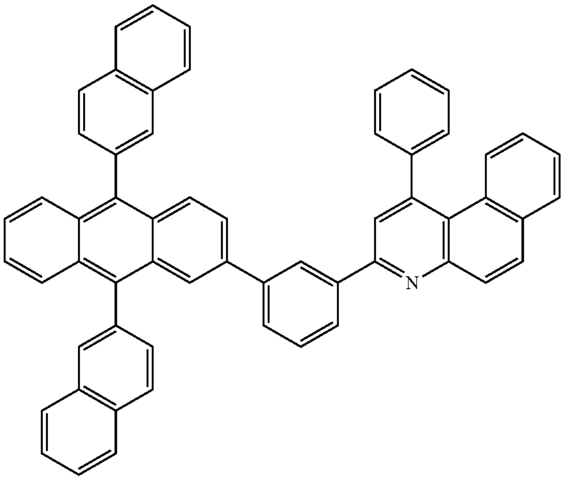
-continued
193
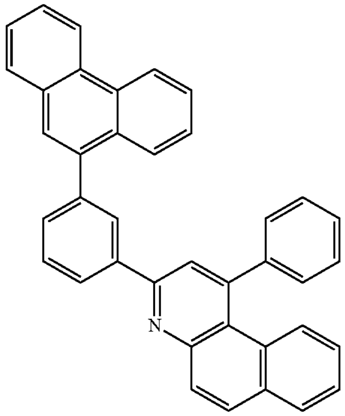
194
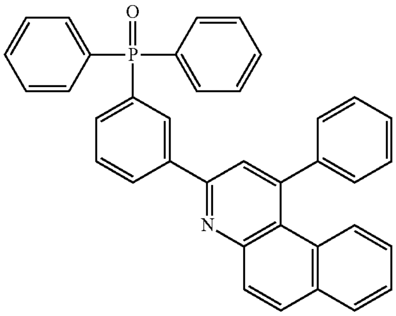
195
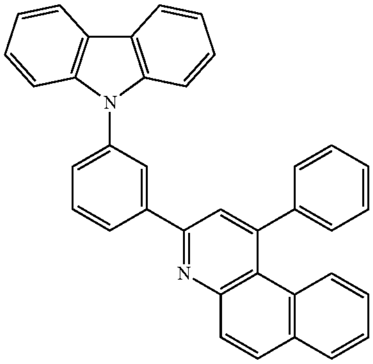
196
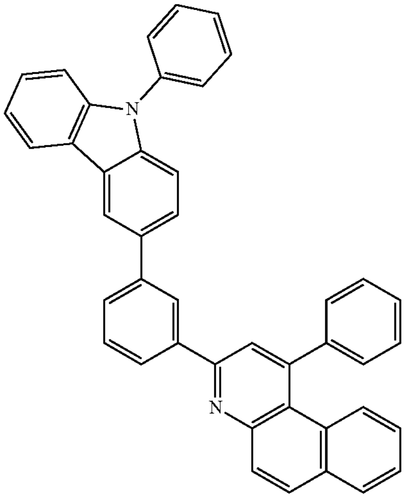

-continued
197
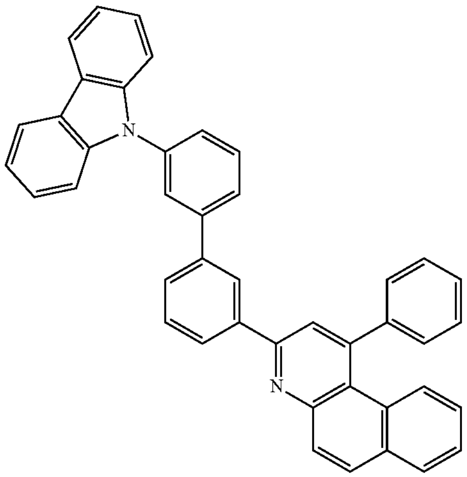
198
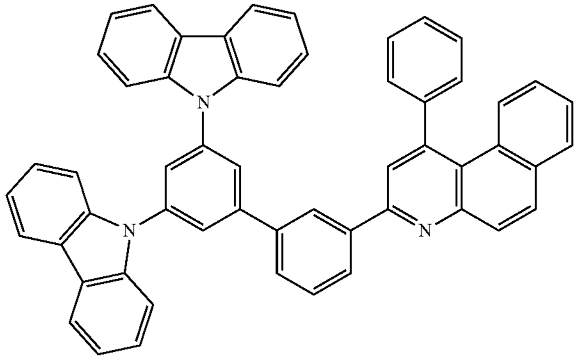
199
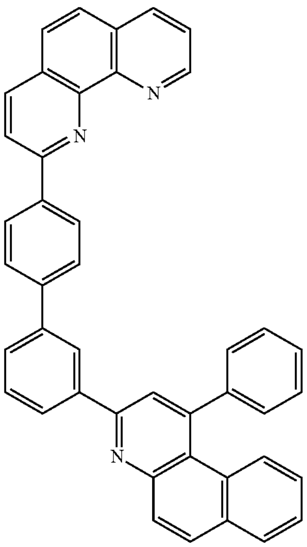
-continued
200
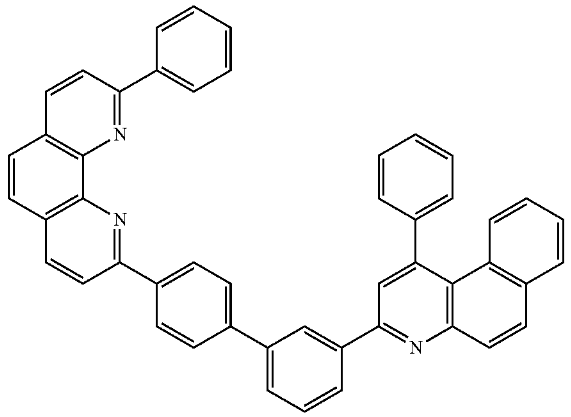
201
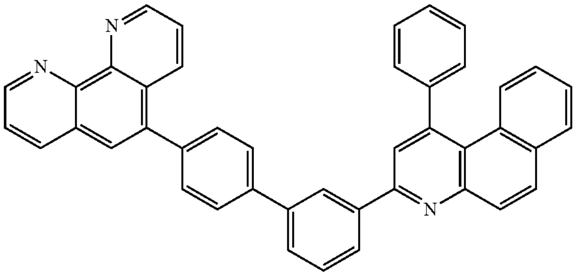
202
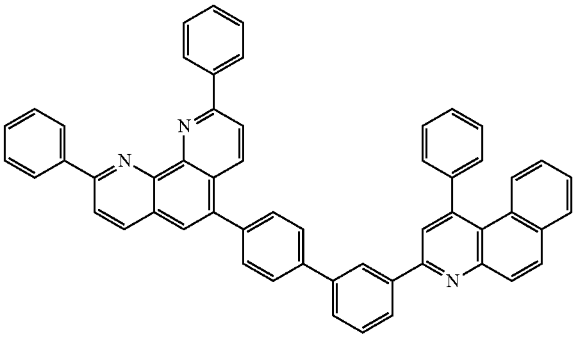
203
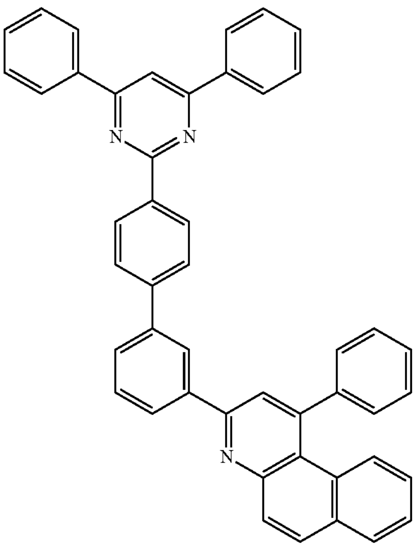

204
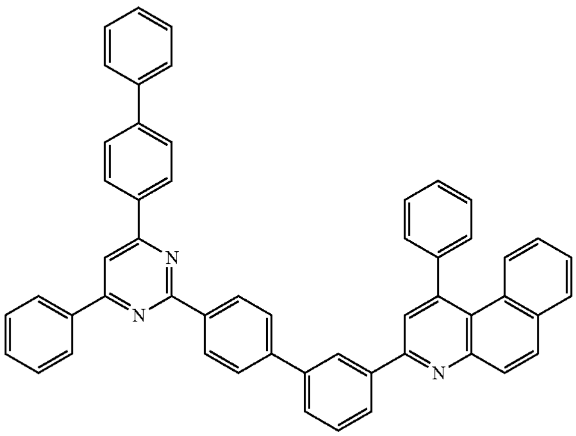
205
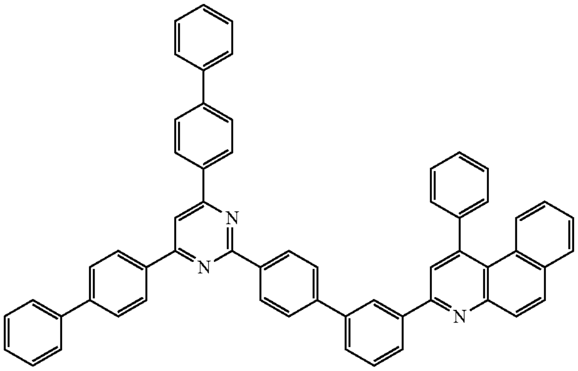
206
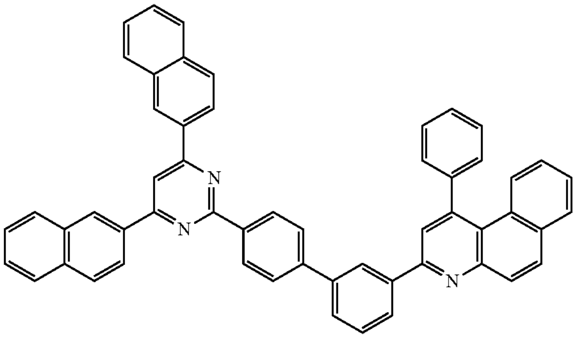
207
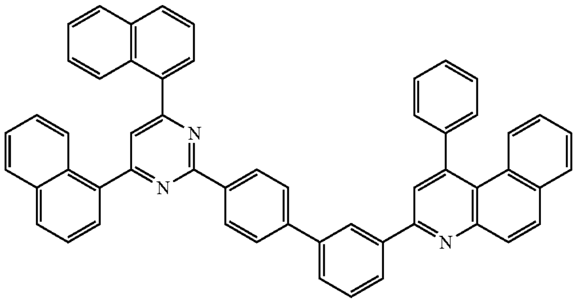
208
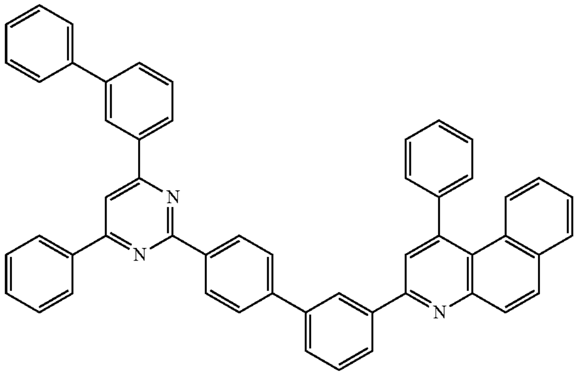
209
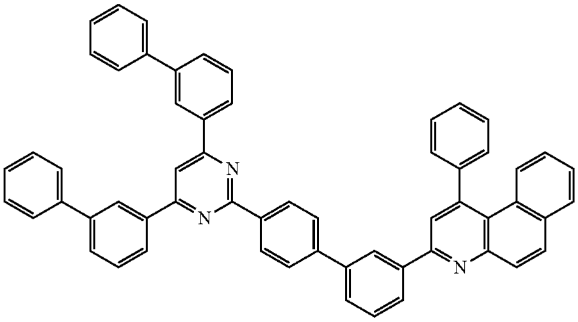
210
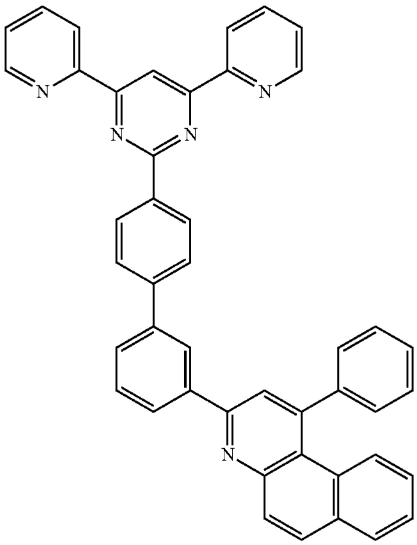

-continued
211
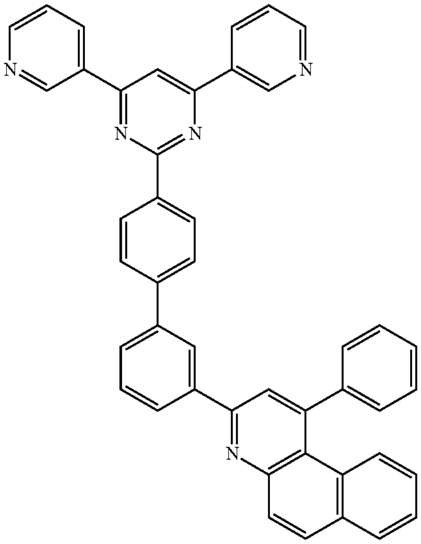
212
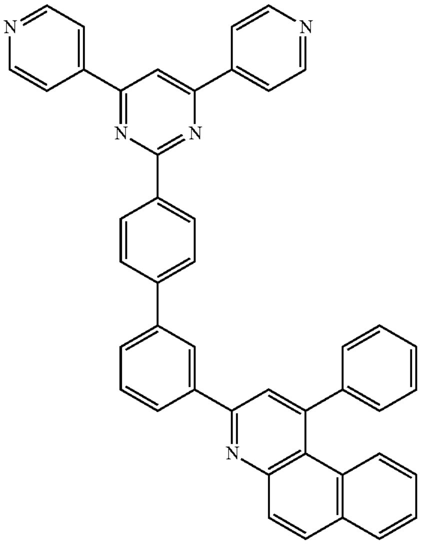
213
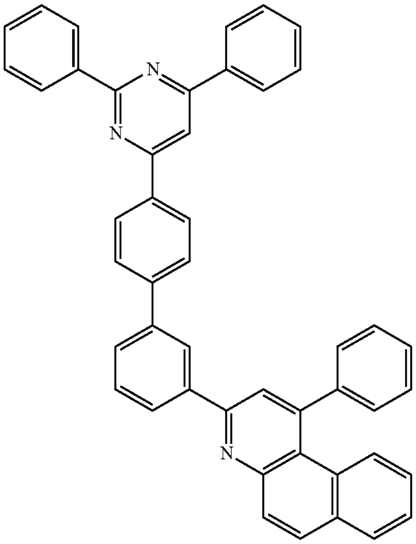
-continued
214
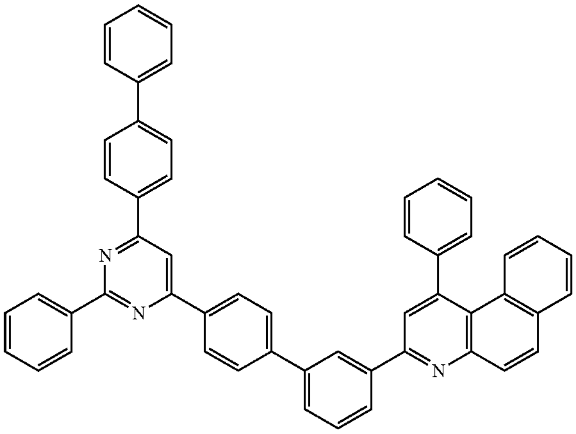
215
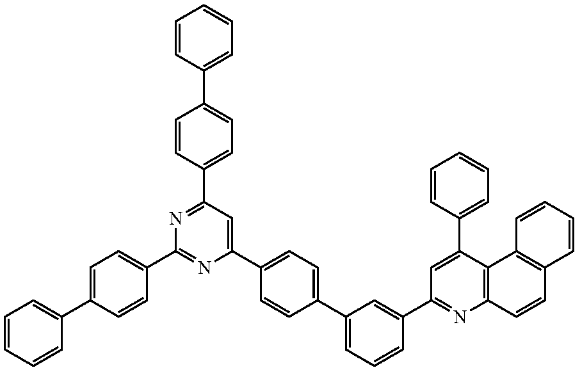
216
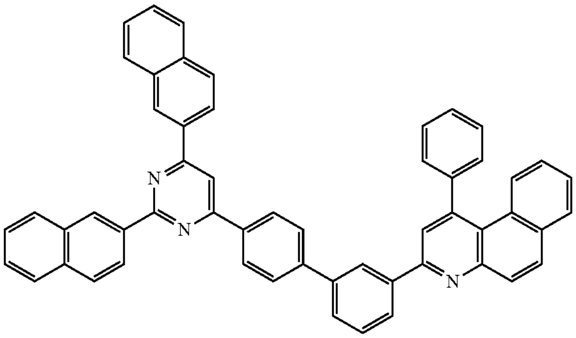
217
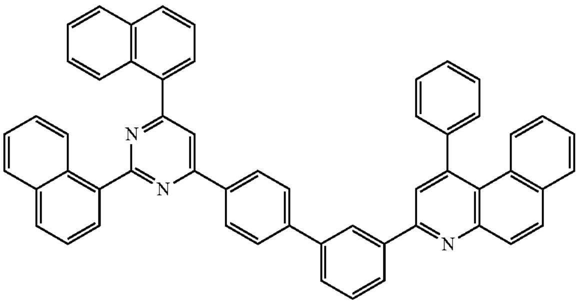

-continued
218
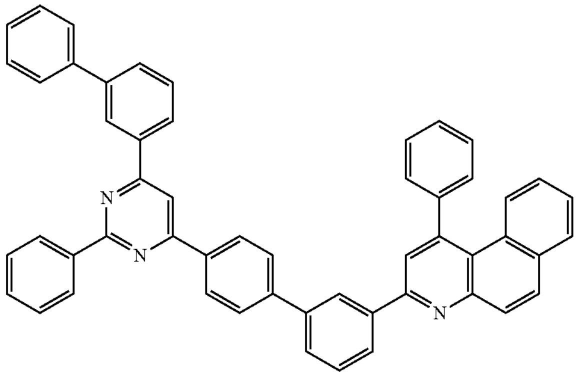
219
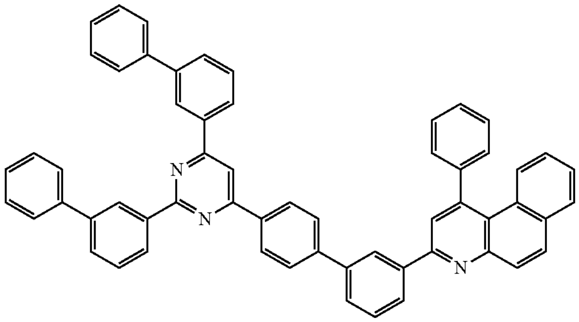
220
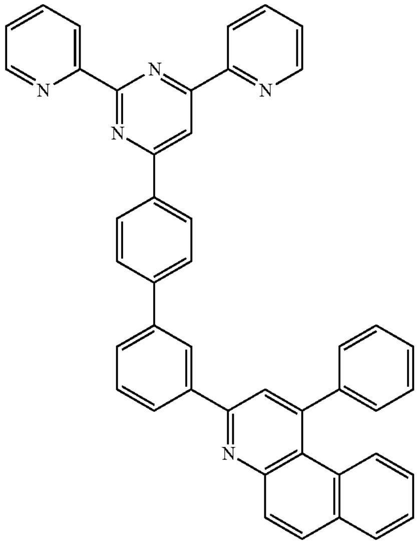
221
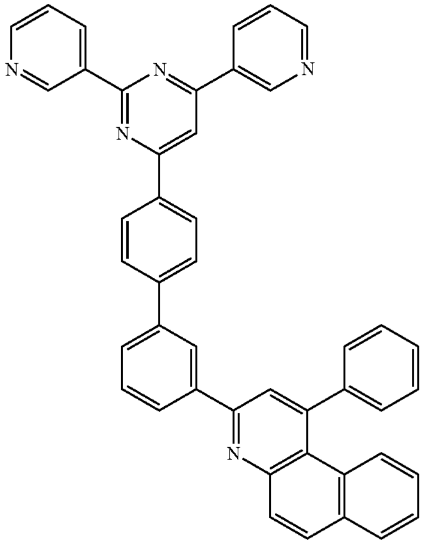
222
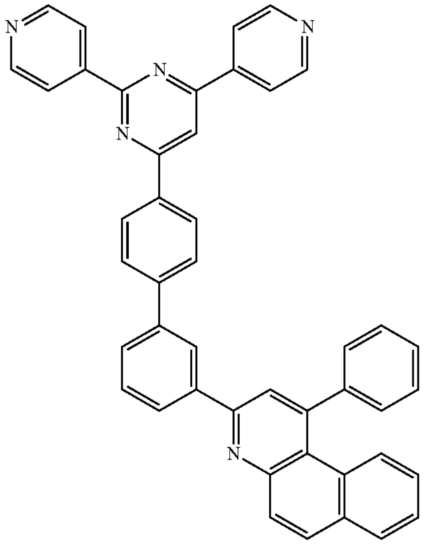
223
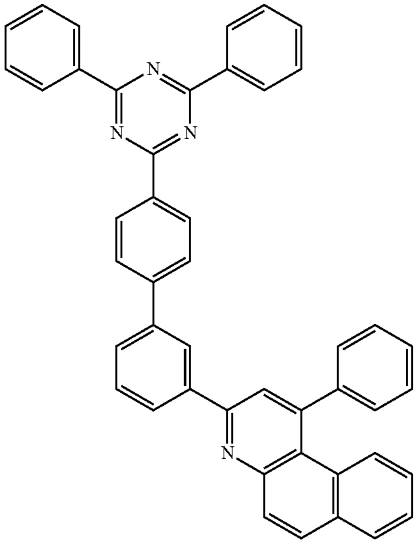

-continued
224
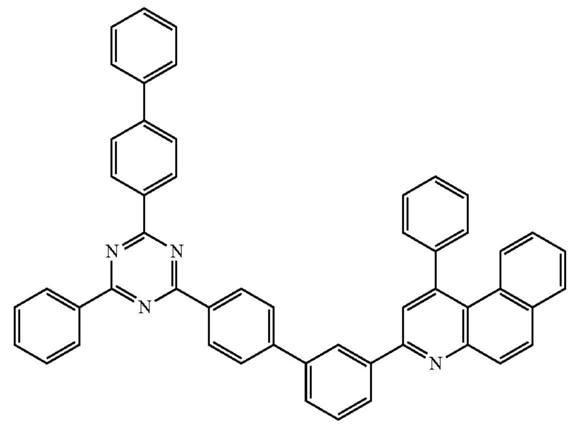
225
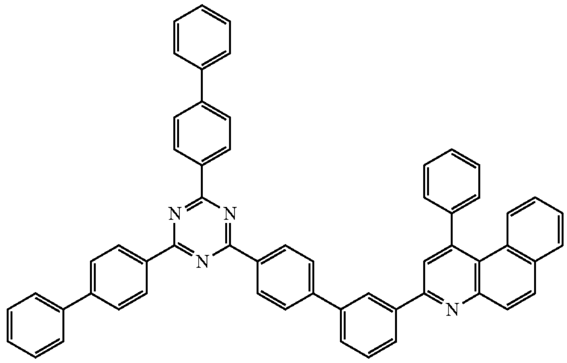
226
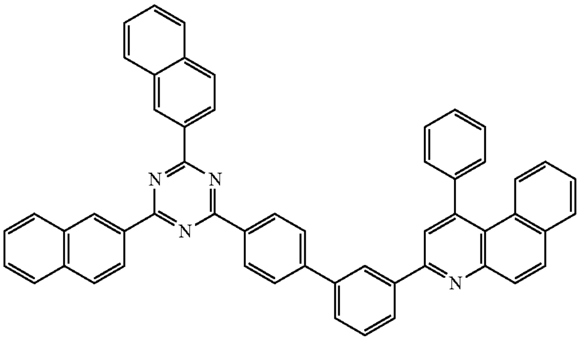
227
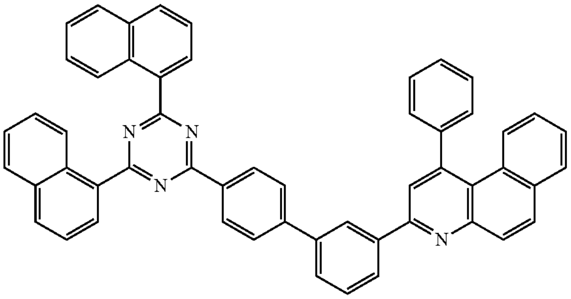
-continued
228
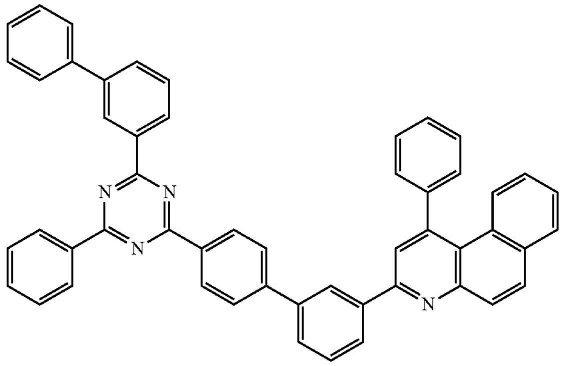
229
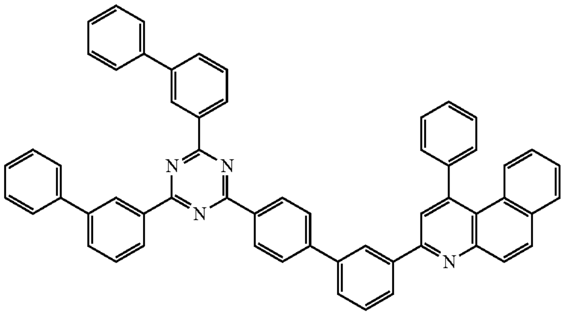
230
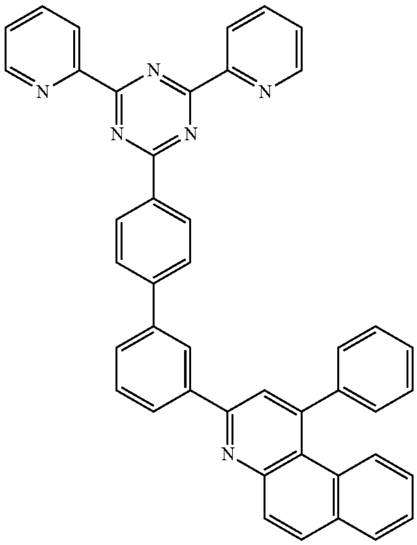

-continued
231
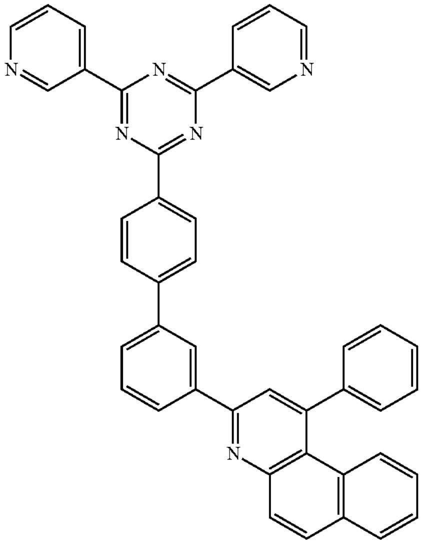
232
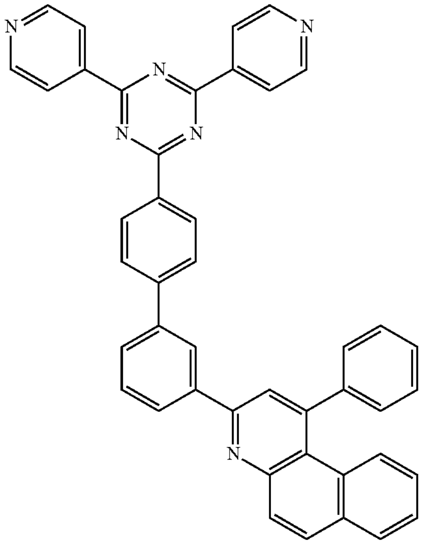
233
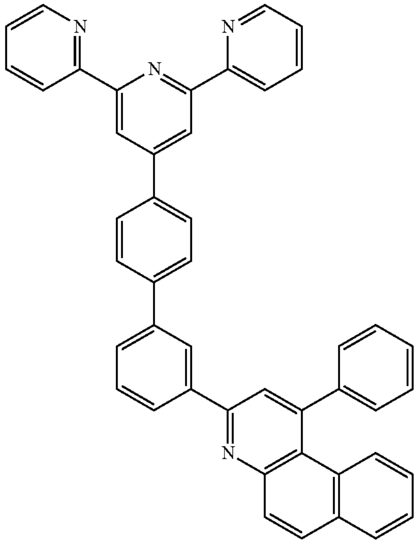
-continued
234
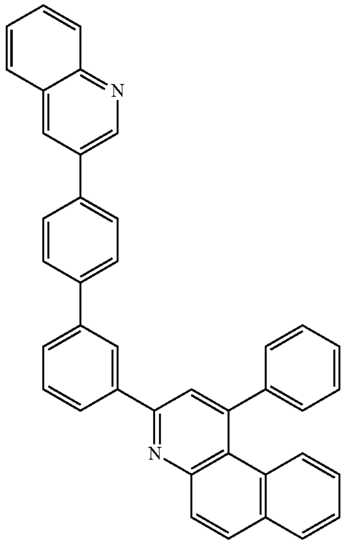
235
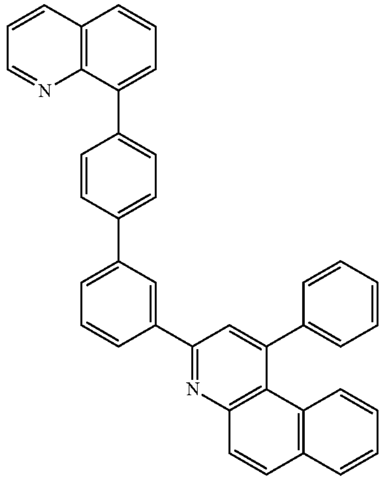
236
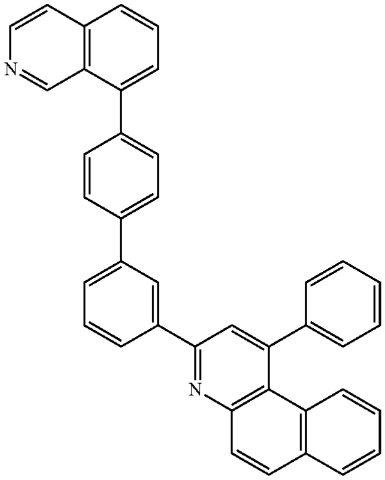

-continued
237
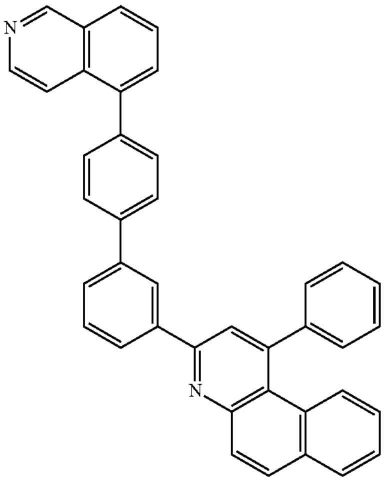
238
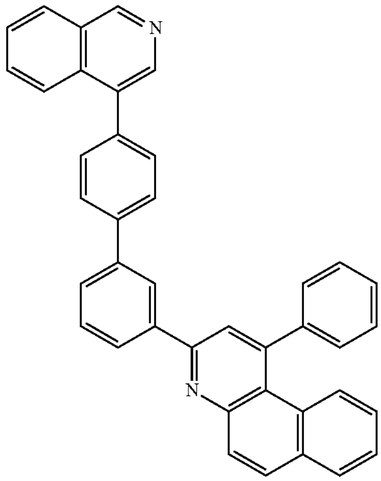
239
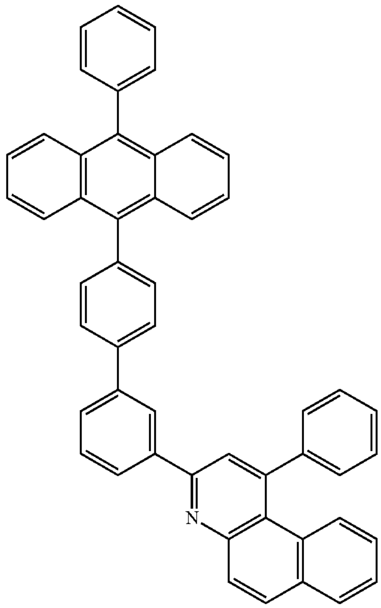
-continued
240
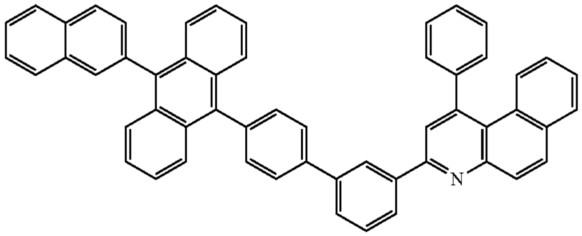
241
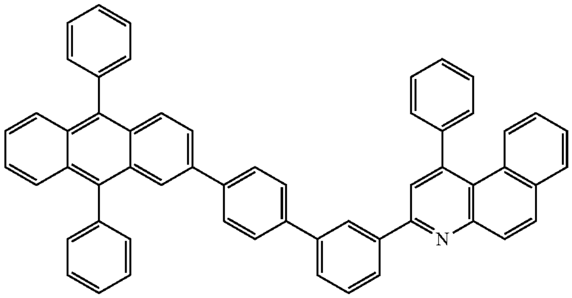
242
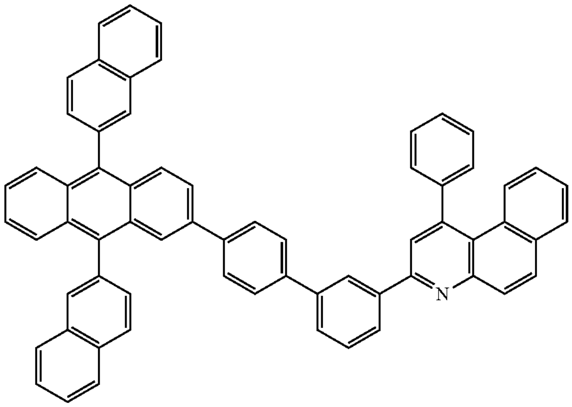
243
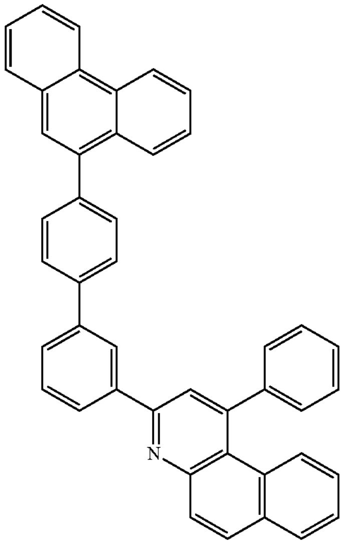

-continued
244
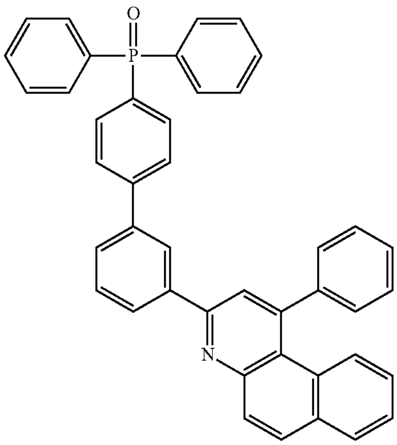
245
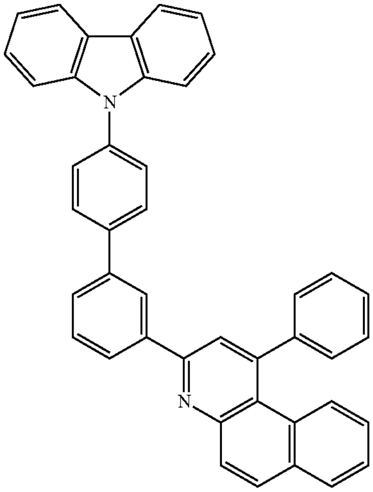
246
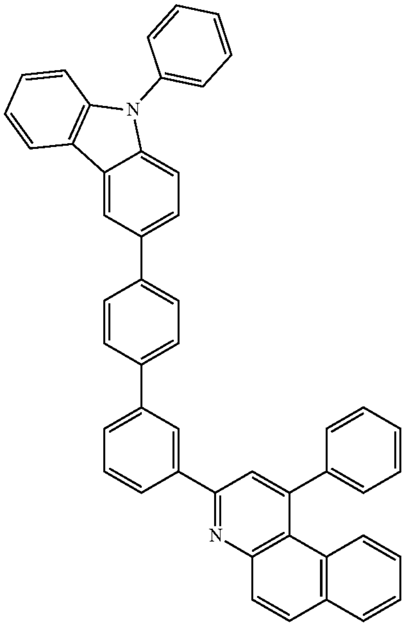
-continued
247
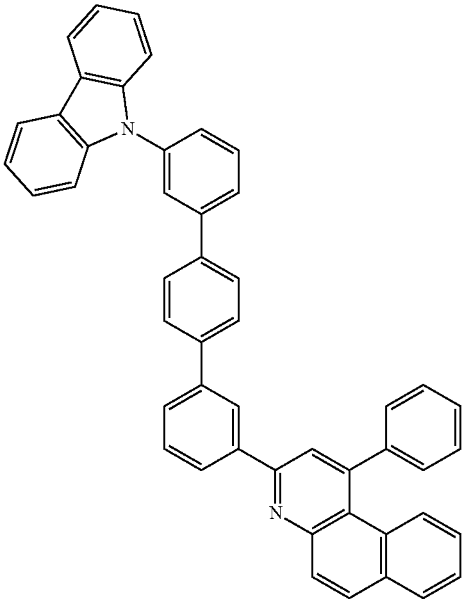
248
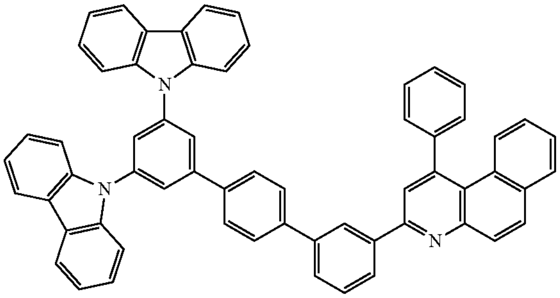
249
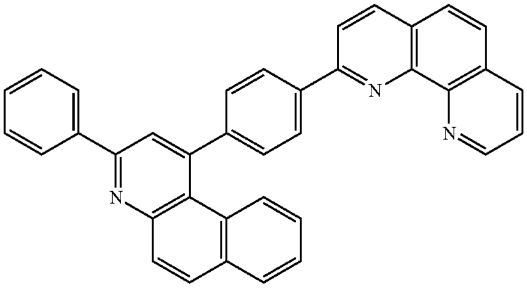
250
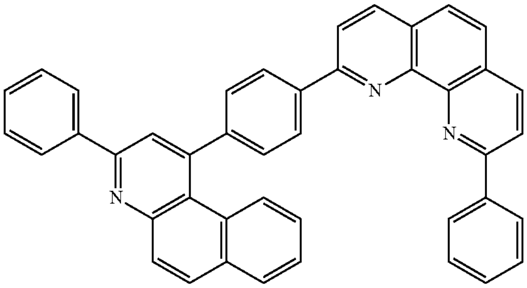

-continued
251
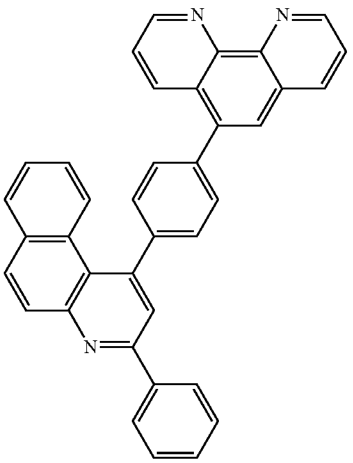
252
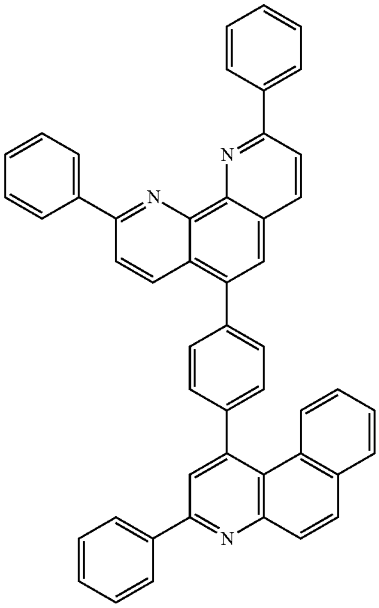
253
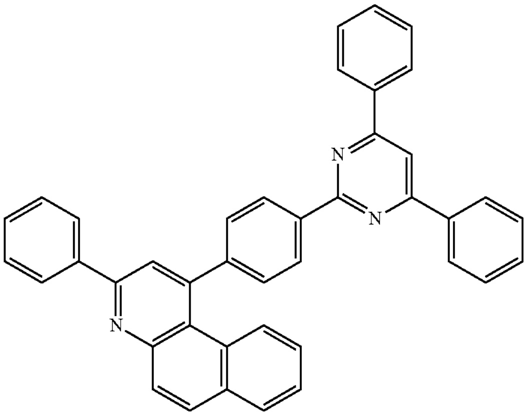
-continued
254
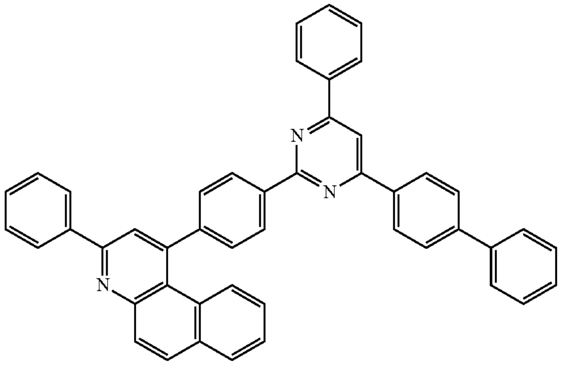
255
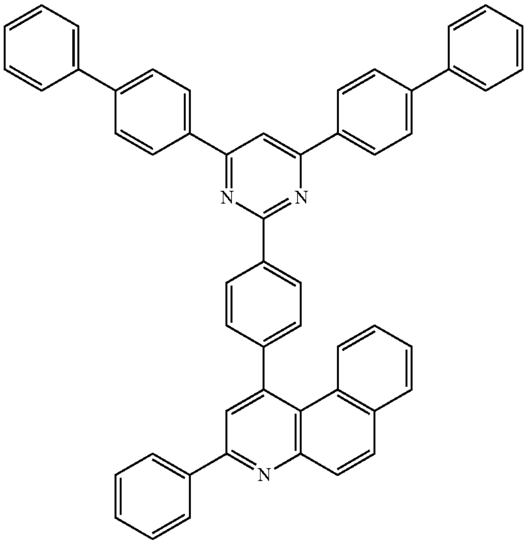
256
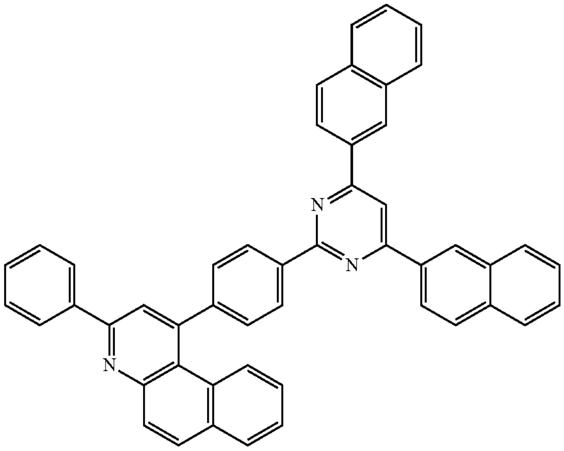

-continued
257
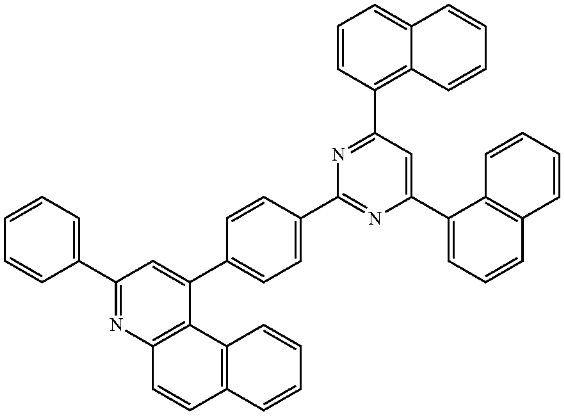
258
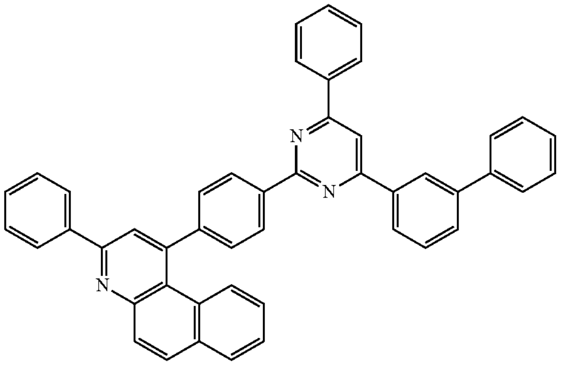
259
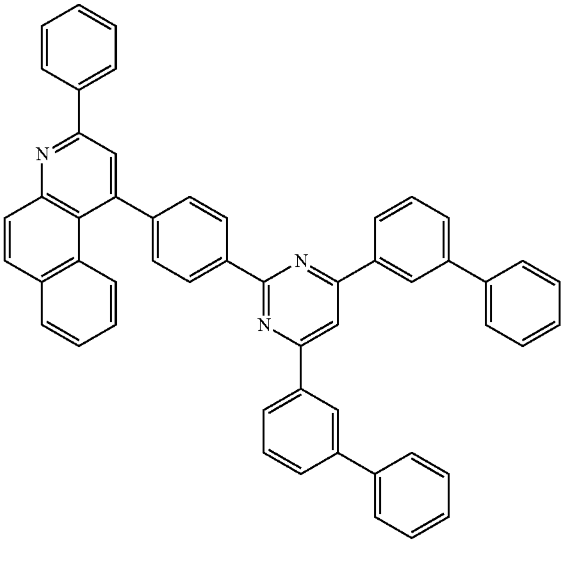
-continued
260
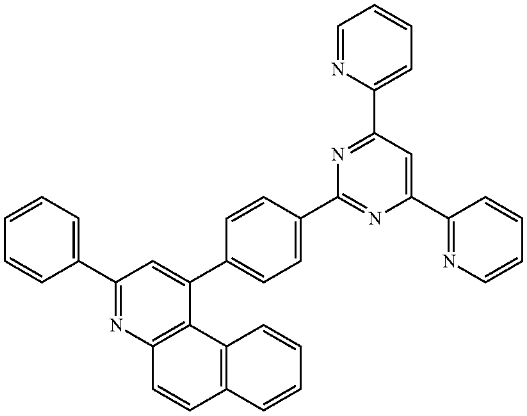
261
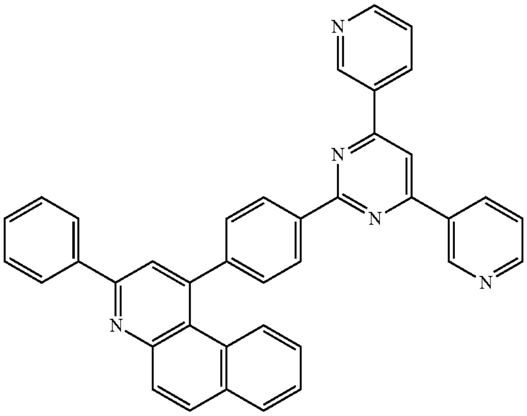
262
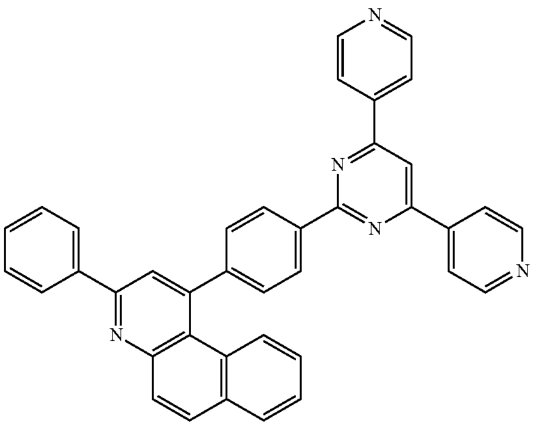

263
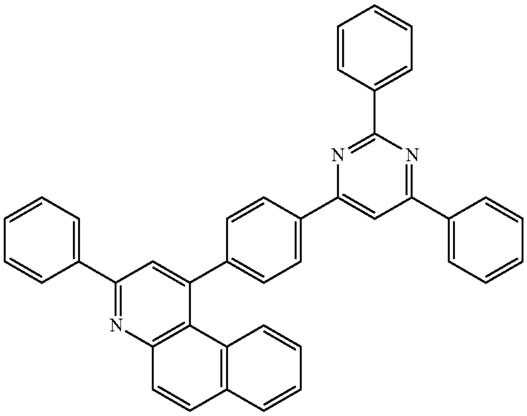
264
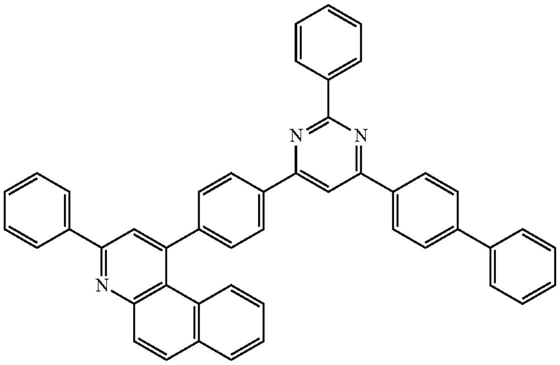
265
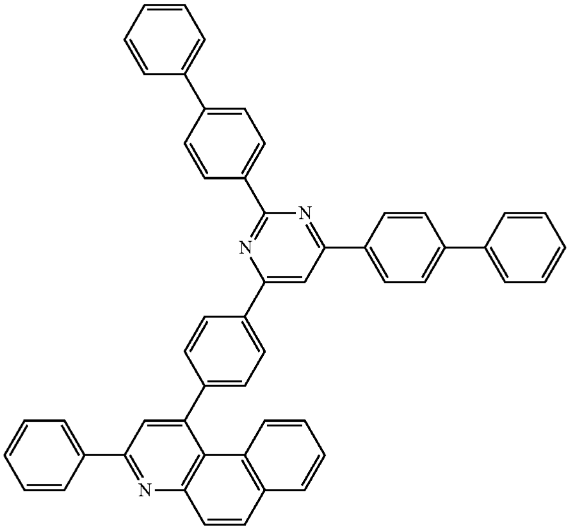
266
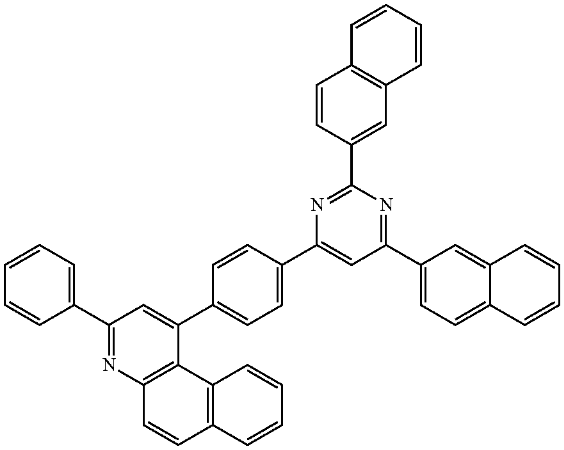
267
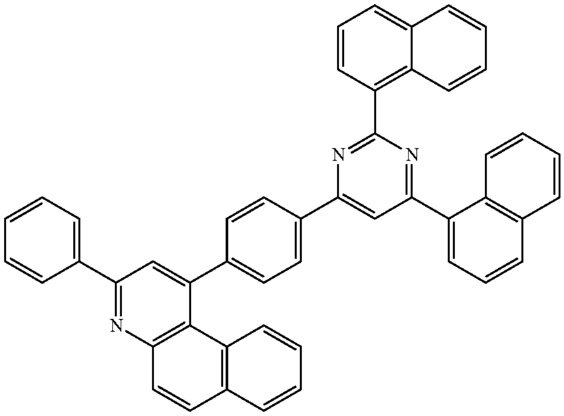
268
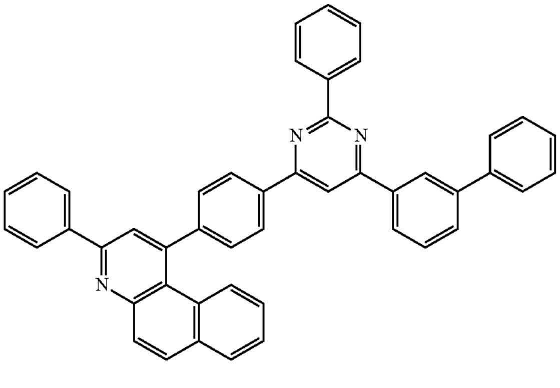

-continued
269
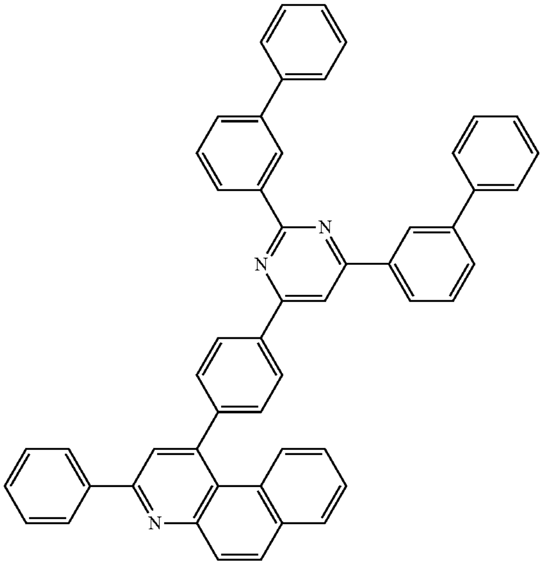
270
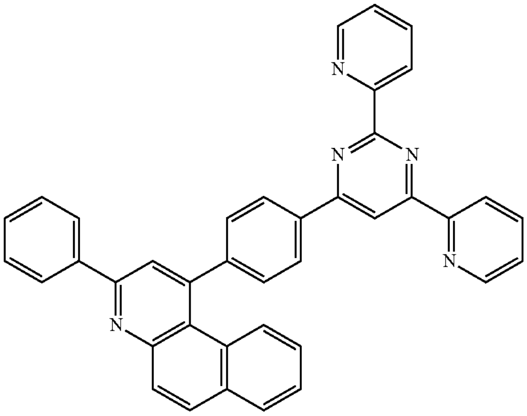
271
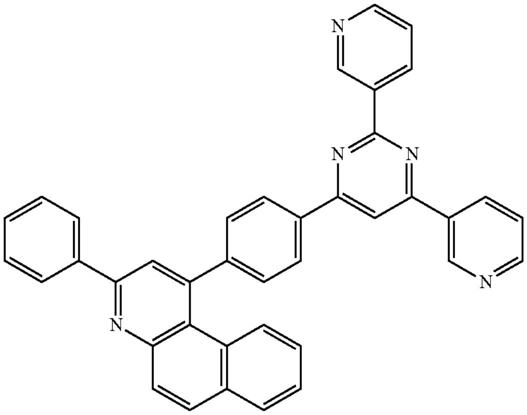
-continued
272
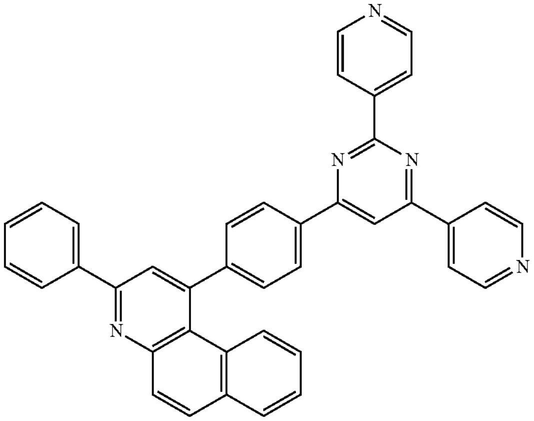
273
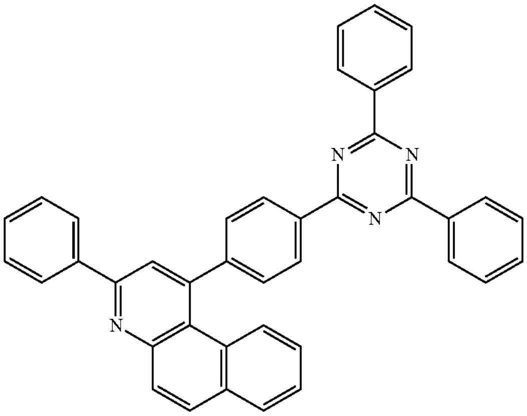
274
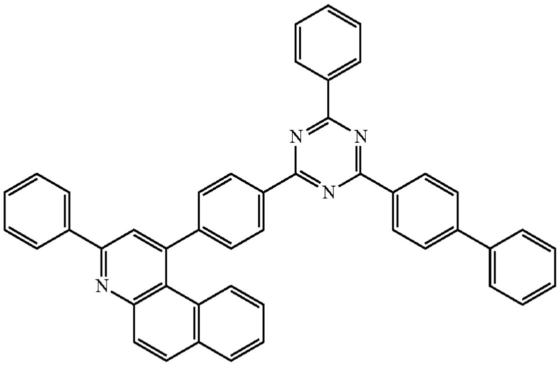

-continued
275
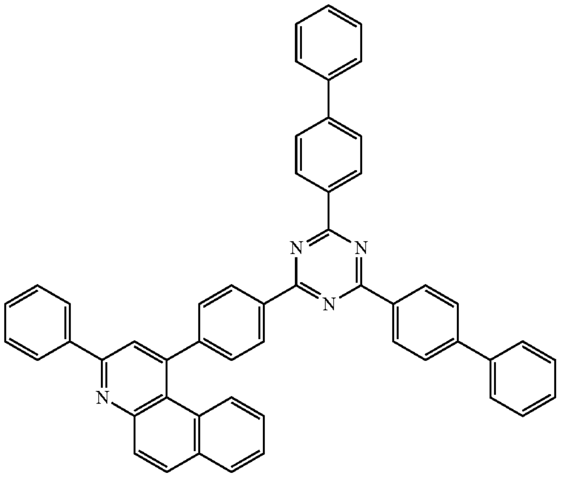
276
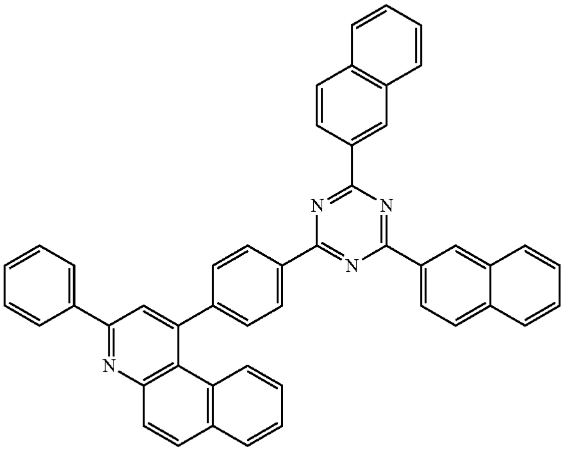
277
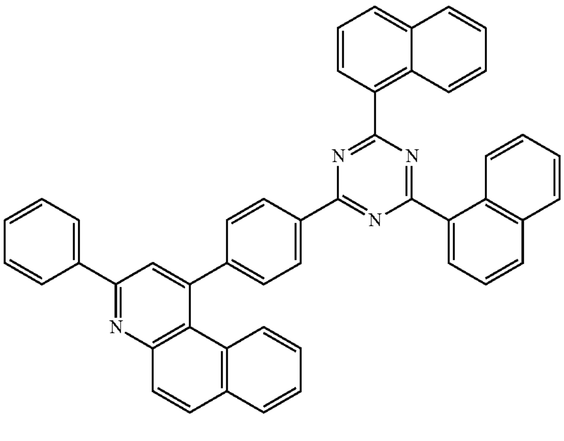
-continued
278
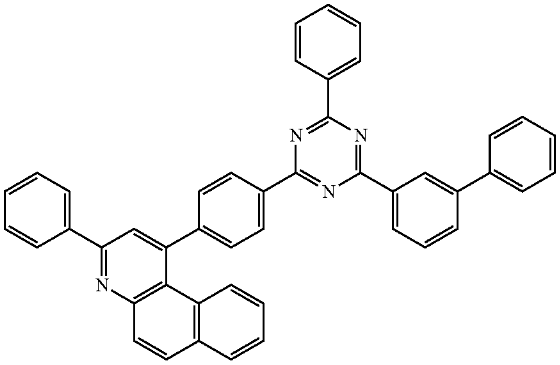
279
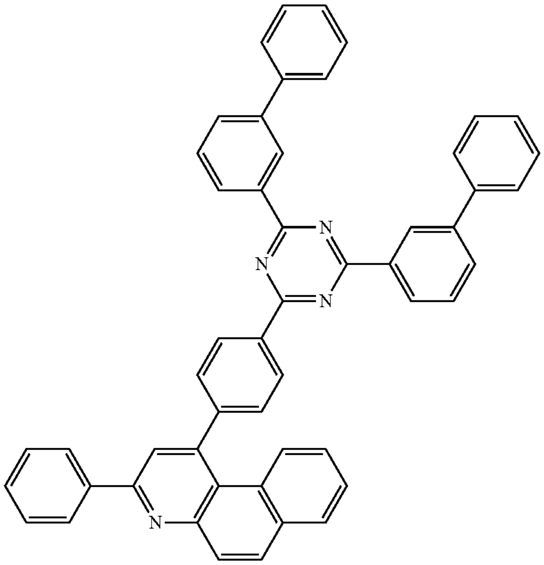
280
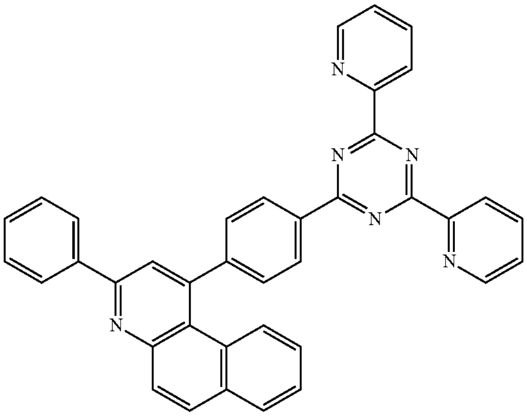

-continued
281
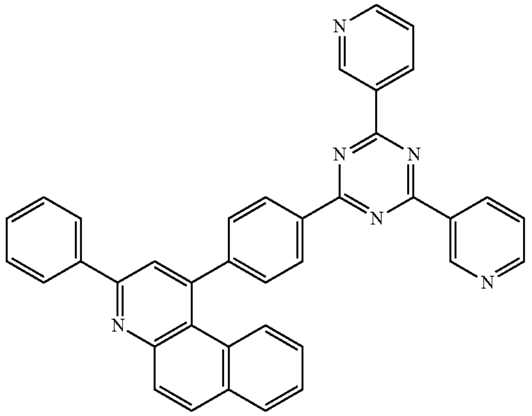
282
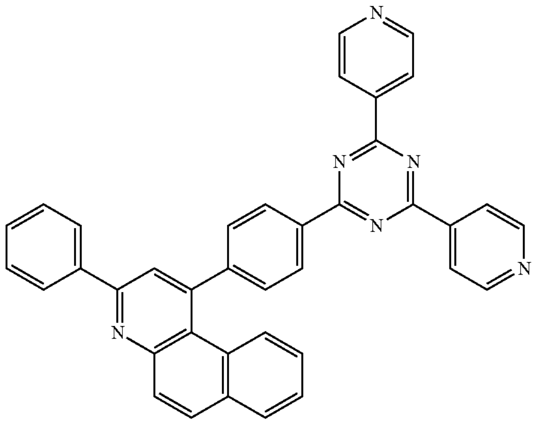
283
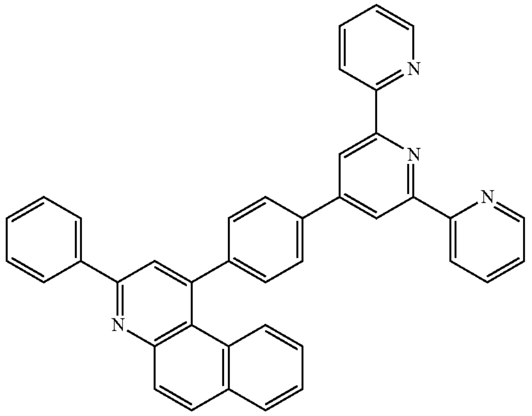
-continued
284
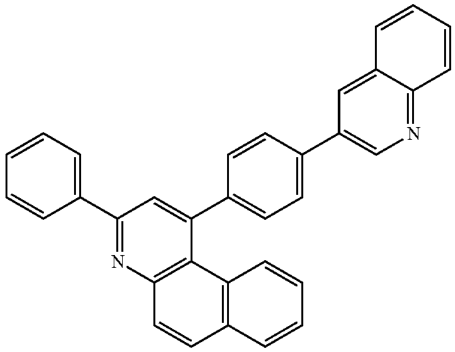
285
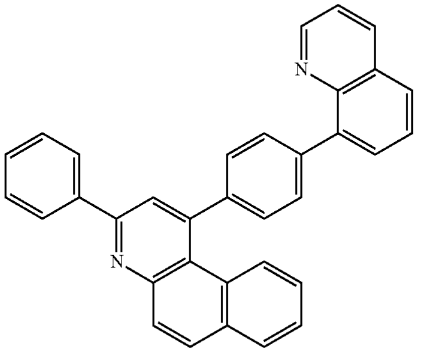
286
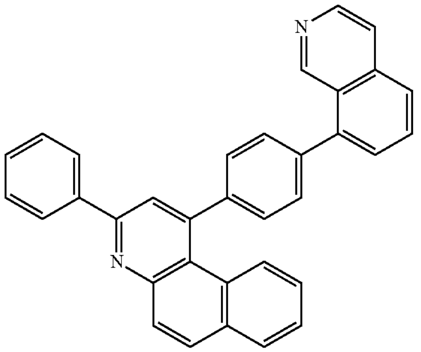
287
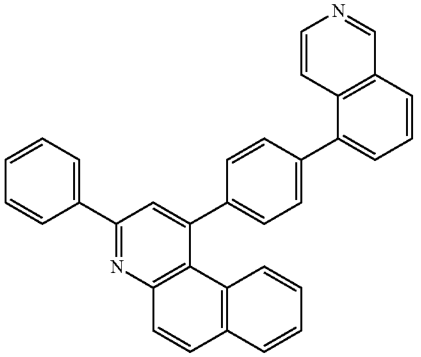

-continued
288
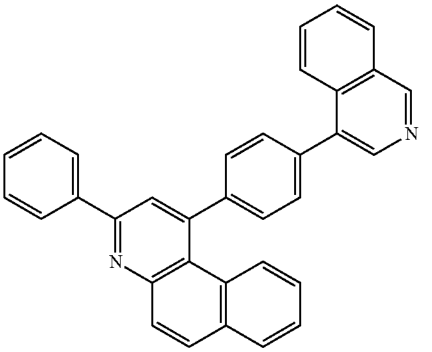
289
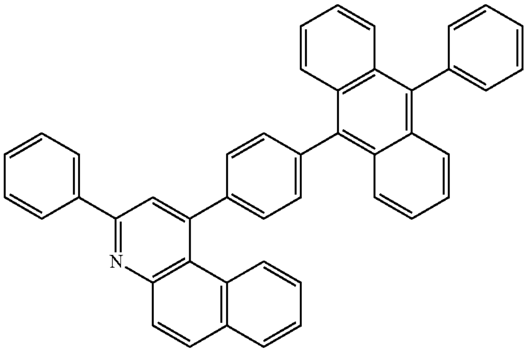
290
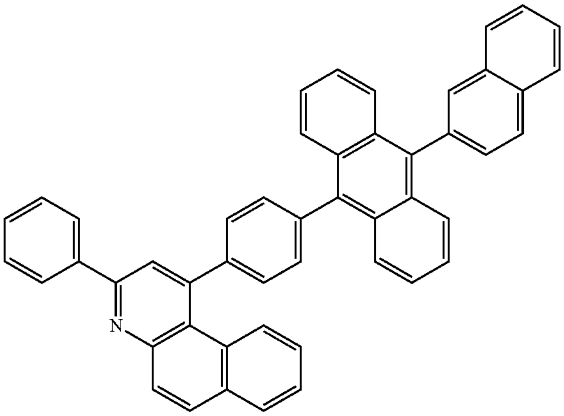
291
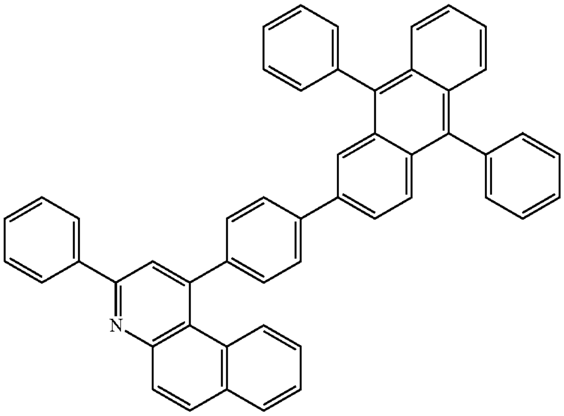
-continued
292
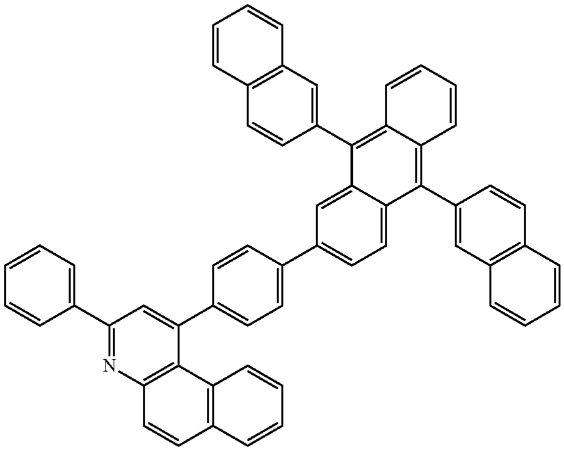
293
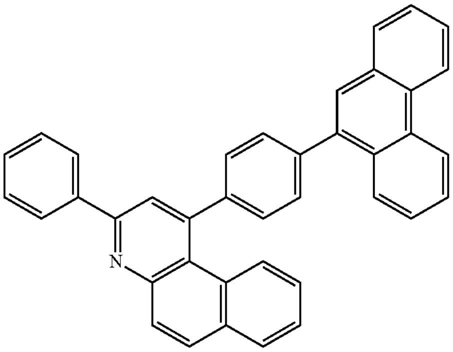
294
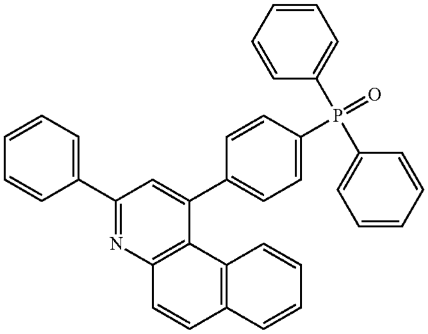
295
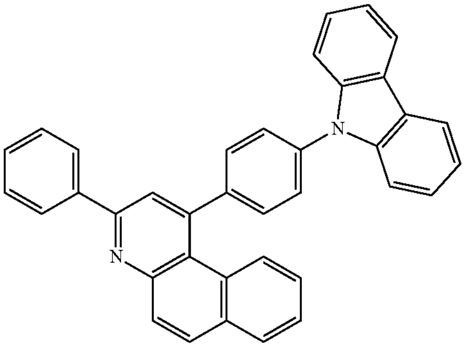

-continued
296
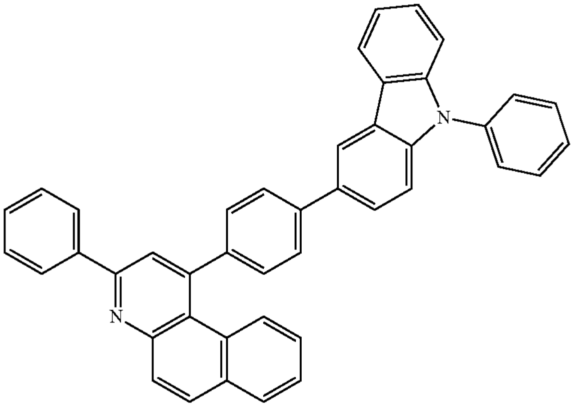
297
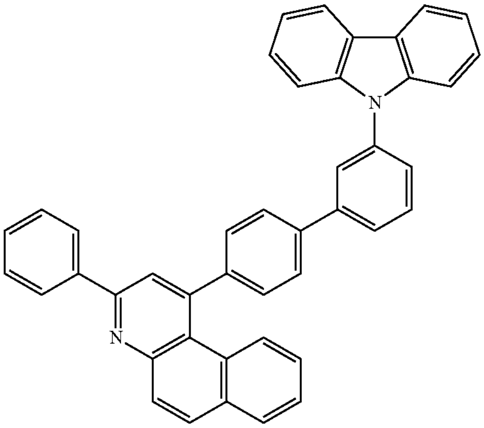
298
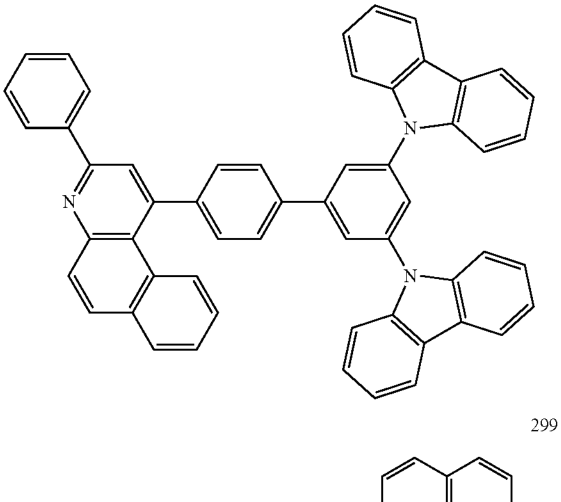
299
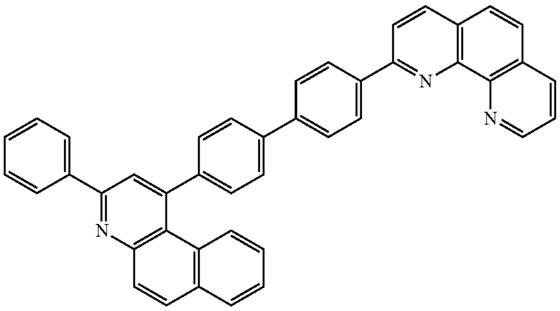
-continued
300
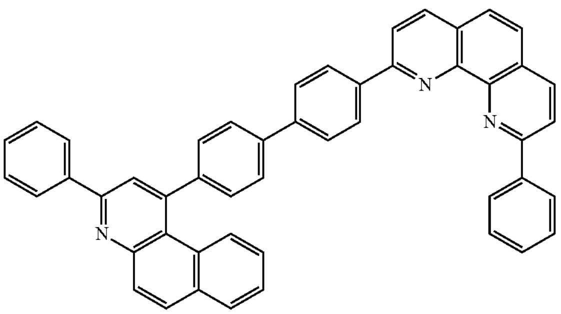
301
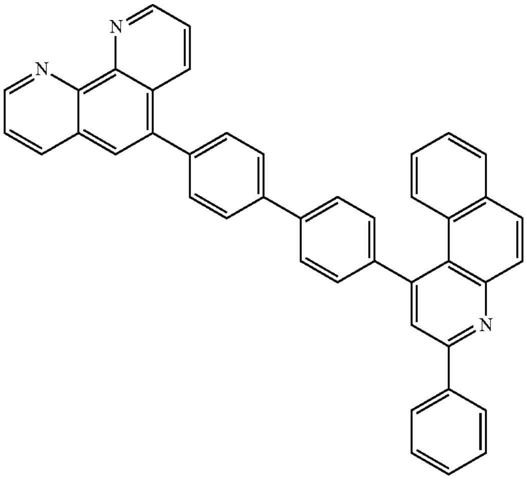
302
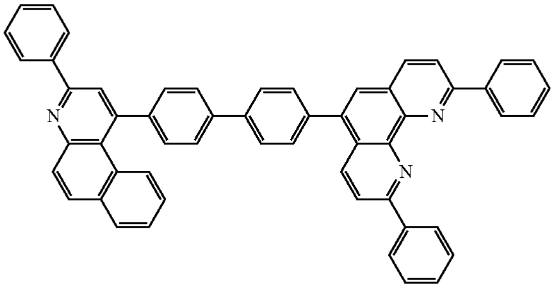
303
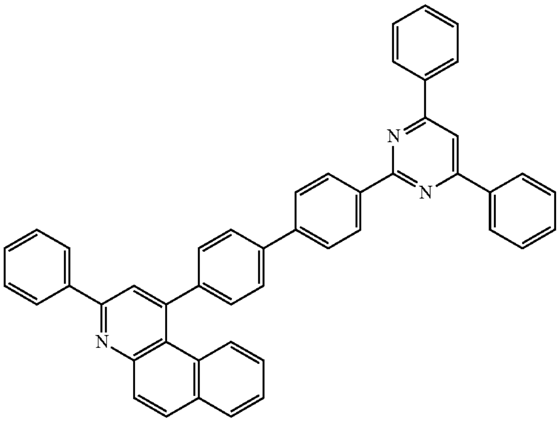

304
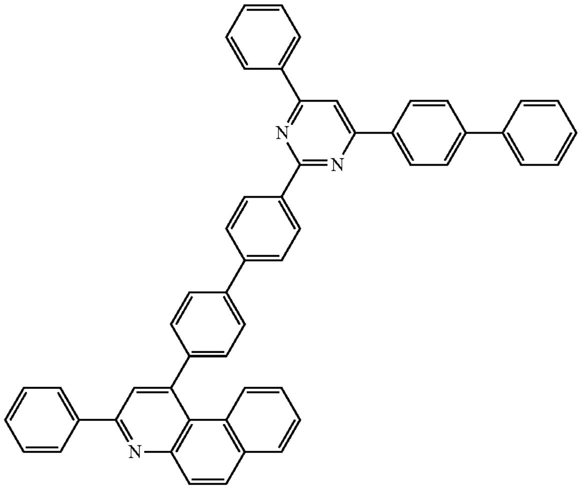
305
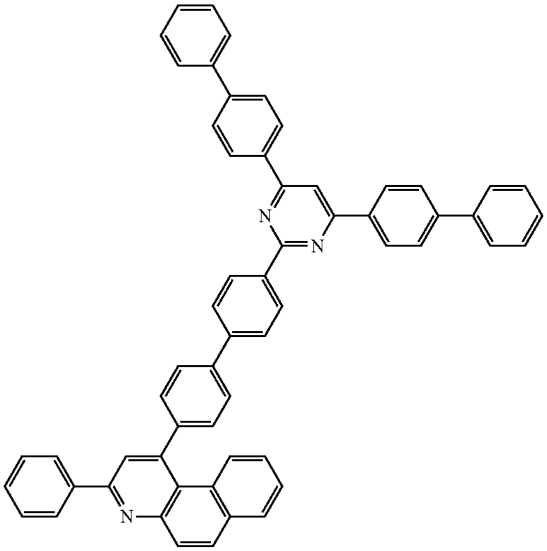
306
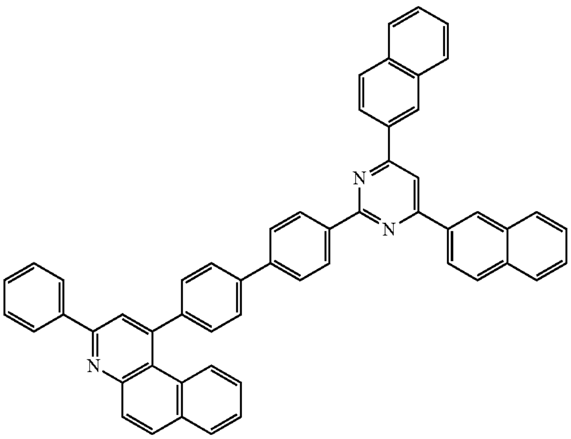
307
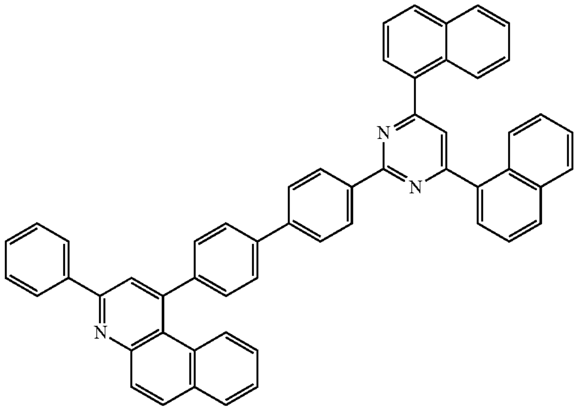
308
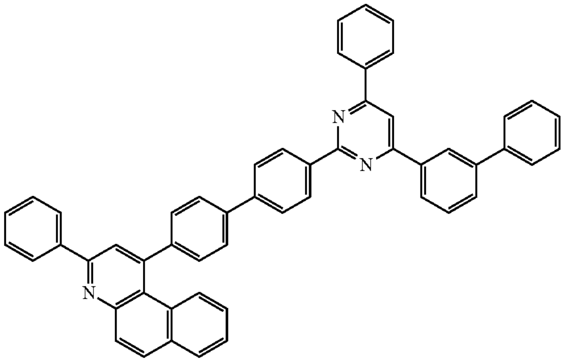
309
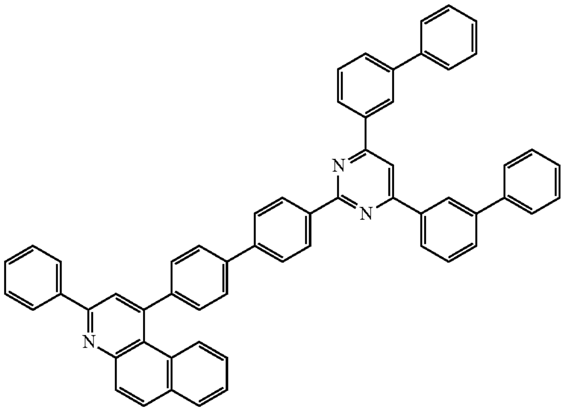

-continued
310
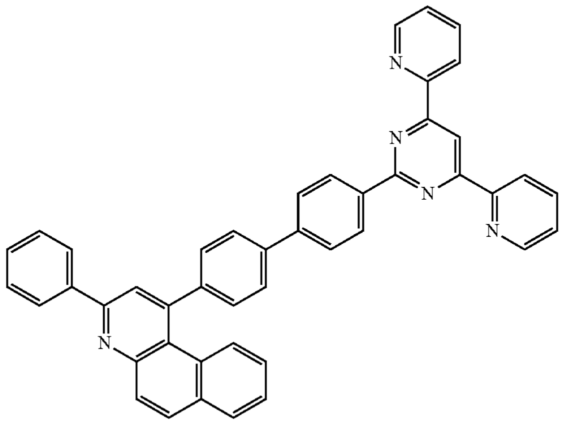
311
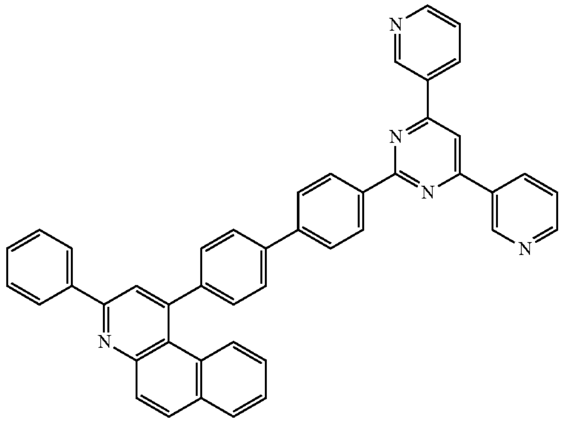
312
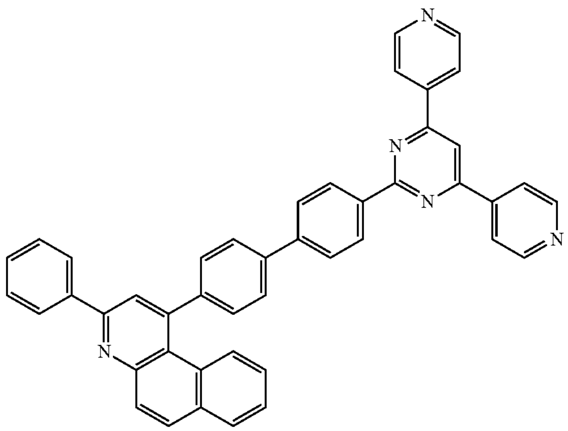
-continued
313
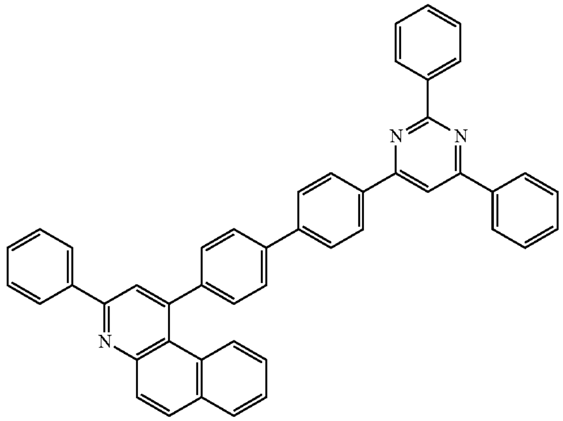
314
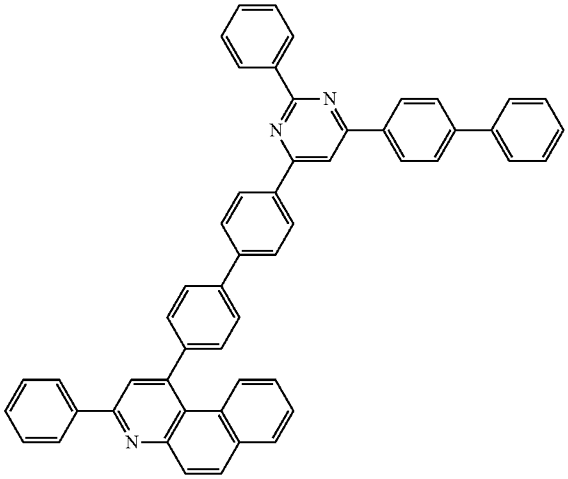
315
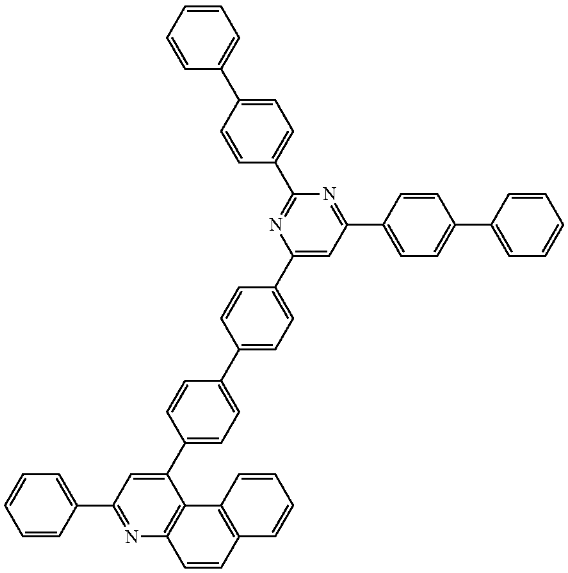

-continued
316
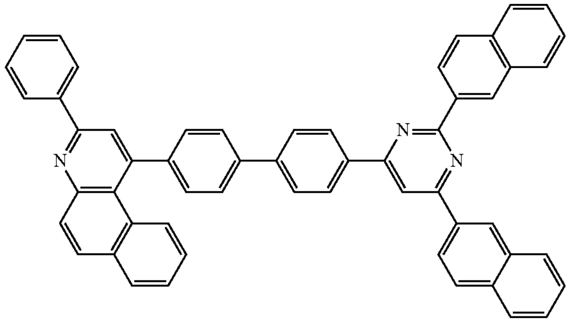
317
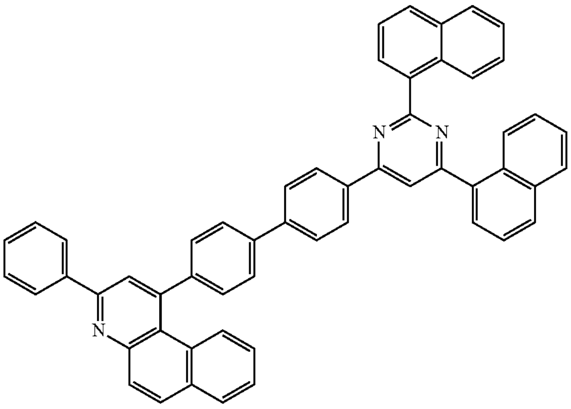
318
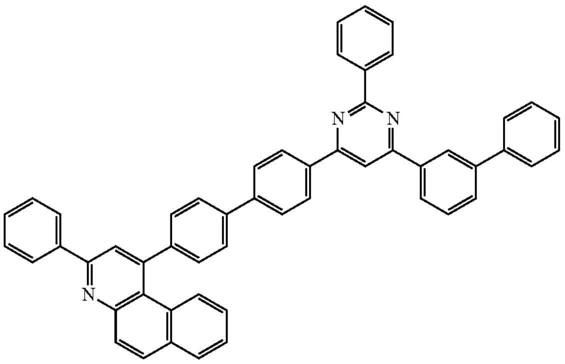
319
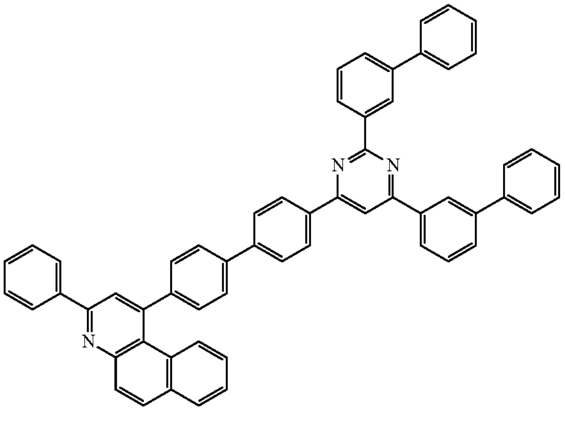
-continued
320
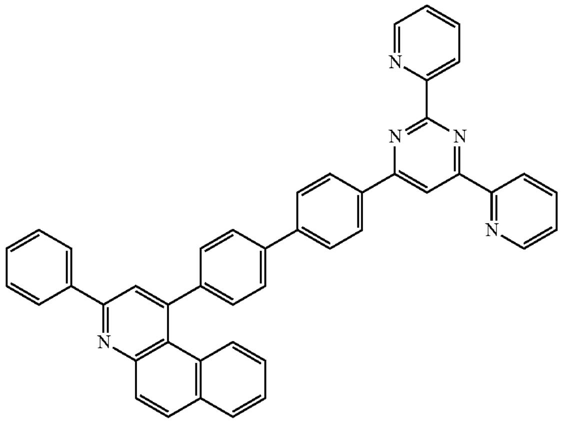
321
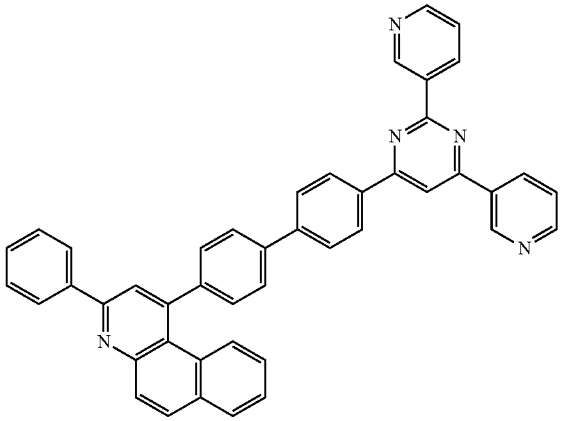
322
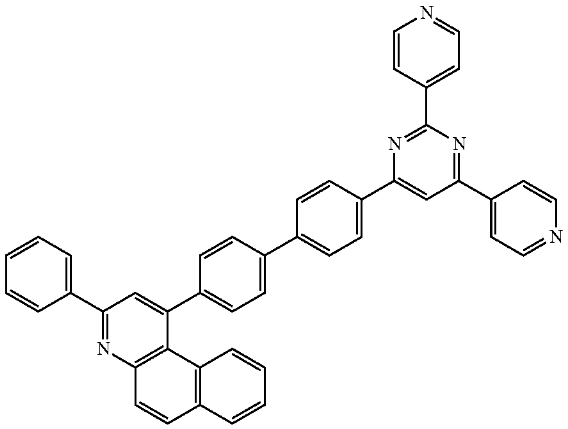

-continued
323
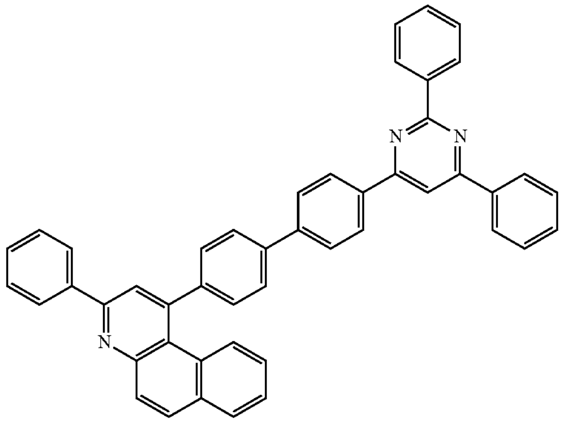
324
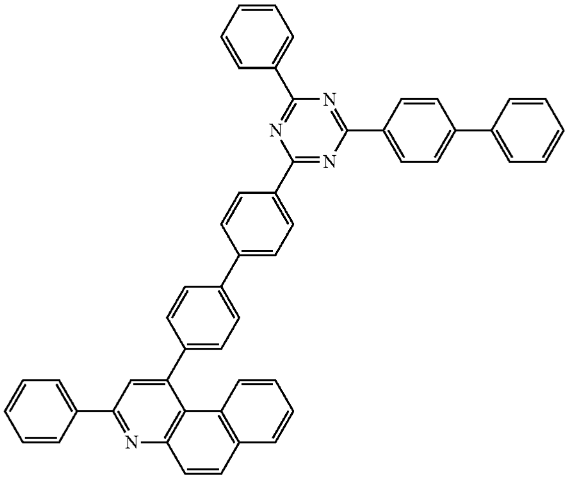
325
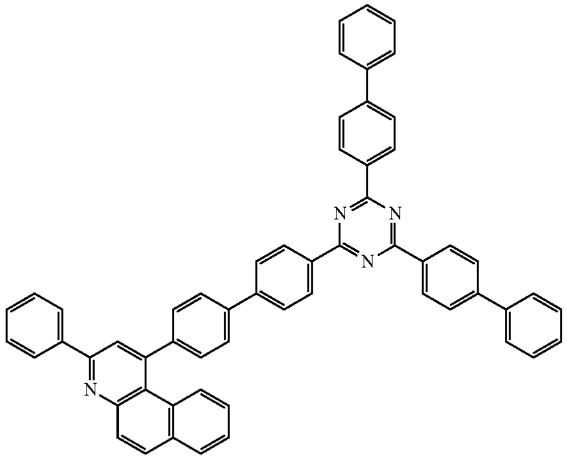
-continued
326
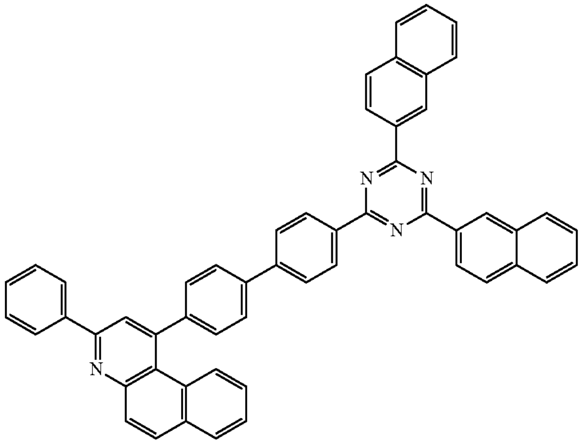
327
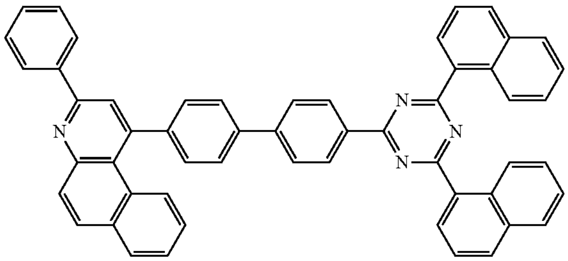
328
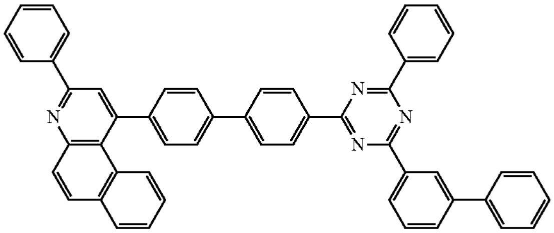
329
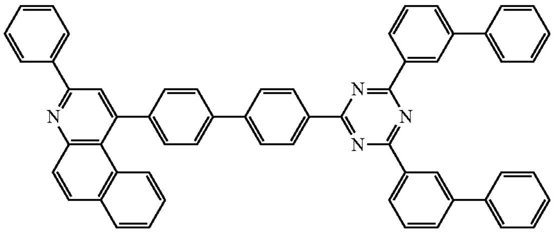

-continued
330
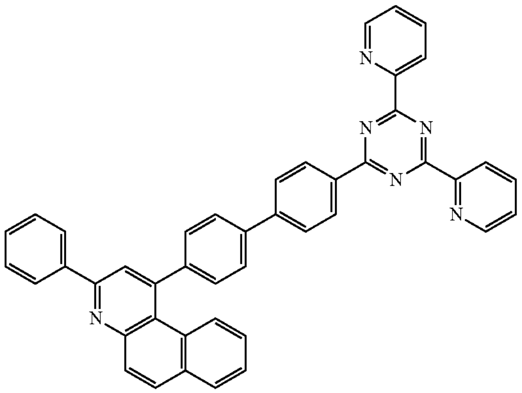
331
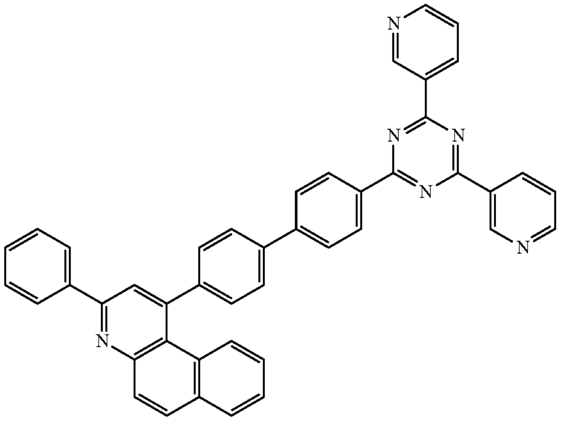
332
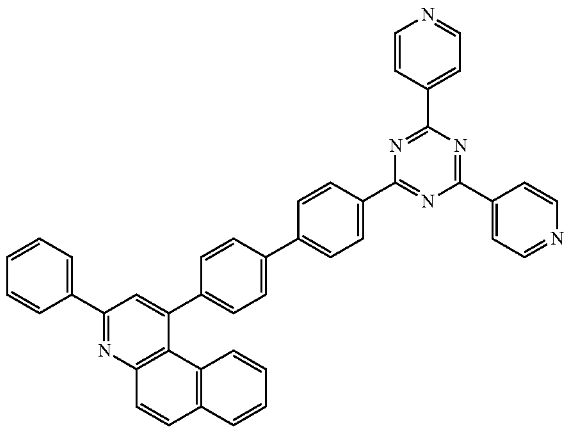
-continued
333
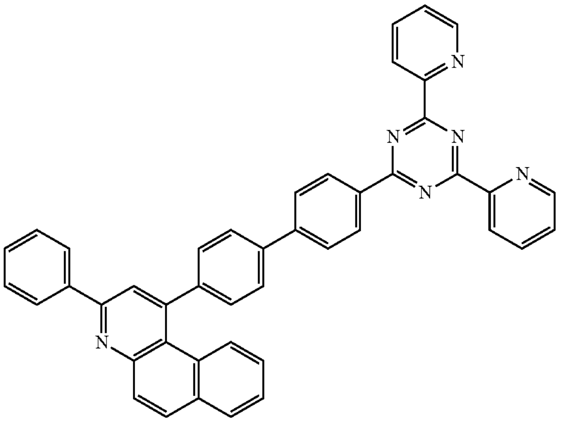
334
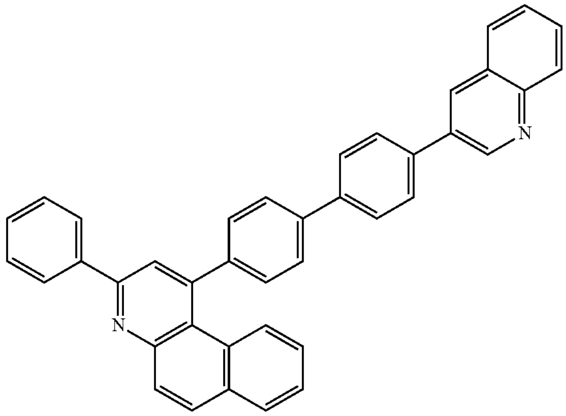
335
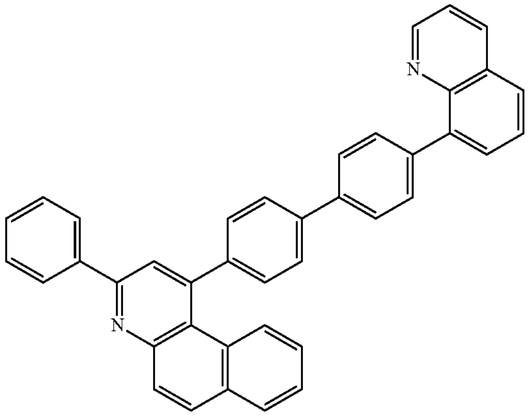

-continued
336
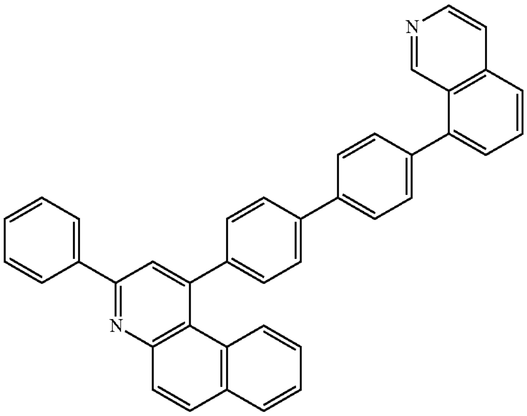
337
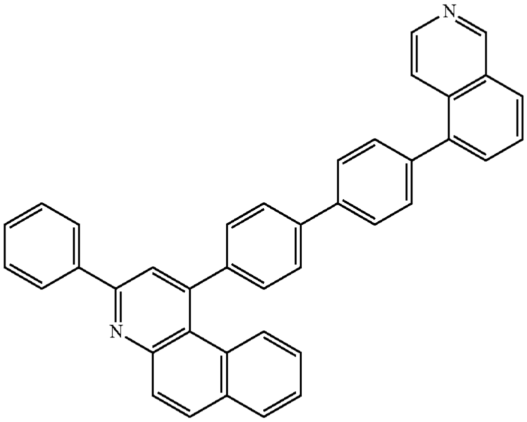
338
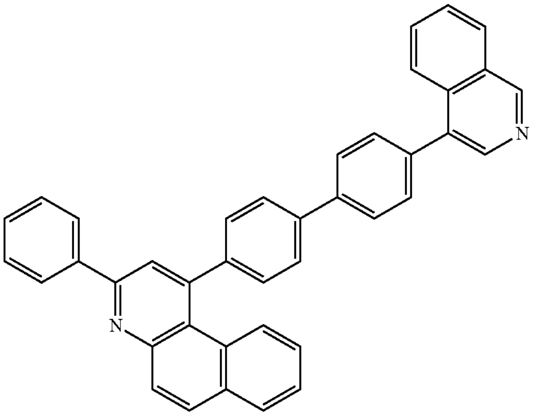
339
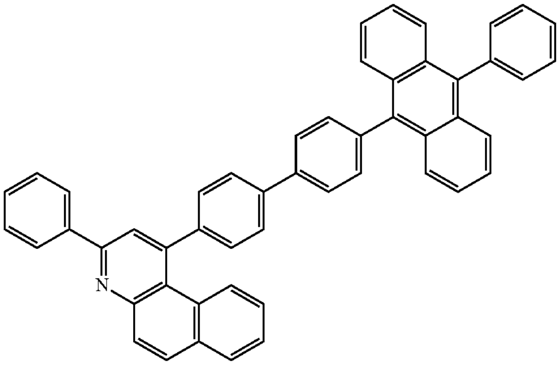
-continued
340
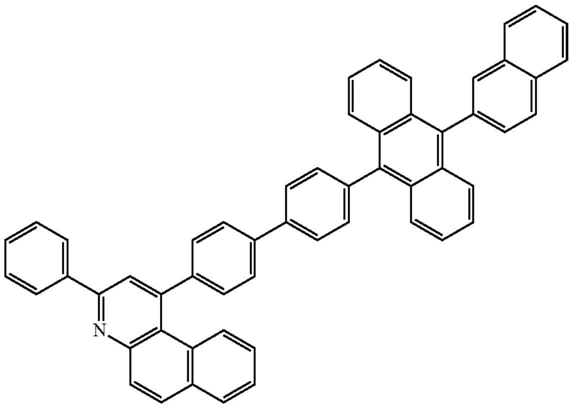
341
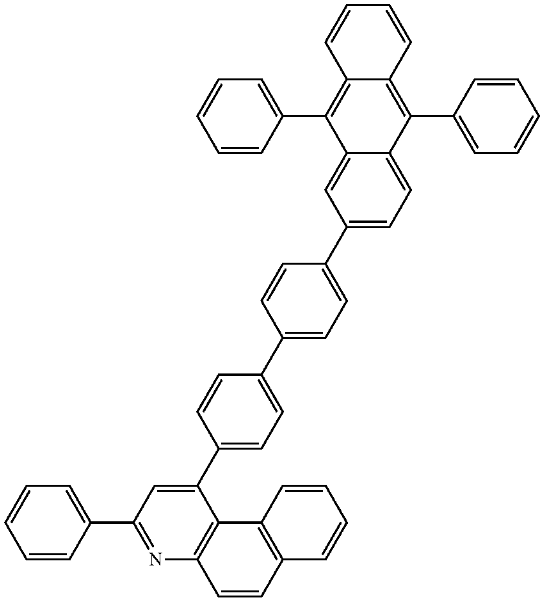
342
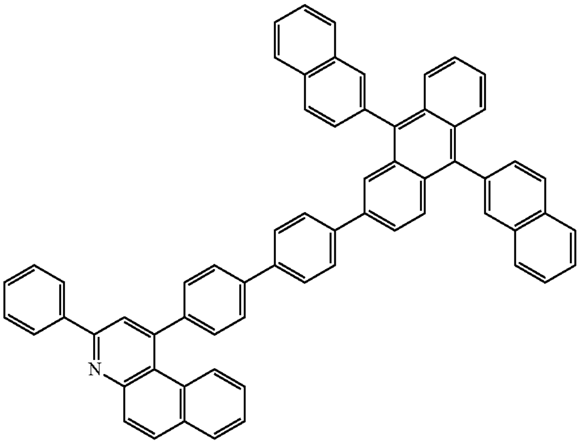

-continued
343
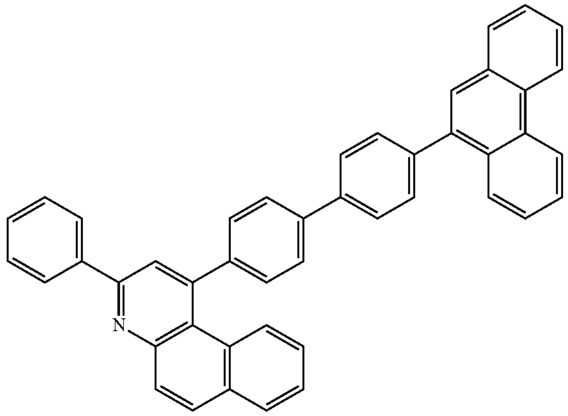
344
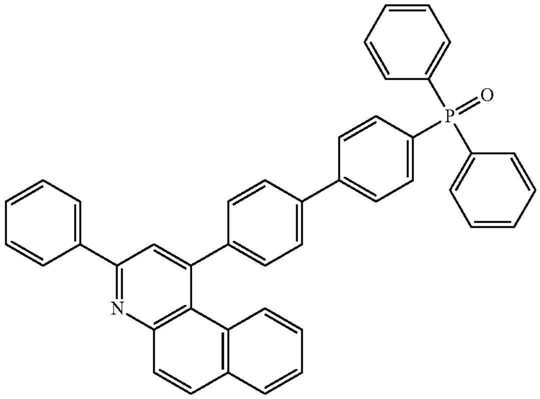
345
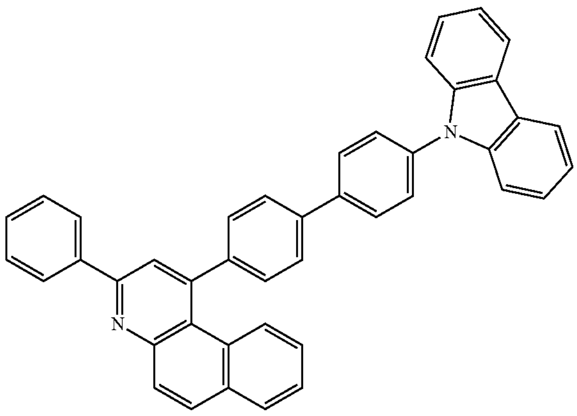
-continued
346
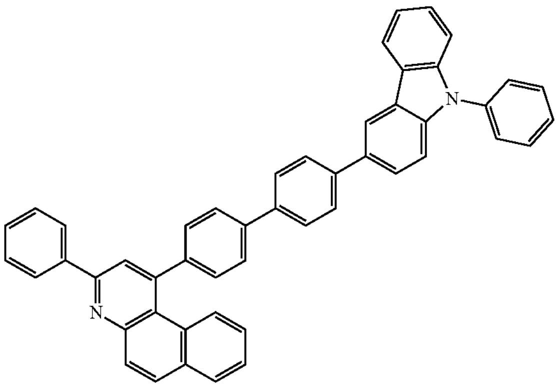
347
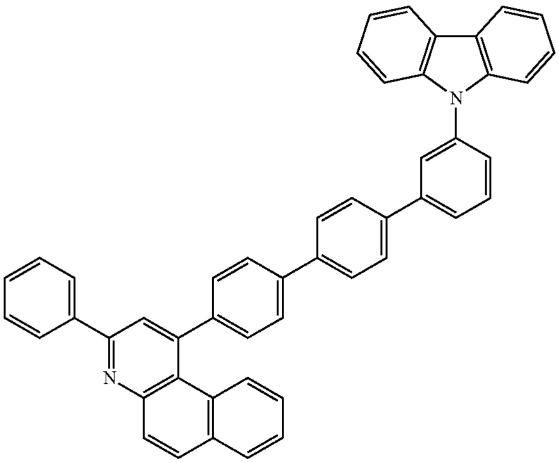
348
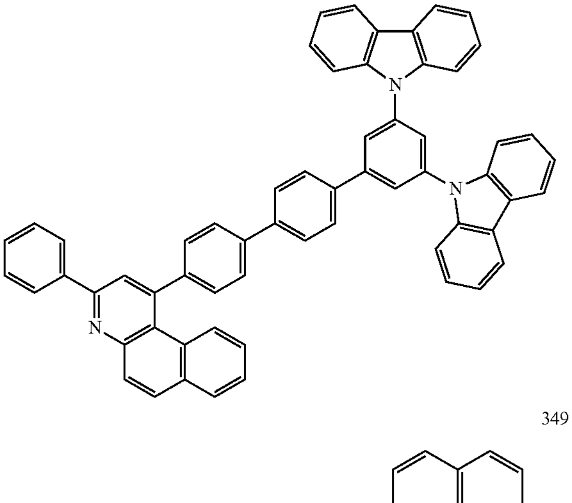
349
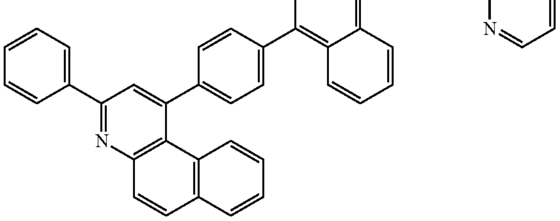

-continued
350
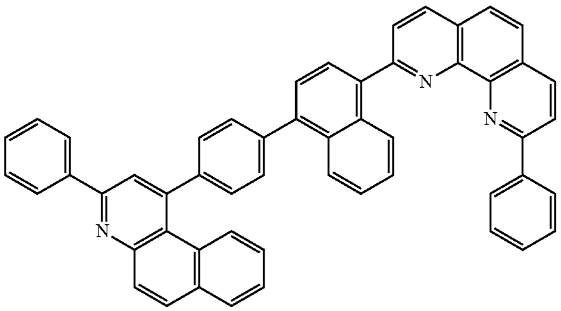
351
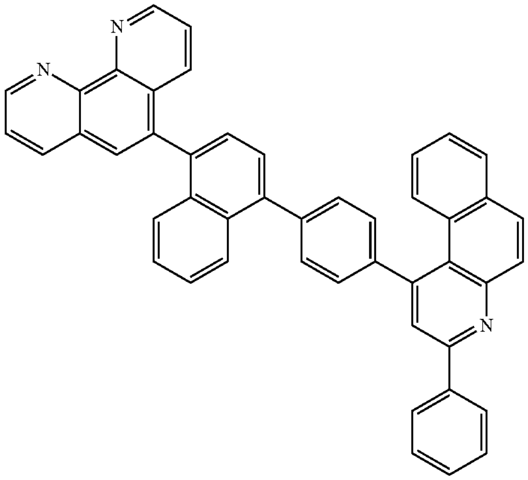
352
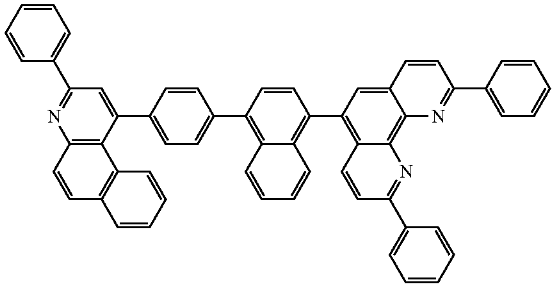
353
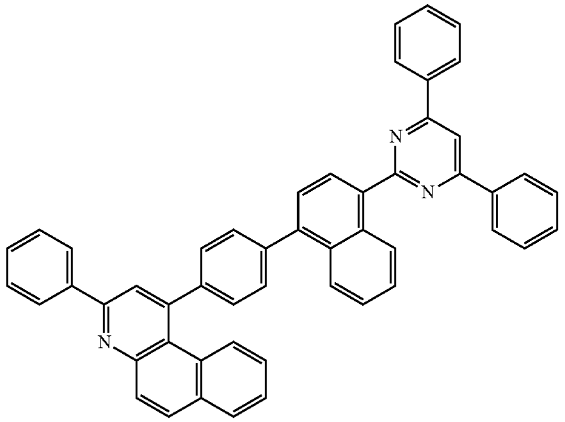
-continued
354
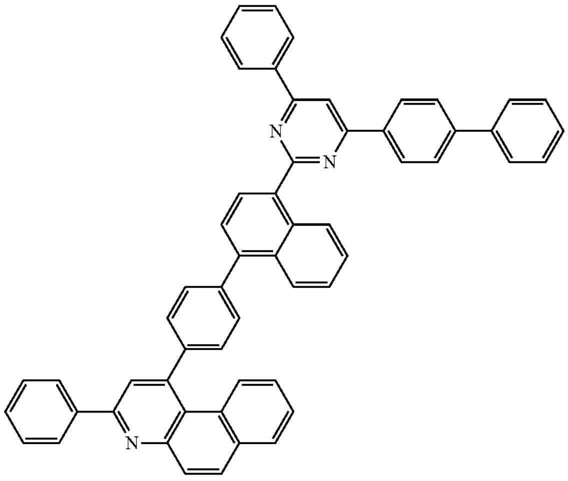
355
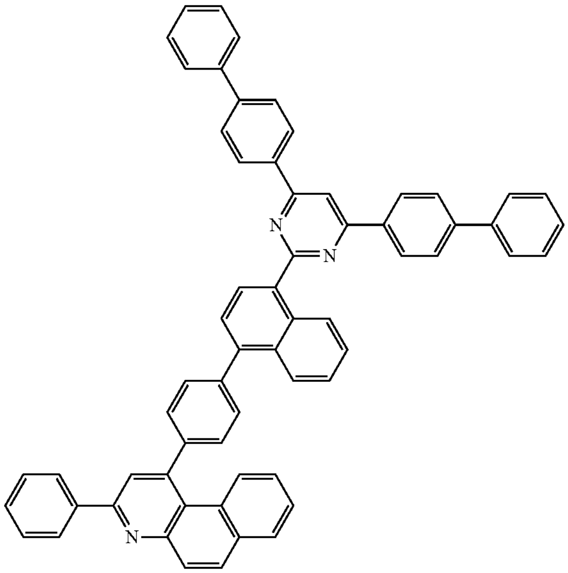
356
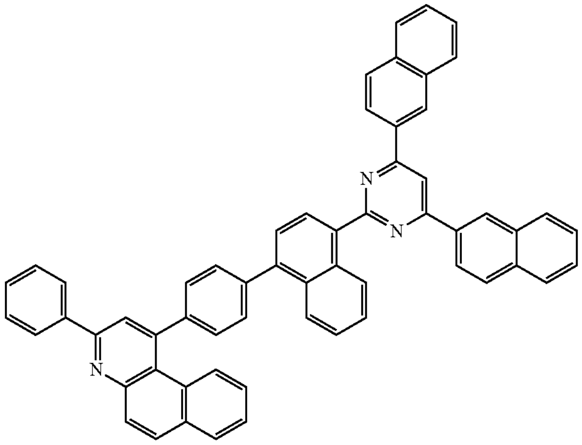

-continued
357
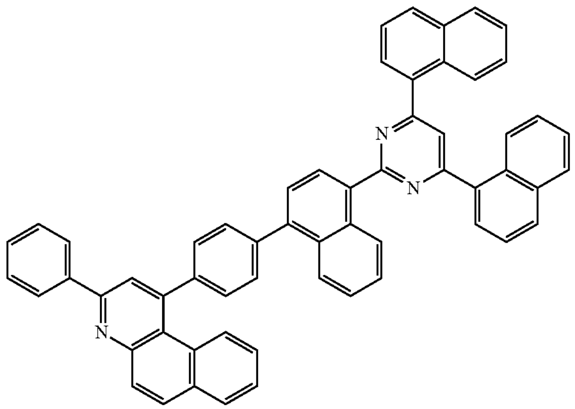
358
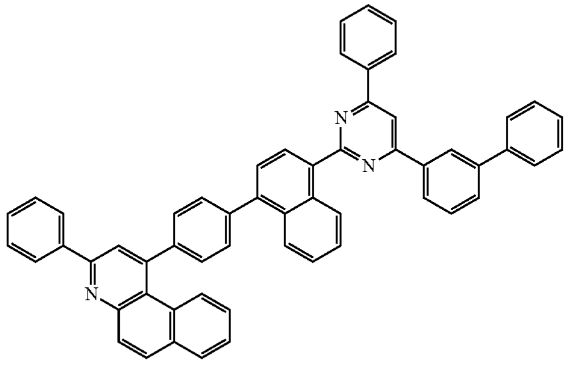
359
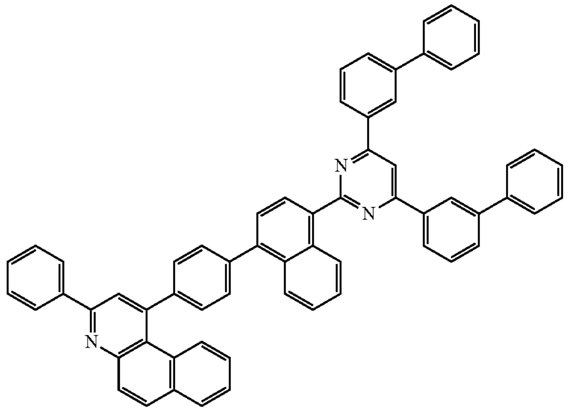
-continued
360
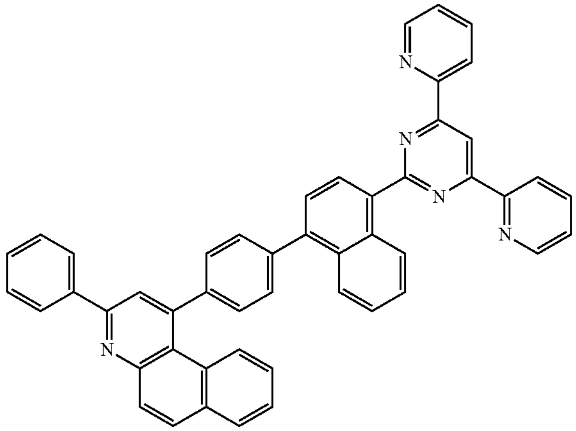
361
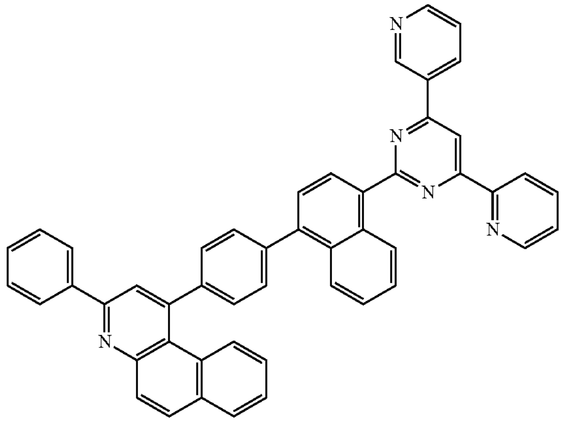
362
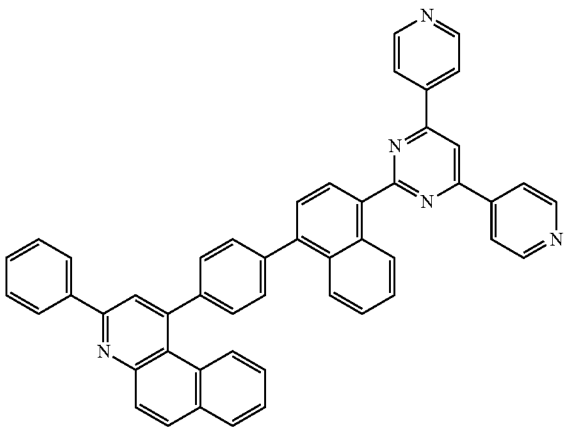

-continued
363
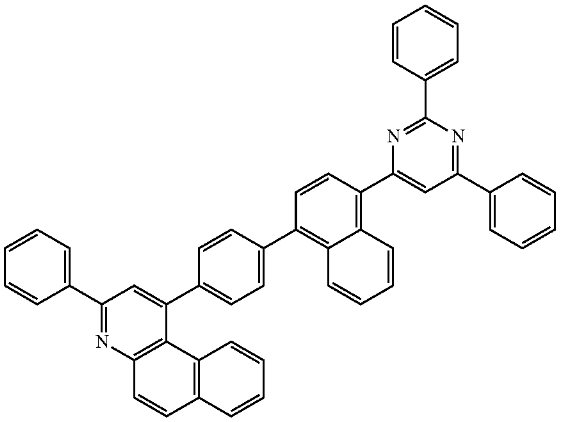
364
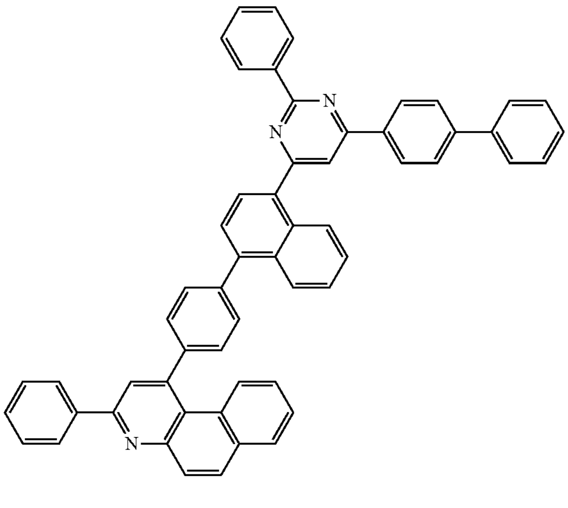
365
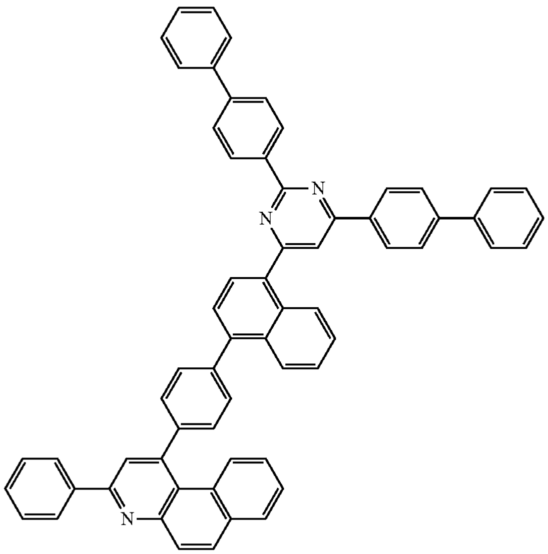
-continued
366
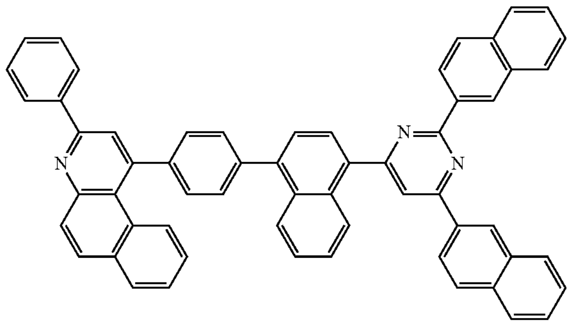
367
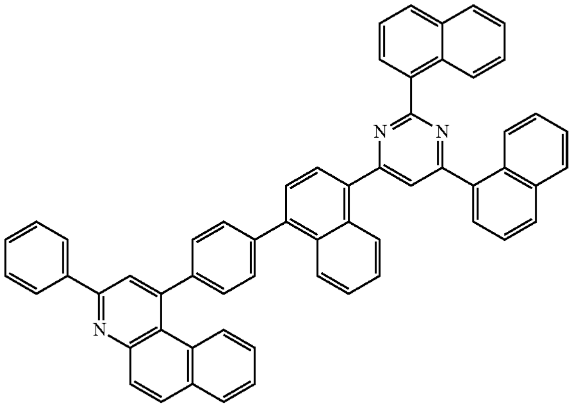
368
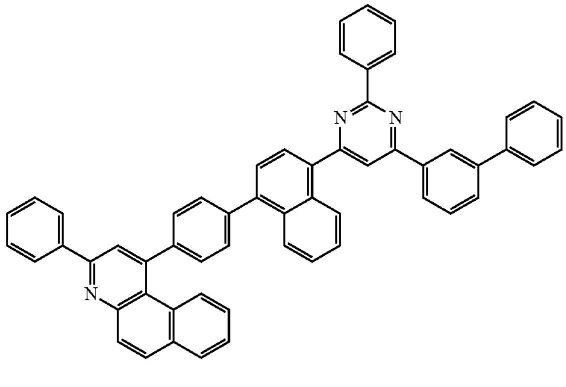
369
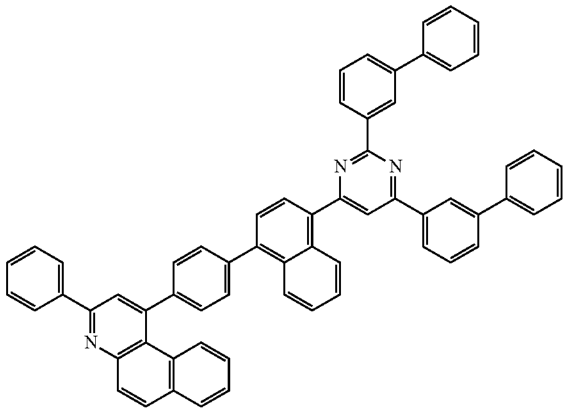

370
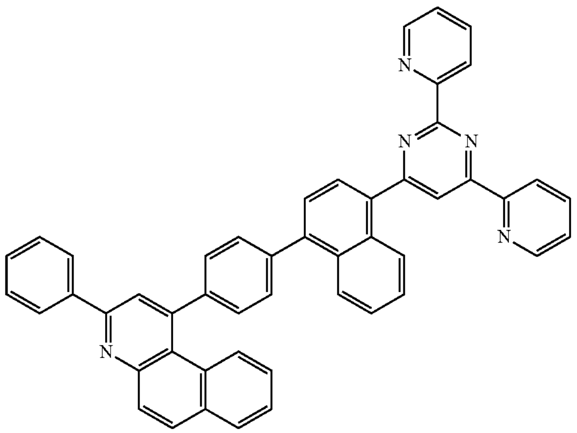
371
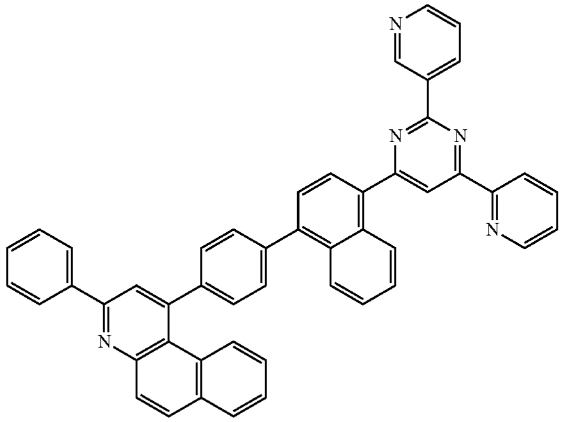
372
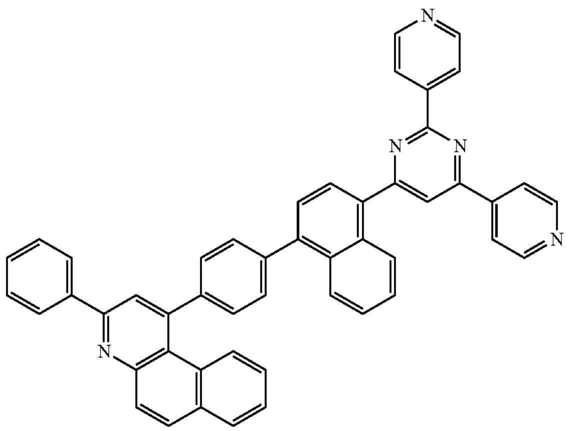
373
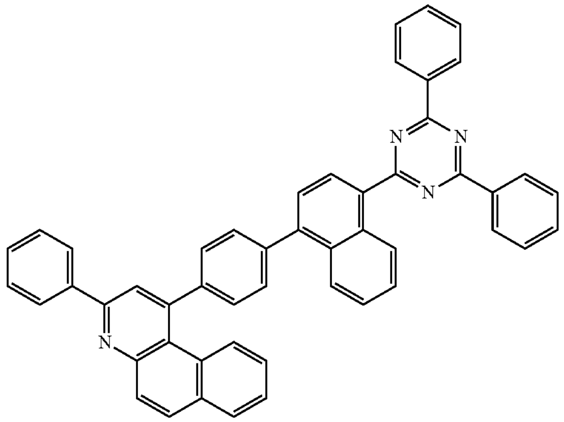
374
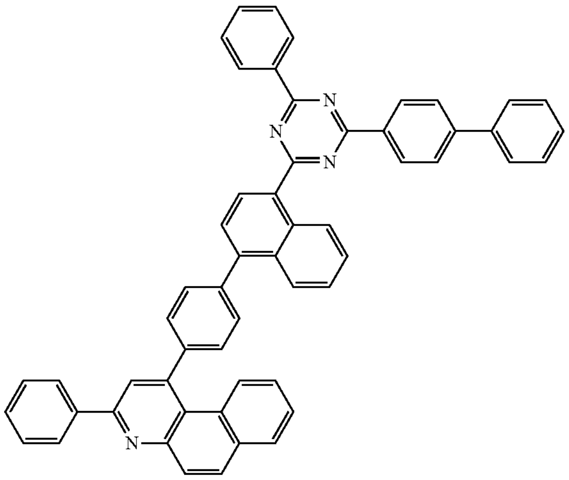
375
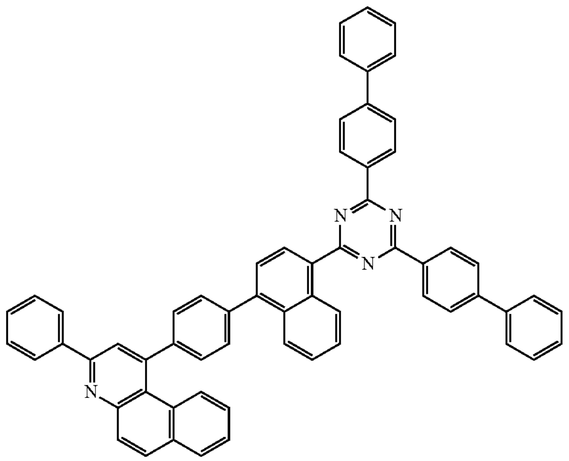

-continued
376
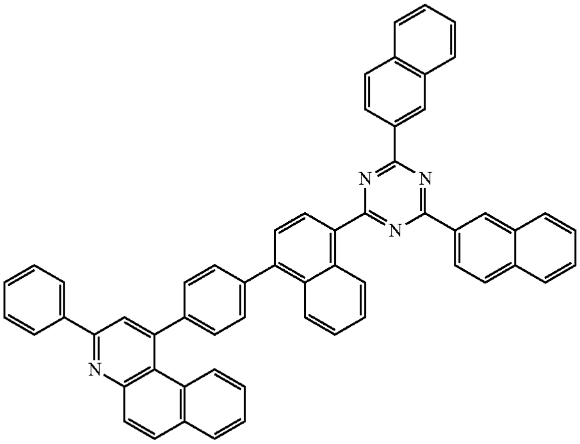
377
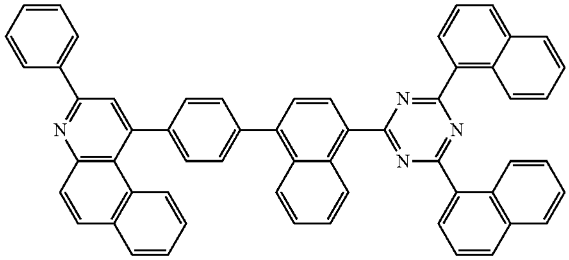
378
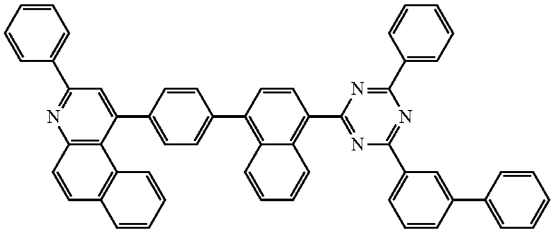
379
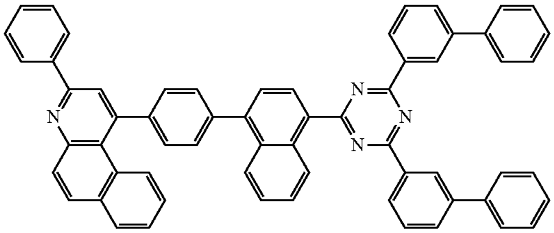
-continued
380
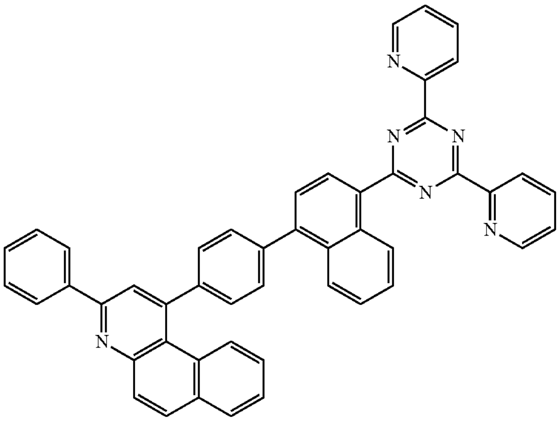
381
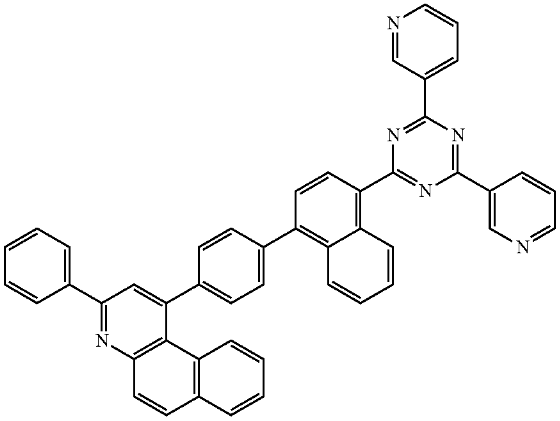
382
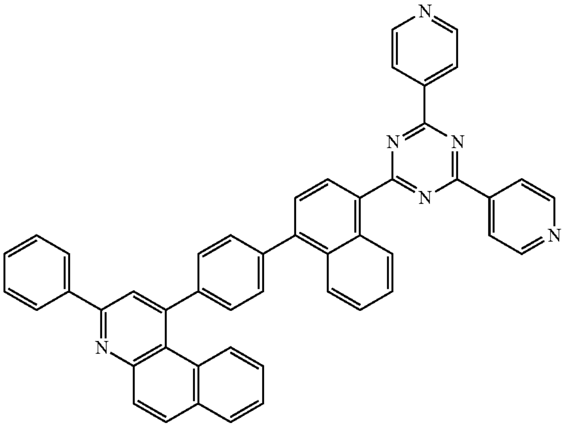

-continued
383
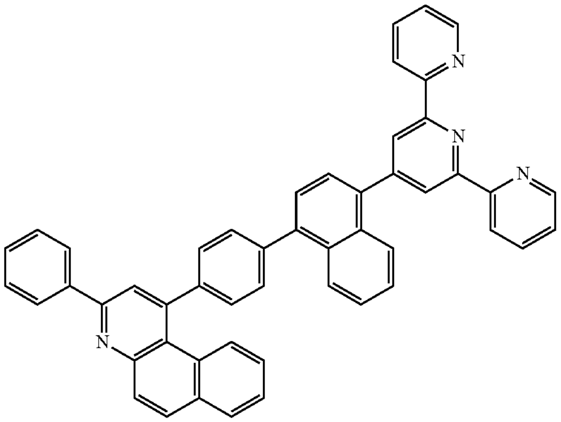
384
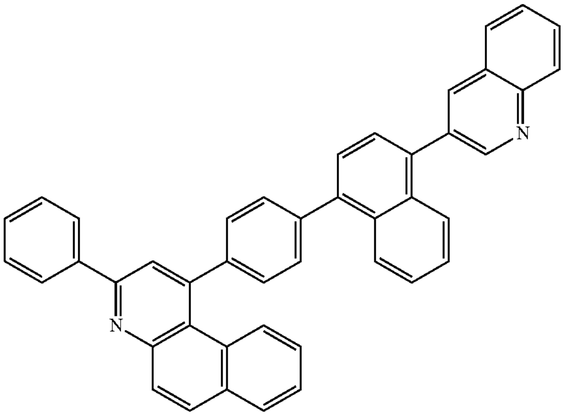
385
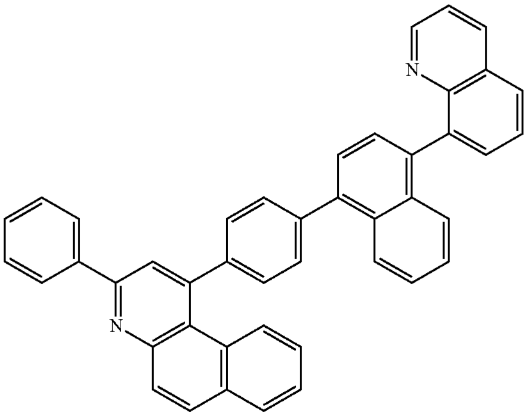
-continued
386
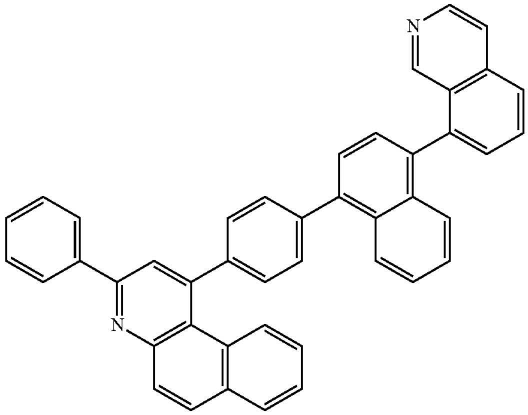
387
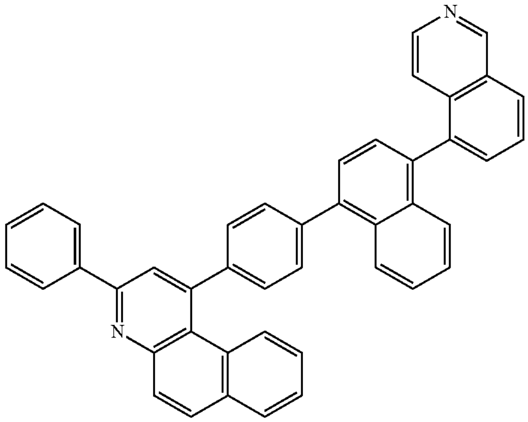
388
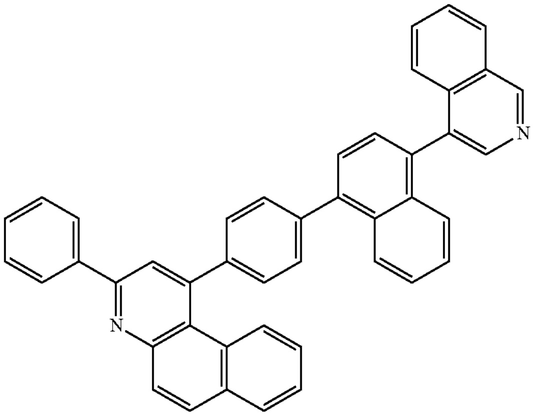

-continued
389
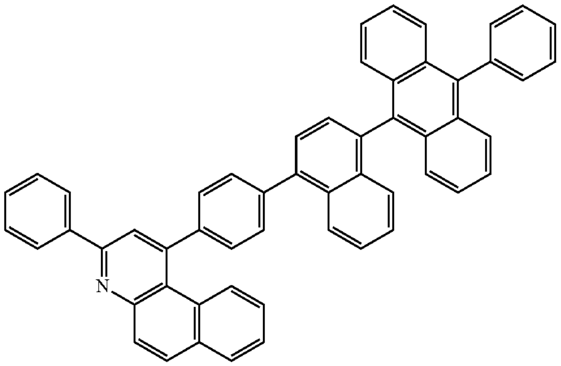
390
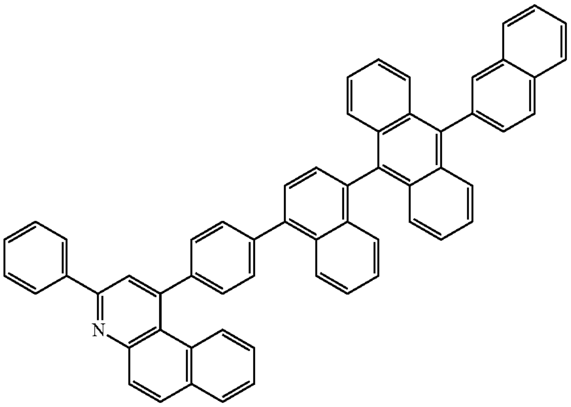
391
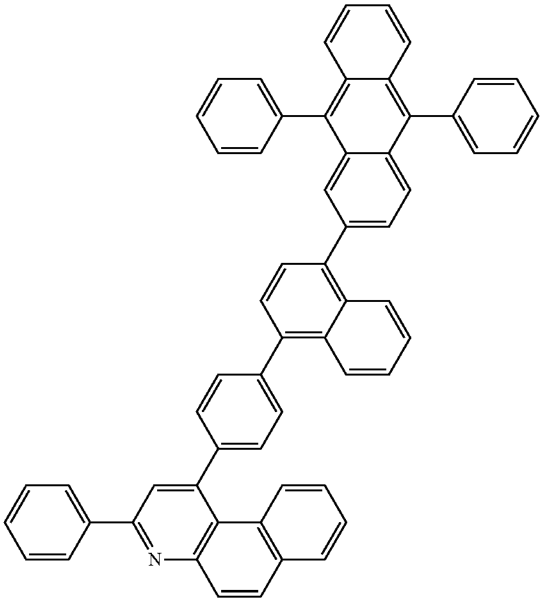
-continued
392
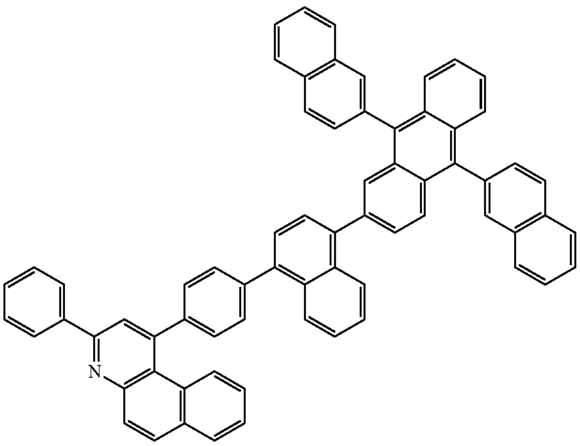
393
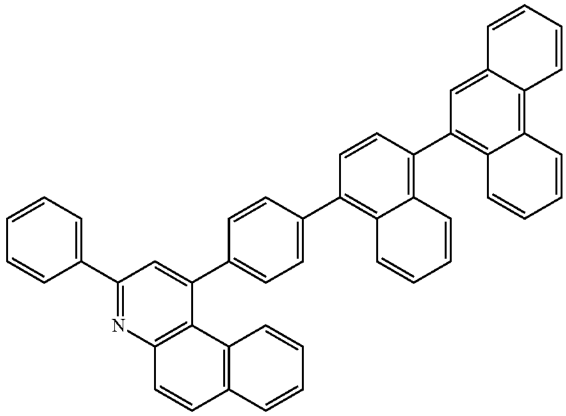
394
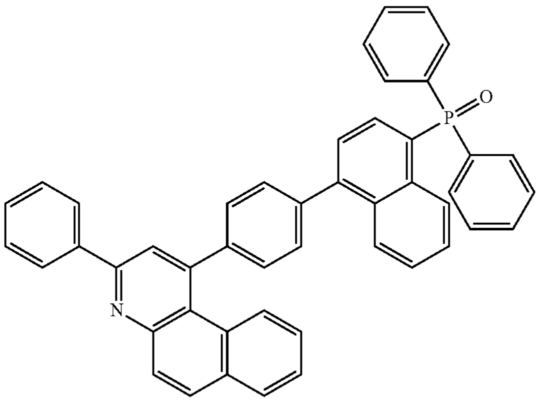

-continued
395
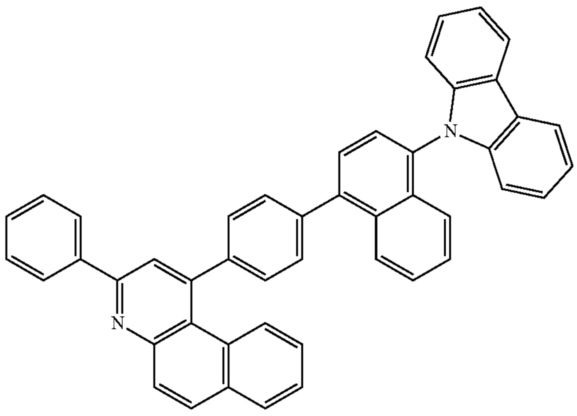
396
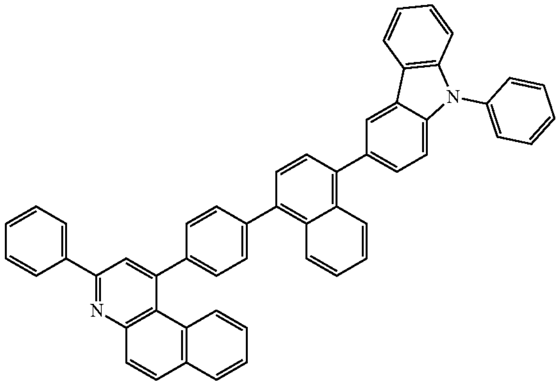
397
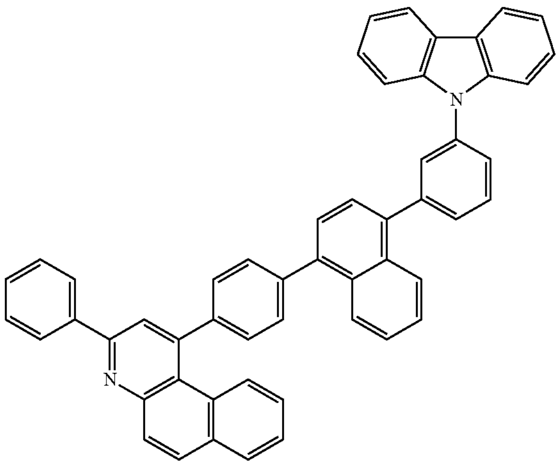
-continued
398
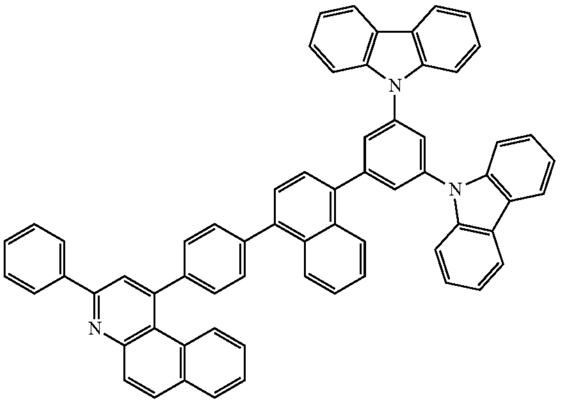
399
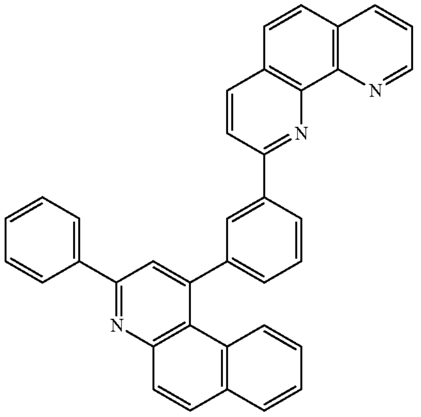
400
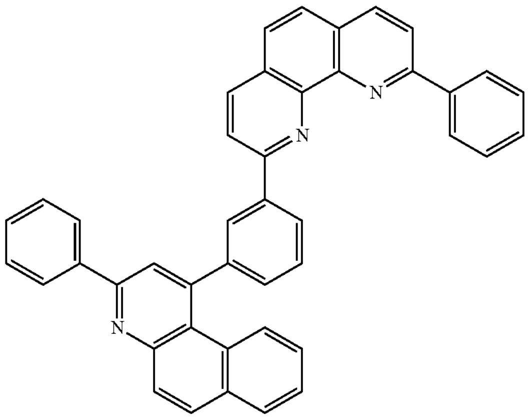

-continued
401
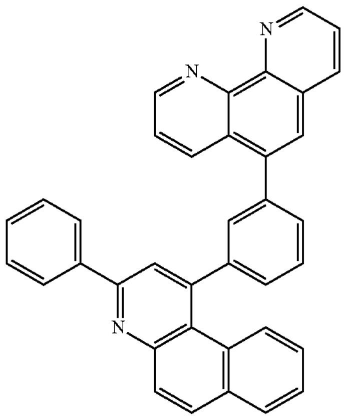
402
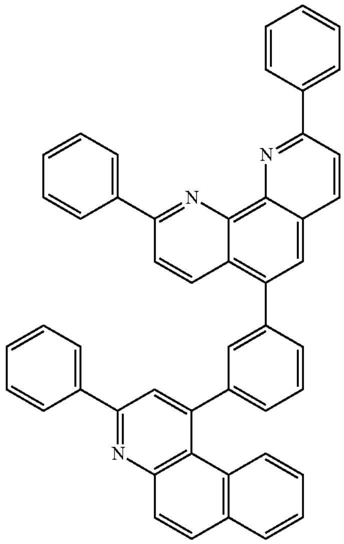
403
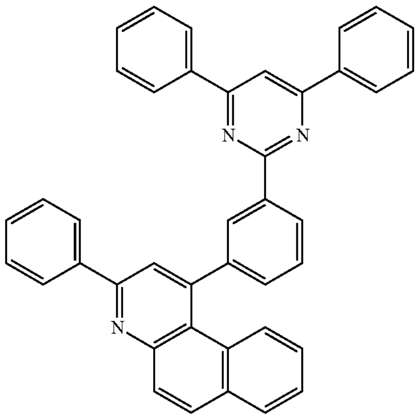
-continued
404
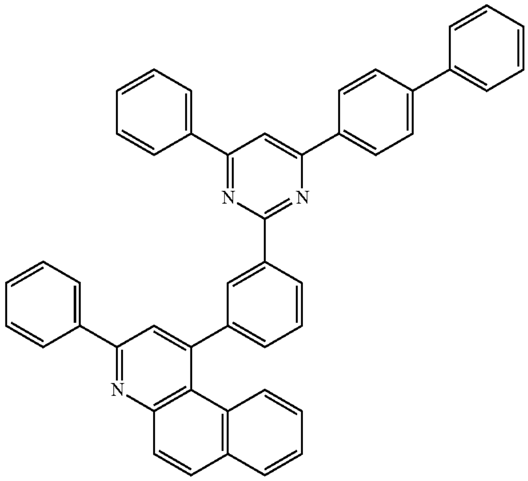
405
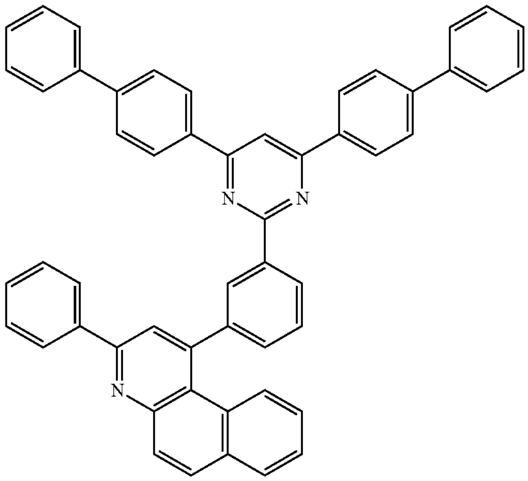
406
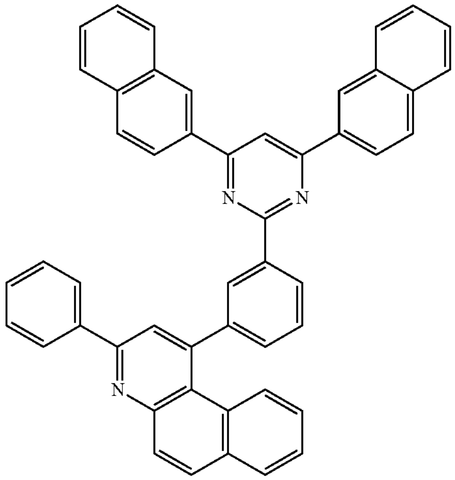

-continued
407
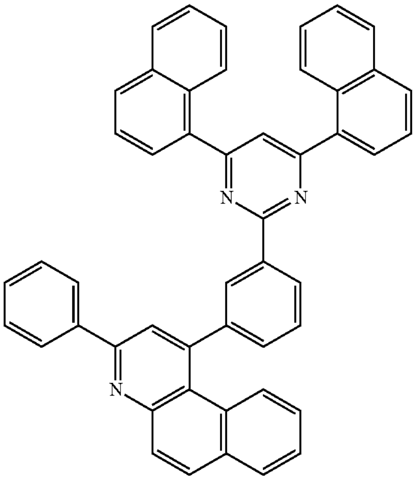
408
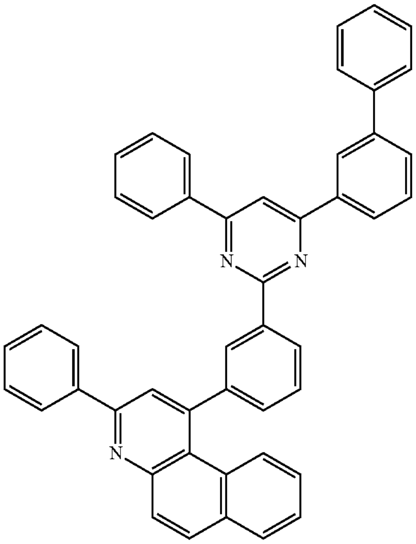
409
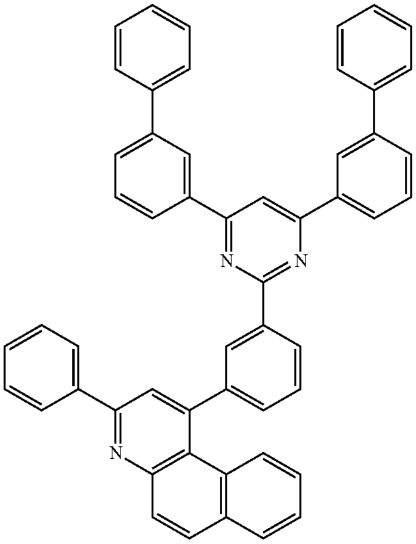
-continued
410
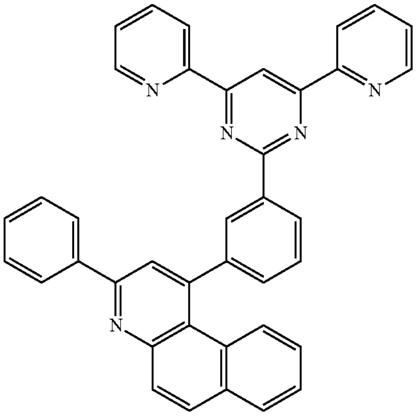
411
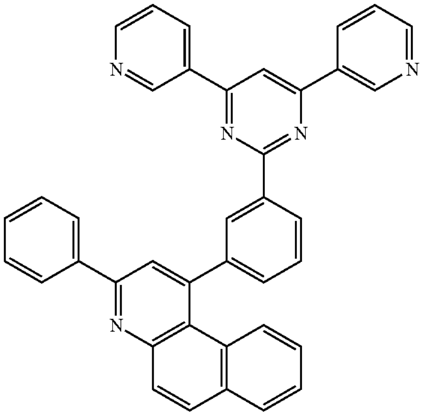
412
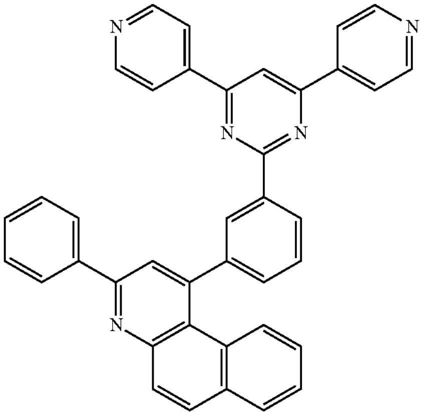

413
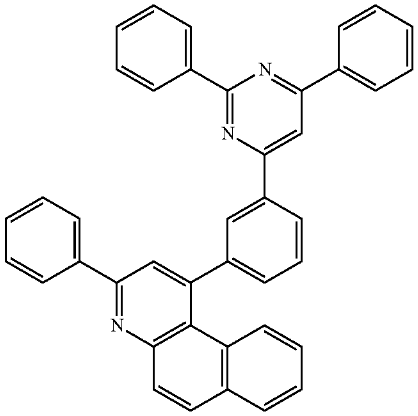
414
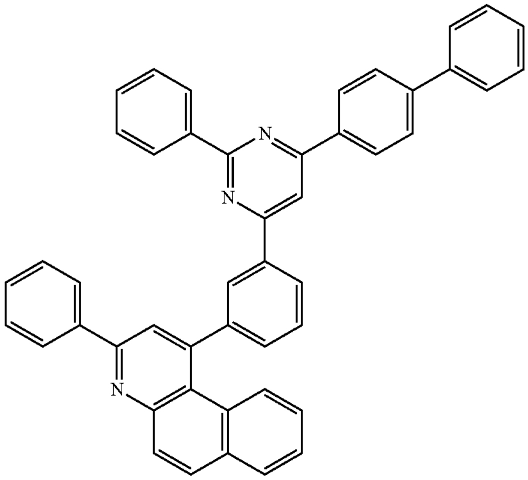
415
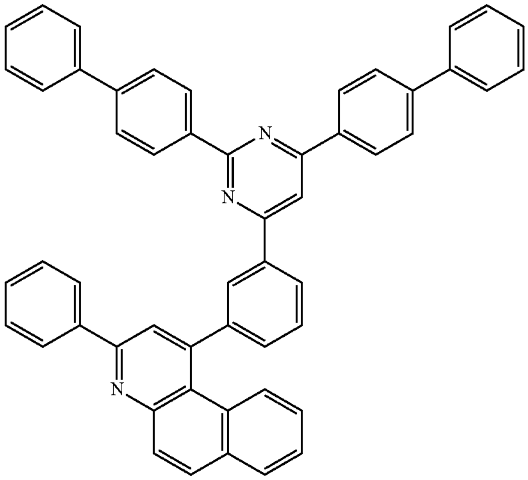
416
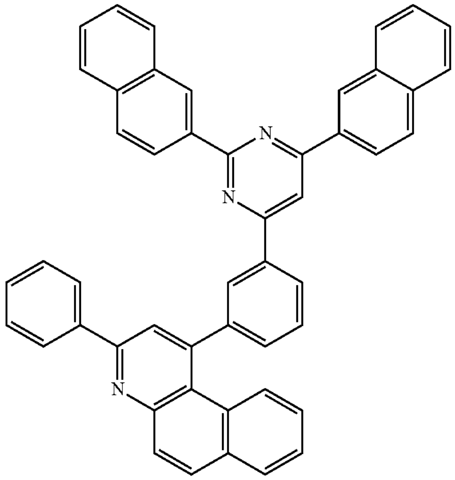
417
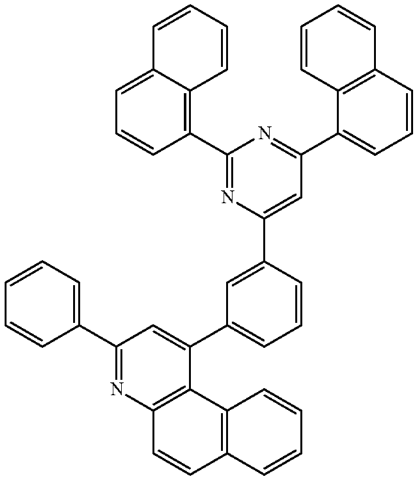
418
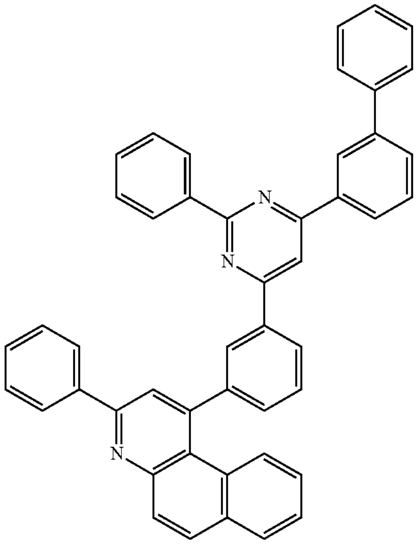

-continued
419
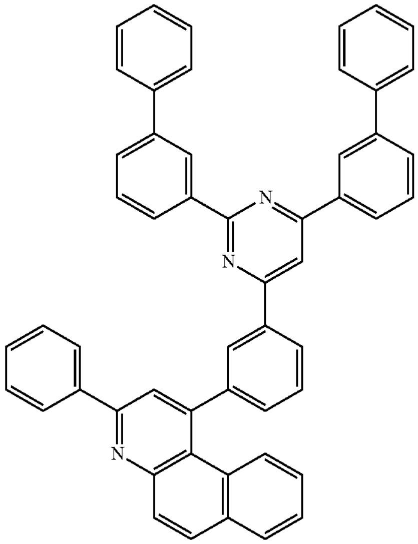
420
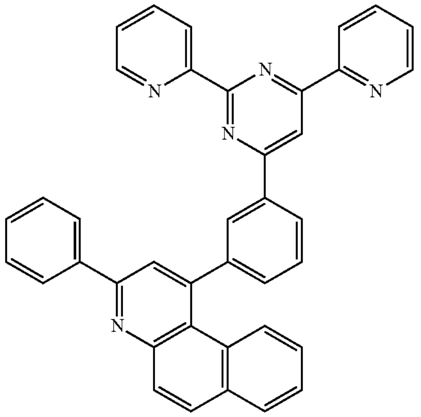
421
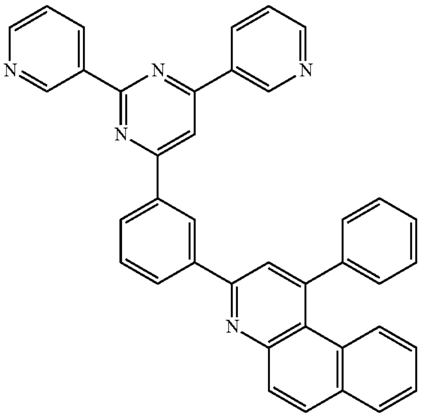
-continued
422
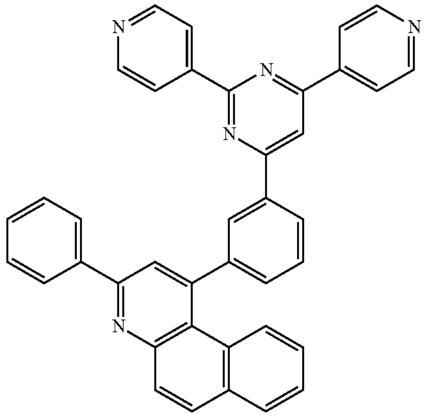
423
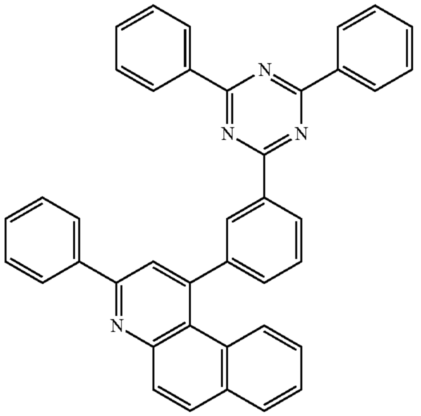
424
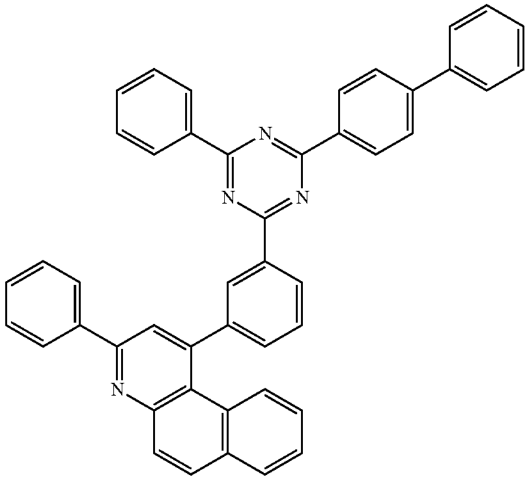

-continued
425
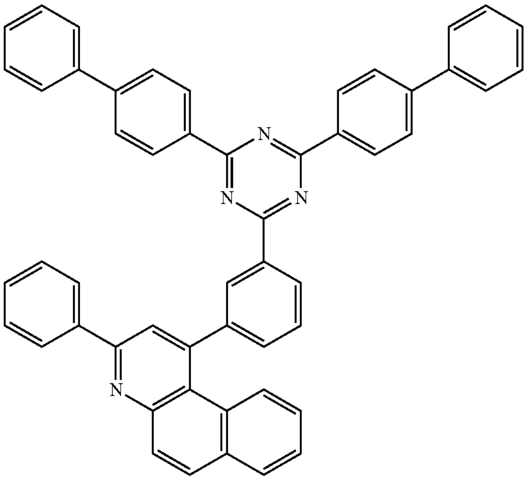
426
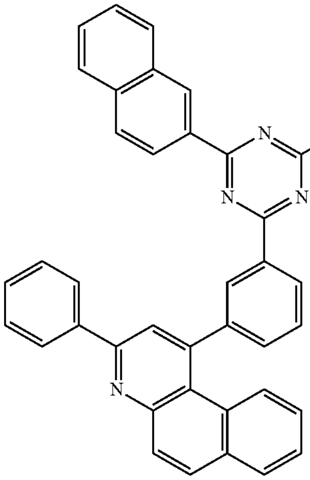
427
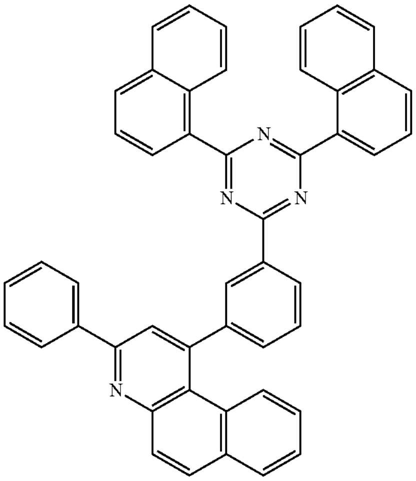
-continued
428
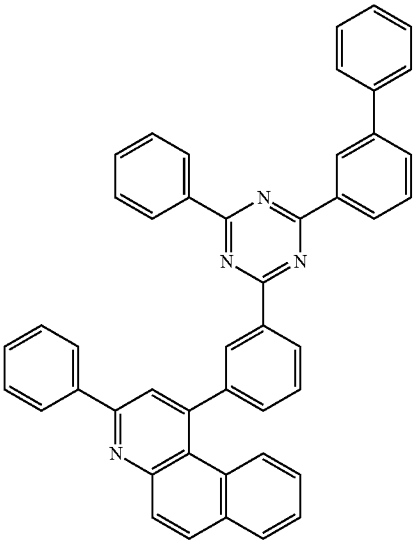
429
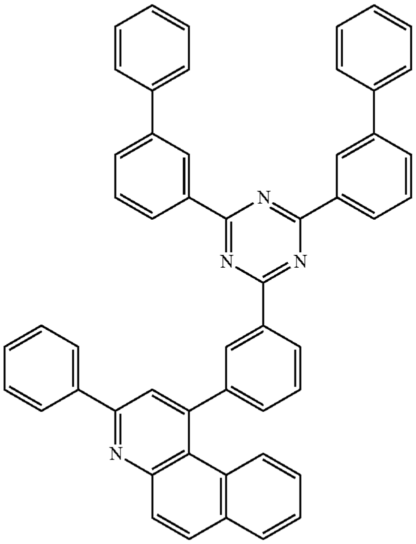
430
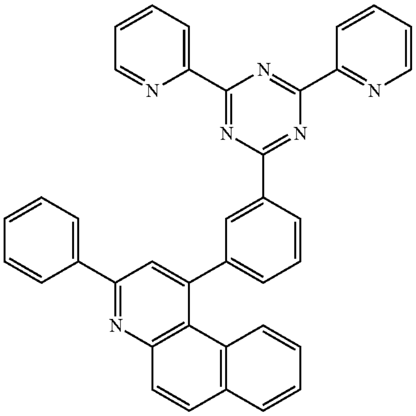

-continued
431
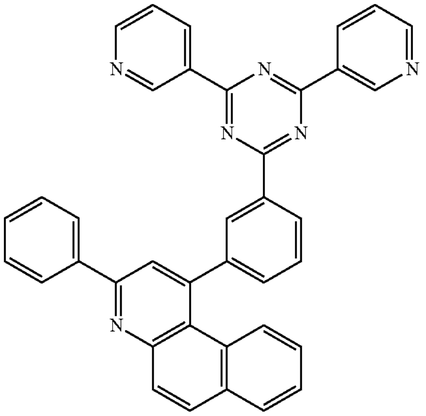
432
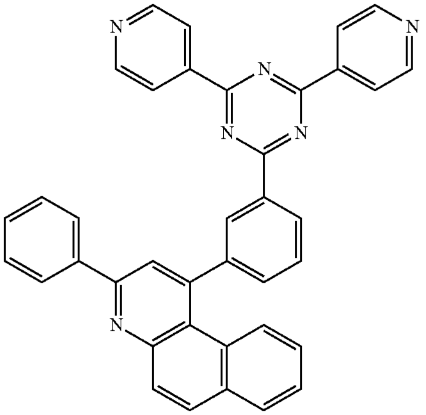
433
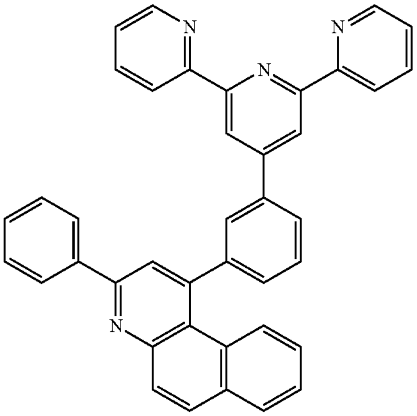
-continued
434
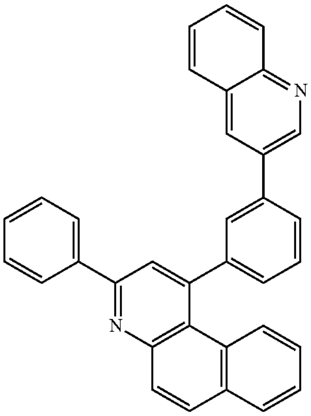
435
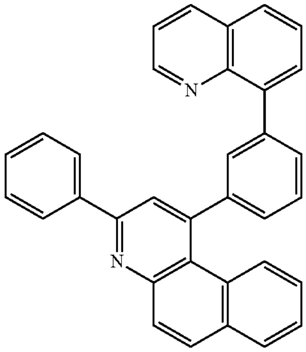
436
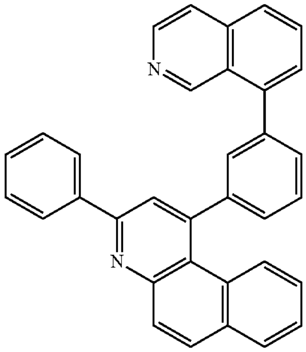
437
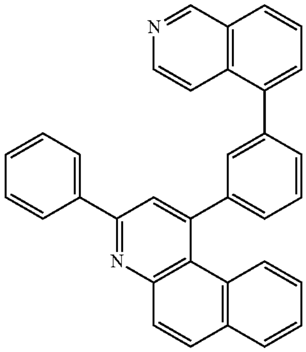

-continued
438
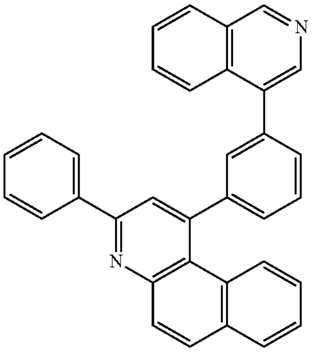
439
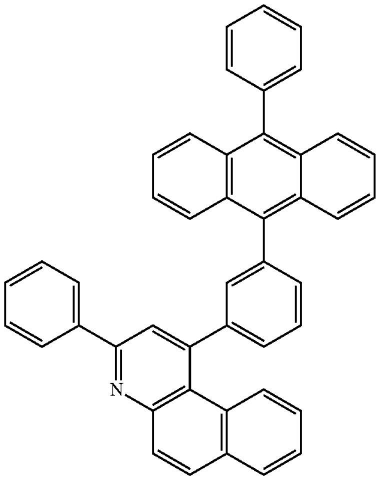
440
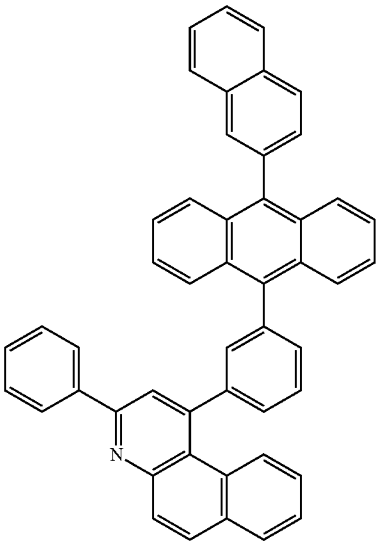
-continued
441
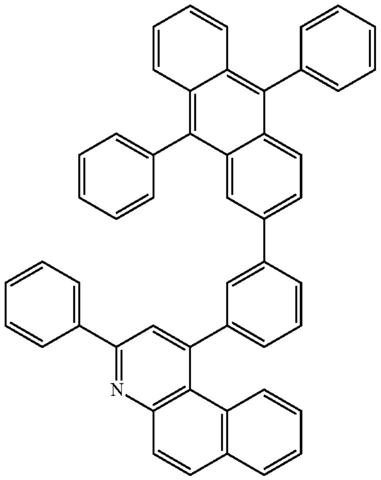
442
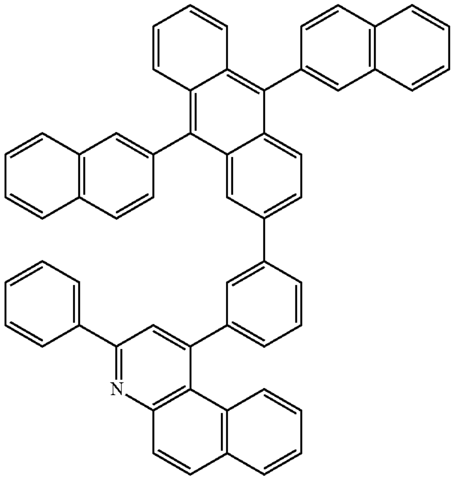
443
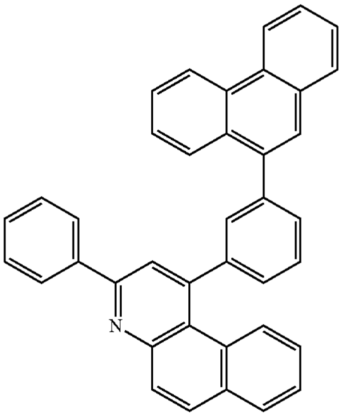

-continued
444
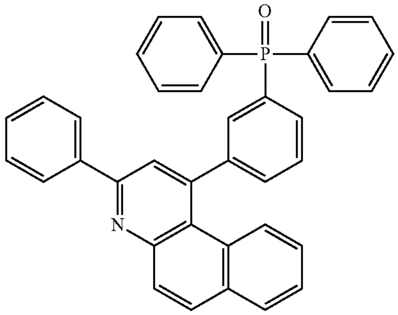
445
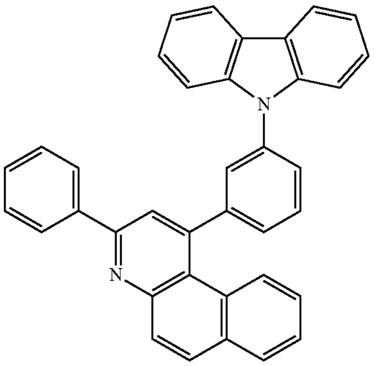
446
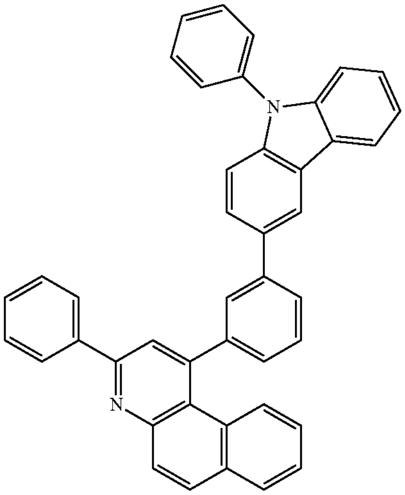
447
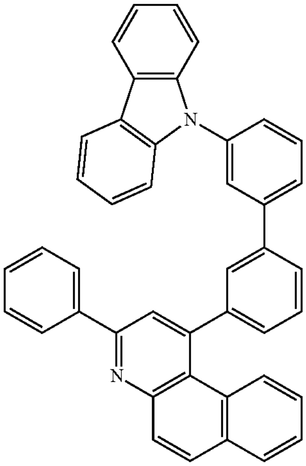
-continued
448
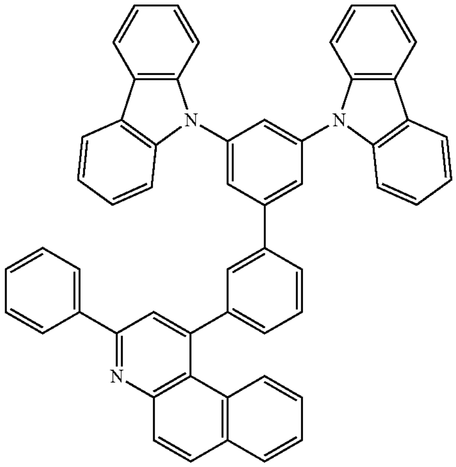
449
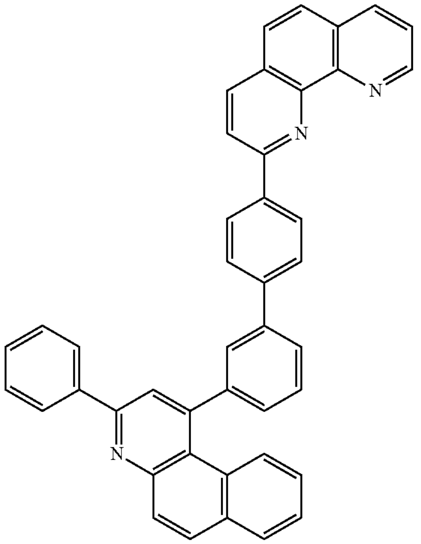
450
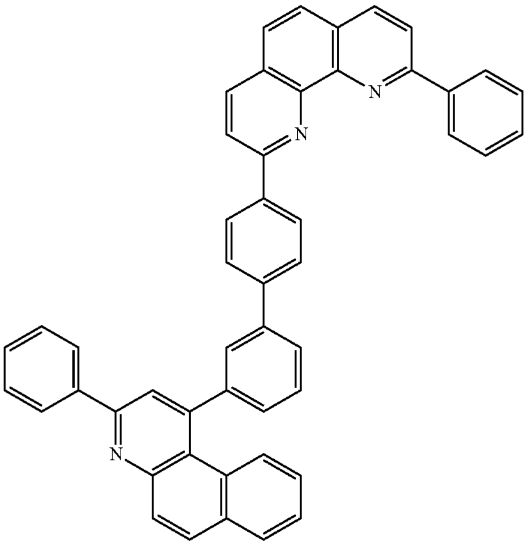

-continued
451
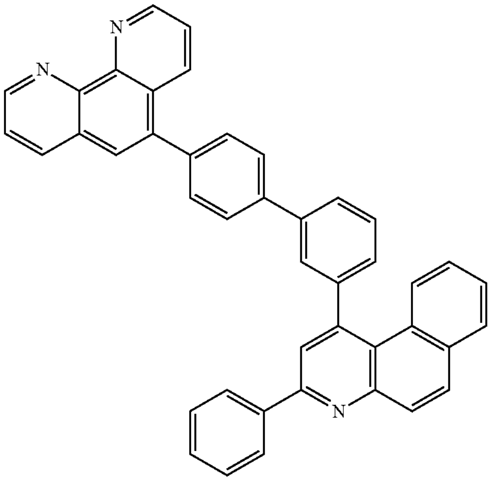
452
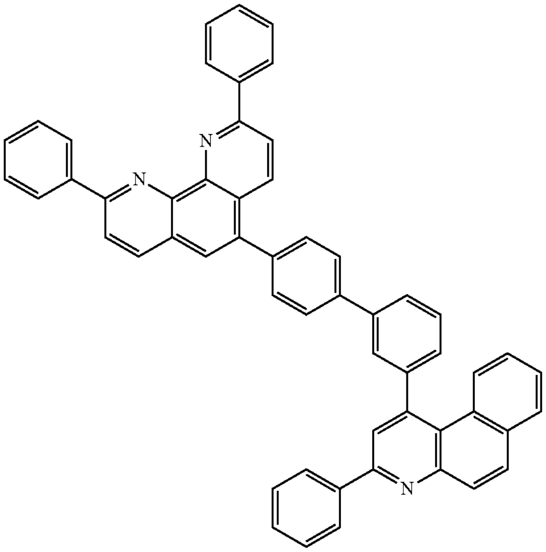
453
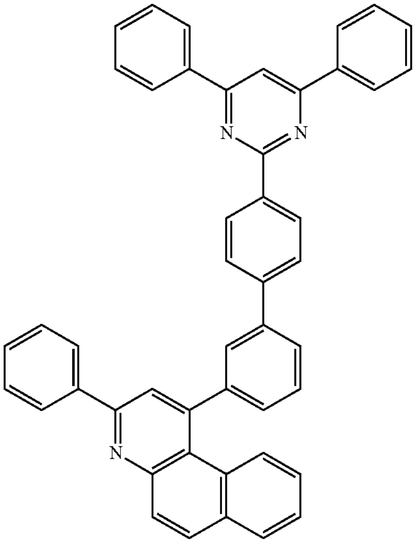
-continued
454
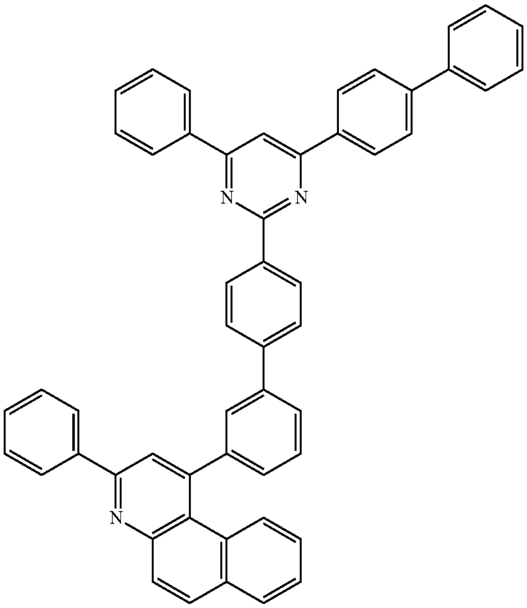
455
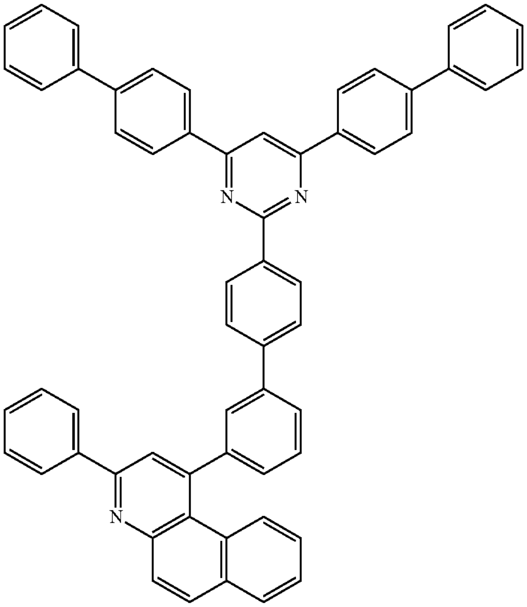

-continued
456
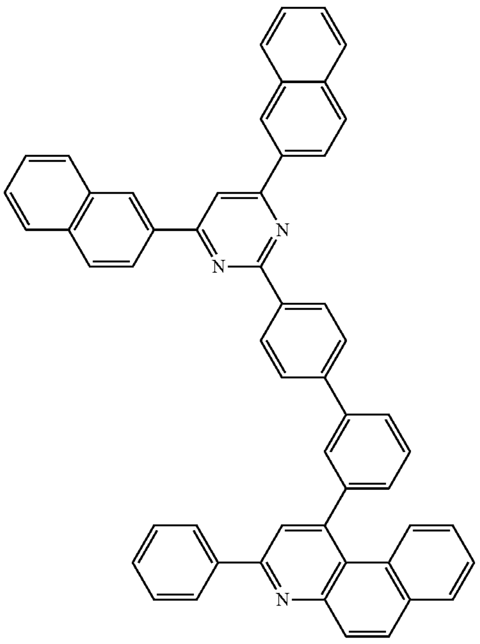
457
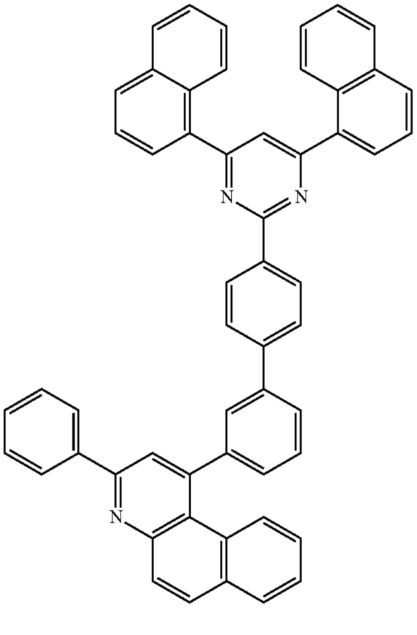
-continued
458
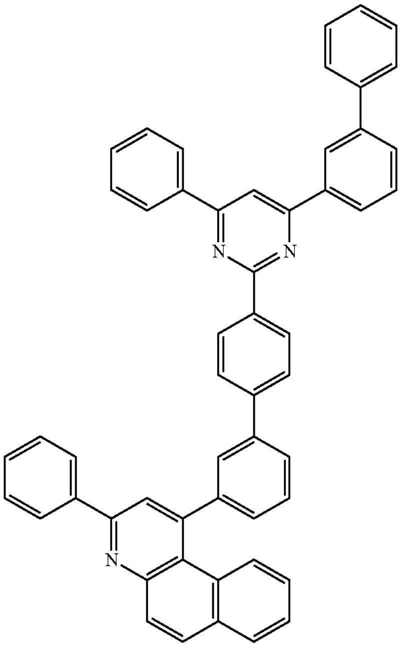
459
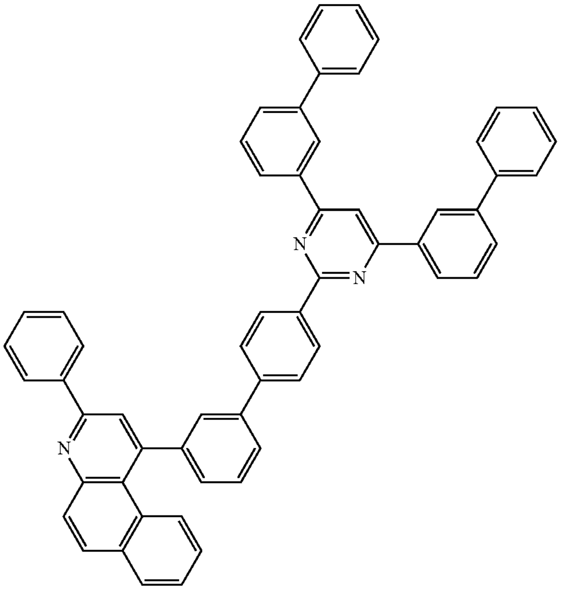

-continued
460
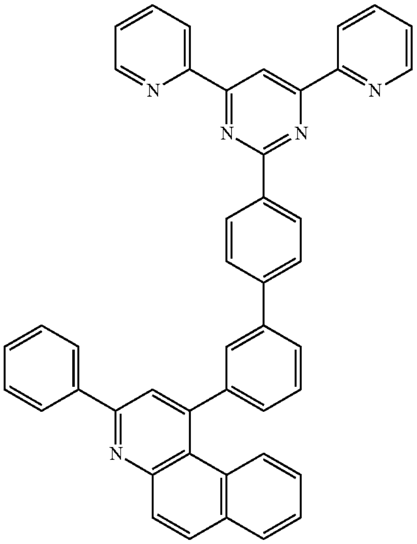
461
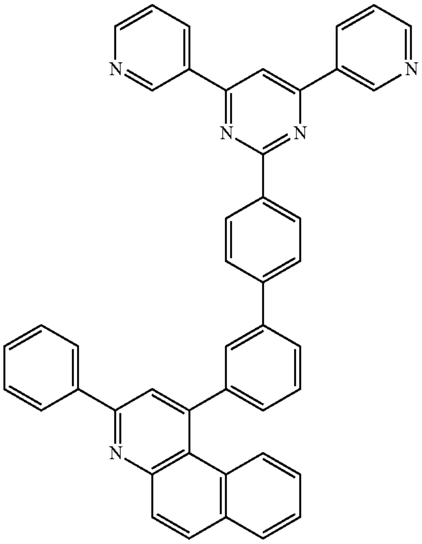
462
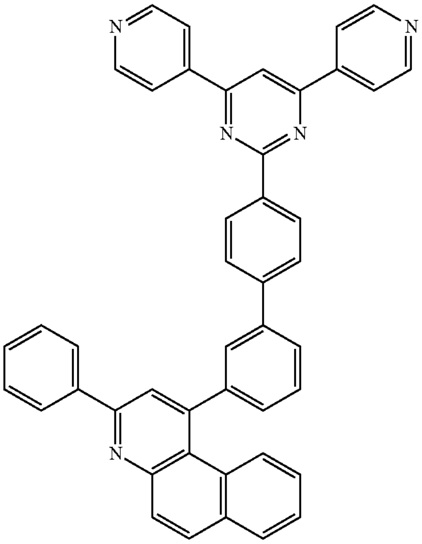
-continued
463
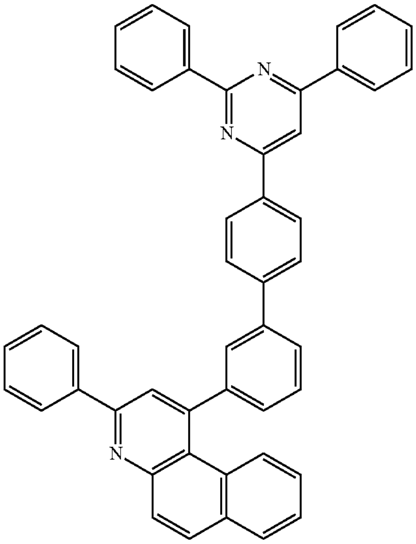
464
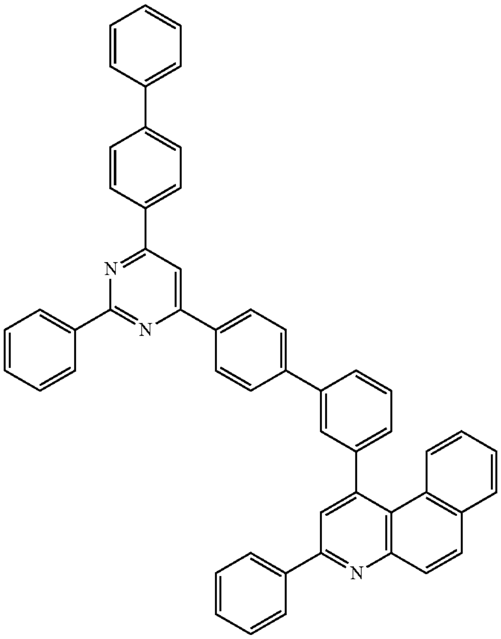

-continued
465
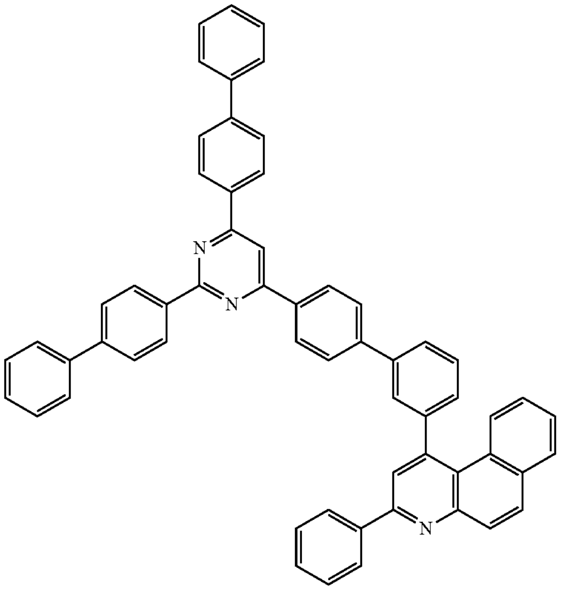
466
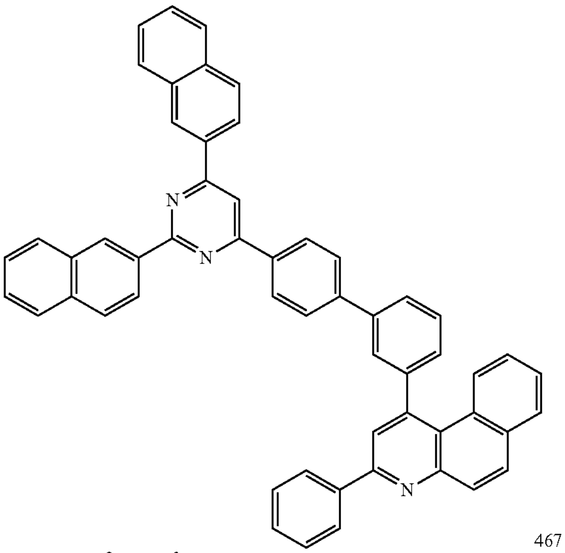
467
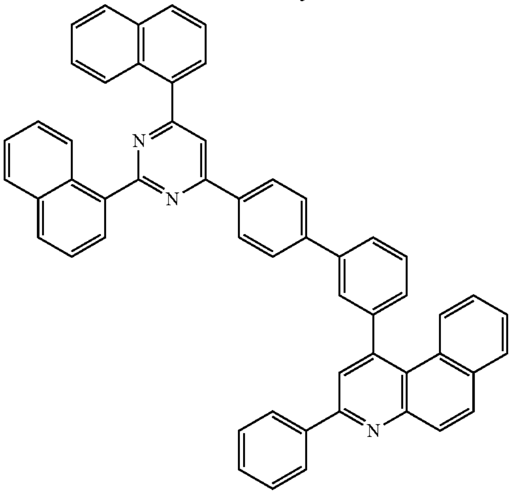
-continued
468
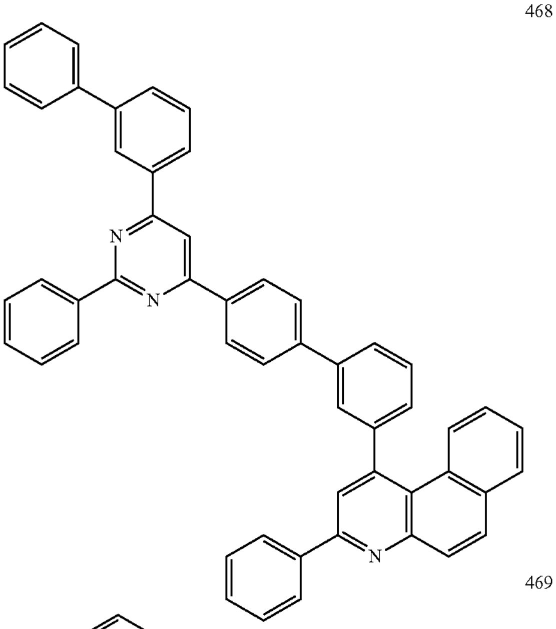
469
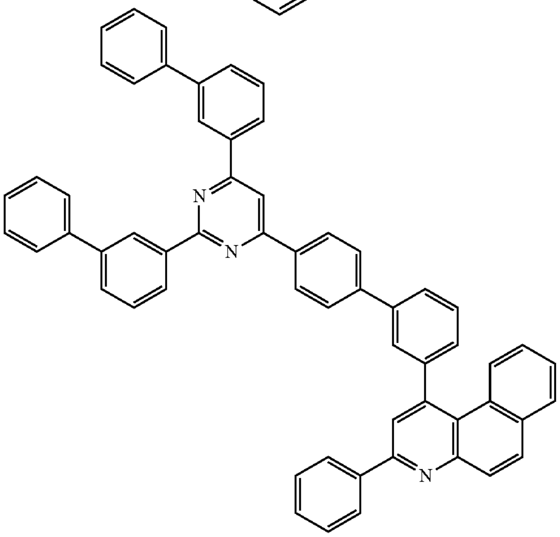
470
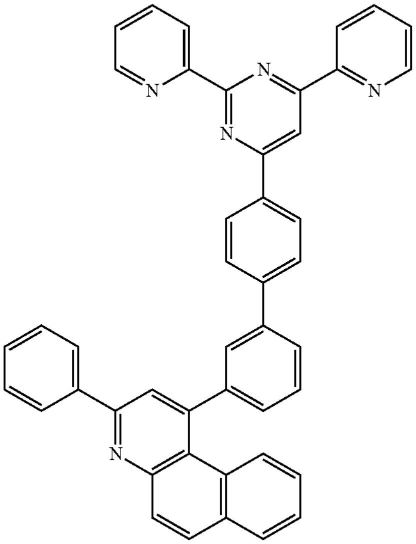

-continued
471
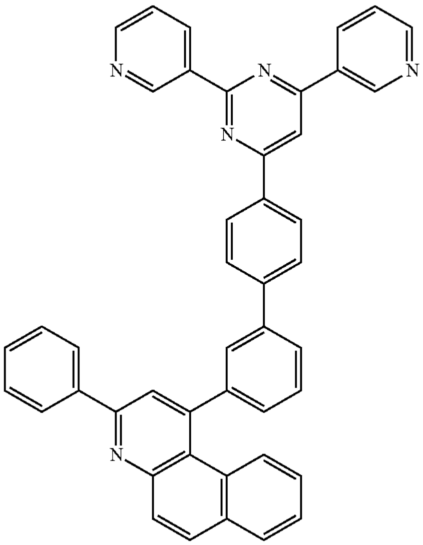
472
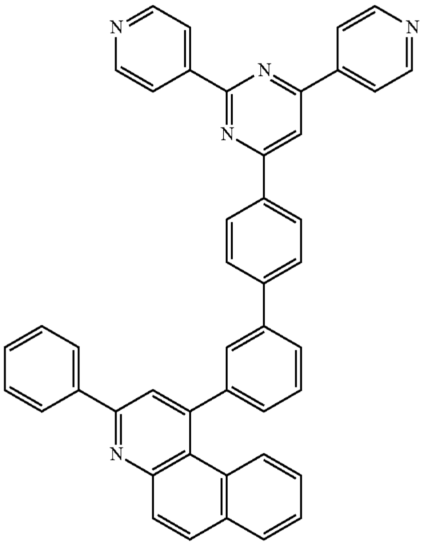
473
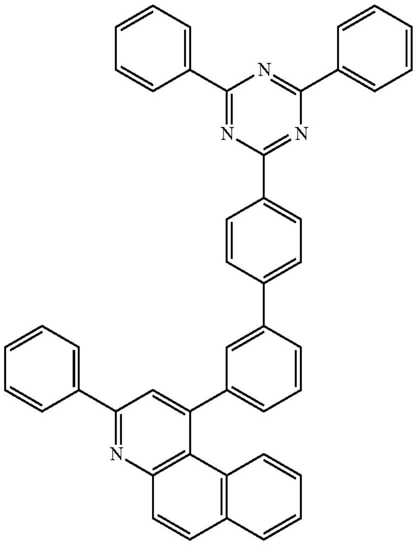
-continued
474
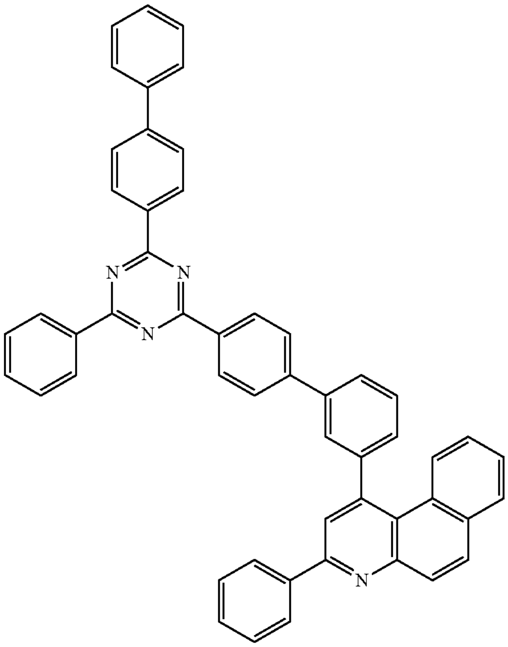
475
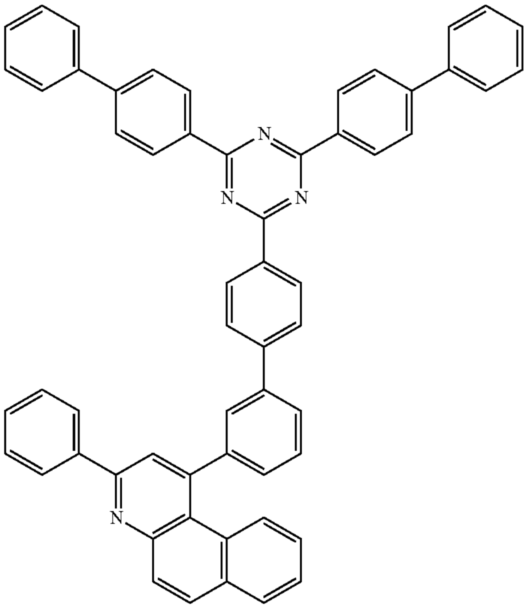

-continued
476
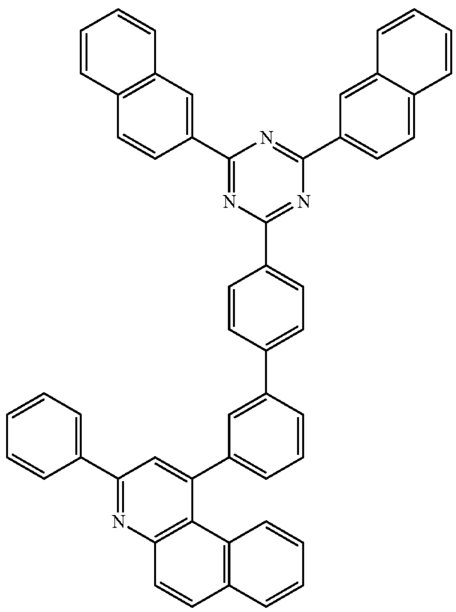
477
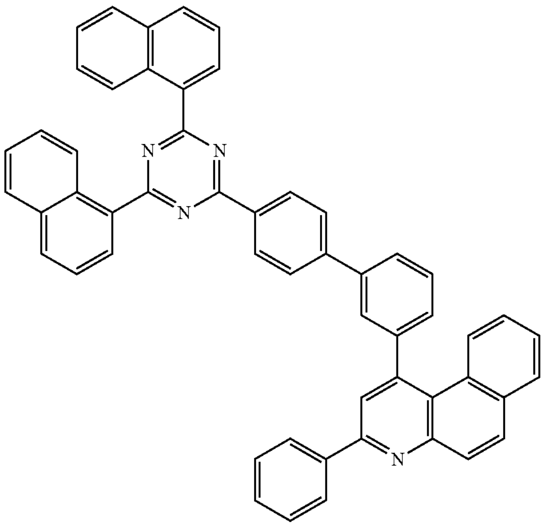
-continued
478
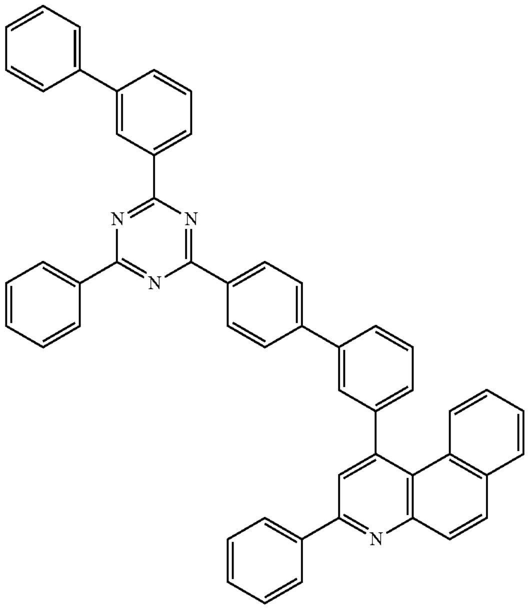
479
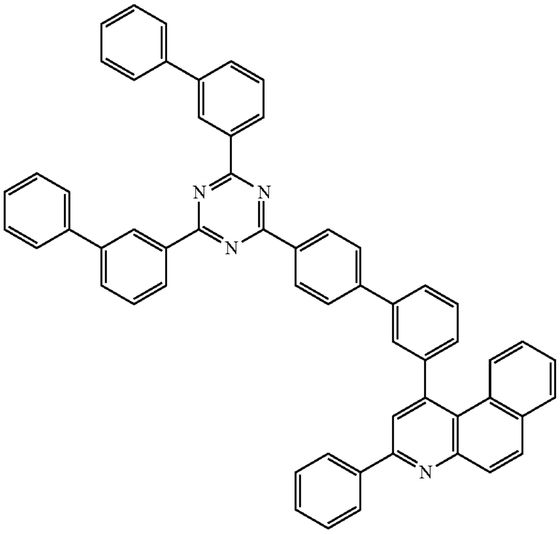

-continued
480
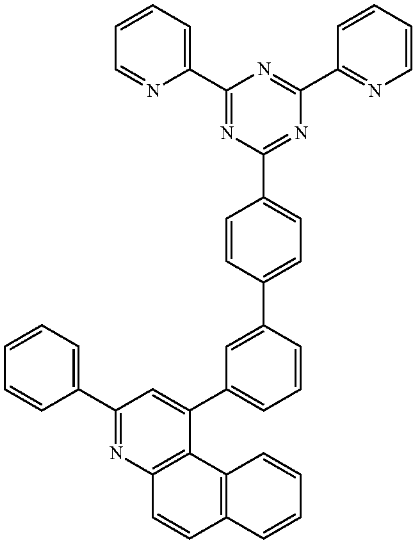
481
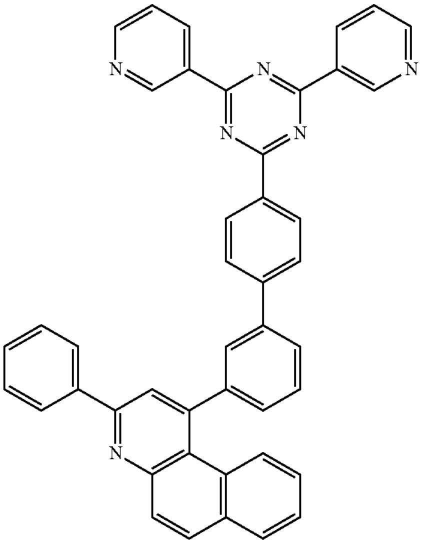
482
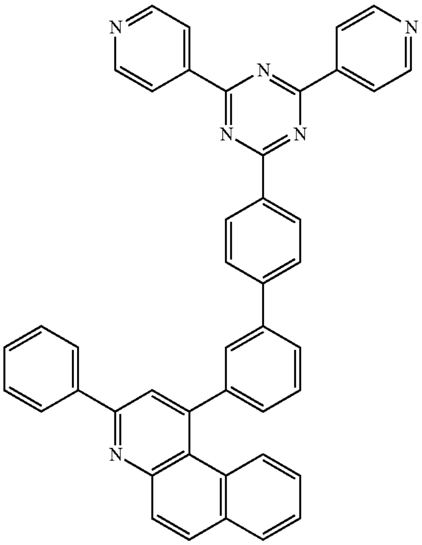
-continued
483
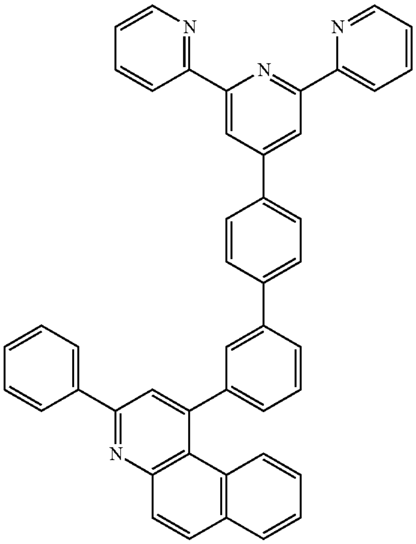
484
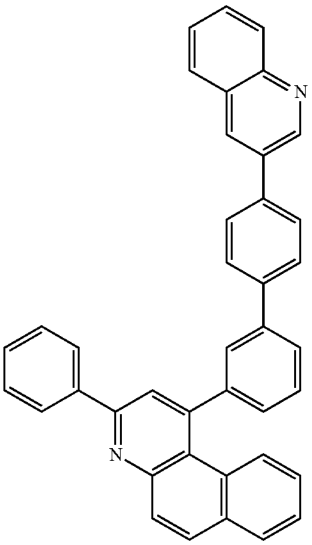
485
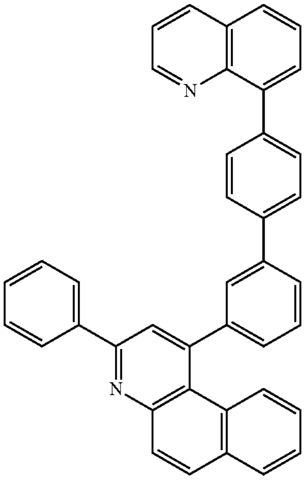

-continued
486
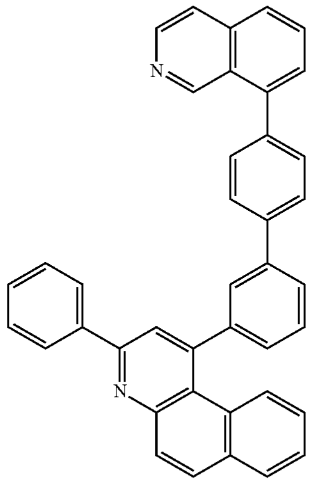
487
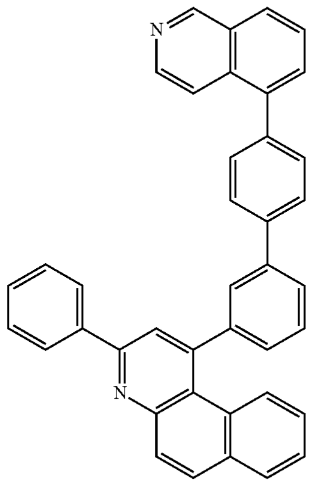
488
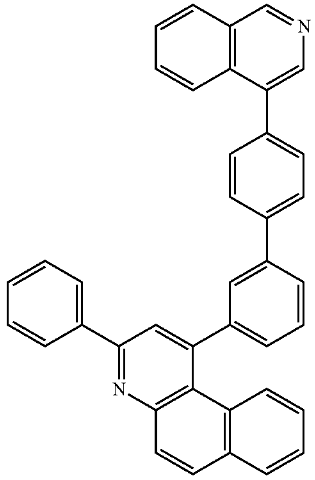
-continued
489
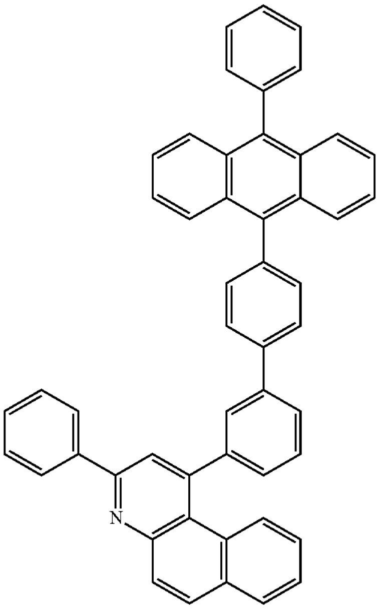
490
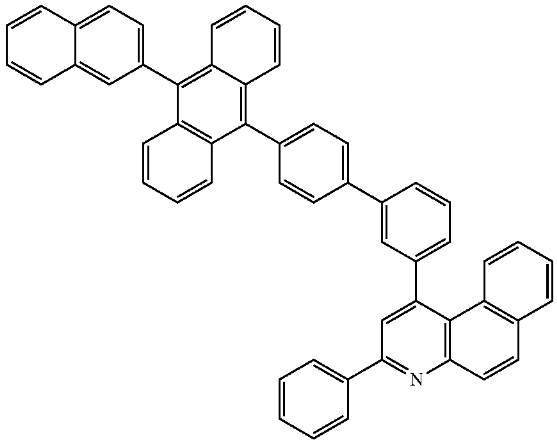
491
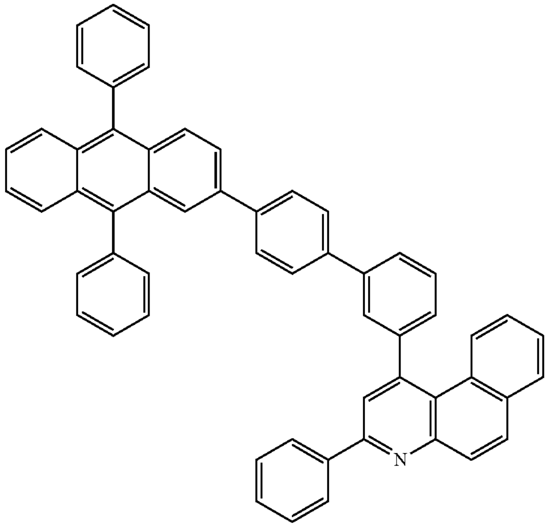

-continued
492
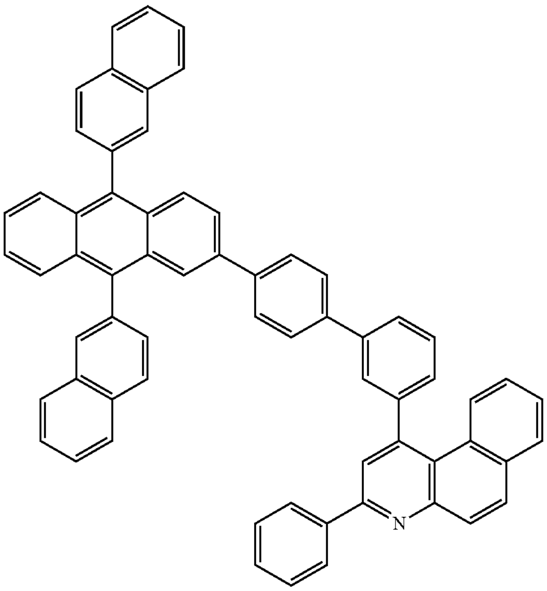
493
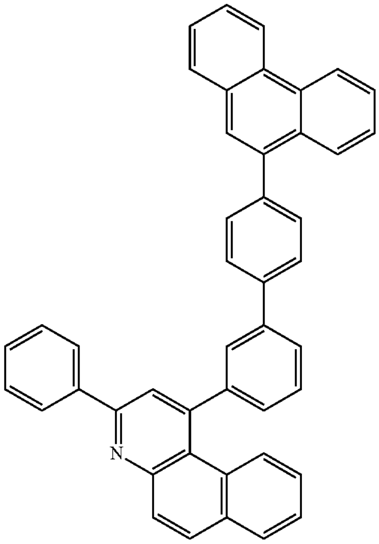
494
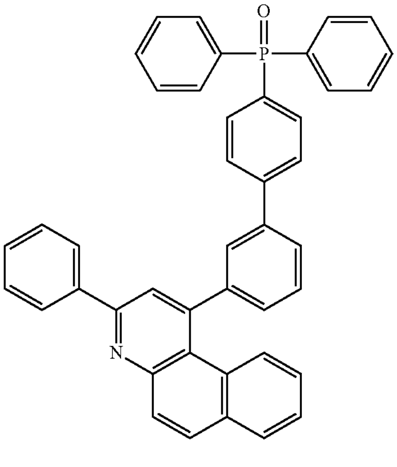
-continued
495
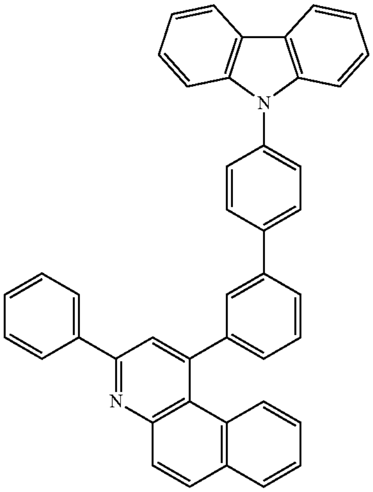
496
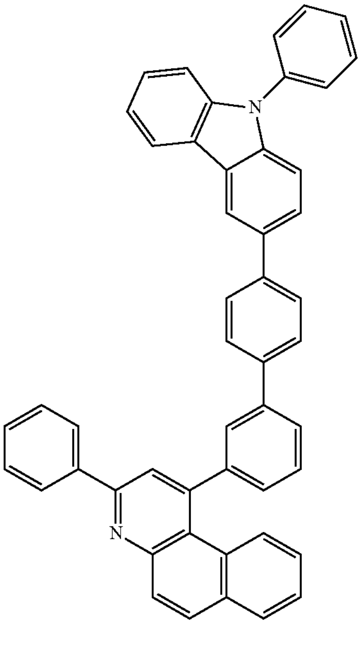

497
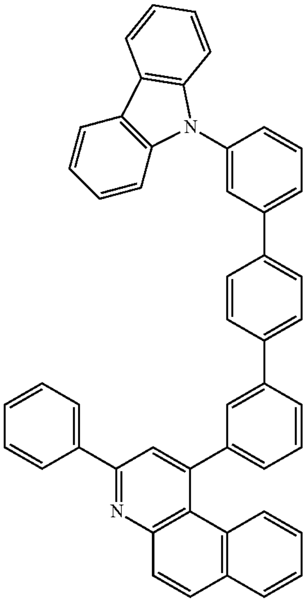
498
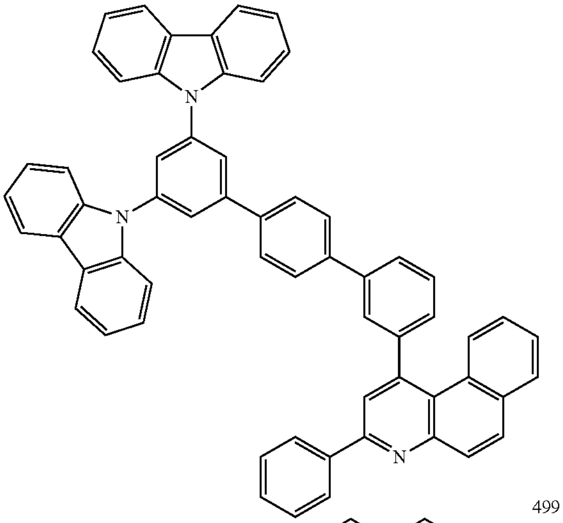
499
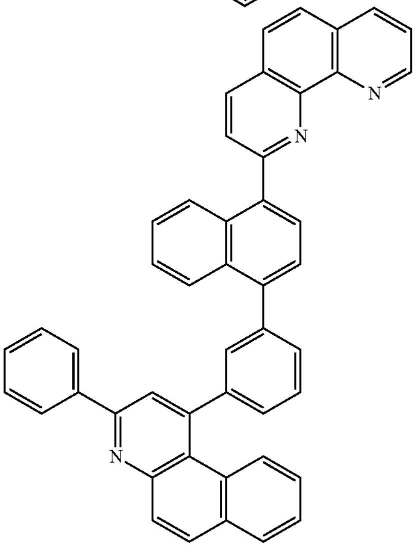
500
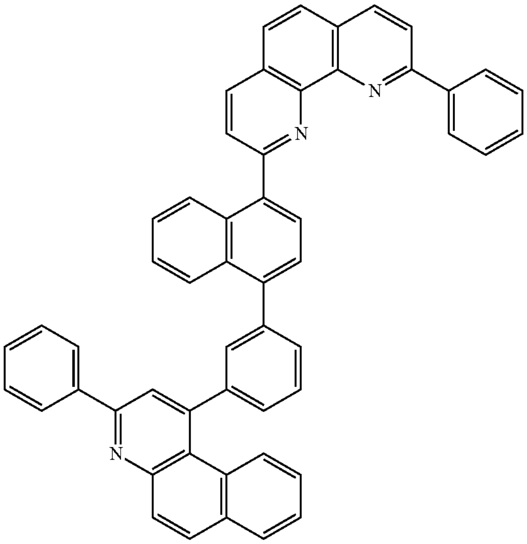
501
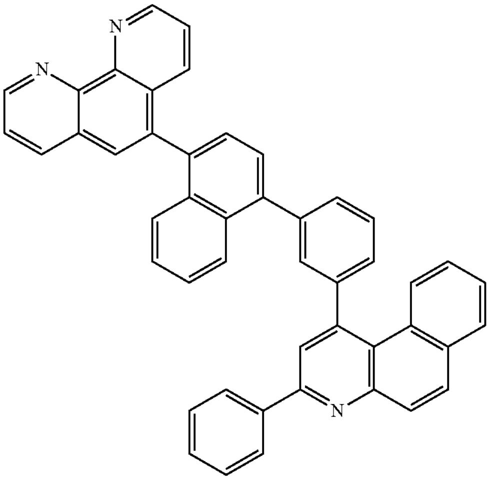
502
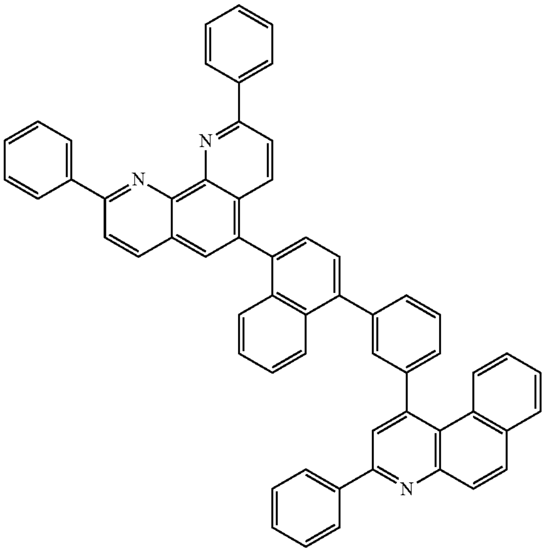

-continued
503
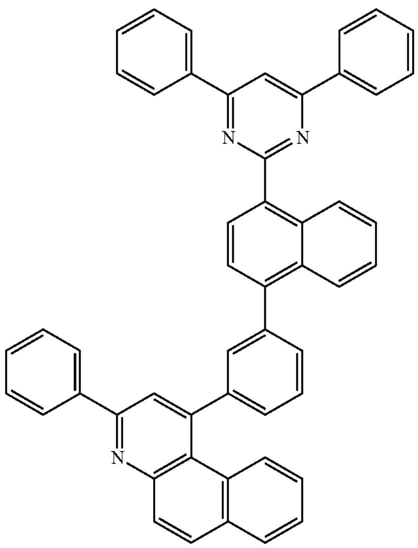
504
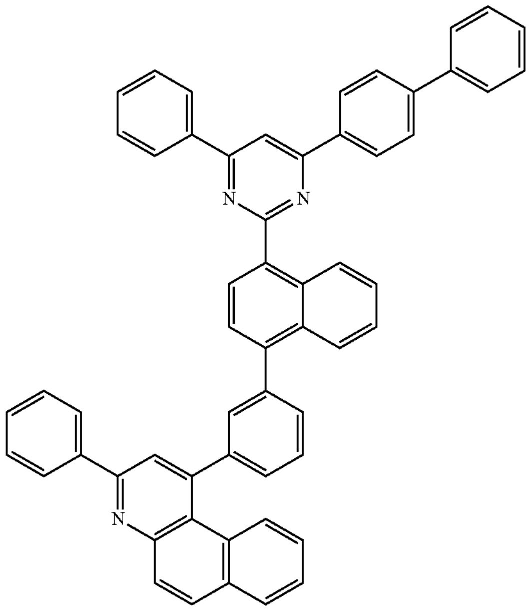
-continued
505
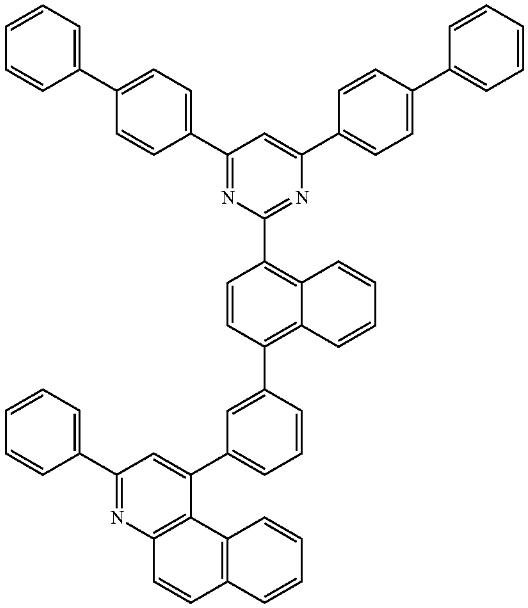
506
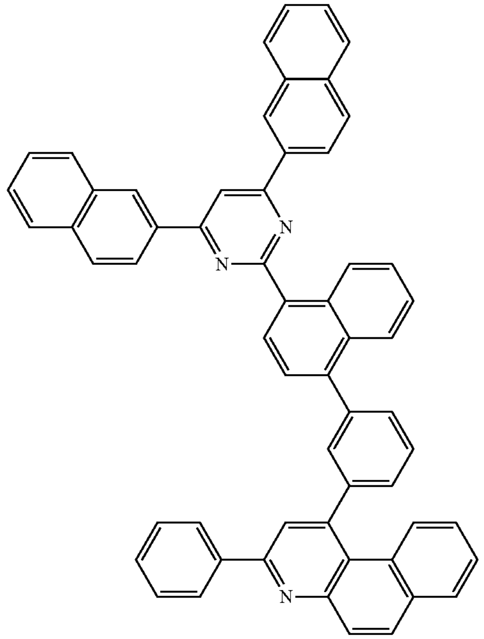

-continued
507
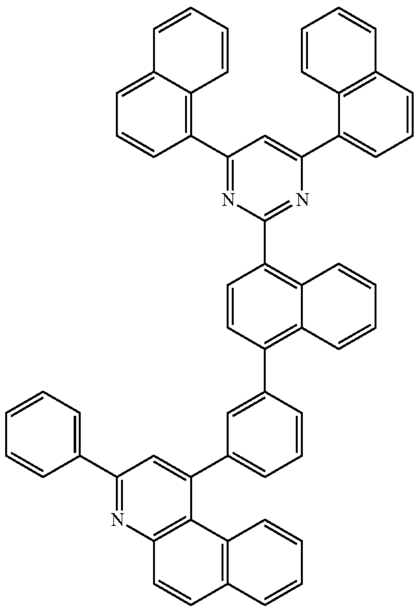
508
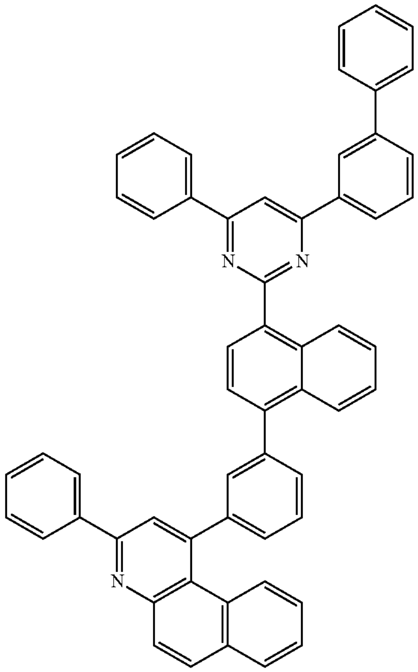
-continued
509
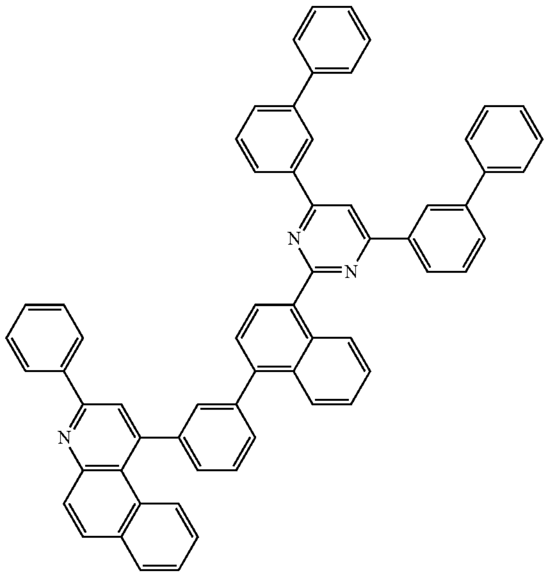
510
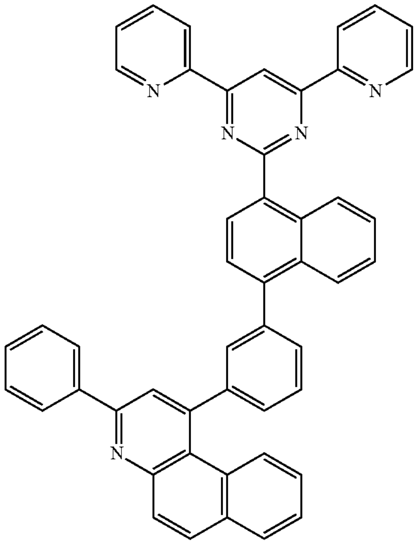

-continued
511
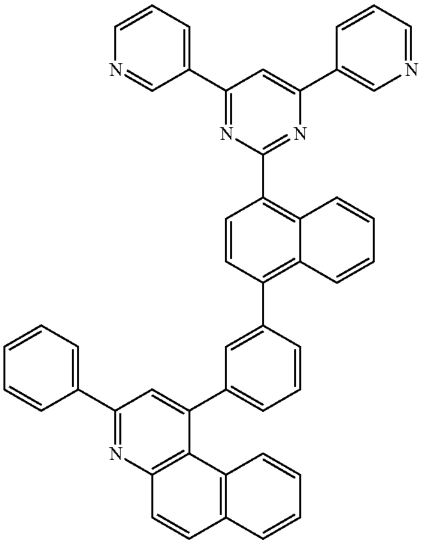
512
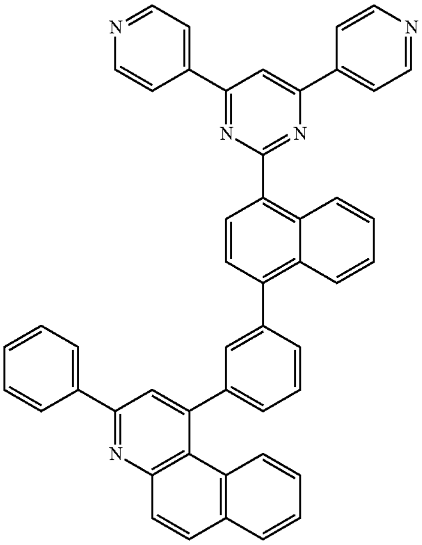
513
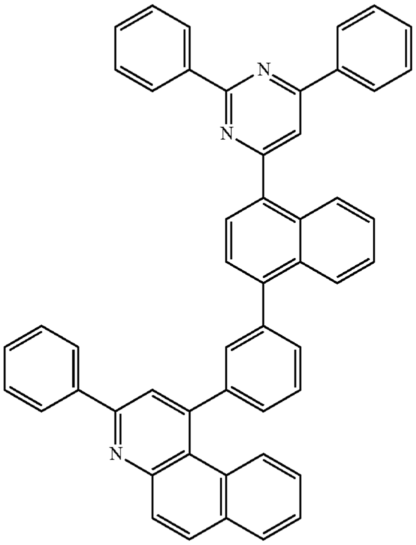
-continued
514
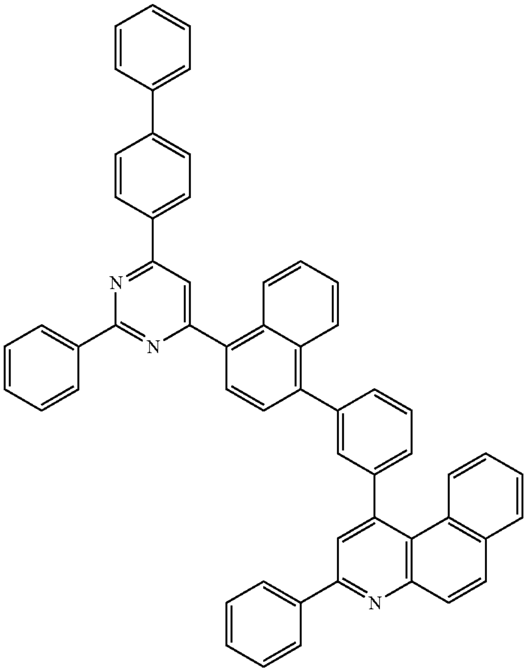
515
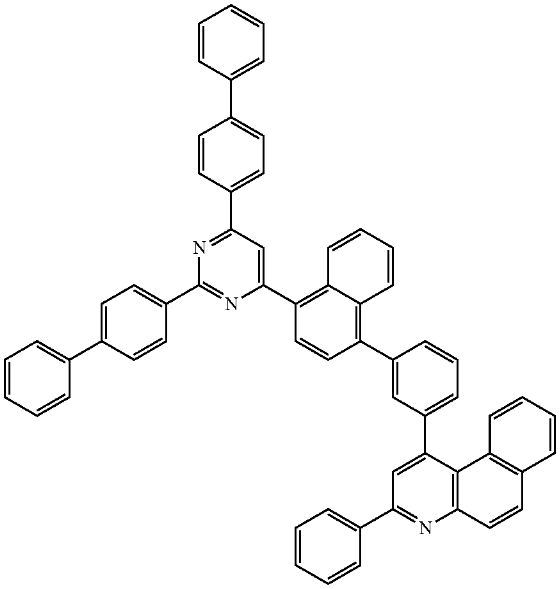

-continued
516
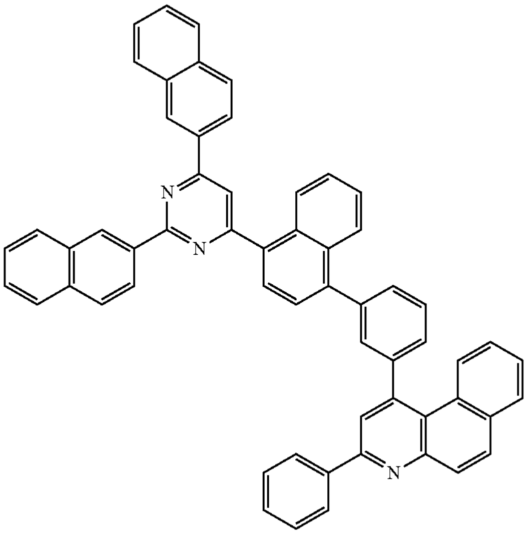
517
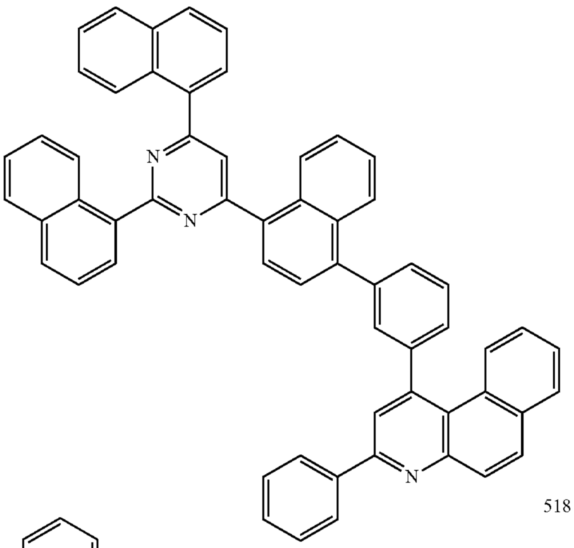
518
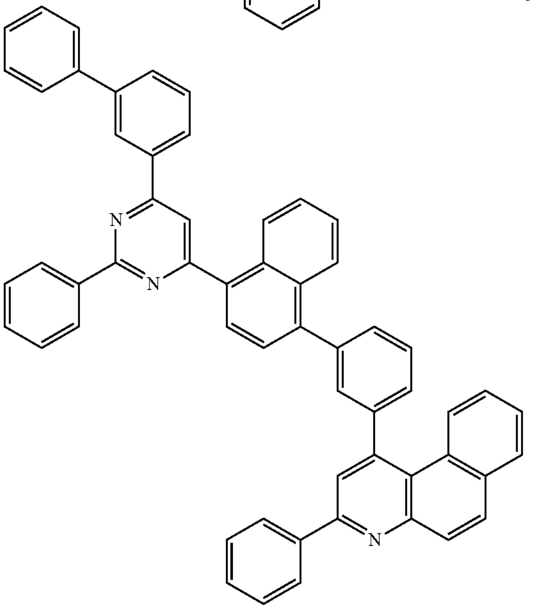
-continued
519
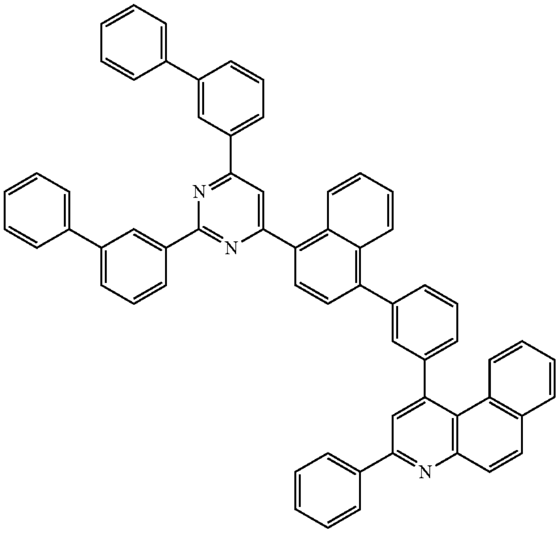
520
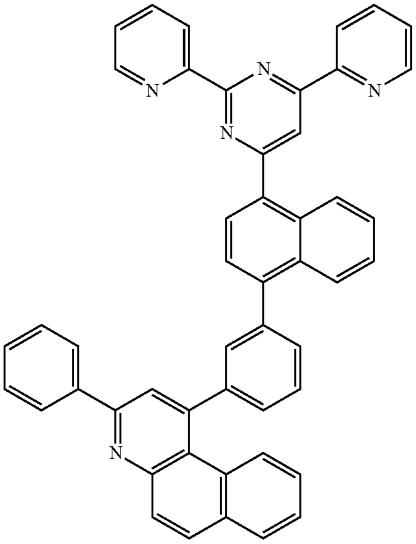
521
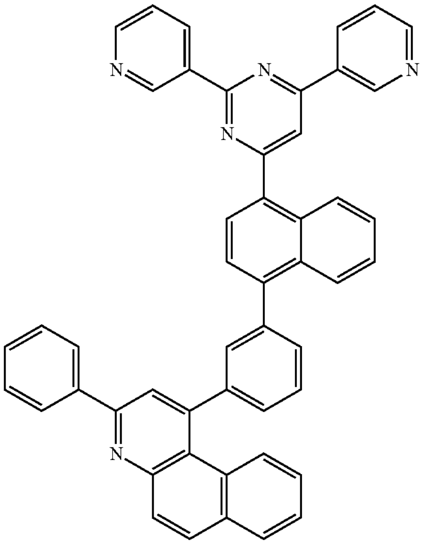

-continued
522
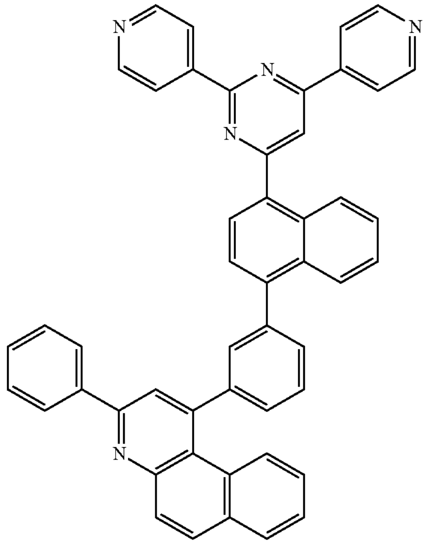
523
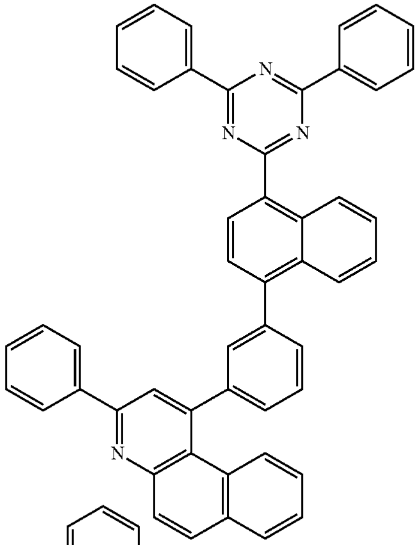
524
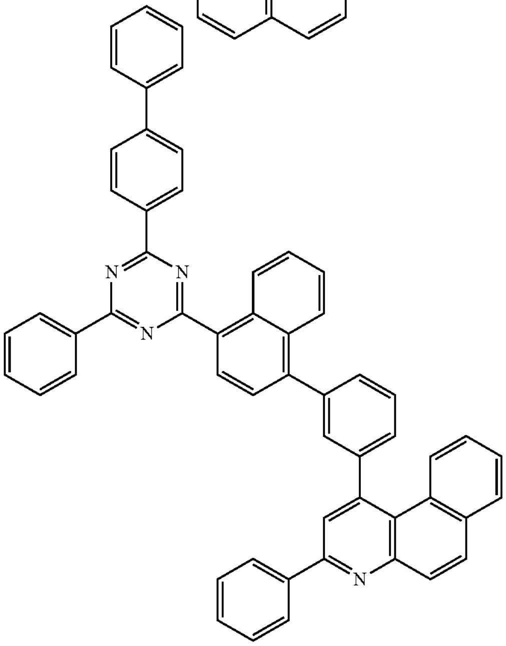
-continued
525
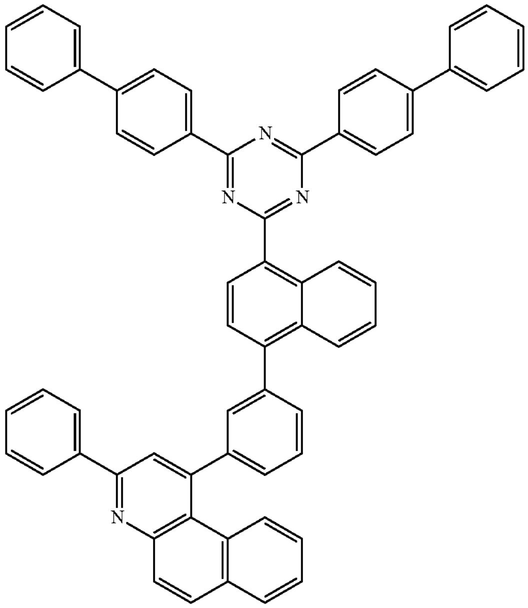
526
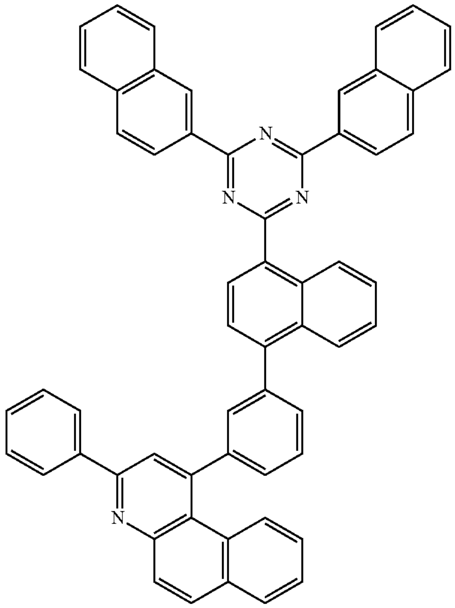

-continued
527
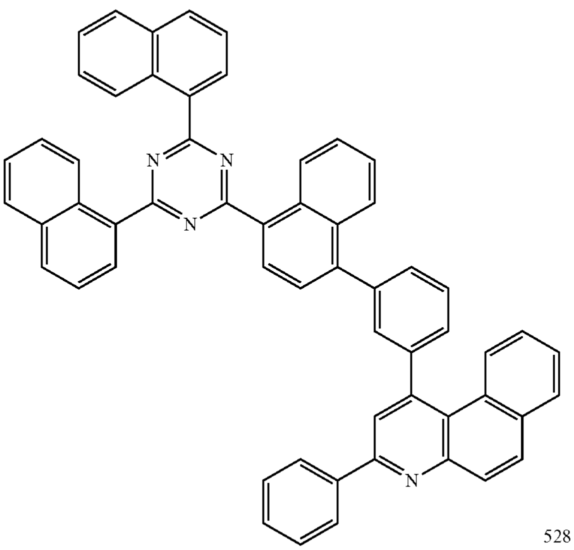
528
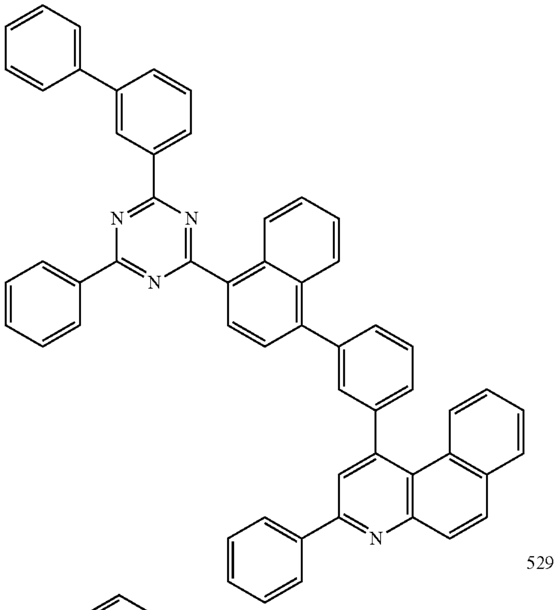
529
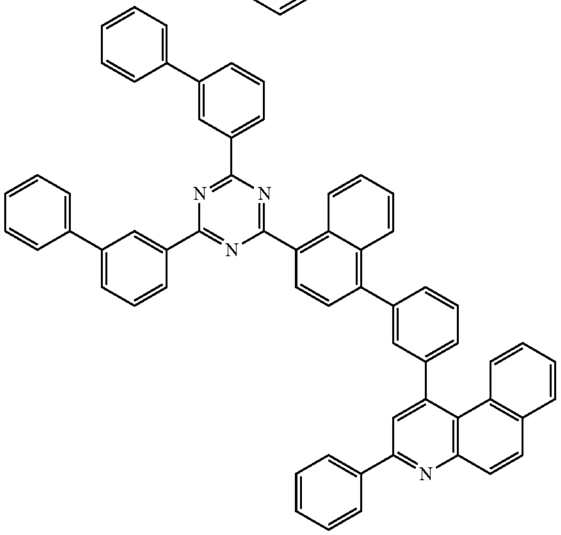
-continued
530
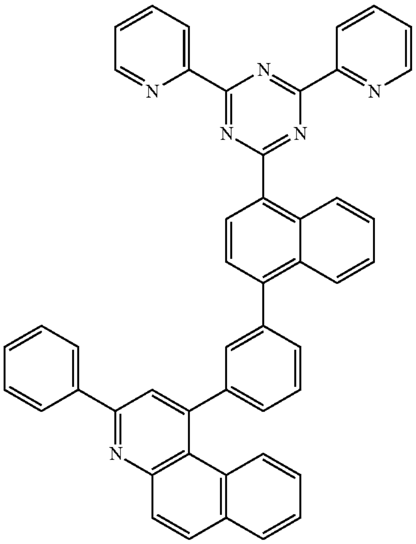
531
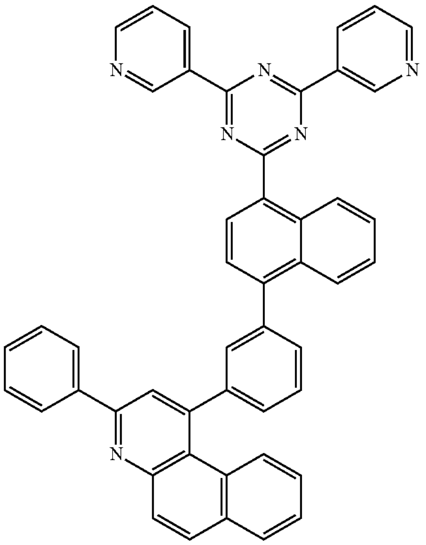
532
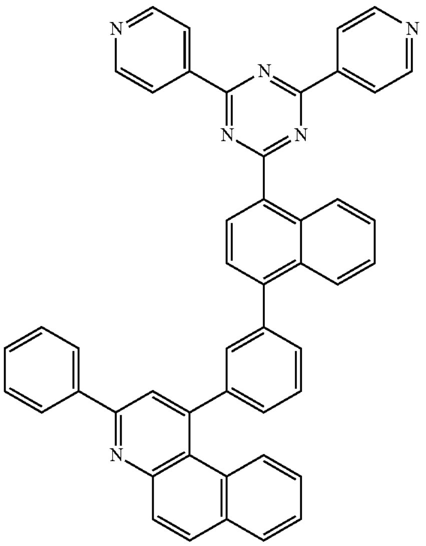

533
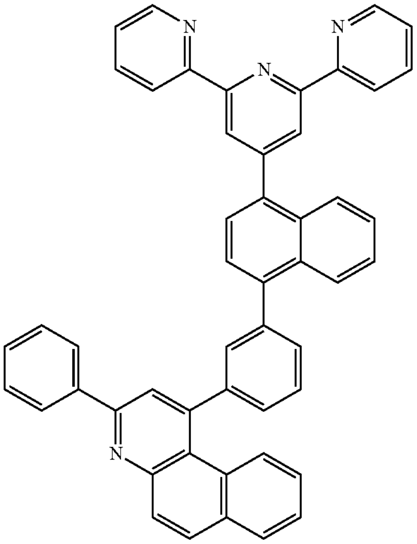
534
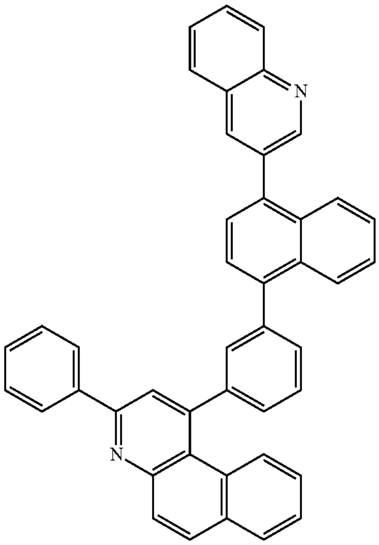
535
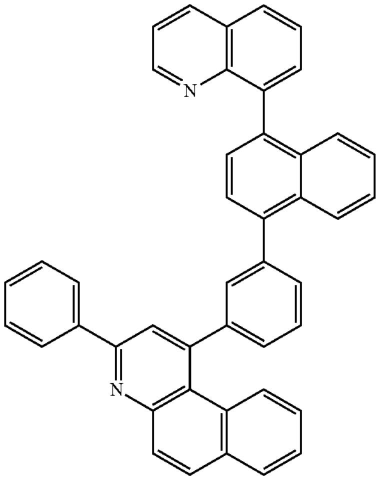
536
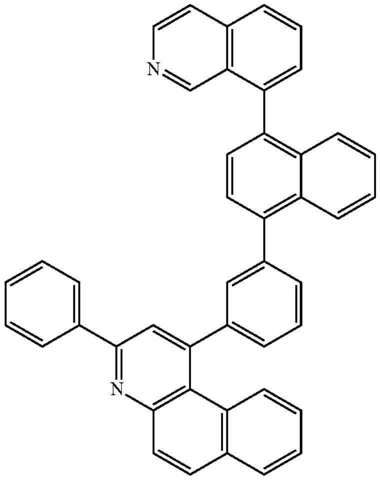
537
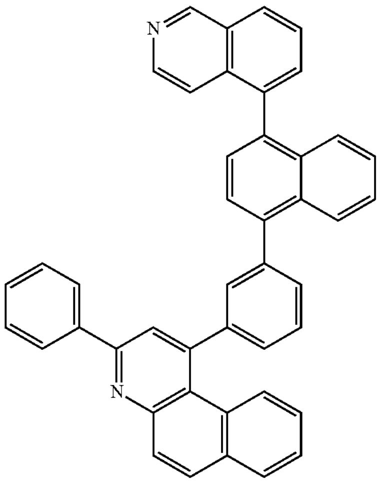
538
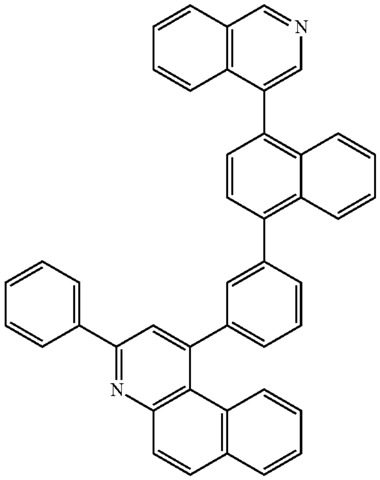

-continued
539
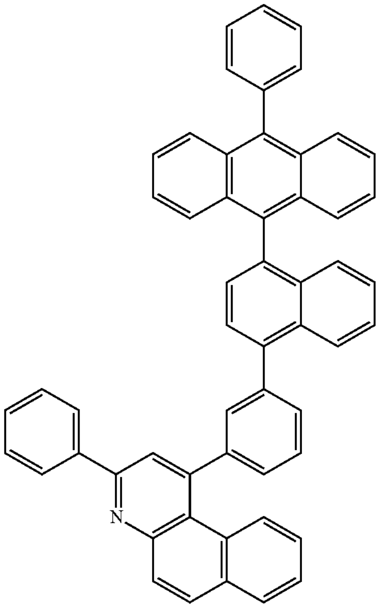
540
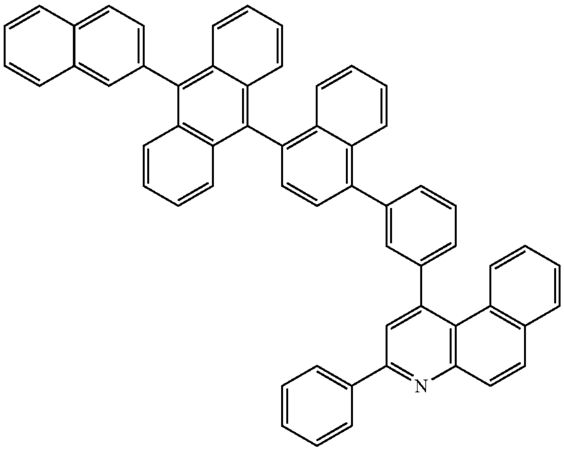
541
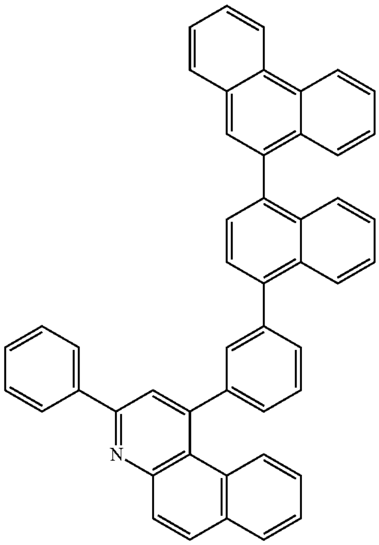
-continued
542
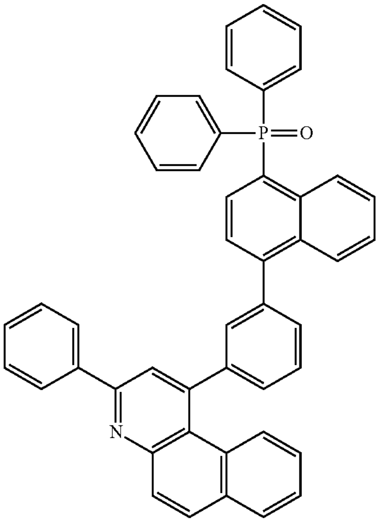
543
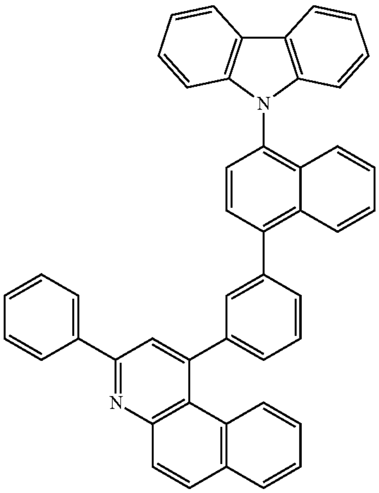
544
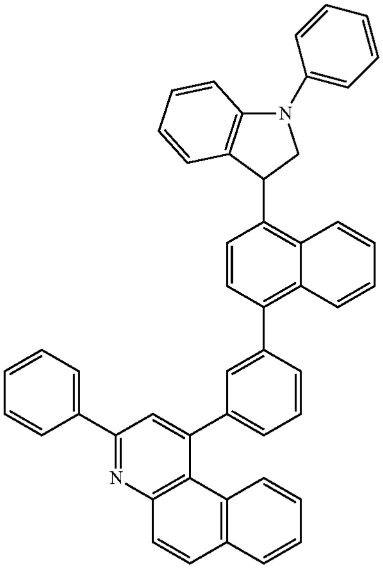

-continued
545
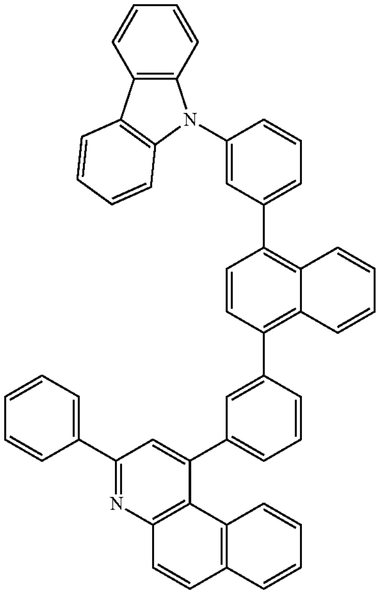
546
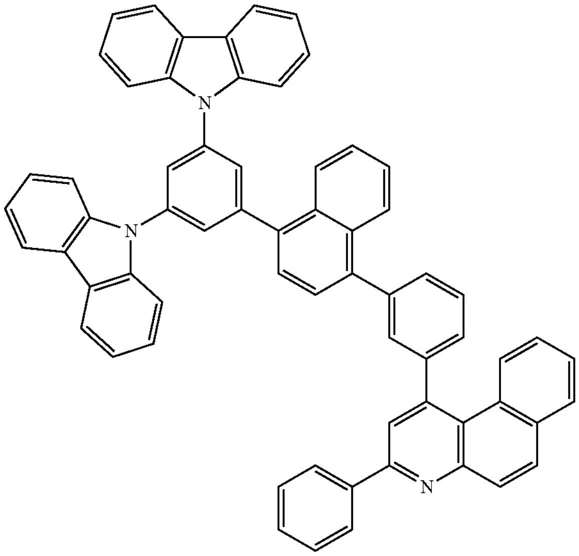
547
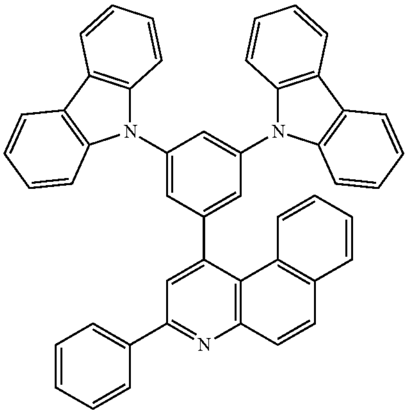
-continued
548
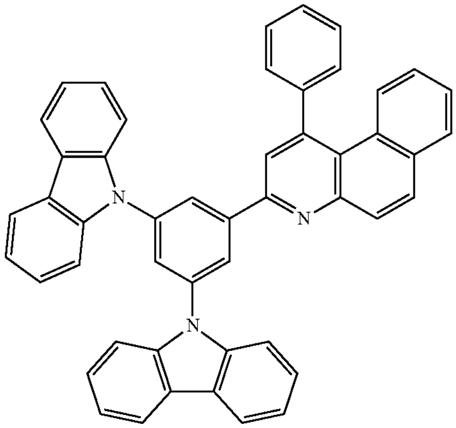
549
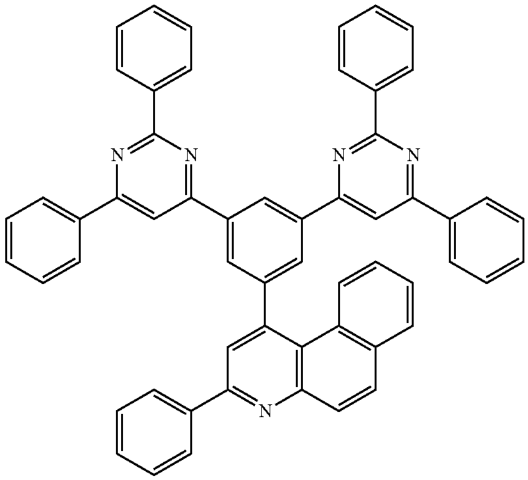
550
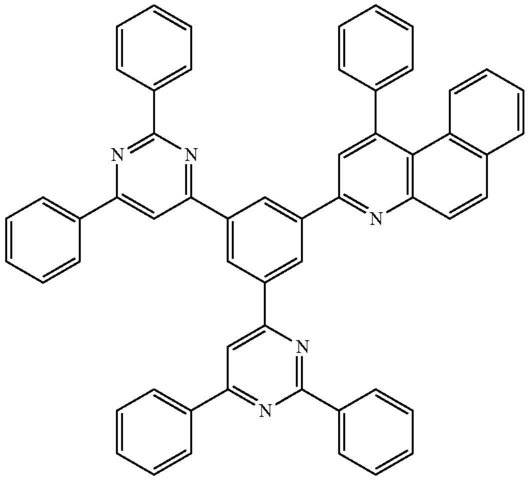

-continued
551
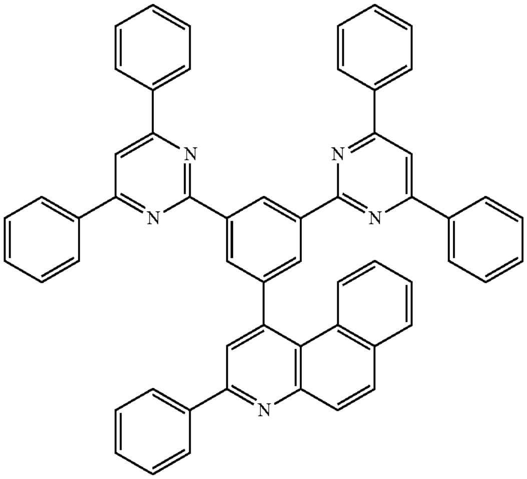
552
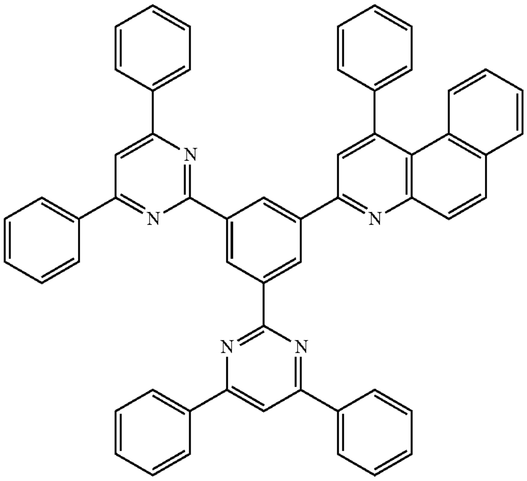
553
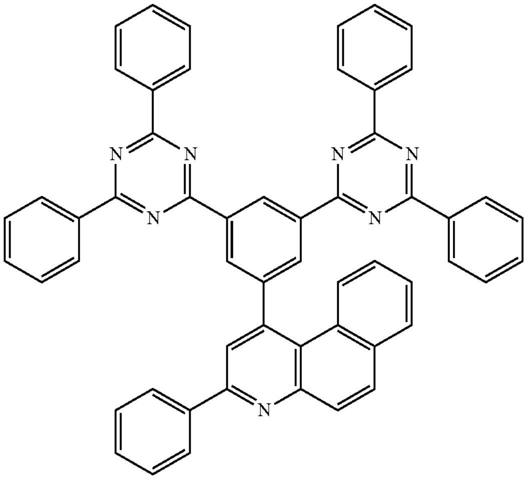
-continued
554
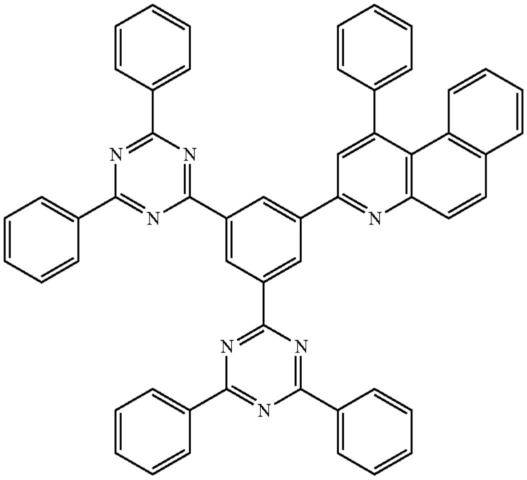
555
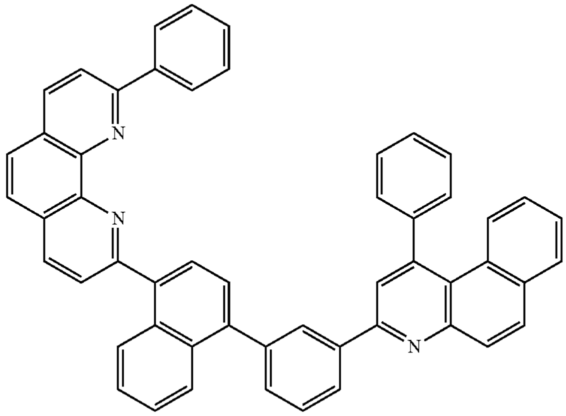
556
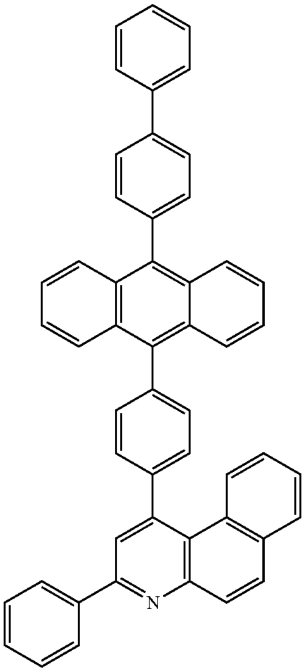

-continued
557
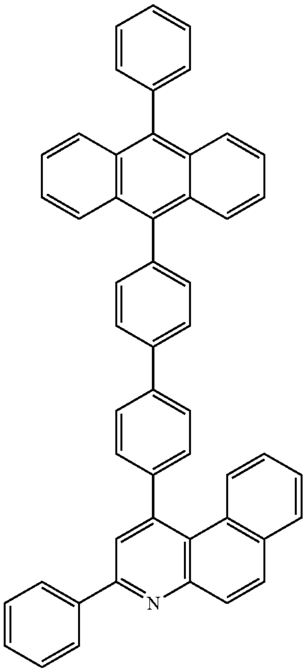
558
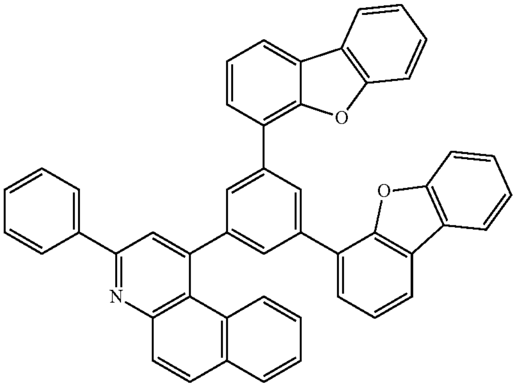
559
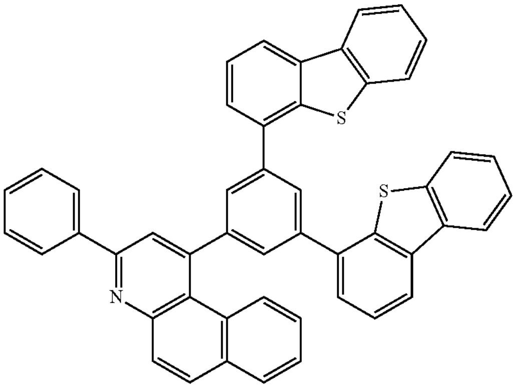
-continued
560
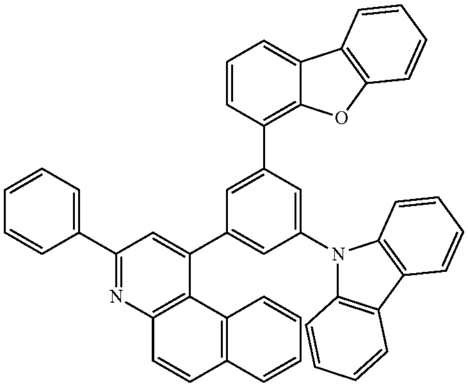
561
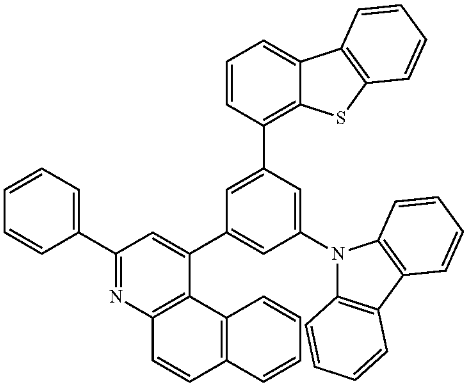
562
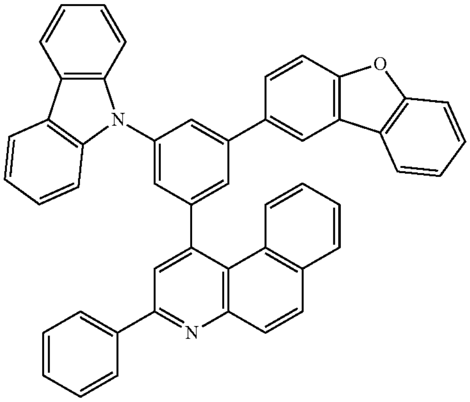

563
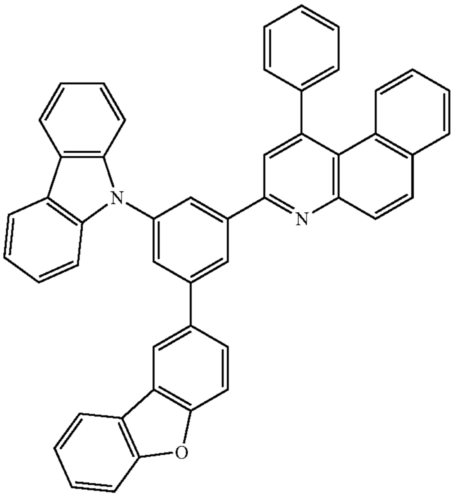
564
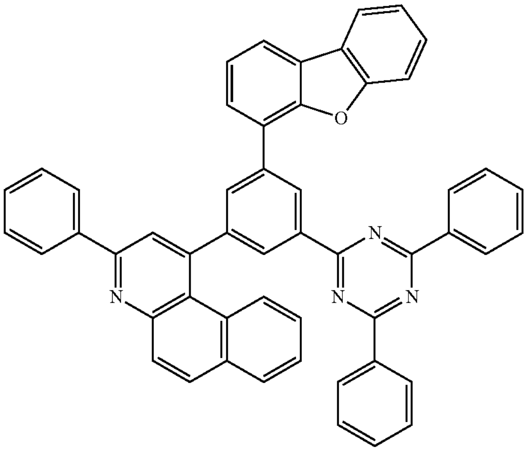
565
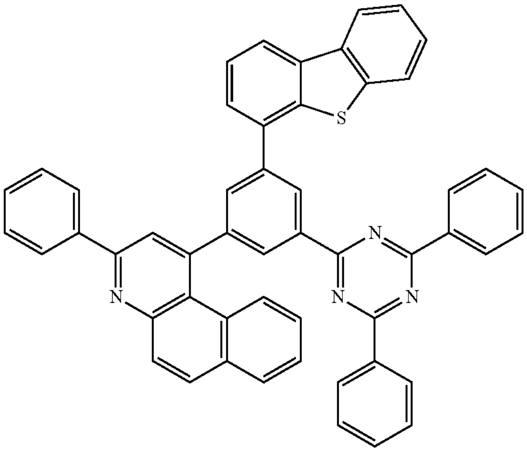
566
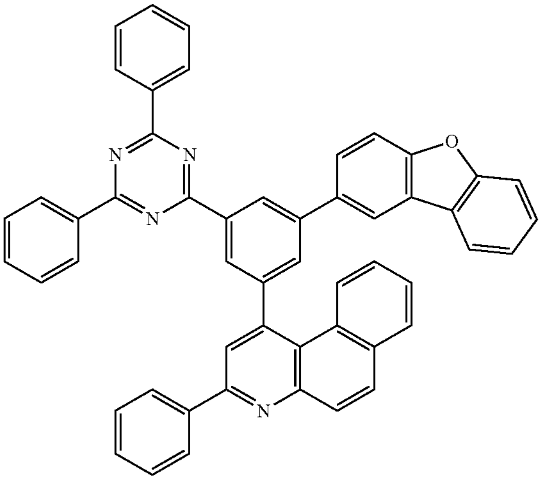
567
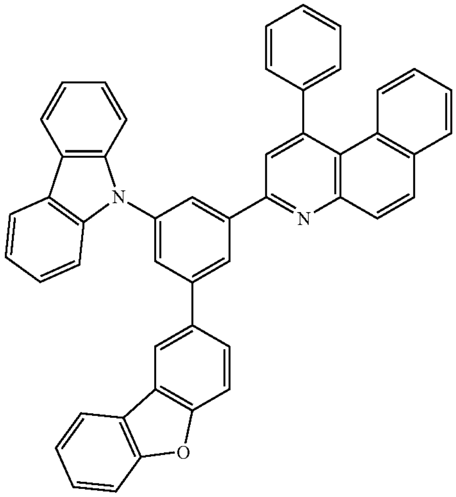
568
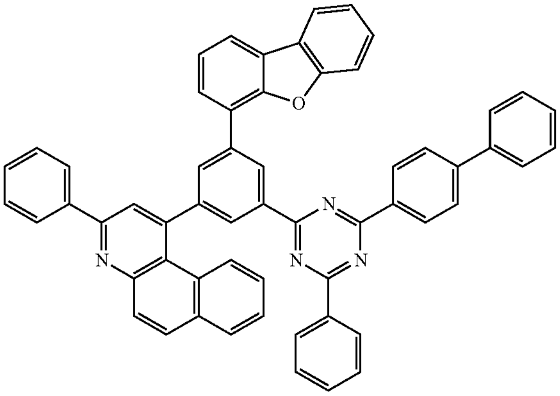

-continued
569
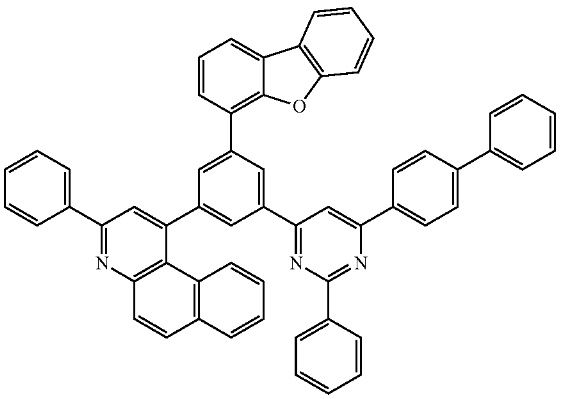
570
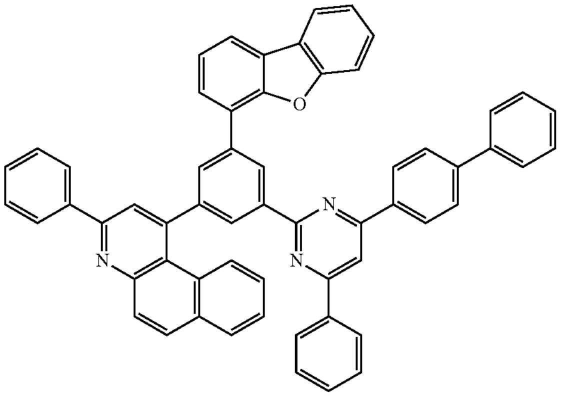
571
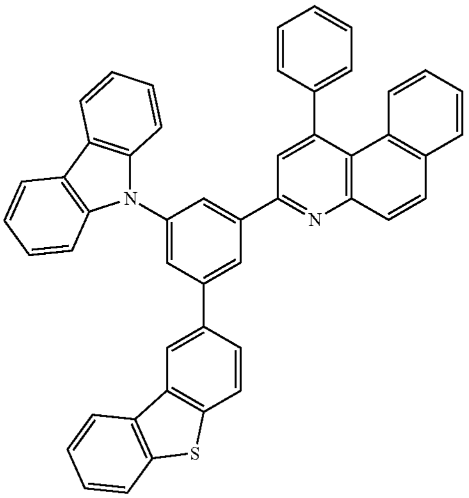
-continued
572
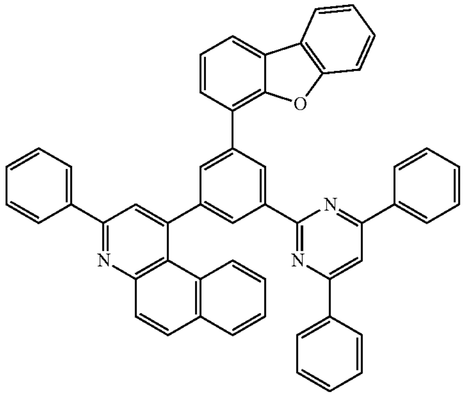
573
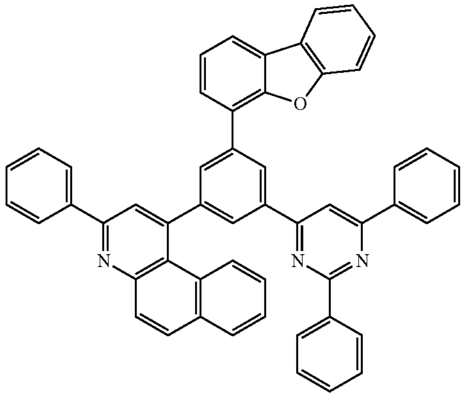
574
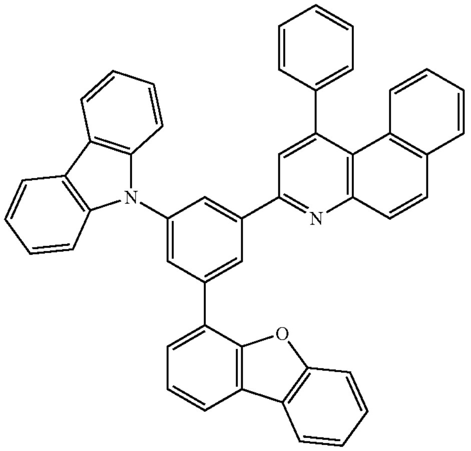

-continued
575
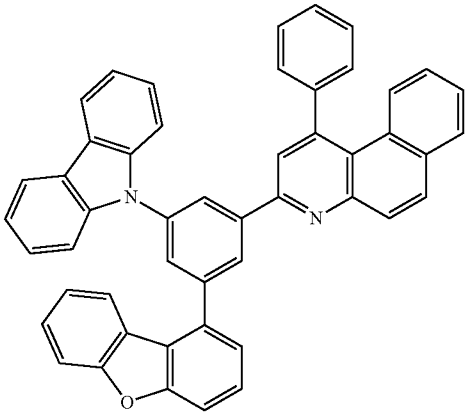
576
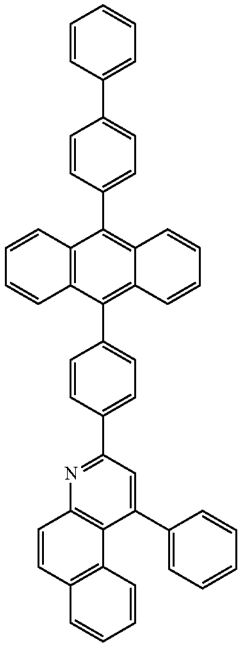
-continued
577
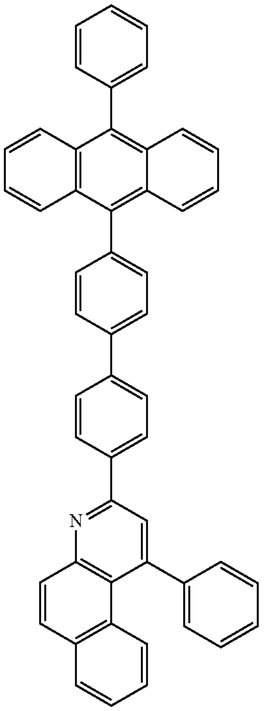
578
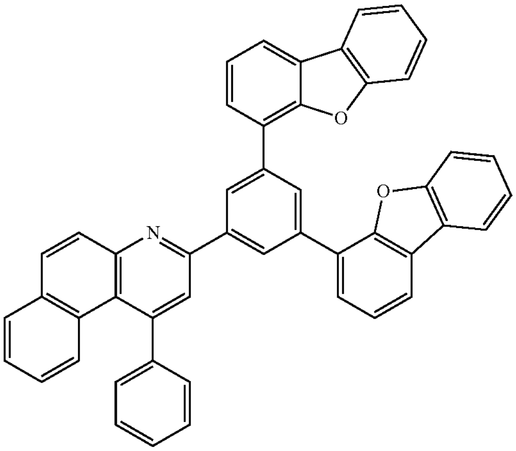
579
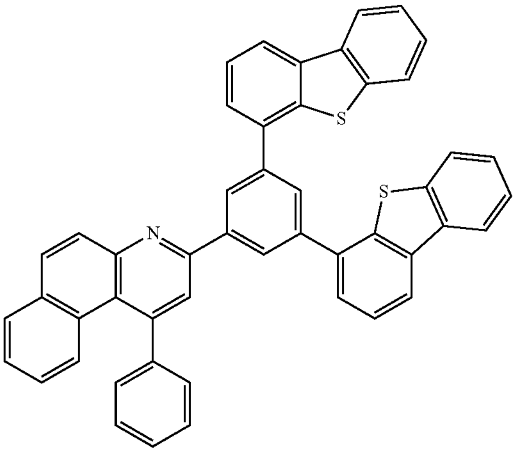

-continued
580
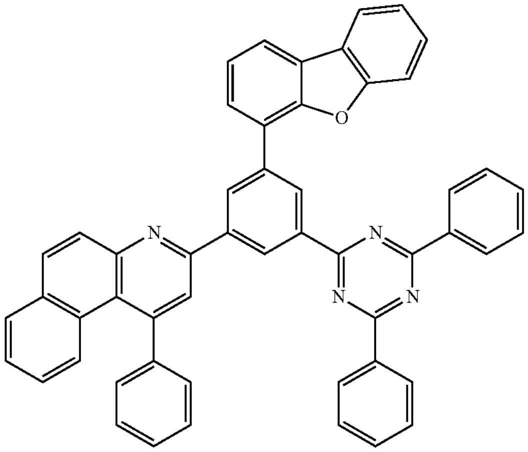
581
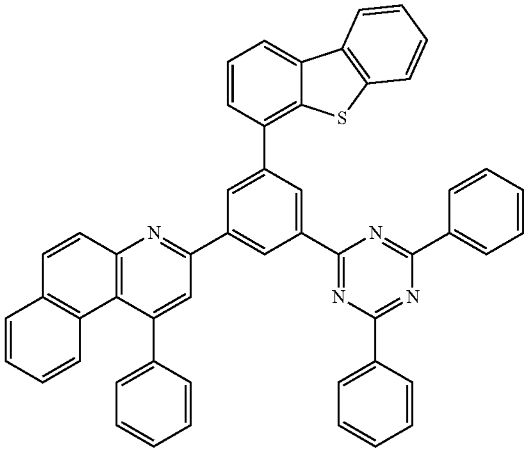
582
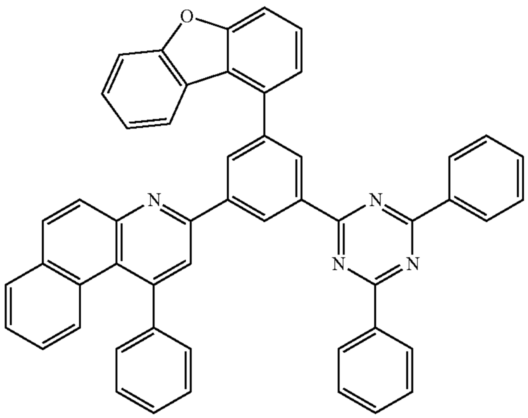
-continued
583
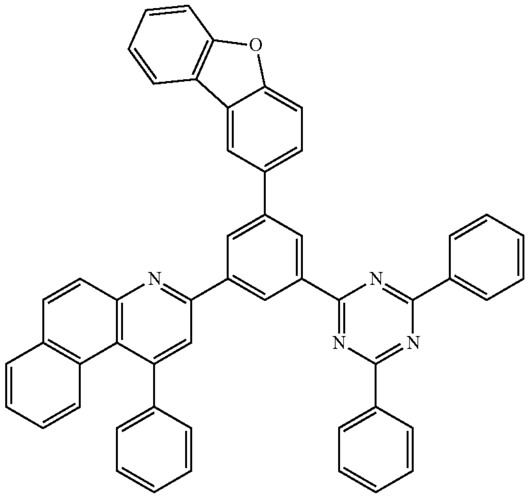
584
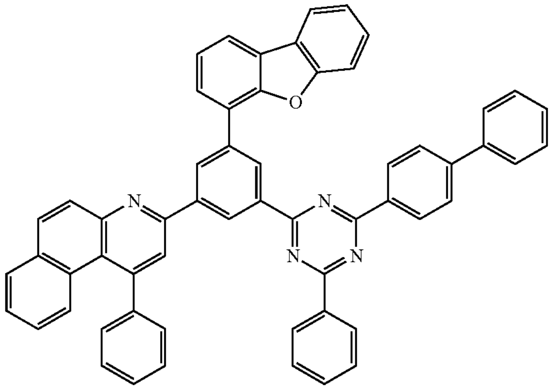
585
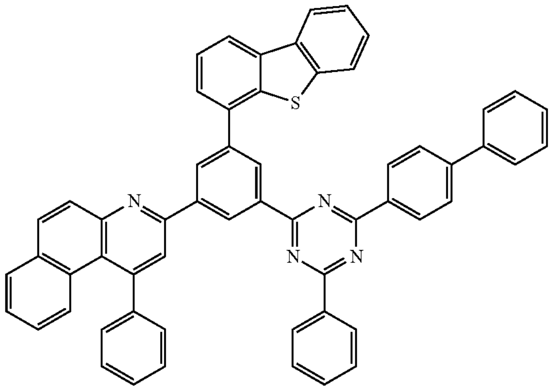

-continued
586
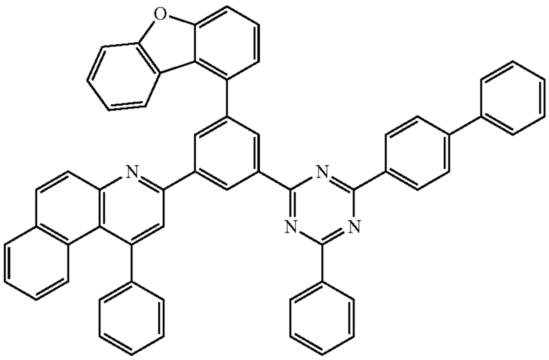
587
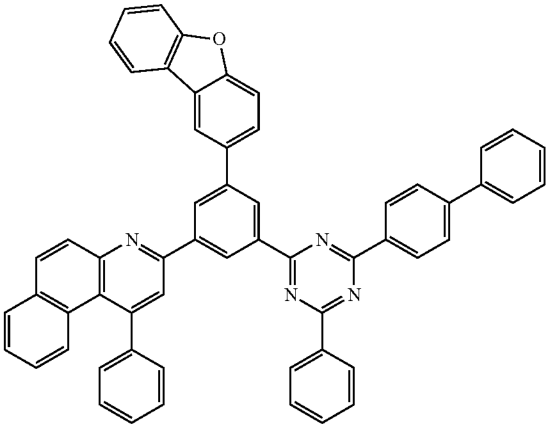
588
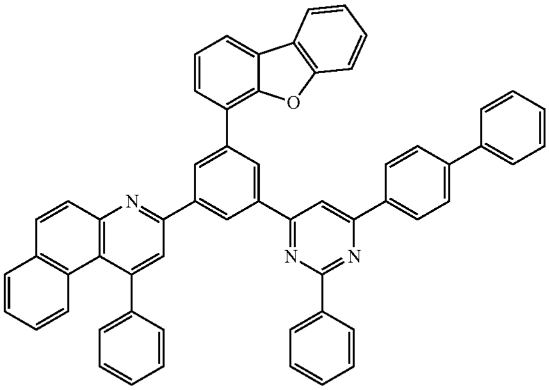
589
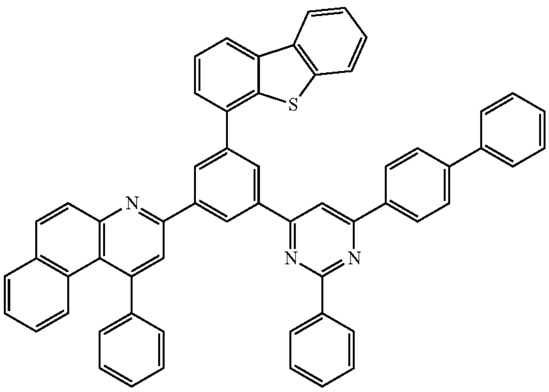
-continued
590
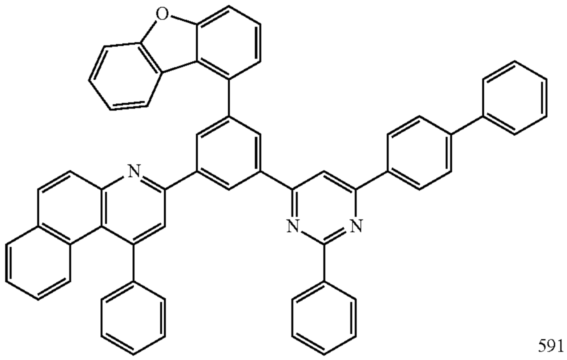
591
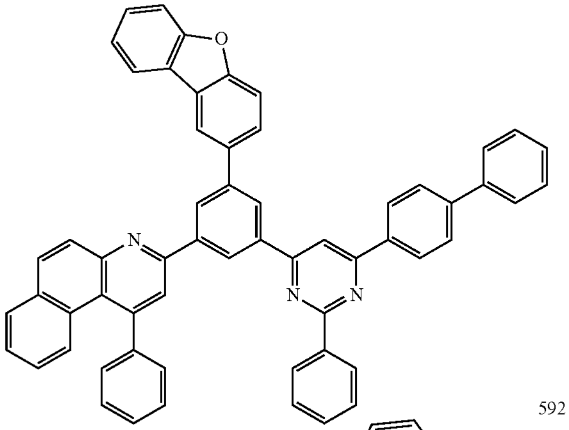
592
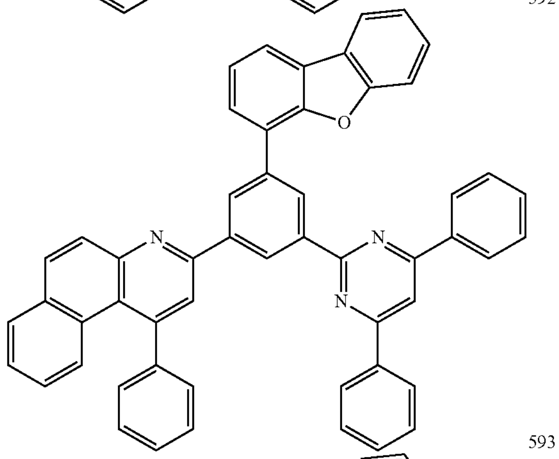
593
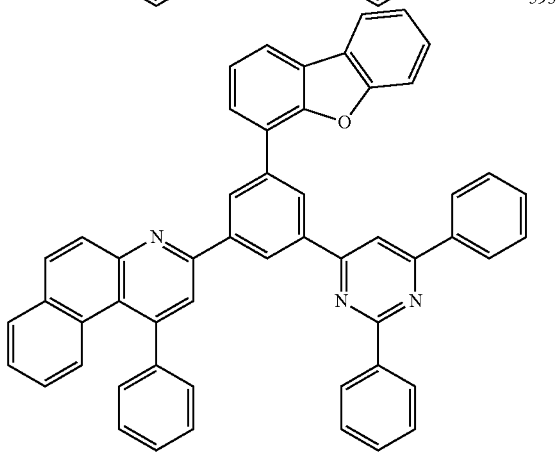

-continued

594

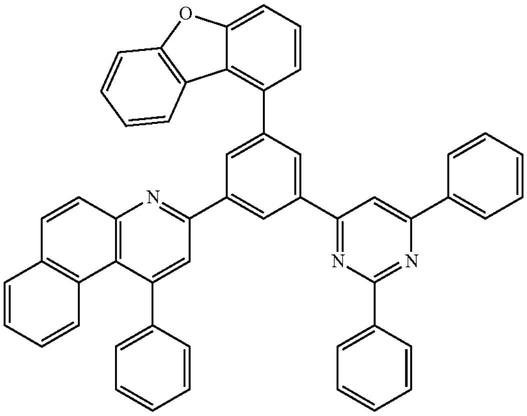

595

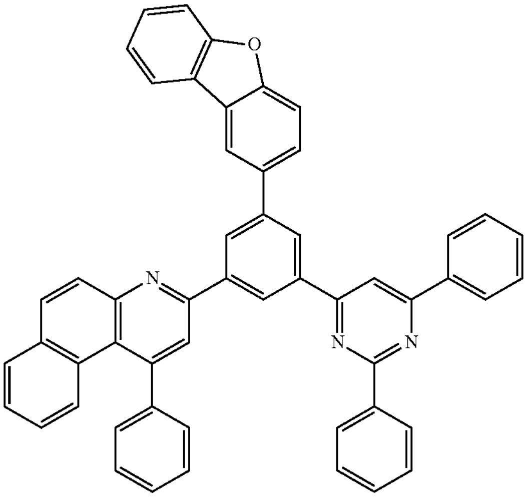

3. An organic light emitting device comprising:

an anode;

a cathode; and one or more organic material layers provided between the anode and the cathode, wherein one or more layers of the organic material layers comprise the hetero-cyclic compound of claim 1.

4. The organic light emitting device of claim 3, wherein the organic material layer comprises at least one of a hole blocking layer, an electron injection layer and an electron transfer layer, and at least one of the hole blocking layer, the electron injection layer and the electron transfer layer comprises the hetero-cyclic compound.

5. The organic light emitting device of claim 3, wherein the organic material layer comprises a light emitting layer, and the light emitting layer comprises the hetero-cyclic compound.

6. The organic light emitting device of claim 3, wherein the organic material layer comprises one or more of a hole injection layer, a hole transfer layer, and a layer carrying out hole injection and hole transfer at the same time, and one of the above-mentioned layers comprises the hetero-cyclic compound.

7. The organic light emitting device of claim 3, wherein the organic material layer comprises a charge generation layer, and the charge generation layer comprises the hetero-cyclic compound.

8. The organic light emitting device of claim 3, comprising:

an anode;

a first stack provided on the anode and comprising a first light emitting layer;

a charge generation layer provided on the first stack;

a second stack provided on the charge generation layer and comprising a second light emitting layer; and a cathode provided on the second stack.

* * * * *